US012774293B2

(12) United States Patent
Nishimae et al.

(10) Patent No.: US 12,774,293 B2
(45) Date of Patent: Oct. 27, 2026

(54) COMPOUND, MATERIAL FOR ORGANIC ELECTROLUMINESCENT ELEMENT, ORGANIC ELECTROLUMINESCENT ELEMENT AND ELECTRONIC DEVICE

(71) Applicant: IDEMITSU KOSAN CO., LTD., Tokyo (JP)

(72) Inventors: Yuichi Nishimae, Basel (CH); Annemarie Wolleb, Basel (CH); Pierre Boufflet, Basel (CH); Thomas Schaefer, Basel (CH)

(73) Assignee: IDEMITSU KOSAN CO., LTD., Tokyo (JP)

( * ) Notice: Subject to any disclaimer, the term of this patent is extended or adjusted under 35 U.S.C. 154(b) by 1139 days.

(21) Appl. No.: 17/865,693

(22) Filed: Jul. 15, 2022

(65) Prior Publication Data

US 2023/0106429 A1 Apr. 6, 2023

(30) Foreign Application Priority Data

Jul. 16, 2021 (JP) ................................. 2021-118158

(51) Int. Cl.
*C07F 5/02* (2006.01)
*C07C 15/28* (2006.01)
(Continued)

(52) U.S. Cl.
CPC .............. *C07F 5/027* (2013.01); *C07C 15/28* (2013.01); *C07C 15/30* (2013.01); *C07C 15/38* (2013.01);
(Continued)

(58) Field of Classification Search
None
See application file for complete search history.

(56) References Cited

U.S. PATENT DOCUMENTS

2010/0295444 A1 11/2010 Kuma et al.

FOREIGN PATENT DOCUMENTS

CN 106467554 A 3/2017
KR 20210010407 A * 1/2021
(Continued)

*Primary Examiner* — Tae H Yoon
(74) *Attorney, Agent, or Firm* — Foley & Lardner LLP

(57) ABSTRACT

A compound has, in a molecule, a cyclic structure represented by a formula (1) below; and at least one cyclic structure selected from the group consisting of a cyclic structure represented by a formula (10) below and a cyclic structure represented by a formula (11) below. In the formula (1): $R_1$ to $R_{16}$ are each independently a hydrogen atom, an alkyl group or the like; and $R_X$ and $R_Y$ are each independently an alkyl group.

(1)

(10)

(Continued)

-continued

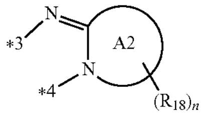

(11)

15 Claims, 3 Drawing Sheets

Figure 1:
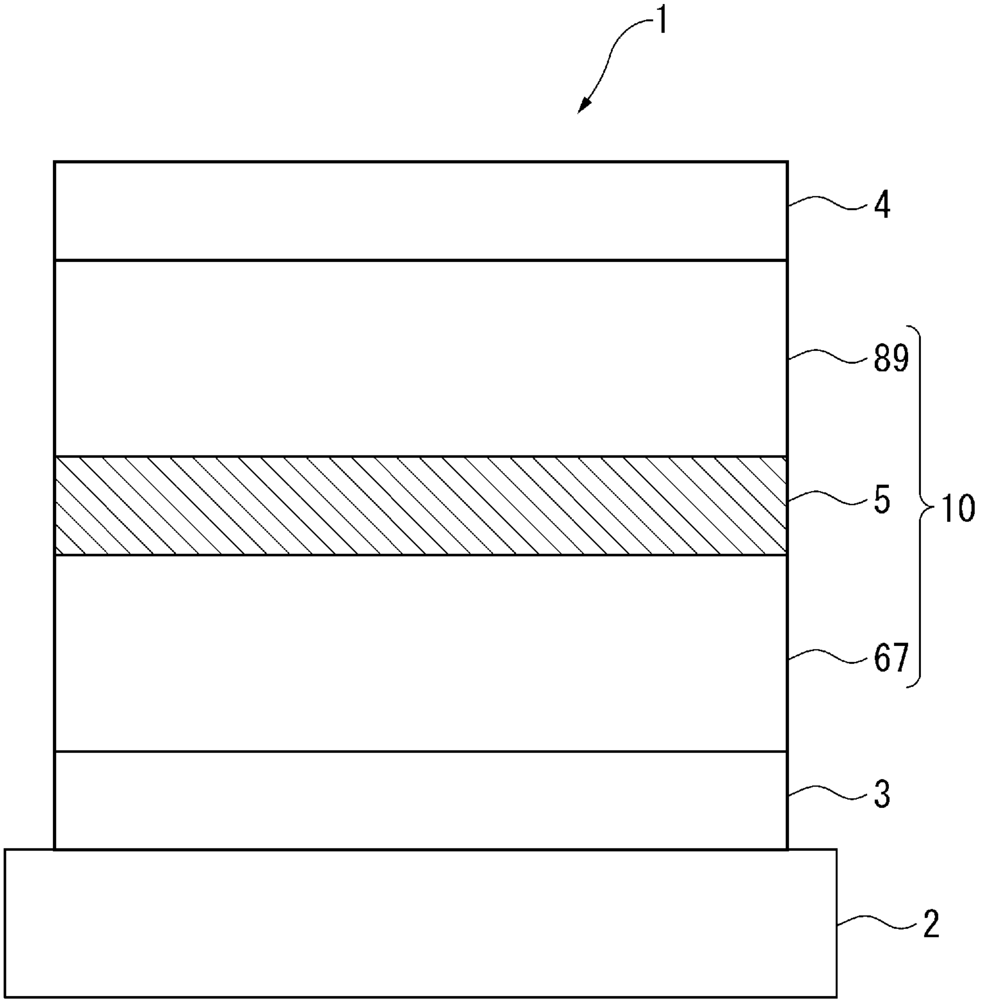

(51) Int. Cl.

| | |
|---|---|
| ***C07C 15/30*** | (2006.01) |
| ***C07C 15/38*** | (2006.01) |
| ***C07D 307/91*** | (2006.01) |
| ***C07D 333/76*** | (2006.01) |
| ***C07D 487/22*** | (2006.01) |
| ***C07F 7/08*** | (2006.01) |
| ***H01L 51/00*** | (2006.01) |
| ***H01L 51/50*** | (2006.01) |
| ***H10K 50/125*** | (2023.01) |
| ***H10K 85/40*** | (2023.01) |
| ***H10K 85/60*** | (2023.01) |

(52) U.S. Cl.

CPC ......... *C07D 307/91* (2013.01); *C07D 333/76* (2013.01); *C07D 487/22* (2013.01); *C07F 7/0805* (2013.01); *H10K 50/125* (2023.02); *H10K 85/40* (2023.02); *H10K 85/615* (2023.02); *H10K 85/622* (2023.02); *H10K 85/623* (2023.02); *H10K 85/636* (2023.02); *H10K 85/652* (2023.02); *H10K 85/657* (2023.02); *H10K 85/6572* (2023.02); *H10K 85/6574* (2023.02); *H10K 85/658* (2023.02); *C07B 2200/05* (2013.01)

(56) References Cited

FOREIGN PATENT DOCUMENTS

| | | | |
|---|---|---|---|
| KR | 1020210010407 | A | 1/2021 |
| WO | WO-2010/134350 | A1 | 11/2010 |
| WO | WO-2020/251049 | A1 | 12/2020 |

* cited by examiner

COMPOUND, MATERIAL FOR ORGANIC ELECTROLUMINESCENT ELEMENT, ORGANIC ELECTROLUMINESCENT ELEMENT AND ELECTRONIC DEVICE

THE ENTIRE DISCLOSURE OF JAPANESE PATENT APPLICATION NO. 2021-118158, FILED Jul. 16, 2021, IS EXPRESSLY INCORPORATED BY REFERENCE HEREIN.

TECHNICAL FIELD

The present invention relates to a compound, an organic-electroluminescence-device material, an organic electroluminescence device, and an electronic device.

BACKGROUND ART

When a voltage is applied to an organic electroluminescence device (hereinafter, occasionally referred to as an organic EL device), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies have been made to improve a performance of the organic EL device.

Examples of literatures regarding an organic EL device and a compound used for the organic EL device include Literature 1 (Chinese Patent No. 106467554), Literature 2 (International Publication No. WO. 2020/251049), and Literature 3 (Korean Patent Publication No. 10-2021-0010407).

A further improvement in performance of the organic EL device has been demanded for an improvement in performance of an electronic device such as a display. The performance of the organic EL device is evaluable in terms of, for instance, luminance, emission wavelength, chromaticity, luminous efficiency, drive voltage, and lifetime. As a factor for improving the luminous efficiency, for instance, a compound having a high photoluminescence quantum yield (PLQY) is usable. Moreover, a blue emitting material among emitting materials used for the organic EL device is required to exhibit emission peak wavelength in a desired wavelength band in a fluorescence spectrum waveform.

SUMMARY OF THE INVENTION

An object of the invention is to provide a compound having a high PLQY and exhibiting an emission peak wavelength in a desired wavelength band in a fluorescence spectrum waveform. Another object of the invention is to provide an organic-electroluminescence-device material and an organic electroluminescence device which contain a compound having a high PLQY and exhibiting an emission peak wavelength in a desired wavelength band in a fluorescence spectrum waveform, and an electronic device including the organic electroluminescence device.

An aspect of the invention provides a compound having, in a molecule, a cyclic structure represented by a formula (1) below and at least one cyclic structure of a cyclic structure represented by a formula (10) below or a cyclic structure represented by a formula (11) below.

(1)

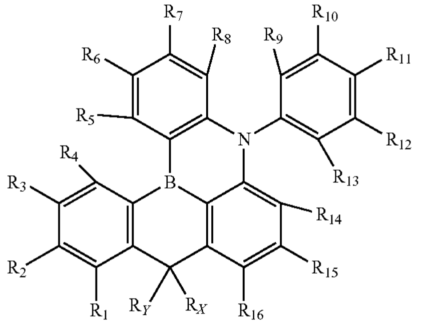

(10)

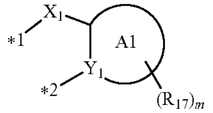

(11)

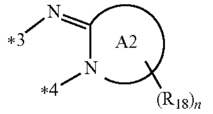

In the formula (1):

at least one combination of adjacent two or more of $R_1$ to $R_{16}$ are mutually bonded to form a substituted or unsubstituted monocyclic ring, mutually bonded to form a substituted or unsubstituted fused ring, or not mutually bonded;

at least one combination of adjacent two or more of $R_1$ to $R_{16}$ are mutually bonded to form the cyclic structure represented by the formula (10) or (11);

a combination of $R_4$ and $R_5$, a combination of $R_8$ and $R_9$, and a combination of $R_{13}$ and $R_{14}$ are not mutually bonded and form neither the cyclic structure represented by the formula (10) nor the cyclic structure represented by the formula (11);

$R_1$ to $R_{16}$ forming neither the cyclic structure represented by the formula (10) nor the cyclic structure represented by the formula (11) are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—N(R_{131})(R_{132})$, a group represented by $—Si(R_{133})(R_{134})(R_{135})$, a group represented by $—O—(R_{136})$, a group represented by $—S—(R_{137})$, a substituted or unsubstituted aralkyl group having 7 to 50 carbon atoms, a group represented by $—C(=O)R_{138}$, a group represented by $—COOR_{139}$, a halogen atom, a cyano group, a nitro group, a group represented by $—P(=O)(R_{140})(R_{141})$, a group represented by $—Ge(R_{142})(R_{143})(R_{144})$, a group represented by $—B(R_{145})(R_{146})$, a substituted or unsubstituted aryl group having 6 to 50 ring carbon atoms, or a substituted or unsubstituted heterocyclic group having 5 to 50 ring atoms;

a combination of $R_X$ and $R_Y$ are mutually bonded to form a substituted or unsubstituted monocyclic ring, mutually bonded to form a substituted or unsubstituted fused ring, or not mutually bonded; and $R_X$ and $R_Y$ forming neither the substituted or unsubstituted monocyclic ring nor the substituted or unsubstituted fused ring are each independently a substituted or unsubstituted alkyl group having 1 to 50 carbon atoms.

In the formula (10):

a ring A1 is a substituted or unsubstituted aliphatic hydrocarbon ring having 3 to 50 ring carbon atoms, a substituted or unsubstituted aromatic hydrocarbon ring having 6 to 50 ring carbon atoms, or a substituted or unsubstituted heterocycle having 5 to 50 ring atoms;

m represents the number of $R_{17}$ bonded to the ring A1 and is an integer of 1 or more;

when a plurality of $R_{17}$ are present, the plurality of $R_{17}$ are mutually the same or different;

$X_1$ is $NR_{100}$, an oxygen atom, or a sulfur atom;

when a plurality of $X_1$ are present, the plurality of $X_1$ are mutually the same or different;

$Y_1$ is a carbon atom or a nitrogen atom; and 1 and *2 each represent a bonding position to the cyclic structure represented by the formula (1).

In the formula (11):

a ring A2 is a substituted or unsubstituted aliphatic hydrocarbon ring having 3 to 50 ring carbon atoms, a substituted or unsubstituted aromatic hydrocarbon ring having 6 to 50 ring carbon atoms, or a substituted or unsubstituted heterocycle having 5 to 50 ring atoms;

n represents the number of $R_{18}$ bonded to the ring A2 and is an integer of 1 or more;

when a plurality of $R_{18}$ are present, the plurality of $R_{18}$ are mutually the same or different;

3 and *4 each represent a bonding position to the cyclic structure represented by the formula (1);

at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{16}$, $R_{17}$ or $R_{18}$ is a group represented by $—N(R_{131})(R_{132})$;

a combination of $R_{100}$, and one adjacent to $R_{100}$ among $R_1$ to $R_{16}$, $R_{17}$, $R_{18}$, $R_{131}$ and $R_{132}$ that form neither the cyclic structure represented by the formula (10) nor the cyclic structure represented by the formula (11) are mutually bonded to form a substituted or unsubstituted monocyclic ring, mutually bonded to form a substituted or unsubstituted fused ring, or not mutually bonded;

a combination of $R_{131}$ and $R_{132}$ are mutually bonded to form a substituted or unsubstituted monocyclic ring, mutually bonded to form a substituted or unsubstituted fused ring, or not mutually bonded;

a combination of: at least one of $R_{131}$ or $R_{132}$ forming neither the substituted or unsubstituted monocyclic ring nor the substituted or unsubstituted fused ring; and at least one adjacent to $R_{131}$ or $R_{132}$ among $R_1$ to $R_{16}$, $R_{17}$, $R_{18}$, and $R_{100}$ that form neither the cyclic structure represented by the formula (10) nor the cyclic structure represented by the formula (11) are mutually bonded to form a substituted or unsubstituted monocyclic ring, mutually bonded to form a substituted or unsubstituted fused ring, or not mutually bonded;

$R_{17}$ and $R_{18}$ forming neither the substituted or unsubstituted monocyclic ring nor the substituted or unsubstituted fused ring each independently represent the same as $R_1$ to $R_{16}$ forming neither the cyclic structure represented by the formula (10) nor the cyclic structure represented by the formula (11);

$R_{100}$, $R_{131}$ and $R_{132}$ forming neither the substituted or unsubstituted monocyclic ring nor the substituted or unsubstituted fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{100}$ are present, the plurality of $R_{100}$ are mutually the same or different;

when a plurality of $R_{131}$ are present, the plurality of $R_{131}$ are mutually the same or different;

when a plurality of $R_{132}$ are present, the plurality of $R_{132}$ are mutually the same or different;

$R_{133}$ to $R_{146}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{133}$ are present, the plurality of $R_{133}$ are mutually the same or different;

when a plurality of $R_{134}$ are present, the plurality of $R_{134}$ are mutually the same or different;

when a plurality of $R_{135}$ are present, the plurality of $R_{135}$ are mutually the same or different;

when a plurality of $R_{136}$ are present, the plurality of $R_{136}$ are mutually the same or different;

when a plurality of $R_{137}$ are present, the plurality of $R_{137}$ are mutually the same or different;

when a plurality of $R_{138}$ are present, the plurality of $R_{138}$ are mutually the same or different;

when a plurality of $R_{139}$ are present, the plurality of $R_{139}$ are mutually the same or different;

when a plurality of $R_{140}$ are present, the plurality of $R_{140}$ are mutually the same or different;

when a plurality of $R_{141}$ are present, the plurality of $R_{141}$ are mutually the same or different;

when a plurality of $R_{142}$ are present, the plurality of $R_{142}$ are mutually the same or different;

when a plurality of $R_{143}$ are present, the plurality of $R_{143}$ are mutually the same or different;

when a plurality of $R_{144}$ are present, the plurality of $R_{144}$ are mutually the same or different;

when a plurality of $R_{145}$ are present, the plurality of $R_{145}$ are mutually the same or different; and when a plurality of $R_{146}$ are present, the plurality of $R_{146}$ are mutually the same or different.

Another aspect of the invention provides an organic-electroluminescence-device material containing the compound according to the above aspect of the invention.

Still another aspect of the invention provides an organic electroluminescence device including: a cathode, an anode, and at least one organic layer provided between the cathode and the anode, in which at least one of the at least one organic layer contains the compound according to the above aspect of the invention.

The above aspect of the invention provides the organic electroluminescence device in which the at least one organic layer includes an emitting layer, and the emitting layer contains the compound according to the above aspect of the invention.

A further aspect of the invention provides an electronic device including the organic electroluminescence device according to the above aspect of the invention.

According to the above aspect of the invention, a compound having a high PLQY and an emission peak wavelength in a desired wavelength band in a fluorescence spectrum waveform can be provided. According to the above aspect of the invention, an organic-electroluminescence-device material or organic electroluminescence device containing a compound having a high PLQY and an emission peak wavelength in a desired wavelength band in a fluorescence spectrum waveform can be provided. Moreover, according to the above aspect of the invention, an electronic device including the above organic electroluminescence device can be provided.

BRIEF DESCRIPTION OF DRAWING(S)

FIG. 1 schematically shows an exemplary arrangement of an organic electroluminescence device according to a third exemplary embodiment of the invention.

Figure 2:
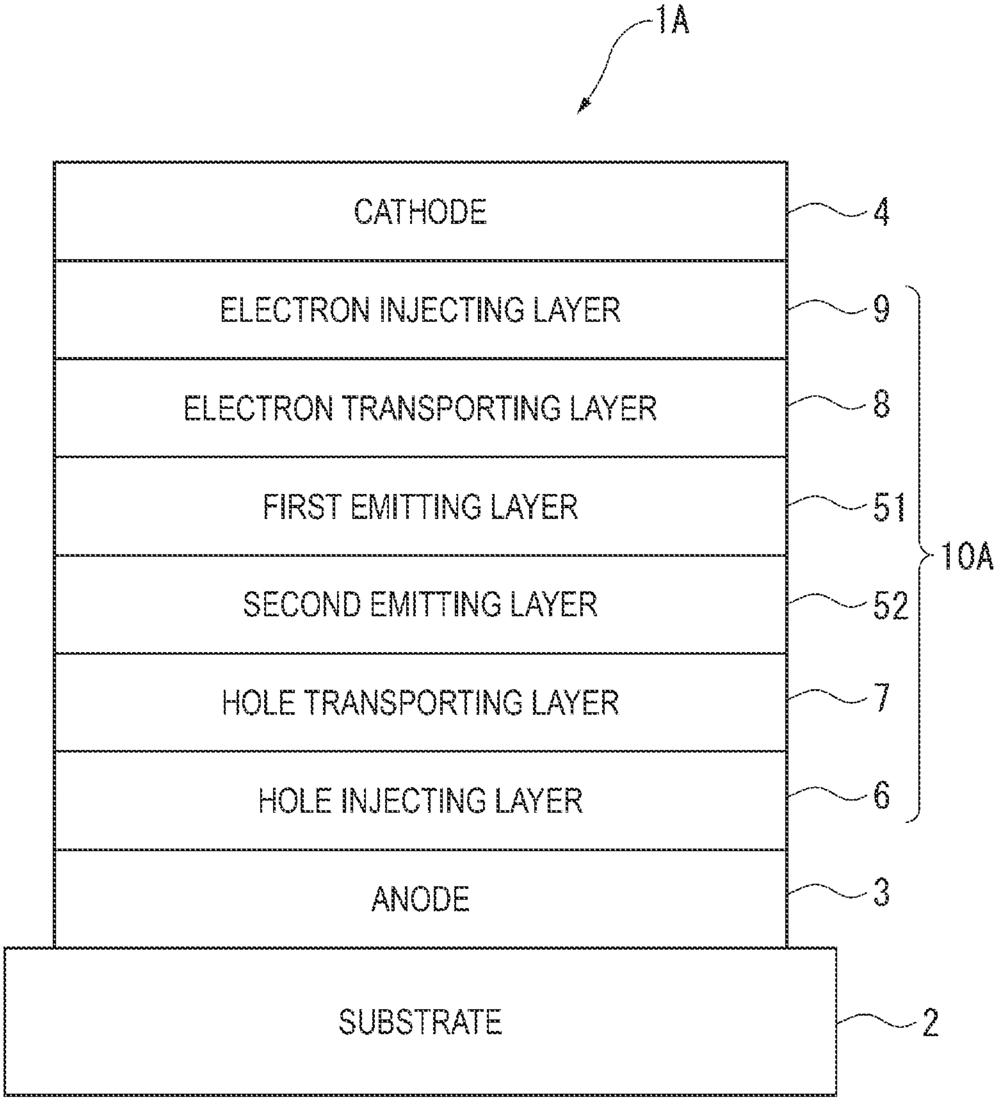

FIG. 2 schematically shows an exemplary arrangement of an organic electroluminescence device according to a fourth exemplary embodiment of the invention.

Figure 3:
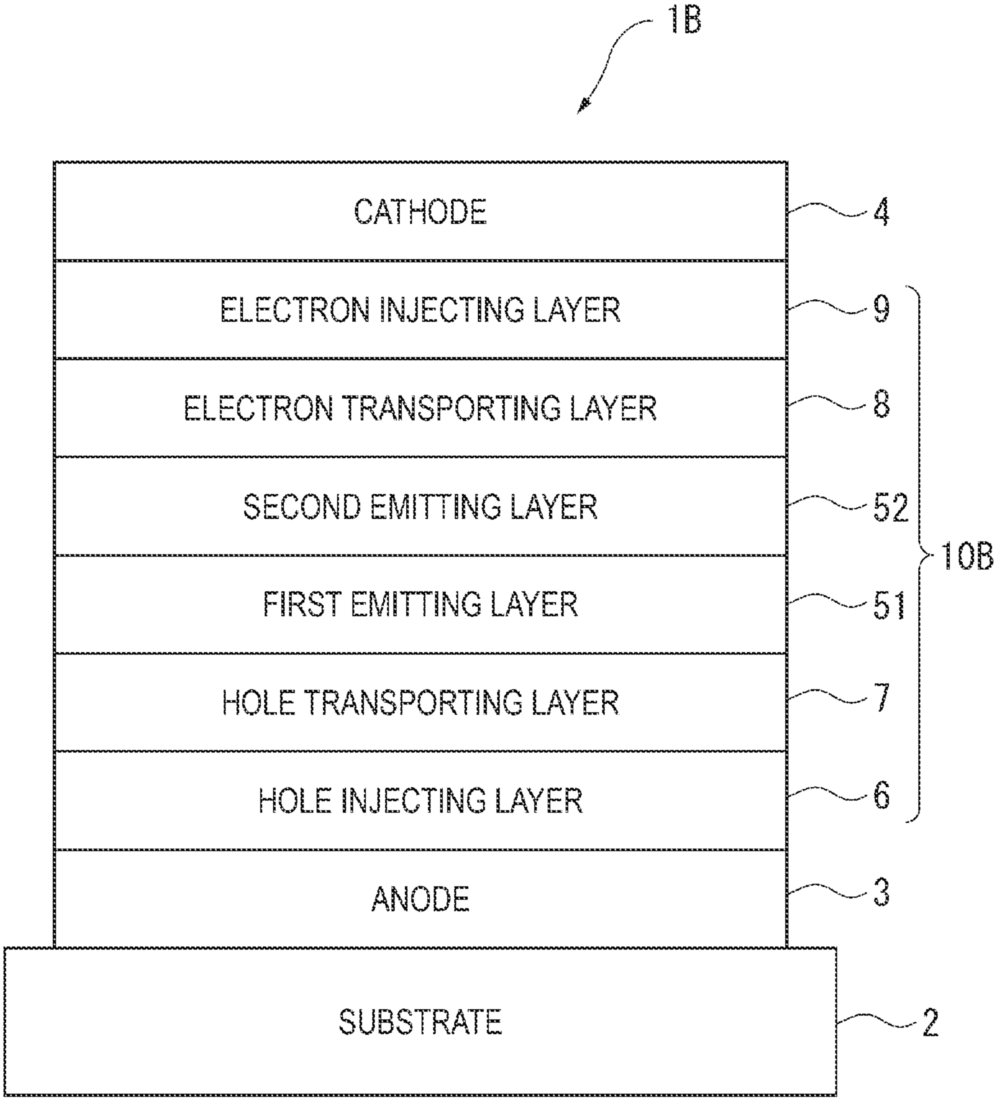

FIG. 3 schematically shows another exemplary arrangement of the organic electroluminescence device according to the fourth exemplary embodiment of the invention.

DESCRIPTION OF EMBODIMENT(S)

Definitions

Herein, a hydrogen atom includes isotopes having different numbers of neutrons, specifically, protium, deuterium and tritium.

In chemical formulae herein, it is assumed that a hydrogen atom (i.e. protium, deuterium and tritium) is bonded to each of bondable positions that are not annexed with signs "R" or the like or "D" representing a deuterium.

Herein, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded with each other to form the ring. When the ring is substituted by a substituent(s), carbon atom(s) contained in the substituent(s) is not counted in the ring carbon atoms. Unless otherwise specified, the same applies to the "ring carbon atoms" described later. For instance, a benzene ring has 6 ring carbon atoms, a naphthalene ring has 10 ring carbon atoms, a pyridine ring has 5 ring carbon atoms, and a furan ring has 4 ring carbon atoms. Further, for instance, 9,9-diphenylfluorenyl group has 13 ring carbon atoms and 9,9'-spirobifluorenyl group has 25 ring carbon atoms.

When a benzene ring is substituted by a substituent in a form of, for instance, an alkyl group, the number of carbon atoms of the alkyl group is not counted in the number of the ring carbon atoms of the benzene ring. Accordingly, the benzene ring substituted by an alkyl group has 6 ring carbon atoms. When a naphthalene ring is substituted by a substituent in a form of, for instance, an alkyl group, the number of carbon atoms of the alkyl group is not counted in the number of the ring carbon atoms of the naphthalene ring. Accordingly, the naphthalene ring substituted by an alkyl group has 10 ring carbon atoms.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, and ring assembly). Atom(s) not forming the ring (e.g., hydrogen atom(s) for saturating the valence of the atom which forms the ring) and atom(s) in a substituent by which the ring is substituted are not counted as the ring atoms. Unless otherwise specified, the same applies to the "ring atoms" described later. For instance, a pyridine ring has 6 ring atoms, a quinazoline ring has 10 ring atoms, and a furan ring has 5 ring atoms. For instance, the number of hydrogen atom(s) bonded to a pyridine ring or the number of atoms forming a substituent are not counted as the pyridine ring atoms. Accordingly, a pyridine ring bonded with a hydrogen atom(s) or a substituent(s) has 6 ring atoms. For instance, the hydrogen atom(s) bonded to carbon atom(s) of a quinazoline ring or the atoms forming a substituent are not counted as the quinazoline ring atoms. Accordingly, a quinazoline ring bonded with hydrogen atom(s) or a substituent(s) has 10 ring atoms.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group. Herein, "YY" is larger than "XX," "XX" representing an integer of 1 or more and "YY" representing an integer of 2 or more.

Herein, "XX to YY atoms" in the description of "substituted or unsubstituted ZZ group having XX to YY atoms" represent atoms of an unsubstituted ZZ group and do not include atoms of a substituent(s) of the substituted ZZ group. Herein, "YY" is larger than "XX," "XX" representing an integer of 1 or more and "YY" representing an integer of 2 or more.

Herein, an unsubstituted ZZ group refers to an "unsubstituted ZZ group" in a "substituted or unsubstituted ZZ group," and a substituted ZZ group refers to a "substituted ZZ group" in a "substituted or unsubstituted ZZ group."

Herein, the term "unsubstituted" used in a "substituted or unsubstituted ZZ group" means that a hydrogen atom(s) in the ZZ group is not substituted with a substituent(s). The hydrogen atom(s) in the "unsubstituted ZZ group" is protium, deuterium, or tritium.

Herein, the term "substituted" used in a "substituted or unsubstituted ZZ group" means that at least one hydrogen atom in the ZZ group is substituted with a substituent. Similarly, the term "substituted" used in a "BB group substituted by AA group" means that at least one hydrogen atom in the BB group is substituted with the AA group.

Substituents Mentioned Herein

Substituents mentioned herein will be described below.

An "unsubstituted aryl group" mentioned herein has, unless otherwise specified herein, 6 to 50, preferably 6 to 30, more preferably 6 to 18 ring carbon atoms.

An "unsubstituted heterocyclic group" mentioned herein has, unless otherwise specified herein, 5 to 50, preferably 5 to 30, more preferably 5 to 18 ring atoms.

An "unsubstituted alkyl group" mentioned herein has, unless otherwise specified herein, 1 to 50, preferably 1 to 20, more preferably 1 to 6 carbon atoms.

An "unsubstituted alkenyl group" mentioned herein has, unless otherwise specified herein, 2 to 50, preferably 2 to 20, more preferably 2 to 6 carbon atoms.

An "unsubstituted alkynyl group" mentioned herein has, unless otherwise specified herein, 2 to 50, preferably 2 to 20, more preferably 2 to 6 carbon atoms.

An "unsubstituted cycloalkyl group" mentioned herein has, unless otherwise specified herein, 3 to 50, preferably 3 to 20, more preferably 3 to 6 ring carbon atoms.

An "unsubstituted arylene group" mentioned herein has, unless otherwise specified herein, 6 to 50, preferably 6 to 30, more preferably 6 to 18 ring carbon atoms.

An "unsubstituted divalent heterocyclic group" mentioned herein has, unless otherwise specified herein, 5 to 50, preferably 5 to 30, more preferably 5 to 18 ring atoms.

An "unsubstituted alkylene group" mentioned herein has, unless otherwise specified herein, 1 to 50, preferably 1 to 20, more preferably 1 to 6 carbon atoms.

Substituted or Unsubstituted Aryl Group

Specific examples (specific example group G1) of the "substituted or unsubstituted aryl group" mentioned herein include unsubstituted aryl groups (specific example group G1A) below and substituted aryl groups (specific example group G1B). Herein, an unsubstituted aryl group refers to an "unsubstituted heterocyclic group" in a "substituted or unsubstituted aryl group," and a substituted aryl group refers to a "substituted aryl group" in a "substituted or unsubstituted aryl group." A simply termed "aryl group" herein includes both of an "unsubstituted aryl group" and a "substituted aryl group."

The "substituted aryl group" refers to a group derived by substituting at least one hydrogen atom in an "unsubstituted aryl group" with a substituent. Examples of the "substituted aryl group" include a group derived by substituting at least one hydrogen atom in the "unsubstituted aryl group" in the specific example group G1A below with a substituent, and examples of the substituted aryl group in the specific example group G1B below. It should be noted that the examples of the "unsubstituted aryl group" and the "substituted aryl group" mentioned herein are merely exemplary, and the "substituted aryl group" mentioned herein includes a group derived by further substituting a hydrogen atom bonded to a carbon atom of a skeleton of a "substituted aryl group" in the specific example group G1B below, and a group derived by further substituting a hydrogen atom of a substituent of the "substituted aryl group" in the specific example group G1B below.

Unsubstituted Aryl Group (Specific Example Group G1A):

phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, benzanthryl group, phenanthryl group, benzophenanthryl group, phenalenyl group, pyrenyl group, chrysenyl group, benzochrysenyl group, triphenylenyl group, benzotriphenylenyl group, tetracenyl group, pentacenyl group, fluorenyl group, 9,9'-spirobifluorenyl group, benzofluorenyl group, dibenzofluorenyl group, fluoranthenyl group, benzofluoranthenyl group, perylenyl group, and a monovalent aryl group derived by removing one hydrogen atom from cyclic structures represented by formulae (TEMP-1) to (TEMP-15) below.

(TEMP-1)

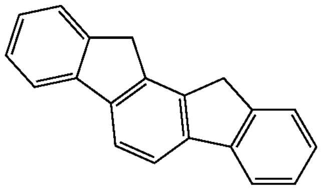

-continued (TEMP-2)

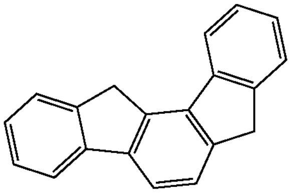

(TEMP-3)

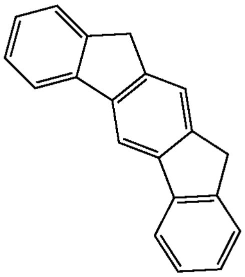

(TEMP-4)

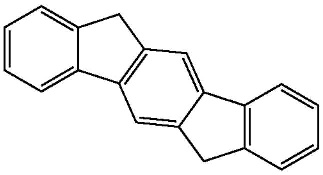

(TEMP-5)

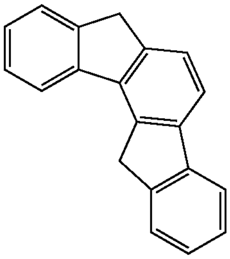

(TEMP-6)

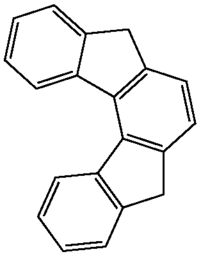

(TEMP-7)

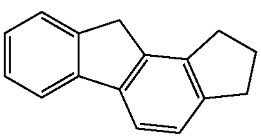

(TEMP-8)

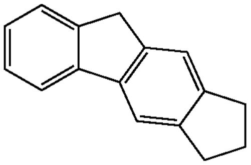

-continued (TEMP-9)

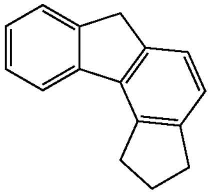

(TEMP-10)

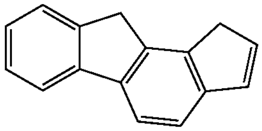

(TEMP-11)

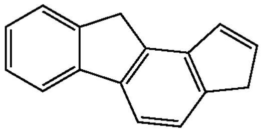

(TEMP-12)

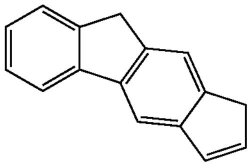

(TEMP-13)

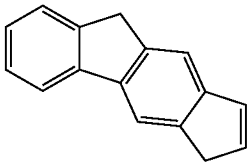

(TEMP-14)

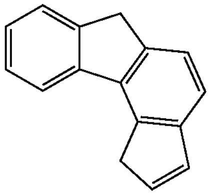

(TEMP-15)

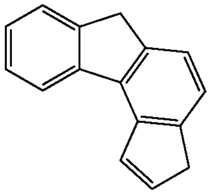

Substituted Aryl Group (Specific Example Group G1B):

o-tolyl group, m-tolyl group, p-tolyl group, para-xylyl group, meta-xylyl group, ortho-xylyl group, para-isopropylphenyl group, meta-isopropylphenyl group, ortho-isopropylphenyl group, para-t-butylphenyl group, meta-t-butylphenyl group, ortho-t-butylphenyl group, 3,4,5-trimethylphenyl group, 9,9-dimethylfluorenyl group, 9,9-diphenylfluorenyl group, 9,9-bis(4-methylphenyl)fluorenyl group, 9,9-bis(4-isopropylphenyl)fluorenyl group, 9,9-bis(4-t-butylphenyl)fluorenyl group, cyanophenyl group, triphenylsilylphenyl group, trimethylsilylphenyl group, phenylnaphthyl group, naphthylphenyl group, and a group derived by substituting at least one hydrogen atom of a monovalent group derived from the cyclic structures represented by the formulae (TEMP-1) to (TEMP-15) with a substituent.

Substituted or Unsubstituted Heterocyclic Group

The "heterocyclic group" mentioned herein refers to a cyclic group having at least one hetero atom in the ring atoms. Specific examples of the hetero atom include a nitrogen atom, oxygen atom, sulfur atom, silicon atom, phosphorus atom, and boron atom.

The "heterocyclic group" mentioned herein is a monocyclic group or a fused-ring group.

The "heterocyclic group" mentioned herein is an aromatic heterocyclic group or a non-aromatic heterocyclic group.

Specific examples (specific example group G2) of the "substituted or unsubstituted heterocyclic group" mentioned herein include unsubstituted heterocyclic groups (specific example group G2A) and substituted heterocyclic groups (specific example group G2B). Herein, an unsubstituted heterocyclic group refers to an "unsubstituted heterocyclic group" in a "substituted or unsubstituted heterocyclic group," and a substituted heterocyclic group refers to a "substituted heterocyclic group" in a "substituted or unsubstituted heterocyclic group." A simply termed "heterocyclic group" herein includes both of an "unsubstituted heterocyclic group" and a "substituted heterocyclic group."

The "substituted heterocyclic group" refers to a group derived by substituting at least one hydrogen atom in an "unsubstituted heterocyclic group" with a substituent. Specific examples of the "substituted heterocyclic group" include a group derived by substituting at least one hydrogen atom in the "unsubstituted heterocyclic group" in the specific example group G2A below with a substituent, and examples of the substituted heterocyclic group in the specific example group G2B below. It should be noted that the examples of the "unsubstituted heterocyclic group" and the "substituted heterocyclic group" mentioned herein are merely exemplary, and the "substituted heterocyclic group" mentioned herein includes a group derived by further substituting a hydrogen atom bonded to a ring atom of a skeleton of a "substituted heterocyclic group" in the specific example group G2B below, and a group derived by further substituting a hydrogen atom of a substituent of the "substituted heterocyclic group" in the specific example group G2B below.

The specific example group G2A includes, for instance, unsubstituted heterocyclic groups including a nitrogen atom (specific example group G2A1) below, unsubstituted heterocyclic groups including an oxygen atom (specific example group G2A2) below, unsubstituted heterocyclic groups including a sulfur atom (specific example group G2A3) below, and monovalent heterocyclic groups (specific example group G2A4) derived by removing a hydrogen atom from cyclic structures represented by formulae (TEMP-16) to (TEMP-33) below.

The specific example group G2B includes, for instance, substituted heterocyclic groups including a nitrogen atom (specific example group G2B1) below, substituted heterocyclic groups including an oxygen atom (specific example group G2B2) below, substituted heterocyclic groups including a sulfur atom (specific example group G2B3) below, and groups derived by substituting at least one hydrogen atom of the monovalent heterocyclic groups (specific example group G2B4) derived from the cyclic structures represented by formulae (TEMP-16) to (TEMP-33) below.

Unsubstituted Heterocyclic Groups Including Nitrogen Atom (Specific Example Group G2A1):

pyrrolyl group, imidazolyl group, pyrazolyl group, triazolyl group, tetrazolyl group, oxazolyl group, isoxazolyl group, oxadiazolyl group, thiazolyl group, isothiazolyl group, thiadiazolyl group, pyridyl group, pyridazynyl group, pyrimidinyl group, pyrazinyl group, triazinyl group, indolyl group, isoindolyl group, indolizinyl group, quinolizinyl group, quinolyl group, isoquinolyl group, cinnolyl group, phthalazinyl group, quinazolinyl group, quinoxalinyl group, benzimidazolyl group, indazolyl group, phenanthrolinyl group, phenanthridinyl group, acridinyl group, phenazinyl group, carbazolyl group, benzocarbazolyl group, morpholino group, phenoxazinyl group, phenothiazinyl group, azacarbazolyl group, and diazacarbazolyl group.

Unsubstituted Heterocyclic Groups Including Oxygen Atom (Specific Example Group G2A2):

furyl group, oxazolyl group, isoxazolyl group, oxadiazolyl group, xanthenyl group, benzofuranyl group, isobenzofuranyl group, dibenzofuranyl group, naphthobenzofuranyl group, benzoxazolyl group, benzisoxazolyl group, phenoxazinyl group, morpholino group, dinaphthofuranyl group, azadibenzofuranyl group, diazadibenzofuranyl group, azanaphthobenzofuranyl group, and diazanaphthobenzofuranyl group.

Unsubstituted Heterocyclic Groups Including Sulfur Atom (Specific Example Group G2A3):

thienyl group, thiazolyl group, isothiazolyl group, thiadiazolyl group, benzothiophenyl group (benzothienyl group), isobenzothiophenyl group (isobenzothienyl group), dibenzothiophenyl group (dibenzothienyl group), naphthobenzothiophenyl group (nahthobenzothienyl group), benzothiazolyl group, benzisothiazolyl group, phenothiazinyl group, dinaphthothiophenyl group (dinaphthothienyl group), azadibenzothiophenyl group (azadibenzothienyl group), diazadibenzothiophenyl group (diazadibenzothienyl group), azanaphthobenzothiophenyl group (azanaphthobenzothienyl group), and diazanaphthobenzothiophenyl group (diazanaphthobenzothienyl group). Monovalent Heterocyclic Groups Derived by Removing One Hydrogen Atom from Cyclic Structures Represented by Formulae (TEMP-16) to (TEMP-33) (Specific Example Group G2A4):

(TEMP-16)

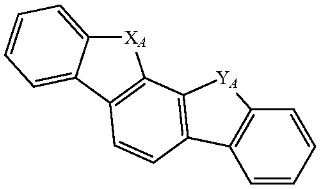

(TEMP-17)

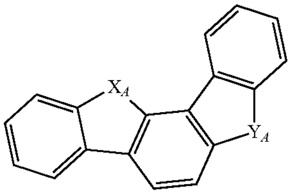

(TEMP-18)

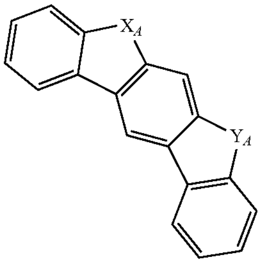

-continued (TEMP-19)

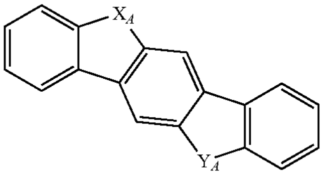

(TEMP-20)

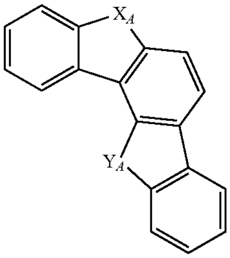

(TEMP-21)

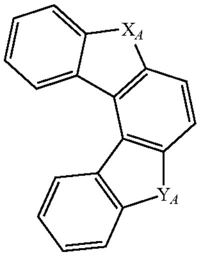

(TEMP-22)

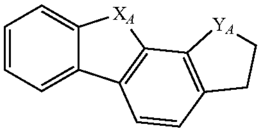

(TEMP-23)

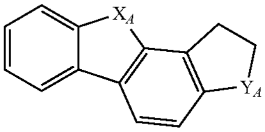

(TEMP-24)

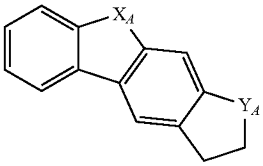

(TEMP-25)

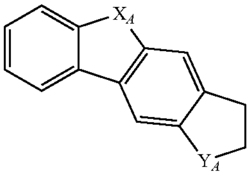

(TEMP-26)

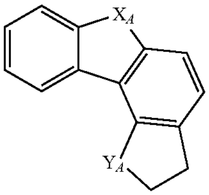

-continued (TEMP-27)

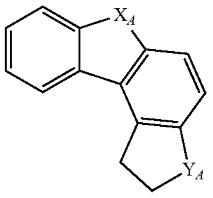

(TEMP-28)

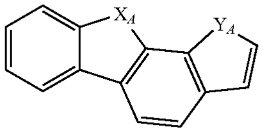

(TEMP-29)

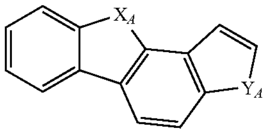

(TEMP-30)

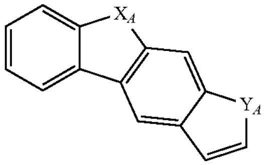

(TEMP-31)

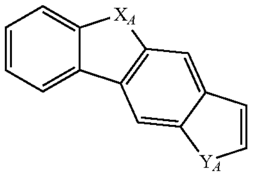

(TEMP-32)

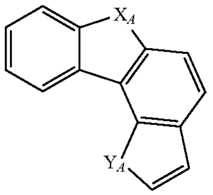

(TEMP-33)

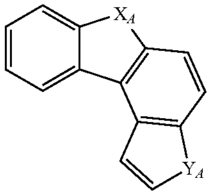

In the formulae (TEMP-16) to (TEMP-33), $X_A$ and $Y_A$ are each independently an oxygen atom, a sulfur atom, NH, or $CH_2$. However, at least one of $X_A$ or $Y_A$ is an oxygen atom, a sulfur atom, or NH.

When at least one of $X_A$ or $Y_A$ in the formulae (TEMP-16) to (TEMP-33) is NH or $CH_2$, the monovalent heterocyclic groups derived from the cyclic structures represented by the formulae (TEMP-16) to (TEMP-33) include a monovalent group derived by removing one hydrogen atom from NH, or $CH_2$.

Substituted Heterocyclic Groups Including Nitrogen Atom (Specific Example Group G2B1):

(9-phenyl)carbazolyl group, (9-biphenylyl)carbazolyl group, (9-phenyl)phenylcarbazolyl group, (9-naphthyl)carbazolyl group, diphenylcarbazole-9-yl group, phenylcarbazole-9-yl group, methylbenzimidazolyl group, ethylbenzimidazolyl group, phenyltriazinyl group, biphenylyltriazinyl group, diphenyltriazinyl group, phenylquinazolinyl group, and biphenylquinazolinyl group.

Substituted Heterocyclic Groups Including Oxygen Atom (Specific Example Group G2B2):

phenyldibenzofuranyl group, methyldibenzofuranyl group, t-butyldibenzofuranyl group, and monovalent residue of spiro[9H-xanthene-9,9'-[9H]fluorene].

Substituted Heterocyclic Groups Including Sulfur Atom (Specific Example Group G2B3):

phenyldibenzothiophenyl group, methyldibenzothiophenyl group, t-butyldibenzothiophenyl group, and monovalent residue of spiro[9H-thioxanthene-9, 9'-[9H]fluorene].

Groups Obtained by Substituting at Least One Hydrogen Atom of Monovalent Heterocyclic Group Derived from Cyclic Structures Represented by Formulae (TEMP-16) to (TEMP-33) with Substituent (Specific Example Group G2B4):

The "at least one hydrogen atom of a monovalent heterocyclic group" means at least one hydrogen atom selected from a hydrogen atom bonded to a ring carbon atom of the monovalent heterocyclic group, a hydrogen atom bonded to a nitrogen atom of at least one of $X_A$ or $Y_A$ in a form of NH, and a hydrogen atom of one of $X_A$ and $Y_A$ in a form of a methylene group ($CH_2$).

Substituted or Unsubstituted Alkyl Group

Specific examples (specific example group G3) of the "substituted or unsubstituted alkyl group" mentioned herein include unsubstituted alkyl groups (specific example group G3A) and substituted alkyl groups (specific example group G3B below). Herein, an unsubstituted alkyl group refers to an "unsubstituted alkyl group" in a "substituted or unsubstituted alkyl group," and a substituted alkyl group refers to a "substituted alkyl group" in a "substituted or unsubstituted alkyl group." A simply termed "alkyl group" herein includes both of an "unsubstituted alkyl group" and a "substituted alkyl group."

The "substituted alkyl group" refers to a group derived by substituting at least one hydrogen atom in an "unsubstituted alkyl group" with a substituent. Specific examples of the "substituted alkyl group" include a group derived by substituting at least one hydrogen atom of an "unsubstituted alkyl group" (specific example group G3A) below with a substituent, and examples of the substituted alkyl group (specific example group G3B) below. Herein, the alkyl group for the "unsubstituted alkyl group" refers to a chain alkyl group. Accordingly, the "unsubstituted alkyl group" include linear "unsubstituted alkyl group" and branched "unsubstituted alkyl group." It should be noted that the examples of the "unsubstituted alkyl group" and the "substituted alkyl group" mentioned herein are merely exemplary, and the "substituted alkyl group" mentioned herein includes a group derived by further substituting a hydrogen atom of a skeleton of the "substituted alkyl group" in the specific example group G3B, and a group derived by further substituting a hydrogen atom of a substituent of the "substituted alkyl group" in the specific example group G3B.

Unsubstituted Alkyl Group (Specific Example Group G3A):

methyl group, ethyl group, n-propyl group, isopropyl group, n-butyl group, isobutyl group, s-butyl group, and t-butyl group.

Substituted Alkyl Group (Specific Example Group G3B):

heptafluoropropyl group (including isomer thereof), pentafluoroethyl group, 2,2,2-trifluoroethyl group, and trifluoromethyl group.

Substituted or Unsubstituted Alkenyl Group

Specific examples (specific example group G4) of the "substituted or unsubstituted alkenyl group" mentioned herein include unsubstituted alkenyl groups (specific example group G4A) and substituted alkenyl groups (specific example group G4B). Herein, an unsubstituted alkenyl group refers to an "unsubstituted alkenyl group" in a "substituted or unsubstituted alkenyl group," and a substituted alkenyl group refers to a "substituted alkenyl group" in a "substituted or unsubstituted alkenyl group." A simply termed "alkenyl group" herein includes both of an "unsubstituted alkenyl group" and a "substituted alkenyl group."

The "substituted alkenyl group" refers to a group derived by substituting at least one hydrogen atom in an "unsubstituted alkenyl group" with a substituent. Specific examples of the "substituted alkenyl group" include an "unsubstituted alkenyl group" (specific example group G4A) substituted by a substituent, and examples of the substituted alkenyl group (specific example group G4B) below. It should be noted that the examples of the "unsubstituted alkenyl group" and the "substituted alkenyl group" mentioned herein are merely exemplary, and the "substituted alkenyl group" mentioned herein includes a group derived by further substituting a hydrogen atom of a skeleton of the "substituted alkenyl group" in the specific example group G4B with a substituent, and a group derived by further substituting a hydrogen atom of a substituent of the "substituted alkenyl group" in the specific example group G4B with a substituent.

Unsubstituted Alkenyl Group (Specific Example Group G4A):

vinyl group, allyl group, 1-butenyl group, 2-butenyl group, and 3-butenyl group.

Substituted Alkenyl Group (Specific Example Group G4B):

1,3-butanedienyl group, 1-methylvinyl group, 1-methylallyl group, 1,1-dimethylallyl group, 2-methylallyl group, and 1,2-dimethylallyl group.

Substituted or Unsubstituted Alkynyl Group

Specific examples (specific example group G5) of the "substituted or unsubstituted alkynyl group" mentioned herein include unsubstituted alkynyl groups (specific example group G5A) below. Herein, an unsubstituted alkynyl group refers to an "unsubstituted alkynyl group" in a "substituted or unsubstituted alkynyl group," and a substituted alkynylgroup refers to a "substituted alkynyl group" in a "substituted or unsubstituted alkynyl group." A simply termed "alkynyl group" herein includes both of an "unsubstituted alkynyl group" and a "substituted alkynyl group."

The "substituted alkynyl group" refers to a group derived by substituting at least one hydrogen atom in an "unsubstituted alkynyl group" with a substituent. Specific examples of the "substituted alkynyl group" include a group derived by substituting at least one hydrogen atom of the "unsubstituted alkynyl group" (specific example group G5A) below with a substituent.

Unsubstituted Alkynyl Group (Specific Example Group G5A):

ethynyl group.

Substituted or Unsubstituted Cycloalkyl Group

Specific examples (specific example group G6) of the "substituted or unsubstituted cycloalkyl group" mentioned herein include unsubstituted cycloalkyl groups (specific example group G6A) and substituted cycloalkyl groups (specific example group G6B). Herein, an unsubstituted cycloalkyl group refers to an "unsubstituted cycloalkyl group" in a "substituted or unsubstituted cycloalkyl group," and a substituted cycloalkyl group refers to a "substituted cycloalkyl group" in a "substituted or unsubstituted cycloalkyl group." A simply termed "cycloalkyl group" herein includes both of an "unsubstituted cycloalkyl group" and a "substituted cycloalkyl group."

The "substituted cycloalkyl group" refers to a group derived by substituting at least one hydrogen atom of an "unsubstituted cycloalkyl group" with a substituent. Specific examples of the "substituted cycloalkyl group" include a group derived by substituting at least one hydrogen atom of the "unsubstituted cycloalkyl group" (specific example group G6A) below with a substituent, and examples of the substituted cycloalkyl group (specific example group G6B) below. It should be noted that the examples of the "unsubstituted cycloalkyl group" and the "substituted cycloalkyl group" mentioned herein are merely exemplary, and the "substituted cycloalkyl group" mentioned herein includes a group derived by substituting at least one hydrogen atom bonded to a carbon atom of a skeleton of the "substituted cycloalkyl group" in the specific example group G6B with a substituent, and a group derived by further substituting a hydrogen atom of a substituent of the "substituted cycloalkyl group" in the specific example group G6B with a substituent.

Unsubstituted Cycloalkyl Group (Specific Example Group G6A):

cyclopropyl group, cyclobutyl group, cyclopentyl group, cyclohexyl group, 1-adamantyl group, 2-adamantyl group, 1-norbornyl group, and 2-norbornyl group.

Substituted Cycloalkyl Group (Specific Example Group G6B):

4-methylcyclohexyl group

Group Represented by —Si($R_{901}$)($R_{902}$)($R_{903}$)

Specific examples (specific example group G7) of the group represented herein by —Si($R_{901}$)($R_{902}$)($R_{903}$) include: —Si(G1)(G1)(G1); —Si(G1)(G2)(G2); —Si(G1)(G1)(G2); —Si(G2)(G2)(G2); —Si(G3)(G3)(G3); and —Si(G6)(G6)(G6).

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

A plurality of G1 in —Si(G1)(G1)(G1) are mutually the same or different.

A plurality of G2 in —Si(G1)(G2)(G2) are mutually the same or different.

A plurality of G1 in —Si(G1)(G1)(G2) are mutually the same or different.

A plurality of G2 in —Si(G2)(G2)(G2) are mutually the same or different.

The plurality of G3 in —Si(G3)(G3)(G3) are mutually the same or different.

A plurality of G6 in —Si(G6)(G6)(G6) are mutually the same or different.

Group Represented by —O—($R_{904}$).

Specific examples (specific example group G8) of a group represented by —O—($R_{904}$) herein include: —O(G1); —O(G2); —O(G3); and —O(G6).

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —S—($R_{905}$)

Specific examples (specific example group G9) of a group represented herein by —S—($R_{905}$) include: —S(G1); —S(G2); —S(G3); and —S(G6).

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

Group Represented by —N($R_{906}$)($R_{907}$)

Specific examples (specific example group G10) of a group represented herein by —N($R_{906}$)($R_{907}$) include: —N(G1)(G1); —N(G2)(G2); —N(G1)(G2); —N(G3)(G3); and —N(G6)(G6).

Herein: G1 represents a "substituted or unsubstituted aryl group" in the specific example group G1;

G2 represents a "substituted or unsubstituted heterocyclic group" in the specific example group G2;

G3 represents a "substituted or unsubstituted alkyl group" in the specific example group G3; and G6 represents a "substituted or unsubstituted cycloalkyl group" in the specific example group G6.

A plurality of G1 in —N(G1)(G1) are mutually the same or different.

A plurality of G2 in —N(G2)(G2) are mutually the same or different.

A plurality of G3 in —N(G3)(G3) are mutually the same or different.

A plurality of G6 in —N(G6)(G6)) are mutually the same or different.

Halogen Atom

Specific examples (specific example group G11) of "halogen atom" mentioned herein include a fluorine atom, chlorine atom, bromine atom, and iodine atom.

Substituted or Unsubstituted Fluoroalkyl Group

The "substituted or unsubstituted fluoroalkyl group" mentioned herein refers to a group derived by substituting at least one hydrogen atom bonded to at least one of carbon atoms forming an alkyl group in the "substituted or unsubstituted alkyl group" with a fluorine atom, and also includes a group (perfluoro group) derived by substituting all of hydrogen atoms bonded to carbon atoms forming the alkyl group in the "substituted or unsubstituted alkyl group" with fluorine atoms. An "unsubstituted fluoroalkyl group" has, unless otherwise specified herein, 1 to 50, preferably 1 to 30, more preferably 1 to 18 carbon atoms. The "substituted fluoroalkyl group" refers to a group derived by substituting at least one hydrogen atom in a "fluoroalkyl group" with a substituent. It should be noted that the examples of the "substituted fluoroalkyl group" mentioned herein include a group derived by further substituting at least one hydrogen atom bonded to a carbon atom of an alkyl chain of a "substituted fluoroalkyl group" with a substituent, and a group derived by further substituting at least one hydrogen atom of a substituent of the "substituted fluoroalkyl group" with a substituent. Specific examples of the "substituted fluoroalkyl group" include a group derived by substituting at least one hydrogen atom of the "alkyl group" (specific example group G3) with a fluorine atom.

Substituted or Unsubstituted Haloalkyl Group

The "substituted or unsubstituted haloalkyl group" mentioned herein refers to a group derived by substituting at least one hydrogen atom bonded to carbon atoms forming the alkyl group in the "substituted or unsubstituted alkyl group" with a halogen atom, and also includes a group derived by substituting all hydrogen atoms bonded to carbon atoms forming the alkyl group in the "substituted or unsubstituted alkyl group" with halogen atoms. An "unsubstituted haloalkyl group" has, unless otherwise specified herein, 1 to 50, preferably 1 to 30, more preferably 1 to 18 carbon atoms. The "substituted haloalkyl group" refers to a group derived by substituting at least one hydrogen atom in a "haloalkyl group" with a substituent. It should be noted that the examples of the "substituted haloalkyl group" mentioned herein include a group derived by further substituting at least one hydrogen atom bonded to a carbon atom of an alkyl chain of a "substituted haloalkyl group" with a substituent, and a group derived by further substituting at least one hydrogen atom of a substituent of the "substituted haloalkyl group" with a substituent. Specific examples of the "substituted haloalkyl group" include a group derived by substituting at least one hydrogen atom of the "alkyl group" (specific example group G3) with a halogen atom. The haloalkyl group is sometimes referred to as a halogenated alkyl group.

Substituted or Unsubstituted Alkoxy Group

Specific examples of a "substituted or unsubstituted alkoxy group" mentioned herein include a group represented by —O(G3), G3 being the "substituted or unsubstituted alkyl group" in the specific example group G3. An "unsubstituted alkoxy group" has, unless otherwise specified herein, 1 to 50, preferably 1 to 30, more preferably 1 to 18 carbon atoms.

Substituted or Unsubstituted Alkylthio Group

Specific examples of a "substituted or unsubstituted alkylthio group" mentioned herein include a group represented by —S(G3), G3 being the "substituted or unsubstituted alkyl group" in the specific example group G3. An "unsubstituted alkylthio group" has, unless otherwise specified herein, 1 to 50, preferably 1 to 30, more preferably 1 to 18 carbon atoms.

Substituted or Unsubstituted Aryloxy Group

Specific examples of a "substituted or unsubstituted aryloxy group" mentioned herein include a group represented by —O(G1), G1 being the "substituted or unsubstituted aryl group" in the specific example group G1. An "unsubstituted aryloxy group" has, unless otherwise specified herein, 6 to 50, preferably 6 to 30, more preferably 6 to 18 ring carbon atoms.

Substituted or Unsubstituted Arylthio Group

Specific examples of a "substituted or unsubstituted arylthio group" mentioned herein include a group represented by —S(G1), G1 being the "substituted or unsubstituted aryl group" in the specific example group G1. An "unsubstituted arylthio group" has, unless otherwise specified herein, 6 to 50, preferably 6 to 30, more preferably 6 to 18 ring carbon atoms.

Substituted or Unsubstituted Trialkylsilyl Group

Specific examples of a "trialkylsilyl group" mentioned herein include a group represented by —Si(G3)(G3)(G3), G3 being the "substituted or unsubstituted alkyl group" in the specific example group G3. The plurality of G3 in —Si(G3)(G3)(G3) are mutually the same or different. Each of the alkyl groups in the "trialkylsilyl group" has, unless otherwise specified herein, 1 to 50, preferably 1 to 20, more preferably 1 to 6 carbon atoms.

Substituted or Unsubstituted Aralkyl Group

Specific examples of a "substituted or unsubstituted aralkyl group" mentioned herein include a group represented by (G3)-(G1), G3 being the "substituted or unsubstituted alkyl group" in the specific example group G3, G1 being the "substituted or unsubstituted aryl group" in the specific example group G1. Accordingly, the "aralkyl group" is a group derived by substituting a hydrogen atom of the "alkyl group" with a substituent in a form of the "aryl group," which is an example of the "substituted alkyl group." An "unsubstituted aralkyl group," which is an "unsubstituted alkyl group" substituted by an "unsubstituted aryl group," has, unless otherwise specified herein, 7 to 50 carbon atoms, preferably 7 to 30 carbon atoms, more preferably 7 to 18 carbon atoms.

Specific examples of the "substituted or unsubstituted aralkyl group" include a benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-ρ-naphthylethyl group, 2-ρ-naphthylethyl group, 1-β-naphthylisopropyl group, and 2-β-naphthylisopropyl group.

Preferable examples of the substituted or unsubstituted aryl group mentioned herein include, unless otherwise specified herein, a phenyl group, p-biphenyl group, m-biphenyl group, o-biphenyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-terphenyl-4-yl group, o-terphenyl-3-yl group, o-terphenyl-2-yl group, 1-naphthyl group, 2-naphthyl group, anthryl group, phenanthryl group, pyrenyl group, chrysenyl group, triphenylenyl group, fluorenyl group, 9,9'-spirobifluorenyl group, 9,9-dimethylfluorenyl group, and 9,9-diphenylfluorenyl group.

Preferable examples of the substituted or unsubstituted heterocyclic group mentioned herein include, unless otherwise specified herein, a pyridyl group, pyrimidinyl group, triazinyl group, quinolyl group, isoquinolyl group, quinazolinyl group, benzimidazolyl group, phenanthrolinyl group, carbazolyl group (1-carbazolyl group, 2-carbazolyl group, 3-carbazolyl group, 4-carbazolyl group, or 9-carbazolyl group), benzocarbazolyl group, azacarbazolyl group, diazacarbazolyl group, dibenzofuranyl group, naphthobenzofuranyl group, azadibenzofuranyl group, diazadibenzofuranyl group, dibenzothiophenyl group, naphthobenzothiophenyl group, azadibenzothiophenyl group, diazadibenzothiophenyl group, (9-phenyl)carbazolyl group ((9-phenyl)carbazole-1-yl group, (9-phenyl)carbazole-2-yl group, (9-phenyl)carbazole-3-yl group, or (9-phenyl)carbazole-4-yl group), (9-biphenylyl)carbazolyl group, (9-phenyl)phenylcarbazolyl group, diphenylcarbazole-9-yl group, phenylcarbazole-9-yl group, phenyltriazinyl group, biphenylyltriazinyl group, diphenyltriazinyl group, phenyldibenzofuranyl group, and phenyldibenzothiophenyl group.

The carbazolyl group mentioned herein is, unless otherwise specified herein, specifically a group represented by one of formulae below.

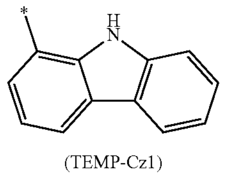

(TEMP-Cz1)

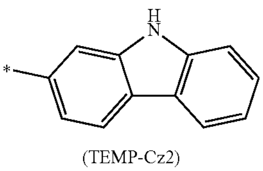

(TEMP-Cz2)

-continued

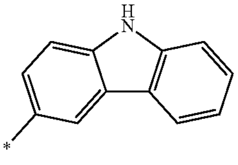

(TEMP-Cz3)

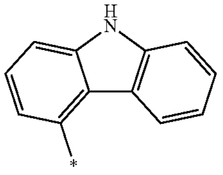

(TEMP-Cz4)

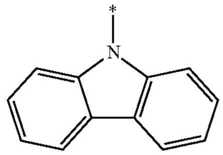

(TEMP-Cz5)

The (9-phenyl)carbazolyl group mentioned herein is, unless otherwise specified herein, specifically a group represented by one of formulae below.

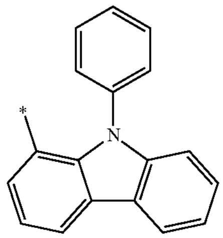

(TEMP-Cz6)

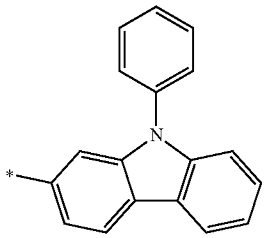

(TEMP-Cz7)

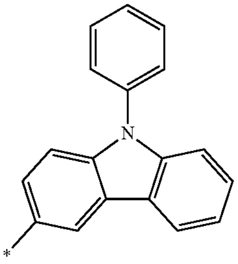

(TEMP-Cz8)

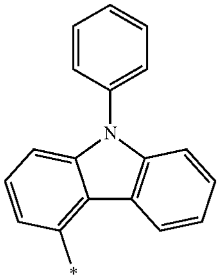

(TEMP-Cz9)

In the formulae (TEMP-Cz1) to (TEMP-Cz9), * represents a bonding position.

The dibenzofuranyl group and dibenzothiophenyl group mentioned herein are, unless otherwise specified herein, each specifically represented by one of formulae below.

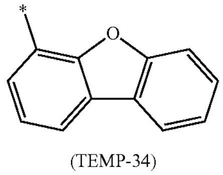

(TEMP-34)

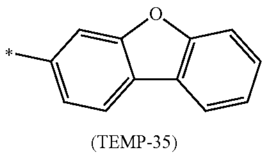

(TEMP-35)

-continued

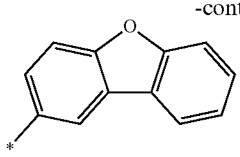

(TEMP-36)

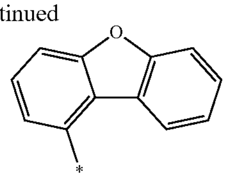

(TEMP-37)

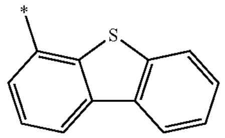

(TEMP-38)

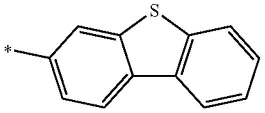

(TEMP-39)

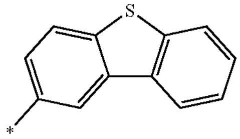

(TEMP-40)

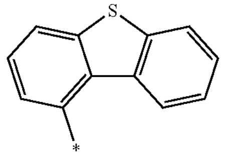

(TEMP-41)

In the formulae (TEMP-34) to (TEMP-41), * represents a bonding position.

Preferable examples of the substituted or unsubstituted alkyl group mentioned herein include, unless otherwise specified herein, a methyl group, ethyl group, propyl group, isopropyl group, n-butyl group, isobutyl group, and t-butyl group.

Substituted or Unsubstituted Arylene Group

The "substituted or unsubstituted arylene group" mentioned herein is, unless otherwise specified herein, a divalent group derived by removing one hydrogen atom on an aryl ring of the "substituted or unsubstituted aryl group." Specific examples of the "substituted or unsubstituted arylene group" (specific example group G12) include a divalent group derived by removing one hydrogen atom on an aryl ring of the "substituted or unsubstituted aryl group" in the specific example group G1.

Substituted or Unsubstituted Divalent Heterocyclic Group

The "substituted or unsubstituted divalent heterocyclic group" mentioned herein is, unless otherwise specified herein, a divalent group derived by removing one hydrogen atom on a heterocyclic ring of the "substituted or unsubstituted heterocyclic group." Specific examples of the "substituted or unsubstituted heterocyclic group" (specific example group G13) include a divalent group derived by removing one hydrogen atom on a heterocyclic ring of the "substituted or unsubstituted heterocyclic group" in the specific example group G2.

Substituted or Unsubstituted Alkylene Group

The "substituted or unsubstituted alkylene group" mentioned herein is, unless otherwise specified herein, a divalent group derived by removing one hydrogen atom on an alkyl ring of the "substituted or unsubstituted alkyl group." Specific examples of the "substituted or unsubstituted alkylene group" (specific example group G14) include a divalent group derived by removing one hydrogen atom on an alkyl ring of the "substituted or unsubstituted alkyl group" in the specific example group G3.

The substituted or unsubstituted arylene group mentioned herein is, unless otherwise specified herein, preferably any one of groups represented by formulae (TEMP-42) to (TEMP-68) below.

(TEMP-42)

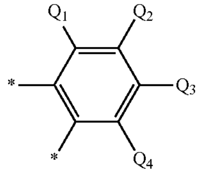

(TEMP-43)

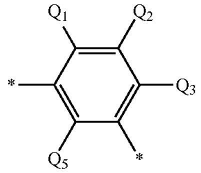

(TEMP-44)

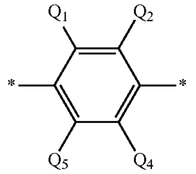

(TEMP-45)

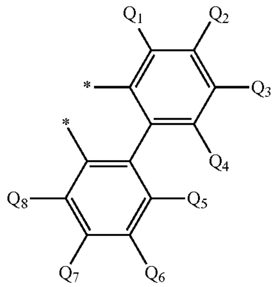

(TEMP-46)

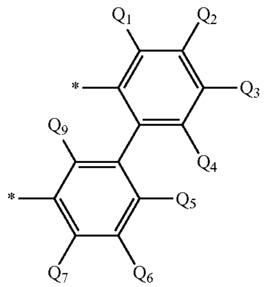

(TEMP-47)

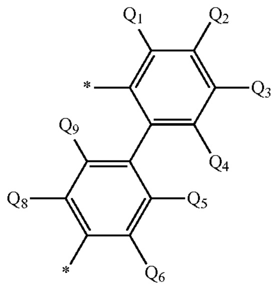

-continued
(TEMP-48)
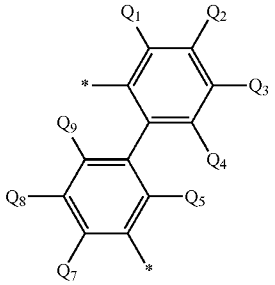
(TEMP-49)
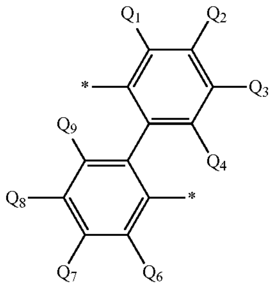
(TEMP-50)
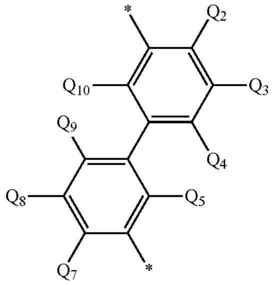
(TEMP-51)
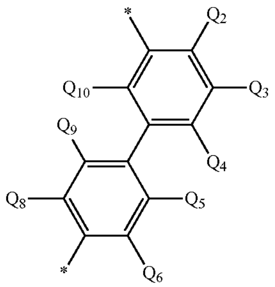
(TEMP-52)
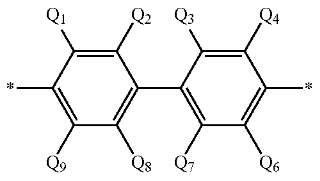
In the formulae (TEMP-42) to (TEMP-52), $Q_1$ to $Q_{10}$ each independently are a hydrogen atom or a substituent.
In the formulae (TEMP-42) to (TEMP-52), * represents a bonding position.
(TEMP-53)
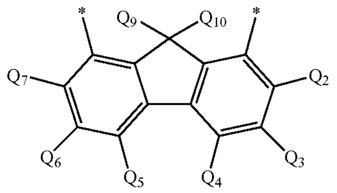
(TEMP-54)
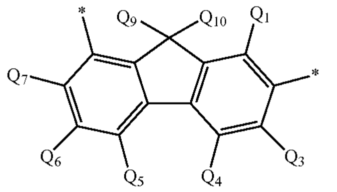
(TEMP-55)
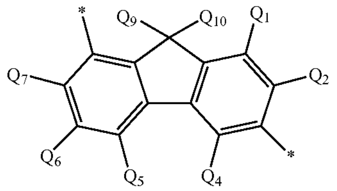
(TEMP-56)
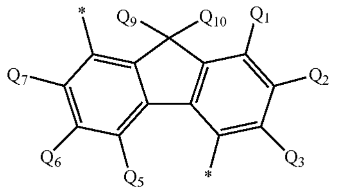
(TEMP-57)
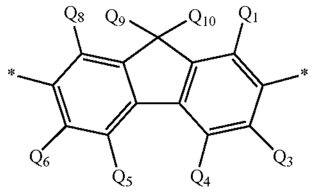
(TEMP-58)
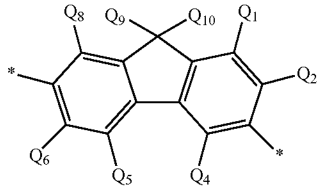
(TEMP-59)
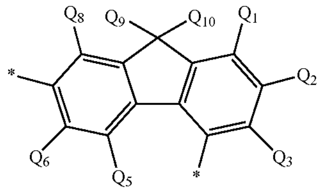
(TEMP-60)
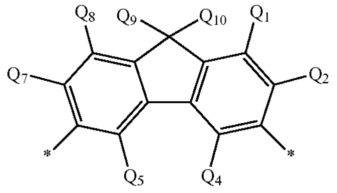

-continued (TEMP-61)

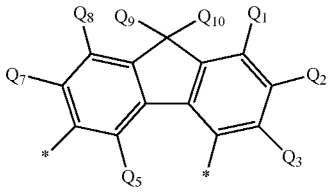

(TEMP-62)

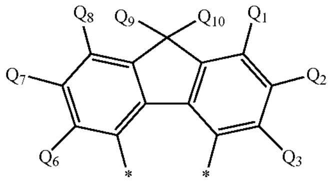

In the formulae (TEMP-53) to (TEMP-62), $Q_1$ to $Q_{10}$ each independently are a hydrogen atom or a substituent.

In the formulae, $Q_9$ and $Q_{10}$ may be mutually bonded through a single bond to form a ring.

In the formulae (TEMP-53) to (TEMP-62), * represents a bonding position.

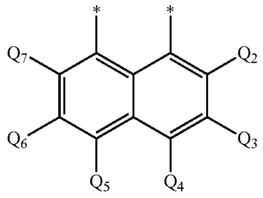

(TEMP-63)

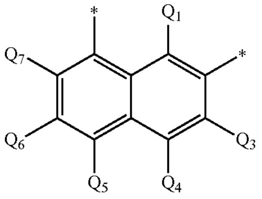

(TEMP-64)

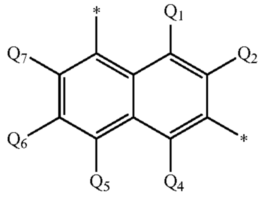

(TEMP-65)

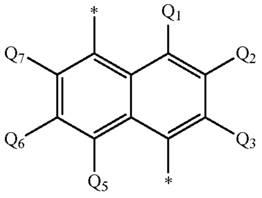

(TEMP-66)

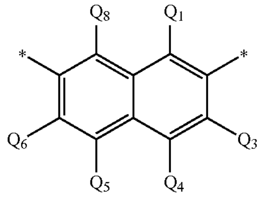

(TEMP-67)

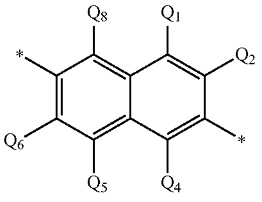

(TEMP-68)

In the formulae (TEMP-63) to (TEMP-68), $Q_1$ to $Q_8$ each independently are a hydrogen atom or a substituent.

In the formulae (TEMP-63) to (TEMP-68), * represents a bonding position.

The substituted or unsubstituted divalent heterocyclic group mentioned herein is, unless otherwise specified herein, preferably a group represented by any one of formulae (TEMP-69) to (TEMP-102) below.

(TEMP-69)

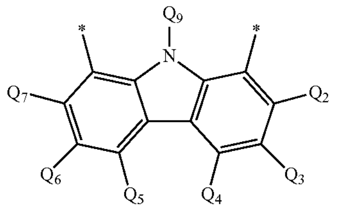

(TEMP-70)

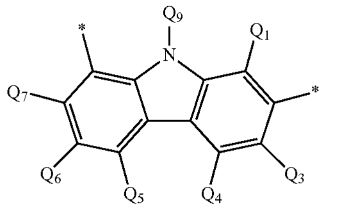

(TEMP-71)

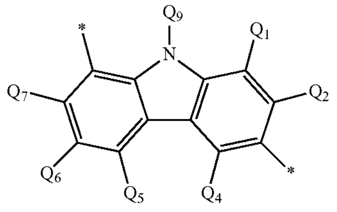

(TEMP-72)

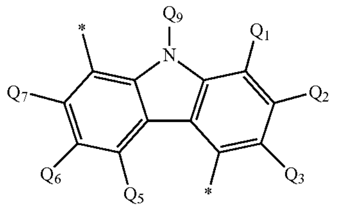

(TEMP-73)

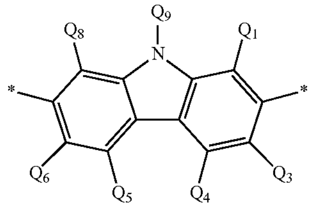

(TEMP-74)

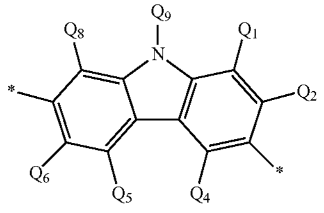

(TEMP-75)

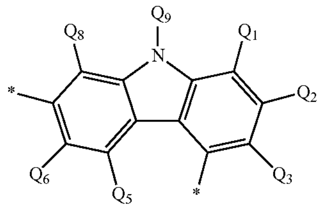

-continued
(TEMP-76)
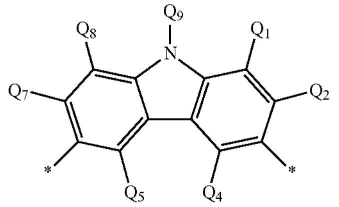
(TEMP-77)
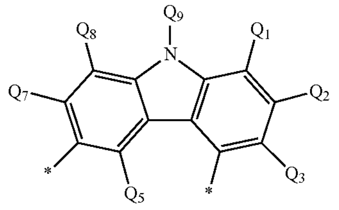
(TEMP-78)
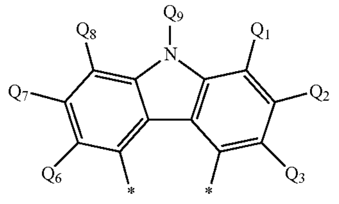
(TEMP-79)
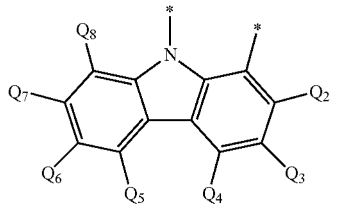
(TEMP-80)
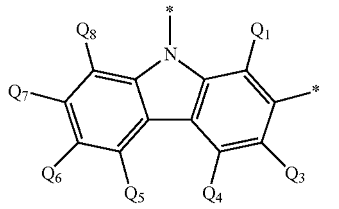
(TEMP-81)
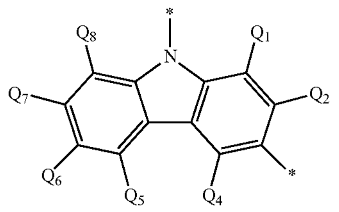
(TEMP-82)
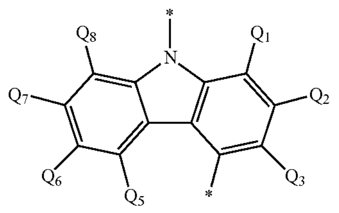
In the formulae (TEMP-69) to (TEMP-82), $Q_1$ to $Q_9$ each independently are a hydrogen atom or a substituent.
(TEMP-83)
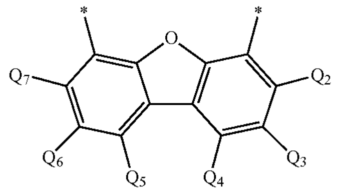
(TEMP-84)
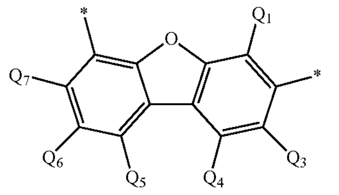
(TEMP-85)
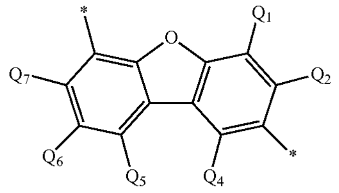
(TEMP-86)
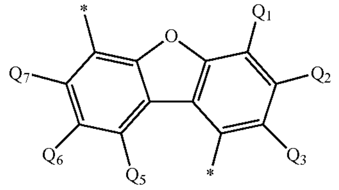
(TEMP-87)
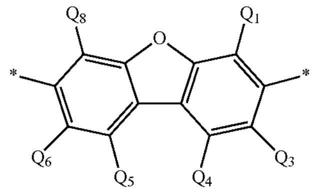
(TEMP-88)
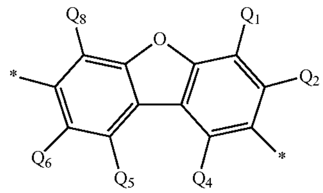
(TEMP-89)
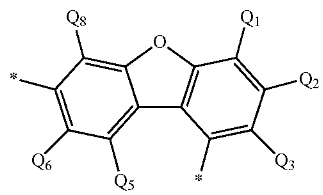
(TEMP-90)
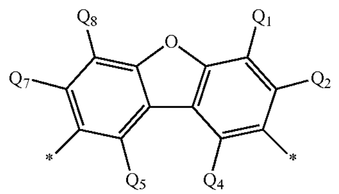

-continued (TEMP-91)

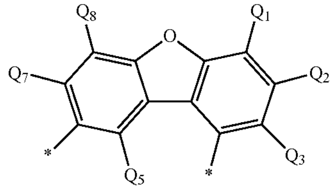

(TEMP-92)

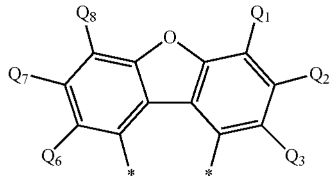

(TEMP-93)

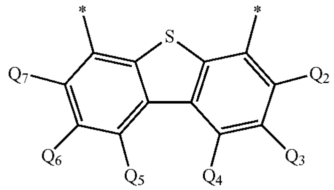

(TEMP-94)

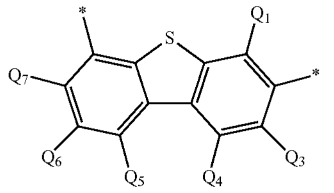

(TEMP-95)

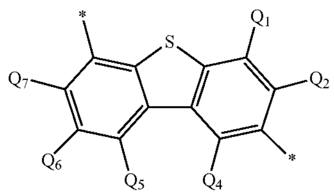

(TEMP-96)

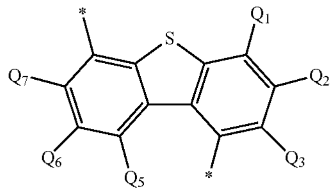

(TEMP-97)

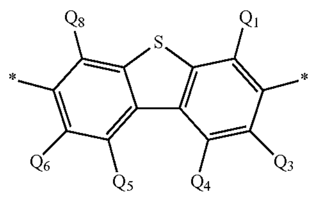

(TEMP-98)

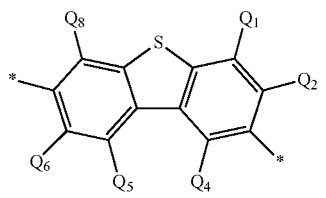

-continued (TEMP-99)

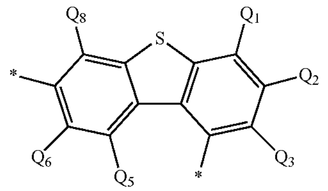

(TEMP-100)

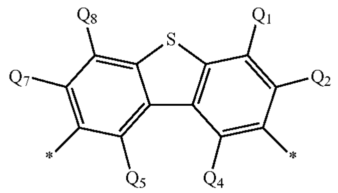

(TEMP-101)

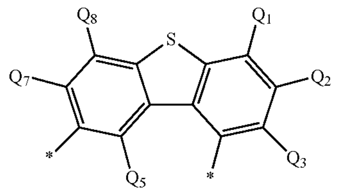

(TEMP-102)

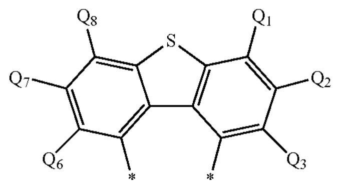

In the formulae (TEMP-83) to (TEMP-102), $Q_1$ to $Q_8$ each independently are a hydrogen atom or a substituent.

The substituent mentioned herein has been described above.

Instance of "Bonded to Form Ring"

Instances where "at least one combination of adjacent two or more (of . . . ) are mutually bonded to form a substituted or unsubstituted monocyclic ring, mutually bonded to form a substituted or unsubstituted fused ring, or not mutually bonded" mentioned herein refer to instances where "at least one combination of adjacent two or more (of . . . ) are mutually bonded to form a substituted or unsubstituted monocyclic ring, "at least one combination of adjacent two or more (of . . . ) are mutually bonded to form a substituted or unsubstituted fused ring," and "at least one combination of adjacent two or more (of . . . ) are not mutually bonded."

Instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (these instances will be sometimes collectively referred to as an instance of "bonded to form a ring" hereinafter) will be described below. An anthracene compound having a basic skeleton in a form of an anthracene ring and represented by a formula (TEMP-103) below will be used as an example for the description.

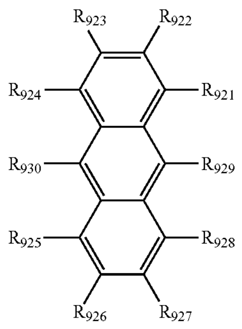

(TEMP-103)

For instance, when "at least one combination of adjacent two or more of" $R_{921}$ to $R_{930}$ "are mutually bonded to form a ring," the combination of adjacent ones of $R_{921}$ to $R_{930}$ (i.e. the combination at issue) is a combination of $R_{921}$ and a combination of $R_{922}$, $R_{922}$ and $R_{923}$, a combination of $R_{923}$ and $R_{924}$, a combination of $R_{924}$ and $R_{930}$, a combination of $R_{930}$ and $R_{925}$, a combination of $R_{925}$ and $R_{926}$, a combination of $R_{926}$ and $R_{927}$, a combination of $R_{927}$ and $R_{928}$, a combination of $R_{928}$ and $R_{929}$, or a combination of $R_{929}$ and $R_{921}$.

The term "at least one combination" means that two or more of the above combinations of adjacent two or more of $R_{921}$ to $R_{930}$ may simultaneously form rings. For instance, when $R_{921}$ and $R_{922}$ are mutually bonded to form a ring $Q_A$ and $R_{925}$ and $R_{926}$ are simultaneously mutually bonded to form a ring $Q_B$, the anthracene compound represented by the formula (TEMP-103) is represented by a formula (TEMP-104) below.

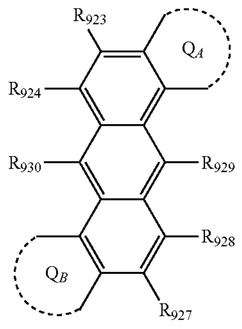

(TEMP-104)

The instance where the "combination of adjacent two or more" form a ring means not only an instance where the "two" adjacent components are bonded but also an instance where adjacent "three or more" are bonded. For instance, $R_{921}$ and $R_{922}$ are mutually bonded to form a ring $Q_A$ and $R_{922}$, $R_{923}$ are mutually bonded to form a ring $Q_C$, and mutually adjacent three components ($R_{921}$, $R_{922}$ and $R_{923}$) are mutually bonded to form a ring fused to the anthracene basic skeleton. In this case, the anthracene compound represented by the formula (TEMP-103) is represented by a formula (TEMP-105) below. In the formula (TEMP-105) below, the ring $Q_A$ and the ring $Q_C$ share $R_{922}$.

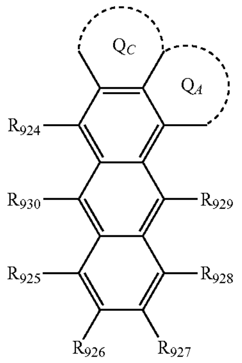

(TEMP-105)

The formed "monocyclic ring" or "fused ring" may be, in terms of the formed ring in itself, a saturated ring or an unsaturated ring. When the "combination of adjacent two" form a "monocyclic ring" or a "fused ring," the "monocyclic ring" or "fused ring" may be a saturated ring or an unsaturated ring. For instance, the ring $Q_A$ and the ring $Q_B$ formed in the formula (TEMP-104) are each independently a "monocyclic ring" or a "fused ring." Further, the ring $Q_A$ and the ring $Q_C$ formed in the formula (TEMP-105) are each a "fused ring." The ring $Q_A$ and the ring $Q_C$ in the formula (TEMP-105) are fused to form a fused ring. When the ring $Q_A$ in the formula (TMEP-104) is a benzene ring, the ring $Q_A$ is a monocyclic ring. When the ring $Q_A$ in the formula (TMEP-104) is a naphthalene ring, the ring $Q_A$ is a fused ring.

The "unsaturated ring" represents an aromatic hydrocarbon ring or an aromatic heterocycle. The "saturated ring" represents an aliphatic hydrocarbon ring or a non-aromatic heterocycle.

Specific examples of the aromatic hydrocarbon ring include a ring formed by terminating a bond of a group in the specific example of the specific example group G1 with a hydrogen atom.

Specific examples of the aromatic heterocyclic ring include a ring formed by terminating a bond of an aromatic heterocyclic group in the specific example of the specific example group G2 with a hydrogen atom.

Specific examples of the aliphatic hydrocarbon ring include a ring formed by terminating a bond of a group in the specific example of the specific example group G6 with a hydrogen atom.

The phrase "to form a ring" herein means that a ring is formed only by a plurality of atoms of a basic skeleton, or by a combination of a plurality of atoms of the basic skeleton and one or more optional atoms. For instance, the ring $Q_A$ formed by mutually bonding $R_{921}$ and $R_{922}$ shown in the formula (TEMP-104) is a ring formed by a carbon atom of the anthracene skeleton bonded with $R_{921}$, a carbon atom of the anthracene skeleton bonded with $R_{922}$, and one or more optional atoms. Specifically, when the ring $Q_A$ is a monocyclic unsaturated ring formed by $R_{921}$ and $R_{922}$, the ring formed by a carbon atom of the anthracene skeleton bonded with $R_{921}$, a carbon atom of the anthracene skeleton bonded with $R_{922}$, and four carbon atoms is a benzene ring.

The "optional atom" is, unless otherwise specified herein, preferably at least one atom selected from the group consisting of a carbon atom, nitrogen atom, oxygen atom, and sulfur atom. A bond of the optional atom (e.g. a carbon atom and a nitrogen atom) not forming a ring may be terminated by a hydrogen atom or the like or may be substituted by an "optional substituent" described later. When the ring includes an optional element other than carbon atom, the resultant ring is a heterocycle.

The number of "one or more optional atoms" forming the monocyclic ring or fused ring is, unless otherwise specified herein, preferably in a range from 2 to 15, more preferably in a range from 3 to 12, further preferably in a range from 3 to 5.

Unless otherwise specified herein, the ring, which may be a "monocyclic ring" or "fused ring," is preferably a "monocyclic ring."

Unless otherwise specified herein, the ring, which may be a "saturated ring" or "unsaturated ring," is preferably an "unsaturated ring."

Unless otherwise specified herein, the "monocyclic ring" is preferably a benzene ring.

Unless otherwise specified herein, the "unsaturated ring" is preferably a benzene ring.

When "at least one combination of adjacent two or more" (of . . . ) are "mutually bonded to form a substituted or unsubstituted monocyclic ring" or "mutually bonded to form a substituted or unsubstituted fused ring," unless otherwise specified herein, at least one combination of adjacent two or more of components are preferably mutually bonded to form a substituted or unsubstituted "unsaturated ring" formed of a plurality of atoms of the basic skeleton, and 1 to 15 atoms of at least one element selected from the group consisting of carbon, nitrogen, oxygen and sulfur.

When the "monocyclic ring" or the "fused ring" has a substituent, the substituent is the substituent described in later-described "optional substituent." When the "monocyclic ring" or the "fused ring" has a substituent, specific examples of the substituent are the substituents described in the above under the subtitle "Substituents Mentioned Herein."

When the "saturated ring" or the "unsaturated ring" has a substituent, the substituent is, for instance, the substituent described in later-described "optional substituent." When the "monocyclic ring" or the "fused ring" has a substituent, specific examples of the substituent are the substituents described in the above under the subtitle "Substituents Mentioned Herein."

The above is the description for the instances where "at least one combination of adjacent two or more (of . . . ) are mutually bonded to form a substituted or unsubstituted monocyclic ring" and "at least one combination of adjacent two or more (of . . . ) are mutually bonded to form a substituted or unsubstituted fused ring" mentioned herein (sometimes referred to as an instance "bonded to form a ring".

Substituent for Substituted or Unsubstituted Group

In an exemplary embodiment herein, the substituent for the substituted or unsubstituted group (sometimes referred to as an "optional substituent") is selected from the group consisting of, for instance, an unsubstituted alkyl group having 1 to 50 carbon atoms, an unsubstituted alkenyl group having 2 to 50 carbon atoms, an unsubstituted alkynyl group having 2 to 50 carbon atoms, an unsubstituted cycloalkyl group having 3 to 50 ring carbon atoms, $—Si(R_{901})(R_{902})(R_{903})$, $—O—(R_{904})$, $—S—(R_{905})$, $—N(R_{906})(R_{907})$, a halogen atom, a cyano group, a nitro group, an unsubstituted aryl group having 6 to 50 ring carbon atoms, and an unsubstituted heterocyclic group having 5 to 50 ring atoms.

Herein, $R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

When two or more $R_{901}$ are present, the two or more $R_{901}$ are mutually the same or different.

When two or more $R_{902}$ are present, the two or more $R_{902}$ are mutually the same or different.

When two or more $R_{903}$ are present, the two or more $R_{903}$ are mutually the same or different.

When two or more $R_{904}$ are present, the two or more $R_{904}$ are mutually the same or different.

When two or more $R_{905}$ are present, the two or more $R_{905}$ are mutually the same or different.

When two or more $R_{906}$ are present, the two or more $R_{906}$ are mutually the same or different.

When two or more $R_{907}$ are present, the two or more $R_{907}$ are mutually the same or different.

In an exemplary embodiment, the substituent for "substituted or unsubstituted" group is selected from the group consisting of an alkyl group having 1 to 50 carbon atoms, an aryl group having 6 to 50 ring carbon atoms, and a heterocyclic group having 5 to 50 ring atoms.

In an exemplary embodiment, the substituent for "substituted or unsubstituted" group is selected from the group consisting of an alkyl group having 1 to 18 carbon atoms, an aryl group having 6 to 18 ring carbon atoms, and a heterocyclic group having 5 to 18 ring atoms.

Specific examples of the above optional substituent are the same as the specific examples of the substituent described in the above under the subtitle "Substituent Mentioned Herein."

Unless otherwise specified herein, adjacent ones of the optional substituents may form a "saturated ring" or an "unsaturated ring," preferably a substituted or unsubstituted saturated five-membered ring, a substituted or unsubstituted saturated six-membered ring, a substituted or unsubstituted saturated five-membered ring, or a substituted or unsubstituted unsaturated six-membered ring, more preferably a benzene ring.

Unless otherwise specified herein, the optional substituent may further include a substituent. Examples of the substituent for the optional substituent are the same as the examples of the optional substituent.

Herein, numerical ranges represented by "AA to BB" represents a range whose lower limit is the value (AA) recited before "to" and whose upper limit is the value (BB) recited after "to."

First Exemplary Embodiment

Compound

A compound according to a first exemplary embodiment is a compound having, in a molecule, a cyclic structure represented by a formula (1) below and at least one cyclic structure selected from the group consisting of a cyclic structure represented by a formula (10) below and a cyclic structure represented by a formula (11) below.

(1)

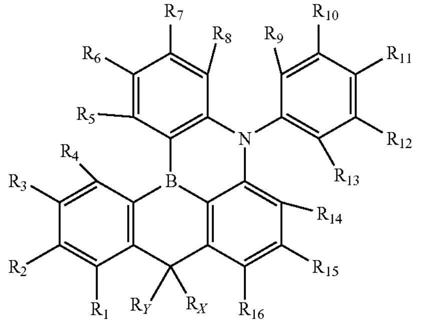

(10)

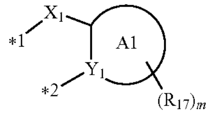

(11)

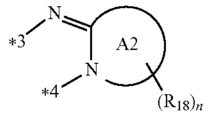

In the formula (1):

at least one combination of adjacent two or more of $R_1$ to $R_{16}$ are mutually bonded to form a substituted or unsubstituted monocyclic ring, mutually bonded to form a substituted or unsubstituted fused ring, or not mutually bonded;

at least one combination of adjacent two or more of $R_1$ to $R_{16}$ are mutually bonded to form the cyclic structure represented by the formula (10) or (11);

a combination of $R_4$ and $R_5$, a combination of $R_8$ and $R_9$, and a combination of $R_{13}$ and $R_{14}$ are not mutually bonded and form neither the cyclic structure represented by the formula (10) nor the cyclic structure represented by the formula (11);

$R_1$ to $R_{16}$ forming neither the cyclic structure represented by the formula (10) nor the cyclic structure represented by the formula (11) are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—N(R_{131})(R_{132})$, a group represented by $—Si(R_{133})(R_{134})(R_{135})$, a group represented by $—O—(R_{136})$, a group represented by $—S—(R_{137})$, a substituted or unsubstituted aralkyl group having 7 to 50 carbon atoms, a group represented by $—C(=O)R_{138}$, a group represented by $—COOR_{139}$, a halogen atom, a cyano group, a nitro group, a group represented by $—P(=O)(R_{140})(R_{141})$, a group represented by $—Ge(R_{142})(R_{143})(R_{144})$, a group represented by $—B(R_{145})(R_{146})$, a substituted or unsubstituted aryl group having 6 to 50 ring carbon atoms, or a substituted or unsubstituted heterocyclic group having 5 to 50 ring atoms;

a combination of $R_X$ and $R_Y$ are mutually bonded to form a substituted or unsubstituted monocyclic ring, mutually bonded to form a substituted or unsubstituted fused ring, or not mutually bonded; and $R_X$ and $R_Y$ forming neither the substituted or unsubstituted monocyclic ring nor the substituted or unsubstituted fused ring are each independently a substituted or unsubstituted alkyl group having 1 to 50 carbon atoms.

In the formula (10):

a ring A1 is a substituted or unsubstituted aliphatic hydrocarbon ring having 3 to 50 ring carbon atoms, a substituted or unsubstituted aromatic hydrocarbon ring having 6 to 50 ring carbon atoms, or a substituted or unsubstituted heterocycle having 5 to 50 ring atoms;

m represents the number of $R_{17}$ bonded to the ring A1 and is an integer of 1 or more, when a plurality of $R_{17}$ are present, the plurality of $R_{17}$ are mutually the same or different;

$X_1$ is $NR_{100}$, an oxygen atom, or a sulfur atom;

when a plurality of $X_1$ are present, the plurality of $X_1$ are mutually the same or different;

$Y_1$ is a carbon atom or a nitrogen atom; and 1 and *2 each represent a bonding position to the cyclic structure represented by the formula (1).

In the formula (11):

a ring A2 is a substituted or unsubstituted aliphatic hydrocarbon ring having 3 to 50 ring carbon atoms, a substituted or unsubstituted aromatic hydrocarbon ring having 6 to 50 ring carbon atoms, or a substituted or unsubstituted heterocycle having 5 to 50 ring atoms;

n represents the number of $R_{18}$ bonded to the ring A2 and is an integer of 1 or more;

when a plurality of $R_{18}$ are present, the plurality of $R_{18}$ are mutually the same or different;

3 and *4 each represent a bonding position to the cyclic structure represented by the formula (1);

at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{16}$, $R_{17}$ or $R_{18}$ is a group represented by $—N(R_{131})(R_{132})$;

a combination of $R_{100}$, and one adjacent to $R_{100}$ among $R_1$ to $R_{16}$, $R_{17}$, $R_{18}$, $R_{131}$ and $R_{132}$ that form neither the cyclic structure represented by the formula (10) nor the cyclic structure represented by the formula (11) are mutually bonded to form a substituted or unsubstituted monocyclic ring, mutually bonded to form a substituted or unsubstituted fused ring, or not mutually bonded;

a combination of $R_{131}$ and $R_{132}$ are mutually bonded to form a substituted or unsubstituted monocyclic ring, mutually bonded to form a substituted or unsubstituted fused ring, or not mutually bonded;

a combination of: at least one of $R_{131}$ or $R_{132}$ forming neither the substituted or unsubstituted monocyclic ring nor the substituted or unsubstituted fused ring;

and at least one adjacent to $R_{131}$ or $R_{132}$ among $R_1$ to $R_{16}$, $R_{17}$, $R_{18}$, and $R_{100}$ that form neither the cyclic structure represented by the formula (10) nor the cyclic structure represented by the formula (11) are mutually bonded to form a substituted or unsubstituted monocyclic ring, mutually bonded to form a substituted or unsubstituted fused ring, or not mutually bonded;

$R_{17}$ and $R_{18}$ forming neither the substituted or unsubstituted monocyclic ring nor the substituted or unsubstituted fused ring each independently represent the same as $R_1$ to $R_{16}$ forming neither the cyclic structure represented by the formula (10) nor the cyclic structure represented by the formula (11);

$R_{100}$, $R_{131}$ and $R_{132}$ forming neither the substituted or unsubstituted monocyclic ring nor the substituted or unsubstituted fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{100}$ are present, the plurality of $R_{100}$ are mutually the same or different;

when a plurality of $R_{131}$ are present, the plurality of $R_{131}$ are mutually the same or different;

when a plurality of $R_{132}$ are present, the plurality of $R_{132}$ are mutually the same or different;

$R_{133}$ to $R_{146}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{133}$ are present, the plurality of $R_{133}$ are mutually the same or different;

when a plurality of $R_{134}$ are present, the plurality of $R_{134}$ are mutually the same or different;

when a plurality of $R_{135}$ are present, the plurality of $R_{135}$ are mutually the same or different;

when a plurality of $R_{136}$ are present, the plurality of $R_{136}$ are mutually the same or different;

when a plurality of $R_{137}$ are present, the plurality of $R_{137}$ are mutually the same or different;

when a plurality of $R_{138}$ are present, the plurality of $R_{138}$ are mutually the same or different;

when a plurality of $R_{139}$ are present, the plurality of $R_{139}$ are mutually the same or different;

when a plurality of $R_{140}$ are present, the plurality of $R_{140}$ are mutually the same or different;

when a plurality of $R_{141}$ are present, the plurality of $R_{141}$ are mutually the same or different;

when a plurality of $R_{142}$ are present, the plurality of $R_{142}$ are mutually the same or different;

when a plurality of $R_{143}$ are present, the plurality of $R_{143}$ are mutually the same or different;

when a plurality of $R_{144}$ are present, the plurality of $R_{144}$ are mutually the same or different;

when a plurality of $R_{145}$ are present, the plurality of $R_{145}$ are mutually the same or different; and when a plurality of $R_{146}$ are present, the plurality of $R_{146}$ are mutually the same or different.

The exemplary embodiment can provide a compound having a high PLQY and an emission peak wavelength in a desired wavelength band in a fluorescence spectrum waveform.

Since the compound according to the exemplary embodiment has a high PLQY, it is considered that an organic EL device having an improved luminous efficiency is obtainable by using the compound according to the exemplary embodiment as a material of an organic electroluminescence device (organic EL device). Therefore, the compound according to the exemplary embodiment can achieve an improvement in the luminous efficiency of the organic electroluminescence device.

The compound according to the exemplary embodiment has an emission peak wavelength in a desired wavelength band in a fluorescence spectrum waveform. The compound according to the exemplary embodiment preferably has the maximum fluorescence peak wavelength of 445 nm or more. The compound according to the exemplary embodiment has the maximum fluorescence peak wavelength of preferably 480 nm or less, more preferably 465 nm or less. When the maximum fluorescence peak wavelength of the compound according to the exemplary embodiment is 445 nm or more, an electronic device (e.g., display) including the organic EL device including the compound according to the exemplary embodiment easily emits target moderate blue light. When the maximum fluorescence peak wavelength of the compound according to the exemplary embodiment is 480 nm or less, an electronic device (e.g., display) including the organic EL device including the compound according to the exemplary embodiment easily emits target moderate blue light.

Herein, the maximum fluorescence peak wavelength means the maximum peak wavelength of a fluorescence spectrum exhibiting a maximum luminous intensity among fluorescence spectra measured in a toluene solution in which a measurement target compound is dissolved at a concentration ranging from $10^{-6}$ mol/l to $10^{-5}$ mol/l. A fluorescence spectrum measurement device (device name: FP-8300, manufactured by JASCO Corporation) is usable as a measurement device. It should be noted that the fluorescence spectrum measurement device is not limited to the device listed herein.

The lowest singlet energy level (hereinafter, sometimes referred to as S1 energy level) of the compound according to the exemplary embodiment is preferably estimated to be low. For instance, the S1 energy level of the compound according to the exemplary embodiment is preferably in a range from 2.6 eV to 2.8 eV. According to an exemplary embodiment, it is considered that an electronic device (e.g., display) including the organic EL device including the compound according to the exemplary embodiment easily emits target moderate blue light.

The S1 energy level can be calculated by TD-DFT calculation through B3LYP as hybrid functional and 6-31 g* as a basis function using the Gaussian 16 software program available from Gaussian Inc.

In the compound according to the exemplary embodiment, when at least one of $R_1$ to $R_{14}$, $R_{16}$ in the formula (1) or $R_{17}$ in the formula (10) is a group represented by $-N(R_{131})(R_{132})$, $R_{15}$ may be or not be a group represented by $-N(R_{131})(R_{132})$.

When at least one of $R_1$ to $R_{14}$, $R_{16}$ in the formula (1) or $R_{18}$ in the formula (11) is a group represented by $-N(R_{131})(R_{132})$, $R_{15}$ may be or not be a group represented by $-N(R_{131})(R_{132})$.

When none of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{16}$, $R_{17}$, and $R_{18}$ is a group represented by $-N(R_{131})(R_{132})$ but only $R_{15}$ is a group represented by $-N(R_{131})(R_{132})$, no target moderate blue emittion is likely to be obtained.

The formula (10) in which $X_1$ is $NR_{100}$ is a cyclic structure represented by a formula (10a) below. The formula (10) in which $X_1$ is an oxygen atom is a cyclic structure represented by a formula (10b) below. The formula (10) in which $X_1$ is a sulfur atom is a cyclic structure represented by a formula (10c) below.

(10a)

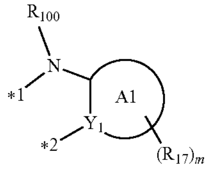

-continued (10b)

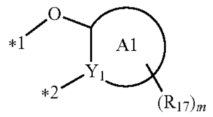

(10c)

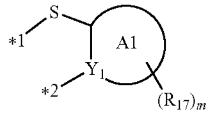

In the formulae (10a), (10b), and (10c), $R_{100}$, ring A1, m, $R_{17}$, $Y_1$, *1, and *2 respectively represent the same as $R_{100}$, ring A1, m, $R_{17}$, $Y_1$, *1 and *2 in the formula (10).

In the compound according to the exemplary embodiment, when at least one combination of adjacent two or more of $R_1$ to $R_{16}$ form a cyclic structure represented by the formula (10a) and at least one of $R_1$ to $R_{16}$ not forming the cyclic structure or $R_{17}$ is a group represented by —$N(R_{131})(R_{132})$, a combination of: one adjacent to $R_{100}$ among $R_1$ to $R_{16}$ not forming the cyclic structure, $R_{17}$, $R_{131}$ and $R_{132}$; and $R_{100}$ may be mutually bonded to form a substituted or unsubstituted monocyclic ring or may be mutually bonded to form a substituted or unsubstituted fused ring. In this case, for instance, a combination of $R_{100}$ and one of $R_1$ to $R_{17}$ adjacent to $R_{100}$ may be mutually bonded directly or via an atom to form a ring.

In the compound according to the exemplary embodiment, when at least one combination of adjacent two or more of $R_1$ to $R_{16}$ form a cyclic structure represented by the formula (10a) and a cyclic structure represented by the formula (11), and at least one of $R_1$ to $R_{16}$ not forming the cyclic structure, $R_{17}$, or $R_{18}$ is a group represented by —$N(R_{131})(R_{132})$, a combination of: one adjacent to $R_{100}$ among $R_1$ to $R_{16}$ not forming the cyclic structure, $R_{17}$, $R_{18}$, $R_{131}$ and $R_{132}$; and $R_{100}$ may be mutually bonded to form a substituted or unsubstituted monocyclic ring or may be mutually bonded to form a substituted or unsubstituted fused ring. In this case, a combination of $R_{100}$ and one of $R_1$ to $R_{18}$ adjacent to $R_{100}$ may be mutually bonded directly or via an atom to form a ring.

In the compound according to the exemplary embodiment, a combination of $R_{100}$ and one of $R_{131}$ and $R_{132}$ in a group represented by —$N(R_{131})(R_{132})$ may be mutually bonded directly or via an atom to form a ring.

In the compound according to the exemplary embodiment, when at least one combination of adjacent two or more of $R_1$ to $R_{16}$ form a cyclic structure represented by the formula (10a) and a cyclic structure represented by the formula (11), a combination of $R_{100}$ and $R_{17}$ adjacent to $R_{100}$ in the ring A1 in the formula (10a) or a combination of $R_{100}$ and $R_{18}$ adjacent to $R_{100}$ in the ring A2 in the formula (11) may be mutually bonded to form a substituted or unsubstituted monocyclic ring or a substituted or unsubstituted fused ring. In this case, for instance, a combination of $R_{100}$ and one of $R_{17}$ in the formula (10a) and $R_{18}$ in the formula (11) may be mutually bonded directly or via an atom to form a ring.

In the compound according to the exemplary embodiment, when one of $R_1$ to $R_{16}$, $R_{17}$ and $R_{18}$ is a group represented by —$N(R_{131})(R_{132})$, a combination of $R_{131}$ and $R_{132}$ may be mutually bonded to form a substituted or unsubstituted monocyclic ring or may be mutually bonded to form a substituted or unsubstituted fused ring. In this case, a combination of $R_{131}$ and $R_{132}$ may be mutually bonded directly or via an atom to form a ring.

A combination of: at least one of $R_{131}$ or $R_{132}$; and at least one of $R_1$ to $R_{16}$ adjacent to $R_{131}$ or $R_{132}$ may be mutually bonded directly or via an atom to form a ring.

Here, when a ring is formed via an atom, a type of the atom is not particularly limited. Examples of the atom include a carbon atom (C), nitrogen atom (N), oxygen atom (O), and sulfur atom (S).

When the compound according to the exemplary embodiment includes a cyclic structure represented by the formula (10a), a combination of $R_{100}$ and one of $R_1$ to $R_{18}$ adjacent to $R_{100}$ may be mutually bonded directly or via an atom to form a ring. In such a case, the compound according to the exemplary embodiment is exemplified by compounds represented by formulae (110A) to (110C) below. The compound according to the exemplary embodiment is not limited to the following examples.

A compound represented by the formula (110A) exemplifies a compound in which a combination of $R_1$ adjacent to $R_{100}$ in a cyclic structure represented by the formula (1) and $R_{100}$ form a cyclic structure via an oxygen atom.

A compound represented by the formula (110B) exemplifies a compound in which a combination of $R_1$ adjacent to $R_{100}$ in a cyclic structure represented by the formula (1) and $R_{100}$ form a cyclic structure via a carbon atom.

A compound represented by the formula (110C) exemplifies a compound in which a combination of $R_1$ adjacent to $R_{100}$ in a cyclic structure represented by the formula (1) and $R_{100}$ form a cyclic structure directly without an atom.

(110A)

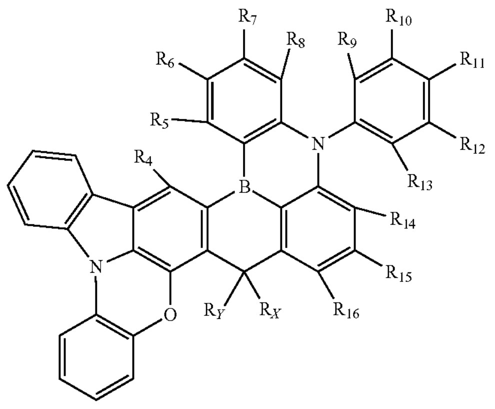

(110B)

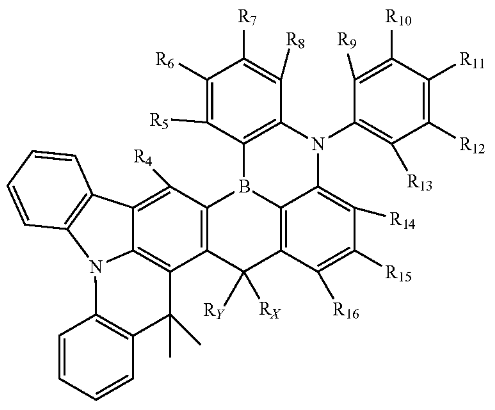

-continued (110C)

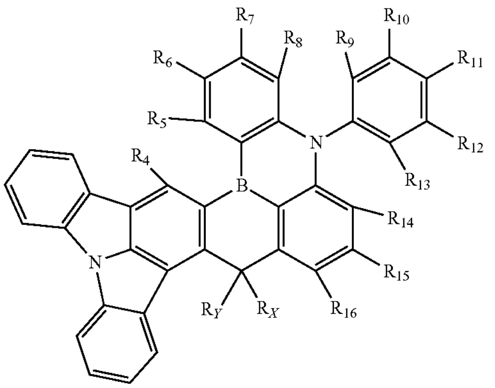

The compound according to the exemplary embodiment having a structure in which $X_1$ in the formula (10) is $NR_{100}$ and $R_{100}$ is bonded to the ring A1 directly or via an atom to form a ring is exemplified by compounds represented by formulae (110D) to (110F) below. The compound according to the exemplary embodiment is not limited to the following examples.

A compound represented by the formula (110D) exemplifies a compound in which a combination of one adjacent to $R_{100}$ of $R_{17}$ in a benzene ring as the ring A1 and $R_{100}$ form a cyclic structure via an oxygen atom.

A compound represented by the formula (110E) exemplifies a compound in which a combination of one adjacent to $R_{100}$ of $R_{17}$ in a benzene ring as the ring A1 and $R_{100}$ form a cyclic structure via a carbon atom.

A compound represented by the formula (110F) exemplifies a compound in which a combination of one adjacent to $R_{100}$ of $R_{17}$ in a benzene ring as the ring A1 and $R_{100}$ form a ring directly without an atom.

(110D)

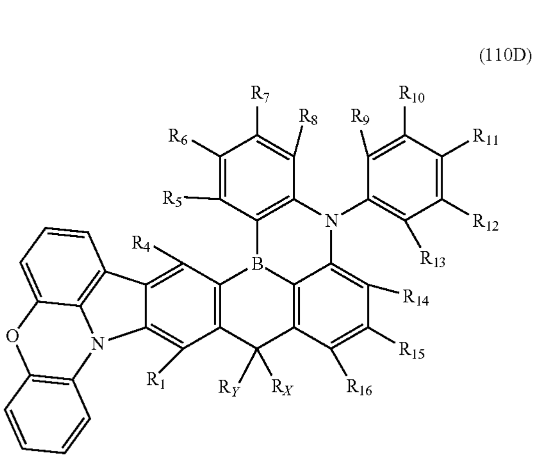

-continued (110E)

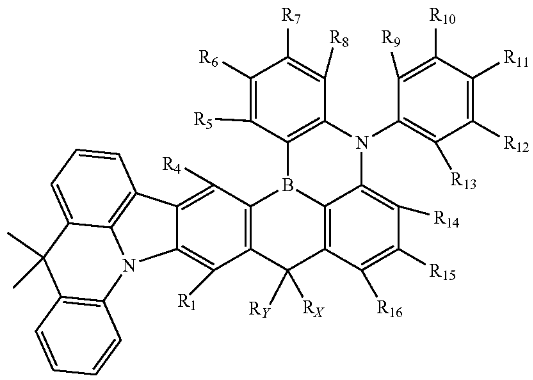

(110F)

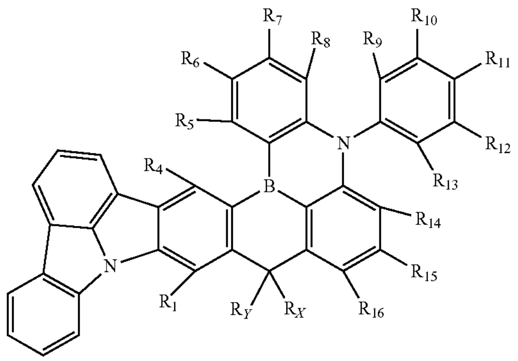

The compound according to the exemplary embodiment having a structure in which a combination of at least one of $R_{131}$ or $R_{132}$, and at least one of $R_1$ to $R_{16}$ adjacent to $R_{131}$ or $R_{132}$ are mutually bonded directly or via an atom to form a ring is exemplified by a compound represented by a formula (110G) below.

The compound according to the exemplary embodiment having a structure in which $R_{131}$ and $R_{132}$ are mutually bonded directly or via an atom to form a ring is exemplified by a compound represented by a formula (110H) below.

The compound according to the exemplary embodiment is not limited to the following examples.

In a compound represented by the formula (110G), $R_7$ is a group represented by —$N(R_{131})(R_{132})$, $R_{131}$ and $R_{132}$ are each a phenyl group, and $R_6$ is adjacent to a phenyl group as $R_{131}$ or $R_{132}$. A combination of the phenyl group and $R_6$ are directly bonded to form a ring without an atom.

In a compound represented by the formula (110H), $R_7$ is a group represented by —$N(R_{131})(R_{132})$, $R_{131}$ and $R_{132}$ are each a phenyl group, and phenyl groups as $R_{131}$ and $R_{132}$ are mutually bonded directly without an atom to form a ring.

(110G)

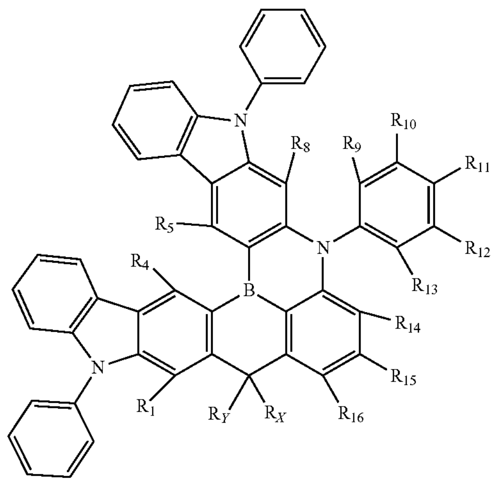

(110H)

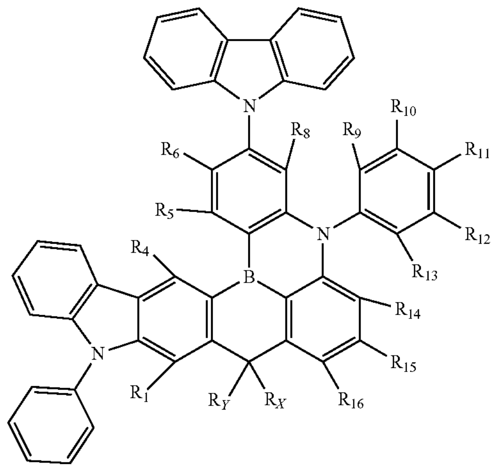

Compounds represented by the formulae (110A) to (110H) exemplify a compound in which a combination of $R_2$ and $R_3$ in a cyclic structure represented by the formula (1) form a cyclic structure represented by the formula (10). In the formulae (110A) to (110H), $R_1$ and $R_4$ to $R_{16}$ each represent the same as $R_1$ to $R_{16}$ in the formula (1).

The structure of the invention is not limited to the structures exemplified for the compounds represented by the formulae (110A) to (110H).

In the compound according to the exemplary embodiment, it is also preferable that a combination of $R_2$ and $R_3$ in the formula (1) form a cyclic structure represented by the formula (10) or a cyclic structure represented by the formula (11).

In the compound according to the exemplary embodiment, it is also preferable that a combination of $R_2$ and $R_3$ in the formula (1) form a cyclic structure represented by the formula (10).

In the compound according to the exemplary embodiment, it is also preferable that a combination of $R_6$ and $R_7$ in the formula (1) form a cyclic structure represented by the formula (10) or a cyclic structure represented by the formula (11).

In the compound according to the exemplary embodiment, it is also preferable that a combination of $R_7$ and $R_8$ in the formula (1) form a cyclic structure represented by the formula (10) or a cyclic structure represented by the formula (11).

In the compound according to the exemplary embodiment, when a combination of $R_X$ and $R_Y$ are mutually bonded to form a substituted or unsubstituted monocyclic ring or a substituted or unsubstituted fused ring, the combination of $R_X$ and $R_Y$ preferably form a substituted or unsubstituted monocyclic ring. When the combination of $R_X$ and $R_Y$ form a substituted or unsubstituted monocyclic ring, the combination of $R_X$ and $R_Y$ are preferably mutually bonded to form a cycloalkyl ring.

In the compound according to the exemplary embodiment, it is preferable that a combination of $R_X$ and $R_Y$ in the formula (1) are not mutually bonded.

In the compound according to the exemplary embodiment, it is preferable that $R_1$ to $R_{16}$ in the formula (1) forming neither a cyclic structure represented by the formula (10) nor a cyclic structure represented by the formula (11) are each independently a hydrogen atom, a substituted or unsubstituted alkyl group having 1 to 50 carbon atoms, a group represented by $-N(R_{131})(R_{132})$, a substituted or unsubstituted aryl group having 6 to 50 ring carbon atoms, or a substituted or unsubstituted heterocyclic group having 5 to 50 ring atoms.

In the compound according to the exemplary embodiment, it is preferable that the ring A1 is a substituted or unsubstituted aliphatic hydrocarbon ring having 3 to 50 ring carbon atoms, or a substituted or unsubstituted aromatic hydrocarbon ring having 6 to 50 ring carbon atoms, $X_1$ is $NR_{100}$ or an oxygen atom, $Y_1$ is a carbon atom in the formula (10), and the ring A2 is a substituted or unsubstituted heterocycle having 5 to 50 ring atoms in the formula (11).

In the compound according to the exemplary embodiment, it is preferable that in the formula (1), a combination of $R_2$ and $R_3$ form a cyclic structure represented by the formula (10), $R_1$ and $R_4$ to $R_{16}$ do not form a cyclic structure represented by the formula (10), $R_5$, $R_{11}$, and $R_{15}$ are each independently a hydrogen atom or a substituted or unsubstituted alkyl group having 1 to 50 carbon atoms, and at least one $R_{17}$ in the formula (10) is $-N(R_{131})(R_{132})$.

In the compound according to the exemplary embodiment, it is preferable that in the formula (1), a combination of $R_2$ and $R_3$ form a cyclic structure represented by the formula (10), $R_5$, $R_{11}$, and $R_{15}$ among $R_1$ and $R_4$ to $R_{16}$ not forming a cyclic structure represented by the formula (10) are each independently a hydrogen atom, a substituted or unsubstituted alkyl group having 1 to 50 carbon atoms or a group represented by $-N(R_{131})(R_{132})$, and at least one of $R_5$ or $R_{11}$ is a group represented by $-N(R_{131})(R_{132})$.

In the compound according to the exemplary embodiment, in the formula (1), it is preferable that $R_1$, $R_4$, $R_5$, $R_7$, $R_8$, $R_9$, $R_{10}$, $R_{12}$, $R_{13}$, $R_{14}$, and $R_{16}$ among $R_1$ and $R_4$ to $R_{16}$ not forming a cyclic structure represented by the formula (10) are each a hydrogen atom.

In the compound according to the exemplary embodiment, it is preferable that in the formula (1), a combination of $R_2$ and $R_3$ form a cyclic structure represented by the formula (10), $R_1$ and $R_4$ to $R_{16}$ do not form a cyclic structure represented by the formula (10), $R_1$, $R_4$, $R_5$, $R_7$, $R_8$, $R_9$, $R_{10}$, $R_{12}$, $R_{13}$, $R_{14}$, and $R_{16}$ are each a hydrogen atom, and at least one $R_{17}$ in the formula (10) is a group represented by $-N(R_{131})(R_{132})$.

In the compound according to the exemplary embodiment, it is preferable that a combination of $R_{131}$ and $R_{132}$ in a group represented by $-N(R_{131})(R_{132})$ in the formula (1) are not mutually bonded.

In the compound according to the exemplary embodiment, it is preferable that a cyclic structure represented by the formula (10) is at least one cyclic structure selected from the group consisting of a cyclic structure represented by a formula (101) below, a cyclic structure represented by a formula (102) below, and a cyclic structure represented by a formula (103) below, and a cyclic structure represented by the formula (11) is a cyclic structure represented by a formula (111) below.

(101)

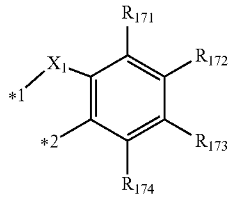

(102)

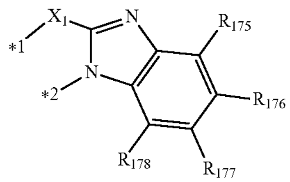

(111)

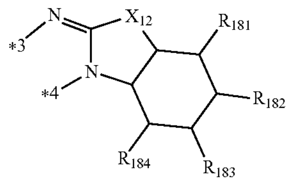

(103)

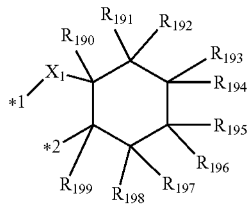

In the formula (101):

at least one combination of adjacent two or more of $R_{171}$ to $R_{174}$ are mutually bonded to form a substituted or unsubstituted monocyclic ring, mutually bonded to form a substituted or unsubstituted fused ring, or not mutually bonded;

$R_{171}$ to $R_{174}$ forming neither a substituted or unsubstituted monocyclic ring nor a substituted or unsubstituted fused ring each independently represent the same as $R_{17}$ in the formula (10); and $X_1$ represents the same as $X_1$ in the formula (10).

In the formula (102):

at least one combination of adjacent two or more of $R_{175}$ to $R_{178}$ are mutually bonded to form a substituted or unsubstituted monocyclic ring, mutually bonded to form a substituted or unsubstituted fused ring, or not mutually bonded;

$R_{175}$ to $R_{178}$ forming neither a substituted or unsubstituted monocyclic ring nor a substituted or unsubstituted fused ring each independently represent the same as $R_{17}$ in the formula (10); and $X_1$ represents the same as $X_1$ in the formula (10).

In the formula (103):

at least one combination of adjacent two or more of $R_{190}$ to $R_{199}$ are mutually bonded to form a substituted or unsubstituted monocyclic ring, mutually bonded to form a substituted or unsubstituted fused ring, or not mutually bonded; $R_{190}$ to $R_{199}$ forming neither a substituted or unsubstituted monocyclic ring nor a substituted or unsubstituted fused ring each independently represent the same as $R_{17}$ in the formula (10); and $X_1$ represents the same as $X_1$ in the formula (10).

In the formula (111):

at least one combination of adjacent two or more of $R_{181}$ to $R_{184}$ are mutually bonded to form a substituted or unsubstituted monocyclic ring, mutually bonded to form a substituted or unsubstituted fused ring, or not mutually bonded;

$R_{181}$ to $R_{184}$ forming neither a substituted or unsubstituted monocyclic ring nor a substituted or unsubstituted fused ring each independently represent the same as $R_{18}$ in the formula (11); and $X_{12}$ represents the same as $X_1$ in the formula (10).

*1 and *2 in the formulae (101), (102), and (103) and *3 and *4 in the formula (111) each represent a bonding position to a cyclic structure represented by the formula (1).

In the compound according to the exemplary embodiment, it is preferable in the formula (101) that $R_{171}$ to $R_{174}$ forming neither the substituted or unsubstituted monocyclic ring nor the substituted or unsubstituted fused ring are each independently a hydrogen atom, a substituted or unsubstituted alkyl group having 1 to 50 carbon atoms, or a group represented by $-N(R_{131})(R_{132})$, a combination of $R_{131}$ and $R_{132}$ are mutually bonded to form a substituted or unsubstituted monocyclic ring, mutually bonded to form a substituted or unsubstituted fused ring, or not mutually bonded.

In the compound according to the exemplary embodiment, it is preferable in the formula (102) that $R_{175}$ to $R_{178}$ forming neither the substituted or unsubstituted monocyclic ring nor the substituted or unsubstituted fused ring are each independently a hydrogen atom, a substituted or unsubstituted alkyl group having 1 to 50 carbon atoms, or a group represented by $-N(R_{131})(R_{132})$, a combination of $R_{131}$ and $R_{132}$ are mutually bonded to form a substituted or unsubstituted monocyclic ring, mutually bonded to form a substituted or unsubstituted fused ring, or not mutually bonded.

In the compound according to the exemplary embodiment, it is preferable in the formula (103) that $R_{190}$ to $R_{199}$ forming neither the substituted or unsubstituted monocyclic ring nor the substituted or unsubstituted fused ring are each independently a hydrogen atom, a substituted or unsubstituted alkyl group having 1 to 50 carbon atoms, or a group represented by $-N(R_{131})(R_{132})$, a combination of $R_{131}$ and $R_{132}$ are mutually bonded to form a substituted or unsubstituted monocyclic ring, mutually bonded to form a substituted or unsubstituted fused ring, or not mutually bonded.

In the compound according to the exemplary embodiment, it is preferable in the formula (111) that $R_{181}$ to $R_{184}$ forming neither the substituted or unsubstituted monocyclic ring nor the substituted or unsubstituted fused ring are each independently a hydrogen atom, a substituted or unsubstituted alkyl group having 1 to 50 carbon atoms, or a group represented by $-N(R_{131})(R_{132})$, a combination of $R_{131}$ and $R_{132}$ are mutually bonded to form a substituted or unsubstituted monocyclic ring, mutually bonded to form a substituted or unsubstituted fused ring, or not mutually bonded.
The compound according to the exemplary embodiment is preferably a compound represented by a formula (131), (132), (133), (134), (135), (136), (137), or (138).
(131)
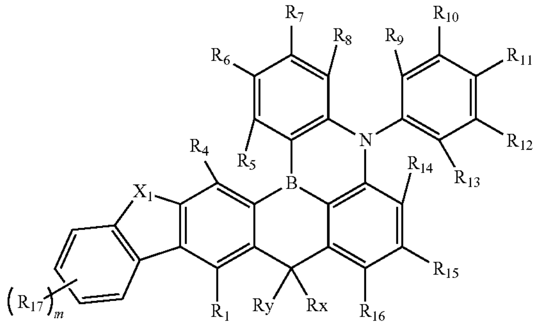
(132)
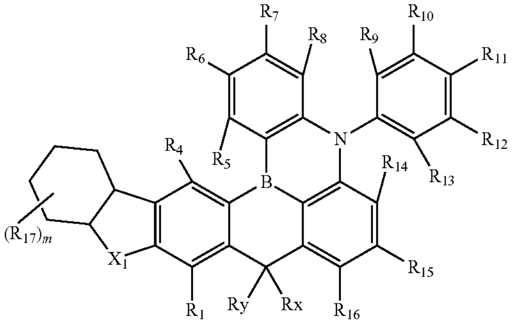
(133)
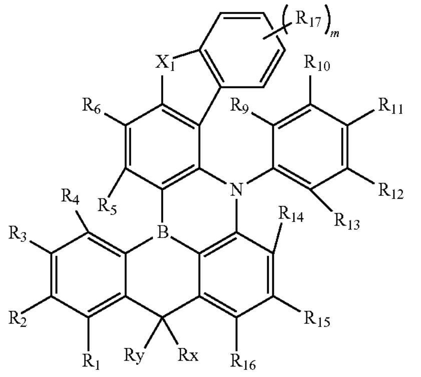
(134)
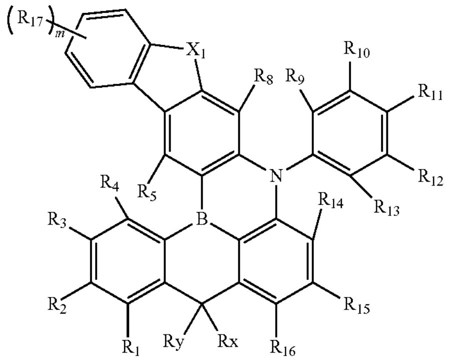
-continued
(135)
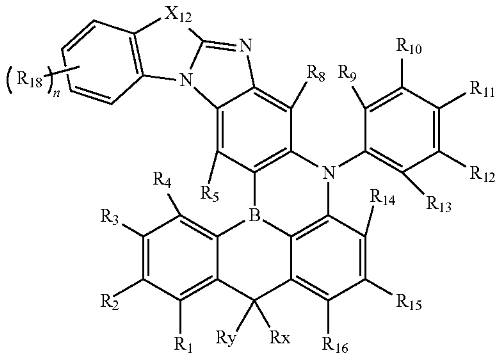
(136)
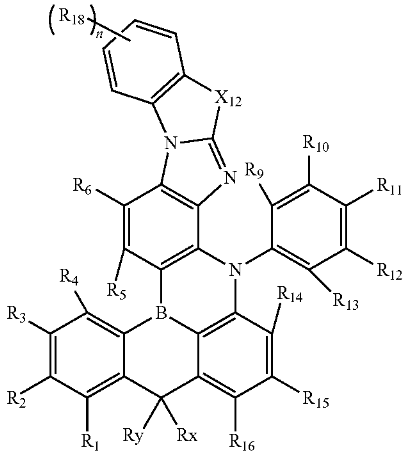
(137)
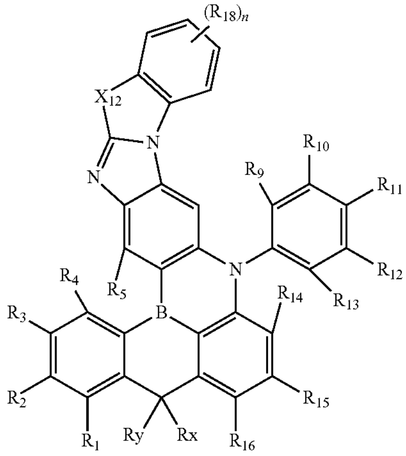

-continued (138)

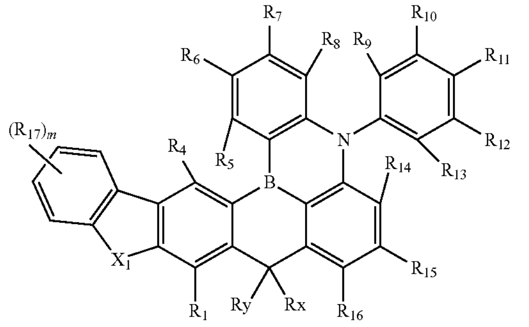

In the formulae (131), (132), (133), (134), (135), (136), (137), and (138):

$R_1$ to $R_{16}$ respectively represent the same as $R_1$ to $R_{16}$ in the formula (1);

$R_{17}$ represent the same as $R_{17}$ in the formula (10);

$R_{18}$ represent the same as $R_{18}$ in the formula (11);

$R_X$ and $R_Y$ respectively represent the same as $R_X$ and $R_Y$ in the formula (1);

$X_1$ and $X_{12}$ each represent the same as $X_1$ in the formula (10);

m represent the same as m for $R_{17}$ in the formula (10); and n represent the same as n for $R_{18}$ in the formula (11).

In the compound according to the exemplary embodiment, it is preferable that a compound represented by the formula (131) is a compound represented by a formula (131-1), (131-2), or (131-3); a compound represented by the formula (132) is a compound represented by a formula (132-1); a compound represented by the formula (133) is a compound represented by a formula (133-1); a compound represented by the formula (134) is a compound represented by a formula (134-1); a compound represented by the formula (135) is a compound represented by a formula (135-1); a compound represented by the formula (136) is a compound represented by a formula (136-1); a compound represented by the formula (137) is a compound represented by a formula (137-1); and a compound represented by the formula (138) is a compound represented by a formula (138-1).

(131-1)

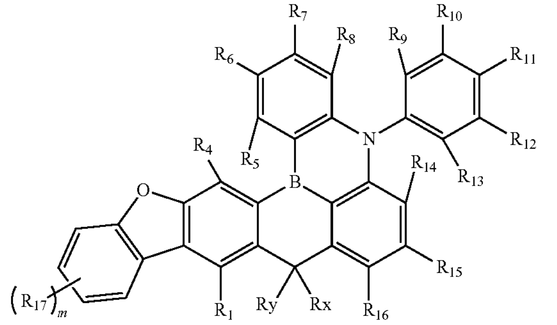

-continued (131-2)

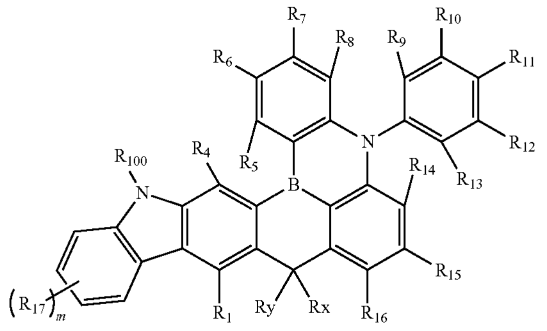

(131-3)

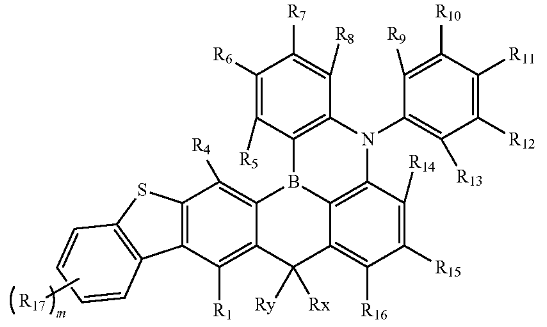

(132-1)

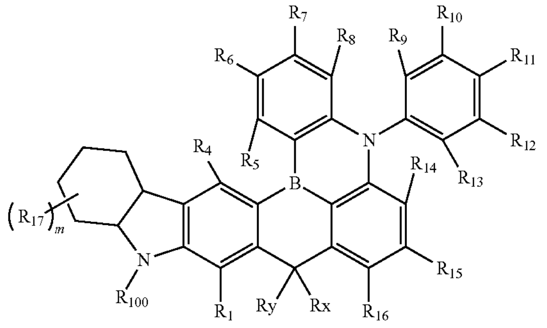

(133-1)

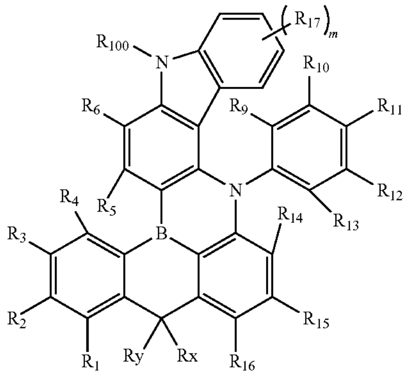

-continued (134-1)

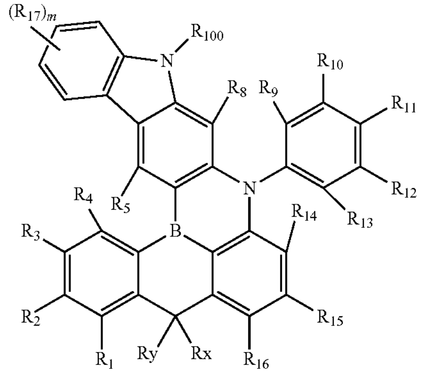

(135-1)

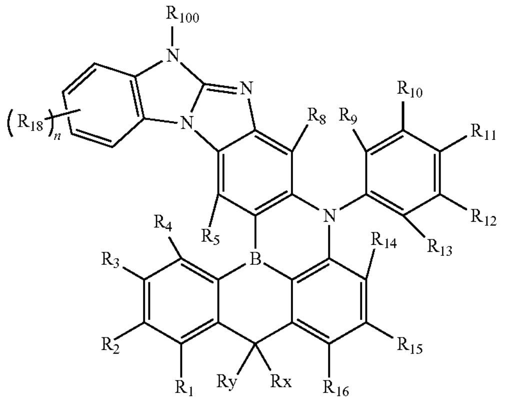

In the formulae (131-1) to (131-3), (132-1), (133-1), (134-1), (135-1), (136-1), (137-1), and (138-1):

$R_1$ to $R_{16}$ each represent the same as $R_1$ to $R_{16}$ in the formula (1);

$R_{17}$ represent the same as $R_{17}$ in the formula (10);

$R_{18}$ represent the same as $R_{18}$ in the formula (11);

$R_X$ and $R_Y$ respectively represent the same as $R_X$ and $R_Y$ in the formula (1);

$R_{100}$ represent the same as $R_{100}$ in the formula (10);

m represent the same as m for $R_{17}$ in the formula (10); and n represent the same as n for $R_{18}$ in the formula (11).

In the compound according to the exemplary embodiment, it is preferable that the substituent for "substituted or unsubstituted" group is a halogen atom, an unsubstituted alkyl group having 1 to 25 carbon atoms, an unsubstituted aryl group having 6 to 25 ring carbon atoms, or an unsubstituted heterocyclic group having 5 to 25 ring atoms.

In the compound according to the exemplary embodiment, it is preferable that the substituent for "substituted or unsubstituted" group is an unsubstituted alkyl group having 1 to 10 carbon atoms, an unsubstituted aryl group having 6 to 12 ring carbon atoms, or an unsubstituted heterocyclic group having 5 to 12 ring atoms.

In the compound according to the exemplary embodiment, it is preferable that all of the "substituted or unsubstituted" groups are "unsubstituted" groups.

Manufacturing Method of Compound According to First Exemplary Embodiment

The compound according to the exemplary embodiment can be manufactured by application of known substitution reactions and materials depending on a target compound, in accordance with or based on synthesis methods described later in Examples.

Specific Examples of Compound According to First Exemplary Embodiment

Examples of the compound according to the exemplary embodiment include the following compounds. However, the invention is not limited to these specific examples. In the chemical formulae herein, a deuterium atom is denoted by D and a protium atom is denoted by H or a description for a protium is omitted.

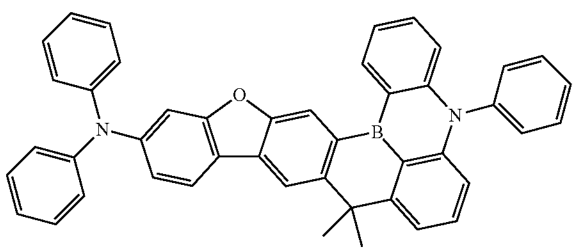

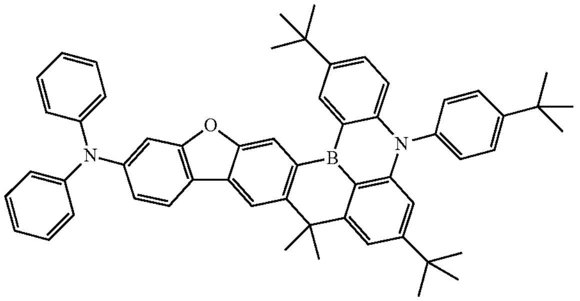

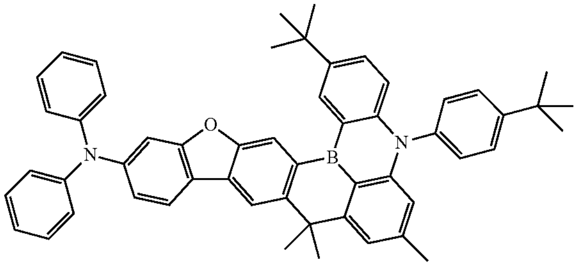

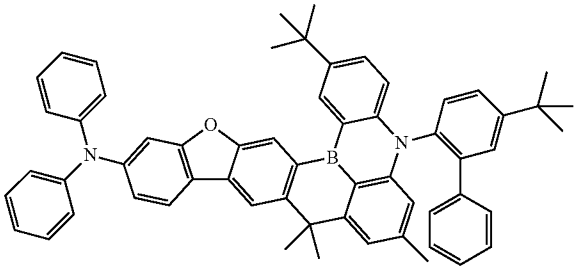

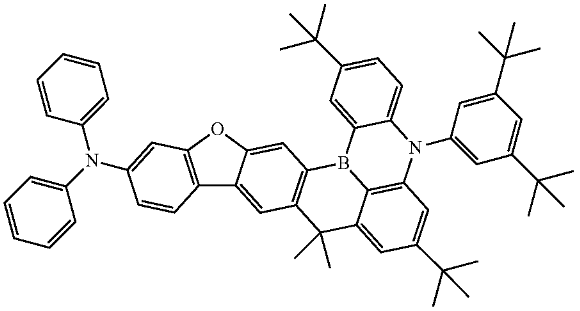

-continued
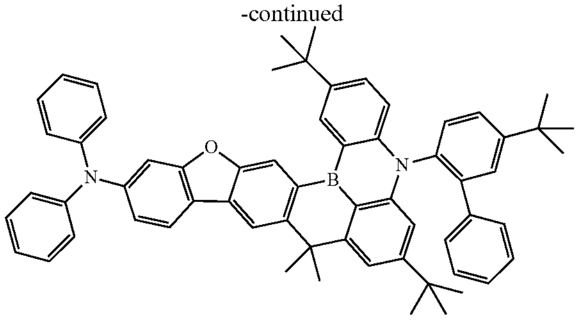
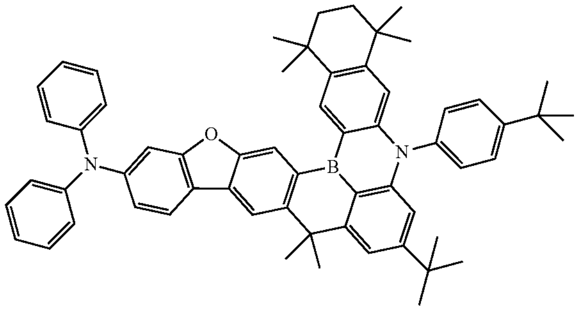
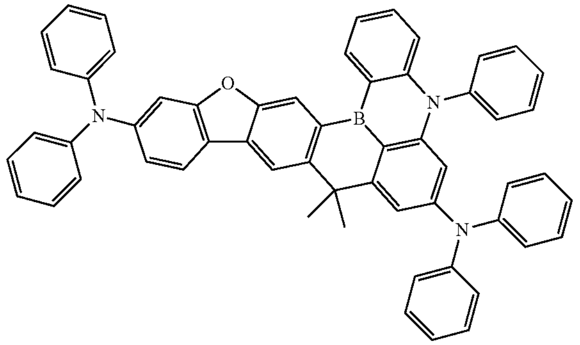
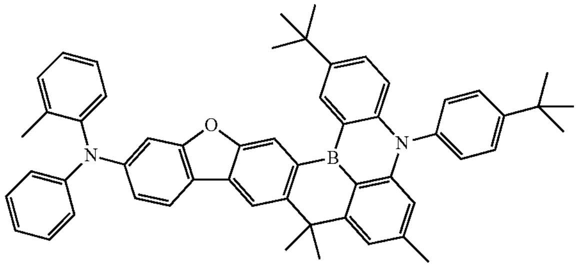
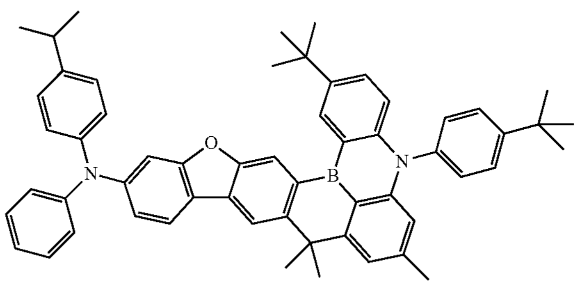
-continued
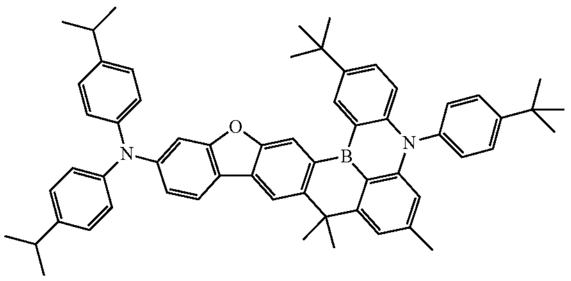
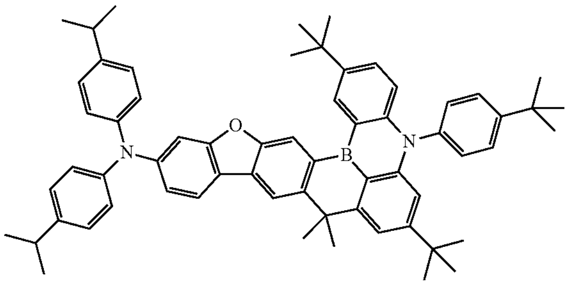
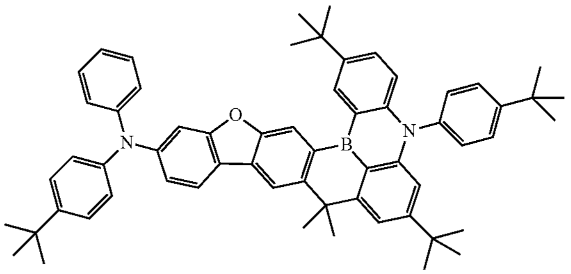
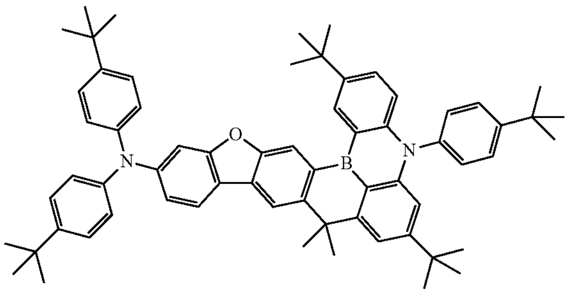
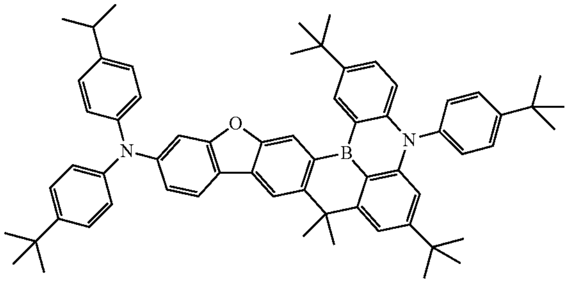
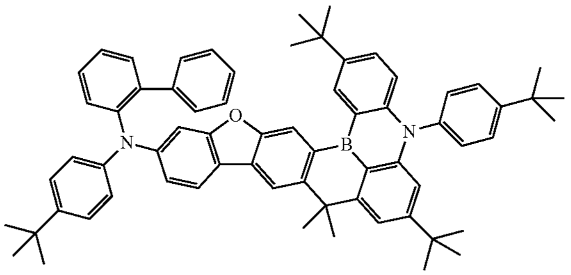

-continued
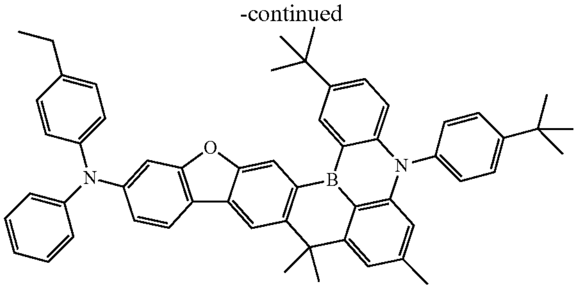
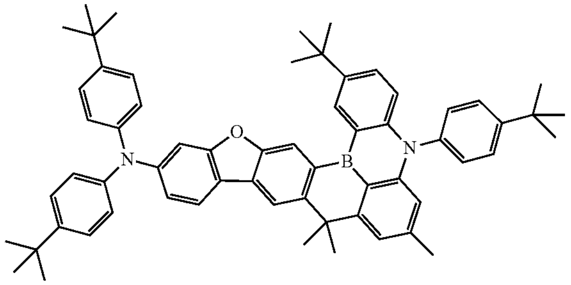
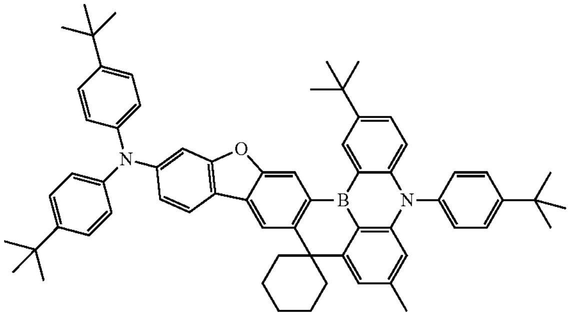
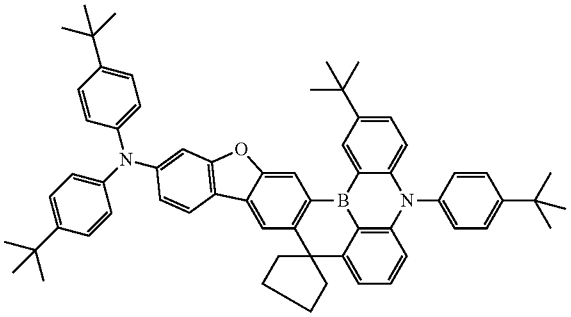
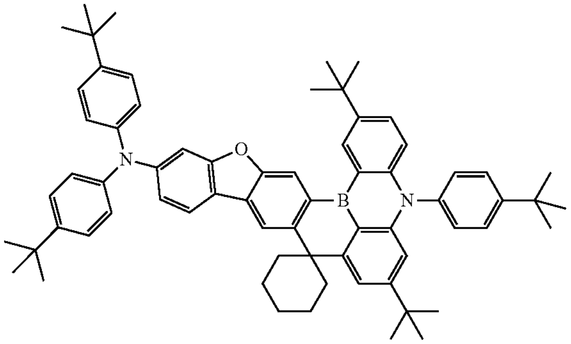
-continued
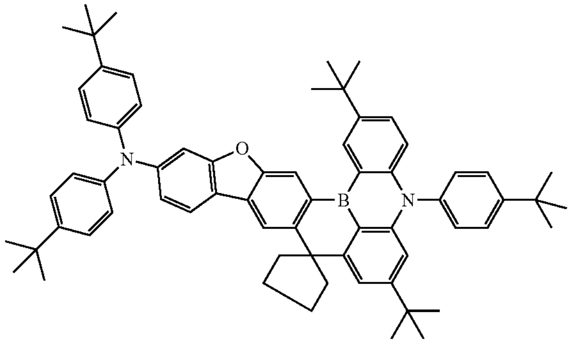
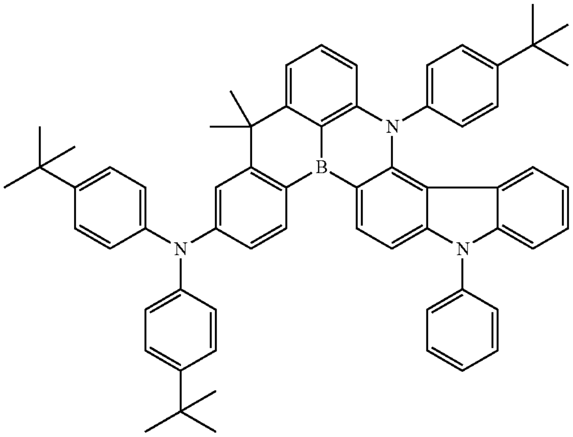
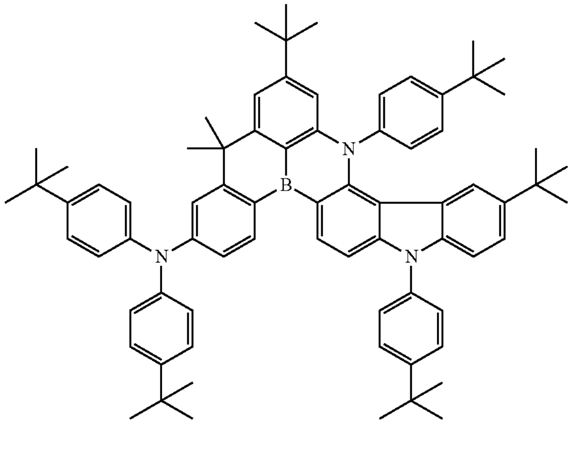
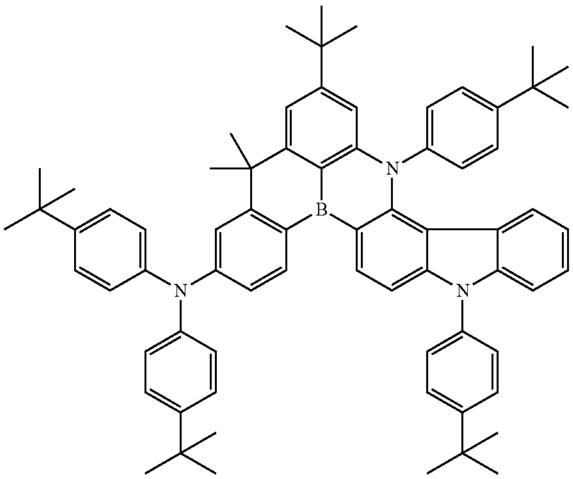

-continued
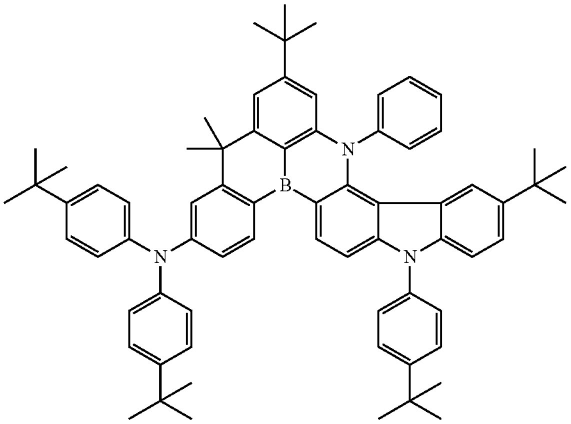
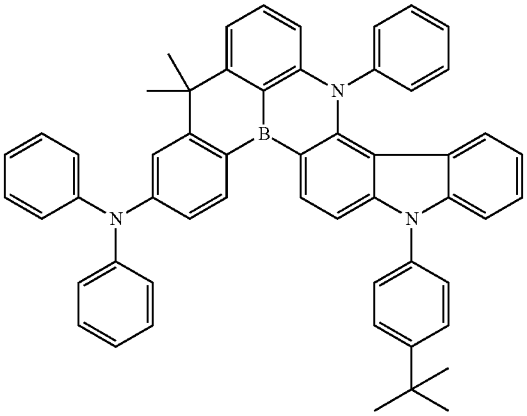
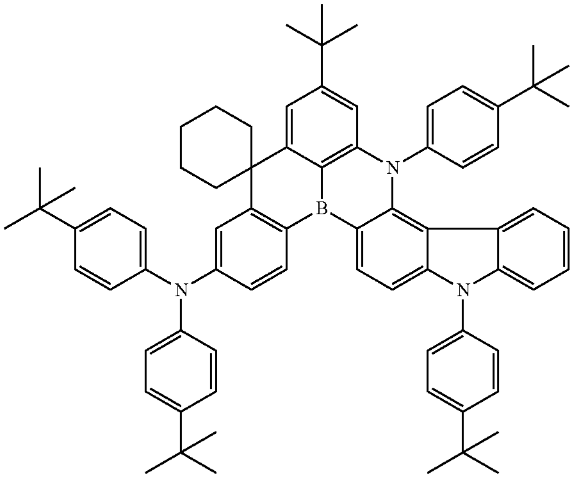
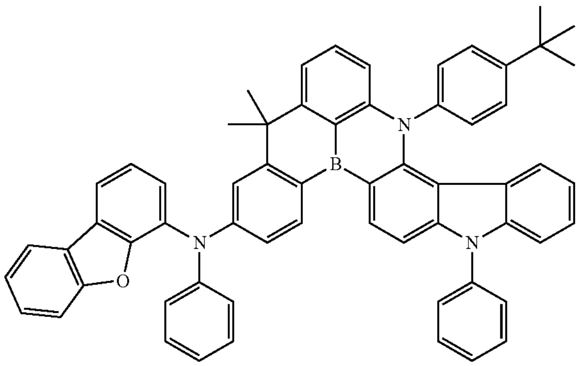
-continued
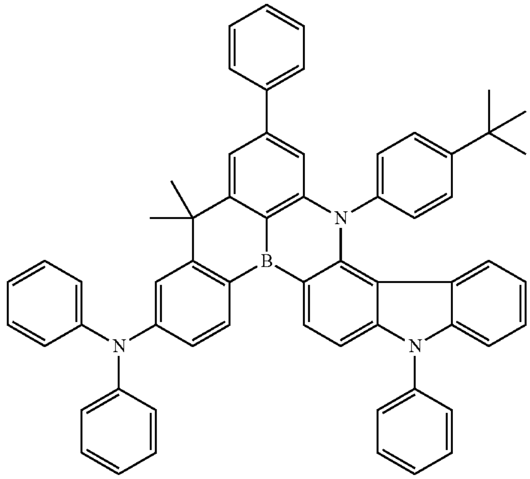
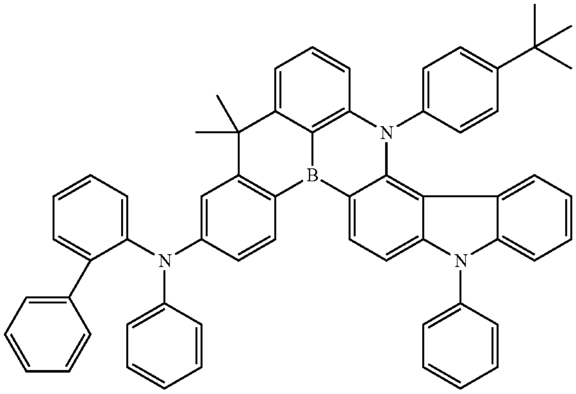
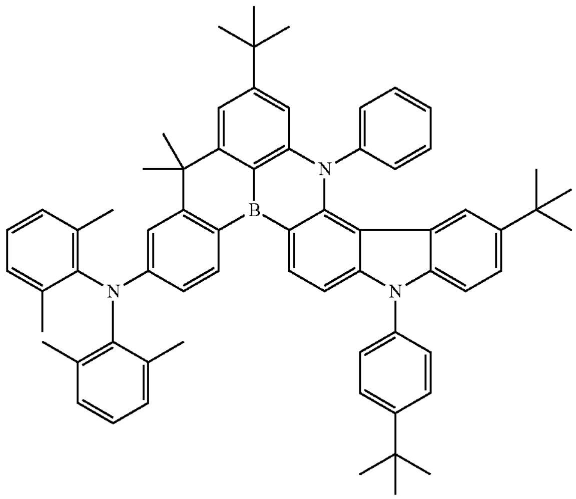

-continued
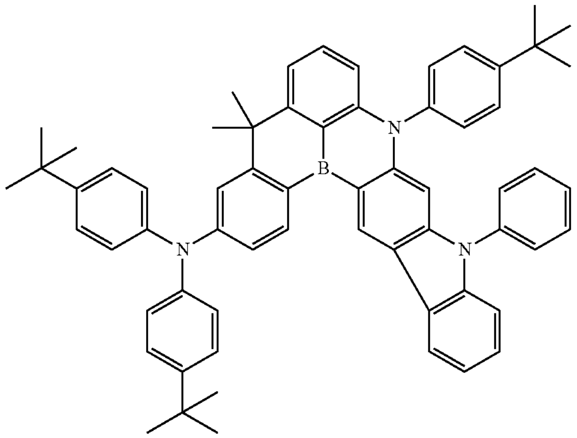
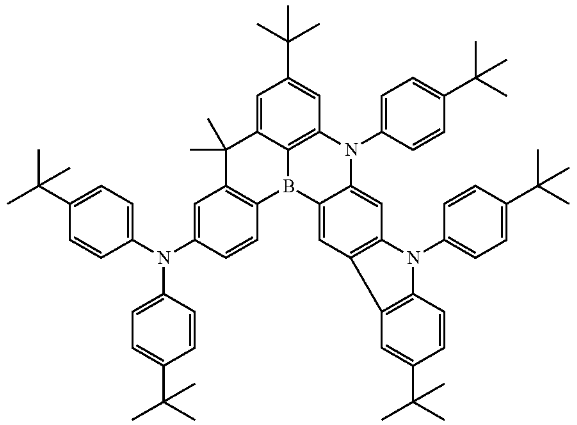
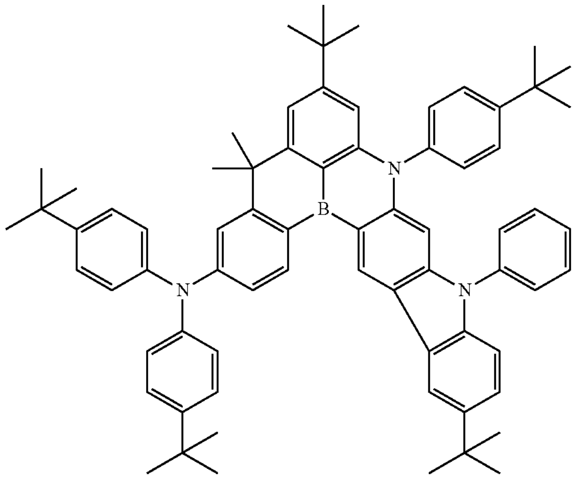
-continued
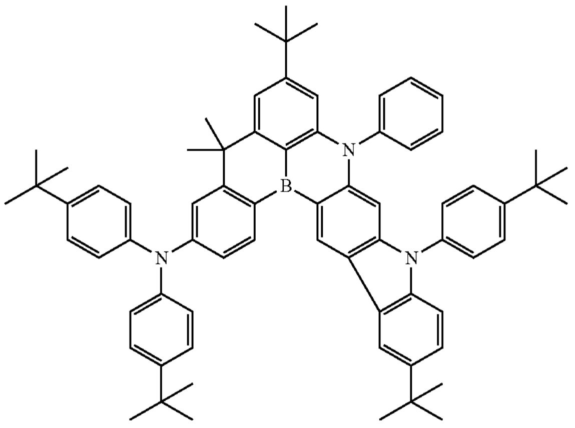
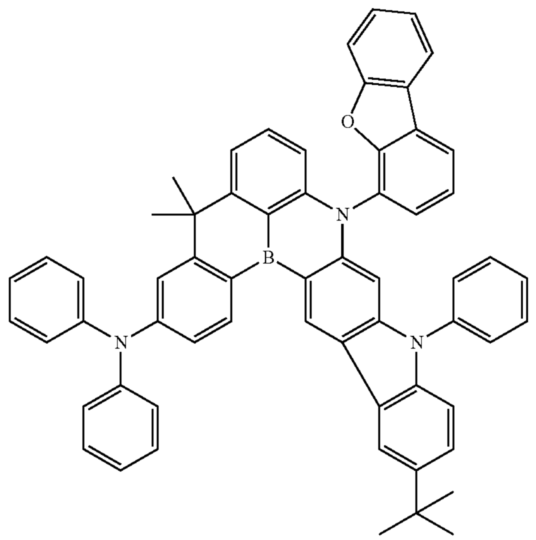
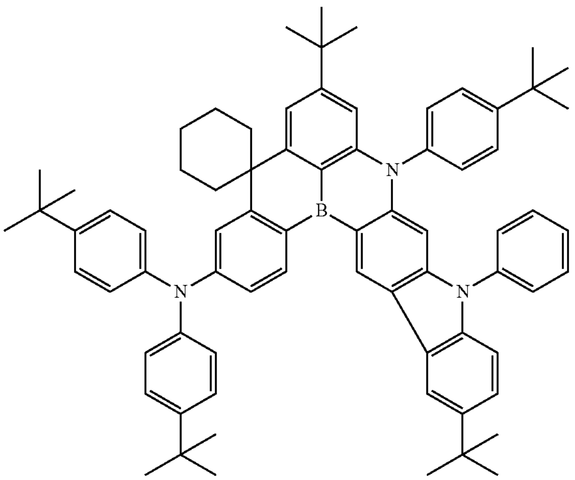

-continued
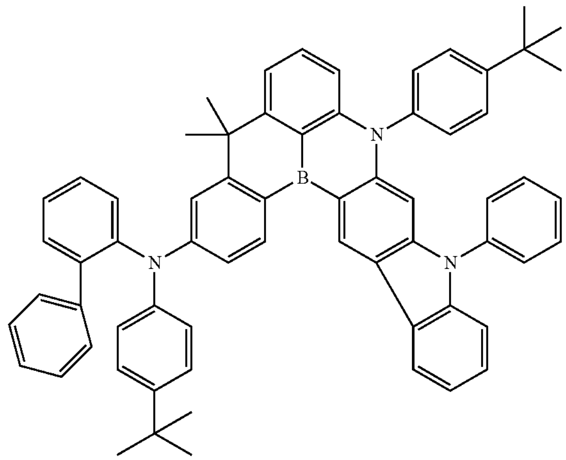
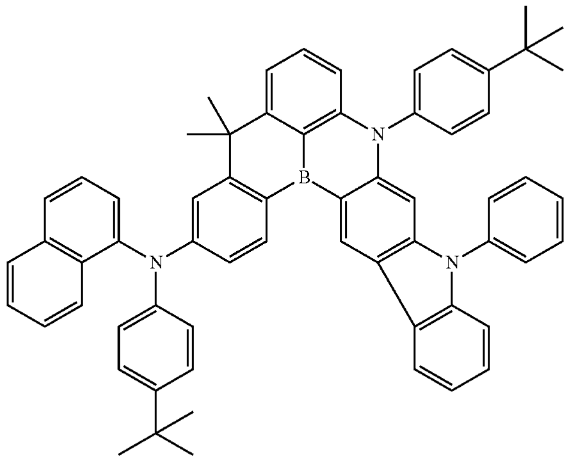
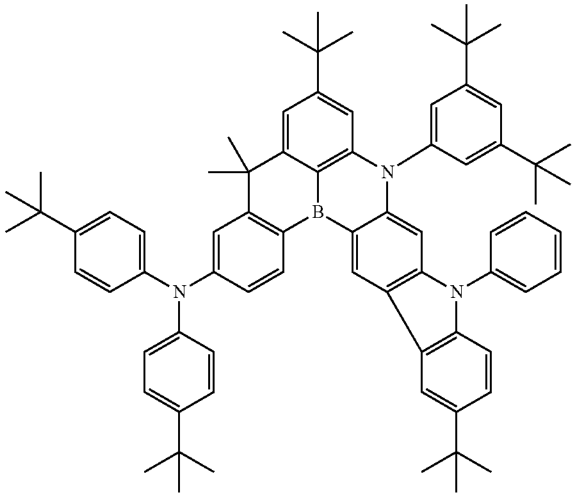
-continued
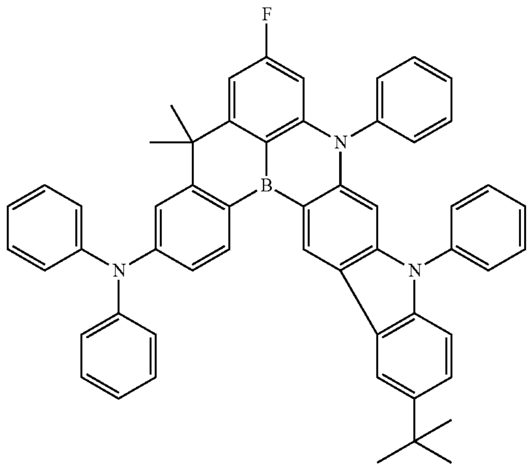
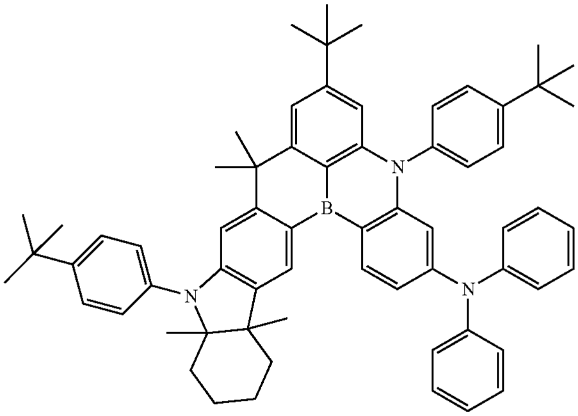
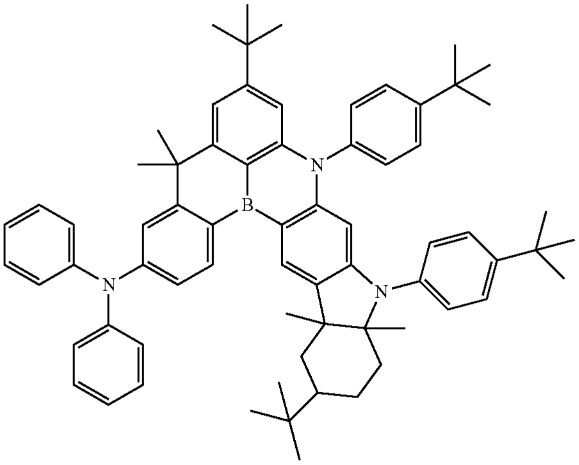

-continued
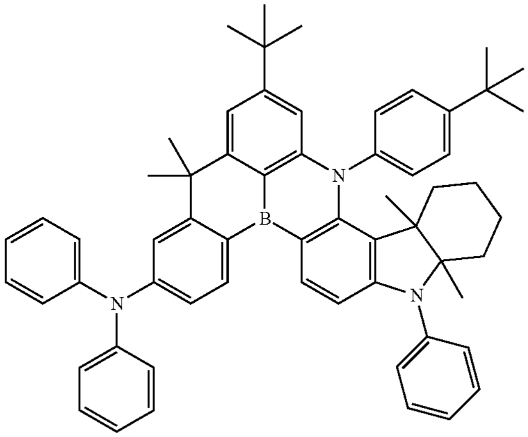
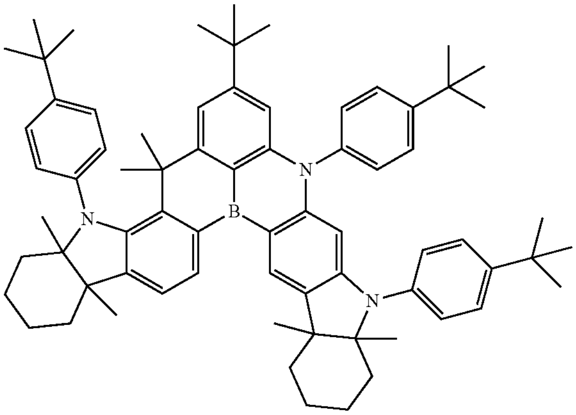
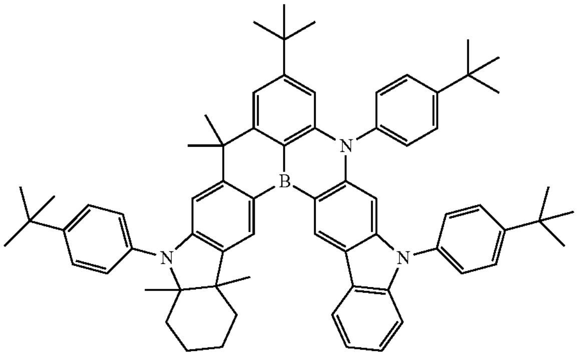
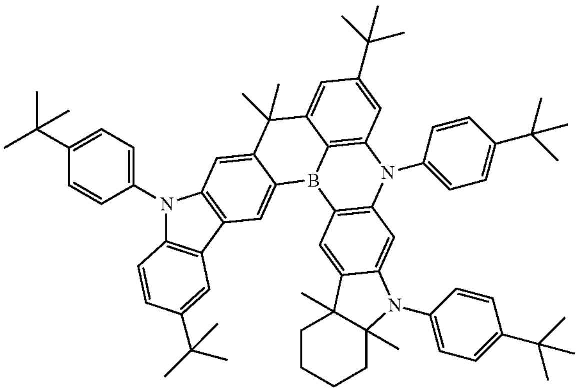
-continued
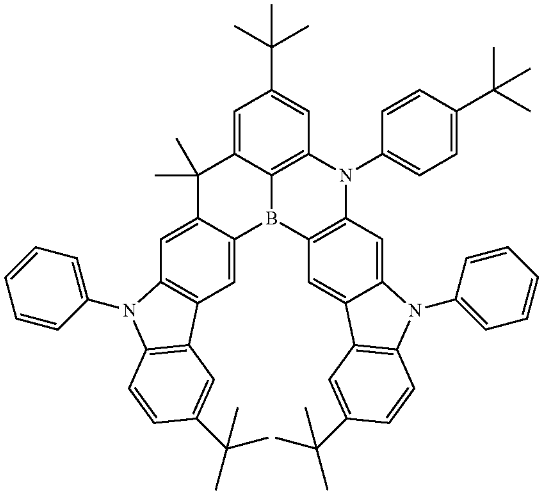
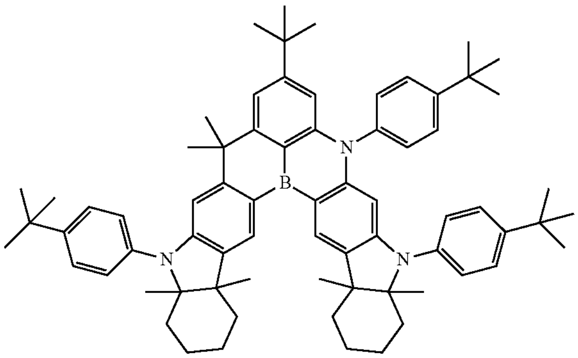
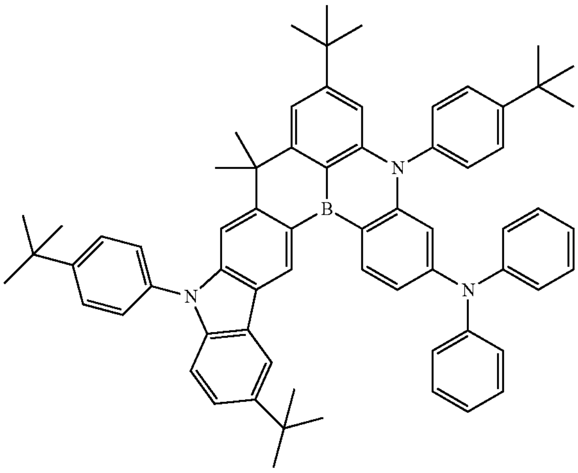

-continued
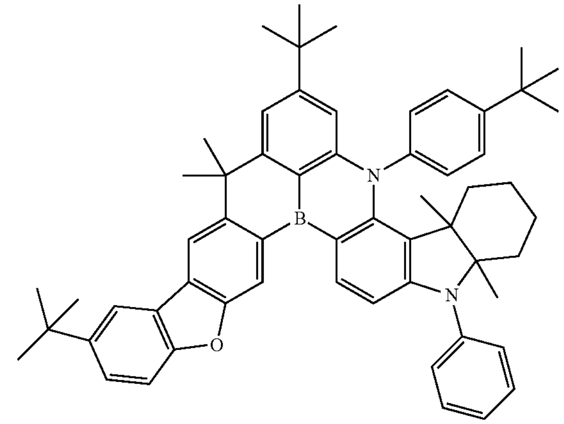
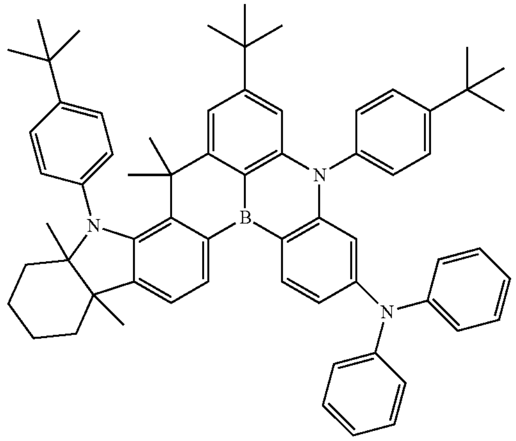
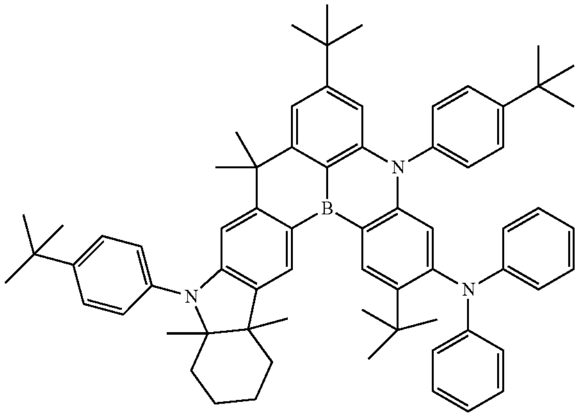
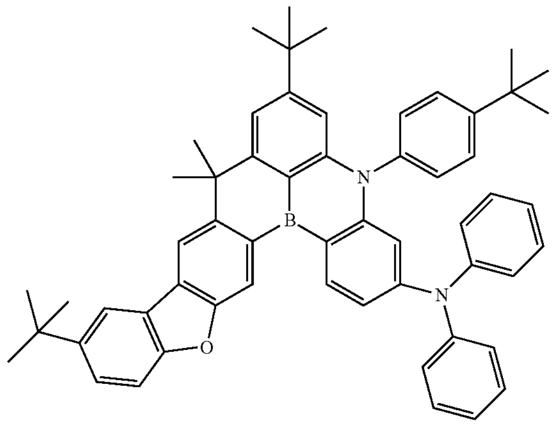
-continued
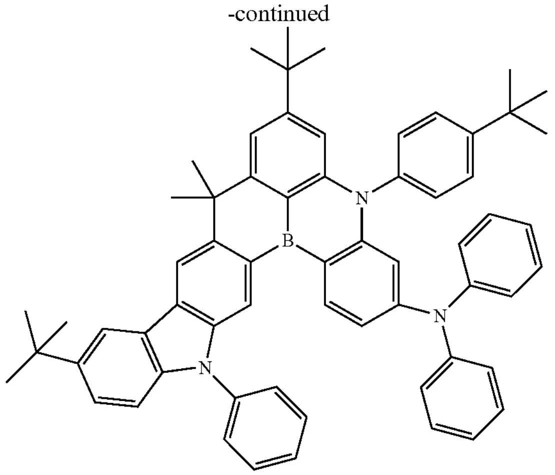
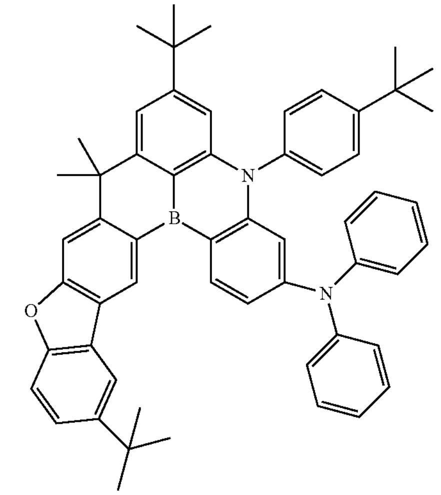
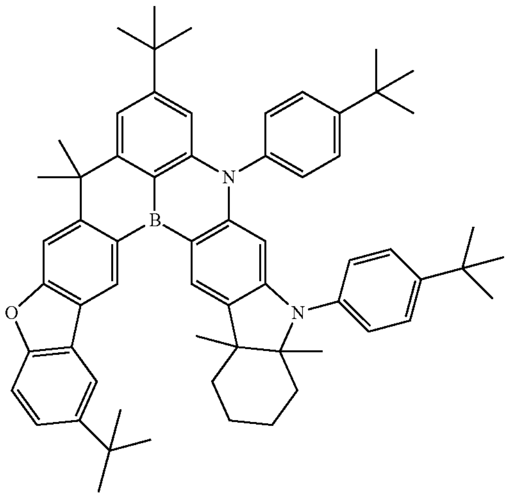

-continued
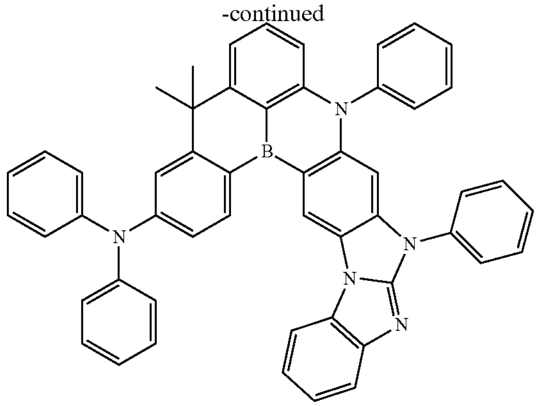
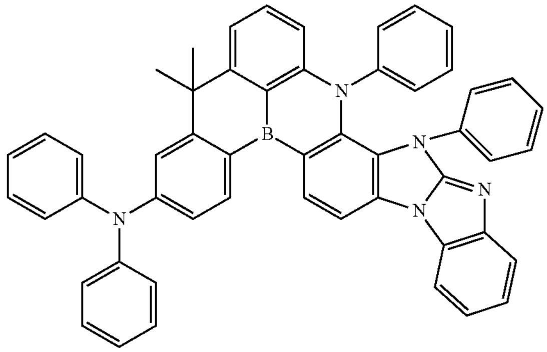
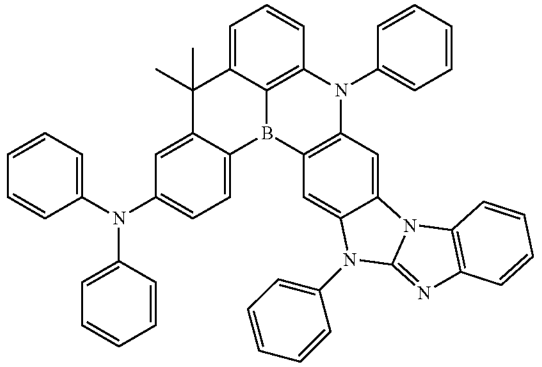
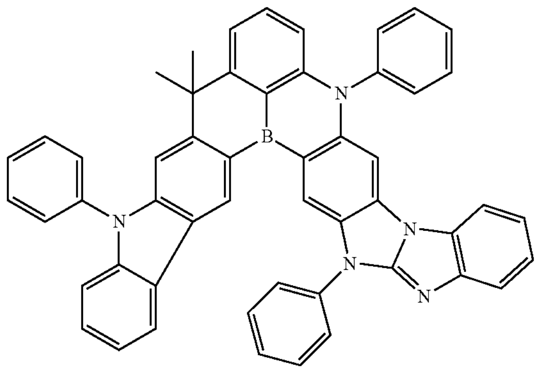
-continued
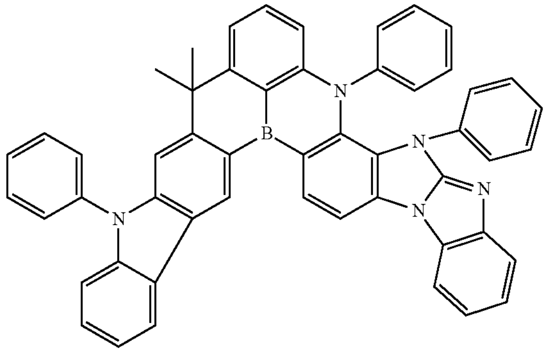
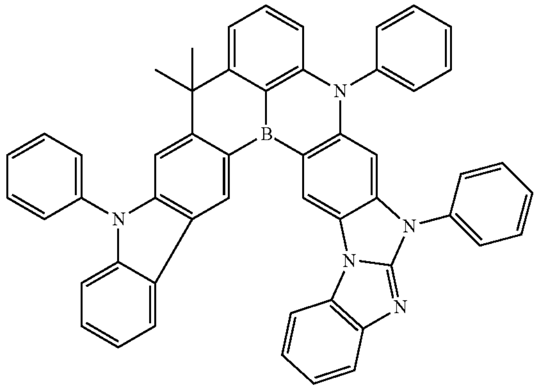
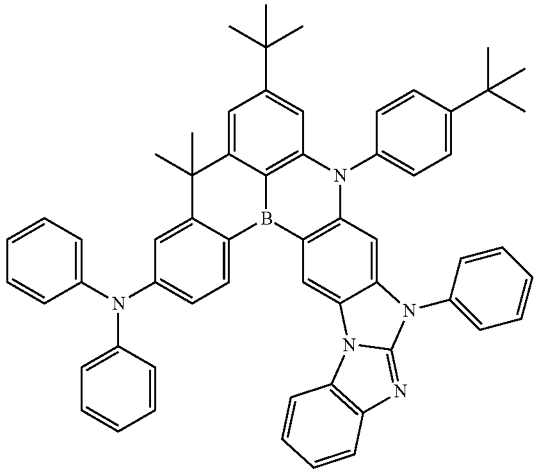
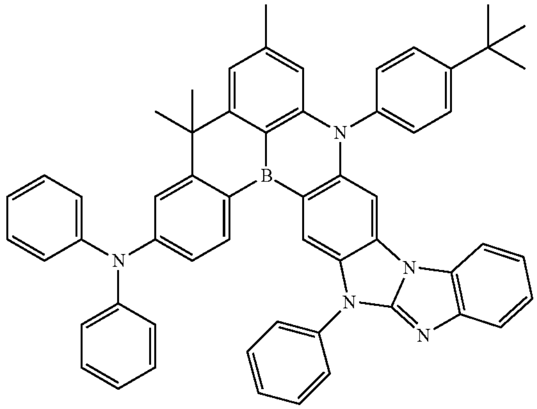

-continued
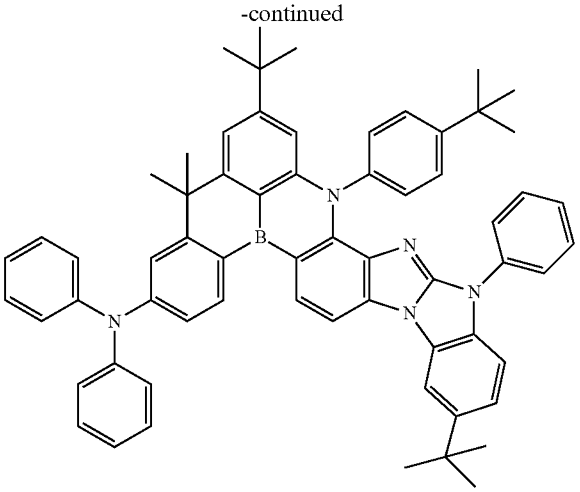
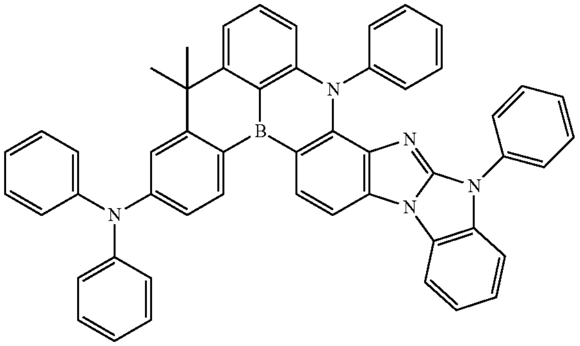
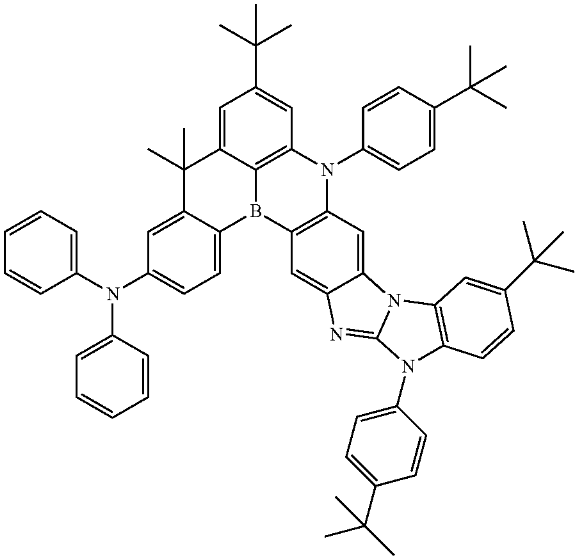
-continued
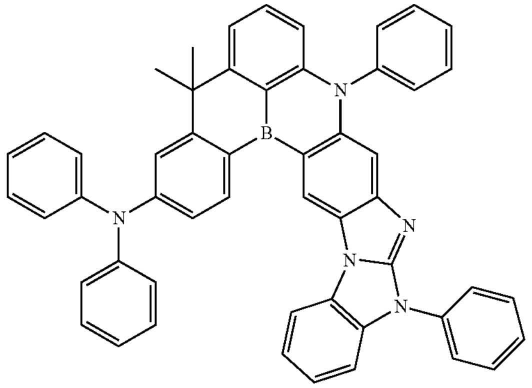
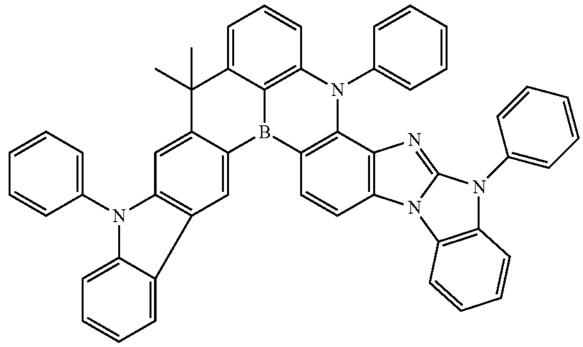
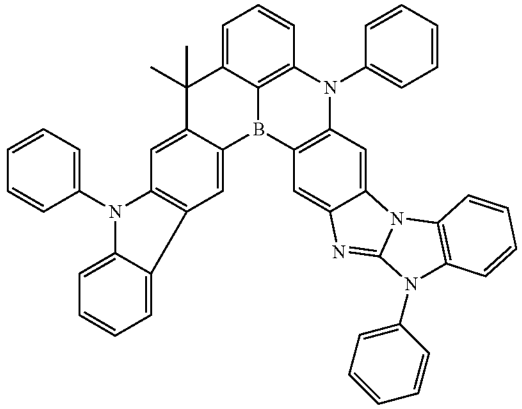
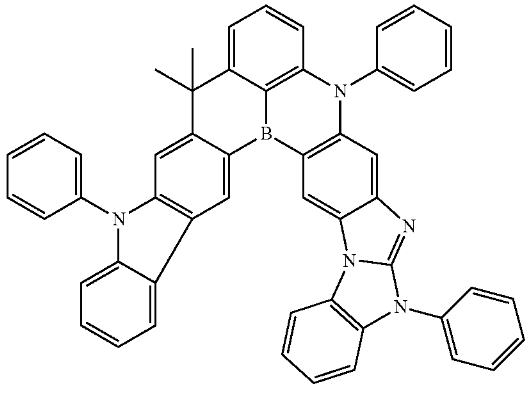

-continued
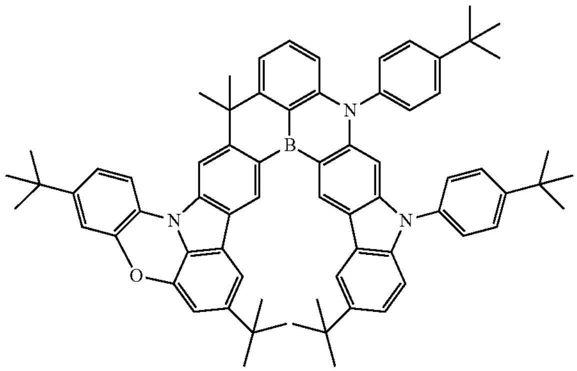
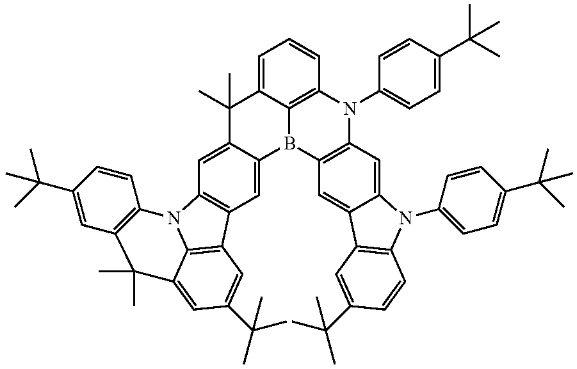
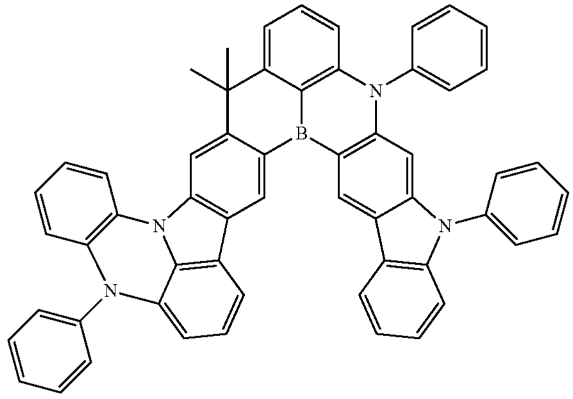
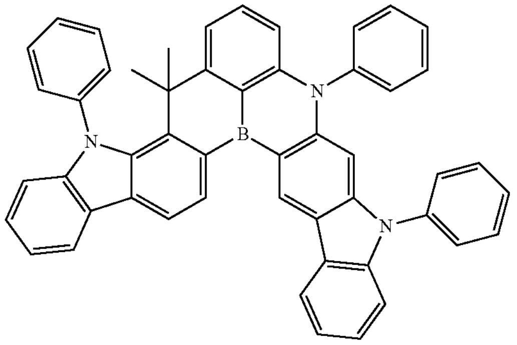
-continued
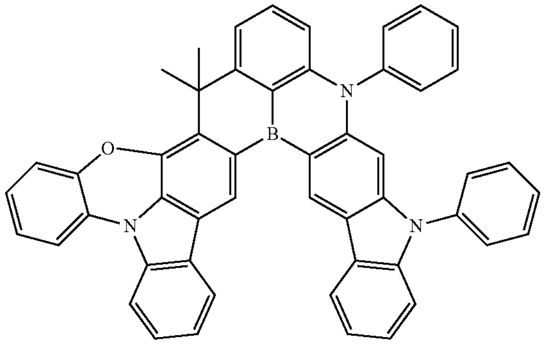
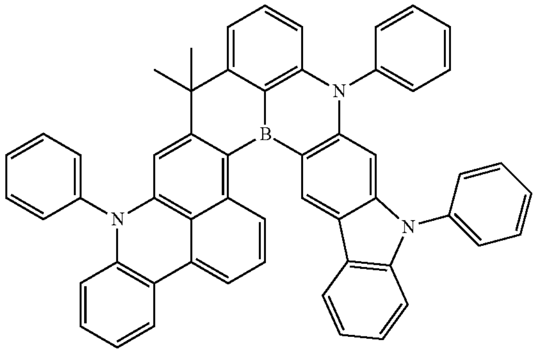
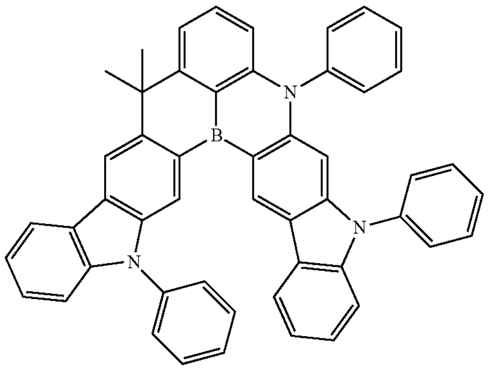
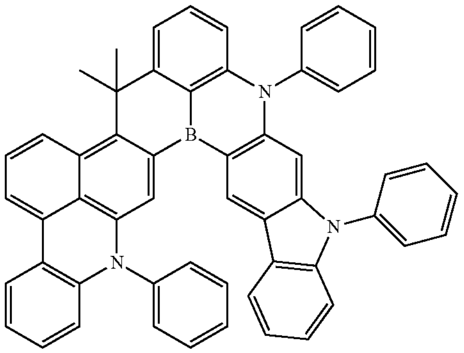

-continued
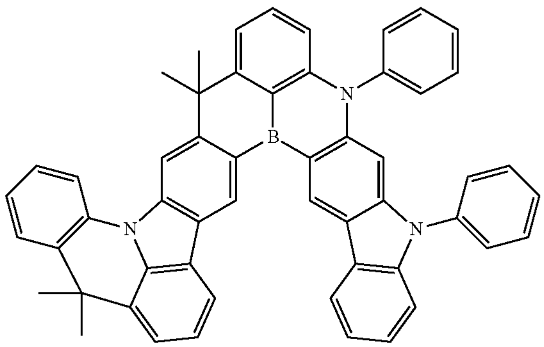
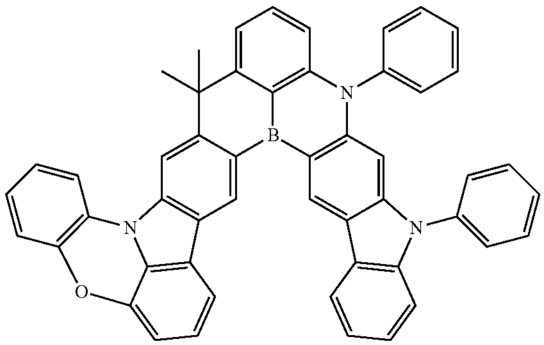
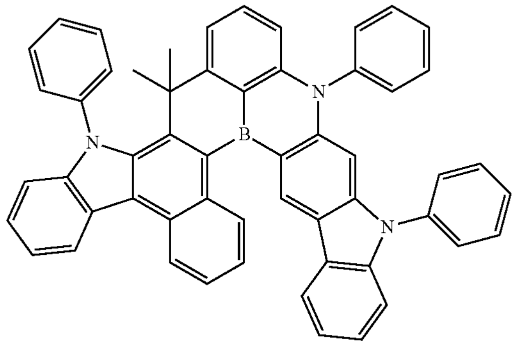
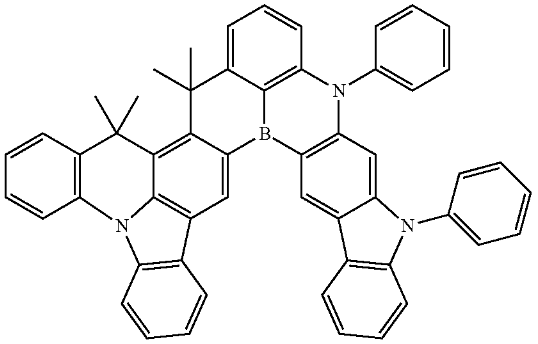
-continued
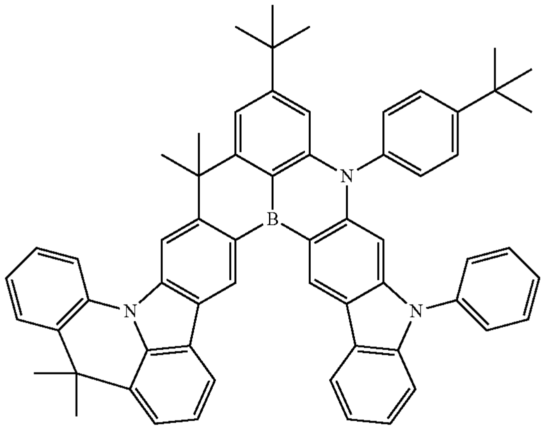
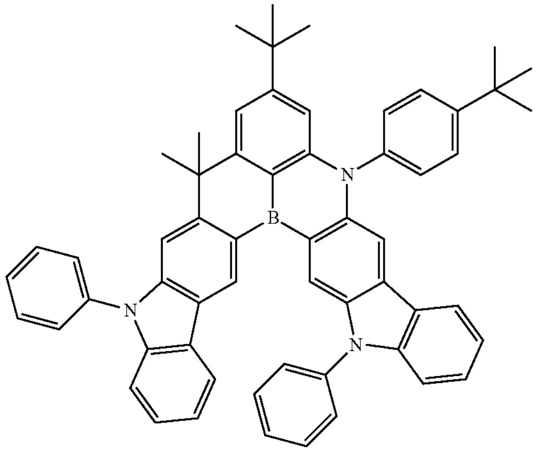
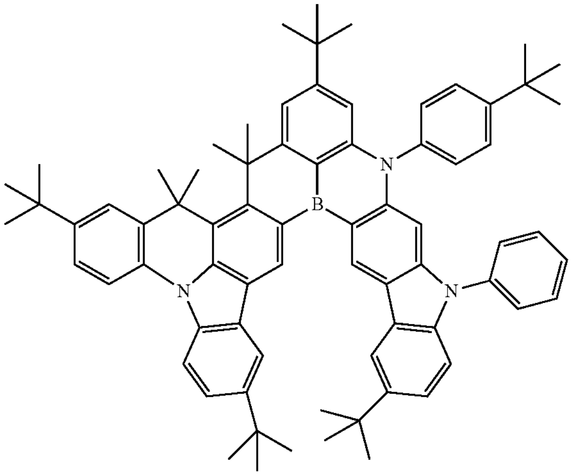
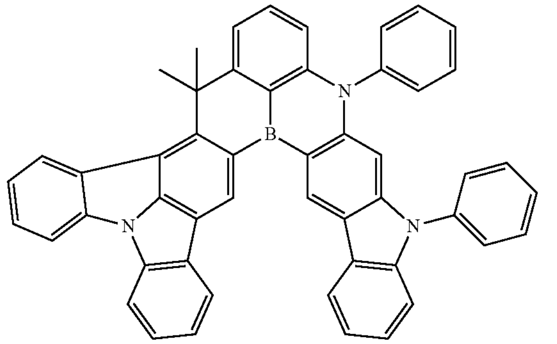

-continued
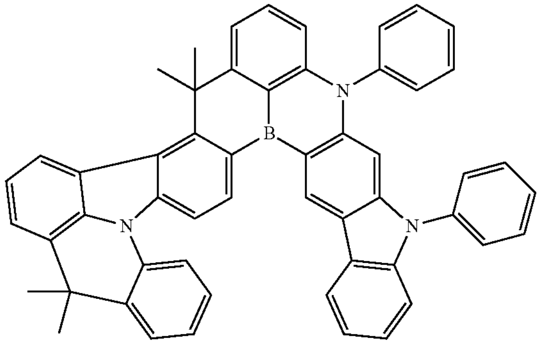
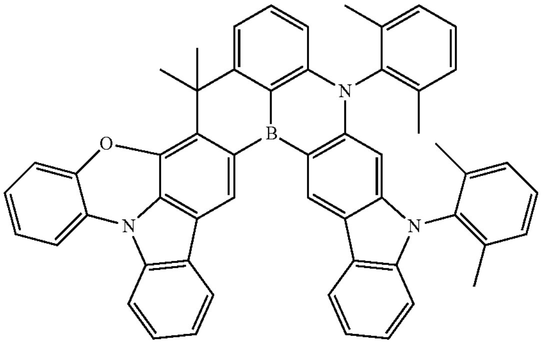
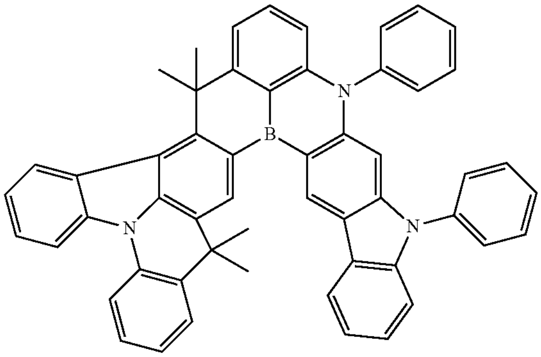
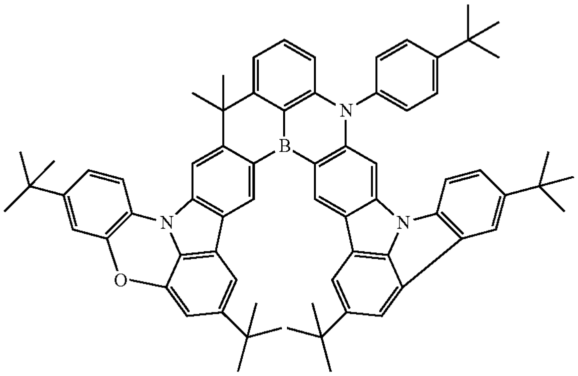
-continued
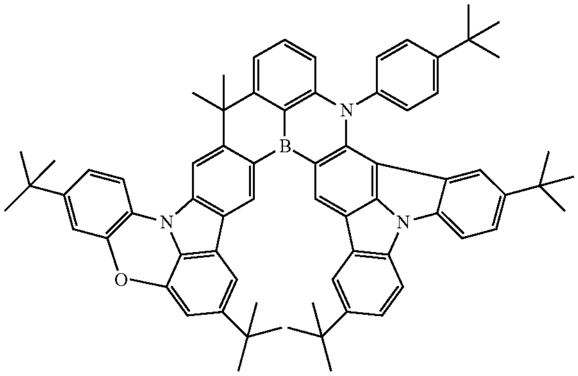
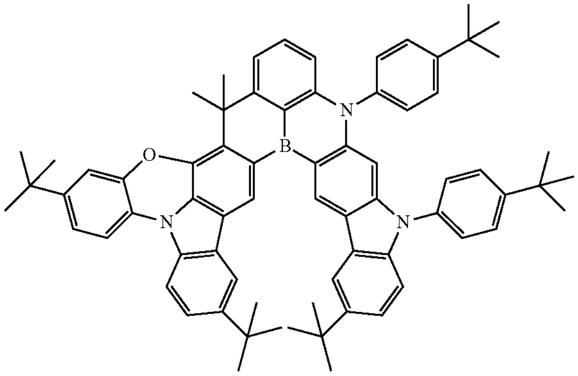
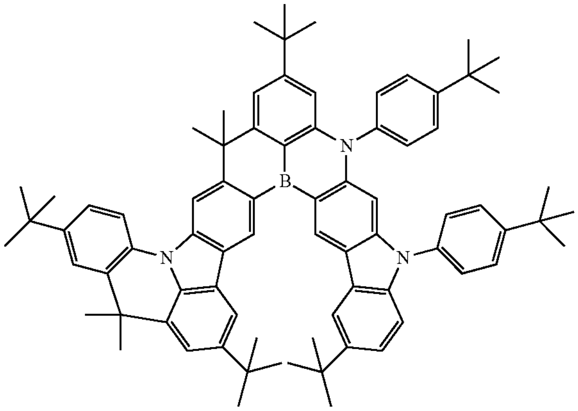
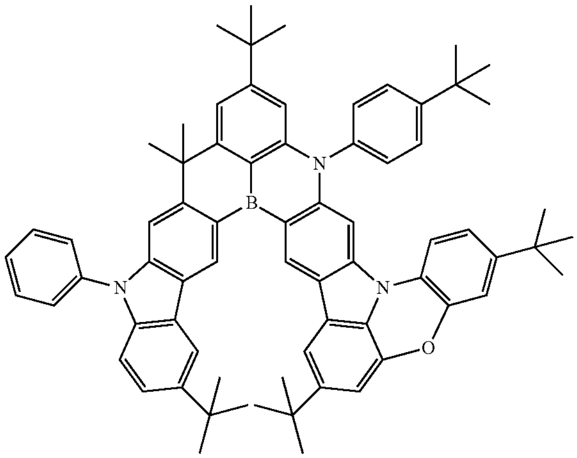

-continued
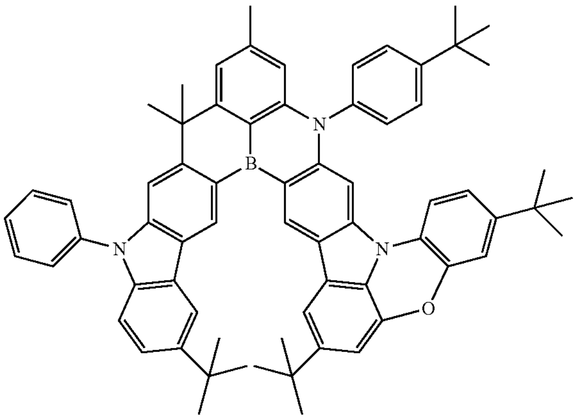
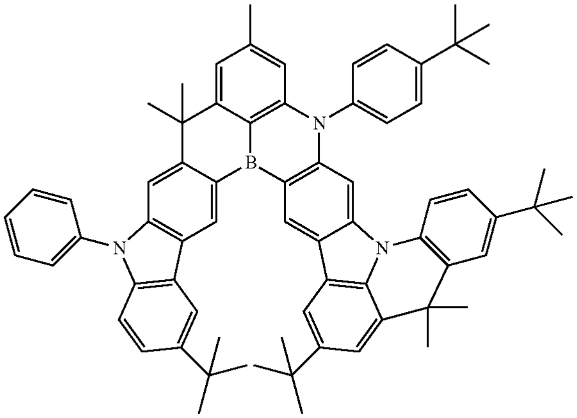
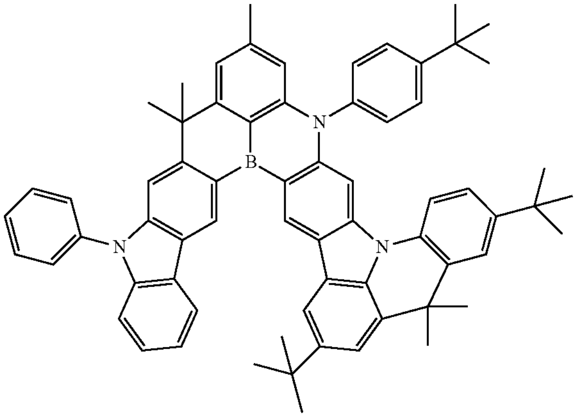
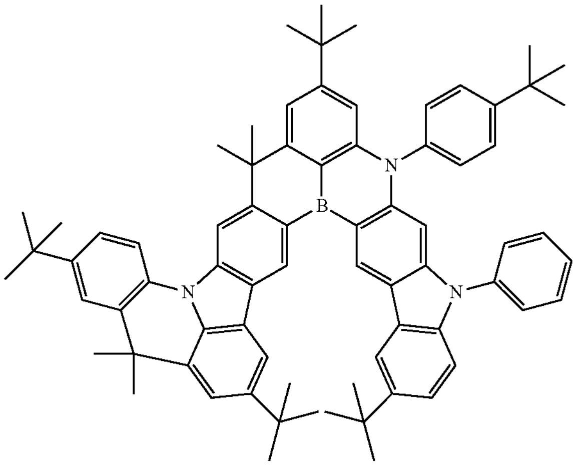
-continued
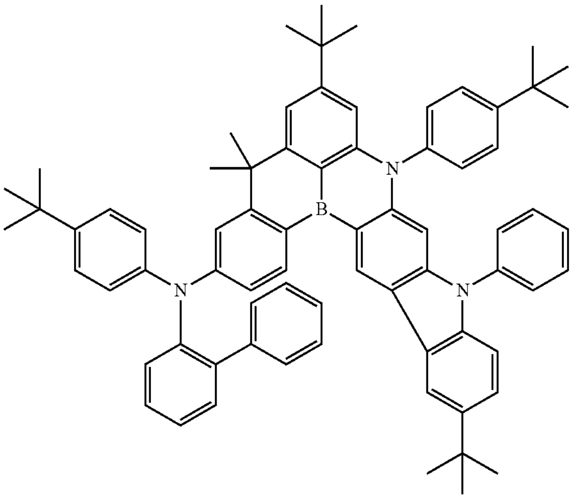
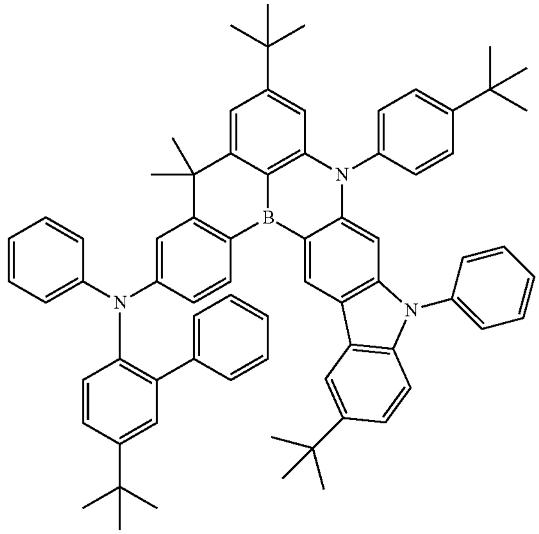
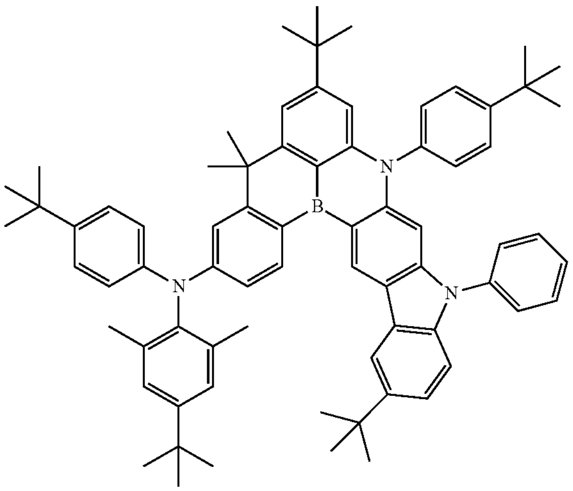

-continued
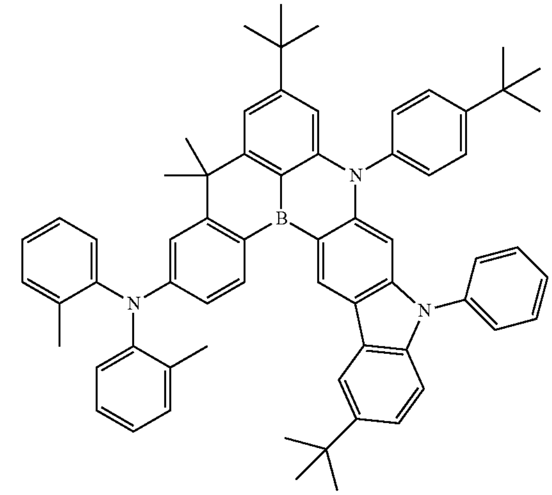
-continued
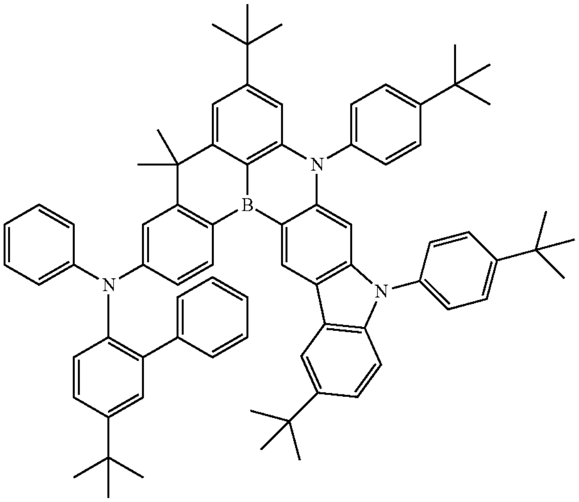
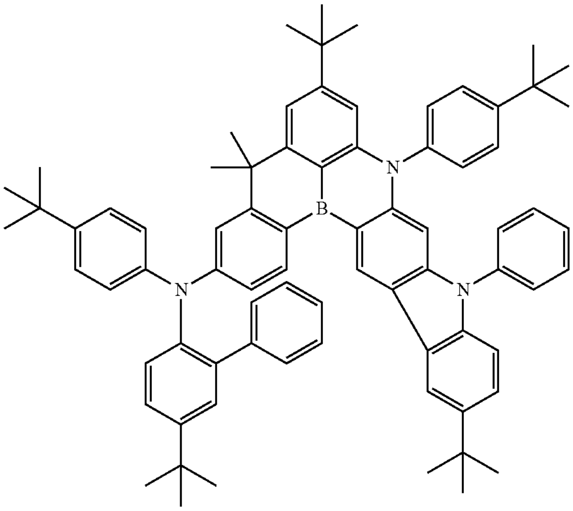
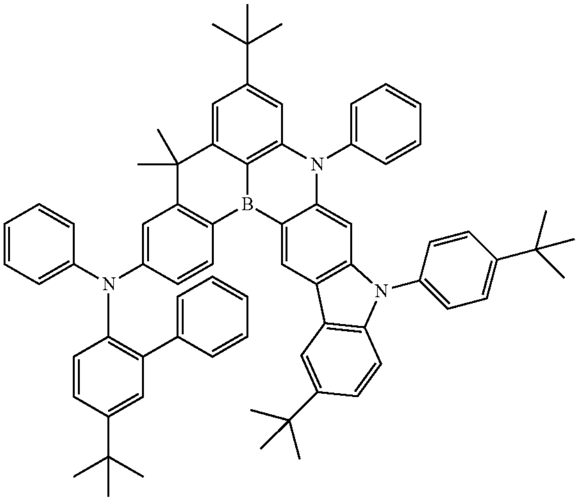
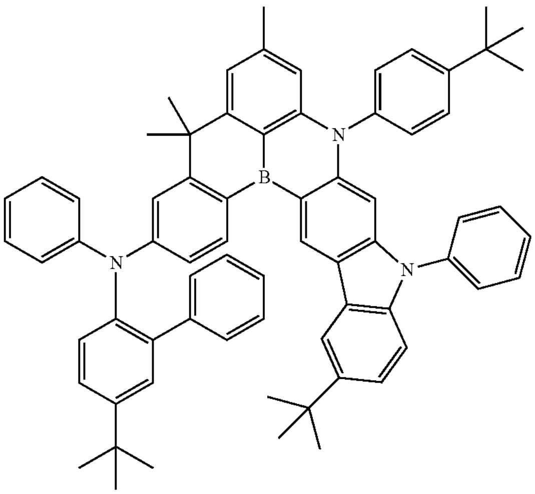
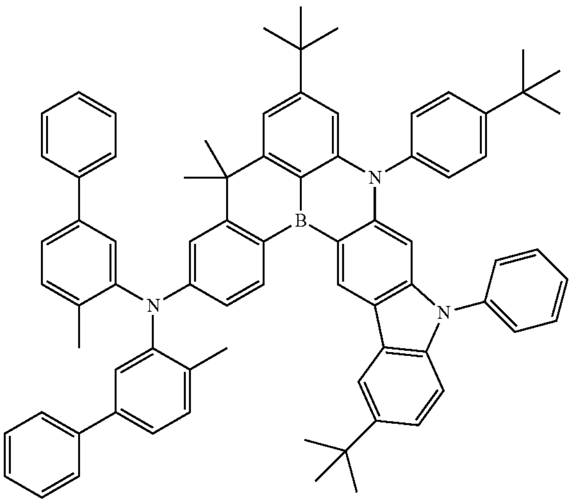

-continued
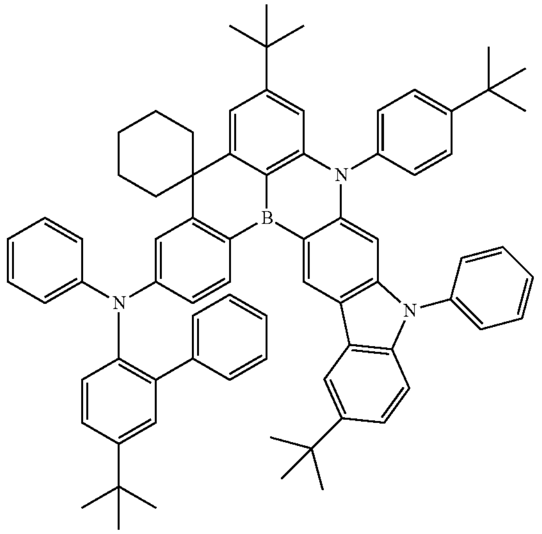
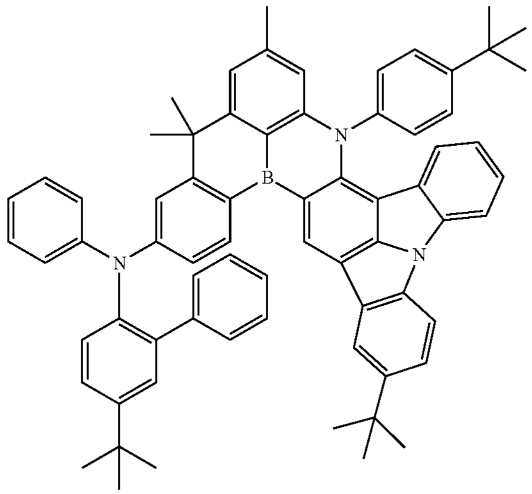
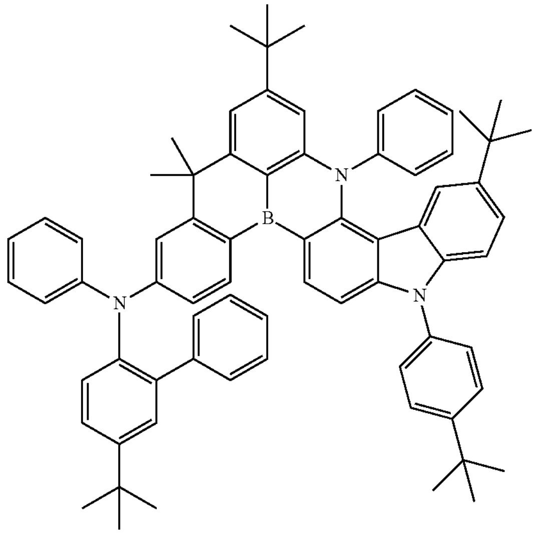
-continued
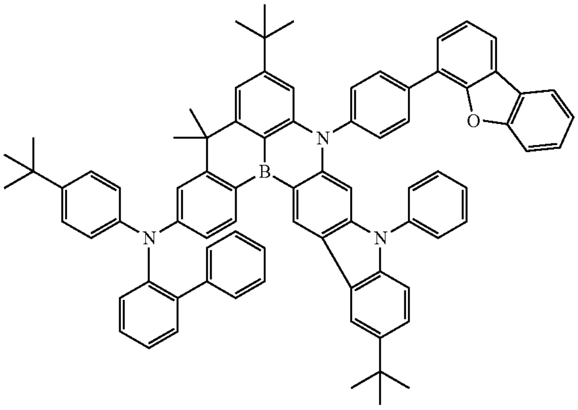
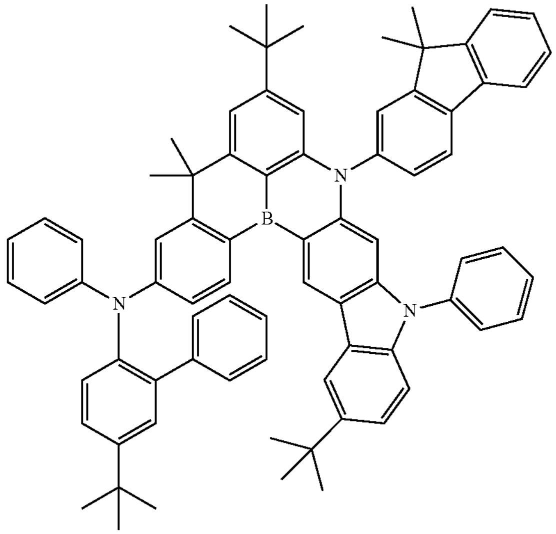
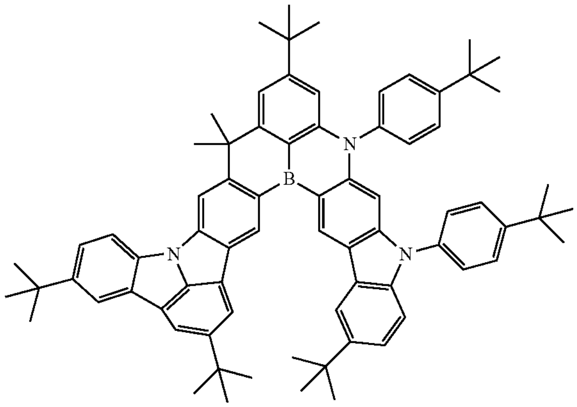

-continued
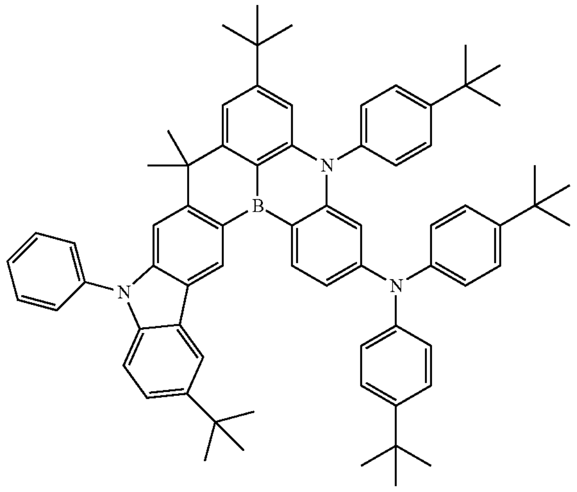
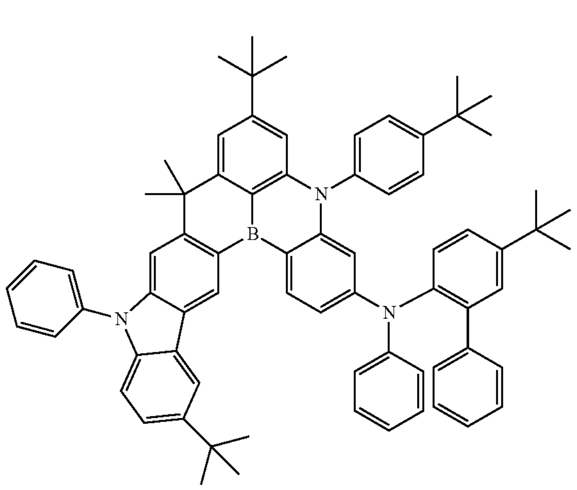
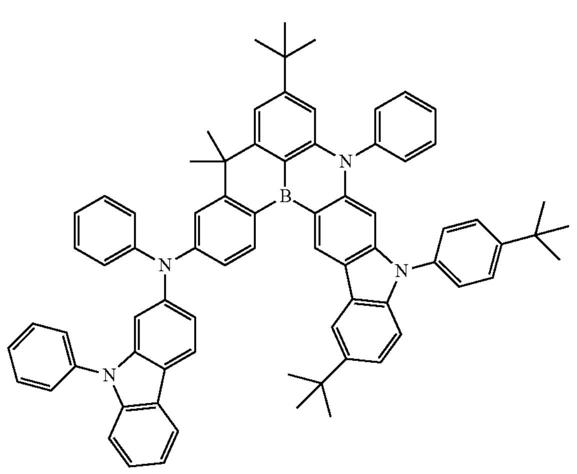
-continued
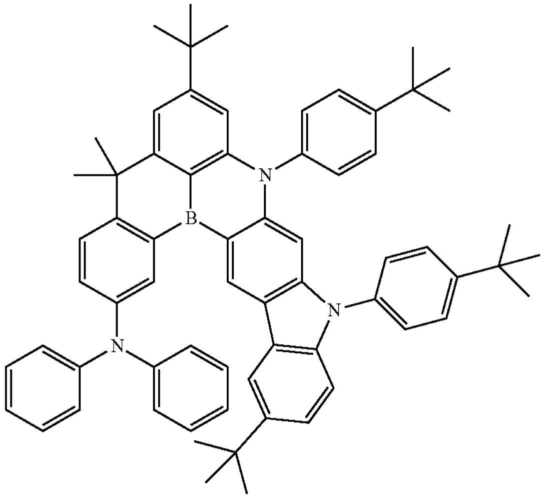
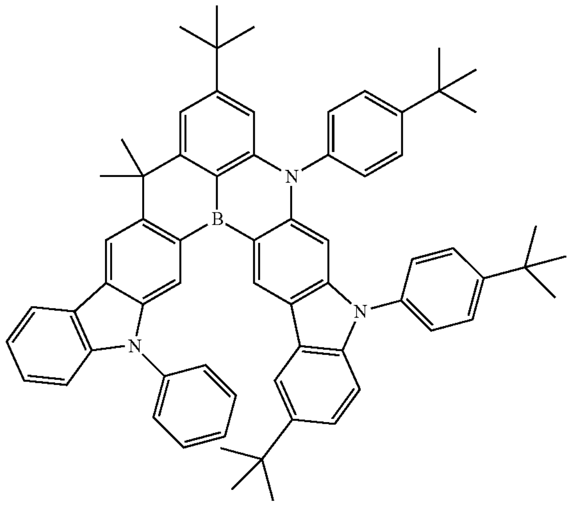
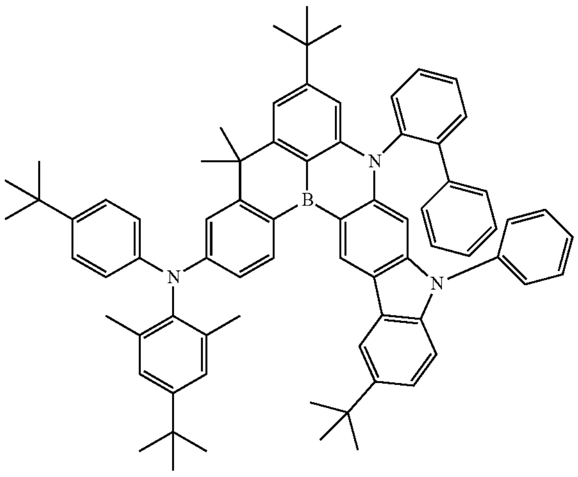

-continued

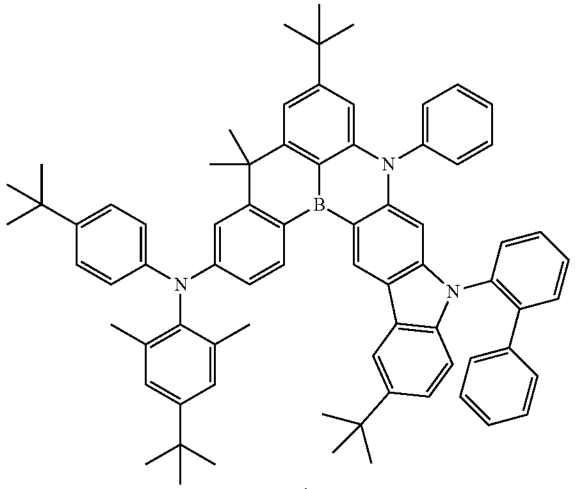

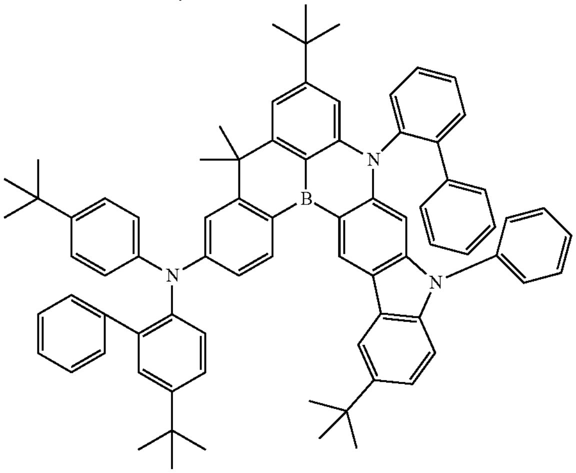

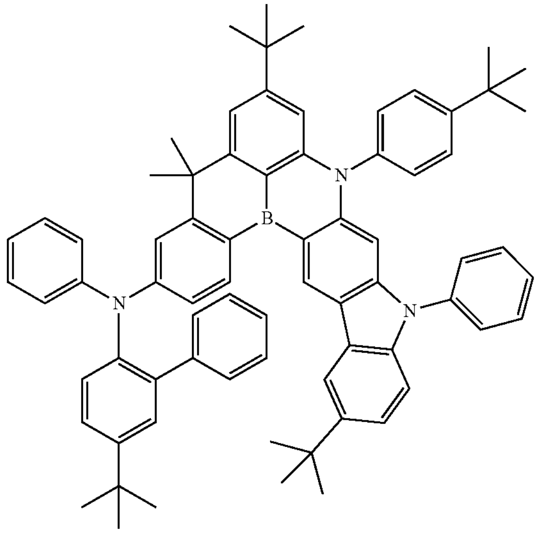

Second Exemplary Embodiment

Organic-Electroluminescence-Device Material

An organic-electroluminescence-device material according to a second exemplary embodiment contains the compound according to the first exemplary embodiment. As one example, the organic-electroluminescence-device material contains only the compound according to the first exemplary embodiment. As another example, the organic-electroluminescence-device material contains the compound according to the first exemplary embodiment and another compound(s) different from the compound according to the first exemplary embodiment.

In the organic-electroluminescence-device material according to the second exemplary embodiment, the compound according to the first exemplary embodiment is preferably a dopant material. In this arrangement, the organic-electroluminescence-device material may contain the compound according to the first exemplary embodiment as the dopant material and another compound(s) such as a host material.

The compound according to the first exemplary embodiment is useful for the organic-electroluminescence-device material and useful for a material for an emitting layer of an organic EL device, particularly, for a blue emitting material for the emitting layer.

Third Exemplary Embodiment

Organic Electroluminescence Device

An organic EL device according to a third exemplary embodiment will be described.

The organic EL device according to the exemplary embodiment includes an anode, a cathode, and at least one organic layer. The at least one organic layer includes at least one layer formed of an organic compound. Alternatively, the at least one organic layer is provided by a plurality of layers each formed of an organic compound and layered. The organic layer(s) may further contain an inorganic compound.

In the organic EL device according to the exemplary embodiment, the at least one organic layer contains the compound according to the first exemplary embodiment. Specifically, the organic EL device according to the exemplary embodiment includes the cathode, the anode, and an organic layer provided between the cathode and the anode, in which the organic layer contains the compound according to the first exemplary embodiment.

In the organic EL device according to the exemplary embodiment, it is preferable that the organic layer includes an emitting layer, in which the emitting layer contains the compound according to the first exemplary embodiment.

The organic EL device according to the exemplary embodiment includes the cathode, the anode, and at least one organic layer provided between the cathode and the anode, in which at least one of the at least one organic layer contains the compound according to the first exemplary embodiment.

The organic EL device according to the exemplary embodiment includes the cathode, the anode, and at least one emitting layer provided between the cathode and the anode, in which at least one of the at least one emitting layer contains the compound according to an exemplary embodiment of the invention.

The organic EL device according to the exemplary embodiment may be an organic EL device having a single emitting layer as the third exemplary embodiment.

An organic EL device according to an exemplary embodiment of the invention will be described with reference to FIG. 1. FIG. 1 schematically shows an example of an organic EL device according to the third exemplary embodiment.

An organic EL device 1 according to an exemplary embodiment of the invention includes a substrate 2, an anode 3, a cathode 4, and an organic layer 10 provided between the anode 3 and the cathode 4. The organic layer 10 includes a first organic layer 67, an emitting layer 5, and a second organic layer 89, which are sequentially layered on the anode 3. Each of the first organic layer 67 and the second organic layer 89 may be a single layer or includes a plurality of layers.

The first organic layer 67 may also include a hole transporting zone. The hole transporting zone may include at least one layer selected from the group consisting of a hole injecting layer, a hole transporting layer, and an electron blocking layer. The second organic layer 89 may also include an electron transporting zone. The electron transporting zone may include at least one layer selected from the group consisting of an electron injecting layer, an electron transporting layer, and a hole blocking layer. For instance, the first organic layer 67 may include the hole injecting layer and the hole transporting layer, which are sequentially layered on the anode 3. The second organic layer 89 may include the electron transporting layer and the electron injecting layer, which are sequentially layered on the anode 3. The organic EL device 1 may include the hole injecting layer, the hole transporting layer, the emitting layer 5, the electron transporting layer, and the electron injecting layer, which are sequentially layered on the anode 3. The invention is not limited to the organic EL device having the structure shown in FIG. 1.

The compound according to the first exemplary embodiment is contained in the first organic layer 67, the emitting layer 5, or the second organic layer 89. In an exemplary embodiment, the compound according to the first exemplary embodiment is contained in the emitting layer 5. The compound according to the first exemplary embodiment can serve as a dopant material in the emitting layer 5.

In the organic EL device according to the third exemplary embodiment, a compound according to an exemplary embodiment of the invention and a compound represented by a formula (H10) described later can be used in combination in the emitting layer of the organic EL device.

A compound represented by the formula (H10) will be described below.

Compound Represented by Formula (H10)

A compound represented by the formula (H10) will be described.

(H10)

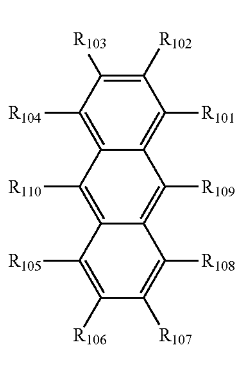

In the formula (H10):

at least one combination of adjacent two or more of $R_{101}$ to $R_{110}$ are mutually bonded to form a substituted or unsubstituted monocyclic ring, mutually bonded to form a substituted or unsubstituted fused ring, or not mutually bonded;

$R_{101}$ to $R_{110}$ neither forming the substituted or unsubstituted monocyclic ring nor forming the substituted or unsubstituted fused ring are each independently a hydrogen atom, a substituent R, or a group represented by a formula (H11) below;

at least one of $R_{101}$ to $R_{110}$ neither forming the substituted or unsubstituted monocyclic ring nor forming the substituted or unsubstituted fused ring is a group represented by the formula (H11) below; and when two or more groups each represented by a formula (H11) below are present, the two or more groups each represented by the formula (H11) are mutually the same or different.

$$-L_{101}-Ar_{101} \quad (H11)$$

In the formula (H11):

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

the substituent R is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a group represented by $—N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms;

when two or more substituents R are present, the two or more substituents R are mutually the same or different;

$R_{901}$ to $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different; and when a plurality of $R_{907}$ are present, the plurality of $R_{907}$ are mutually the same or different.

A compound represented by the formula (H10) may have a deuterium atom as a hydrogen atom.

In an exemplary embodiment, at least one of $Ar_{101}$ in the formula (H10) is a substituted or unsubstituted aryl group having 6 to 50 ring carbon atoms.

In an exemplary embodiment, at least one of $Ar_{101}$ in the formula (H10) is a substituted or unsubstituted monovalent heterocyclic group having 5 to 50 ring atoms.

In an exemplary embodiment, all of $Ar_{101}$ in the formula (H10) are each a substituted or unsubstituted aryl group having 6 to 50 ring carbon atoms. A plurality of $Ar_{101}$ may be mutually the same or different.

In an exemplary embodiment, one of $Ar_{101}$ in the formula (H10) is a substituted or unsubstituted heterocyclic group having 5 to 50 ring atoms and the rest of $Ar_{101}$ is a substituted or unsubstituted aryl group having 6 to 50 ring carbon atoms. A plurality of $Ar_{101}$ may be mutually the same or different.

In an exemplary embodiment, at least one of $L_{101}$ in the formula (H10) is a single bond.

In an exemplary embodiment, all of $L_{101}$ in the formula (H10) are each a single bond.

In an exemplary embodiment, at least one of $L_{101}$ in the formula (H10) is a substituted or unsubstituted arylene group having 6 to 50 ring carbon atoms.

In an exemplary embodiment, at least one of $L_{101}$ in the formula (H10) is a substituted or unsubstituted phenylene group or a substituted or unsubstituted naphthylene group.

In an exemplary embodiment, a group represented by $-L_{101}-Ar_{101}$ in the formula (H10) is selected from the group consisting of a substituted or unsubstituted phenyl group, a substituted or unsubstituted naphthyl group, a substituted or unsubstituted biphenyl group, a substituted or unsubstituted phenanthrenyl group, a substituted or unsubstituted benzophenanthrenyl group, a substituted or unsubstituted fluorenyl group, a substituted or unsubstituted benzofluorenyl group, a substituted or unsubstituted dibenzofuranyl group, a substituted or unsubstituted naphthobenzofuranyl group, a substituted or unsubstituted dibenzothiophenyl group, and a substituted or unsubstituted carbazolyl group.

In an exemplary embodiment, the substituent R in the formula (H10) is each independently a substituted or unsubstituted alkyl group having 1 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, or a substituted or unsubstituted aryl group having 6 to 50 ring carbon atoms; and $R_{901}$ to $R_{907}$ represent the same as $R_{901}$ to $R_{907}$ defined in the formula (H10).

In an exemplary embodiment, "a substituted or unsubstituted" substituent in the formula (H10) is each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, a substituted or unsubstituted aryl group having 6 to 50 ring carbon atoms, or a substituted or unsubstituted heterocyclic group having 5 to 50 ring atoms; and $R_{901}$ to $R_{907}$ represent the same as $R_{901}$ to $R_{907}$ defined in the formula (H10).

In an exemplary embodiment, "a substituted or unsubstituted" substituent in the formula (H10) is each independently a substituted or unsubstituted alkyl group having 1 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a group represented by $-N(R_{906})(R_{907})$, a halogen atom, a cyano group, a nitro group, or a substituted or unsubstituted aryl group having 6 to 50 ring carbon atoms; and $R_{901}$ to $R_{907}$ represent the same as $R_{901}$ to $R_{907}$ defined in the formula (H10).

In an exemplary embodiment, a "substituted or unsubstituted" substituent in the formula (H10) is selected from the group consisting of an alkyl group having 1 to 18 carbon atoms, an aryl group having 6 to 18 ring carbon atoms, and a heterocyclic group having 5 to 18 ring atoms.

In an exemplary embodiment, a "substituted or unsubstituted" substituent in the formula (H10) is an alkyl group having 1 to 5 carbon atoms.

In an exemplary embodiment, a compound represented by the formula (H10) is a compound represented by a formula (H20) below.

(H20)

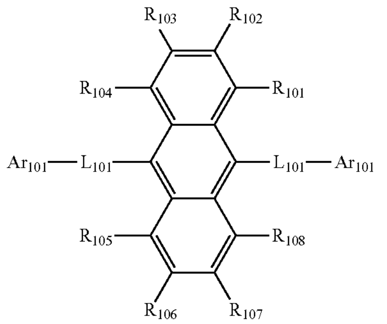

In the formula (H20), $R_{101}$ to $R_{108}$, $L_{101}$ and $Ar_{101}$ are the same as defined in the formula (H10).

A compound represented by the formula (H20) may have a deuterium atom as a hydrogen atom.

Specifically, in an exemplary embodiment, a compound represented by the formula (H10) or the formula (H20) has at least two groups represented by the formula (H11).

In an exemplary embodiment, a compound represented by the formula (H10) or the formula (H20) has two or three groups represented by the formula (H11).

In an exemplary embodiment, none of combinations of adjacent two or more of $R_{101}$ to $R_{110}$ in the formula (H10) and the formula (H20) are not mutually bonded.

In an exemplary embodiment, all of $R_{101}$ to $R_{110}$ in the formula (H10) and the formula (H20) are each a hydrogen atom.

In an exemplary embodiment, a compound represented by the formula (H20) is a compound represented by a formula (H30) below.

(H30)

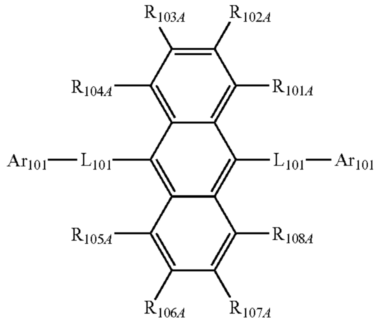

In the formula (H30):

$L_{101}$ and $Ar_{101}$ are the same as defined in the formula (H10);

none of combinations of adjacent two or more of $R_{101A}$ to $R_{108A}$ are mutually bonded;

$R_{101A}$ to $R_{108A}$ are each independently a hydrogen atom or a substituent R;

and the substituent R is the same as defined in the formula (H10).

In other words, a compound represented by the formula (H30) is a compound having two groups represented by the formula (H11).

A compound represented by the formula (H30) substantially has only a protium atom as a hydrogen atom.

The phrase "substantially has only a protium atom" means that in a compound (protium isotope) having only a protium atom as a hydrogen atom and a compound (deuterium isotope) having a deuterium atom as a hydrogen atom, the compounds having the same structure, a ratio of the protium isotope to the total of the compounds is 90 mol % or more, 95 mol % or more, or 99 mol % or more.

In an exemplary embodiment, a compound represented by the formula (H30) is a compound represented by a formula (H31) below.

(H31)

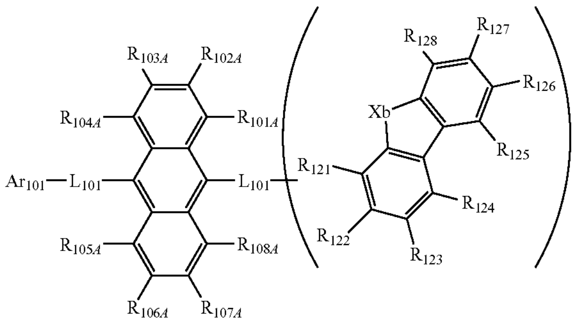

In the formula (H31):

$L_{101}$ and $Ar_{101}$ are the same as defined in the formula (H10);

$R_{101A}$ to $R_{108A}$ represent the same as $R_{101A}$ to $R_{108A}$ defined in the formula (H30);

$X_b$ is an oxygen atom, a sulfur atom, $N(R_{331})$, or $C(R_{332})(R_{333})$;

one of $R_{121}$ to $R_{128}$ and $R_{331}$ to $R_{333}$ is a single bond bonded to $L_{101}$;

at least one combination of adjacent two or more of $R_{121}$ to $R_{128}$ that are not a single bond bonded to $L_{101}$ are mutually bonded to form a substituted or unsubstituted monocyclic ring, mutually bonded to form a substituted or unsubstituted fused ring, or not mutually bonded;

$R_{121}$ to $R_{128}$ not being a single bond bonded to $L_{101}$ and neither forming the substituted or unsubstituted monocyclic ring nor forming the substituted or unsubstituted fused ring are each independently a hydrogen atom, or a substituent R;

the substituent R represents the same as defined in the formula (H10);

$R_{331}$ to $R_{333}$ not being a single bond bonded to $L_{101}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{331}$ are present, the plurality of $R_{331}$ are mutually the same or different;

when a plurality of $R_{3321}$ are present, the plurality of $R_{332}$ are mutually the same or different; and when a plurality of $R_{333}$ are present, the plurality of $R_{333}$ are mutually the same or different.

In an exemplary embodiment, a compound represented by the formula (H31) is a compound represented by a formula (H32) below.

(H32)

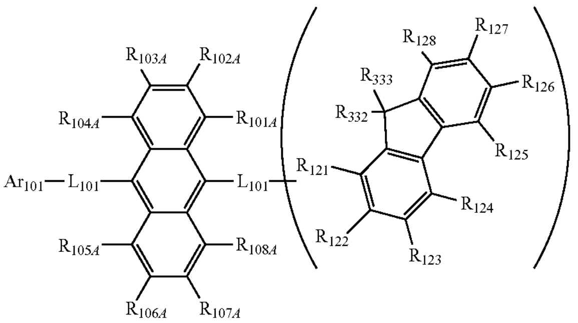

In the formula (H32), $R_{101A}$ to $R_{108A}$, $L_{101}$, $Ar_{101}$, $R_{121}$ to $R_{128}$, $R_{332}$ and $R_{333}$ are the same as defined in the formula (H31).

In an exemplary embodiment, a compound represented by the formula (H31) is a compound represented by a formula (H33) below.

(H33)

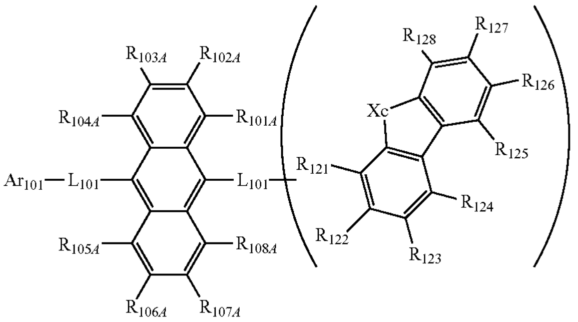

In the formula (H33):

$R_{101A}$ to $R_{108A}$, $L_{101}$, $Ar_{101}$, and $R_{121}$ to $R_{128}$ are the same as defined in the formula (H31);

$X_c$ is an oxygen atom, a sulfur atom, or $NR_{331}$; and $R_{331}$ is the same as defined in the formula (H31).

In an exemplary embodiment, a compound represented by the formula (H31) is a compound represented by a formula (H34) below.

(H34)

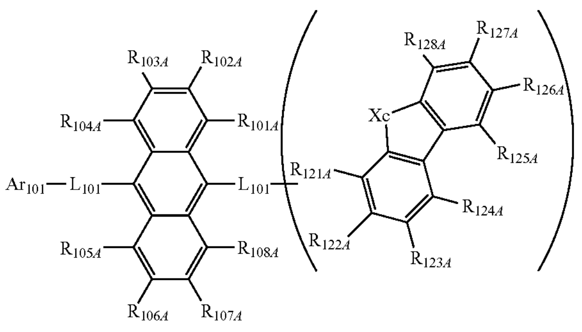

In the formula (H34):

$R_{101A}$ to $R_{108A}$, $L_{101}$ and $Ar_{101}$ are the same as defined in the formula (H31);

$X_c$ is an oxygen atom, a sulfur atom, or $NR_{331}$;

$R_{331}$ represents the same as $R_{331}$ defined in the formula (H31);

one of $R_{121A}$ to $R_{128A}$ is a single bond bonded to $L_{101}$;

none of combinations of adjacent two or more of $R_{121A}$ to $R_{128A}$ not being a single bond to bonded to $L_{101}$ are mutually bonded;

$R_{121A}$ to $R_{128A}$ not being a single bond to $L_{101}$ are each independently a hydrogen atom, or a substituent R; and the substituent R is the same as defined in the formula (H10).

In an exemplary embodiment, a compound represented by the formula (H31) is a compound represented by a formula (H35) below.

(H35)

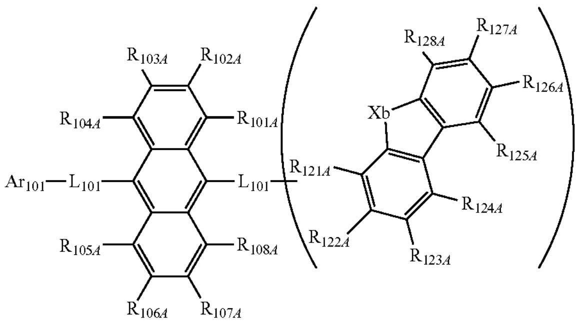

In the formula (H35):

$R_{101A}$ to $R_{108A}$, $L_{101}$, $Ar_{101}$ and $X_b$ are the same as defined in the formula (H31);

none of combinations of adjacent two or more of $R_{121A}$ to $R_{124A}$ are mutually bonded; and one combination of a combination of $R_{125A}$ and $R_{126A}$, a combination of $R_{126A}$ and $R_{127A}$, and a combination of $R_{127A}$ and $R_{128A}$ are mutually bonded to form a ring represented by a formula (H35a) or a formula (H35b) below.

(H35a)

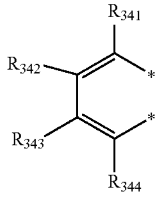

(H35b)

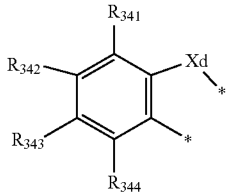

In the formulae (H35a) and (H35b):

two * are respectively bonded to one combination of a combination of $R_{125A}$ and $R_{126A}$, a combination of $R_{126A}$ and $R_{127A}$, and a combination of $R_{127A}$ and $R_{128A}$;

$R_{341}$ to $R_{344}$ are each independently a hydrogen atom, or a substituent R;

the substituent R represents the same as defined in the formula (H10); and $X_d$ is an oxygen atom or a sulfur atom;

one of $R_{125A}$ to $R_{128A}$ not forming a ring represented by the formula (H35a) or (H35b), $R_{341}$ to $R_{344}$, and $R_{121A}$ to $R_{124A}$ is a single bond bonded to $L_{101}$;

$R_{121A}$ to $R_{124A}$ not being a single bond to $L_{101}$, and $R_{125A}$ to $R_{128A}$ neither being a single bond to $L_{101}$ nor forming a ring represented by the formula (H35a) or (H35b) are each independently a hydrogen atom, or a substituent R; and the substituent R represent the same as defined in the formula (H10).

In an exemplary embodiment, a compound represented by the formula (H35) is a compound represented by a formula (H36) below.

(H36)

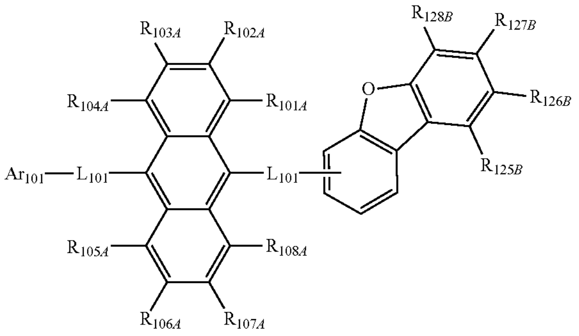

In the formula (H36), $R_{101A}$ to $R_{108A}$, $L_{101}$ and $Ar_{101}$ are the same as defined in the formula (H35), and $R_{125B}$ to $R_{128B}$ each independently represent the same as $R_{125A}$ to $R_{128A}$ in the formula (H35).

In an exemplary embodiment, a compound represented by the formula (H34) is a compound represented by a formula (H37) below.

(H37)

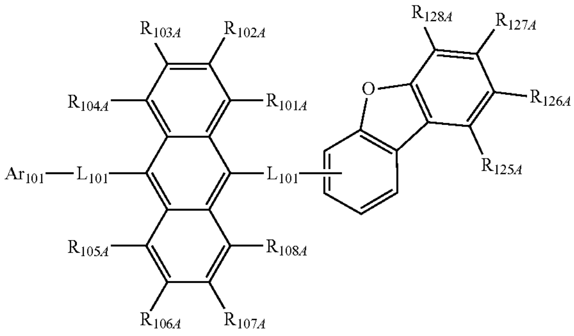

In the formula (H37), $R_{101A}$ to $R_{108A}$, $R_{125A}$ to $R_{128A}$, $L_{101}$ and $Ar_{101}$ are the same as defined in the formula (H34).

In an exemplary embodiment, $R_{101A}$ to $R_{108A}$ in the formulae (H30) to (H37) are each a hydrogen atom.

In an exemplary embodiment, a compound represented by the formula (H10) is a compound represented by a formula (H40) below.

(H40)

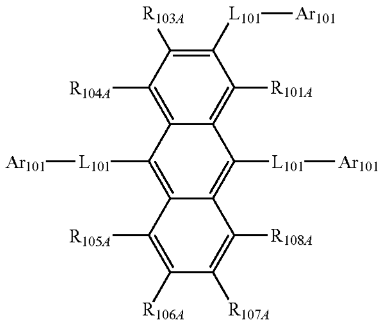

In the formula (H40):

$L_{101}$ and $Ar_{101}$ are the same as defined in the formula (H10);

at least one combination of adjacent two or more of $R_{101A}$ and $R_{103A}$ to $R_{108A}$ are mutually bonded to form a substituted or unsubstituted monocyclic ring, mutually bonded to form a substituted or unsubstituted fused ring, or not mutually bonded;

$R_{101A}$ and $R_{103A}$ to $R_{108A}$ forming neither the substituted or unsubstituted monocyclic ring nor the substituted or unsubstituted fused ring are each independently a hydrogen atom or a substituent R; and the substituent R is the same as defined in the formula (H10).

In other words, a compound represented by the formula (H40) is a compound having three groups represented by the formula (H11). Moreover, a compound represented by the formula (H40) substantially has only a protium atom as a hydrogen atom.

In an exemplary embodiment, a compound represented by the formula (H40) is a compound represented by a formula (H41) below.

(H41)

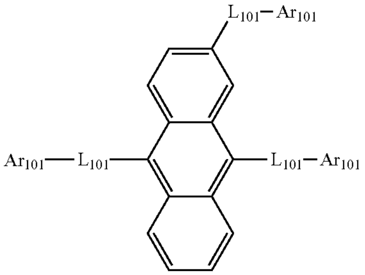

In the formula (H41), $L_{101}$ and $Ar_{101}$ are the same as defined in the formula (H40).

In an exemplary embodiment, a compound represented by the formula (H40) is a compound represented by one of formulae (H42-1) to (H42-3) below.

(H42-1)

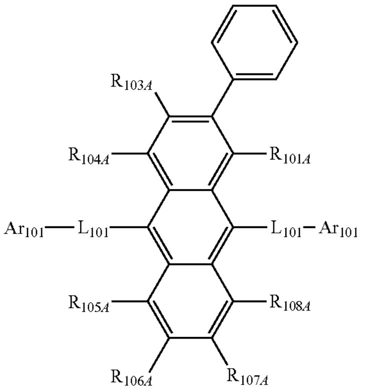

(H42-2)

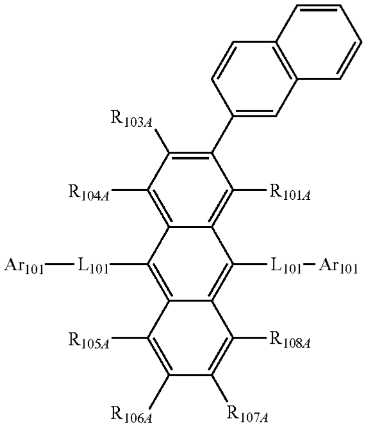

-continued (H42-3)

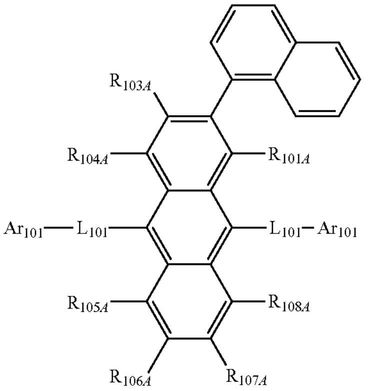

In the formulae (H42-1) to (H42-3), $R_{101A}$ to $R_{108A}$, $L_{101}$ and $Ar_{101}$ are the same as defined in the formula (H40).

In an exemplary embodiment, each of the compounds represented by the formulae (H42-1) to (H42-3) is a compound represented by one of formulae (H43-1) to (H43-3) below.

(H43-1)

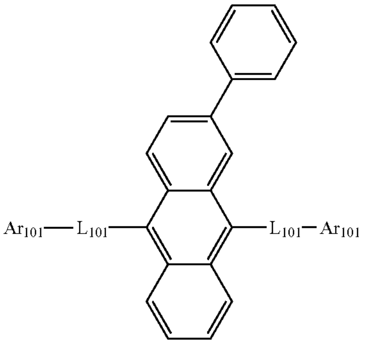

(H43-2)

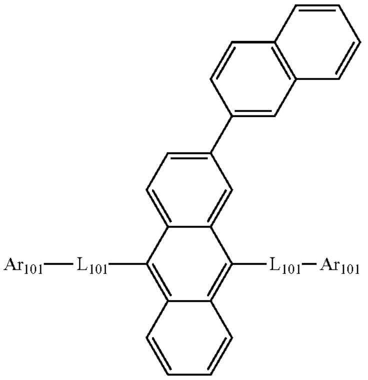

-continued (H43-3)

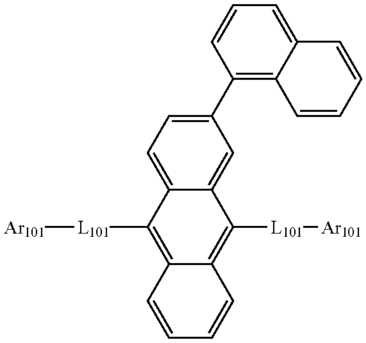

In the formulae (H43-1) to (H43-3), $L_{101}$ and $Ar_{101}$ are the same as defined in the formula (H40).

In an exemplary embodiment, a group represented by $-L_{101}-Ar_{101}$ in the formulae (H40), (H41), (H42-1) to (H42-3), and (H43-1) to (H43-3) is selected from the group consisting of a substituted or unsubstituted phenyl group, a substituted or unsubstituted naphthyl group, a substituted or unsubstituted biphenyl group, a substituted or unsubstituted phenanthrenyl group, a substituted or unsubstituted benzophenanthrenyl group, a substituted or unsubstituted fluorenyl group, a substituted or unsubstituted benzofluorenyl group, a substituted or unsubstituted dibenzofuranyl group, a substituted or unsubstituted naphthobenzofuranyl group, a substituted or unsubstituted dibenzothiophenyl group, and a substituted or unsubstituted carbazolyl group.

In an exemplary embodiment, a compound represented by the formula (H10) or (H20) includes a compound in which at least one of hydrogen atoms is a deuterium atom.

In an exemplary embodiment, in the formula (H20), at least one of hydrogen atoms as $R_{101}$ to $R_{108}$, hydrogen atoms contained in $R_{101}$ to $R_{108}$ being the substituent R, a hydrogen atom contained in $L_{101}$, a hydrogen atom contained in a substituent for $L_{101}$, a hydrogen atom contained in $Ar_{101}$, or a hydrogen atom contained in a substituent for $Ar_{101}$ is a deuterium atom.

The compounds represented by the formulae (H30) to (H37) each include a compound in which at least one of hydrogen atoms is a deuterium atom.

In an exemplary embodiment, at least one of hydrogen atoms bonded to carbon atoms forming an anthracene skeleton in the compounds represented by the formulae (H30) to (H37) is a deuterium atom.

In an exemplary embodiment, a compound represented by the formula (H30) is a compound represented by a formula (H30D) below.

(H30D)

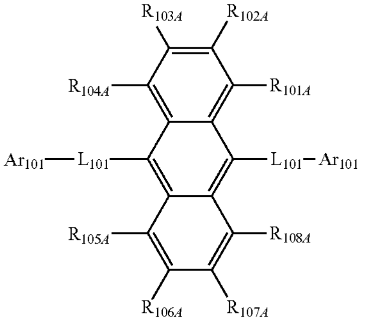

In the formula (H30D), $R_{101A}$ to $R_{108A}$, $L_{101}$ and $Ar_{101}$ are the same as defined in the formula (H30).

At least one of hydrogen atoms as $R_{101A}$ to $R_{108A}$, hydrogen atoms contained in $R_{101A}$ to $R_{108A}$ being the substituent R, a hydrogen atom contained in $L_{101}$, a hydrogen atom contained in a substituent for $L_{101}$, a hydrogen atom contained in $Ar_{101}$, or a hydrogen atom contained in a substituent for $Ar_{101}$ is a deuterium atom.

In other words, a compound represented by the formula (H30D) is a compound represented by the formula (H30) in which at least one of hydrogen atoms is a deuterium atom.

In an exemplary embodiment, at least one of $R_{101A}$ to $R_{108A}$ that are hydrogen atoms in the formula (H30D) is a deuterium atom.

In an exemplary embodiment, a compound represented by the formula (H30D) is a compound represented by a formula (H31D) below.

(H31D)

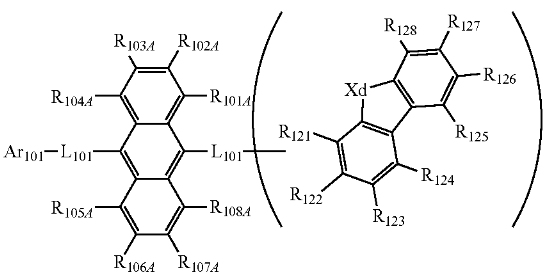

In the formula (H31D):

$R_{101A}$ to $R_{108A}$, $L_{101}$ and $Ar_{101}$ are the same as defined in the formula (H30D);

$X_d$ is an oxygen atom or a sulfur atom;

one of $R_{121}$ to $R_{128}$ is a single bond bonded to $L_{101}$;

at least one combination of adjacent two or more of $R_{121}$ to $R_{128}$ that are not a single bond bonded to $L_{101}$ are mutually bonded to form a substituted or unsubstituted monocyclic ring, mutually bonded to form a substituted or unsubstituted fused ring, or not mutually bonded;

$R_{121}$ to $R_{128}$ not being a single bond bonded to $L_{101}$ and neither forming the substituted or unsubstituted monocyclic ring nor forming the substituted or unsubstituted fused ring are each independently a hydrogen atom, or a substituent R;

the substituent R represent the same as defined in the formula (H10); and at least one of hydrogen atoms as $R_{101A}$ to $R_{108A}$, hydrogen atoms contained in $R_{101A}$ to $R_{108A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$ hydrogen atoms as $R_{121}$ to $R_{128}$, or hydrogen atoms contained in $R_{121}$ to $R_{128}$ being the substituent R is a deuterium atom.

In an exemplary embodiment, a compound represented by the formula (H31D) is a compound represented by a formula (H32D) below.

(H32D)

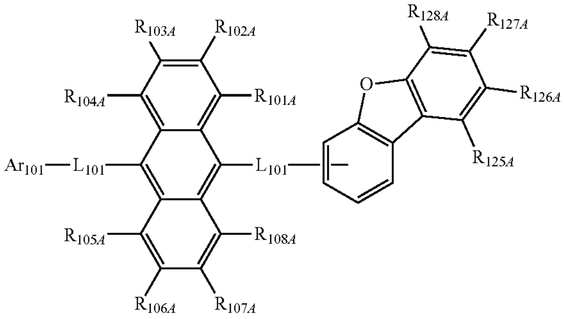

In the formula (H32D), $R_{101A}$ to $R_{108A}$, $L_{101}$ and $Ar_{101}$ are the same as defined in the formula (H31D), and $R_{125A}$ to $R_{128A}$ are each independently the same as $R_{125}$ to $R_{128}$ defined in the formula (H31D).

At least one of hydrogen atoms as $R_{101A}$ to $R_{108A}$, a hydrogen atom contained in $R_{101A}$ to $R_{108A}$ being the substituent R, hydrogen atoms as $R_{125A}$ to $R_{128A}$, a hydrogen atom contained in $R_{125A}$ to $R_{128A}$ being the substituent R, a hydrogen atom bonded to a carbon atom of a dibenzofuran skeleton in the formula (H32D), a hydrogen atom contained in $L_{101}$, a hydrogen atom contained in a substituent for $L_{101}$, a hydrogen atom contained in $Ar_{101}$, or a hydrogen atom contained in a substituent for $Ar_{101}$ is a deuterium atom.

In an exemplary embodiment, a compound represented by the formula (H32D) is a compound represented by a formula (H32D-1) or (H32D-2) below.

(H32D-1)

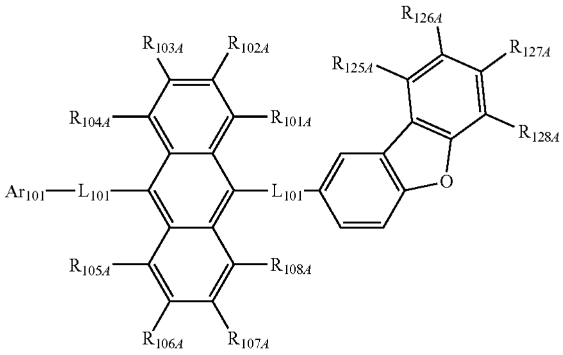

(H32D-2)

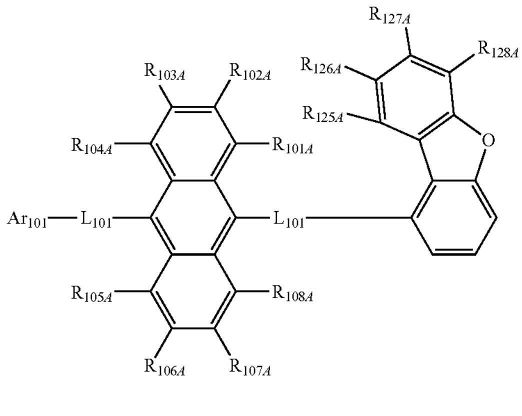

In the formulae (H32D-1) and (H32D-2), $R_{101A}$ to $R_{108A}$, $R_{125A}$ to $R_{128A}$, $L_{101}$ and $Ar_{101}$ are the same as defined in the formula (H32D).

At least one of hydrogen atoms as $R_{101A}$ to $R_{108A}$, a hydrogen atom contained in $R_{101A}$ to $R_{108A}$ being the substituent R, hydrogen atoms as $R_{125A}$ to $R_{128A}$, a hydrogen atom contained in $R_{125A}$ to $R_{128A}$ being the substituent R, a hydrogen atom bonded to a carbon atom of a dibenzofuran skeleton in the formulae (H32D-1) and (H32D-2), a hydrogen atom contained in $L_{101}$, a hydrogen atom contained in a substituent for $L_{101}$, a hydrogen atom contained in $Ar_{101}$, or a hydrogen atom contained in a substituent for $Ar_{101}$ is a deuterium atom.

In an exemplary embodiment, at least one of hydrogen atoms contained in the compounds represented by the formulae (H40), (H41), (H42-1) to (H42-3) or (H43-1) to (H43-3) is a deuterium atom.

In an exemplary embodiment, at least one of hydrogen atoms bonded to carbon atoms forming an anthracene skeleton in a compound represented by the formula (H41) is a deuterium atom.

In an exemplary embodiment, a compound represented by the formula (H40) is a compound represented by a formula (H40D) below.

(H40D)

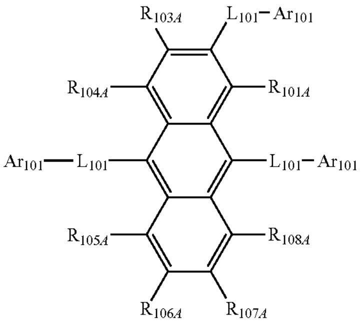

In the formula (H40D):

$L_{101}$ and $Ar_{101}$ are the same as defined in the formula (H10);

none of combinations of adjacent two or more of $R_{101A}$ and $R_{103A}$ to $R_{108A}$ are mutually bonded;

$R_{101A}$ and $R_{103A}$ to $R_{108A}$ are each independently a hydrogen atom, or a substituent R;

the substituent R represent the same as defined in the formula (H10); and at least one of hydrogen atoms as $R_{101A}$ and $R_{103A}$ to $R_{108A}$, a hydrogen atom contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, or a hydrogen atom contained in a substituent for $Ar_{101}$ is a deuterium atom.

In an exemplary embodiment, at least one of $R_{101A}$ or $R_{103A}$ to $R_{108A}$ in the formula (H40D) is a deuterium atom.

In an exemplary embodiment, a compound represented by the formula (H40D) is a compound represented by a formula (H41D) below.

(H41D)

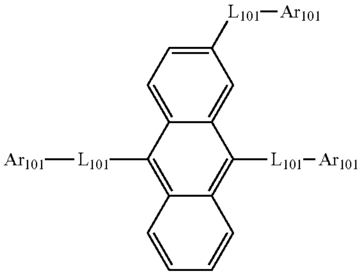

In the formula (H41D), $L_{101}$ and $Ar_{101}$ are the same as defined in the formula (H40D).

In the formula (H41D), at least one of a hydrogen atom bonded to a carbon atom of an anthracene skeleton, a hydrogen atom contained in $L_{101}$, a hydrogen atom contained in a substituent for $L_{101}$, a hydrogen atom contained in $Ar_{101}$, or a hydrogen atom contained in a substituent for $Ar_{101}$ is a deuterium atom.

In an exemplary embodiment, a compound represented by the formula (H40D) is a compound represented by one of formulae (H42D-1) to (H42D-3) below.

(H42D-1)

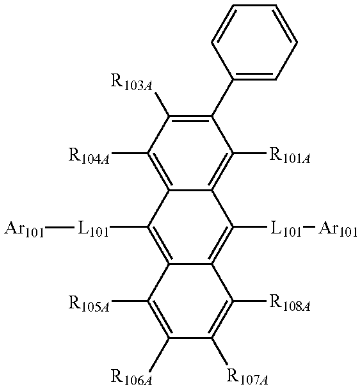

(H42D-2)

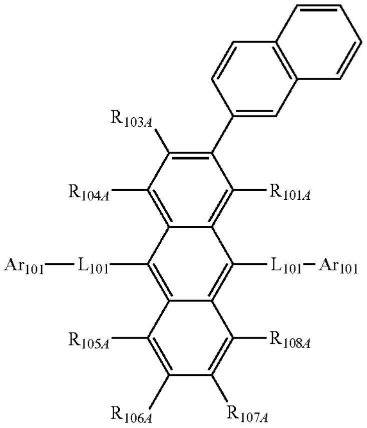

-continued (H42D-3)

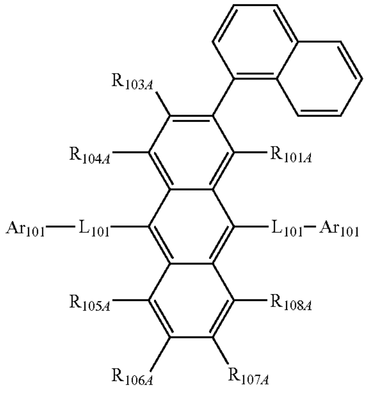

In the formulae (H42D-1) to (H42D-3), $R_{101A}$ to $R_{108A}$, $L_{101}$ and $Ar_{101}$ are the same as defined in the formula (H40D).

In the formula (H42D-1), at least one of hydrogen atoms as $R_{101A}$ and $R_{103A}$ to $R_{108A}$, a hydrogen atom contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, or a hydrogen atom bonded to a carbon atom of a phenyl group in the formula (H42D-1) is a deuterium atom.

In the formula (H42D-2), at least one of hydrogen atoms as $R_{101A}$ and $R_{103A}$ to $R_{108A}$, a hydrogen atom contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, or a hydrogen atom bonded to a carbon atom of a naphthyl group in the formula (H42D-2) is a deuterium atom.

In the formula (H42D-3), at least one of hydrogen atoms as $R_{101A}$ and $R_{103A}$ to $R_{108A}$, a hydrogen atom contained in $R_{101A}$ and $R_{103A}$ to $R_{108A}$ being the substituent R, a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, or a hydrogen atom bonded to a carbon atom of a naphthyl group in the formula (H42D-3) is a deuterium atom.

In an exemplary embodiment, each of the compounds represented by the formulae (H42D-1) to (H42D-3) is a compound represented by one of formulae (H43D-1) to (H43D-3) below.

(H43D-1)

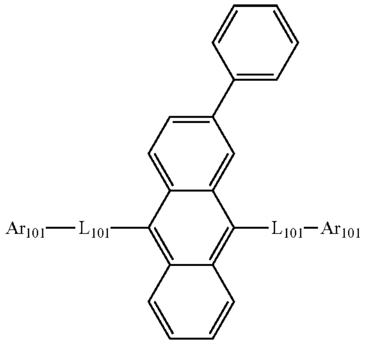

-continued (H43D-2)

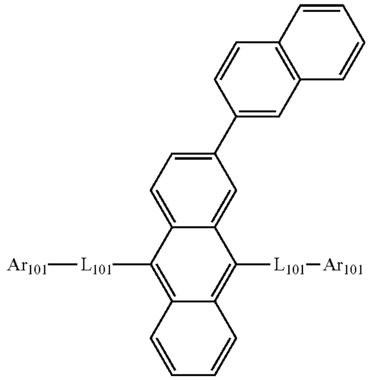

(H43D-3)

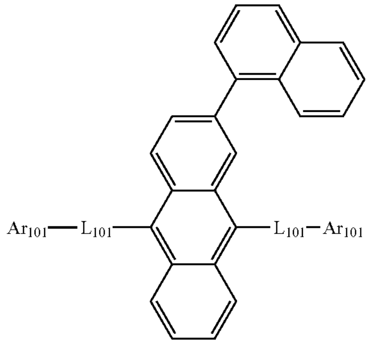

In the formulae (H43D-1) to (H43D-3), $L_{101}$ and $Ar_{101}$ are the same as defined in the formula (H40D).

At least one of a hydrogen atom bonded to a carbon atom of an anthracene skeleton in the formula (H43D-1), a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, or a hydrogen atom bonded to a carbon atom of a phenyl group in the formula (H43D-1) is a deuterium atom.

At least one of a hydrogen atom bonded to a carbon atom of an anthracene skeleton in the formula (H43D-2), a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, or a hydrogen atom bonded to a carbon atom of a naphthyl group in the formula (H43D-2) is a deuterium atom.

At least one of a hydrogen atom bonded to a carbon atom of an anthracene skeleton in the formula (H43D-3), a hydrogen atom contained in $L_{101}$, a hydrogen atom contained in a substituent for $L_{101}$, a hydrogen atom contained in $Ar_{101}$, a hydrogen atom contained in a substituent for $Ar_{101}$, or a hydrogen atom bonded to a carbon atom of a naphthyl group in the formula (H43D-3) is a deuterium atom.

In an exemplary embodiment, in a compound represented by the formula (H20), at least one $Ar_{101}$ is a monovalent group having a structure represented by a formula (H50) below.

(H50)

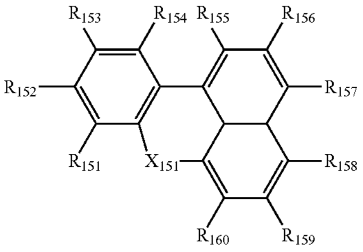

In the formula (H50):

$X_{151}$ is an oxygen atom, a sulfur atom, or $C(R_{161})(R_{162})$;

one of $R_{151}$ to $R_{160}$ is a single bond bonded to $L_{101}$;

at least one combination of adjacent two or more of $R_{151}$ to $R_{154}$ not being a single bond bonded to $L_{101}$ or adjacent two or more of $R_{155}$ to $R_{160}$ not being a single bond bonded to $L_{101}$ are mutually bonded to form a substituted or unsubstituted monocyclic ring, mutually bonded to form a substituted or unsubstituted fused ring, or not mutually bonded;

a combination of $R_{161}$ and $R_{162}$ are mutually bonded to form a substituted or unsubstituted monocyclic ring, mutually bonded to form a substituted or unsubstituted fused ring, or not mutually bonded;

$R_{161}$ and $R_{162}$ forming neither the substituted or unsubstituted monocyclic ring nor the substituted or unsubstituted fused ring, and $R_{151}$ to $R_{160}$ neither being a single bond to $L_{101}$, forming the substituted or unsubstituted saturated or unsaturated monocyclic ring, nor forming the substituted or unsubstituted fused ring are each independently a hydrogen atom or a substituent R;

the substituent R represents the same as defined in the formula (H10); and $Ar_{101}$ not being a monovalent group having a structure represented by the formula (H50) is a substituted or unsubstituted aryl group having 6 to 50 ring carbon atoms or a substituted or unsubstituted heterocyclic group having 5 to 50 ring atoms.

In the formula (H50), a position of a single bond to $L_{101}$ is not particularly limited.

In an exemplary embodiment, one of $R_{151}$ to $R_{154}$ or one of $R_{155}$ to $R_{160}$ in the formula (H50) is a single bond bonded to $L_{101}$.

In an exemplary embodiment, $Ar_{101}$ is a monovalent group represented by a formula (H50-$R_{152}$), (H50-$R_{153}$), (H50-$R_{154}$), (H50-$R_{157}$) or (H50-$R_{158}$) below.

(H50-$R_{152}$)

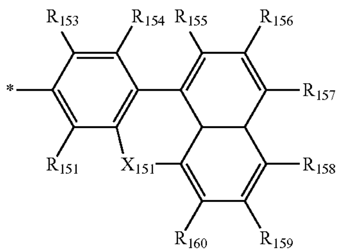

-continued (H50-$R_{153}$)

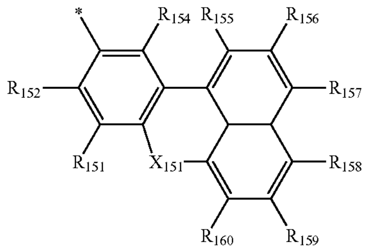

(H50-$R_{154}$)

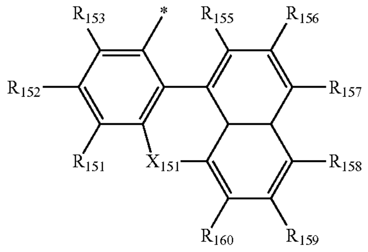

(H50-$R_{157}$)

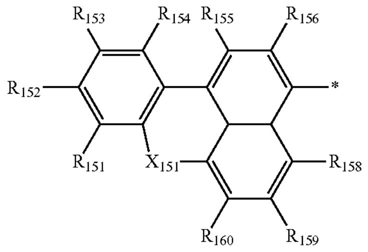

(H50-$R_{158}$)

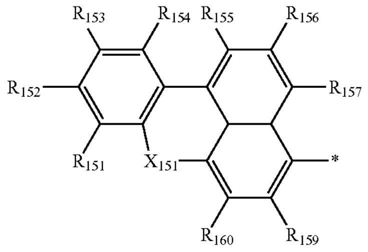

In the formulae (H50-$R_{152}$), (H50-$R_{153}$), (H50-$R_{154}$), (H50-$R_{157}$), and (H50-$R_{158}$), $X_{151}$ and $R_{151}$ to $R_{160}$ are the same as defined in the formula (H50), and

* is bonded to $L_{101}$.

Specific Examples of Compound Represented by Formula (H10)

Specific examples of a compound represented by the formula (H10) include compounds shown below. A compound represented by the formula (H10) is not limited to the specific examples. In the specific examples, D represents a deuterium atom.

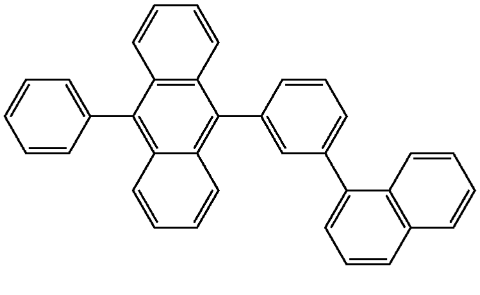

-continued
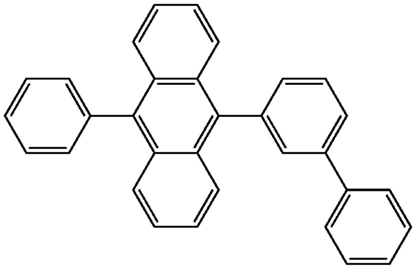
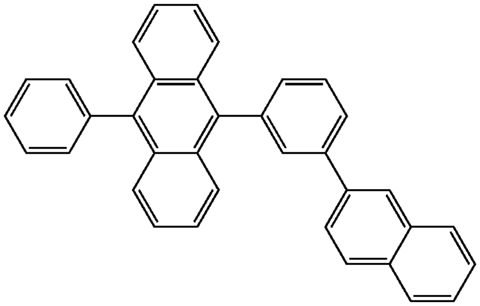
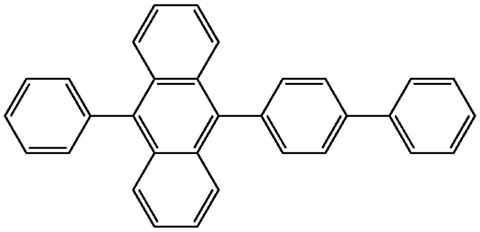
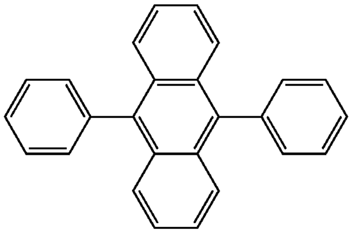
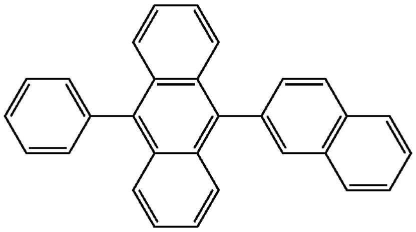
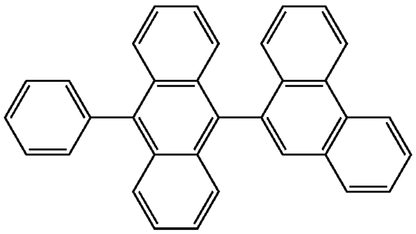
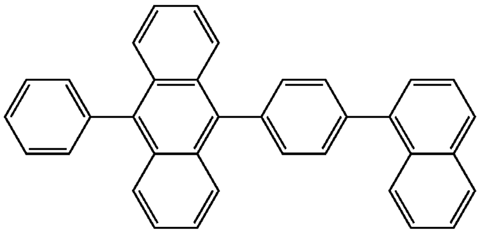
-continued
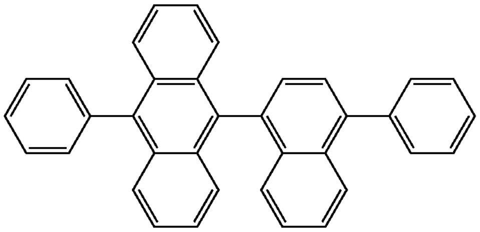
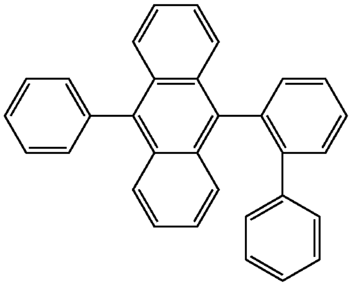
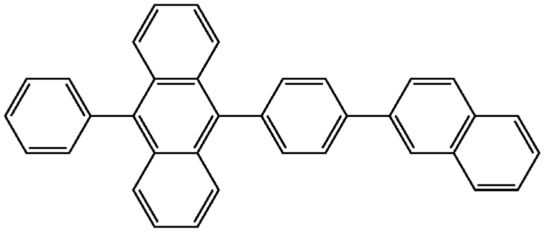
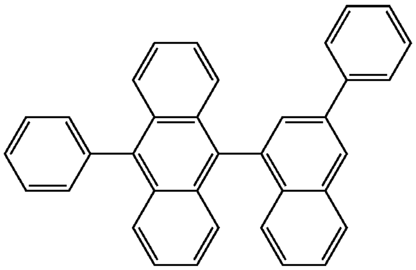
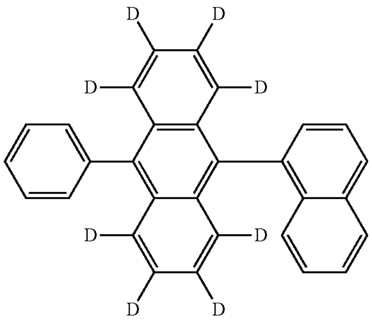
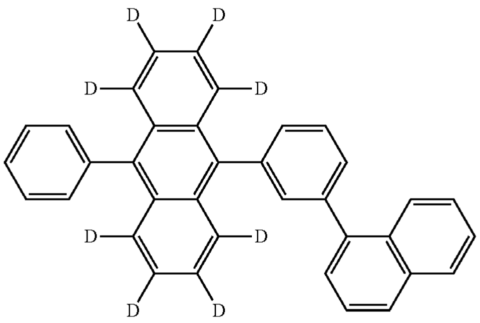

-continued
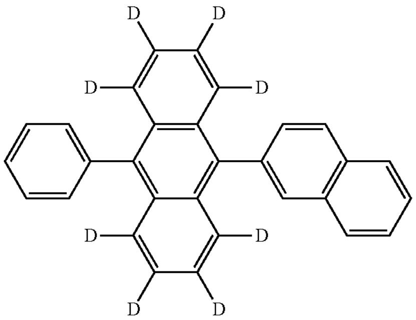
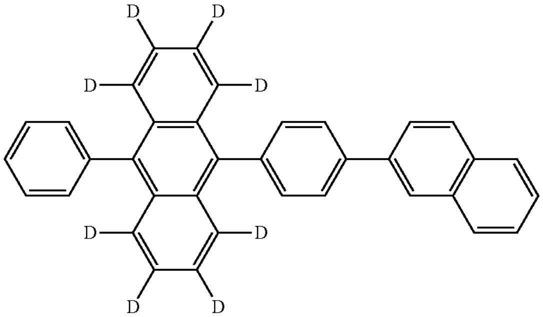
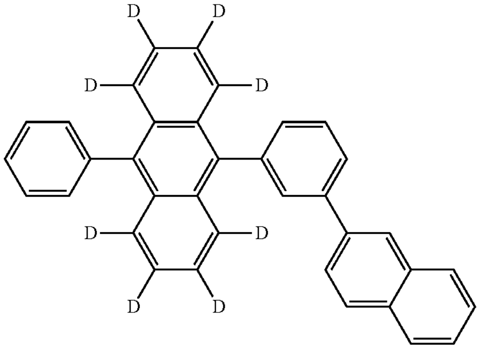
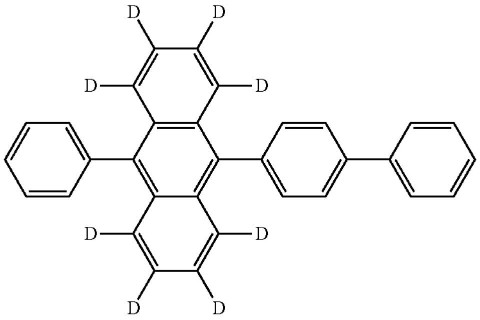
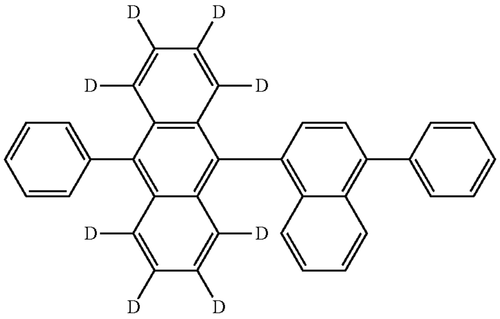
-continued
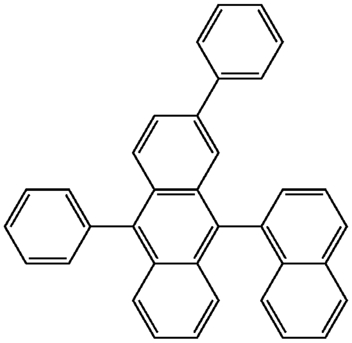
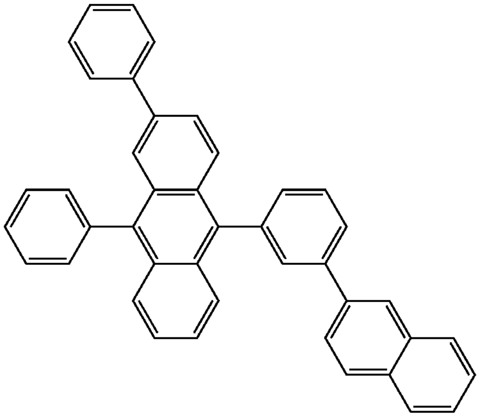
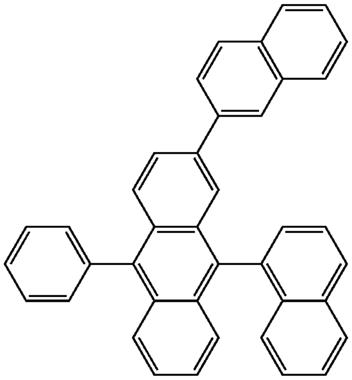
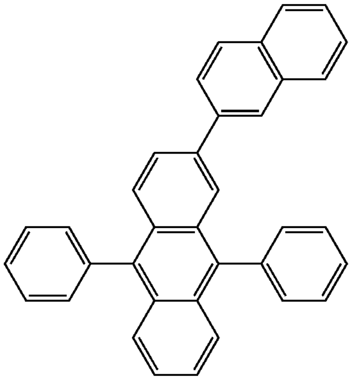

-continued
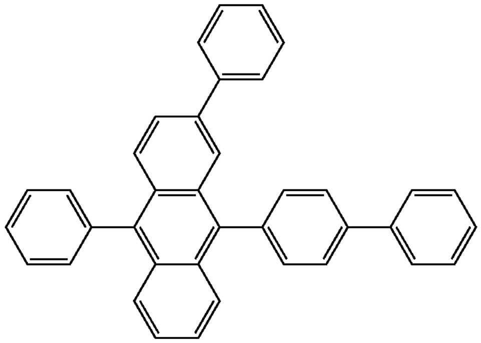
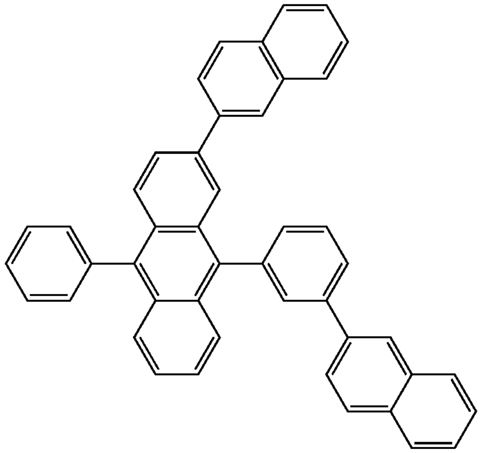
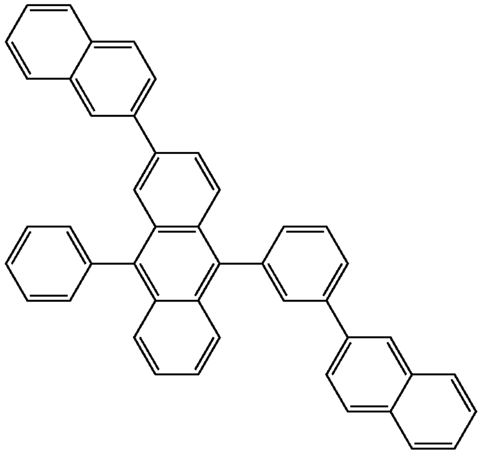
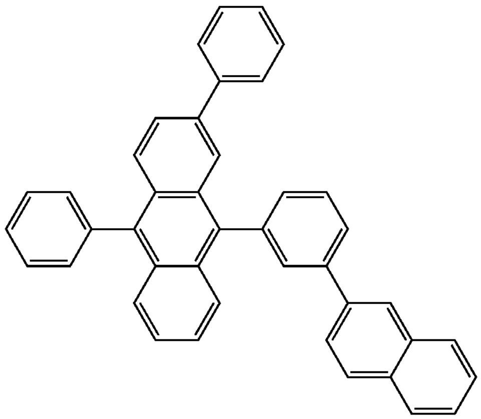
-continued
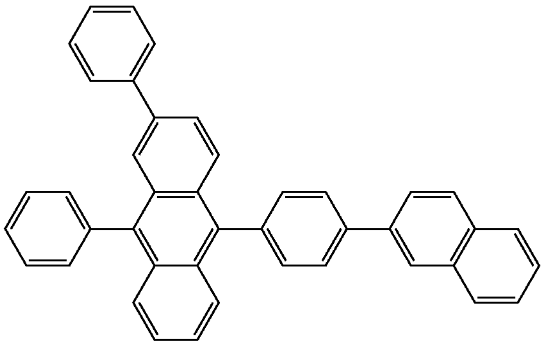
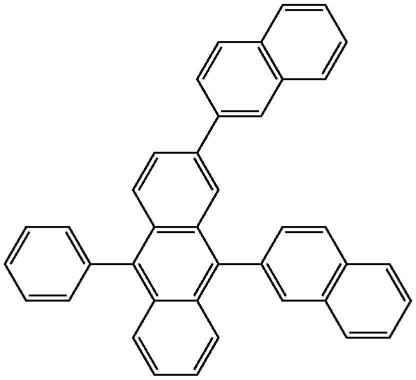
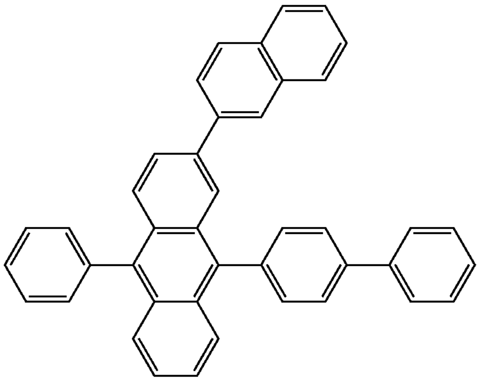
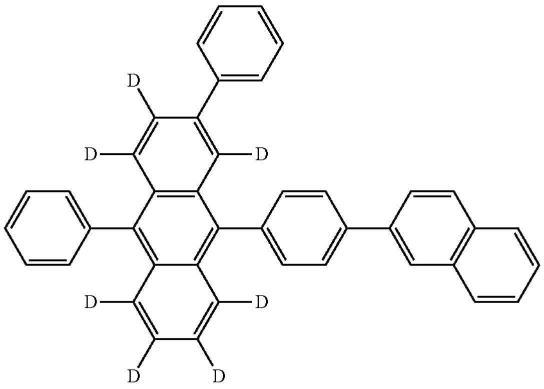

-continued
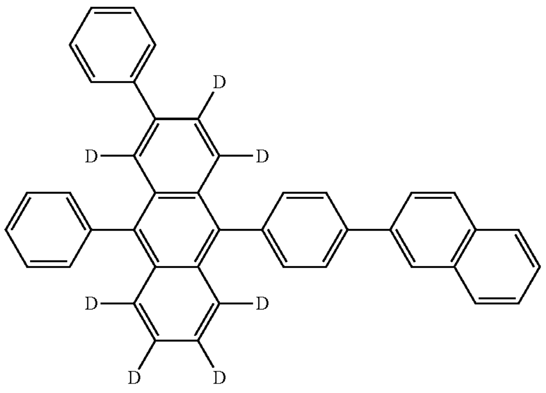
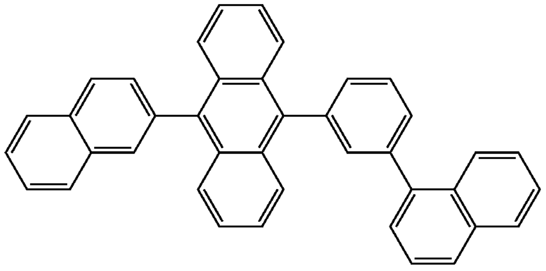
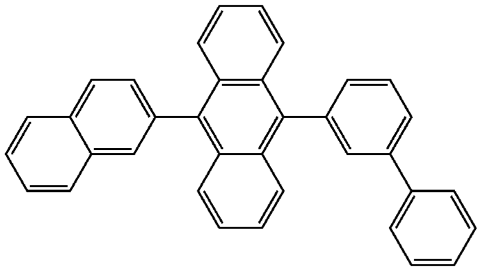
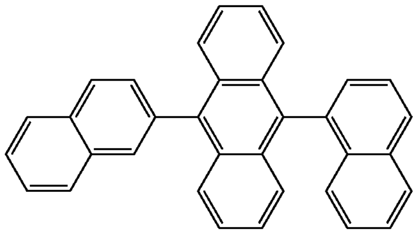
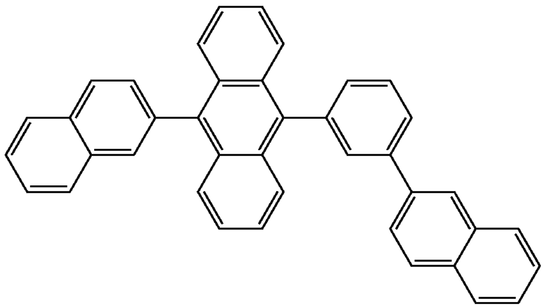
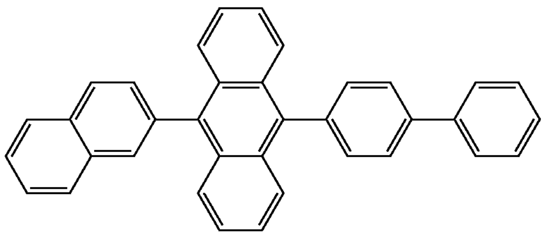
-continued
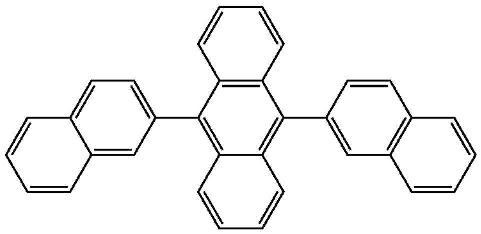
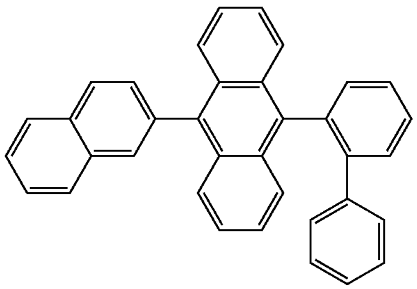
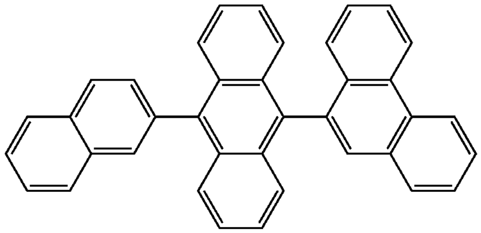
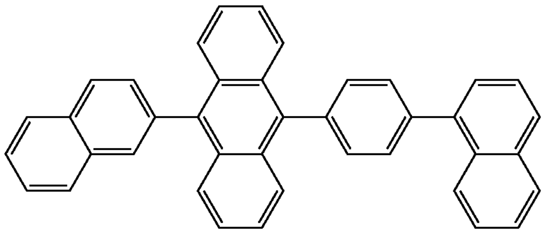
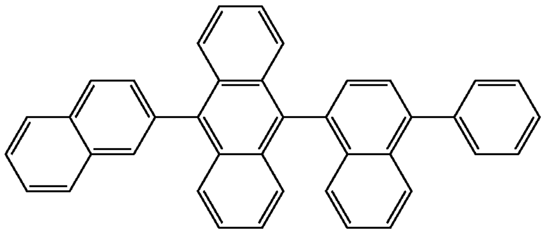
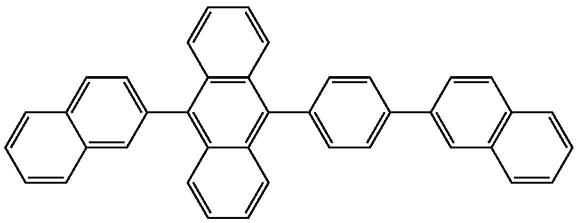
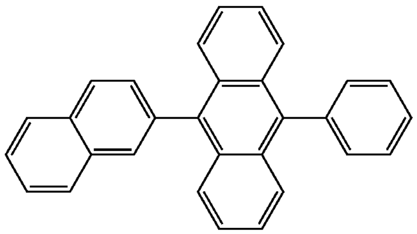

-continued
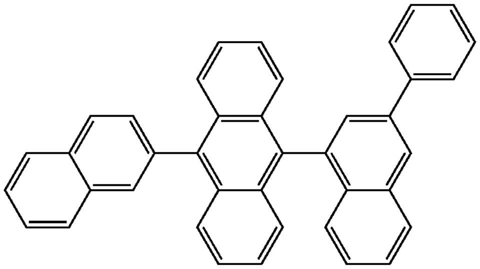
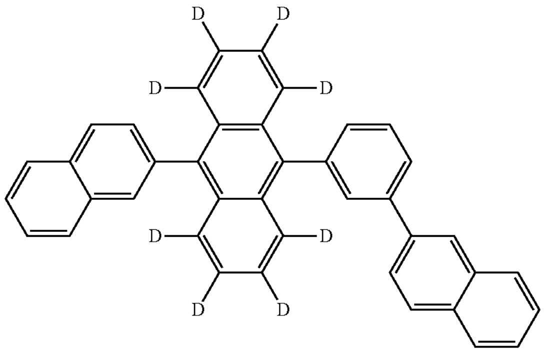
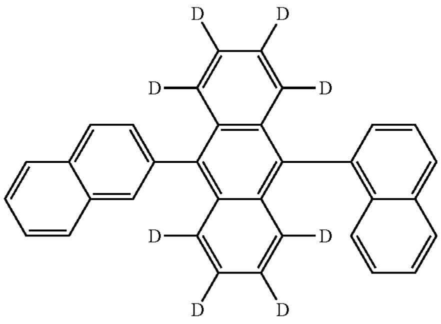
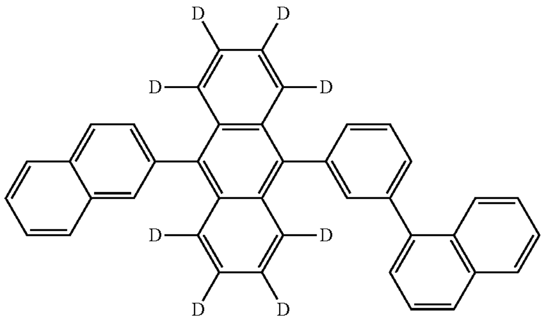
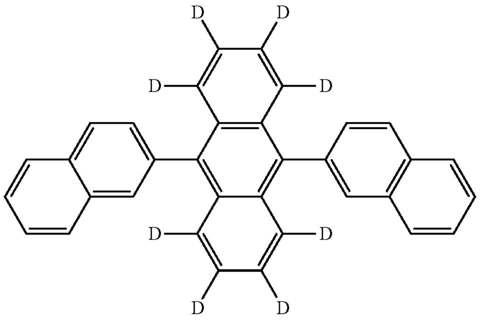
-continued
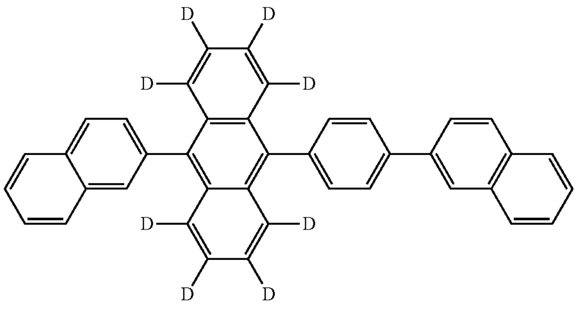
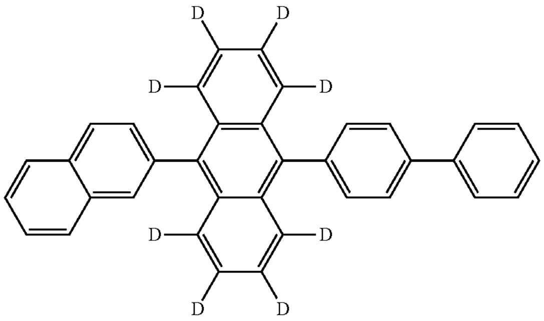
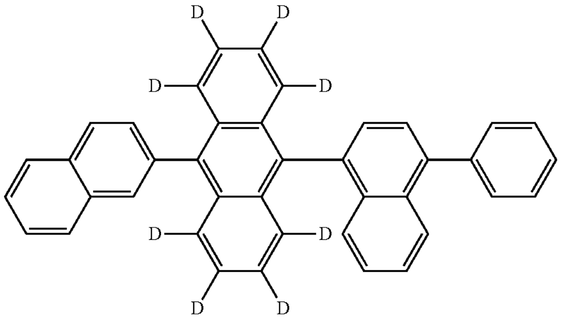
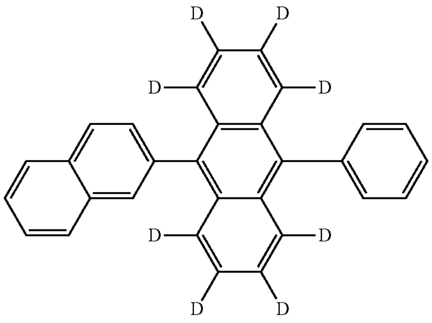
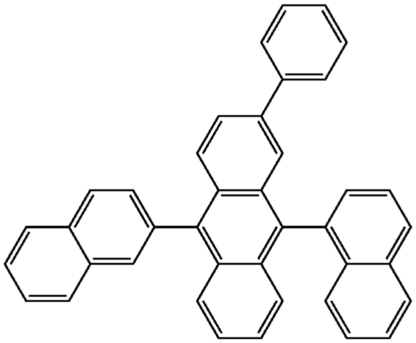

-continued
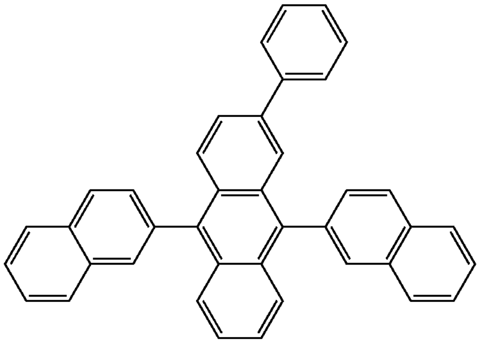
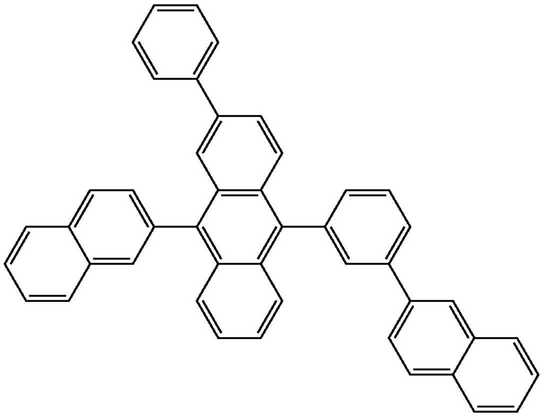
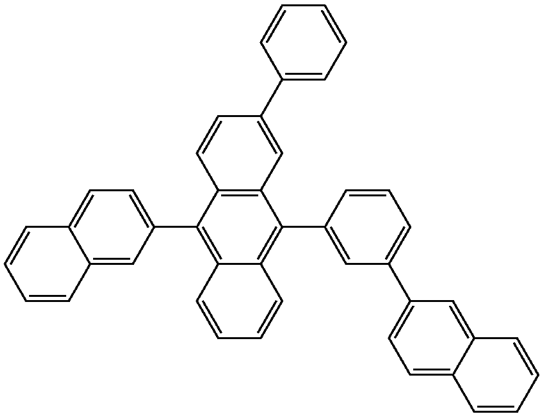
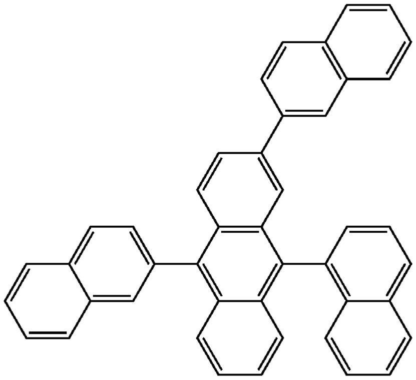
-continued
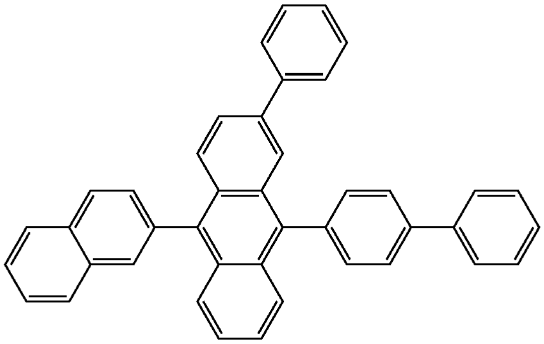
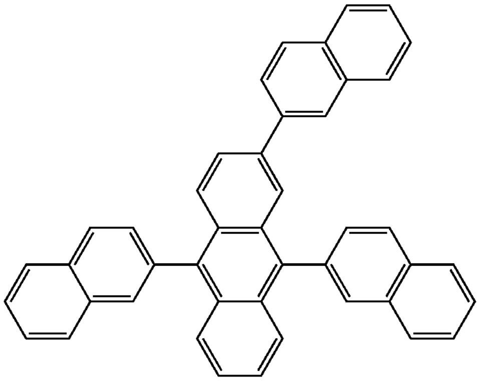
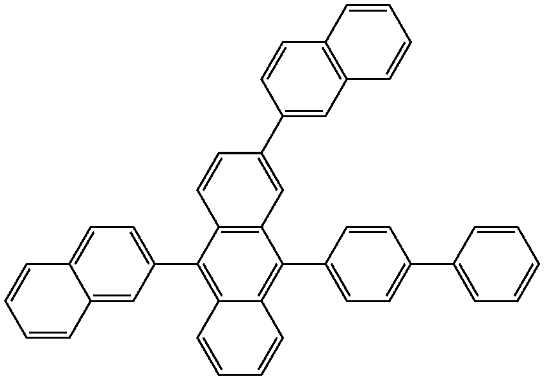
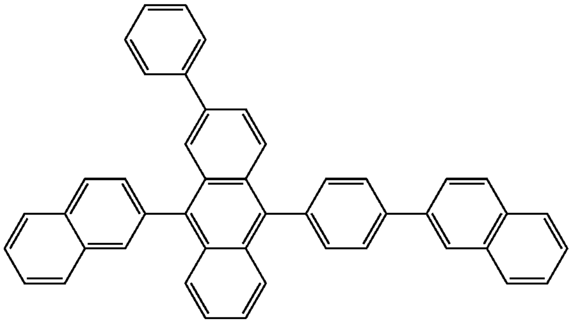

-continued
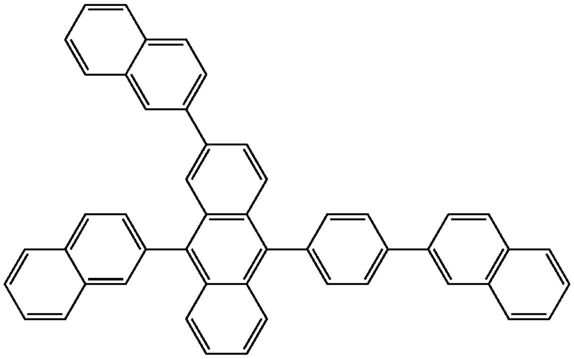
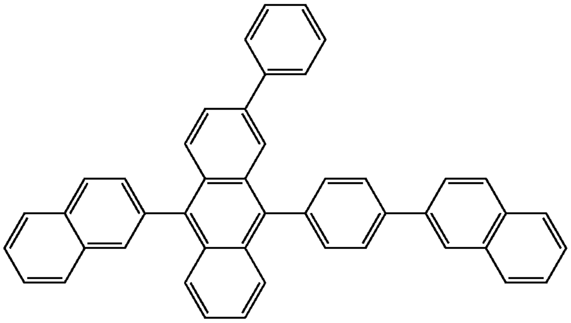
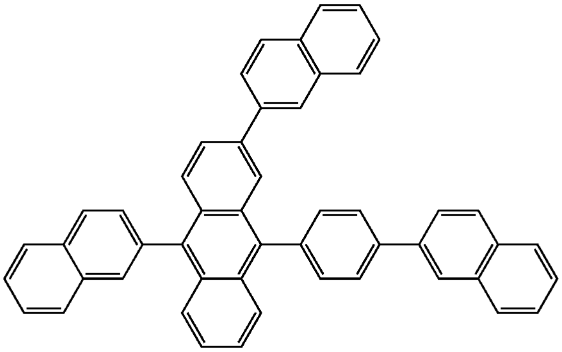
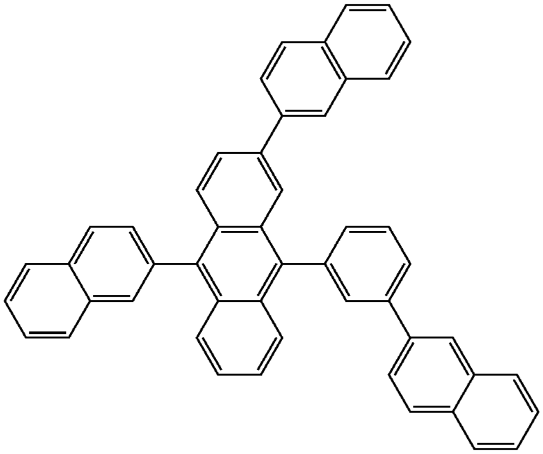
-continued
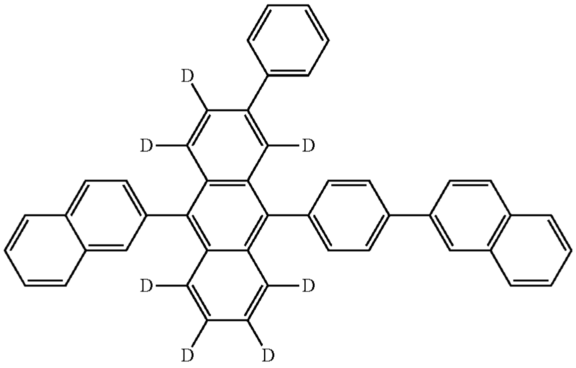
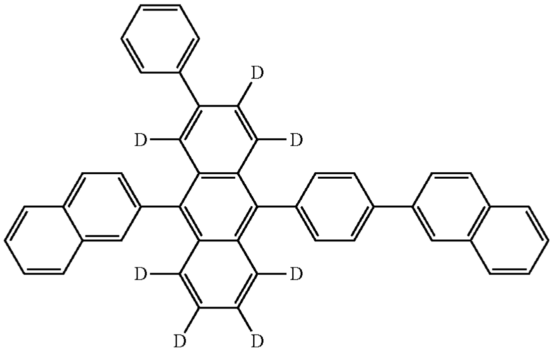
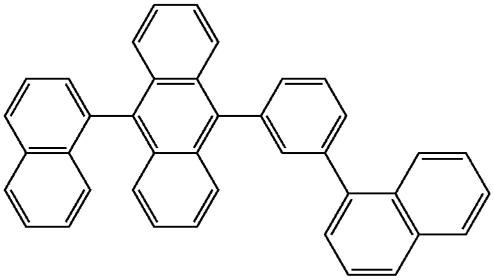
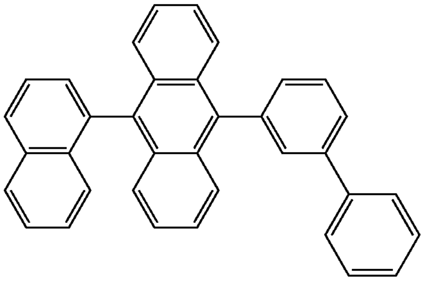
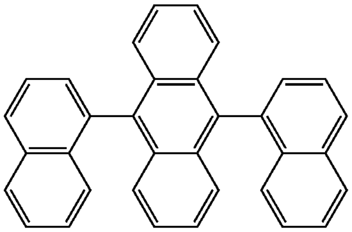

-continued
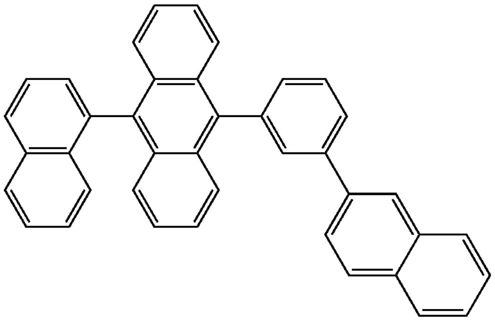
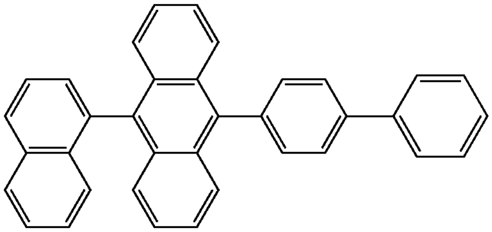
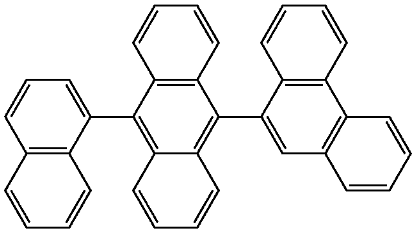
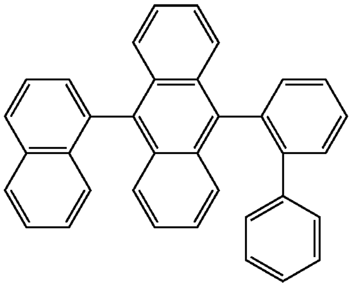
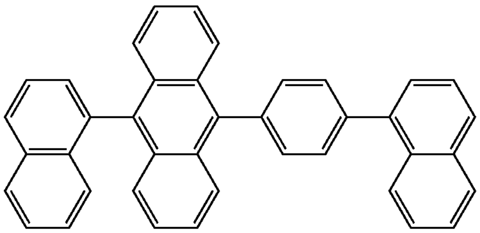
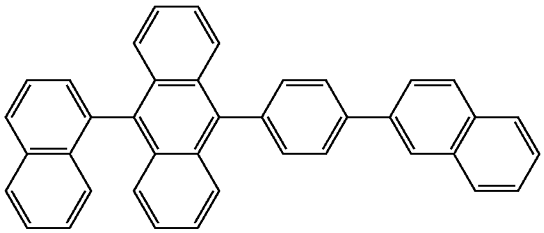
-continued
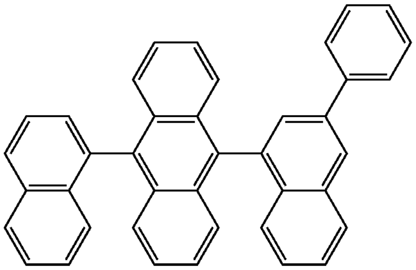
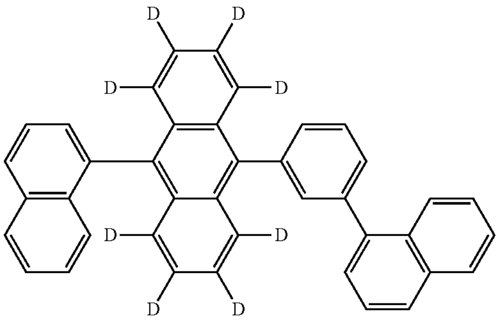
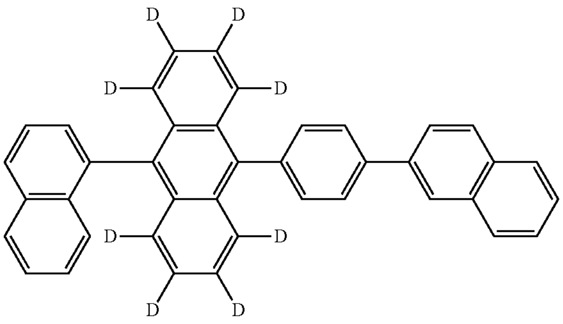
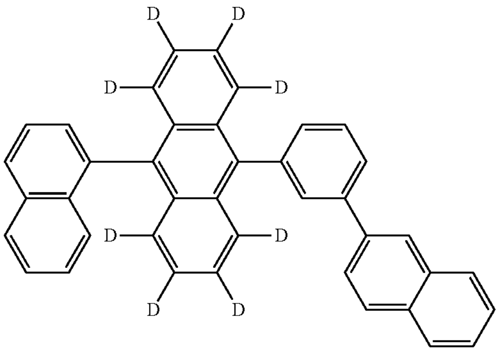
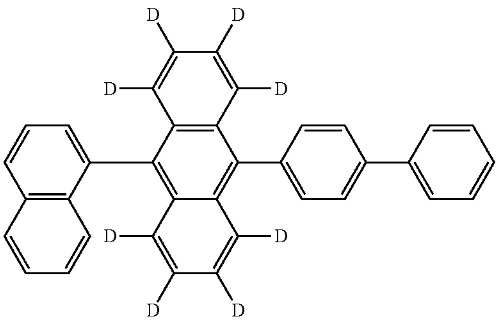

-continued
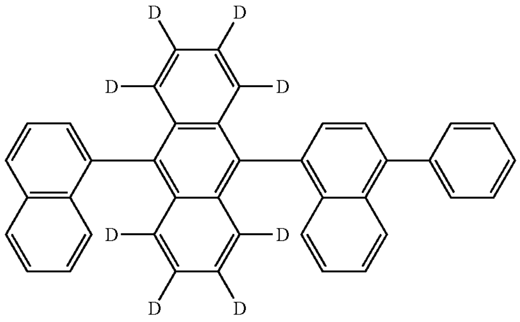
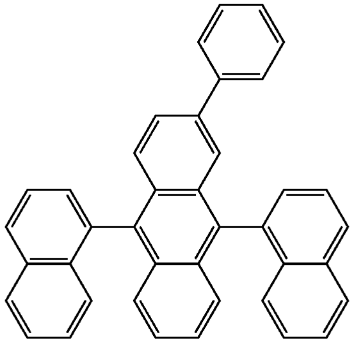
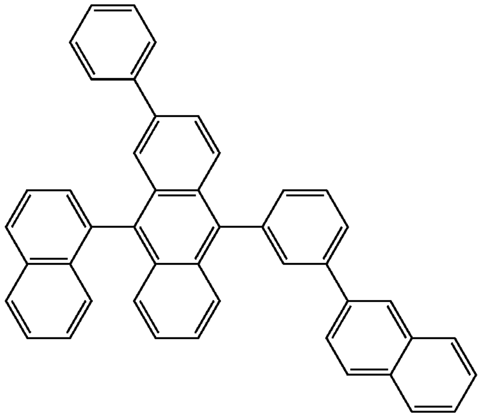
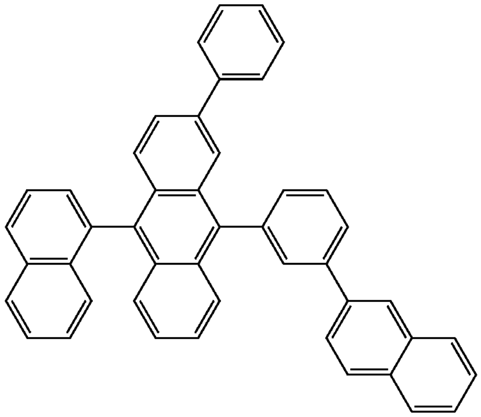
-continued
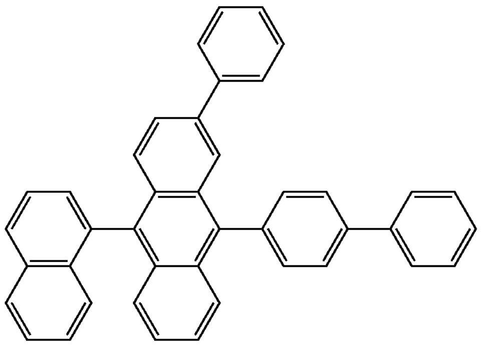
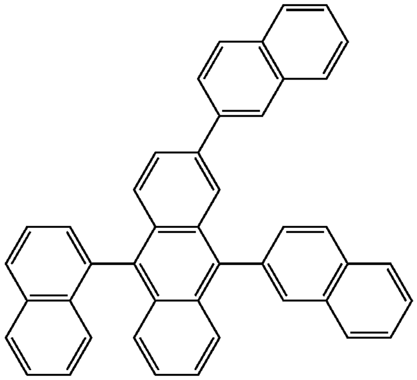
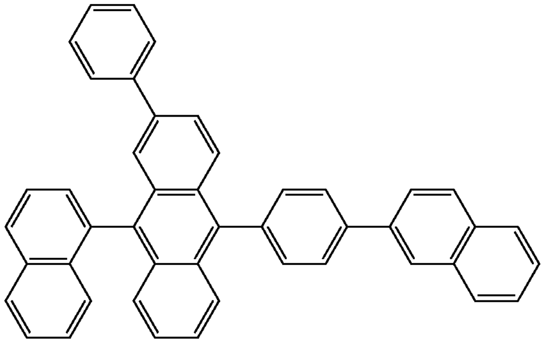
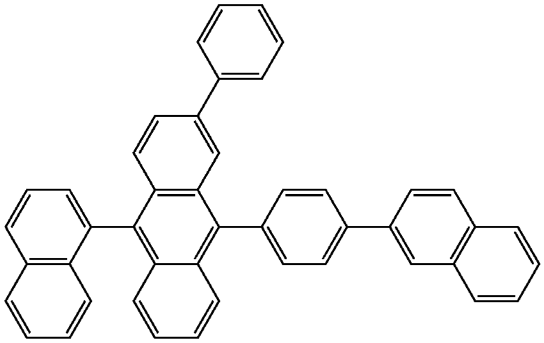

-continued
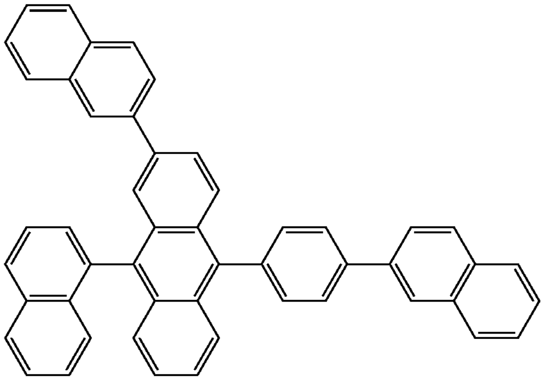
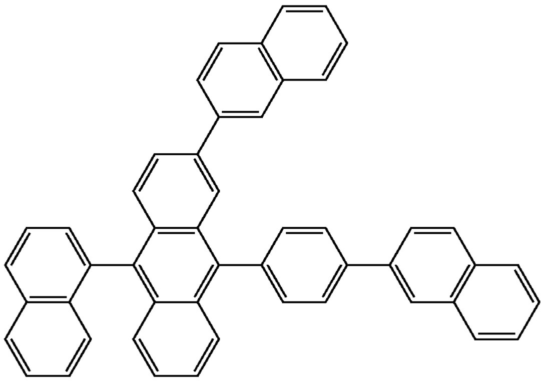
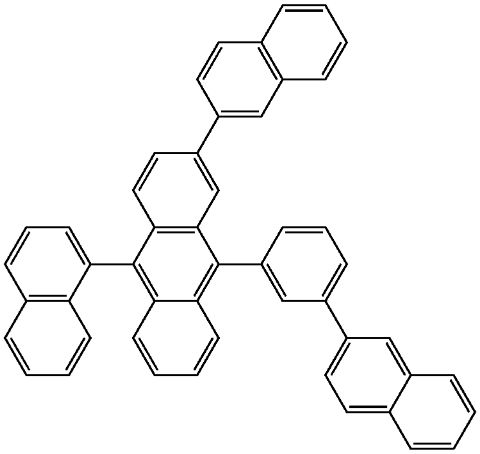
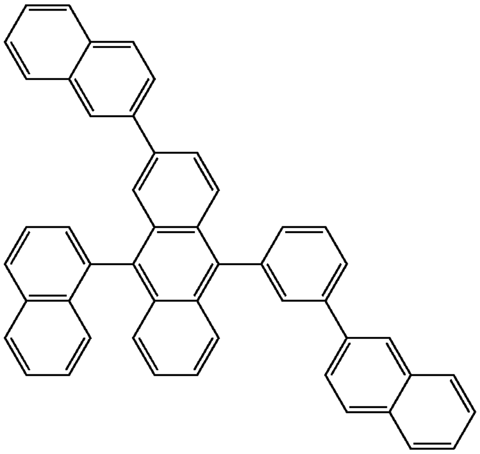
-continued
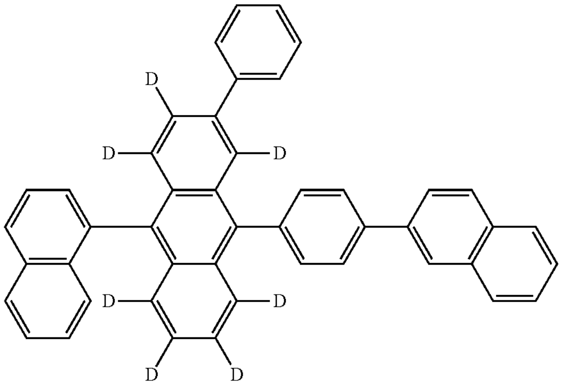
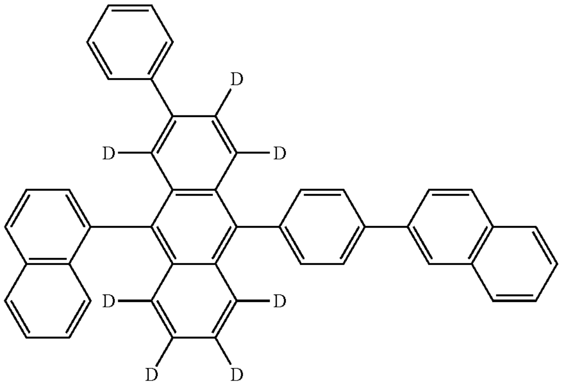
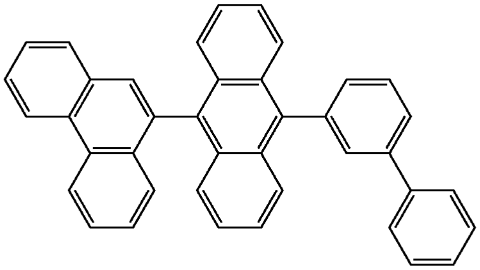
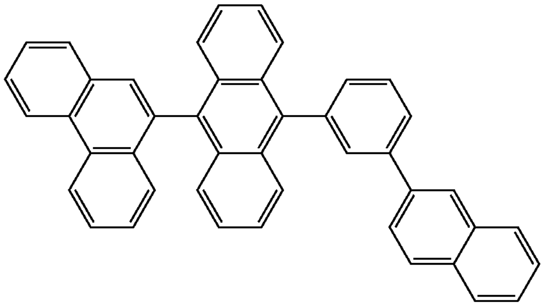
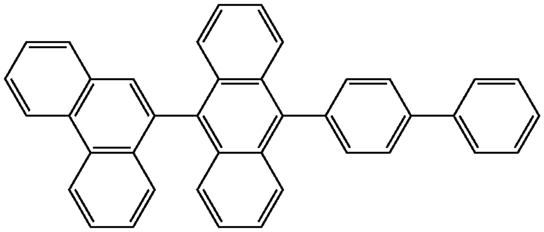

-continued
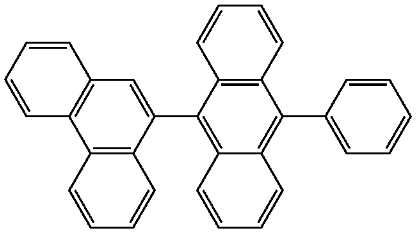
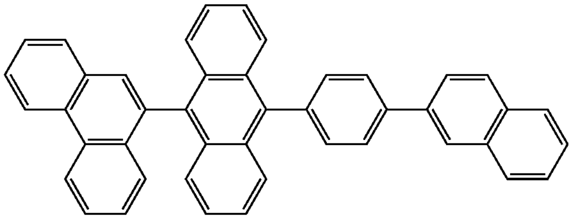
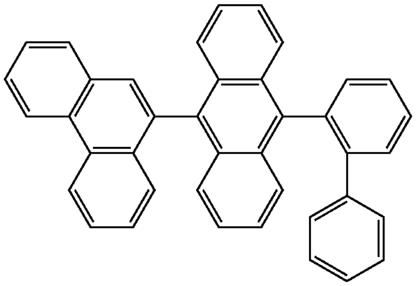
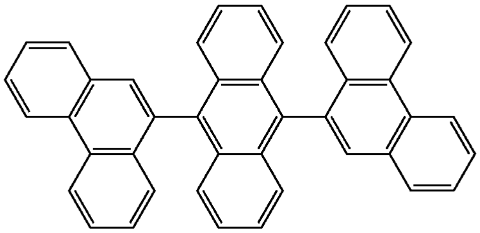
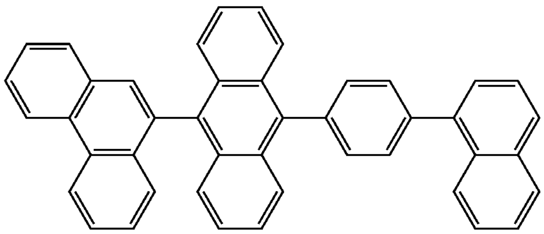
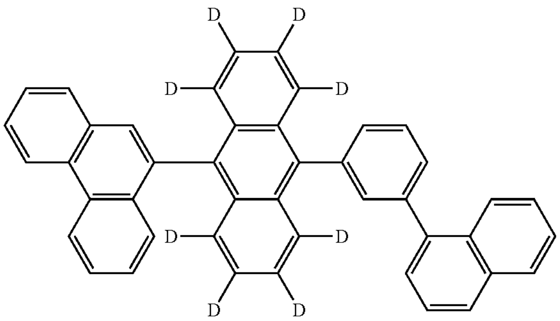
-continued
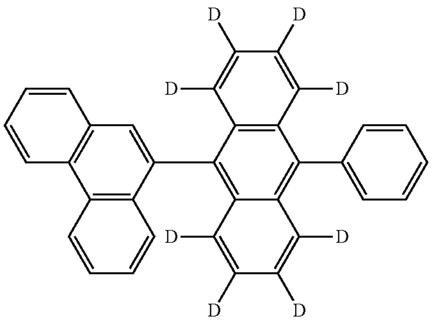
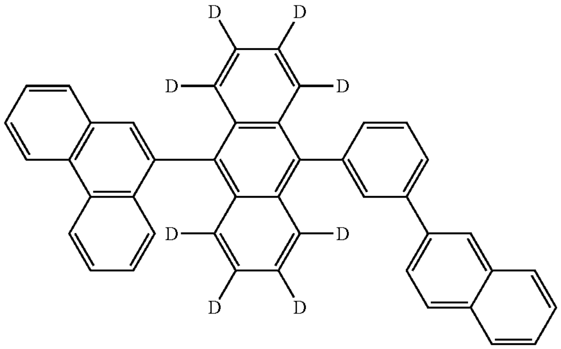
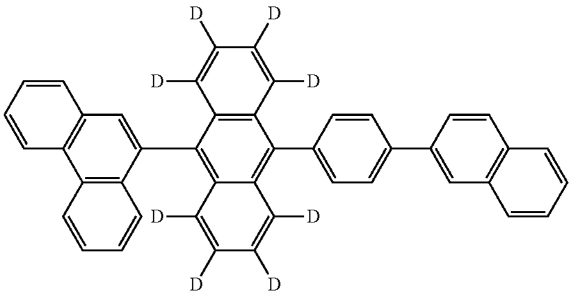
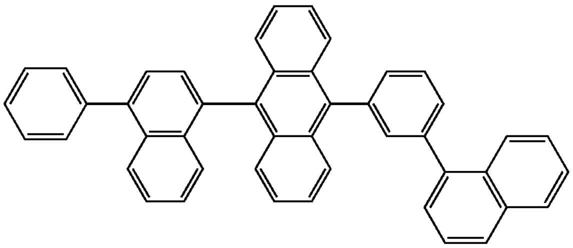
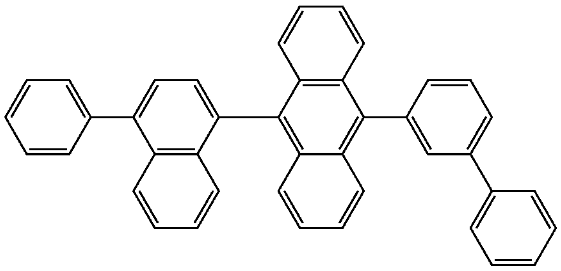

-continued
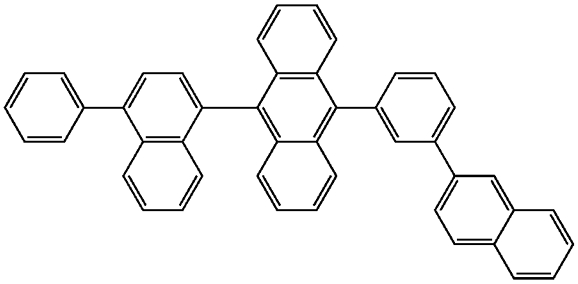
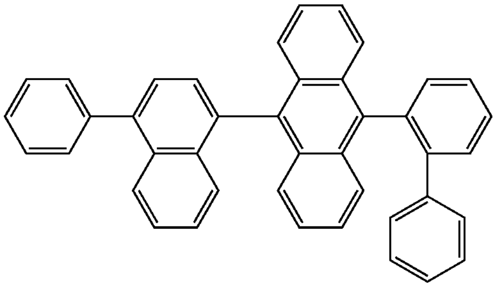
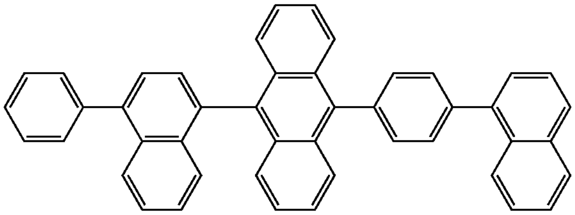
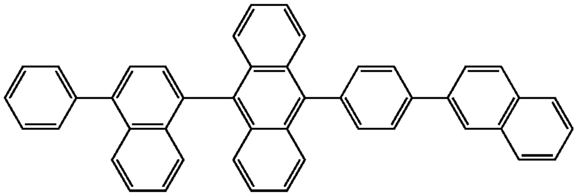
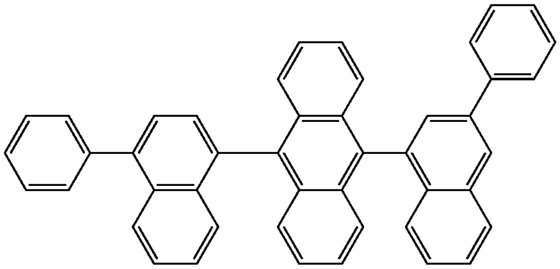
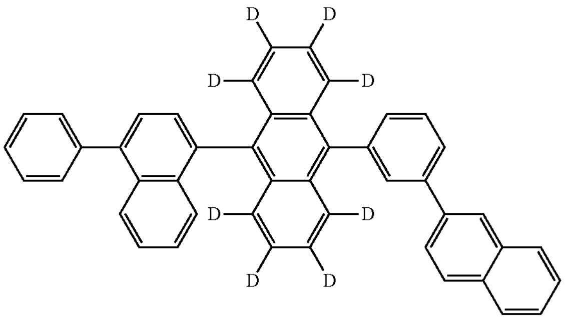
-continued
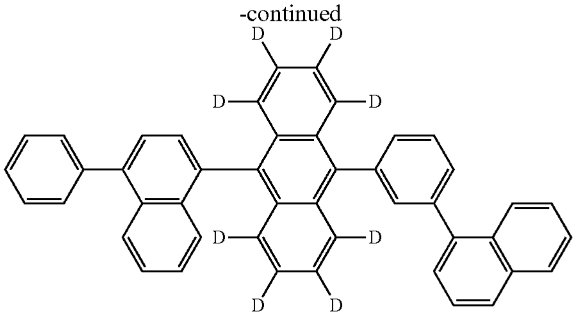
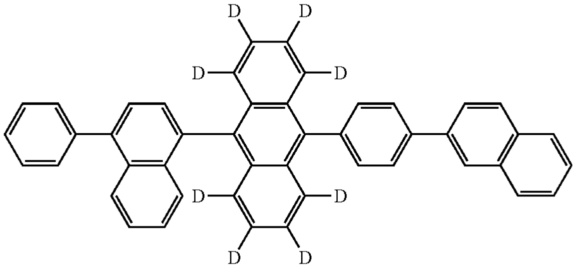
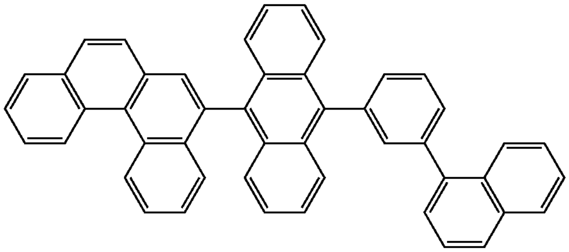
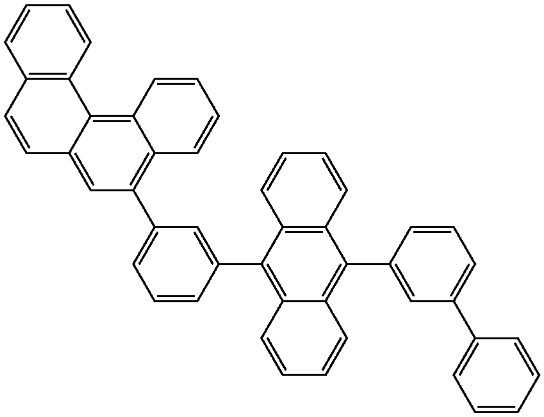
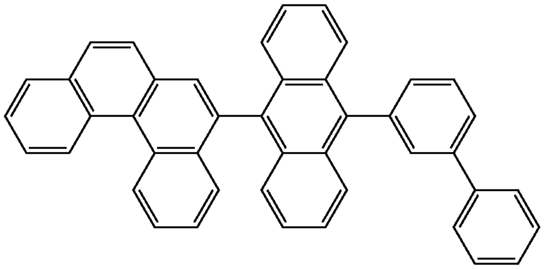
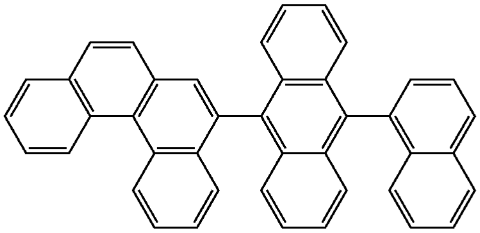

-continued
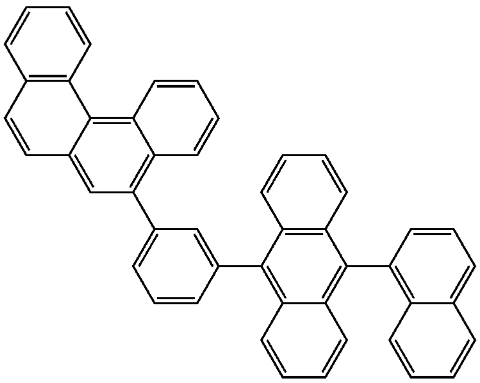
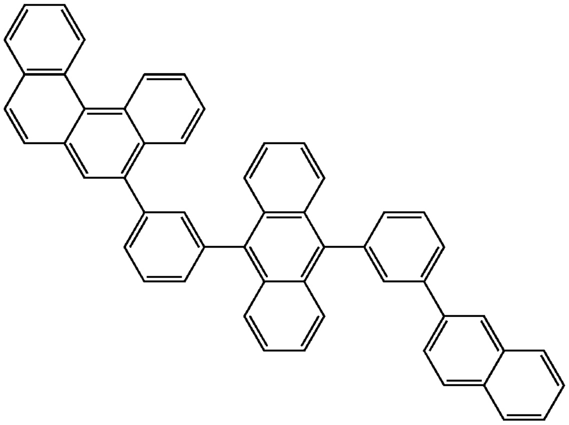
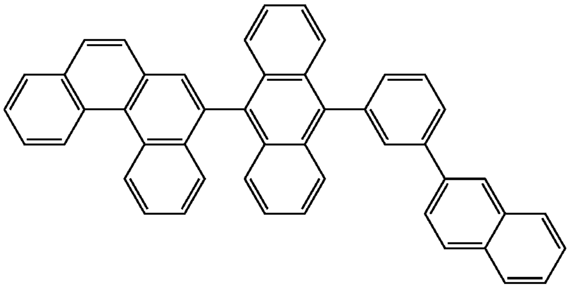
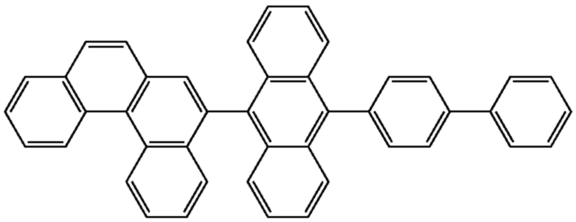
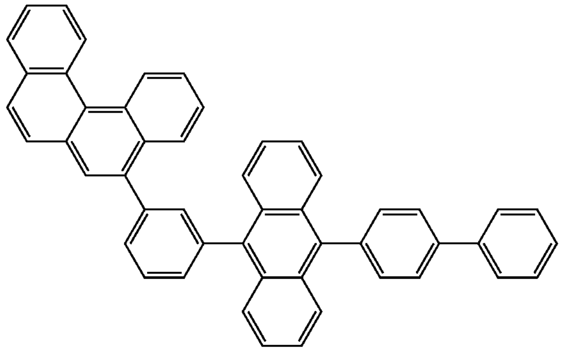
-continued
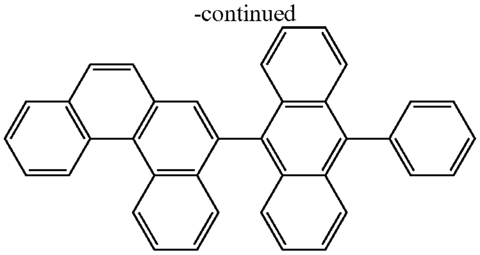
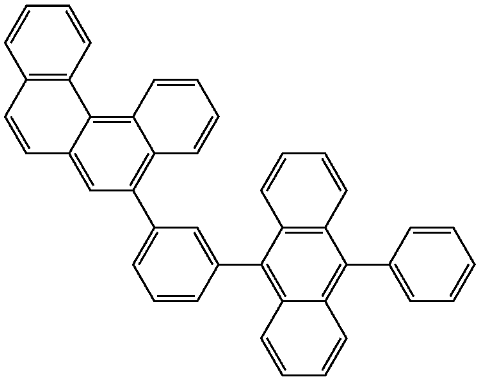
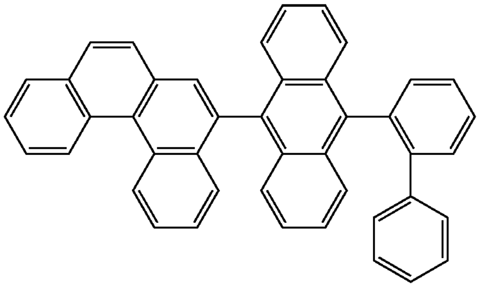
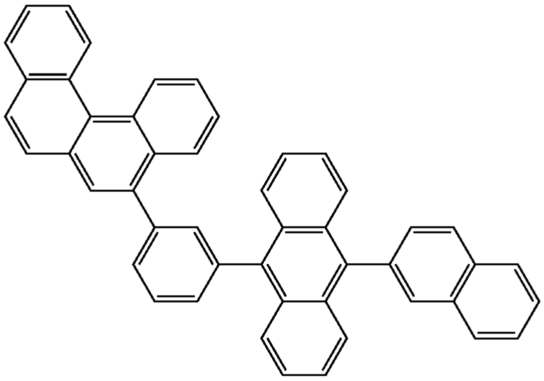
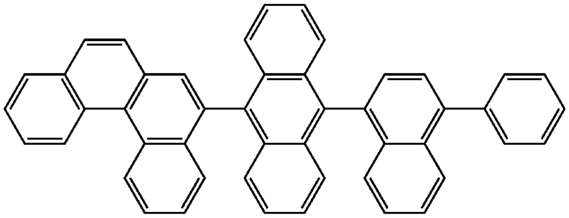
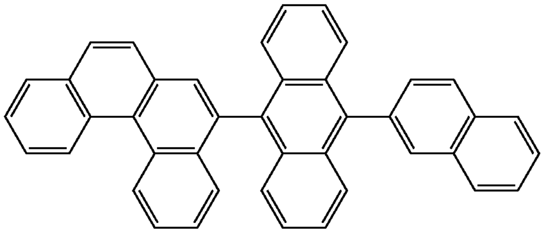

-continued
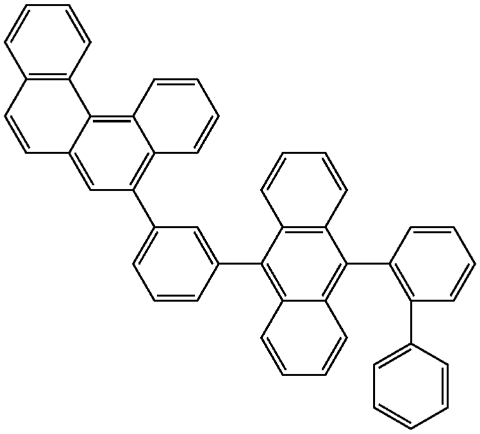
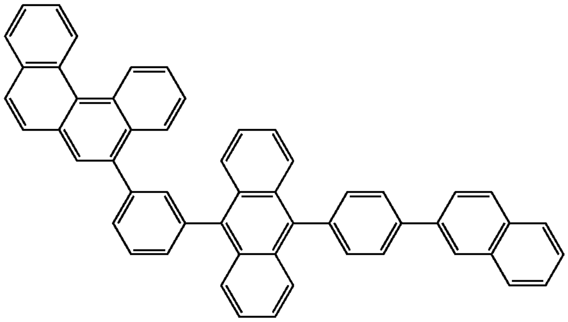
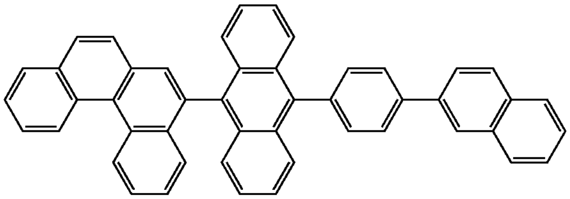
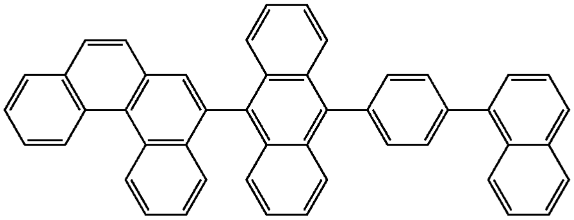
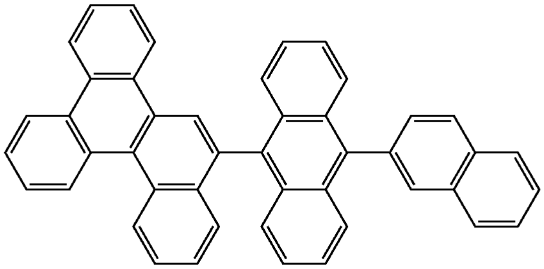
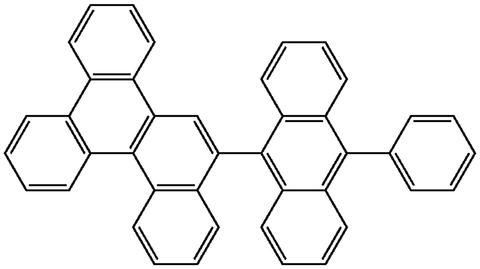
-continued
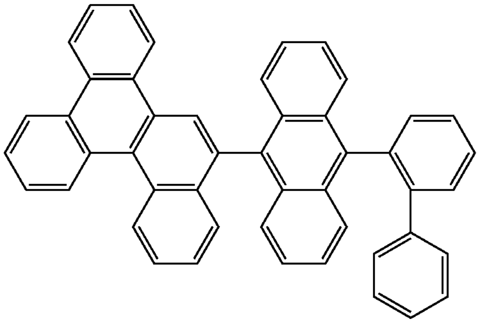
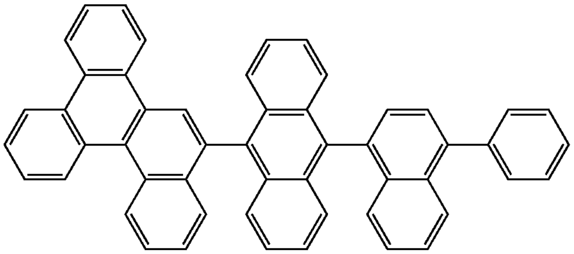
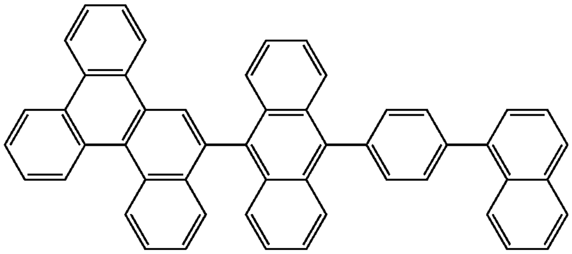
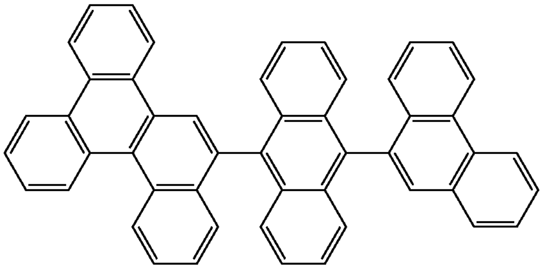
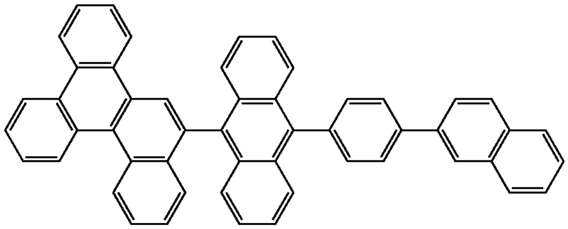
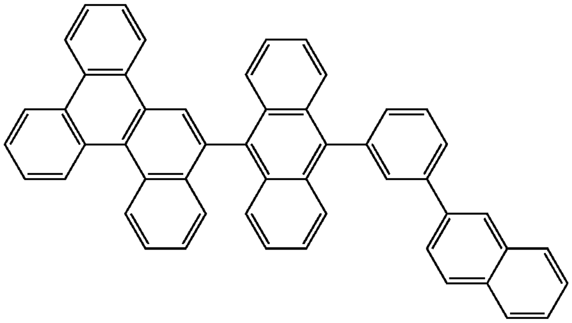

-continued
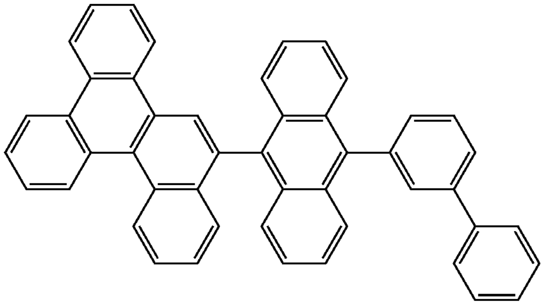
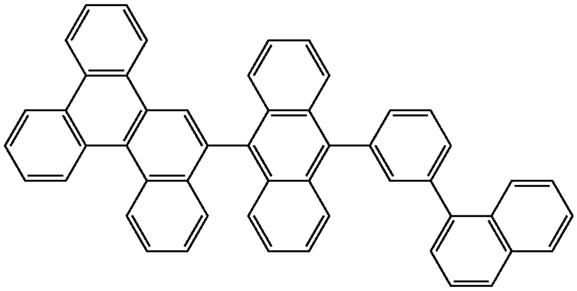
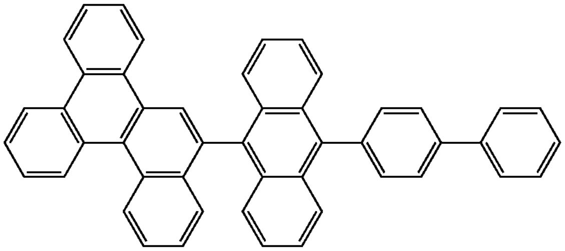
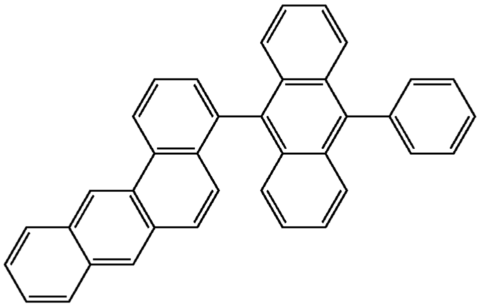
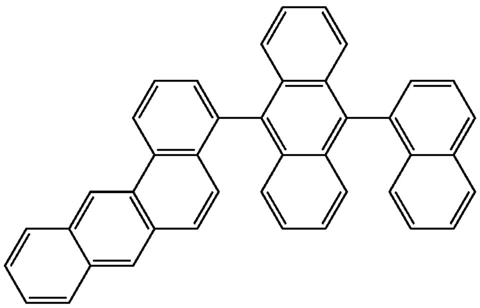
-continued
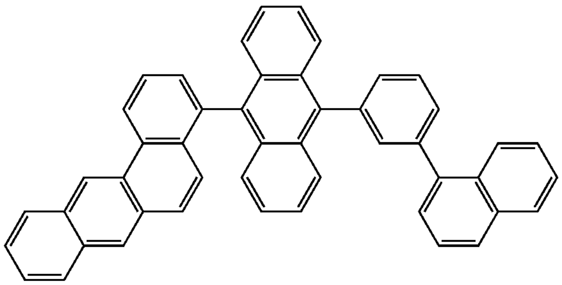
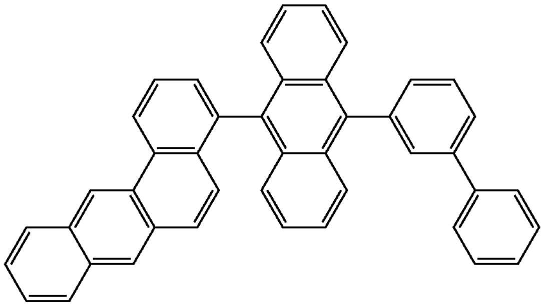
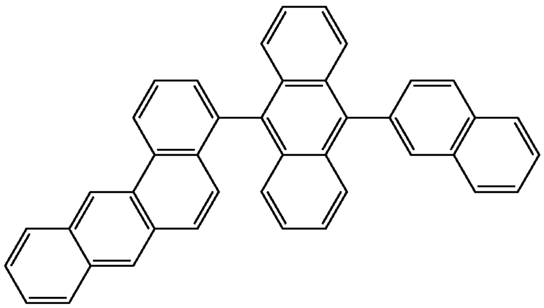
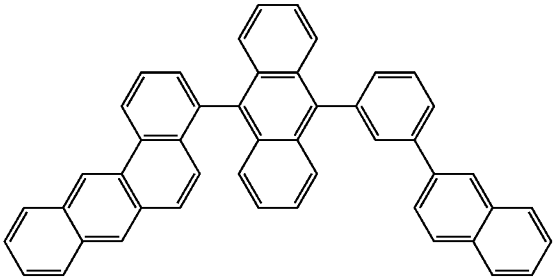
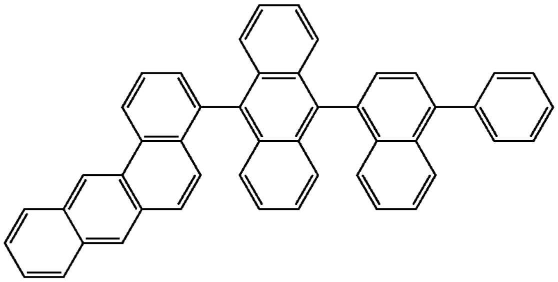

-continued
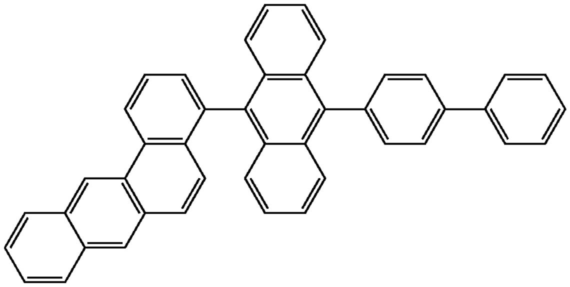
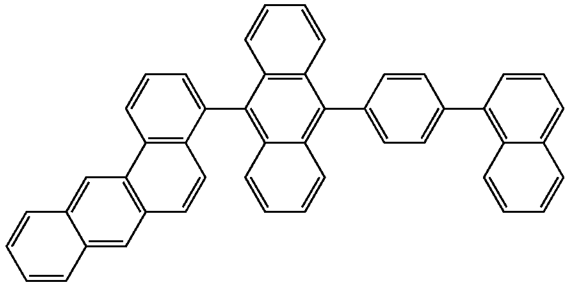
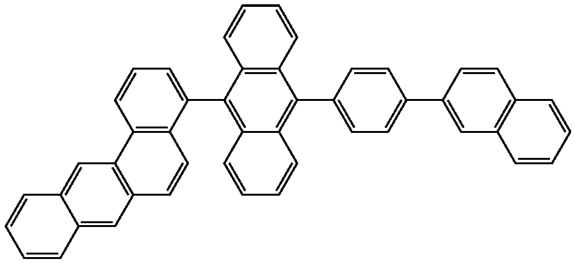
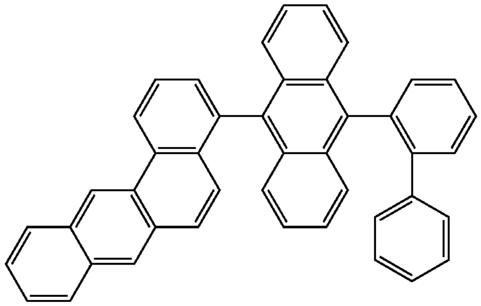
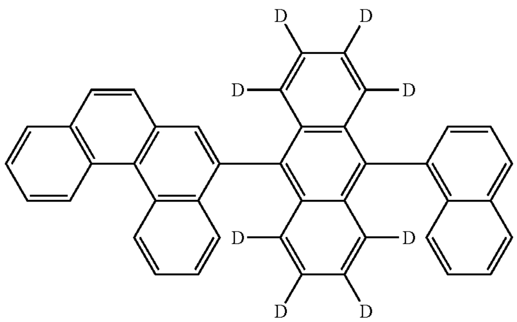
-continued
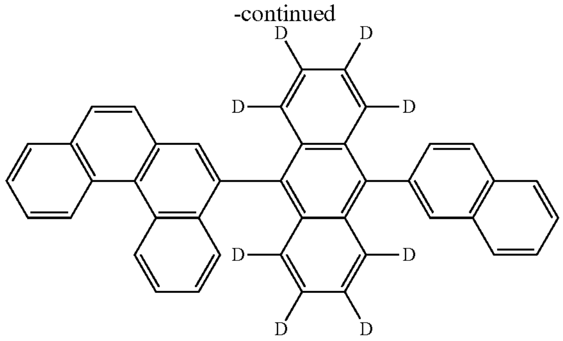
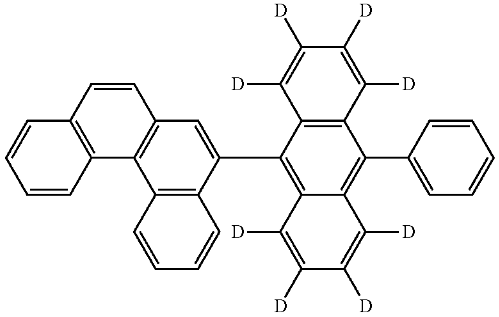
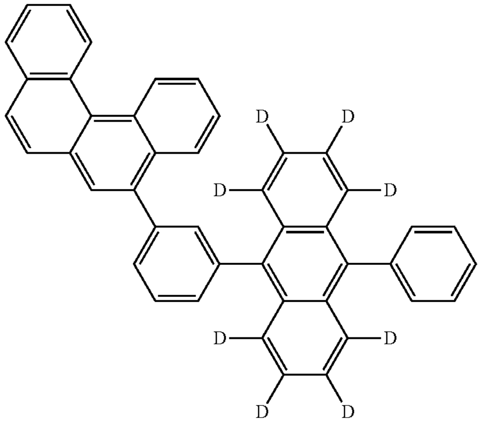
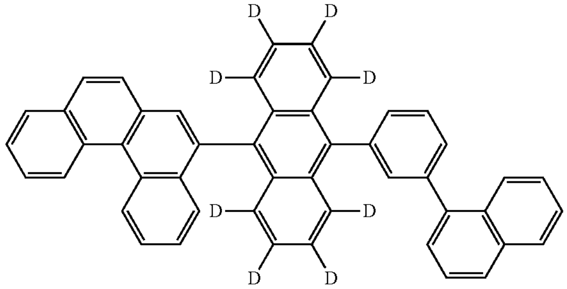
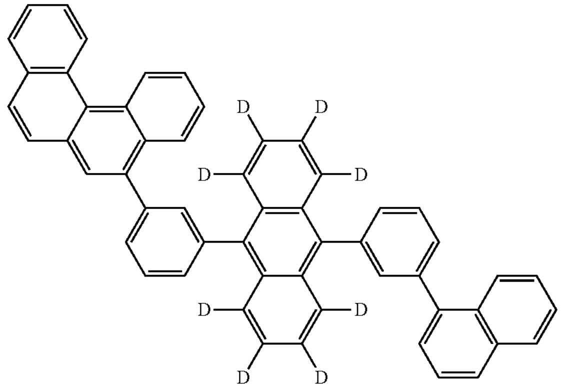

-continued
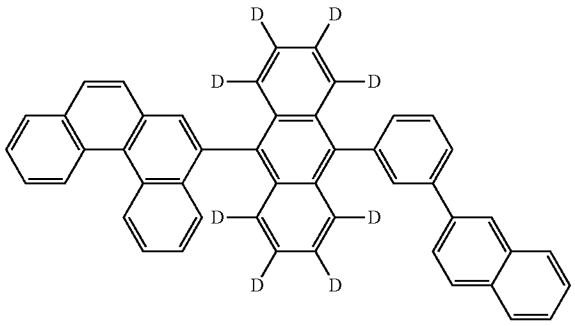
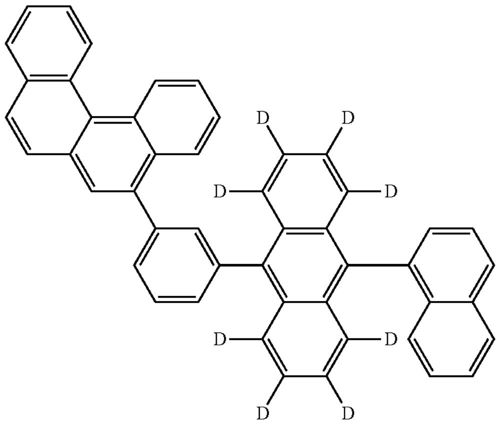
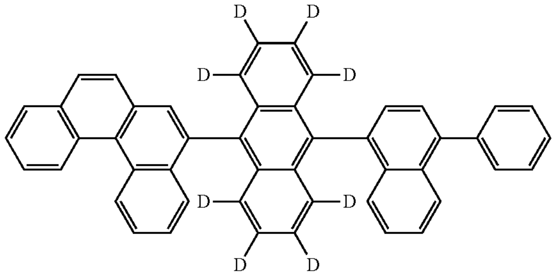
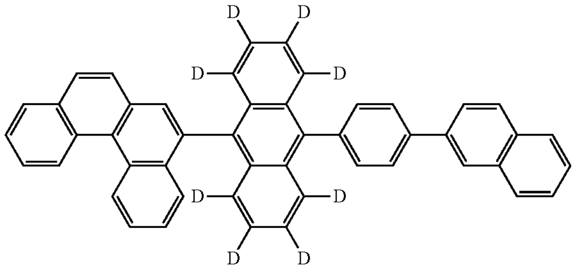
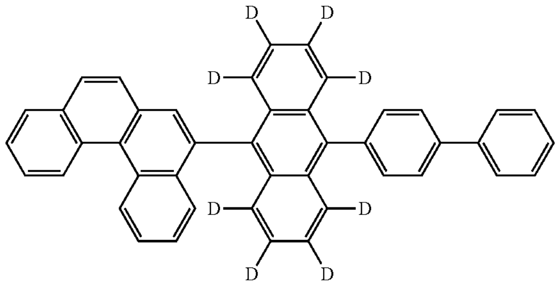
-continued
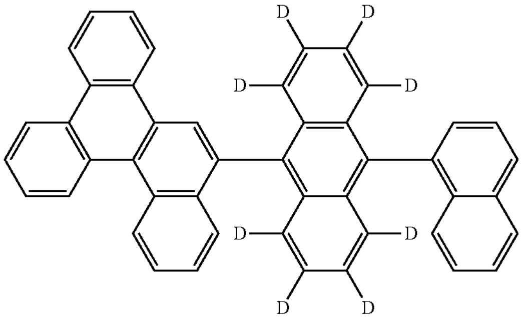
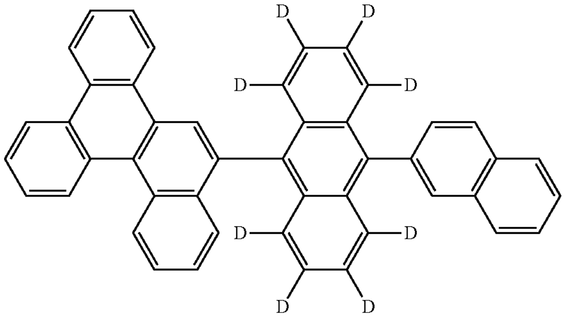
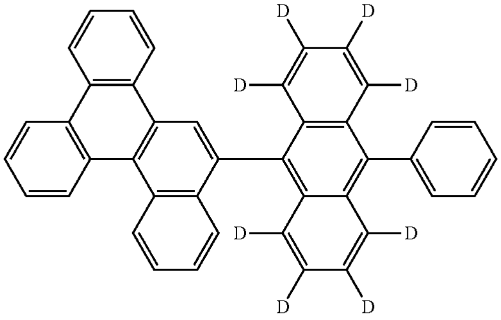
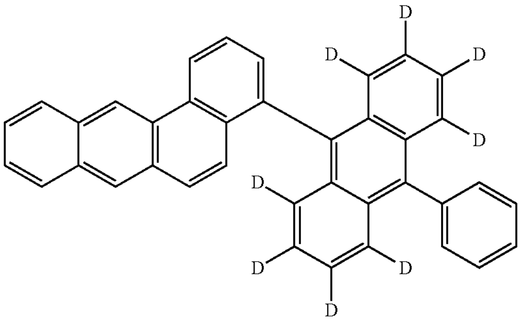
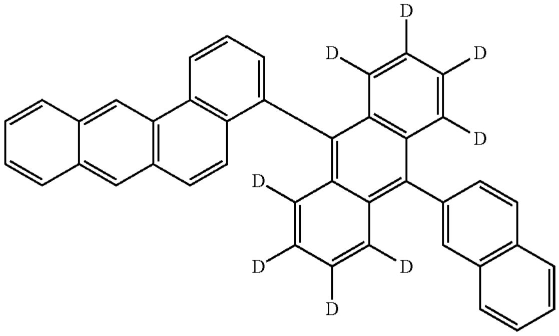

-continued
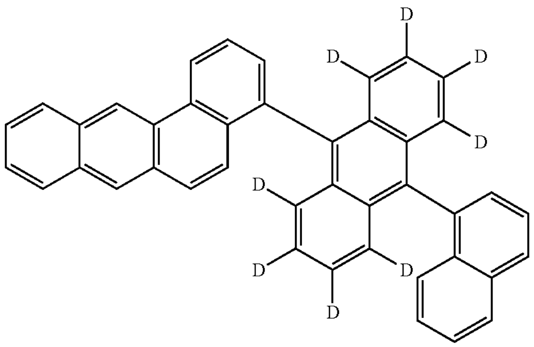
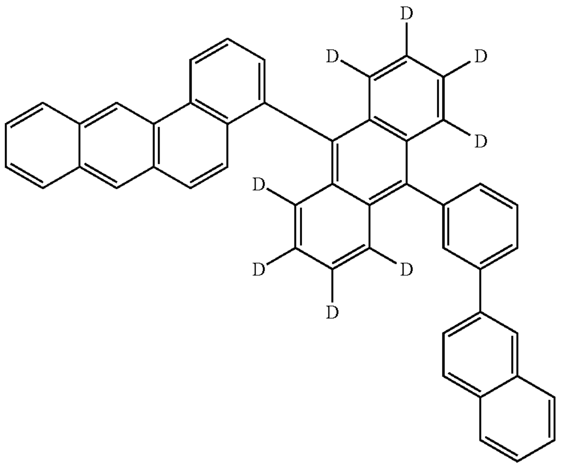
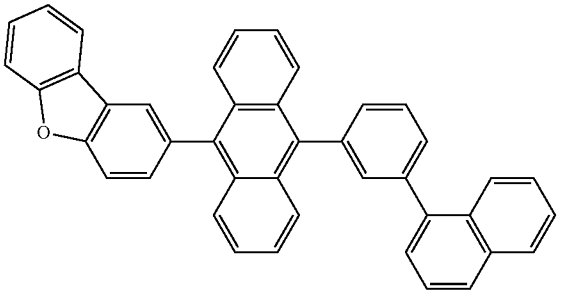
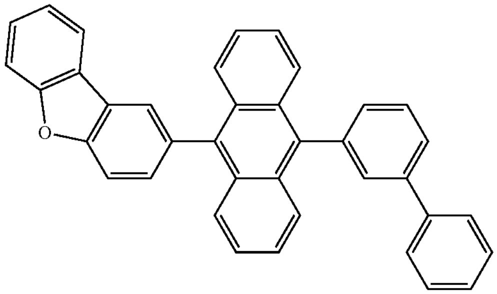
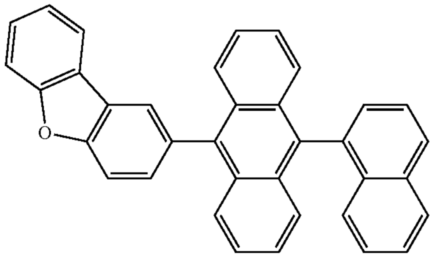
-continued
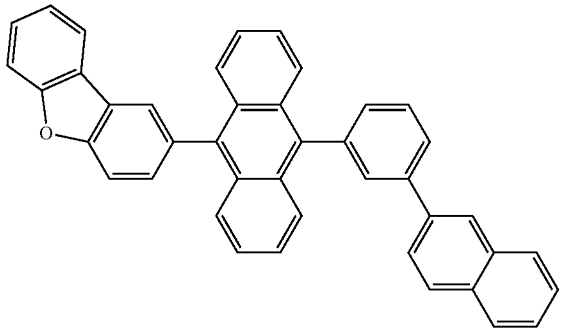
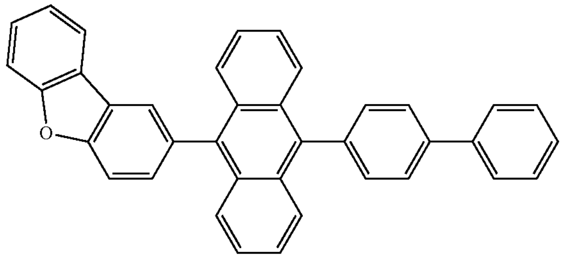
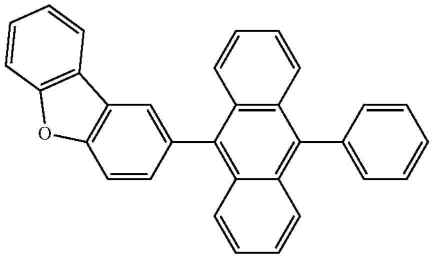
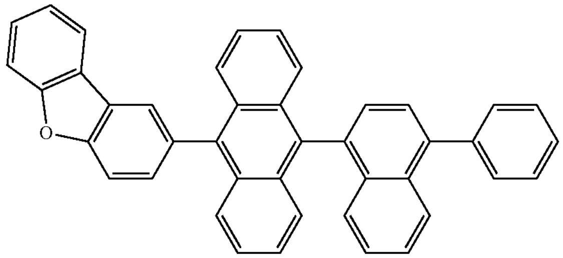
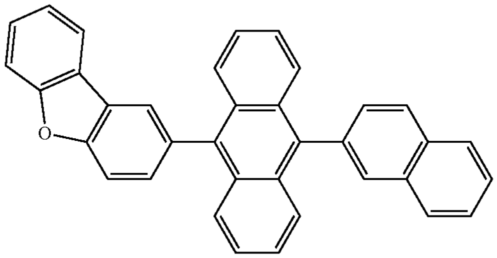
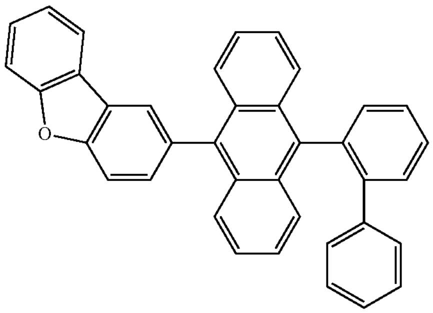

-continued
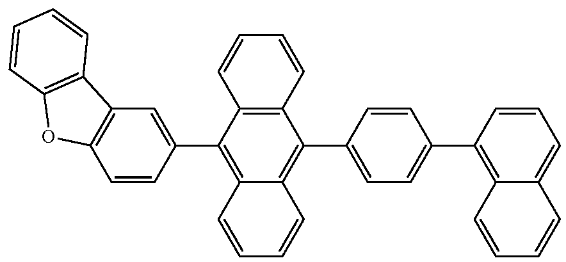
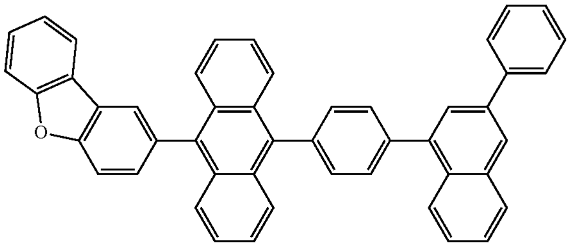
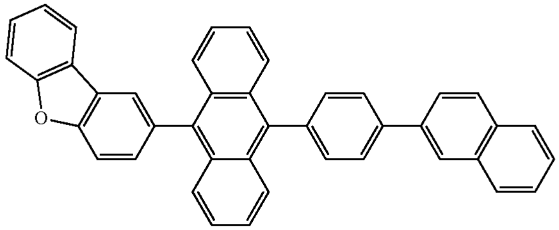
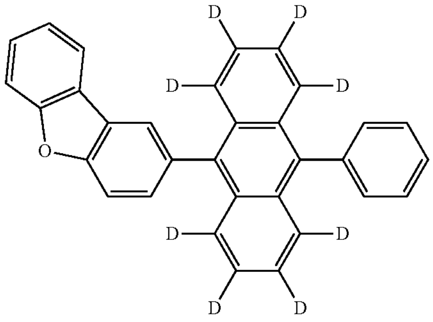
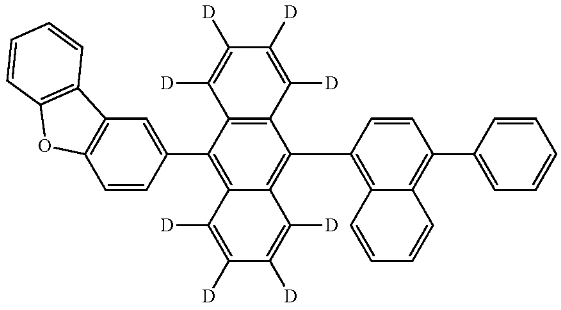
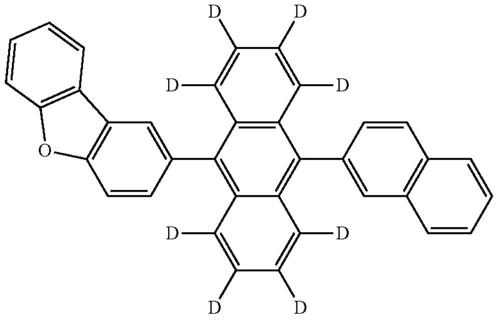
-continued
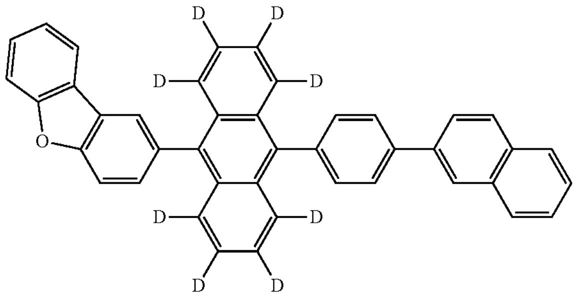
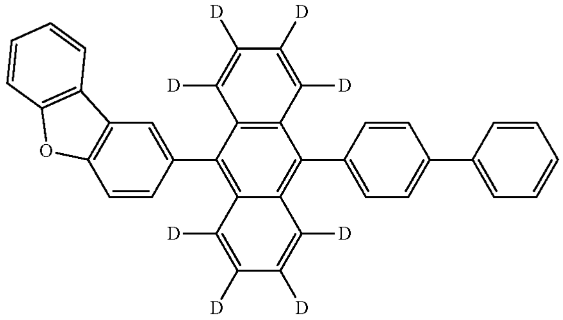
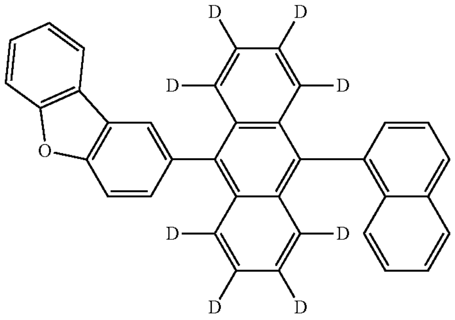
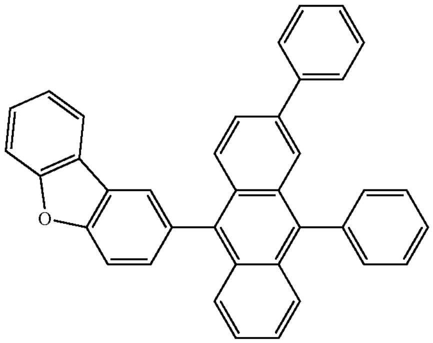
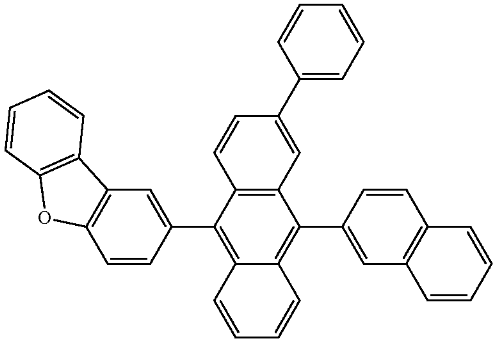

-continued
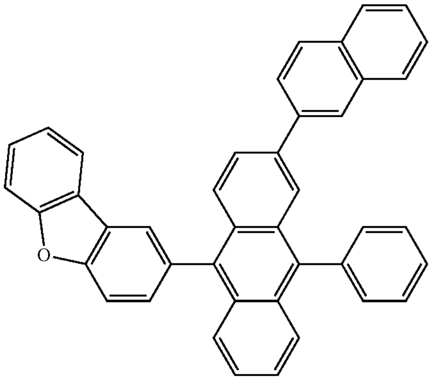
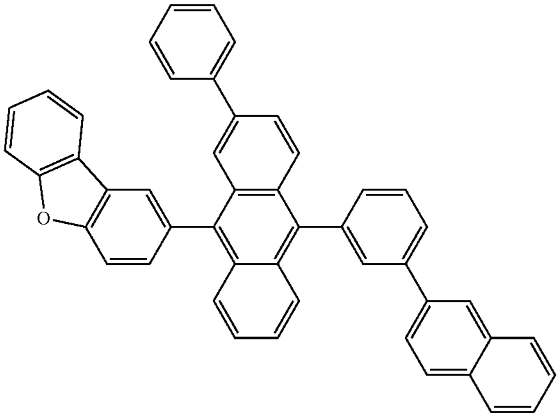
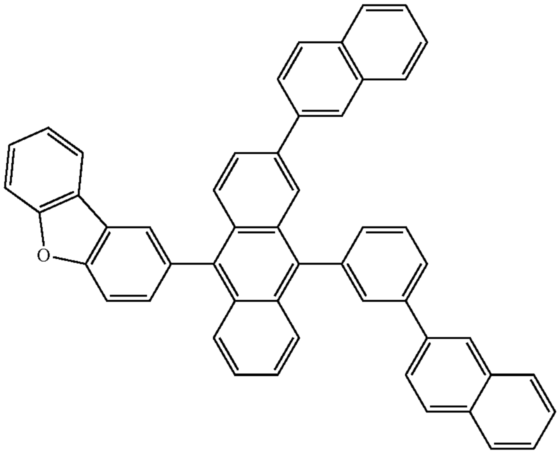
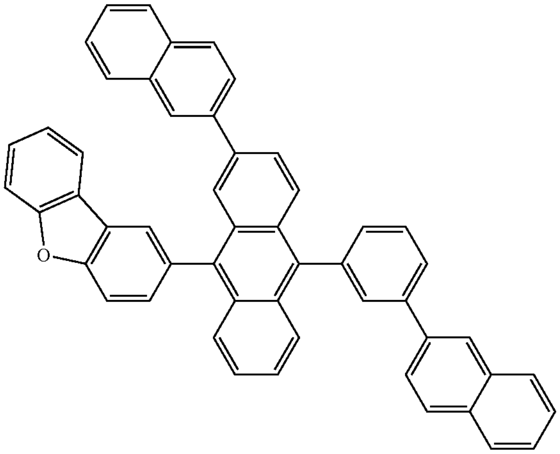
-continued
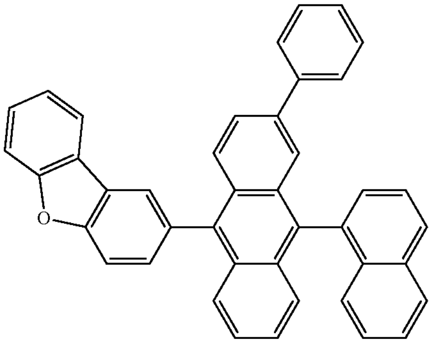
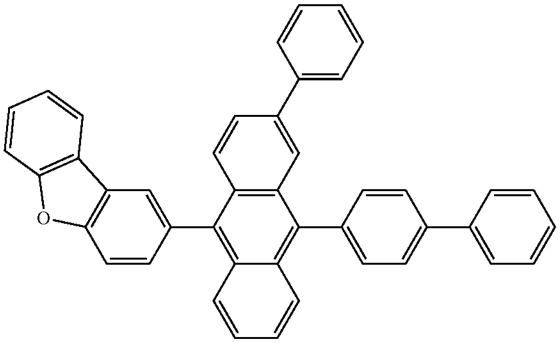
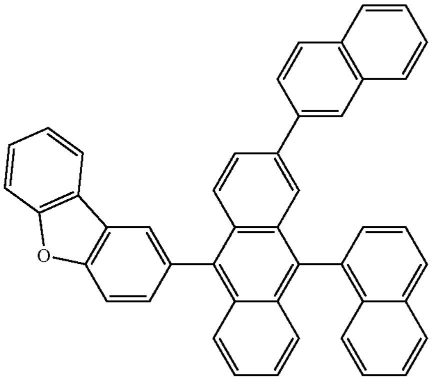
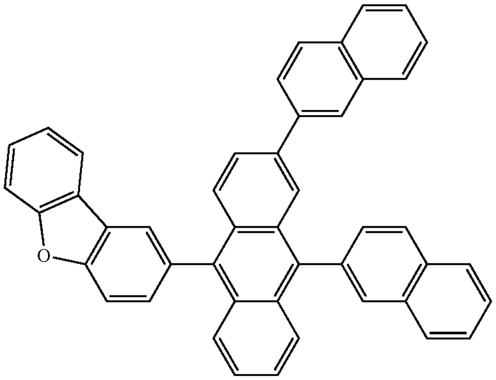

-continued
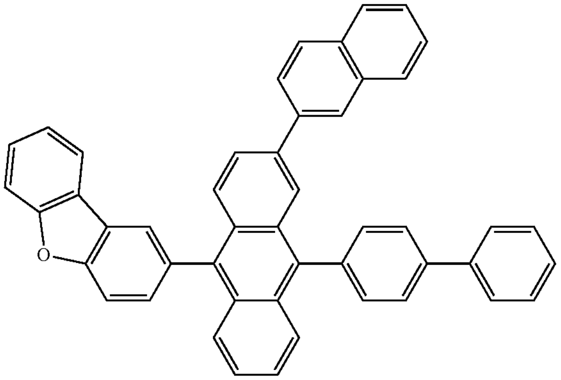
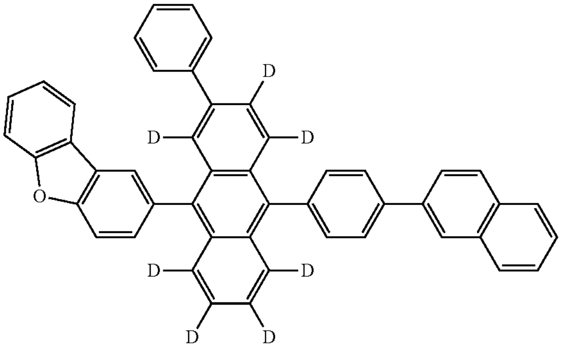
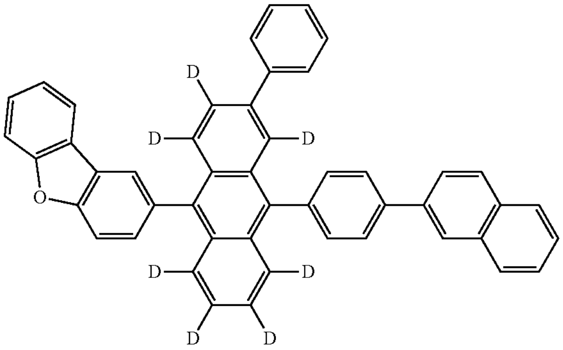
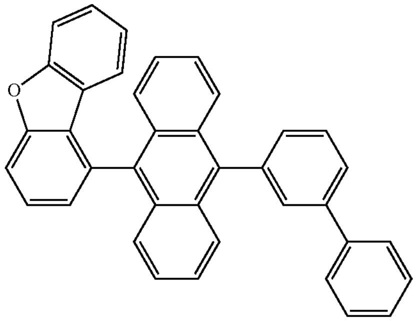
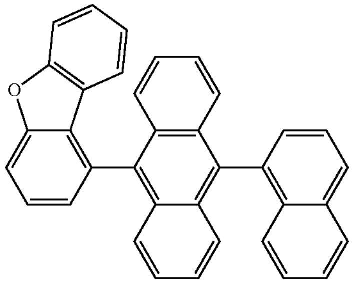
-continued
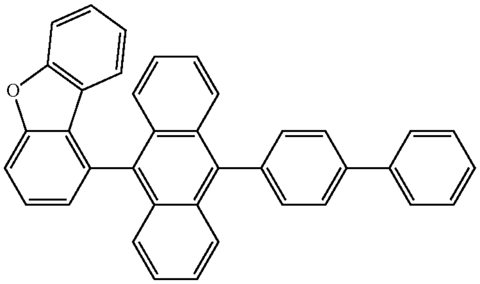
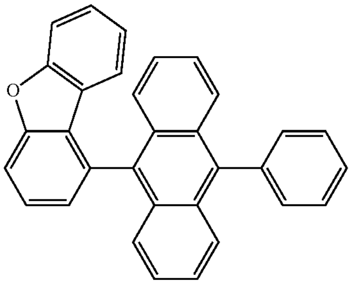
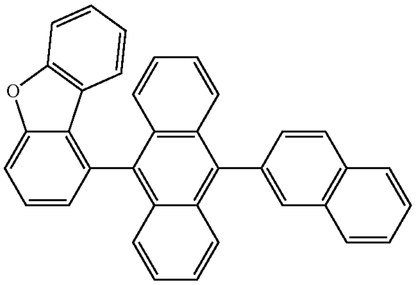
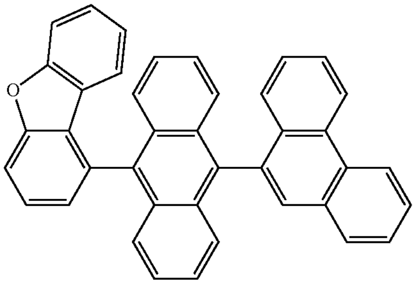
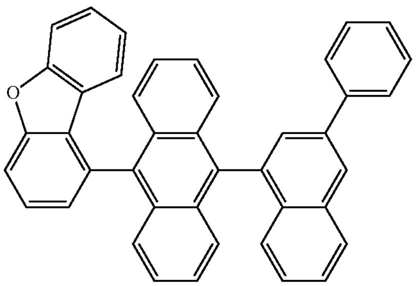

-continued
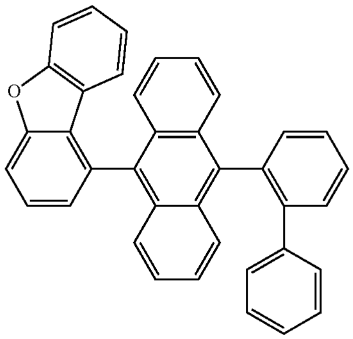
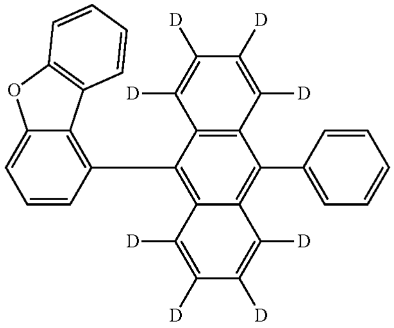
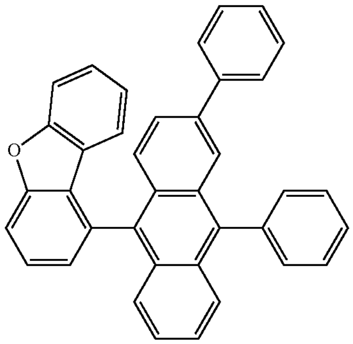
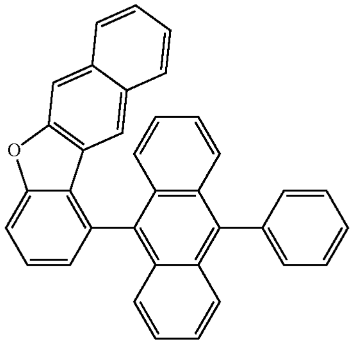
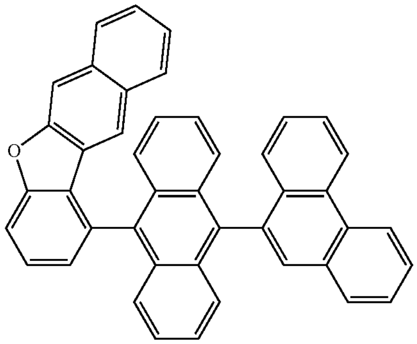
-continued
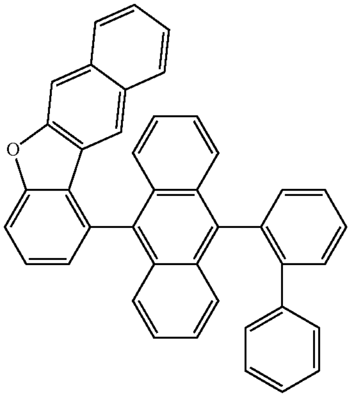
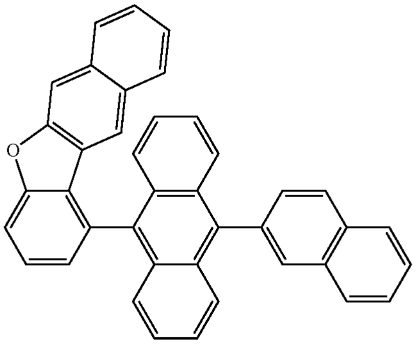
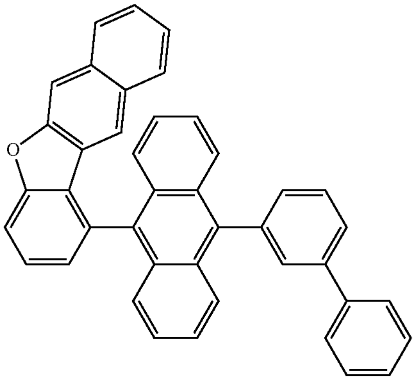
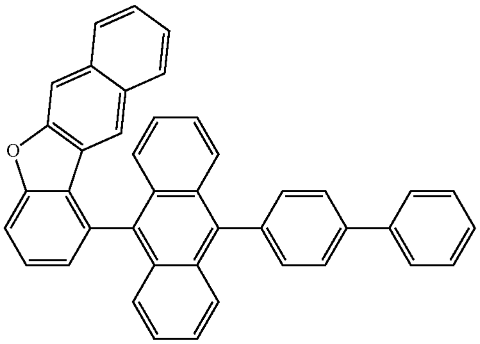

-continued
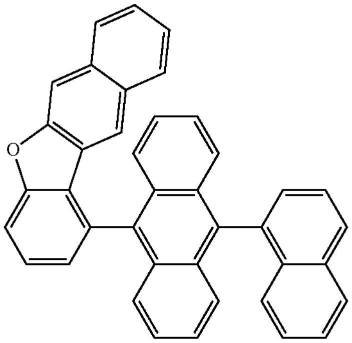
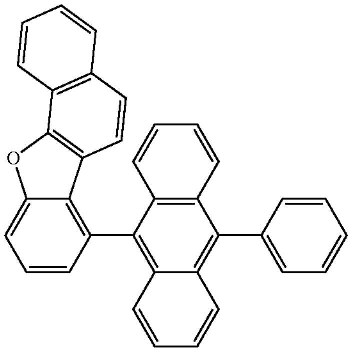
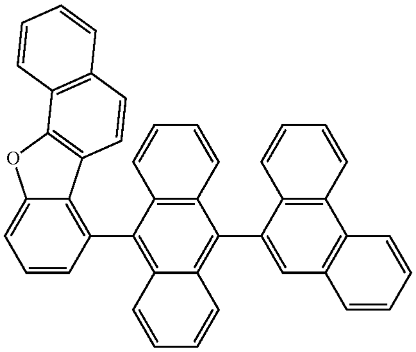
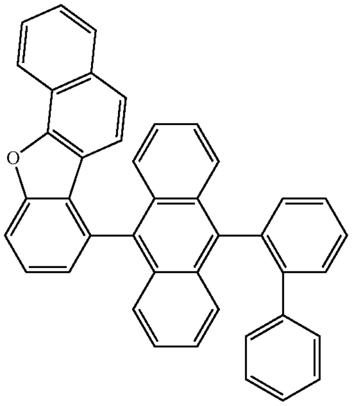
-continued
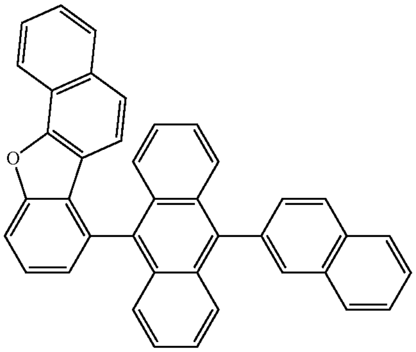
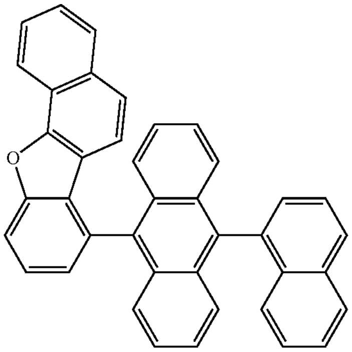
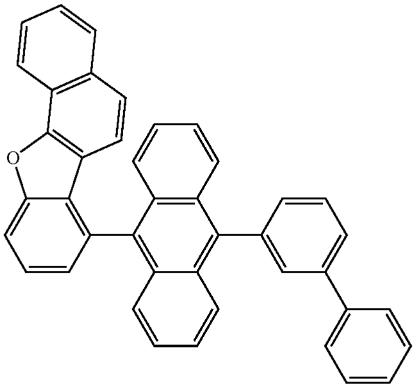
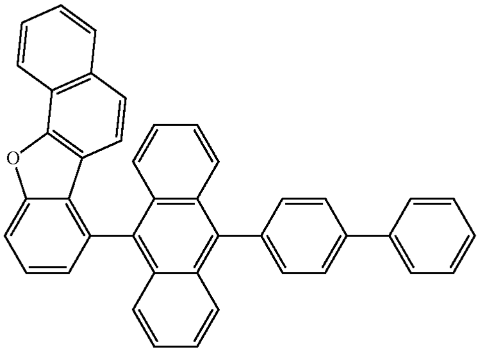
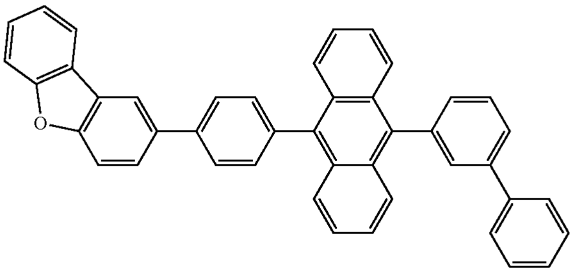

-continued
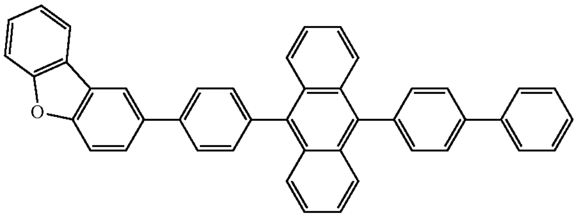
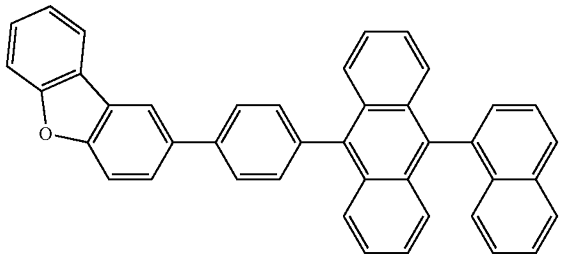
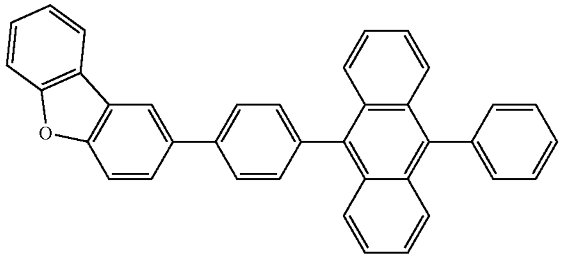
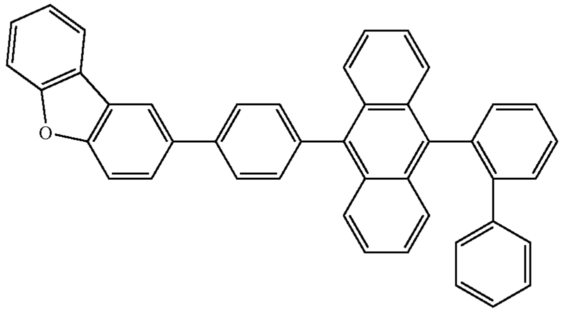
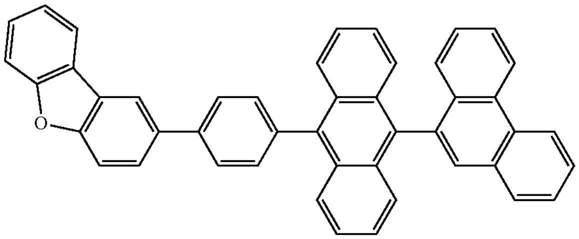
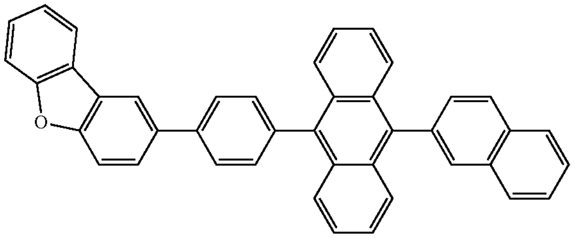
-continued
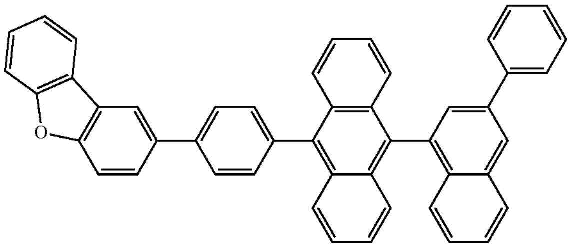
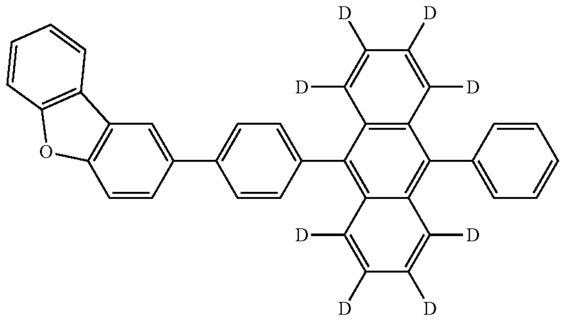
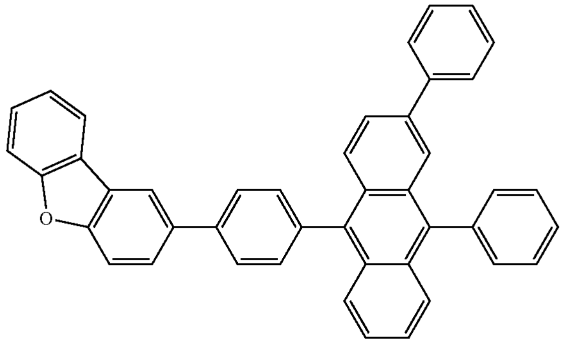
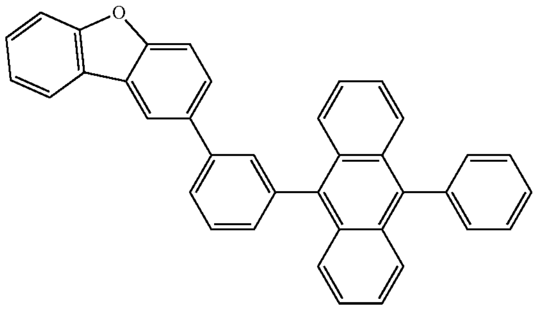
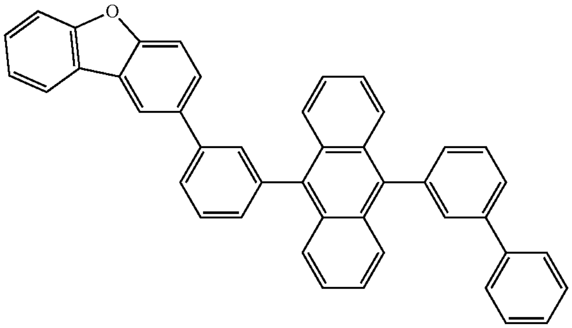

-continued
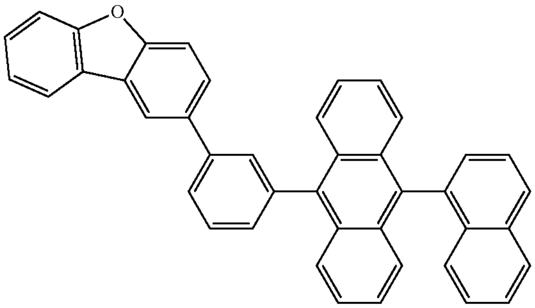
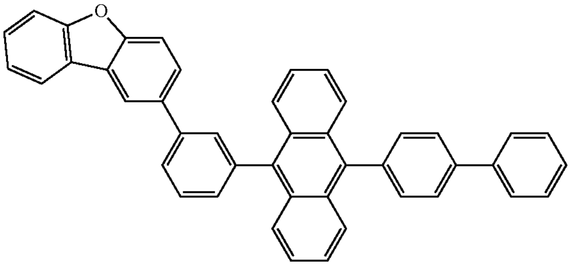
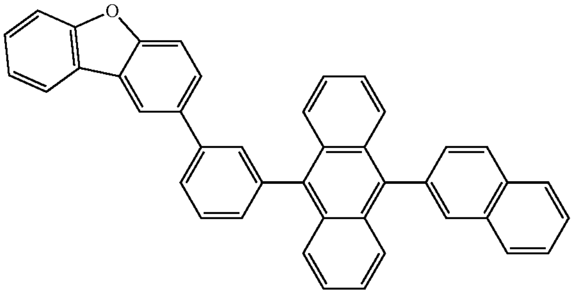
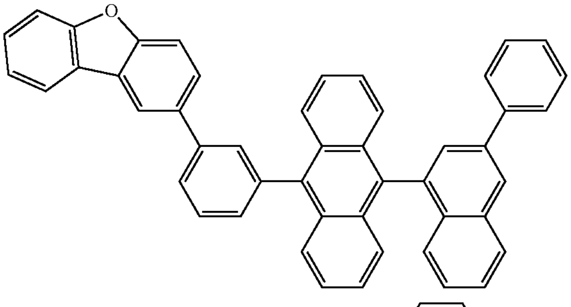
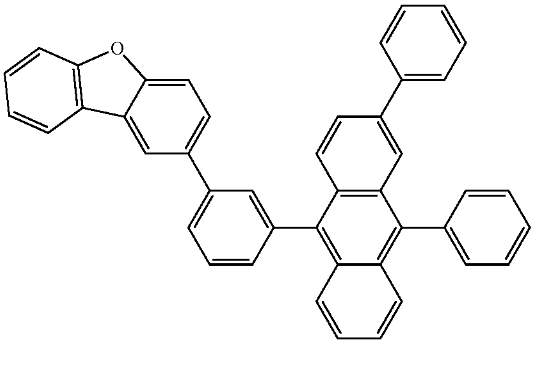
-continued
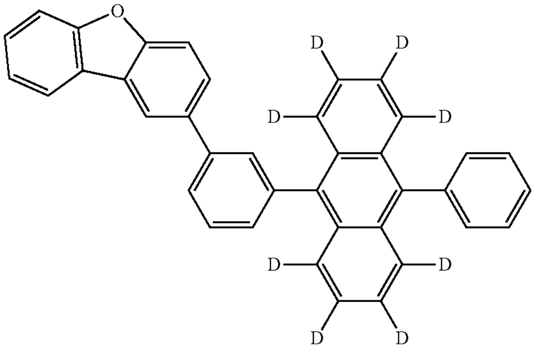
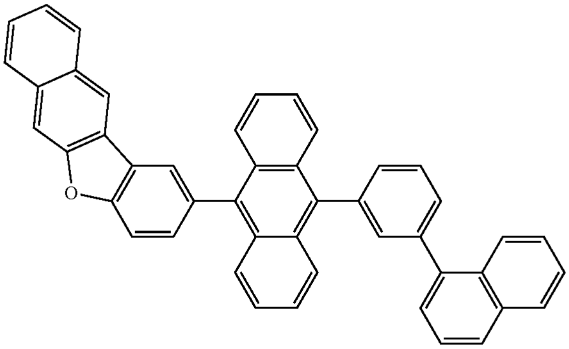
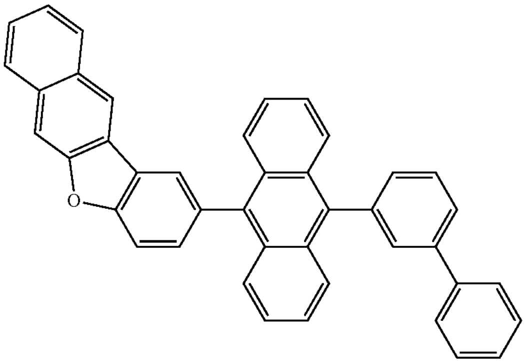
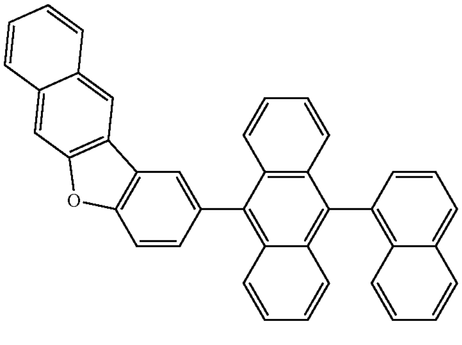

-continued
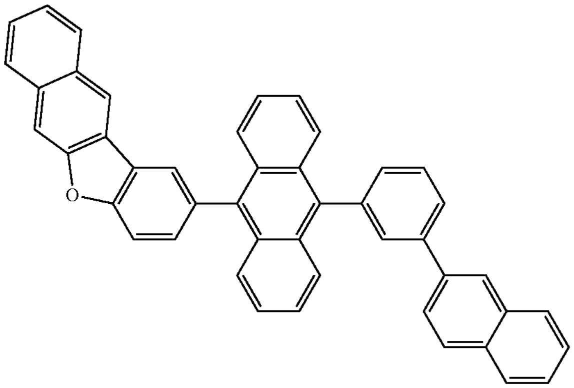
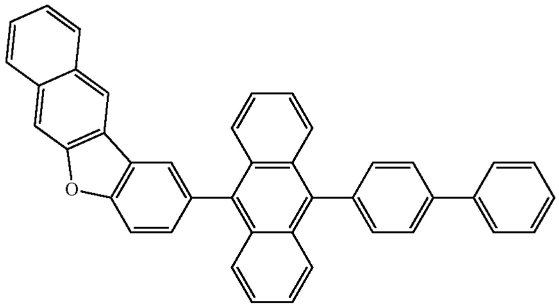
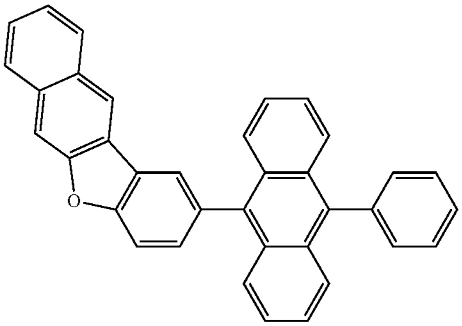
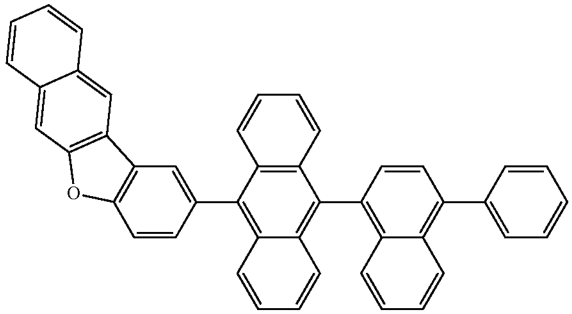
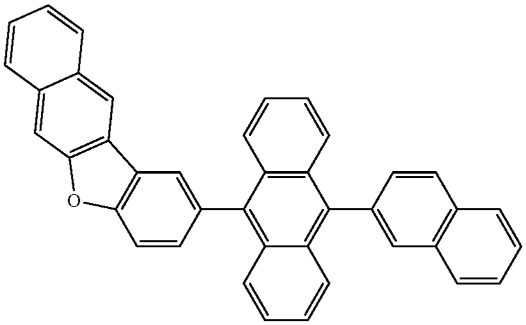
-continued
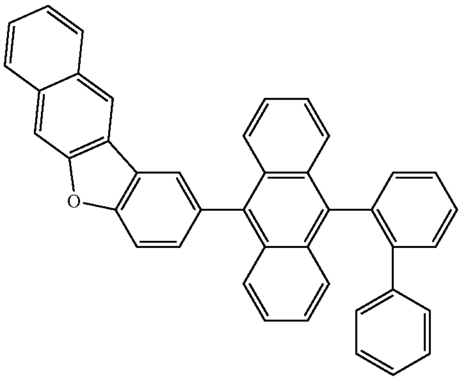
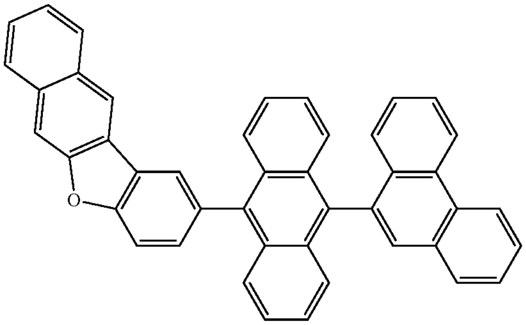
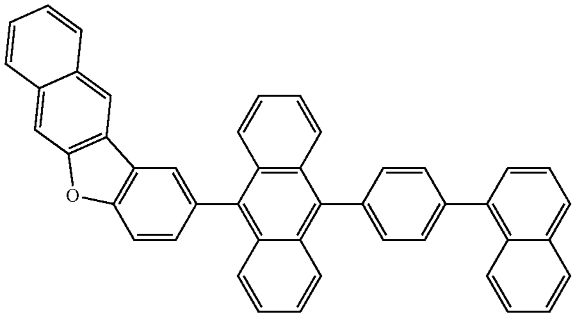
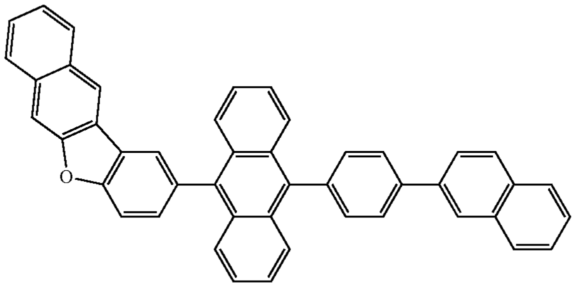
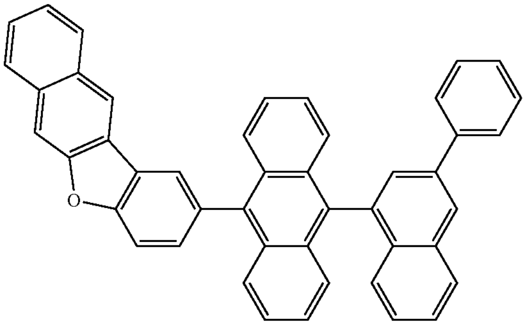

-continued
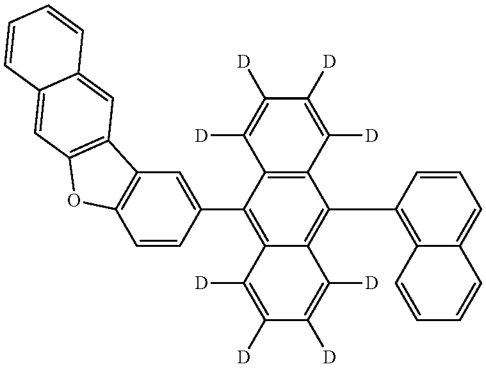
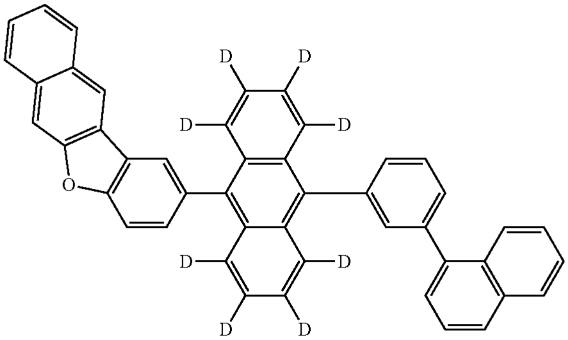
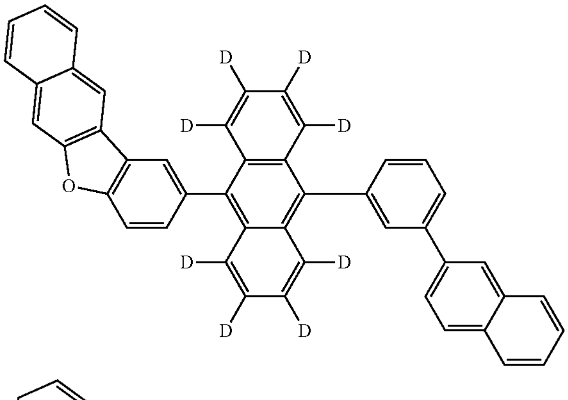
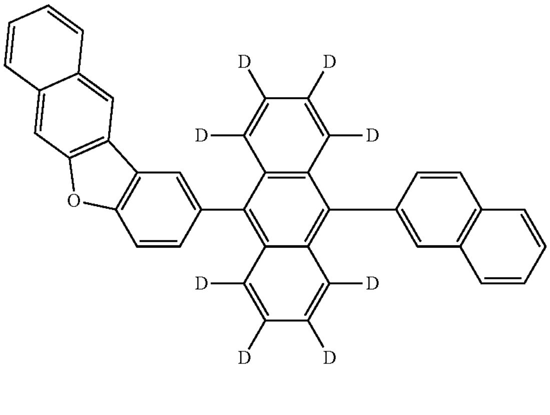
-continued
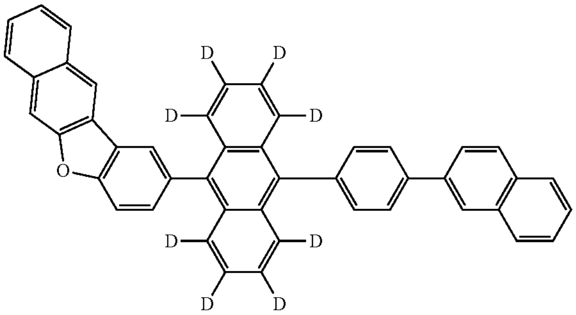
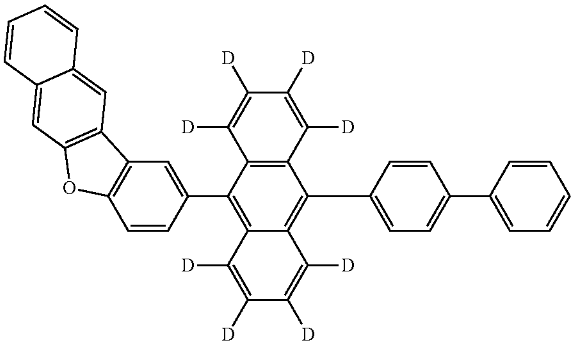
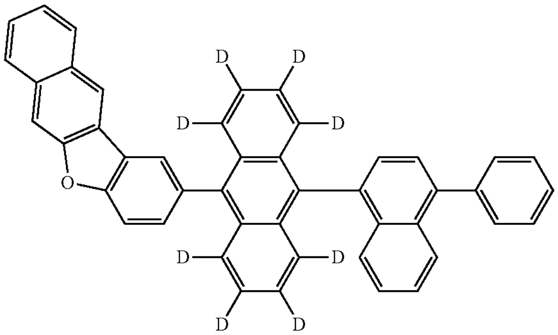
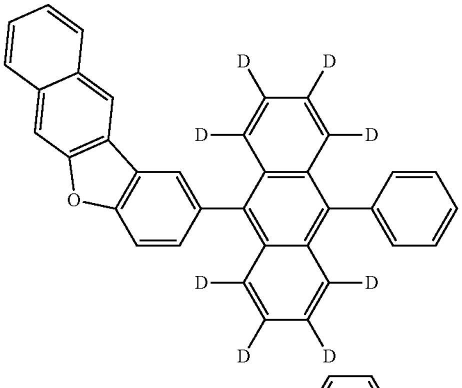
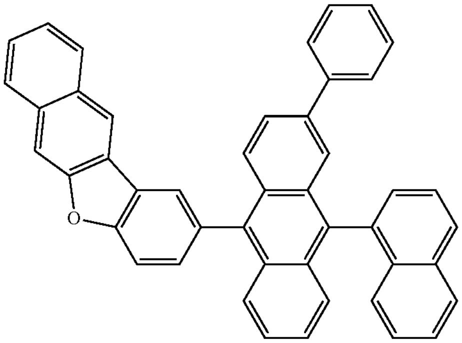

-continued
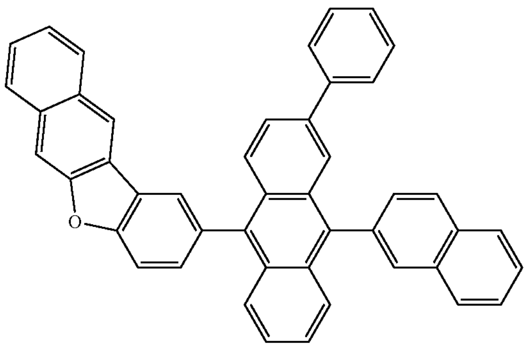
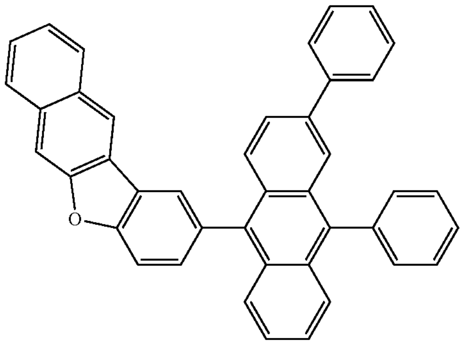
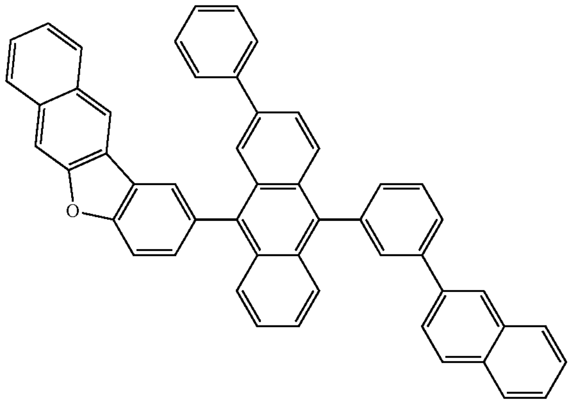
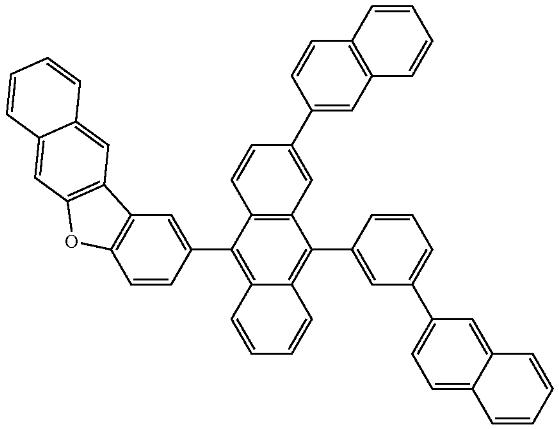
-continued
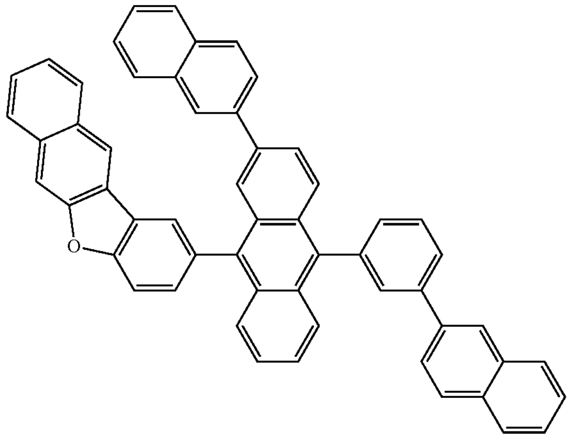
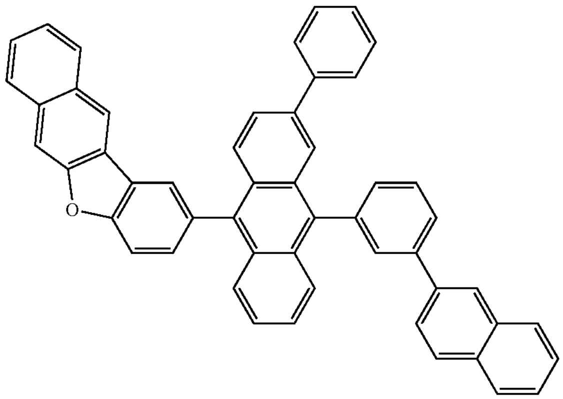
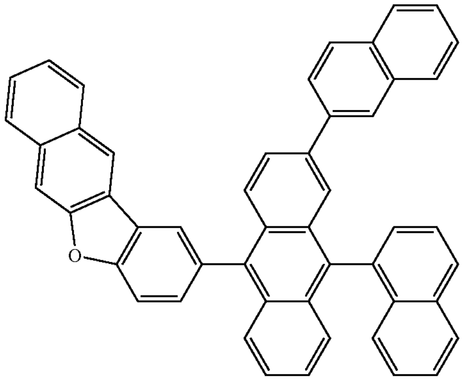
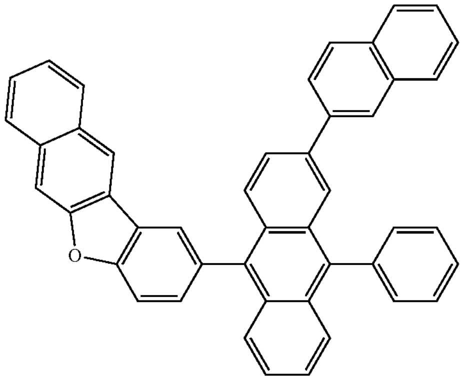

-continued
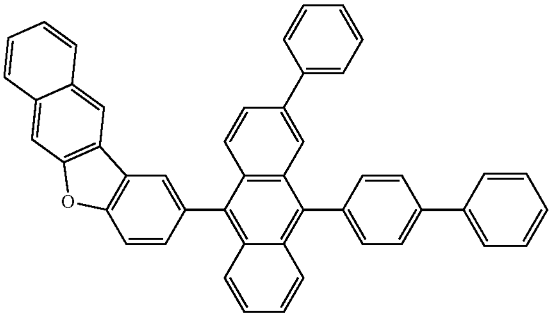
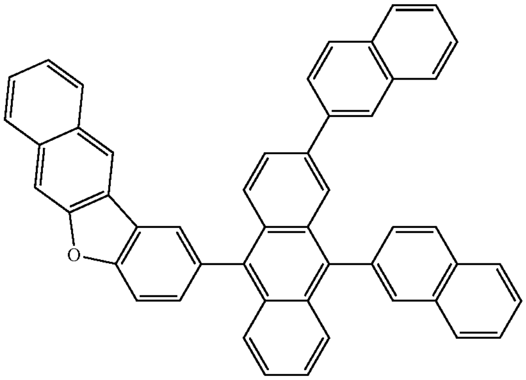
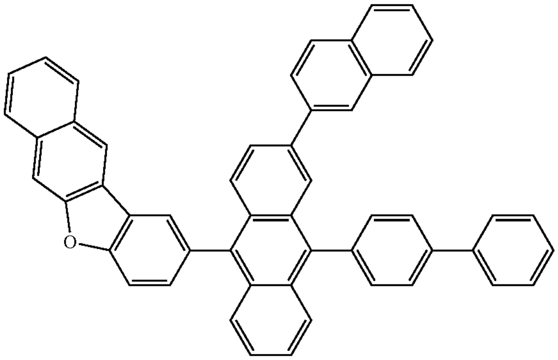
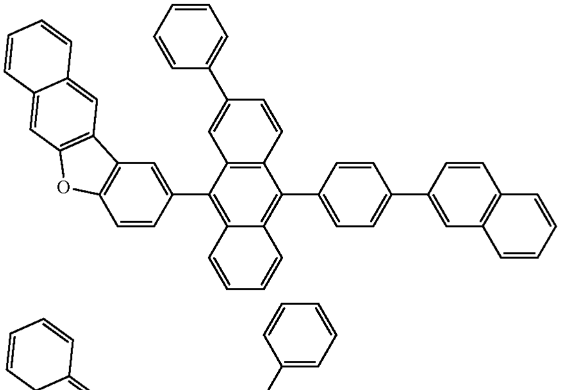
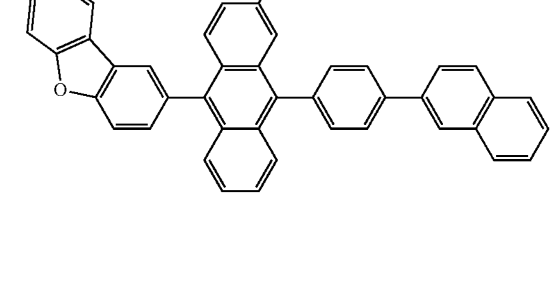
-continued
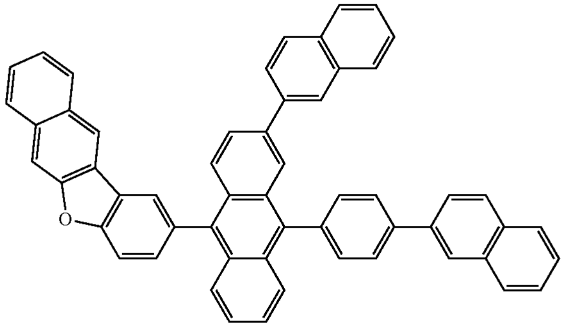
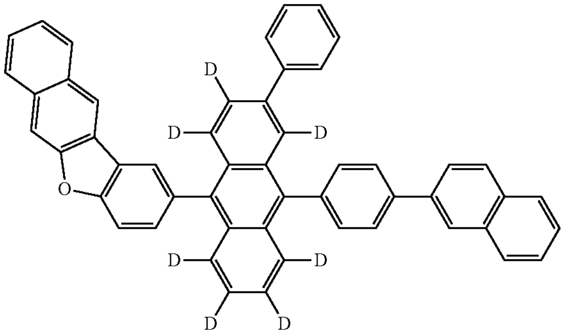
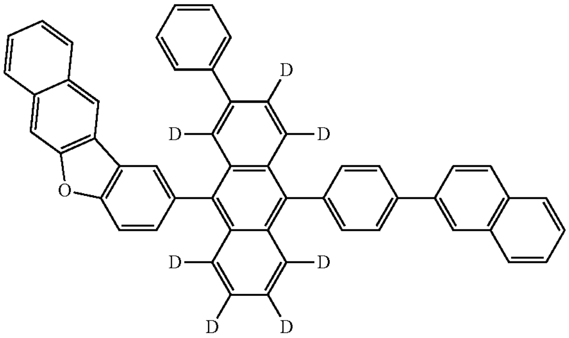
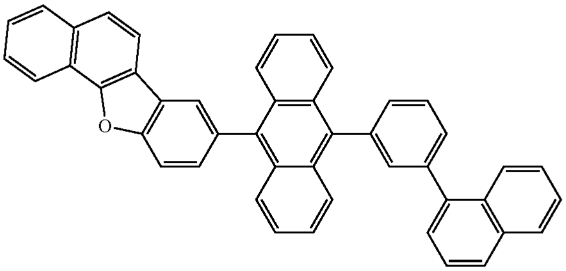
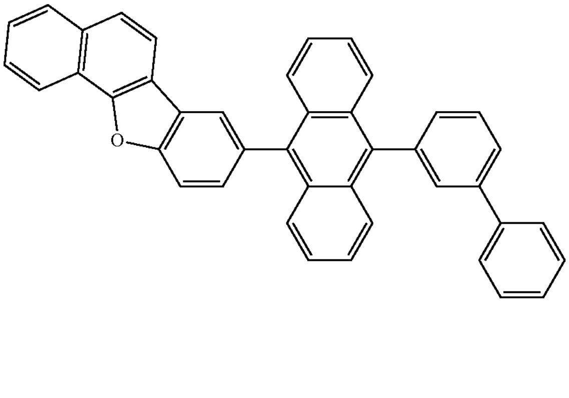

-continued
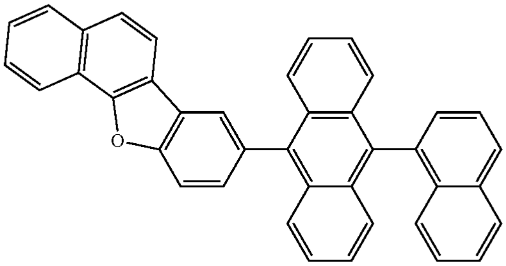
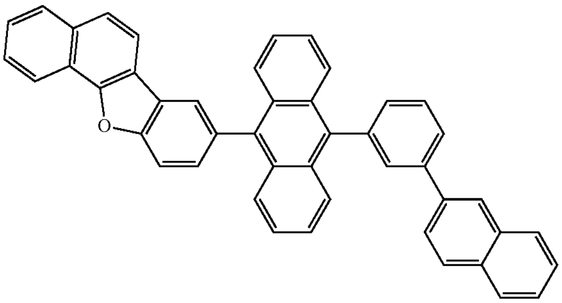
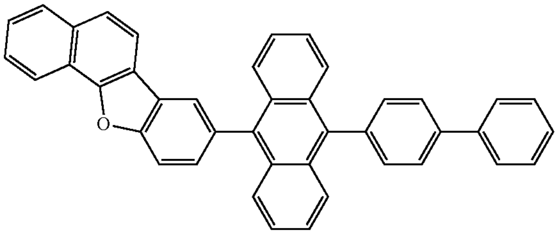
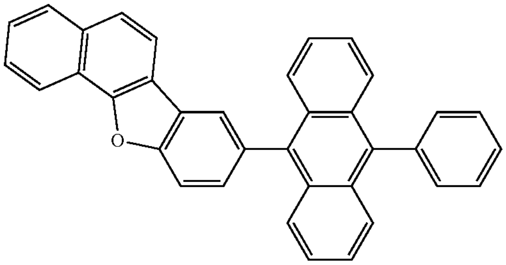
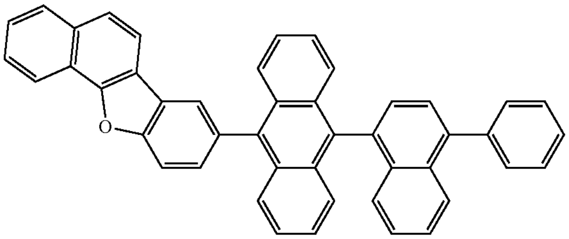
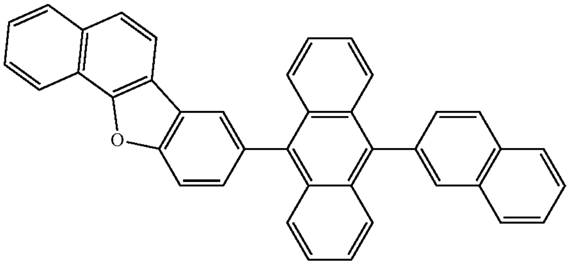
-continued
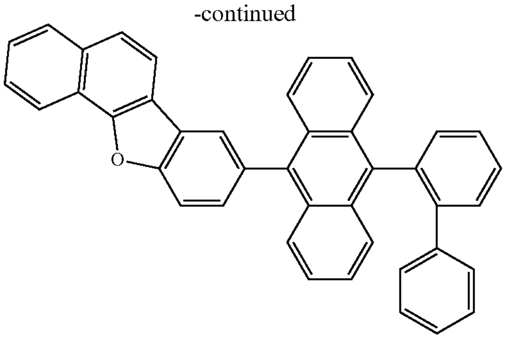
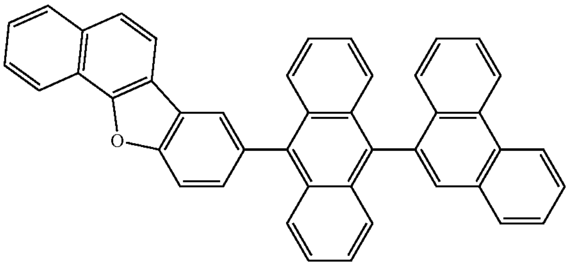
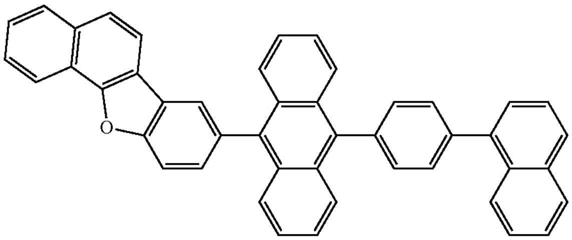
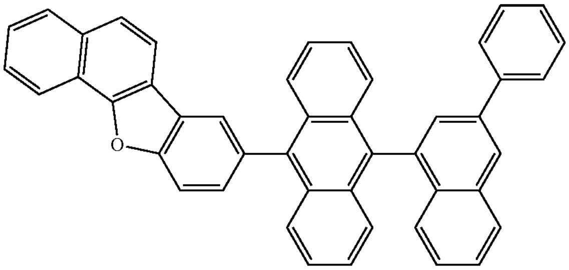
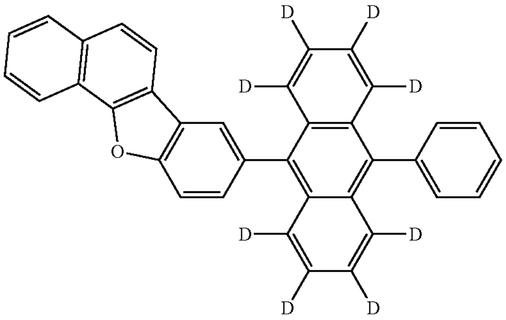
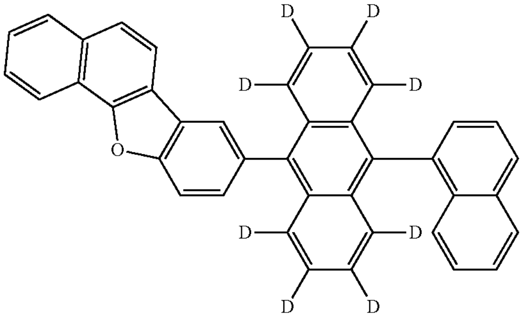

-continued
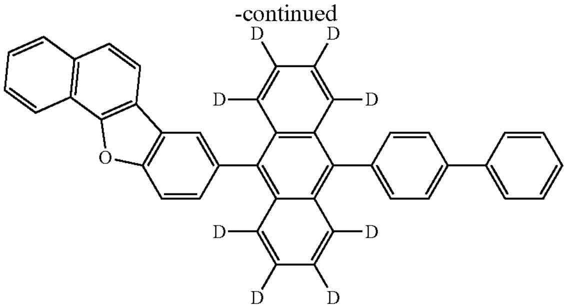
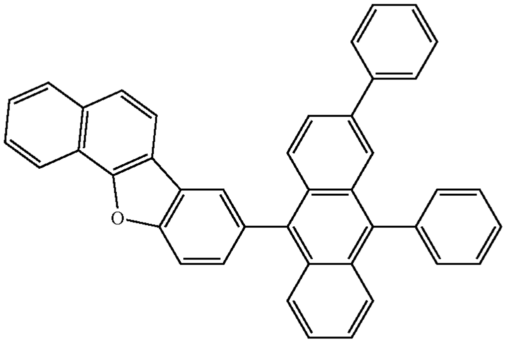
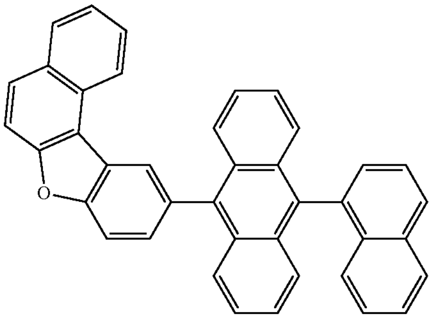
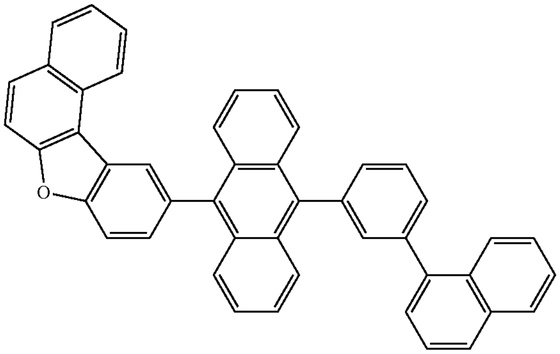
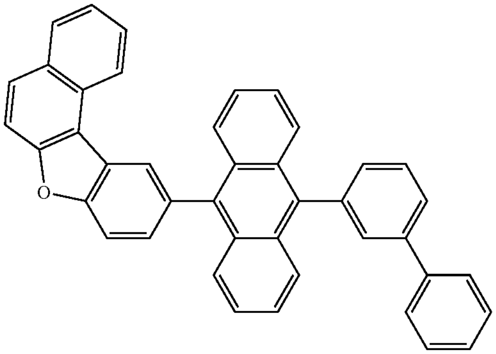
-continued
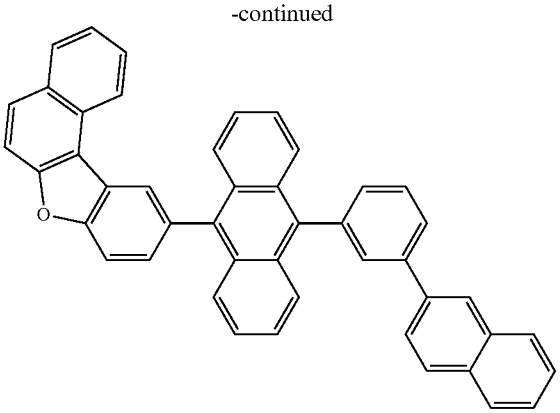
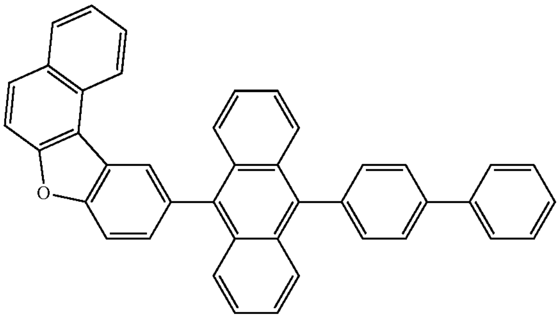
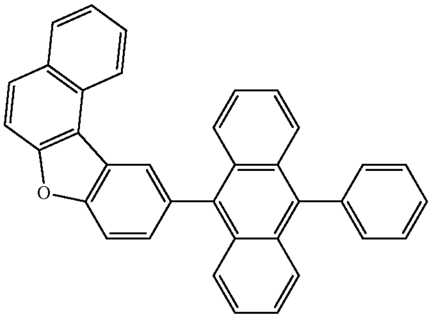
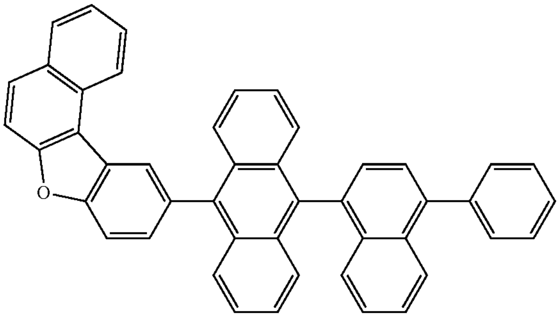
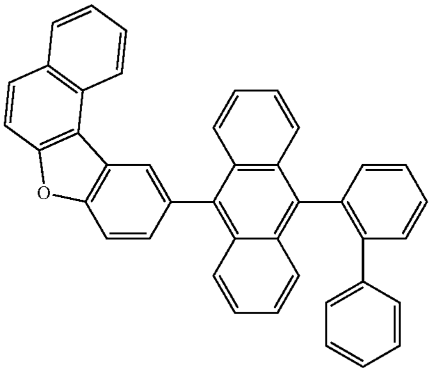

-continued
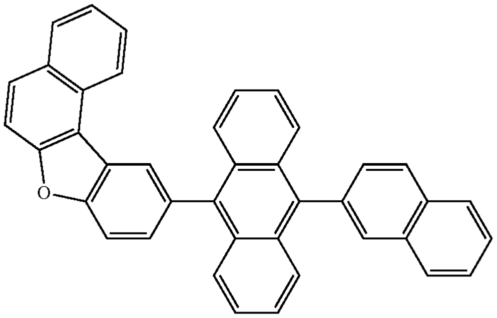
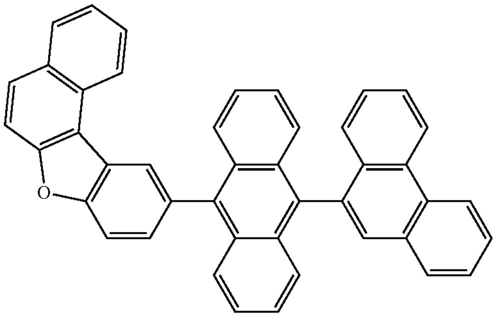
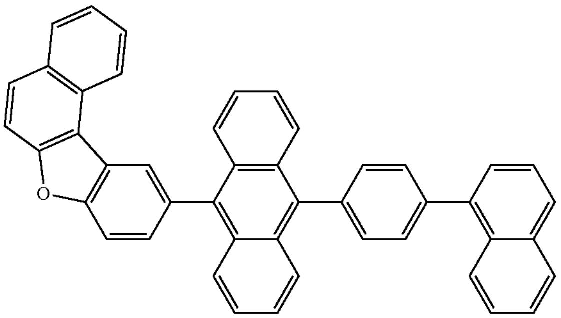
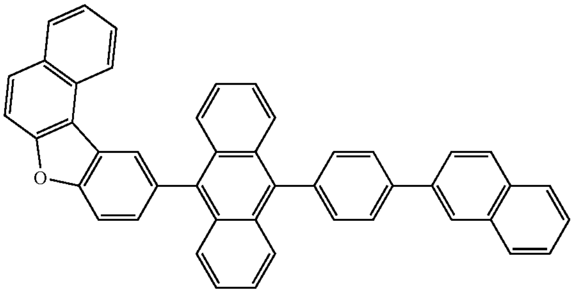
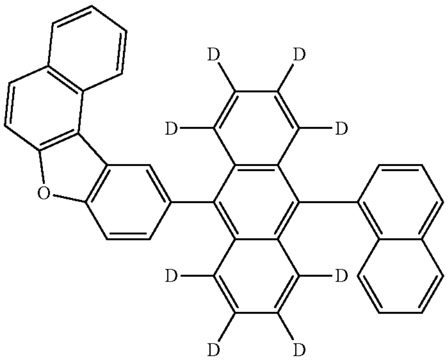
-continued
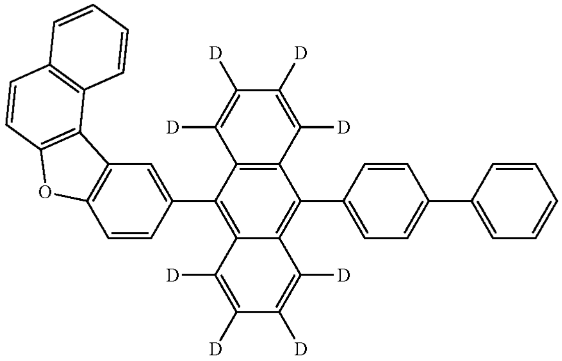
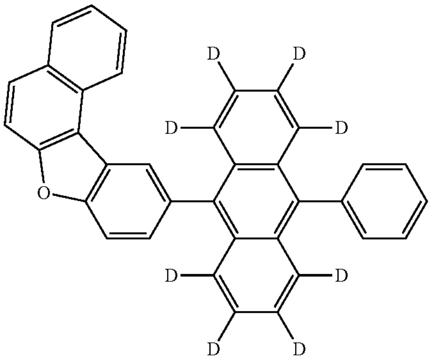
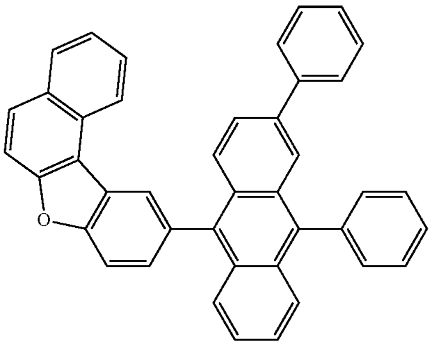
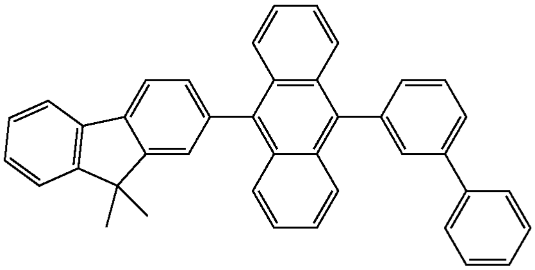
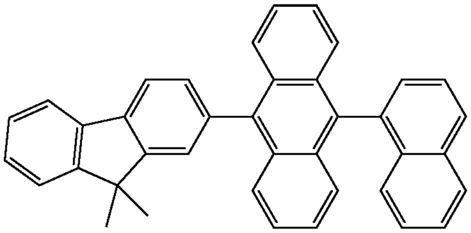

-continued
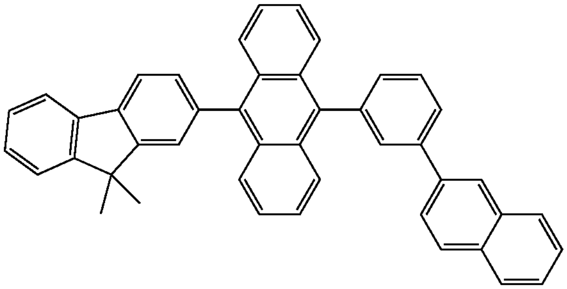
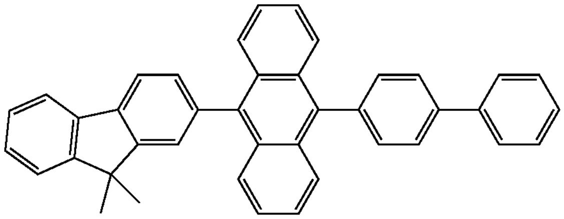
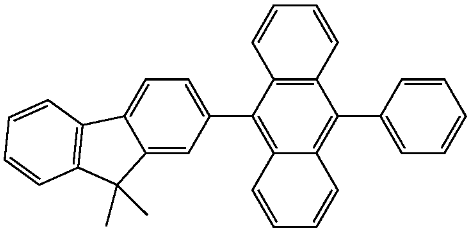
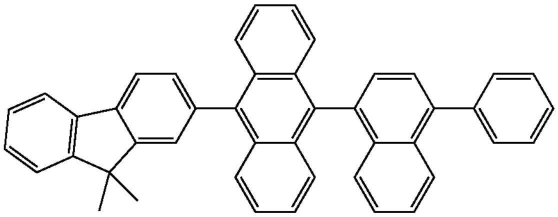
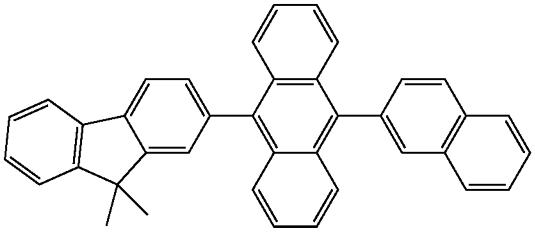
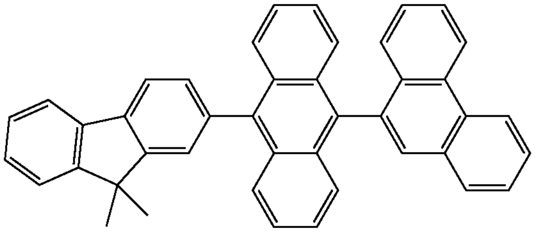
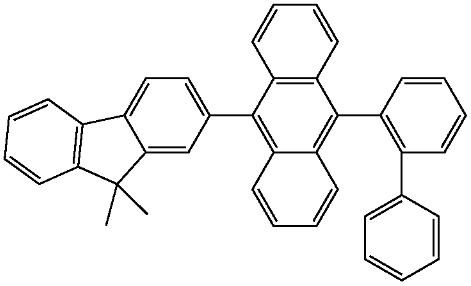
-continued
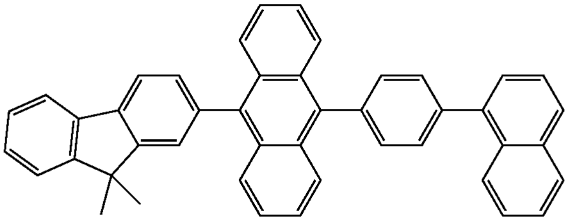
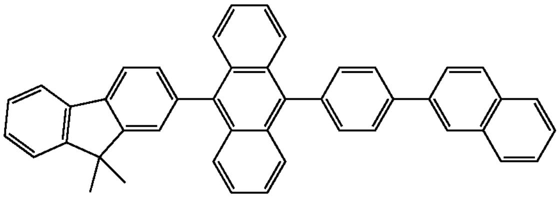
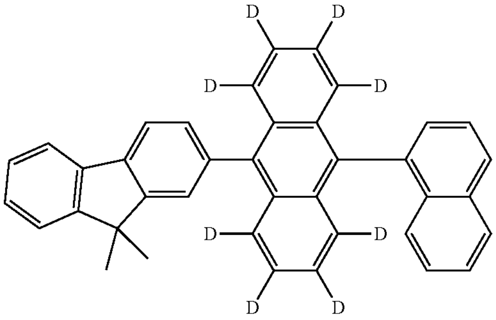
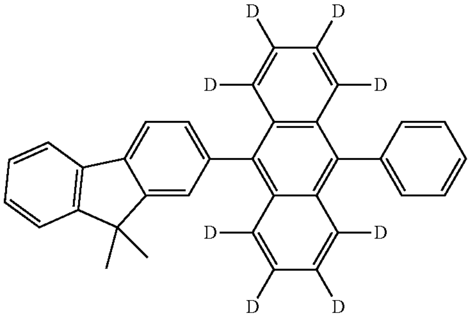
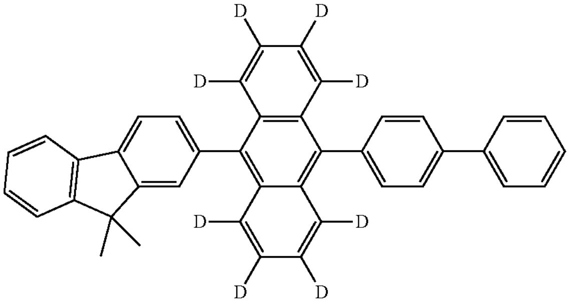
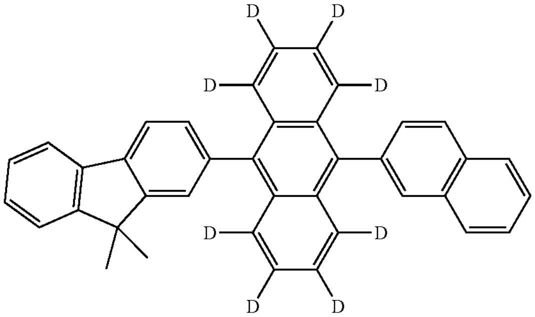

-continued
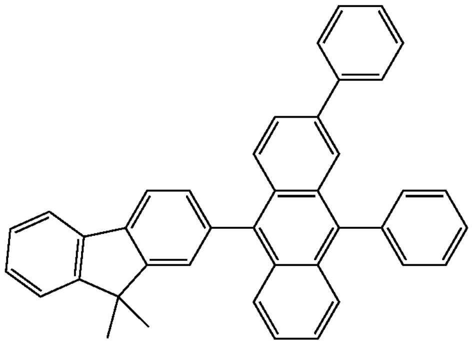
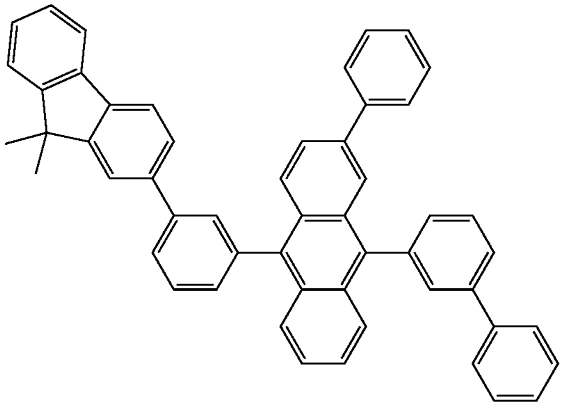
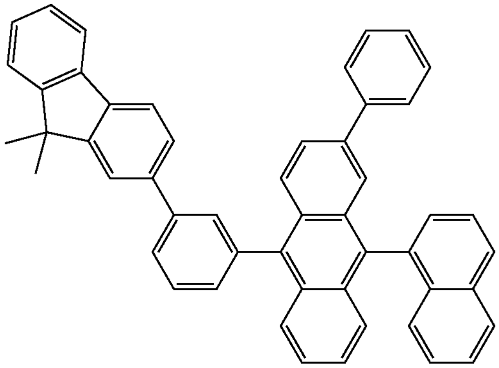
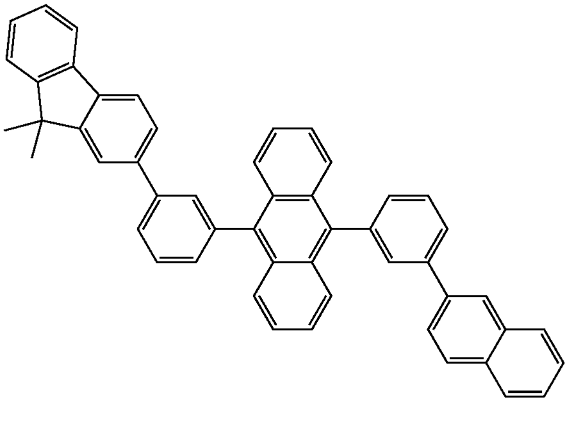
-continued
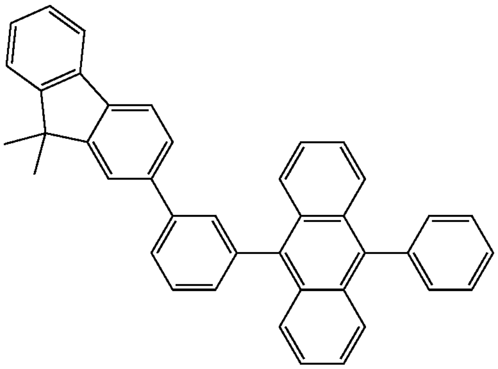
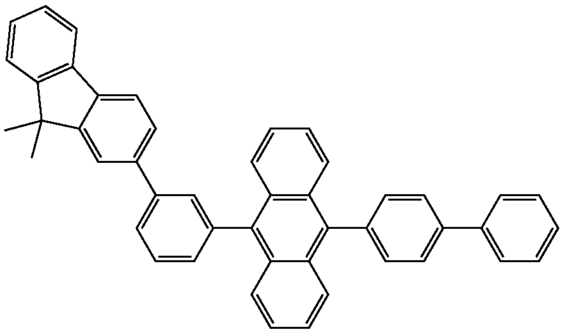
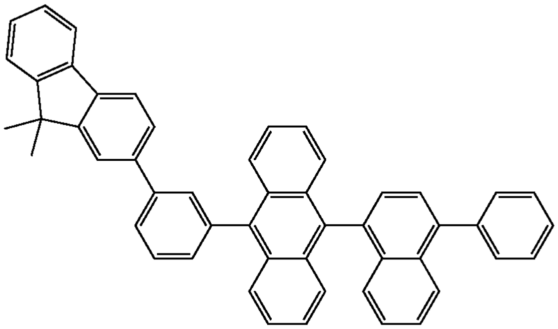
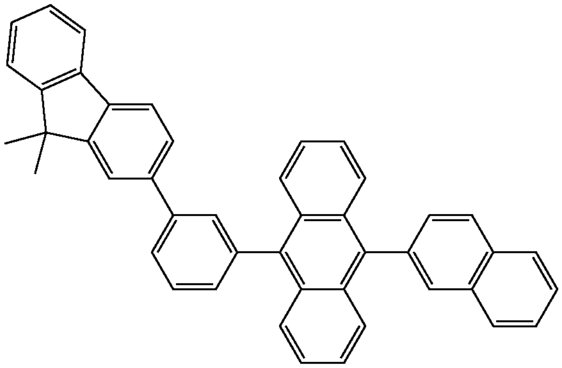

-continued
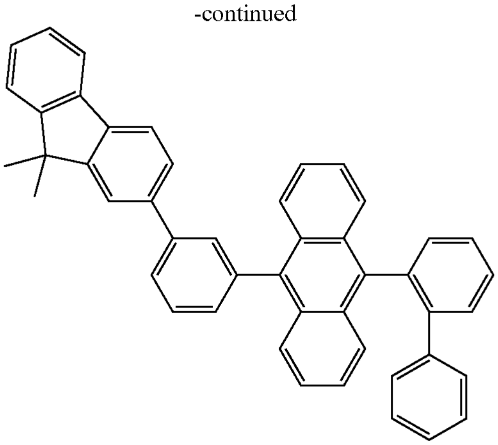
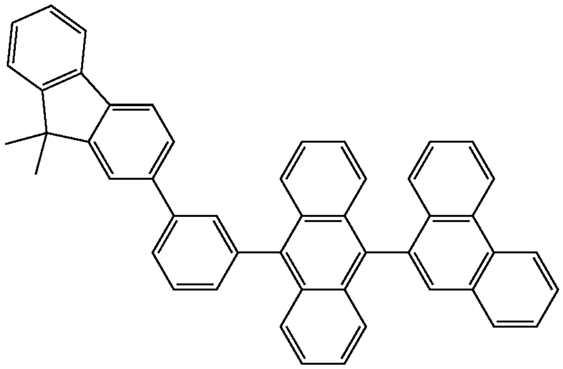
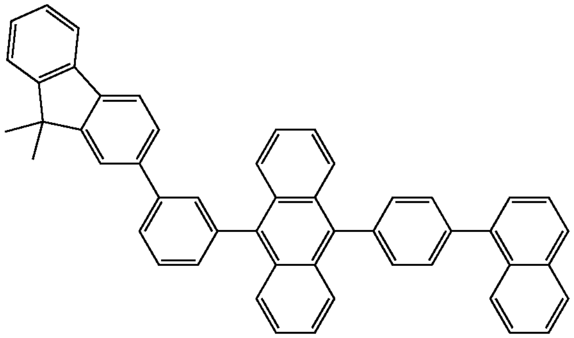
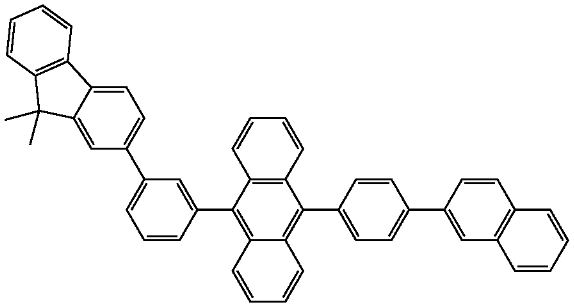
-continued
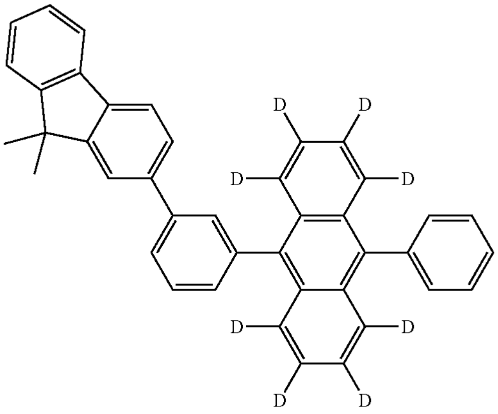
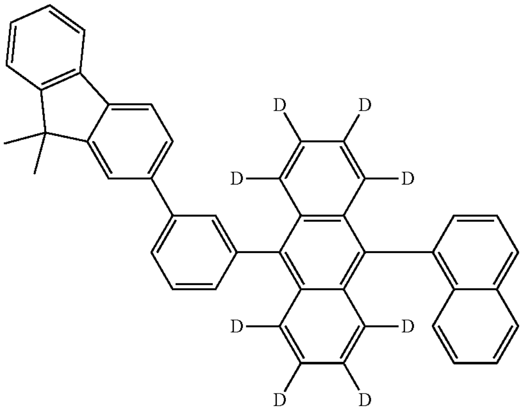
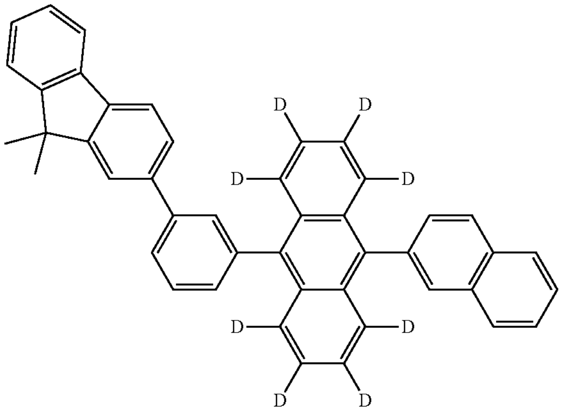
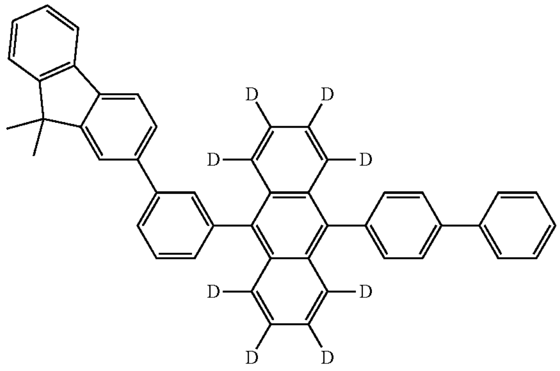

-continued
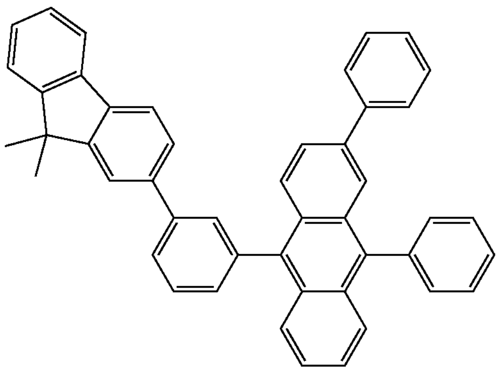
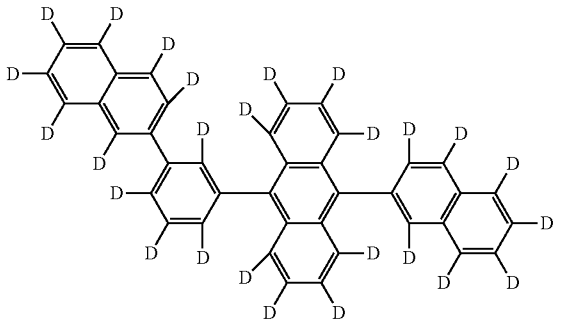
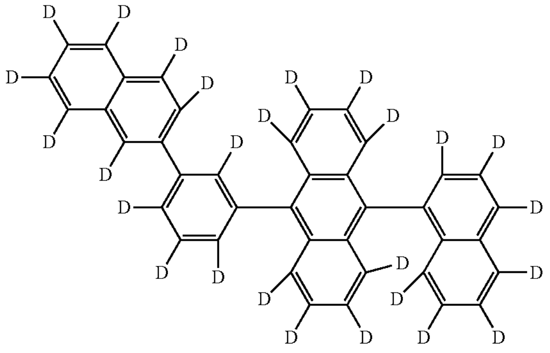
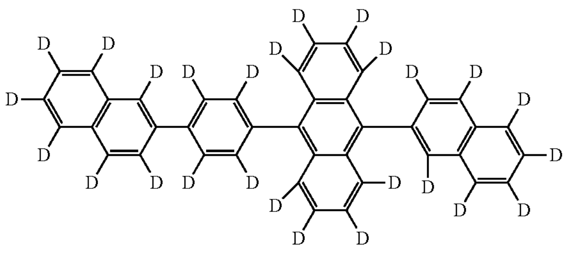
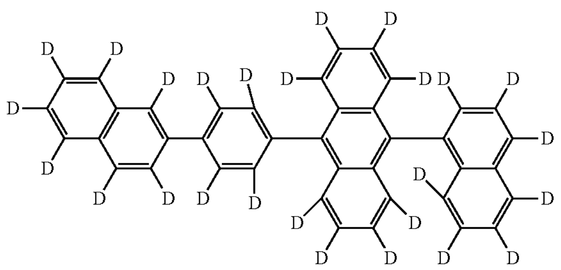
-continued
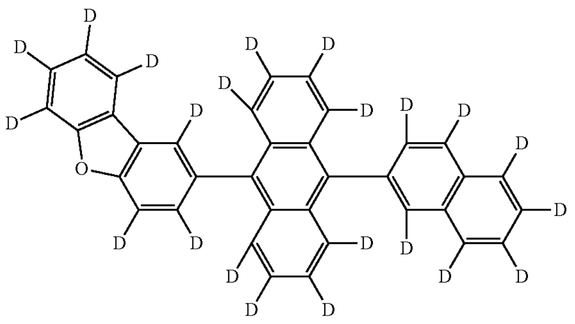
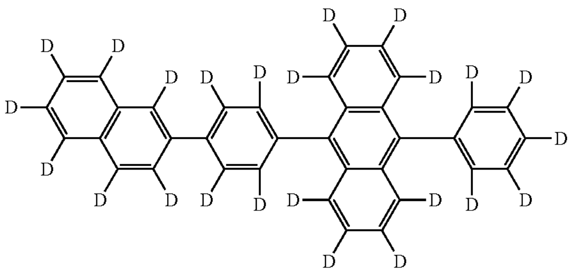
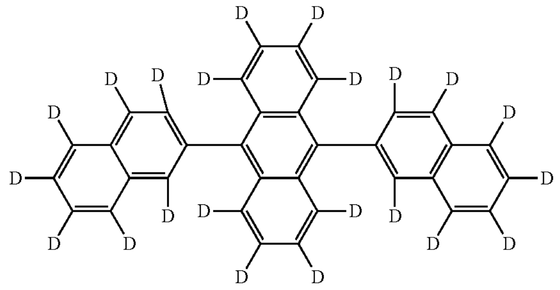
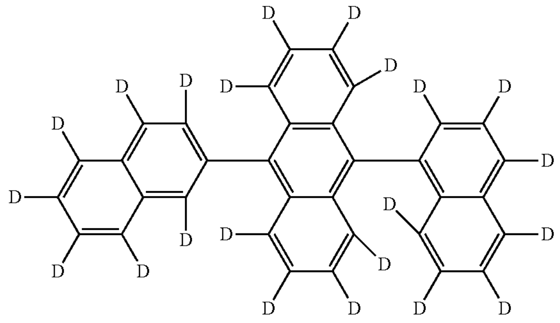
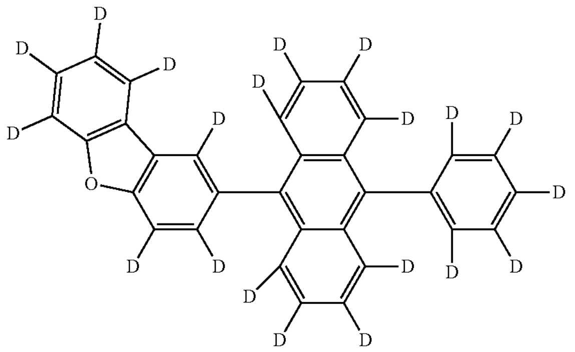

-continued

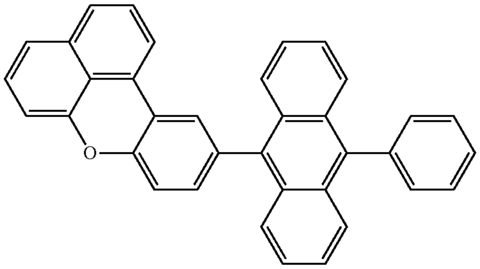

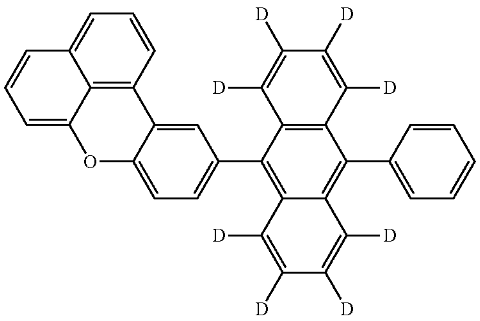

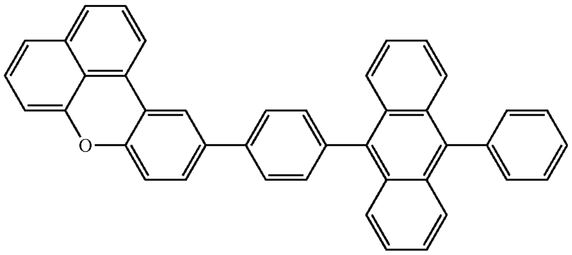

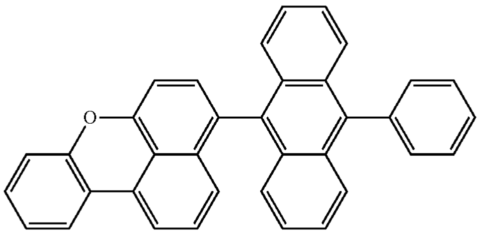

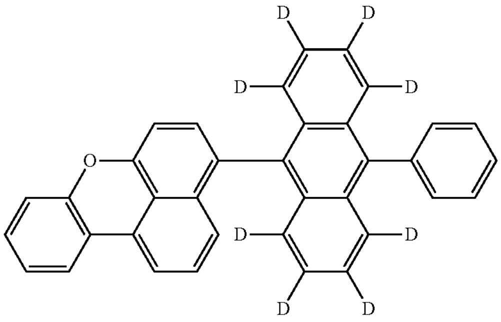

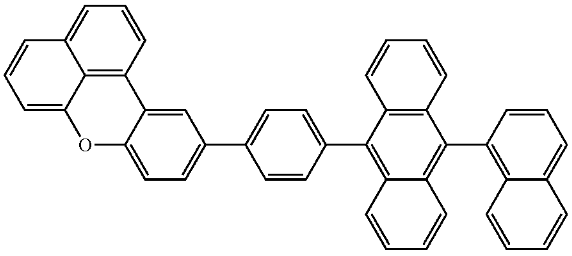

-continued

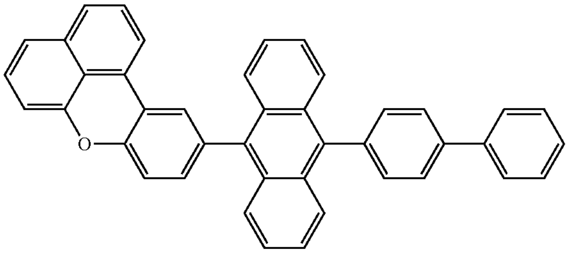

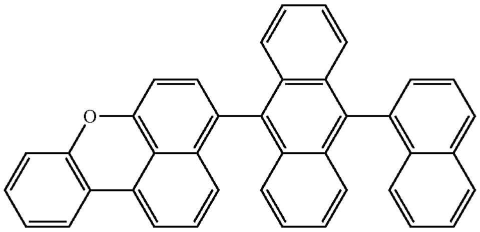

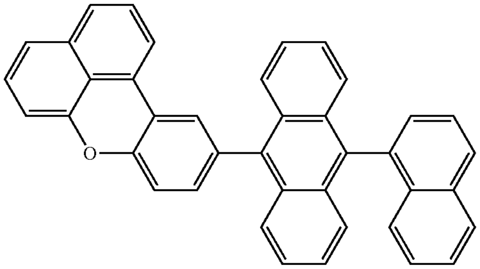

Specific examples of the above groups are as defined herein under subtitle "Definition."

Except that an organic EL device according to an exemplary embodiment of the invention includes the cathode, the anode, and the emitting layer between the cathode and the anode in which the emitting layer contains the compound according to the first exemplary embodiment as described above, conventionally known materials and device arrangements can be applied to the organic EL device according to an exemplary embodiment as long as the effects of the invention are not impaired.

A content of the compound according to the first exemplary embodiment in the emitting layer is preferably in a range from 1 mass % to 20 mass % with respect to a total mass of the emitting layer. The compound according to the first exemplary embodiment is preferably a dopant material.

In the organic EL device according to the exemplary embodiment, when the emitting layer contains a compound represented by the formula (H10), the emitting layer contains the compound represented by the formula (H10) preferably at 60 mass % or more, more preferably 70 mass % or more, and further preferably 80 mass % or more, with respect to the total mass of the emitting layer. The compound represented by the formula (H10) is preferably a host material.

When the emitting layer contains a compound represented by the formula (H10) as the host material and the compound according to the first exemplary embodiment as the dopant material, the upper limit of the total of the respective content ratios of the host material and the dopant material is 100 mass %.

Fourth Exemplary Embodiment

The organic EL device according to the fourth exemplary embodiment may be an organic EL device having two or more emitting layers.

The organic EL device according to the fourth exemplary embodiment is different from the organic EL device according to the third exemplary embodiment in having at least two emitting layers. The rest of the arrangement of the organic EL device according to the fourth exemplary embodiment is the same as in the third exemplary embodiment.

In the description of the fourth exemplary embodiment, the same components as those in the third exemplary embodiment are denoted by the same reference signs and names to simplify or omit an explanation of the components. In the fourth exemplary embodiment, any materials and compounds that are not specified may be the same as materials and compounds described in the first and third exemplary embodiments.

An arrangement of an organic EL device according to the exemplary embodiment will be described.

In the organic EL device according to the exemplary embodiment, the emitting layer includes a first emitting layer and a second emitting layer. The first emitting layer contains a first host material and a first dopant material. The second emitting layer contains a second host material and a second dopant material. The first host material and the second host material are mutually different. The first dopant material and the second dopant material are mutually the same or different.

The organic EL device according to the exemplary embodiment includes at least two layers (e.g., the first emitting layer and the second emitting layer) as the emitting layer. The first emitting layer according to the exemplary embodiment has the similar arrangement of the emitting layer of the organic EL device according to the third exemplary embodiment. In the following, parts different from the first exemplary embodiment are mainly described and duplicate explanations are omitted or simplified.

The organic EL device according to the exemplary embodiment enables a long lifetime and an improved luminous efficiency by using Triplet-Triplet-Annihilation (sometimes referred to as TTA).

TTA is a mechanism in which triplet excitons collide with one another to generate singlet excitons. TTA mechanism is sometimes referred to as TTF mechanism as described in International Publication No. WO2010/134350.

TTF phenomenon is described. Holes injected from an anode and electrons injected from a cathode are recombined in the emitting layer to generate excitons. As for the spin state, as is conventionally known, singlet excitons account for 25% and triplet excitons account for 75%. In a conventionally known fluorescent device, light is emitted when singlet excitons of 25% are relaxed to the ground state. The remaining triplet excitons of 75% are returned to the ground state without emitting light through a thermal deactivation process. Accordingly, the theoretical limit value of the internal quantum efficiency of a conventional fluorescent device is believed to be 25%.

The behavior of triplet excitons generated within an organic substance has been theoretically examined. According to S. M. Bachilo et al. (J. Phys. Chem. A, 104, 7711 (2000)), assuming that high-order excitons such as quintet excitons are quickly returned to triplet excitons, triplet excitons (hereinafter abbreviated as 3A*) collide with one another with an increase in the density thereof, whereby a reaction shown by the following formula occurs. In the formula, $^1A$ represents the ground state and $^1A^*$ represents the lowest singlet excitons.

$$^3A^*+^3A^*\rightarrow(4/9)^1A+(1/9)^1A^*+(13/9)^3A^*$$

In other words, $5^3A^*\rightarrow4^1A+1A^*$ is satisfied, and it is expected that, among triplet excitons initially generated, which account for 75%, one fifth thereof (i.e., 20%) is changed to singlet excitons. Accordingly, the amount of singlet excitons which contribute to emission is 40%, which is a value obtained by adding 15% (75%×(1/5)=15%) to 25%, which is the amount ratio of initially generated singlet excitons. At this time, a ratio of a luminous intensity derived from TTF (TTF ratio) relative to the total luminous intensity is 15/40, i.e., 37.5%. Assuming that singlet excitons are generated by collision of initially generated triplet excitons accounting for 75% (i.e., one singlet exciton is generated from two triplet excitons), a significantly high internal quantum efficiency of 62.5% is obtained, which is a value obtained by adding 37.5% (75%×(1/2)=37.5%) to 25% (the amount ratio of initially generated singlet excitons). At this time, the TTF ratio is 37.5/62.5=60%.

In the organic EL device according to the exemplary embodiment, in terms of expressing the TTF mechanism, a triplet energy $T_1$(H1) of the first host material and a triplet energy $T_1$(H2) of the second host material preferably satisfy a relationship represented by a numerical formula (Numerical Formula 1), more preferably satisfy a relationship represented by a numerical formula (Numerical Formula 2).

$$T_1(H2)>T_1(H1) \quad \text{(Numerical Formula 1)}$$

$$T_1(H2)-T_1(H1)>0.03\text{ eV} \quad \text{(Numerical Formula 2)}$$

In the organic electroluminescence device according to the exemplary embodiment, it is considered that since the relationship represented by the numerical formula (Numerical Formula 1) is satisfied, triplet excitons generated by recombination of holes and electrons in the second emitting layer and present on an interface between the second emitting layer and organic layer(s) in direct contact therewith are not likely to be quenched even under the presence of excessive carriers on the interface between the second emitting layer and the organic layer(s). For instance, the presence of a recombination region locally on an interface between the second emitting layer and a hole transporting layer or an electron blocking layer is considered to cause quenching by excessive electrons. For instance, the presence of a recombination region locally on an interface between the second emitting layer and a hole transporting layer or an electron blocking layer is considered to cause quenching by excessive holes.

In the organic electroluminescence device according to the exemplary embodiment, by including the first emitting layer and the second emitting layer so as to satisfy the numerical formula (Numerical Formula 1), triplet excitons generated in the second emitting layer can transfer to the first emitting layer without being quenched by excessive carriers and be inhibited from back-transferring from the first emitting layer to the second emitting layer. Consequently, the first emitting layer expresses the TTF mechanism to efficiently generate singlet excitons, thereby improving the luminous efficiency.

Accordingly, the organic EL device includes, as different regions, the second emitting layer mainly generating triplet excitons and the first emitting layer mainly exhibiting the TTF mechanism using triplet excitons having transferred from the second emitting layer, and a difference in triplet energy is provided by using a compound having a smaller triplet energy than that of the second host material in the second emitting layer as the first host material in the first emitting layer, thereby improving the luminous efficiency.

The organic EL device according to the exemplary embodiment can prolong a lifetime and further improve the luminous efficiency by selecting a combination of the host materials satisfying the relationship of the numerical formula (Numerical Formula 1) and including the compound according to the first exemplary embodiment in the first emitting layer.

Triplet Energy $T_1$

A method of measuring triplet energy $T_1$ is exemplified by a method below.

A measurement target compound is dissolved in EPA (diethylether:isopentane:ethanol=5:5:2 in volume ratio) so as to fall within a range from $10^{-5}$ mol/L to $10^{-4}$ mol/L, and the obtained solution is put in a quartz cell to provide a measurement sample. A phosphorescence spectrum (ordinate axis:

phosphorescence intensity, abscissa axis: wavelength) of the measurement sample is measured at a low temperature (77K). A tangent is drawn to the rise of the phosphorescence spectrum close to the short-wavelength region. An energy amount is calculated by a conversion equation (F1) below on a basis of a wavelength value $\lambda_{edge}$ [nm] at an intersection of the tangent and the abscissa axis. The calculated energy amount is defined as triplet energy $T_1$.

$$T_1[\text{eV}]=1239.85/\lambda\text{edge} \quad \text{Conversion Equation (F1):}$$

The tangent to the rise of the phosphorescence spectrum close to the short-wavelength region is drawn as follows. While moving on a curve of the phosphorescence spectrum from the short-wavelength region to the local maximum value closest to the short-wavelength region among the local maximum values of the phosphorescence spectrum, a tangent is checked at each point on the curve toward the long-wavelength of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Emission Wavelength of Organic EL Device

The organic EL device according to the exemplary embodiment emits light having the maximum peak wavelength of preferably 500 nm or less when driven, more preferably in a range from 445 nm to 480 nm, and further preferably in a range from 445 nm to 465 nm. The maximum peak wavelength of the light emitted from the organic EL device when being driven is measured as described above.

The maximum peak wavelength of light emitted from the organic EL device when driven is measured as follows. Voltage is applied to the organic EL device such that a current density is 10 mA/$cm^2$, where spectral radiance spectrum is measured by a spectroradiometer CS-2000 (produced by Konica Minolta, Inc.). A peak wavelength of an emission spectrum, at which the luminous intensity of the resultant spectral radiance spectrum is at the maximum, is measured and defined as the maximum peak wavelength (unit: nm).

First Emitting Layer

The first emitting layer contains a first host material and a first dopant material. The first host material is a different compound from the second host material contained in the second emitting layer.

The first emitting layer according to the exemplary embodiment has the similar arrangement of the emitting layer according to the third exemplary embodiment. The first dopant material is preferably the compound according to the first exemplary embodiment (compound represented by the formula (1)). The first host material is preferably a compound represented by the formula (H10).

In the organic EL device according to the fourth exemplary embodiment, the compound according to the first exemplary embodiment and a compound represented by the formula (H10) can be used in combination in the first emitting layer of the organic EL device.

In the organic EL device according to the exemplary embodiment, the emitting layer preferably emits light having the maximum peak wavelength of 500 nm or less when the device is driven.

The maximum peak wavelength of the light emitted from the organic EL device when being driven can be measured by a method described below.

Maximum Peak Wavelength λp of Light Emitted from Emitting Layer when Device is Driven For the maximum peak wavelength $\lambda p_1$ of light emitted from the first emitting layer when the organic EL device is driven, the organic EL device is manufactured by using the same material as the first emitting layer for the second emitting layer, and voltage is applied on the organic EL device so that a current density becomes 10 mA/$cm^2$, where spectral radiance spectrum is measured by a spectroradiometer CS-2000 (manufactured by Konica Minolta, Inc.). The maximum peak wavelength $\lambda p_1$ (unit: nm) is calculated from the obtained spectral radiance spectrum.

For the maximum peak wavelength $\lambda p_2$ of light emitted from the second emitting layer when the organic EL device is driven, the organic EL device is manufactured by using the same material as the second emitting layer for the first emitting layer, and voltage is applied on the organic EL device so that a current density becomes 10 mA/$cm^2$, where spectral radiance spectrum is measured by a spectroradiometer CS-2000 (manufactured by Konica Minolta, Inc.). The maximum peak wavelength $\lambda p_2$ (unit: nm) is calculated from the obtained spectral radiance spectrum.

In the organic EL device according to the exemplary embodiment, a triplet energy $T_1$(D1) of the first dopant material and a triplet energy $T_1$(H1) of the first host material preferably satisfy a relationship represented by a numerical formula (Numerical Formula 4A).

$$T_1(D1)>T_1(H1) \quad \text{(Numerical Formula 4A)}$$

In the organic EL device according to the exemplary embodiment, when the first dopant material and the first host material satisfy the relationship of the numerical formula (Numerical Formula 4A), in transfer of triplet excitons generated in the second emitting layer to the first emitting layer, the triplet excitons energy-transfer not to the first dopant material having higher triplet energy but to molecules of the first host material. In addition, triplet excitons generated by recombination of holes and electrons on the first host material do not transfer to the first dopant material having higher triplet energy. Triplet excitons generated by recombination on molecules of the first dopant material quickly energy-transfer to molecules of the first host material.

Triplet excitons in the first host material do not transfer to the first dopant material but efficiently collide with one another on the first host material to generate singlet excitons by the TTF phenomenon.

In the organic EL device according to the exemplary embodiment, a singlet energy $S_1$(H1) of the first host material and a singlet energy $S_1$(D1) of the first dopant material preferably satisfy a relationship represented by a numerical formula (Numerical Formula 4).

$$S_1(H1)>S_1(D1) \quad \text{(Numerical Formula 4)}$$

In the organic EL device according to the exemplary embodiment, when the first dopant material and the first host material satisfy the relationship of the numerical formula (Numerical formula 4), since the singlet energy of the first dopant material is lower than the singlet energy of the first host material, singlet excitons generated by the TTF phenomenon energy-transfer from the first host material to the first dopant material, thereby contributing to emission (preferably fluorescence) of the first dopant material.

Singlet Energy $S_1$

A method of measuring a singlet energy $S_1$ with use of a solution (occasionally referred to as a solution method) is exemplified by a method below.

A toluene solution of a measurement target compound at a concentration ranging from $10^{-5}$ mol/L to $10^{-4}$ mol/L is prepared and put in a quartz cell. An absorption spectrum (ordinate axis: absorption intensity, abscissa axis: wavelength) of the thus-obtained sample is measured at a normal temperature (300K). A tangent is drawn to the fall of the absorption spectrum close to the long-wavelength region, and a wavelength value λedge (nm) at an intersection of the tangent and the abscissa axis is assigned to a conversion equation (F2) below to calculate singlet energy.

$$S_1[\text{eV}]=1239.85/\lambda\text{edge} \quad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

When the second emitting layer and the first emitting layer are layered in this order from the anode in the organic EL device according to the exemplary embodiment, an electron mobility μe(H2) of the second host material and an electron mobility μe(H1) of the first host material preferably satisfy a relationship of a numerical formula (Numerical Formula 3) below. When the first host material and the second host material satisfy the relationship of the numerical formula (Numerical Formula 3), a recombination ability of holes and electrons in the second emitting layer is improved.

$$\mu e(H1)>\mu e(H2) \quad \text{(Numerical Formula 3)}$$

When the second emitting layer and the first emitting layer are layered in this order from the anode in the organic EL device according to the exemplary embodiment, a hole mobility μh(H2) of the second host material and a hole mobility μh(H1) of the first host material also preferably satisfy a relationship of a numerical formula (Numerical Formula 31) below.

$$\mu h(H2)>\mu h(H1) \quad \text{(Numerical Formula 31)}$$

When the second emitting layer and the first emitting layer are layered in this order from the anode in the organic EL device according to the exemplary embodiment, the hole mobility μh(H2) of the second host material, the electron mobility μe(H2) of the second host material, the hole mobility μh(H1) of the first host material, and the electron mobility μe(H1) of the first host material also preferably satisfy a relationship of a numerical formula (Numerical Formula 32) below.

$$(\mu e(H1)/\mu h(H1))>(\mu e(H2)/\mu h(H2)) \quad \text{(Numerical Formula 32)}$$

The electron mobility can be measured according to an impedance measurement using a mobility evaluation device manufactured by the following steps. The mobility evaluation device is, for instance, manufactured by the following steps.

A compound Target, which is to be measured for an electron mobility, is vapor-deposited on a glass substrate having an aluminum electrode (anode) so as to cover the aluminum electrode, thereby forming a measurement target layer. A compound ET-A below is vapor-deposited on this measurement target layer to form an electron transporting layer. LiF is vapor-deposited on the formed electron transporting layer to form an electron injecting layer. Metal aluminum (Al) is vapor-deposited on the formed electron injecting layer to form a metal cathode.

An arrangement of the mobility evaluation device above is roughly shown as follows.

glass/Al(50)/Target(200)/ET-A(10)/LiF(1)/Al(50)

Numerals in parentheses represent a film thickness (nm).

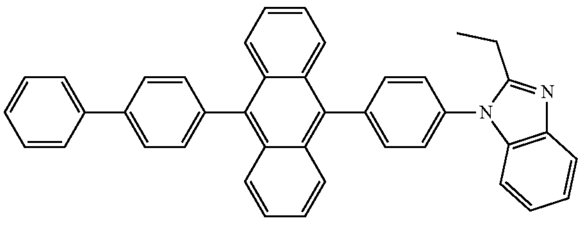

ET-A

The mobility evaluation device for an electron mobility is set in an impedance measurement device to perform an impedance measurement. In the impedance measurement, a measurement frequency is swept from 1 Hz to 1 MHz. At this time, an alternating current amplitude of 0.1 V and a direct current voltage V are applied to the device. A modulus M is calculated from a measured impedance Z using a relationship of a calculation formula (C1) below.

$M=j\omega Z$ Calculation formula (C1):

In the calculation formula (C1), j is an imaginary unit whose square is −1 and ω is an angular frequency [rad/s].

In a bode plot in which an imaginary part of the modulus M is represented by an ordinate axis and the frequency [Hz] is represented by an abscissa axis, an electrical time constant τ of the mobility evaluation device is obtained from a frequency fmax showing a peak using a calculation formula (C2) below.

$\tau=1/(2\pi f\text{max})$ Calculation formula (C2):

π in the calculation formula (C2) is a symbol representing a circumference ratio.

An electron mobility μe is calculated from a relationship of a calculation formula (C3-1) below using τ.

$\mu e=d^2/(V\tau)$ Calculation formula (C3-1):

d in the calculation formula (C3-1) is a total film thickness of organic thin film(s) forming the device. In a case of the arrangement of the mobility evaluation device for an electron mobility, d=210 [nm] is satisfied.

The hole mobility can be measured according to an impedance measurement using a mobility evaluation device manufactured by the following steps. The mobility evaluation device is, for instance, manufactured by the following steps.

A compound HA-2 below is vapor-deposited on a glass substrate having an ITO transparent electrode (anode) so as to cover the transparent electrode, thereby forming a hole injecting layer. A compound HT-A below is vapor-deposited on the formed hole injecting layer to form a hole transporting layer. Subsequently, a compound Target, which is to be measured for a hole mobility, is vapor-deposited to form a measurement target layer. Metal aluminum (Al) is vapor-deposited on this measurement target layer to form a metal cathode.

An arrangement of the mobility evaluation device above is roughly shown as follows.

ITO(130)/HA-2(5)/HT-A(10)/Target(200)/A1(80)

Numerals in parentheses represent a film thickness (nm).

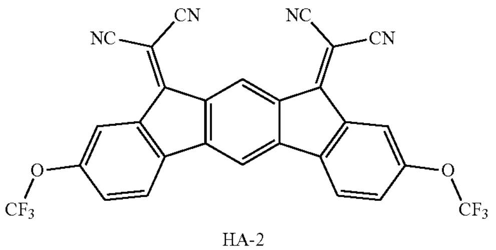

HA-2

-continued

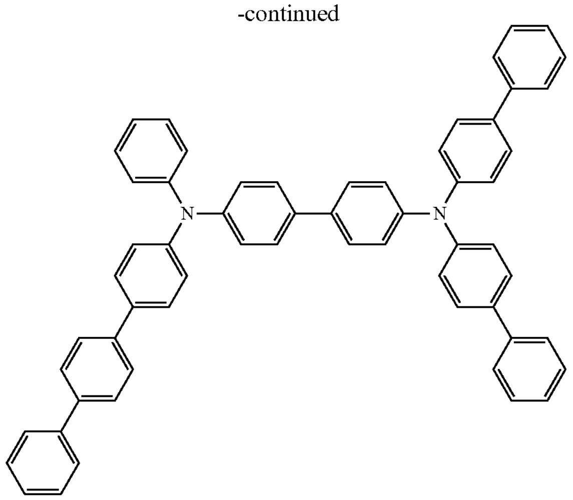

HT-A

The mobility evaluation device for a hole mobility is set in an impedance measurement device to perform an impedance measurement. In the impedance measurement, a measurement frequency is swept from 1 Hz to 1 MHz. At this time, an alternating current amplitude of 0.1 V and a direct current voltage V are applied to the device. A modulus M is calculated from a measured impedance Z using the relationship of the calculation formula (C1).

In a bode plot in which an imaginary part of the modulus M is represented by an ordinate axis and the frequency [Hz] is represented by an abscissa axis, an electrical time constant τ of the mobility evaluation device is obtained from a frequency fmax showing a peak using the calculation formula (C2).

A hole mobility μh is calculated from a relationship of a calculation formula (C3-2) below using τ obtained from the calculation formula (C2).

$\mu h=d^2/(V\tau)$ Calculation formula (C3-2):

d in the calculation formula (C3-2) is a total film thickness of organic thin film(s) forming the device. In a case of the arrangement of the mobility evaluation device for a hole mobility, d=215 [nm] is satisfied.

The electron mobility and the hole mobility herein are each a value obtained in a case where a square root of an electric field intensity meets $E^{1/2}=500$ [$V^{1/2}/cm^{1/2}$]. The square root of the electric field intensity, $E^{1/2}$, can be calculated from a relationship of a calculation formula (C4) below.

$E^{1/2}=V^{1/2}/d^{1/2}$ Calculation formula (C4):

For the impedance measurement, a 1260 type by Solartron Analytical is used as the impedance measurement device, and for a higher accuracy, a 1296 type dielectric constant measurement interface by Solartron Analytical can be used together therewith.

In the organic EL device according to the exemplary embodiment, the first emitting layer contains the first dopant material preferably at 0.5 mass % or more, more preferably at more than 1.1 mass %, further preferably at 1.2 mass % or more, still further preferably at 1.5 mass % or more with respect to the total mass of the first emitting layer.

The first emitting layer contains the first dopant material preferably at 10 mass % or less, more preferably at 7 mass % or less, further preferably at 5 mass % or less with respect to the total mass of the first emitting layer.

In the organic EL device according to the exemplary embodiment, the first emitting layer contains the first host material preferably at 60 mass % or more, more preferably at 70 mass % or more, further preferably at 80 mass % or more, still further preferably at 90 mass % or more, still further preferably at 95 mass % or more, with respect to the total mass of the first emitting layer.

The first emitting layer preferably includes the first host material of 99 mass % or less with respect to a total mass of the first emitting layer.

When the first emitting layer contains the first host material and the first dopant material, the upper limit of a total content ratio of the first host material and the first dopant material is 100 mass %.

It is not excluded that the first emitting layer of the exemplary embodiment further contains a material(s) other than the first host material and the first dopant material.

The first emitting layer may include a single type of the first host material or may include two or more types of the first host material. The first emitting layer may include a single type of the first dopant material or may include two or more types of the first dopant material.

In the organic EL device according to the exemplary embodiment, a film thickness of the first emitting layer is preferably 5 nm or more, more preferably 15 nm or more. When the film thickness of the first emitting layer is 5 nm or more, it is easy to inhibit triplet excitons having transferred from the second emitting layer to the first emitting layer from returning to the second emitting layer. Further, when the film thickness of the first emitting layer is 5 nm or more, triplet excitons can be sufficiently separated from the recombination portion on the second emitting layer.

In the organic EL device according to the exemplary embodiment, the film thickness of the first emitting layer is preferably 20 nm or less. When the film thickness of the first emitting layer is 20 nm or less, the density of the triplet excitons in the second emitting layer is improved to cause the TTF phenomenon more easily.

In the organic EL device according to the exemplary embodiment, the film thickness of the first emitting layer is preferably in a range from 5 nm to 20 nm.

Second Emitting Layer

The second emitting layer contains a second host material and a second dopant material. The second host material is a different compound from the first host material contained in the first emitting layer.

The second dopant material is preferably a compound that emits light having the maximum peak wavelength of 500 nm or less. The second host material is more preferably a compound that emits fluorescence having the maximum peak wavelength of 500 nm or less.

The maximum peak wavelength of a compound is measured as described above.

In the organic EL device according to the exemplary embodiment, the second dopant material and the first dopant material are the same compound or different compounds.

In the organic EL device according to the exemplary embodiment, the second emitting layer preferably does not contain a metal complex. In the organic EL device according to the exemplary embodiment, the first emitting layer also preferably does not contain a boron-containing complex.

In the organic EL device according to the exemplary embodiment, the second emitting layer preferably does not contain a phosphorescent material (dopant material).

Moreover, the second emitting layer preferably does not contain a heavy metal complex and a phosphorescent rare-earth metal complex.

In an emission spectrum of the second dopant material, where a peak exhibiting a maximum luminous intensity is defined as a maximum peak and a height of the maximum peak is defined as 1, heights of other peaks appearing in the emission spectrum are preferably less than 0.6. It should be noted that the peaks in the emission spectrum are defined as local maximal values.

Moreover, in the emission spectrum of the second emitting compound, the number of peaks is preferably less than three.

In the organic EL device according to the exemplary embodiment, the second emitting layer preferably emits light having the maximum peak wavelength of 500 nm or less when the device is driven.

Second Host Material

Examples of the second host material include:

1) a fused aromatic compound such as an anthracene derivative, phenanthrene derivative, pyrene derivative, benzanthracene derivative, fluorene derivative, fluoranthene derivative or chrysene derivative;

2) a heterocyclic compound such as a carbazole derivative, a dibenzofuran derivative, a dibenzothiophene derivative, or a benzoxanthene derivative.

The second host material is preferably a fused aromatic compound, more preferably a pyrene derivative (a later-described compound represented by a formula (H100)).

The second host material is also preferably a benzanthracene derivative (a later-described compound represented by a formula (H1X)) or a benzoxanthene derivative (a later-described compound represented by a formula (H14X)).

When the second host material is a pyrene derivative, the second host material is preferably a compound represented by the formula (H100) below.

Compound Represented by Formula (H100)

(H100)

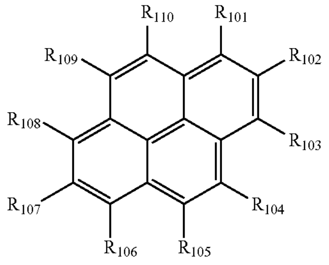

(H110)

$$*\!-\!(L_{101})_{mx}\!-\!Ar_{101}$$

In the formula (H100):

$R_{101}$ to $R_{110}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(=O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (H110);

at least one of $R_{101}$ to $R_{110}$ is a group represented by the formula (H110);

when a plurality of groups represented by the formula (H110) are present, the plurality of groups represented by the formula (H110) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 0, 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (H110) represents a bonding position to a pyrene ring in the formula (H100).

In the second host material, $R_{901}$, $R_{902}$, $R_{903}$, $R_{904}$, $R_{905}$, $R_{906}$, $R_{907}$, $R_{801}$ and $R_{802}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different;

when a plurality of $R_{907}$ are present, the plurality of $R_{907}$ are mutually the same or different;

when a plurality of $R_{801}$ are present, the plurality of $R_{801}$ are mutually the same or different; and when a plurality of $R_{802}$ are present, the plurality of $R_{802}$ are mutually the same or different.

In the organic EL device according to the exemplary embodiment, a group represented by the formula (H110) is preferably a group represented by a formula (H111) below.

(H111)

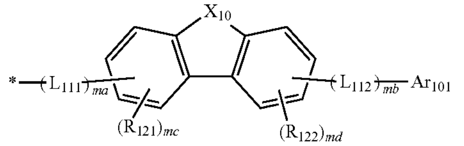

In the formula (H111):

$X_{10}$ is $C(R_{123})(R_{124})$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$Ar_{101}$ represent the same as $Ar_{101}$ in the formula (H110);

$R_{121}$, $R_{122}$, $R_{123}$, $R_{124}$ and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $—Si(R_{901})(R_{902})(R_{903})$, a group represented by $—O—(R_{904})$, a group represented by $—S—(R_{905})$, a substituted or unsubstituted aralkyl group having 7 to 50 carbon atoms, a group represented by $—C(=O)R_{801}$, a group represented by $—COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

and is 3; and three $R_{122}$ are mutually the same or different.

Among positions *1 to *8 of carbon atoms in a cyclic structure represented by a formula (H111a) below in a group represented by the formula (H111), $L_{111}$ is bonded to one of the positions *1 to *4, $R_{121}$ is bonded to each of three positions of the rest of *1 to *4, $L_{112}$ is bonded to one of the positions *5 to *8, and $R_{122}$ is bonded to each of three positions of the rest of *5 to *8.

(H111a)

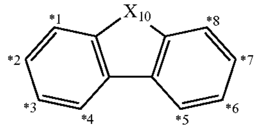

For instance, in a group represented by the formula (H111), when $L_{111}$ is bonded to a carbon atom at a position *2 in the cyclic structure represented by the formula (111a) and $L_{112}$ is bonded to a carbon atom at a position *7 in the cyclic structure represented by the formula (111a), a group represented by the formula (H111) is represented by a formula (H111b) below.

(H111b)

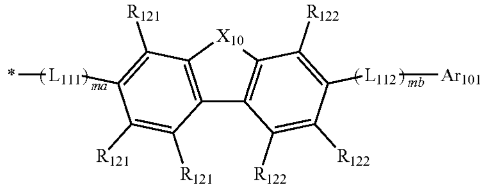

In the formula (H111b):

$X_{10}$, $L_{111}$, $L_{112}$, ma, mb, $Ar_{101}$, $R_{121}$, $R_{122}$, $R_{123}$, $R_{124}$ and $R_{125}$ respectively independently represent the same as $X_{10}$, $L_{111}$, $L_{112}$, ma, mb, $Ar_{101}$, $R_{121}$, $R_{122}$, $R_{123}$, $R_{124}$ and $R_{125}$ in the formula (H111);

a plurality of $R_{121}$ are mutually the same or different; and a plurality of $R_{122}$ are mutually the same or different.

In the organic EL device according to the exemplary embodiment, a group represented by the formula (H111) is preferably a group represented by the formula (H111b).

In the organic EL device according to the exemplary embodiment, it is preferable that ma is 0, 1 or 2 and mb is 0, 1 or 2.

In the organic EL device according to the exemplary embodiment, it is preferable that ma is 0 or 1 and mb is 0 or 1.

In the organic EL device according to the exemplary embodiment, $Ar_{101}$ is preferably a substituted or unsubstituted aryl group having 6 to 50 ring carbon atoms.

In the organic EL device according to the exemplary embodiment, it is preferable that $Ar_{101}$ is a substituted or unsubstituted phenyl group, a substituted or unsubstituted naphthyl group, a substituted or unsubstituted biphenyl group, a substituted or unsubstituted terphenyl group, a substituted or unsubstituted pyrenyl group, a substituted or unsubstituted phenanthryl group, or a substituted or unsubstituted fluorenyl group.

In the organic EL device according to the exemplary embodiment, $Ar_{101}$ is also preferably a group represented by a formula (H120), a formula (H130) or a formula (H140) below.

(H120)

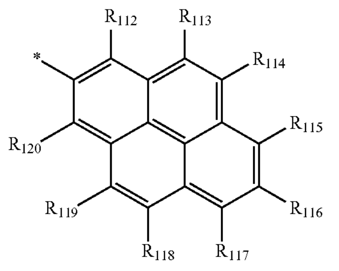

(H130)

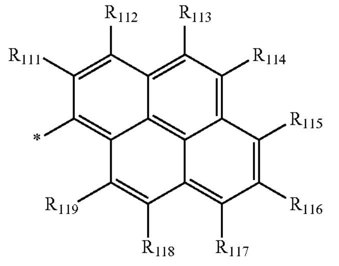

(H140)

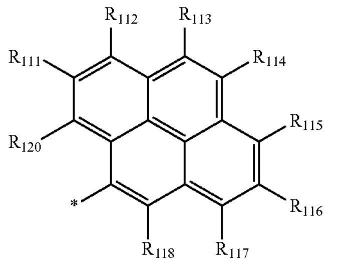

In the formula (H120), the formula (H130), and the formula (H140):

$R_{111}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms; and

* in the formulae (H120), (H130) and (H140) represents a bonding position to $L_{101}$ in the formula (H110) or a bonding position to $L_{112}$ in the formula (H111) or the formula (H111b).

In the organic EL device according to the exemplary embodiment, the second host material is preferably represented by a formula (H101) below.

(H101)

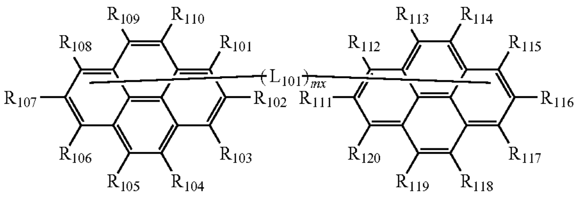

In the formula (H101):

$R_{101}$ to $R_{120}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

one of $R_{101}$ to $R_{110}$ represents a bonding position to $L_{101}$, and one of $R_{111}$ to $R_{120}$ represents a bonding position to $L_{101}$;

$L_{101}$ is a single bond, a substituted or unsubstituted arylene group having 6 to 50 ring carbon atoms, or a substituted or unsubstituted divalent heterocyclic group having 5 to 50 ring atoms;

mx is 0, 1, 2, 3, 4, or 5; and when two or more $L_{101}$ are present, the two or more $L_{101}$ are mutually the same or different.

In the organic EL device according to the exemplary embodiment, it is preferable that $L_{101}$ is a single bond, or a substituted or unsubstituted arylene group having 6 to 50 ring carbon atoms.

In the organic EL device according to the exemplary embodiment, it is preferable that the second host material is represented by a formula (H102) below.

(H102)

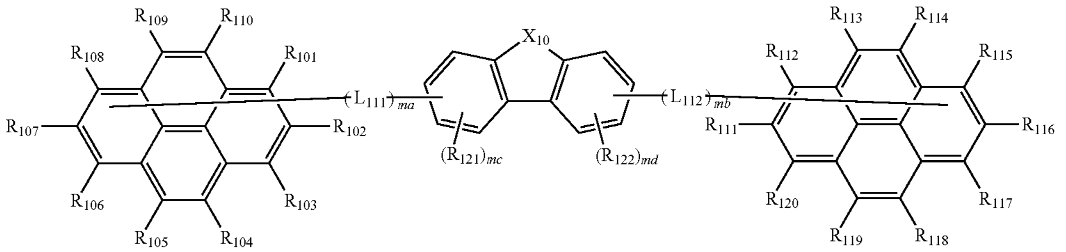

In the formula (H102):

$R_{101}$ to $R_{120}$ respectively represent the same as $R_{101}$ to $R_{120}$ in the formula (H101);

one of $R_{101}$ to $R_{110}$ represents a bonding position to $L_{111}$, and one of $R_{111}$ to $R_{120}$ represents a bonding position to $L_{112}$;

$X_{10}$ is $C(R_{123})(R_{124})$, an oxygen atom, a sulfur atom, or $NR_{125}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 0, 1, 2, 3, or 4;

mb is 0, 1, 2, 3, or 4;

ma+mb is 0, 1, 2, 3, or 4;

$R_{121}$, $R_{122}$, $R_{123}$, $R_{124}$ and $R_{125}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{121}$ are mutually the same or different;

and is 3; and three $R_{122}$ are mutually the same or different.

In the compound represented by the formula (H102), it is preferable that ma is 0, 1 or 2 and mb is 0, 1 or 2.

In the compound represented by the formula (H102), it is preferable that ma is 0 or 1 and mb is 0 or 1.

In the organic EL device according to the exemplary embodiment, it is preferable that two or more of $R_{101}$ to $R_{110}$ are each a group represented by the formula (H110).

In the organic EL device according to the exemplary embodiment, it is preferable that two or more of $R_{101}$ to $R_{110}$ are each a group represented by the formula (H110) and $Ar_{101}$ is a substituted or unsubstituted aryl group having 6 to 50 ring carbon atoms.

In the organic EL device according to the exemplary embodiment, it is preferable that $Ar_{101}$ is not a substituted or unsubstituted pyrenyl group, $L_{101}$ is not a substituted or unsubstituted pyrenylene group, and a substituted or unsubstituted aryl group having 6 to 50 ring carbon atoms as $R_{101}$ to $R_{110}$ not being a group represented by the formula (H110) is not a substituted or unsubstituted pyrenyl group.

In the organic EL device according to the exemplary embodiment, it is preferable that $R_{101}$ to $R_{110}$ not being a group represented by the formula (H110) are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the organic EL device according to the exemplary embodiment, it is preferable that $R_{101}$ to $R_{110}$ not being a group represented by the formula (H110) are each independently a hydrogen atom, a substituted or unsubstituted alkyl group having 1 to 50 carbon atoms, or a substituted or unsubstituted cycloalkyl group having 3 to 50 ring carbon atoms.

In the organic EL device according to the exemplary embodiment, it is preferable that $R_{101}$ to $R_{110}$ not being a group represented by the formula (H110) is each a hydrogen atom.

In a compound represented by the formula (H100), it is preferable that all of the "substituted or unsubstituted" groups are "unsubstituted" groups.

A compound represented by the formula (H100) can be manufactured by a well-known method.

Specific Examples of Compound Represented by Formula (H100)

Specific examples of the compound represented by the formula (H100) include compounds shown below. It should be noted that the compound represented by the formula (H100) is by no means limited to the specific examples below.

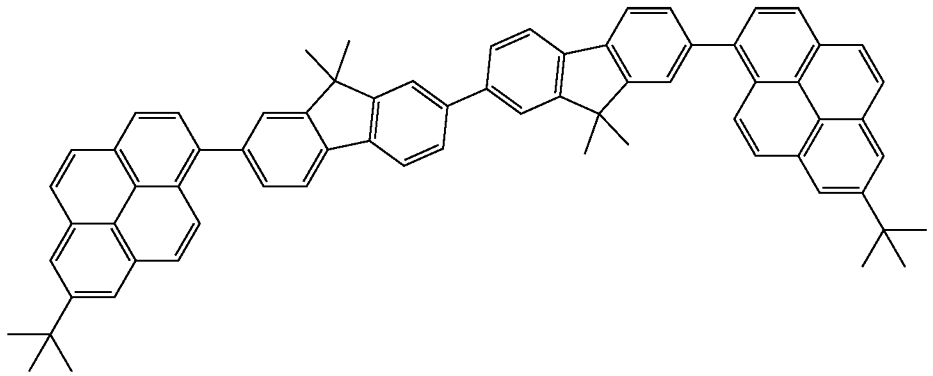
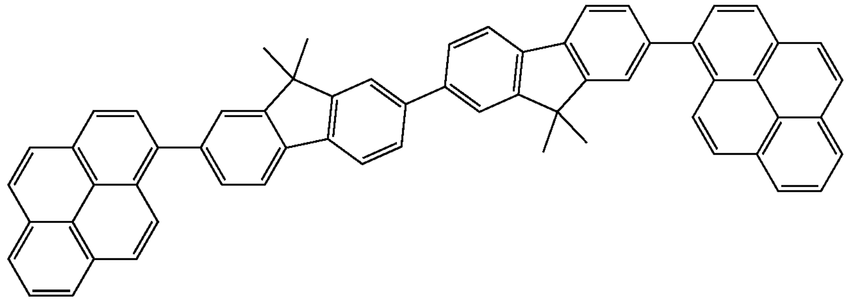
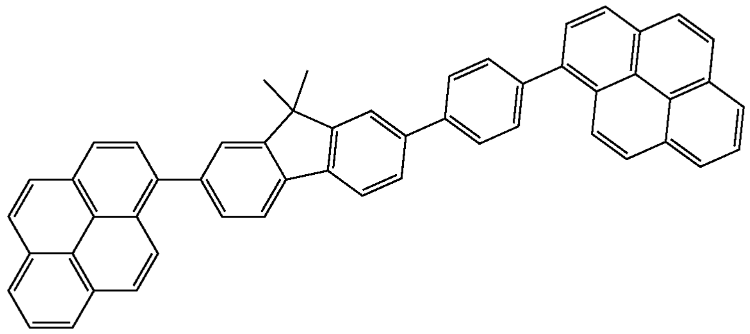
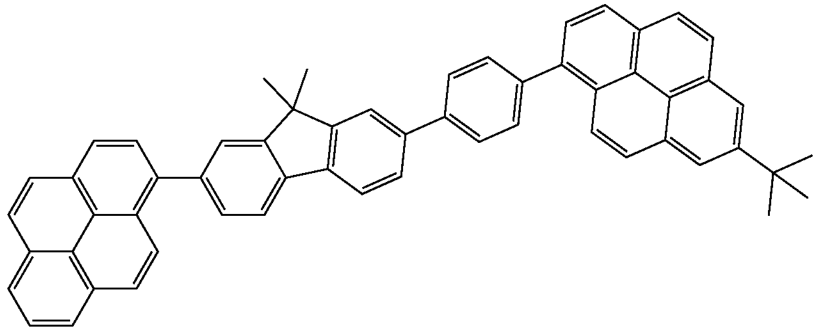
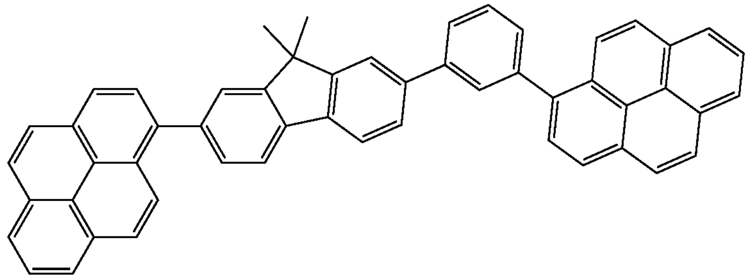

-continued
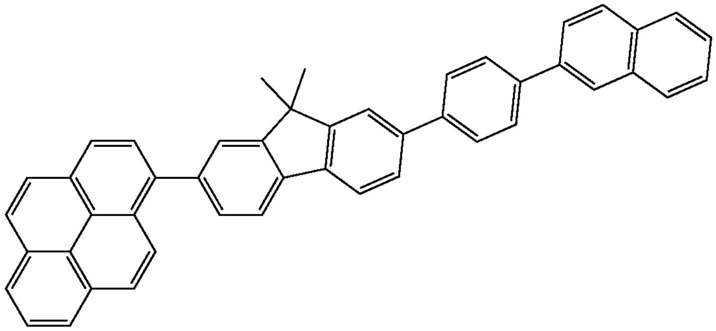
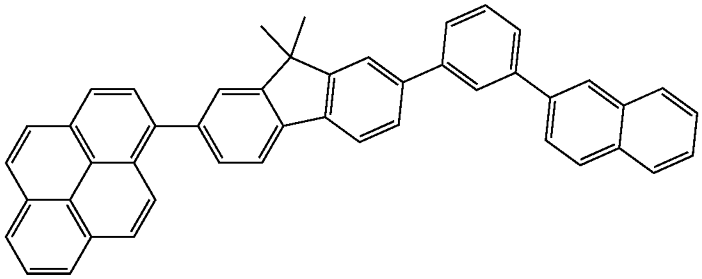
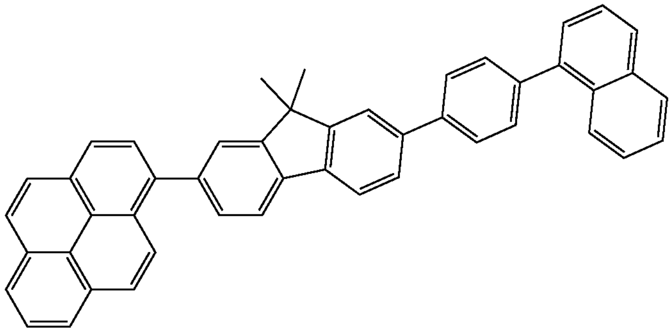
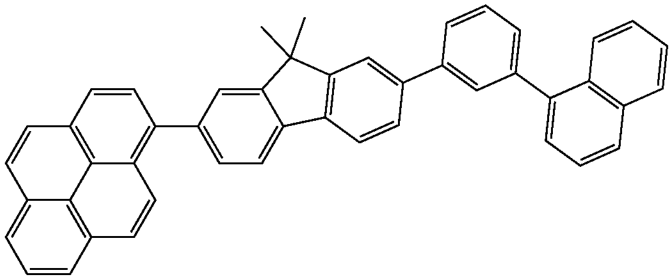
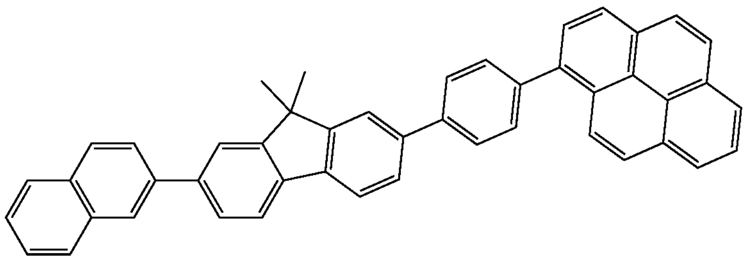
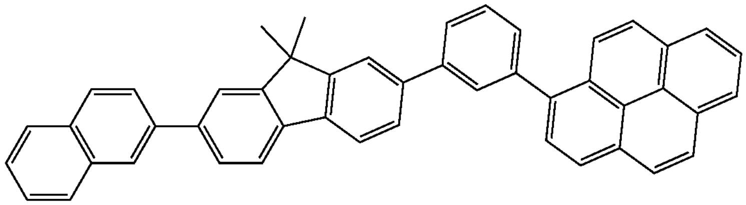

-continued
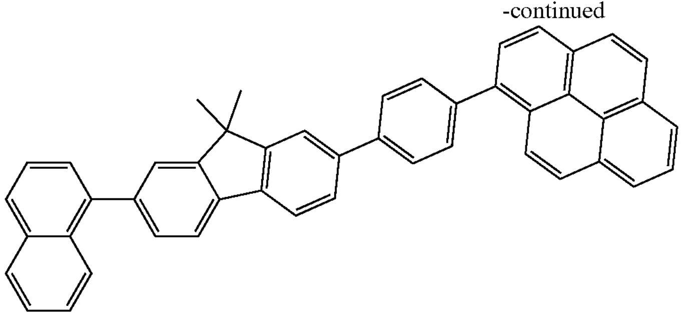
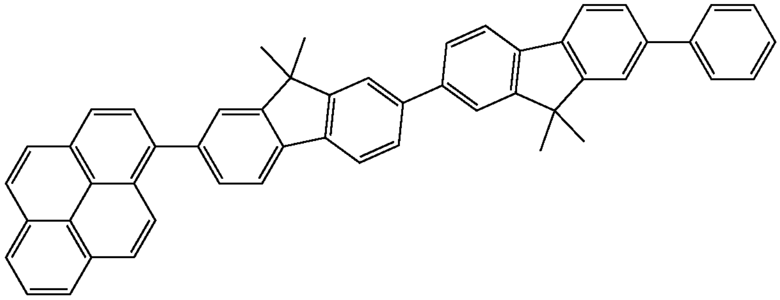
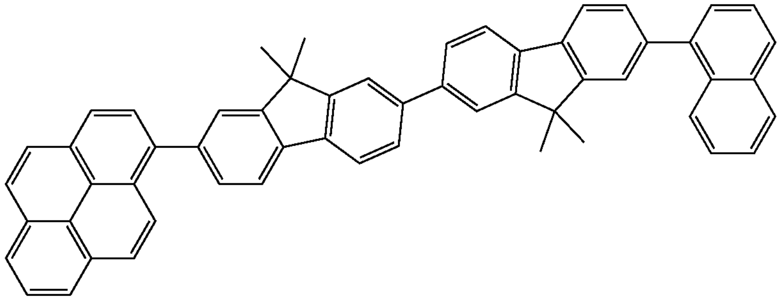
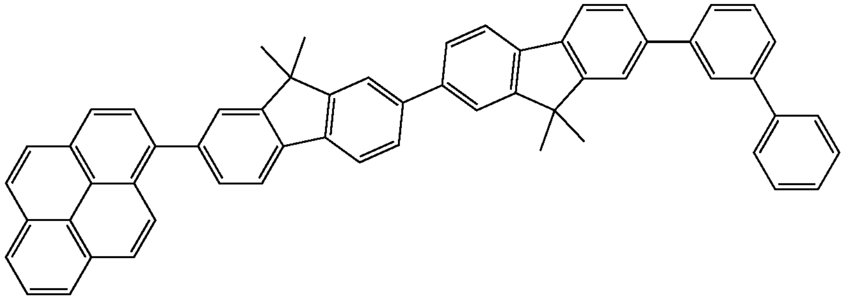
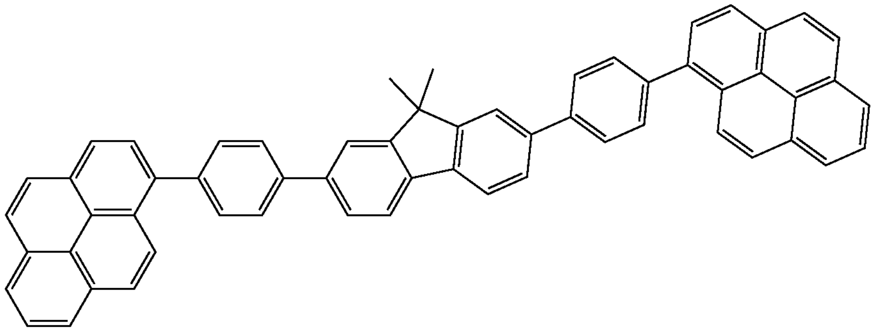

-continued
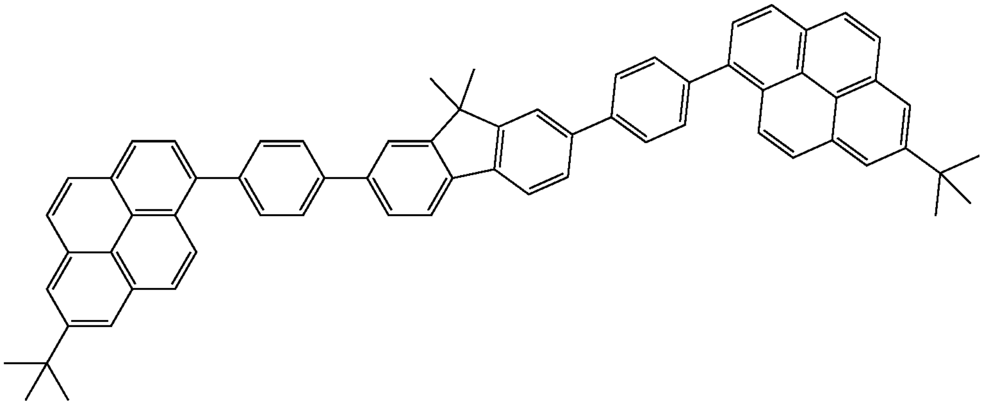
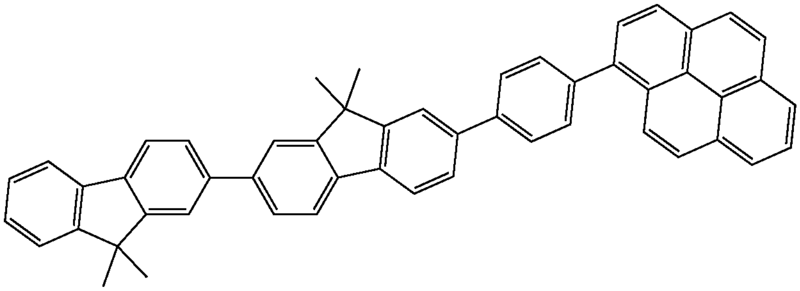
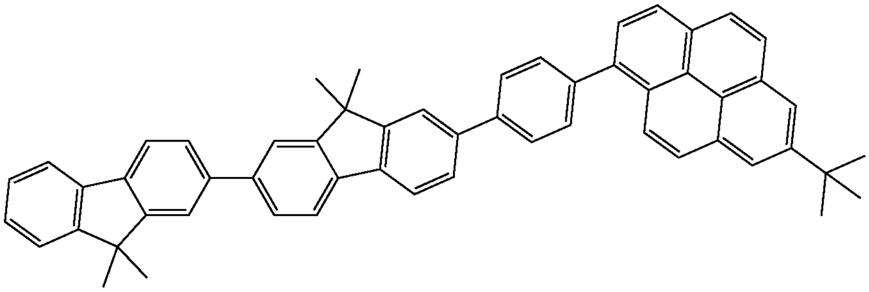
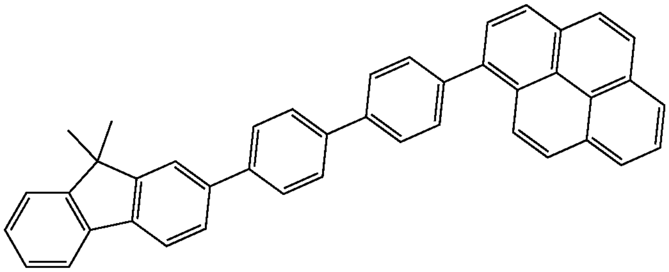
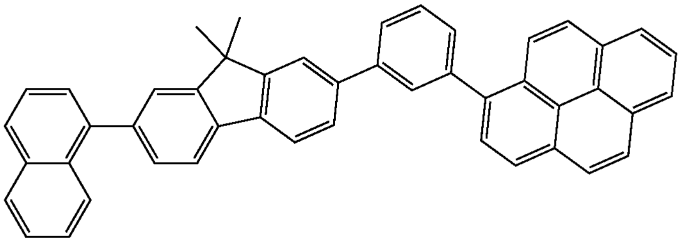

-continued
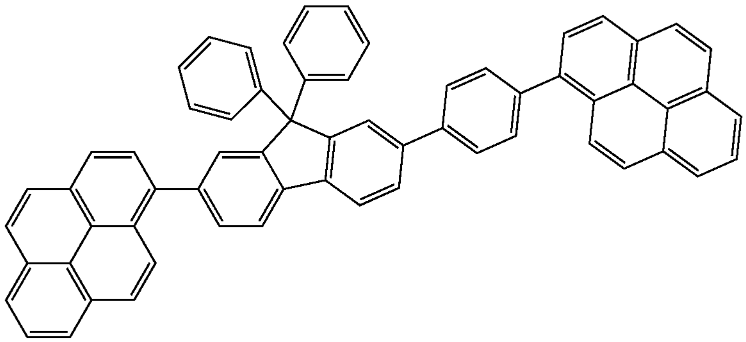
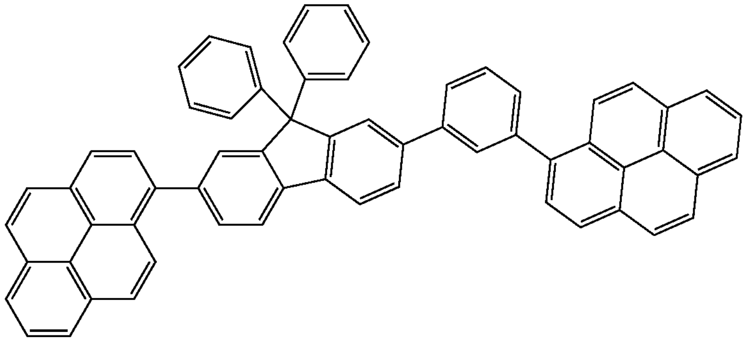
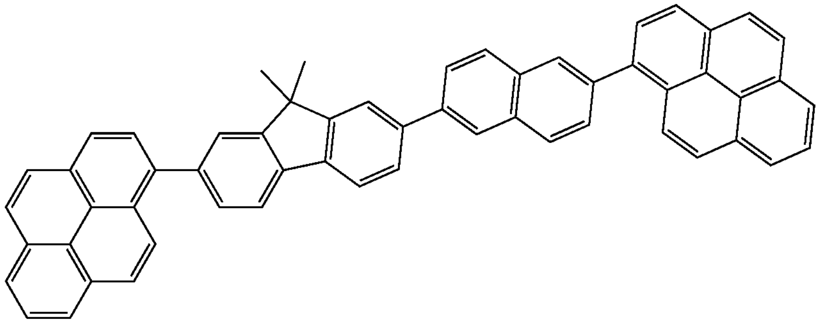
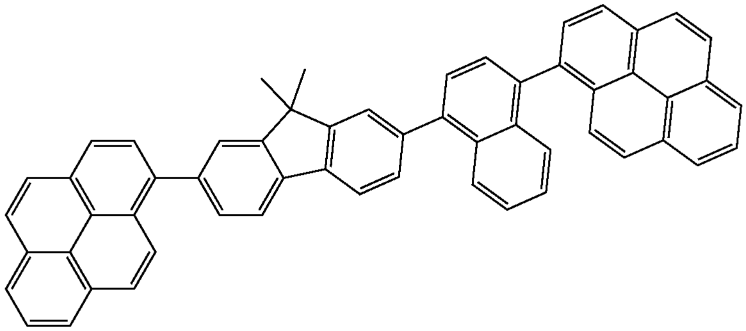
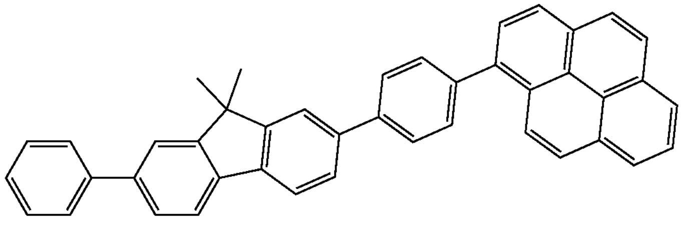

-continued
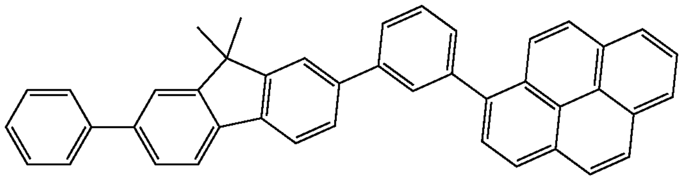
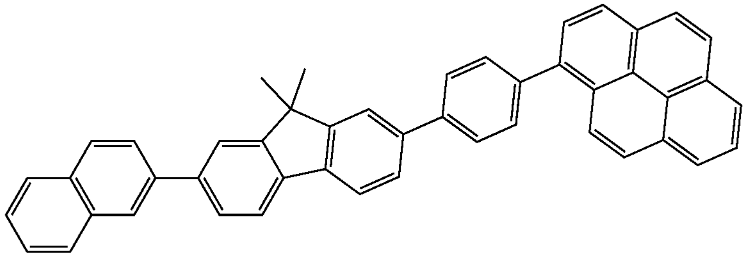
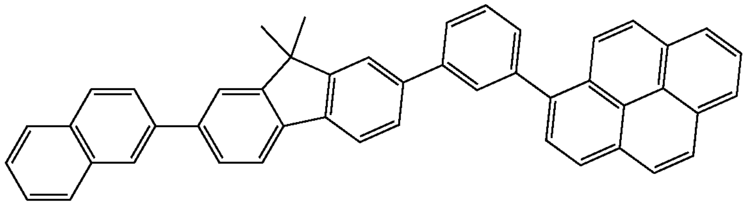
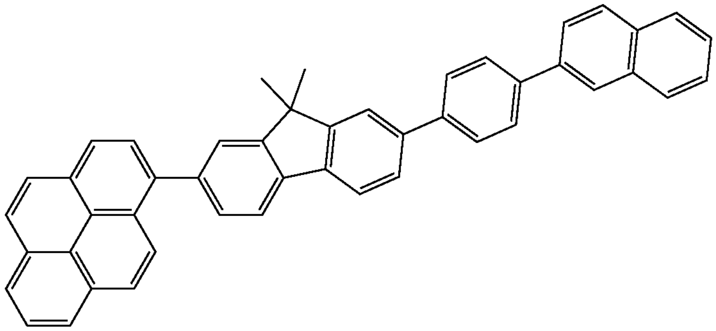
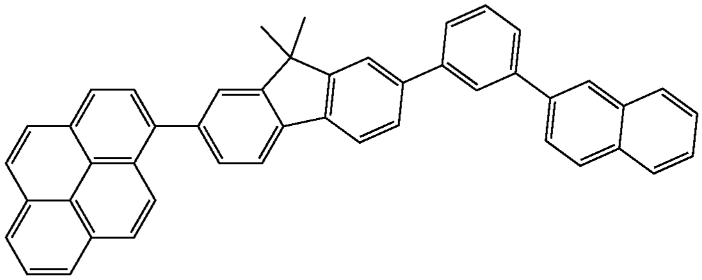
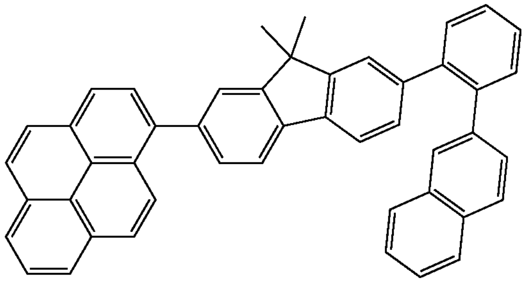

-continued
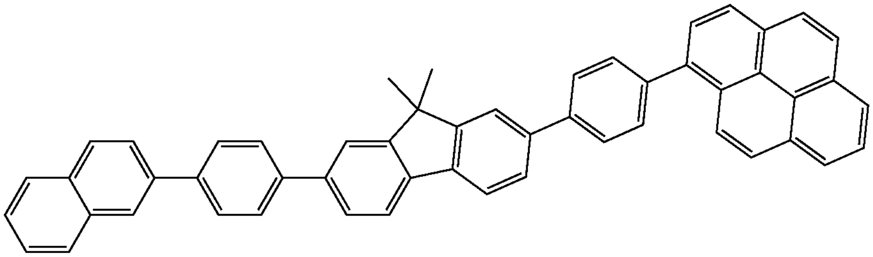
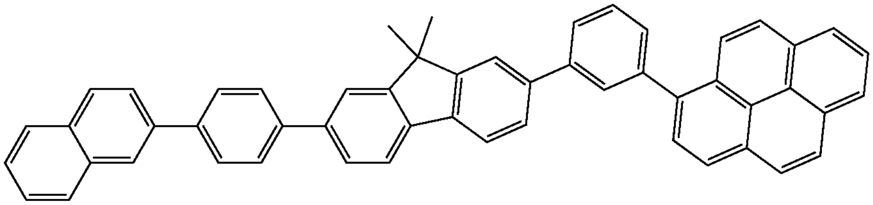
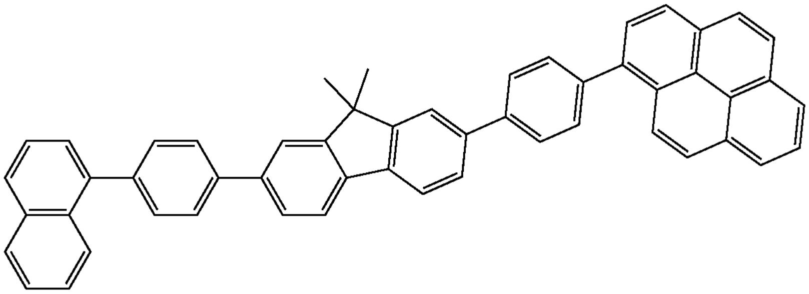
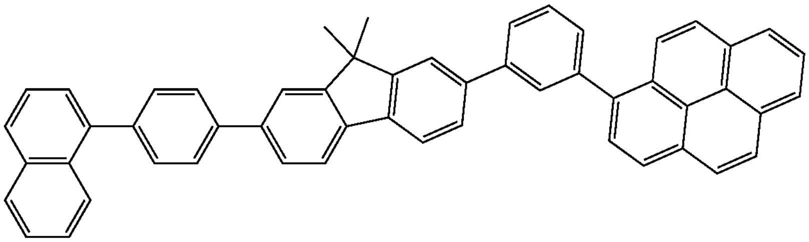
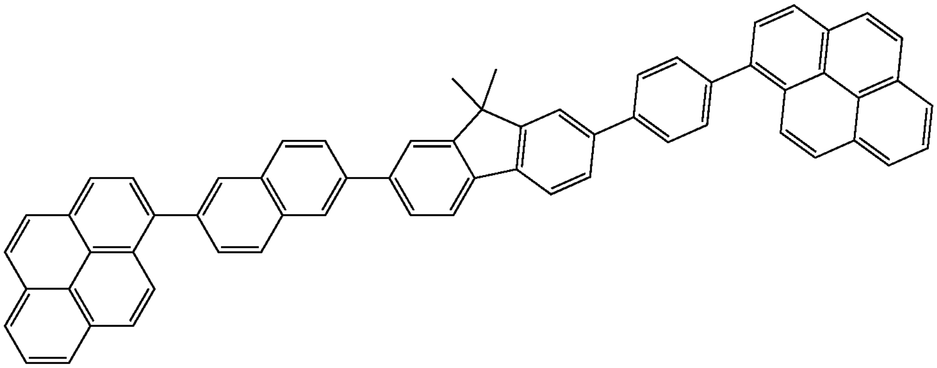
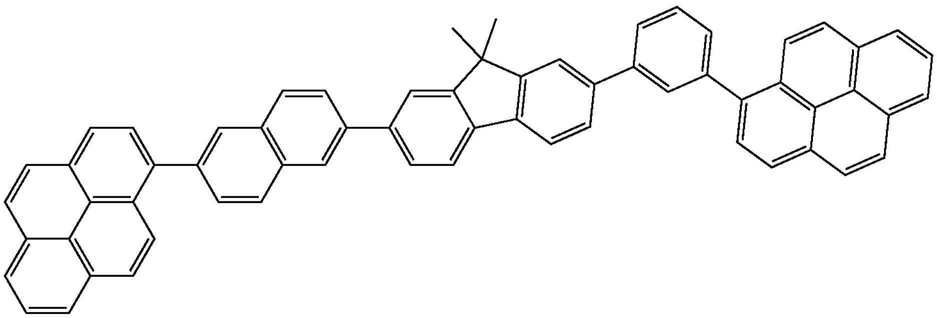

-continued
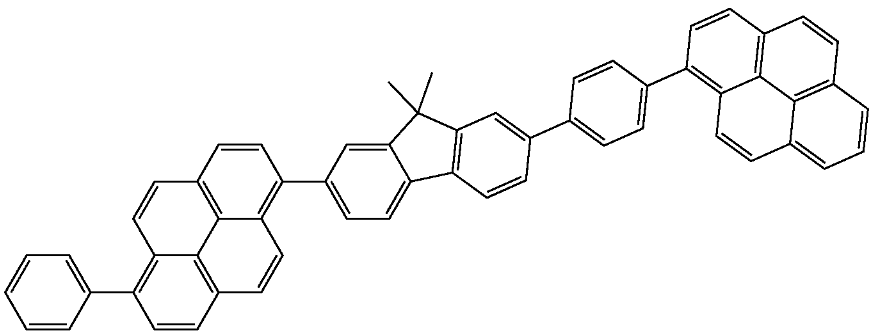
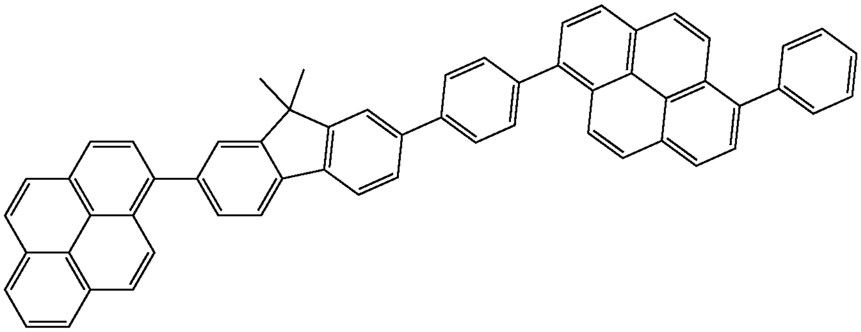
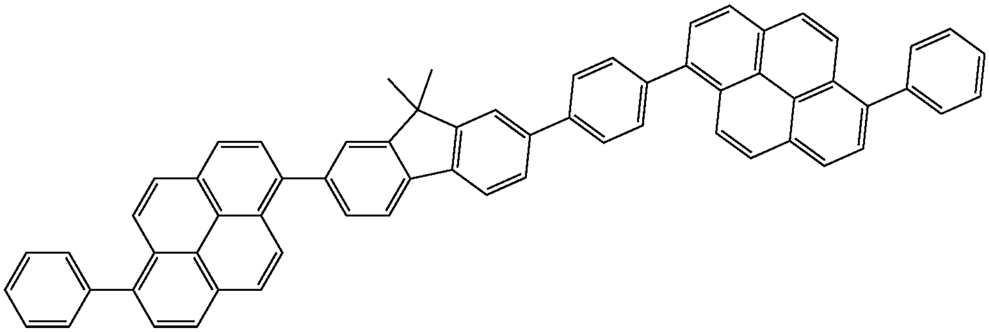
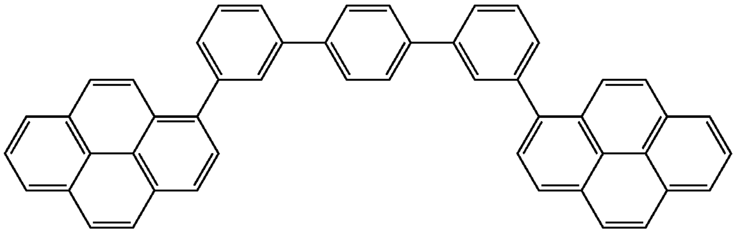
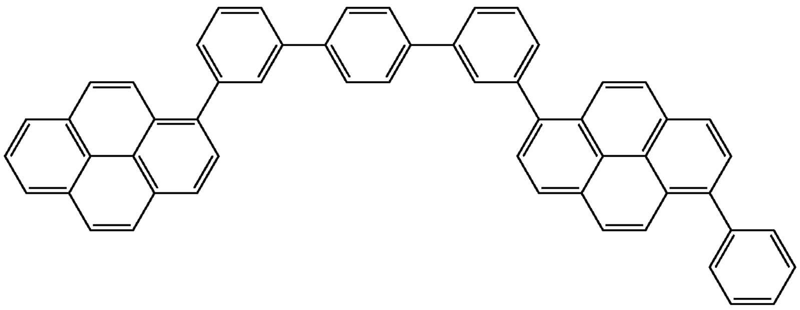

-continued
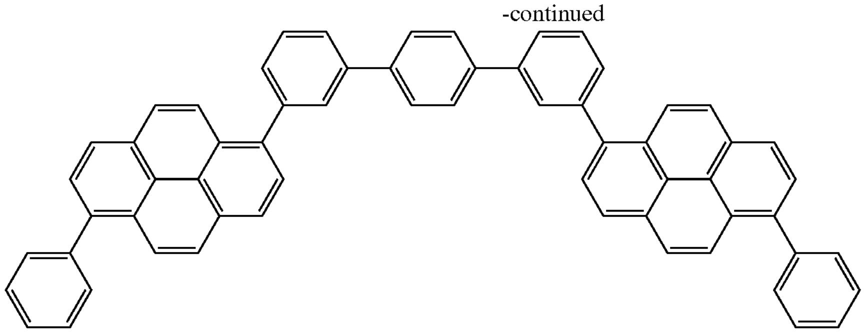
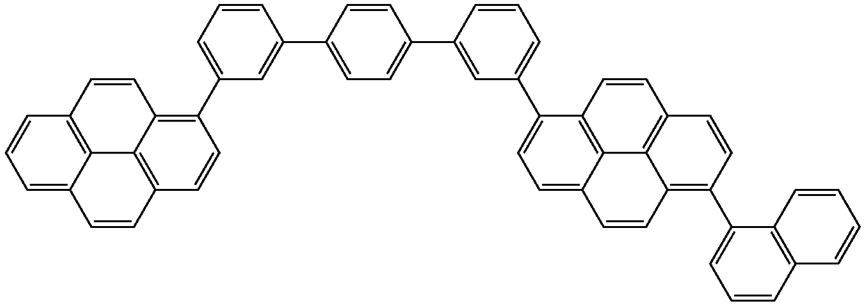
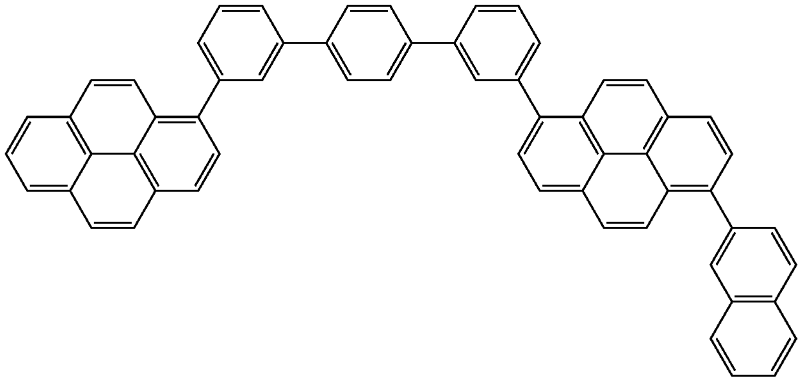
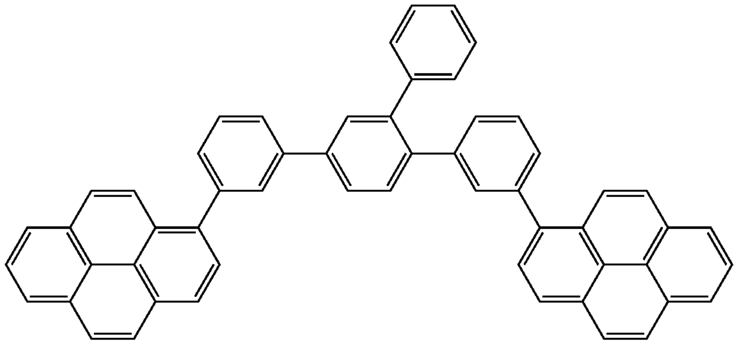

-continued
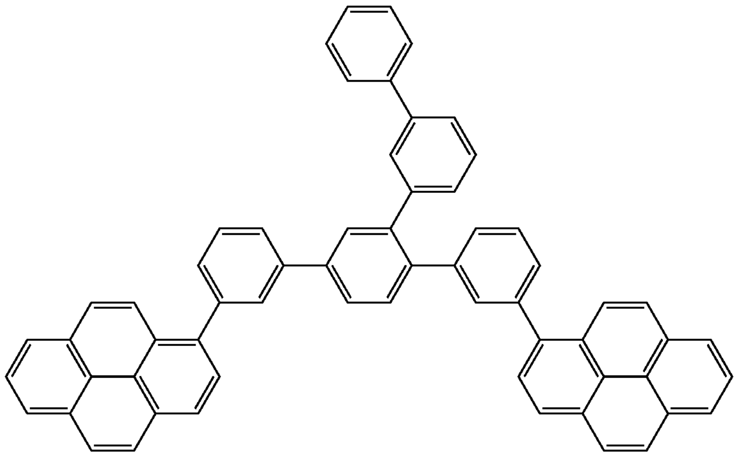
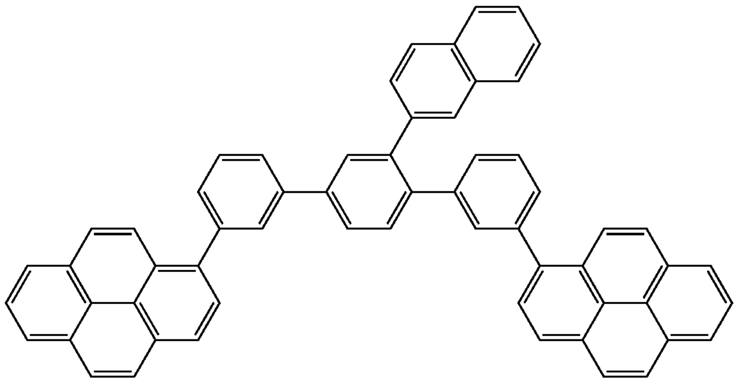
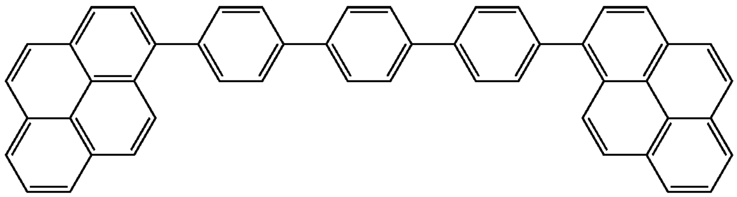
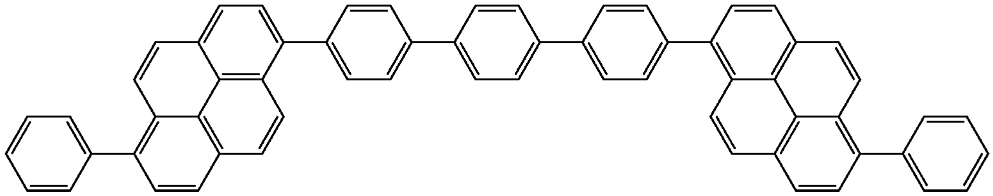
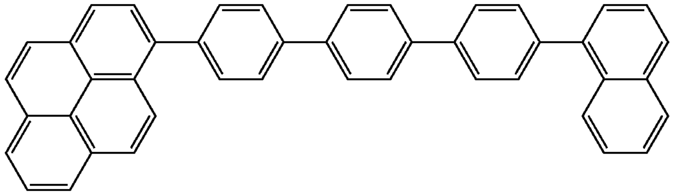
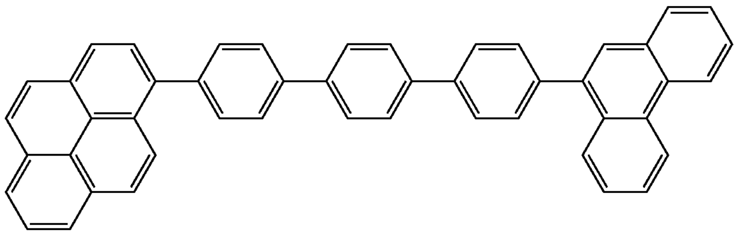

-continued
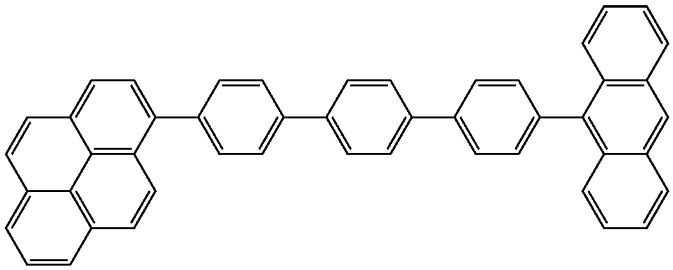
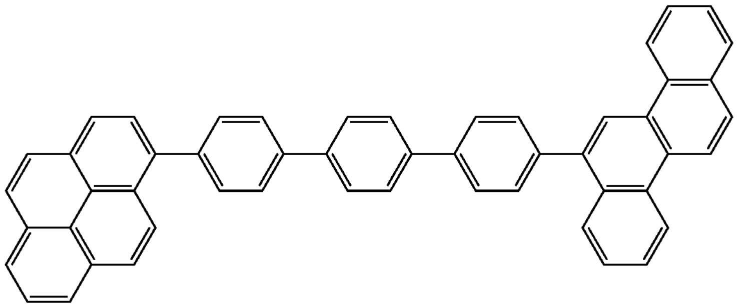
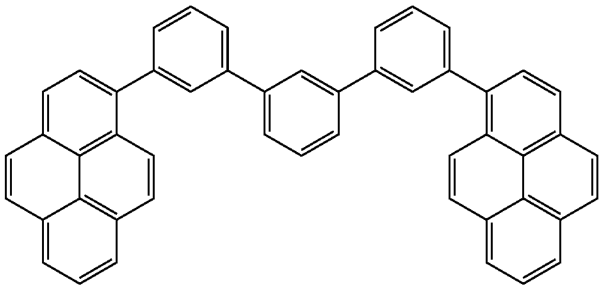
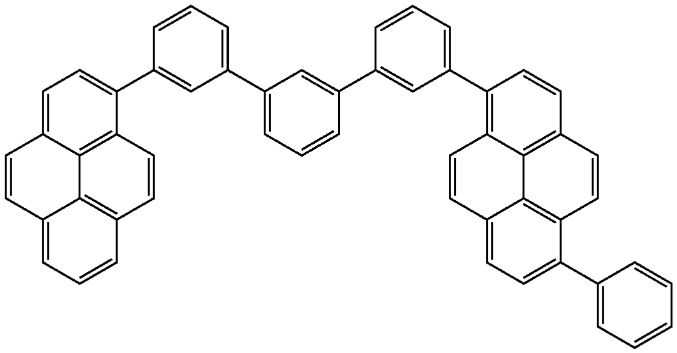
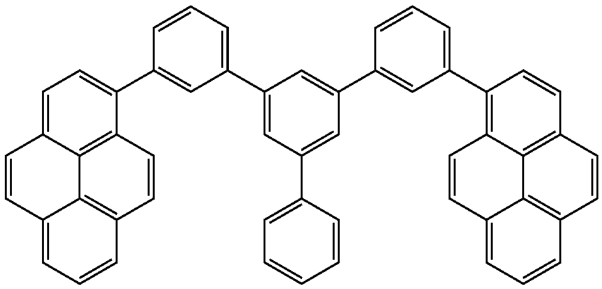

-continued
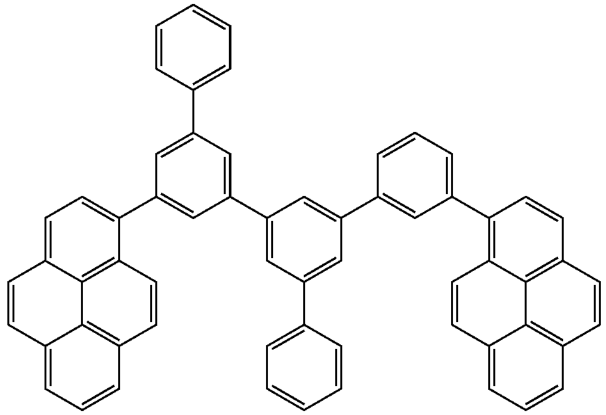
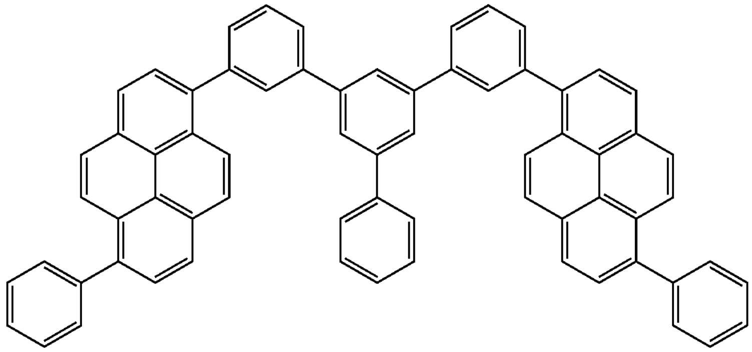
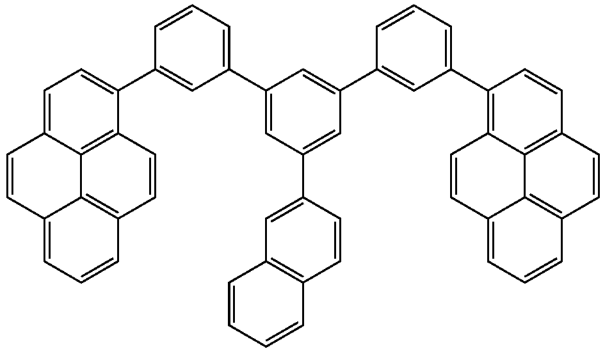
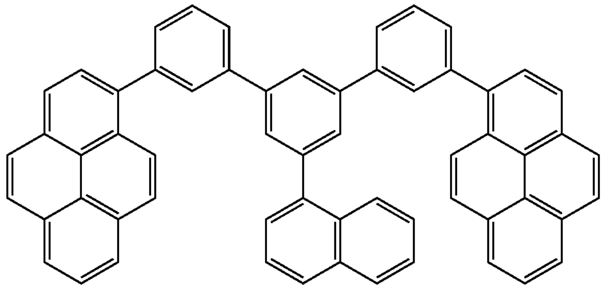
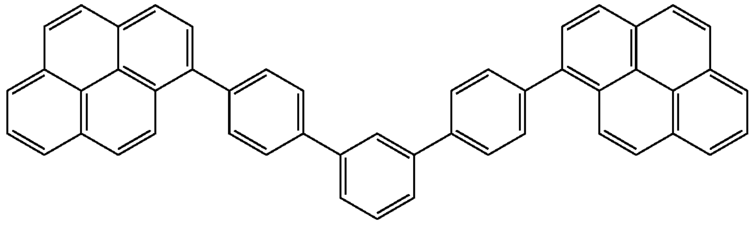

-continued
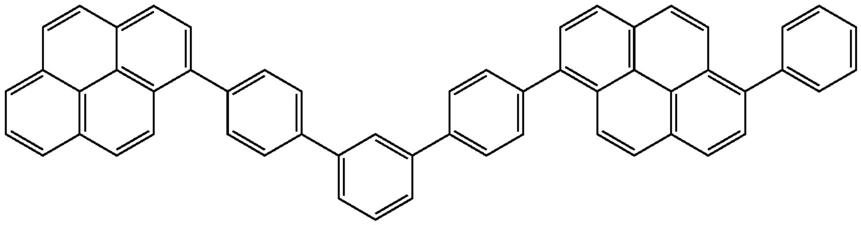
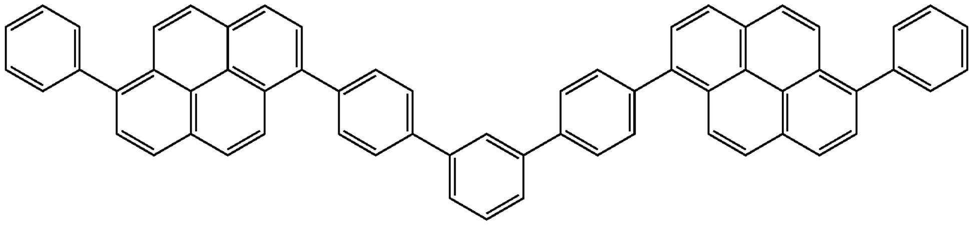
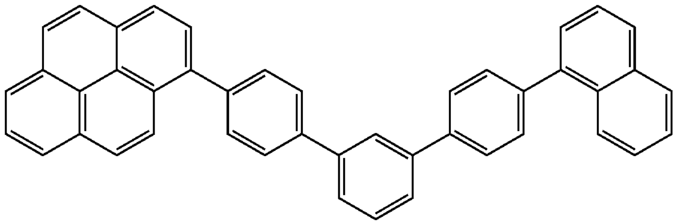
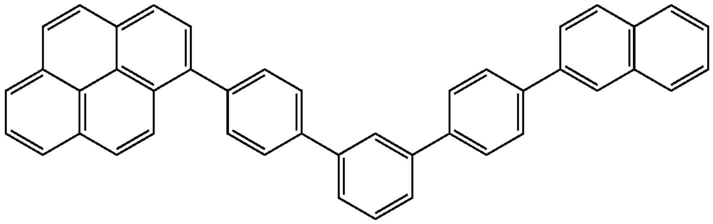
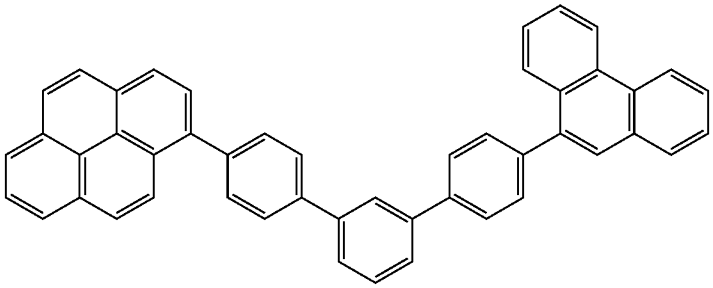
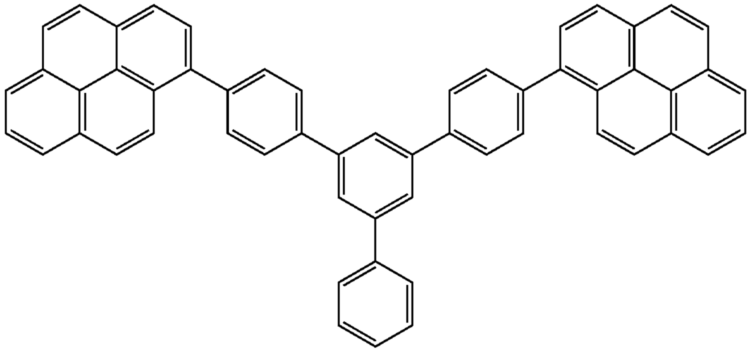

-continued
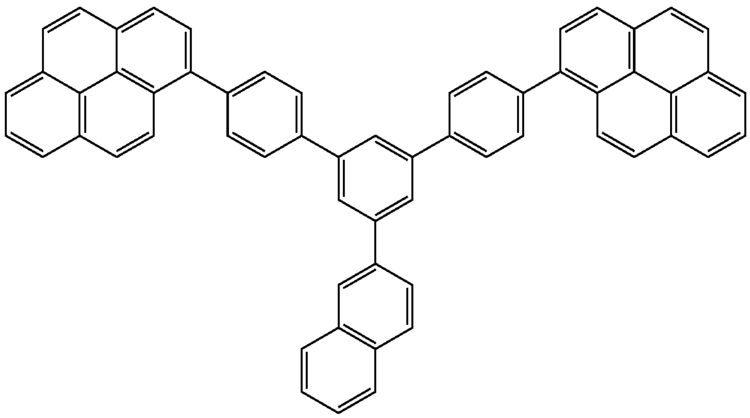
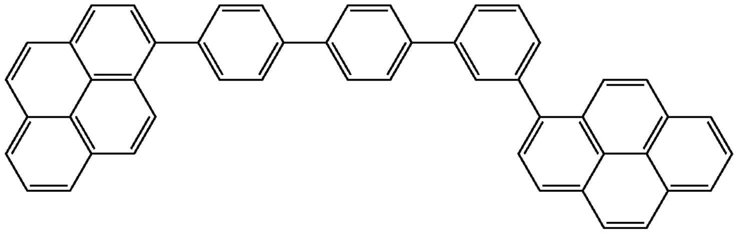
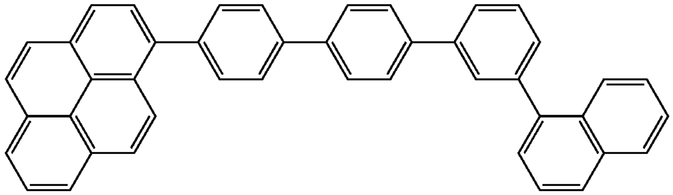
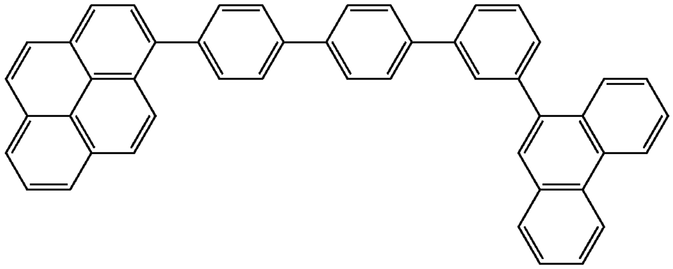
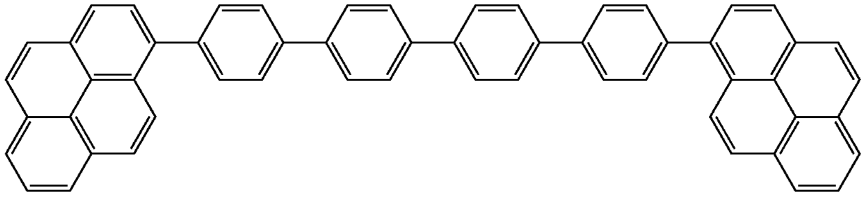
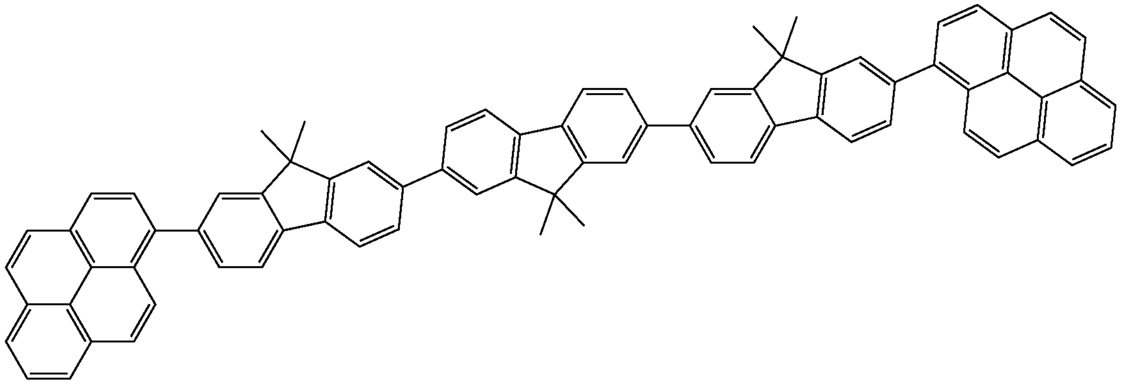

-continued
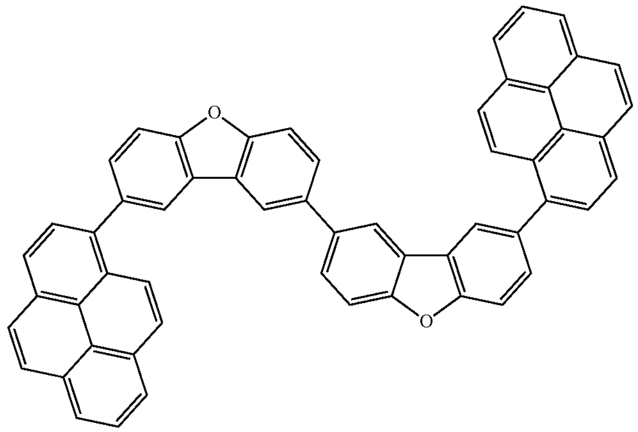
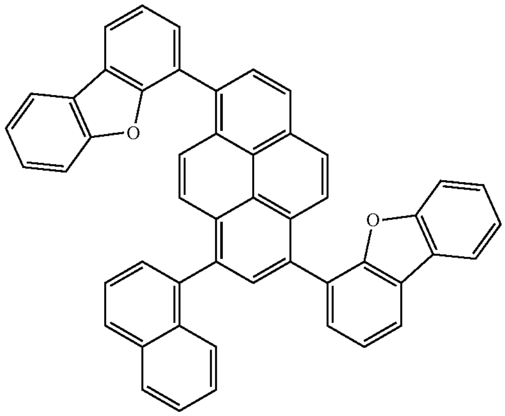
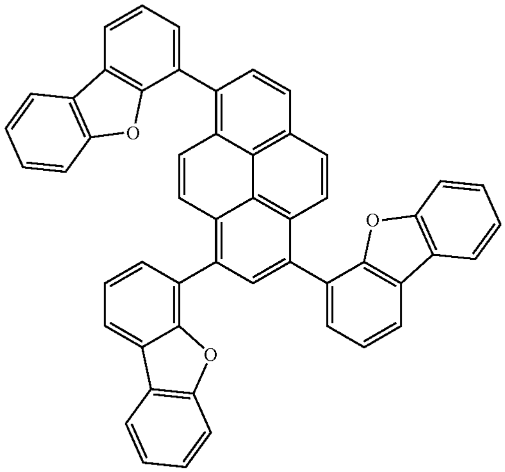
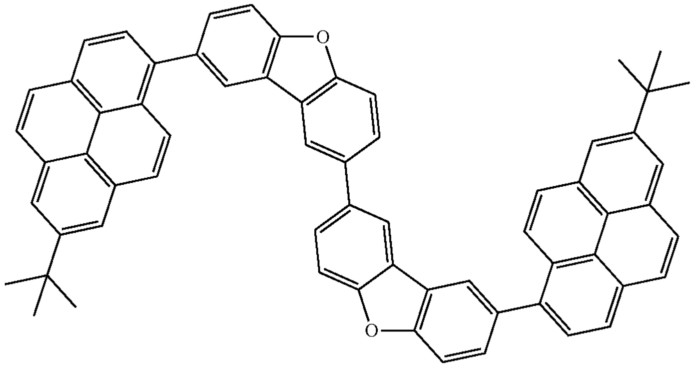
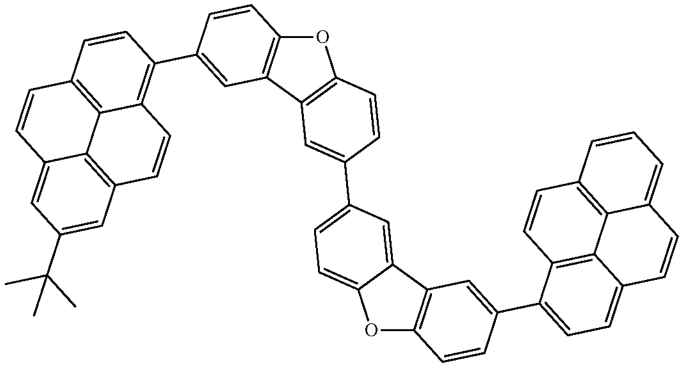

-continued
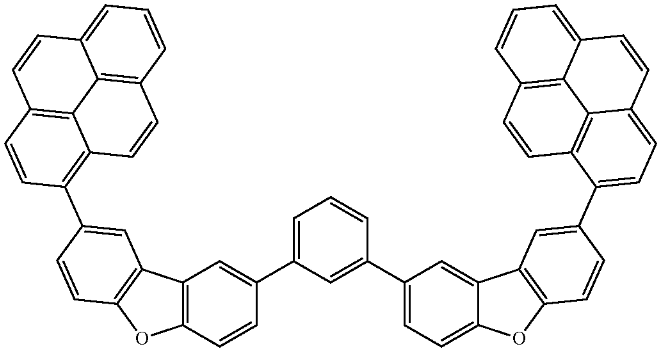
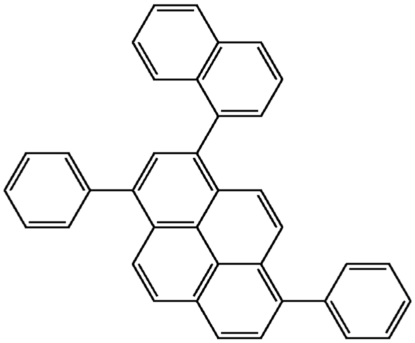
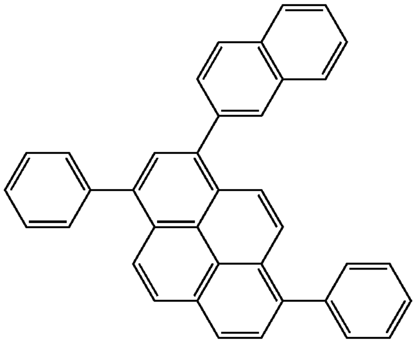
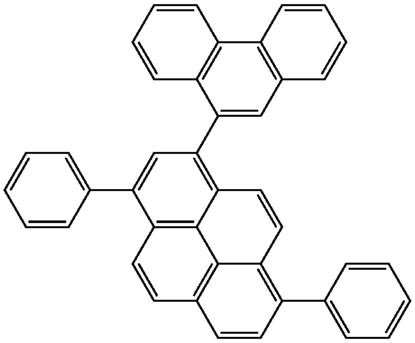
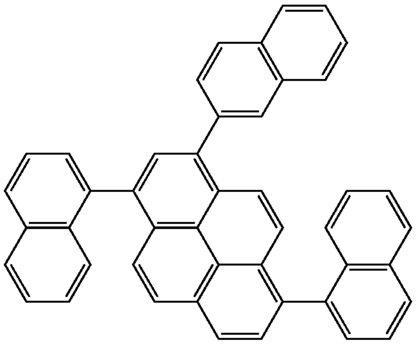
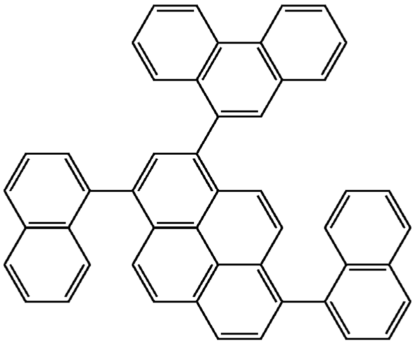
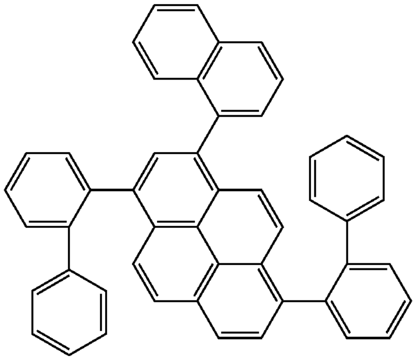
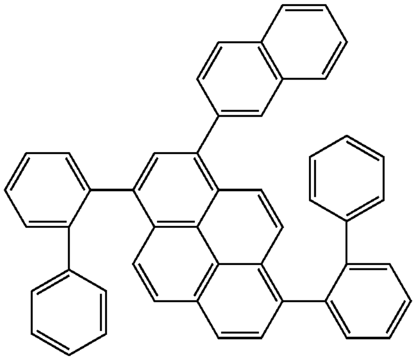

-continued
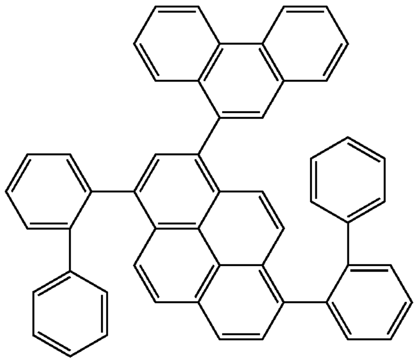
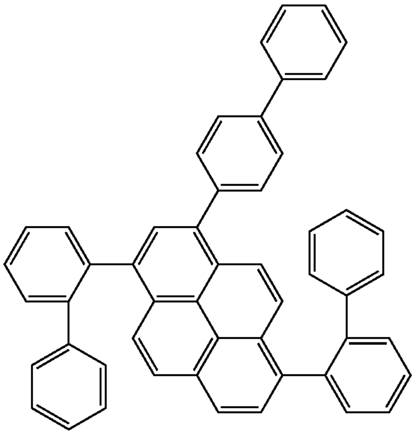
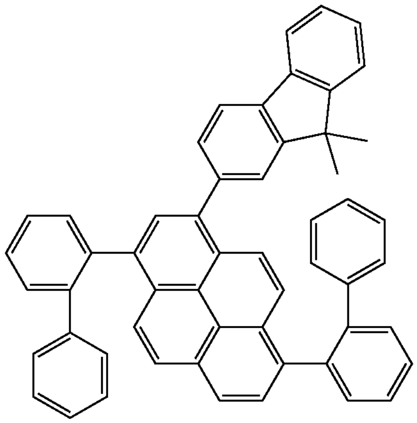
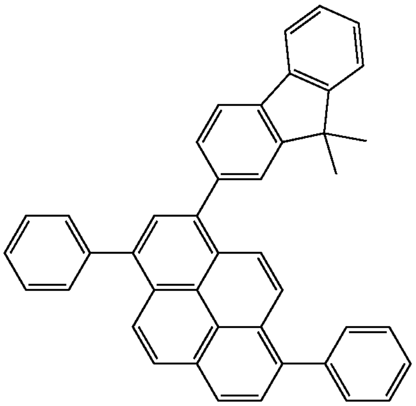
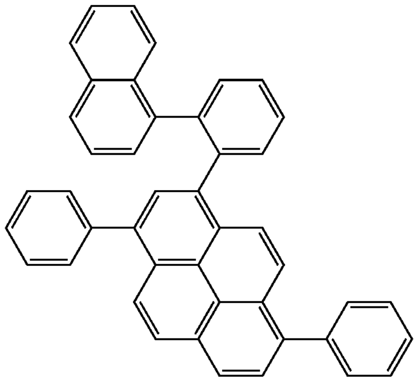
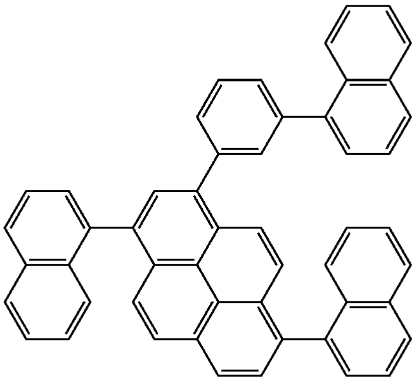
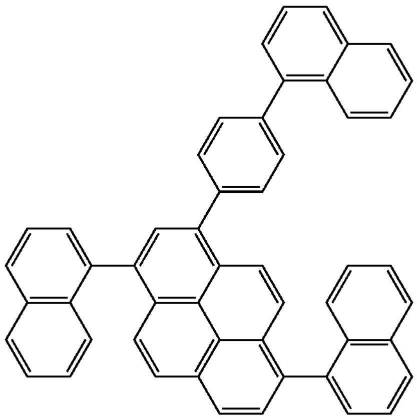
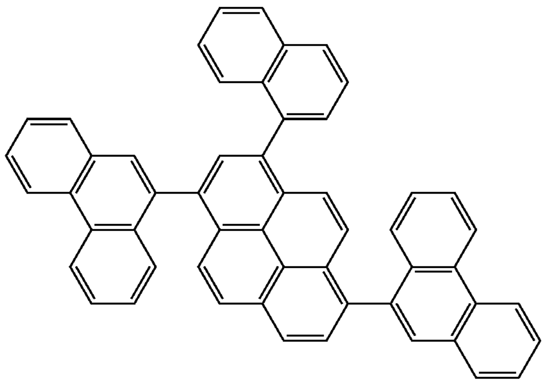

-continued
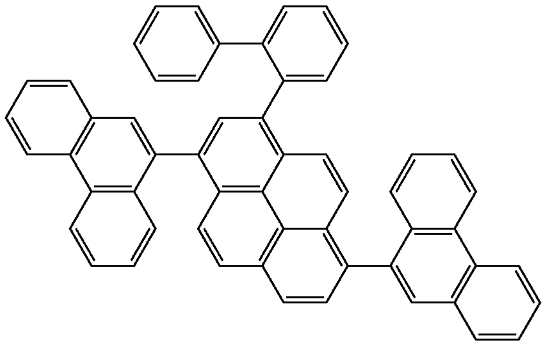
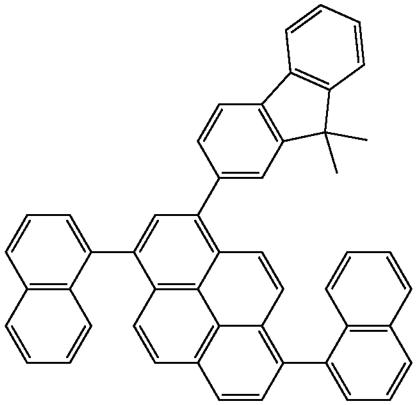
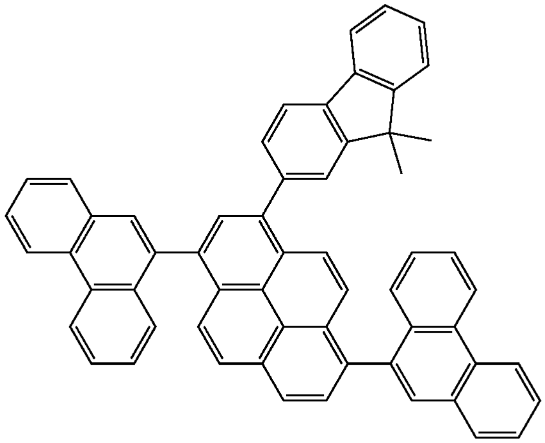
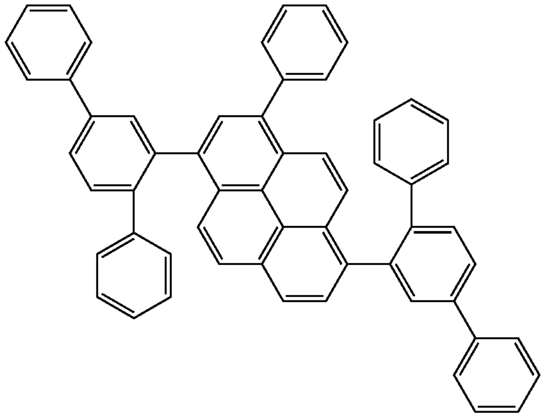
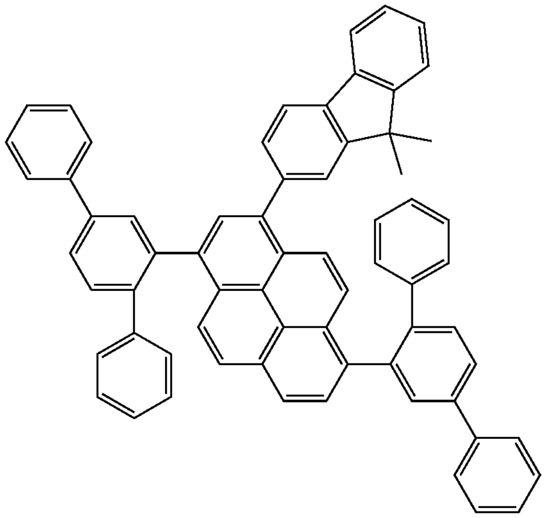
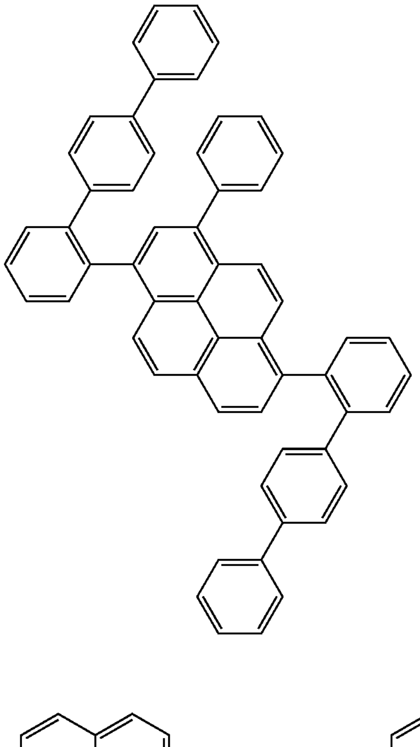
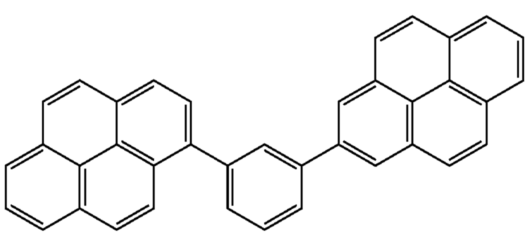
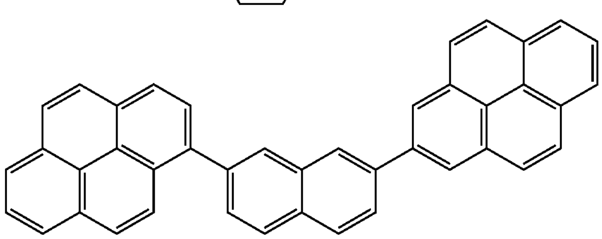

-continued
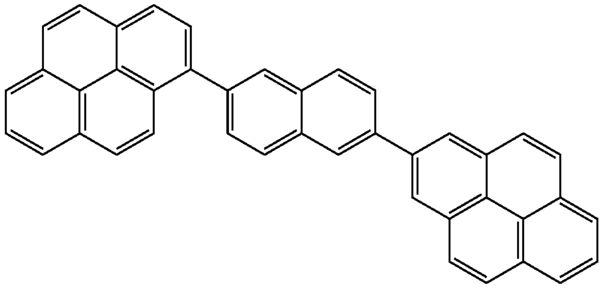
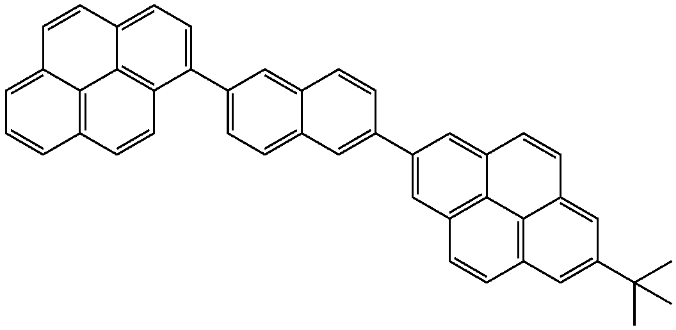
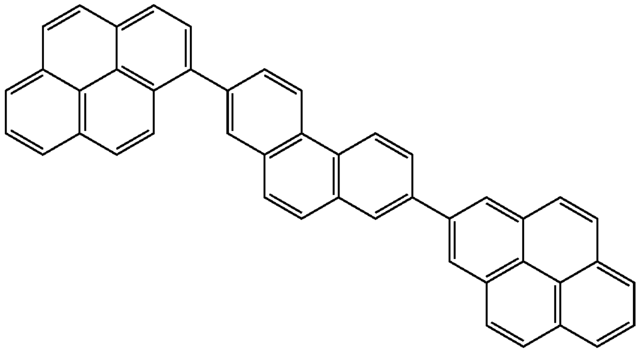
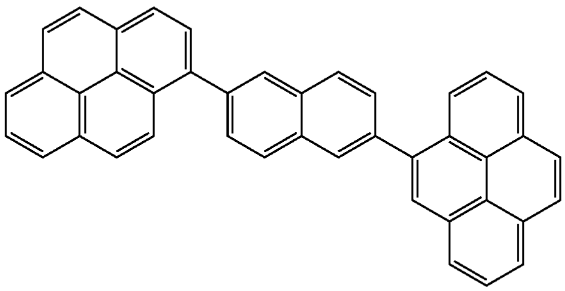
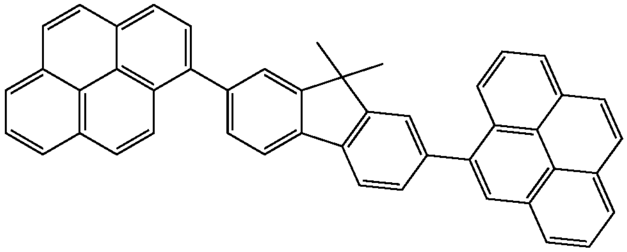

-continued
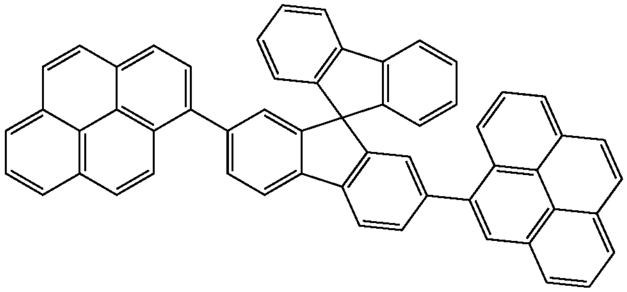
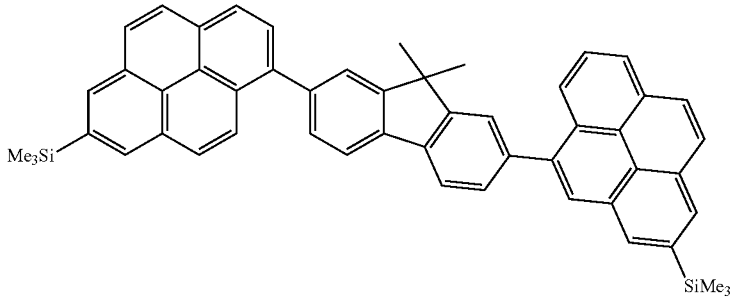
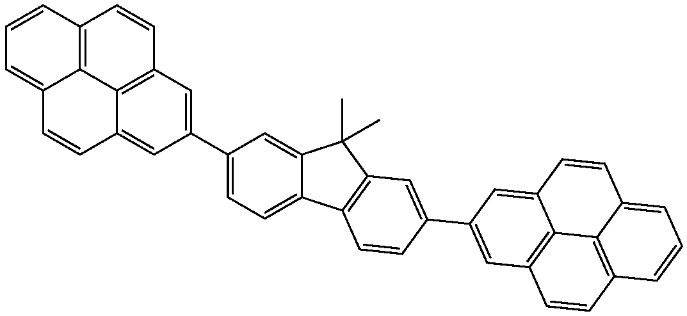
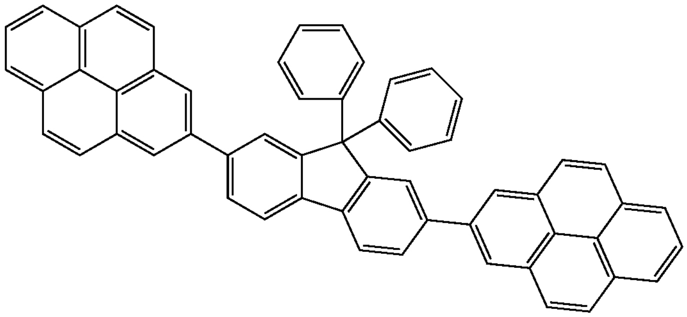
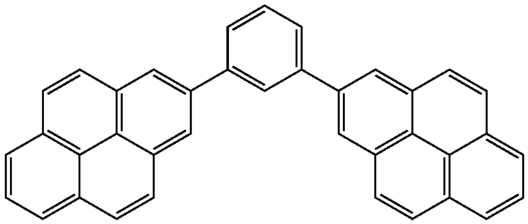
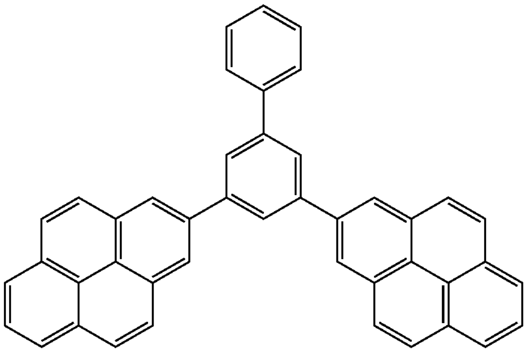

-continued
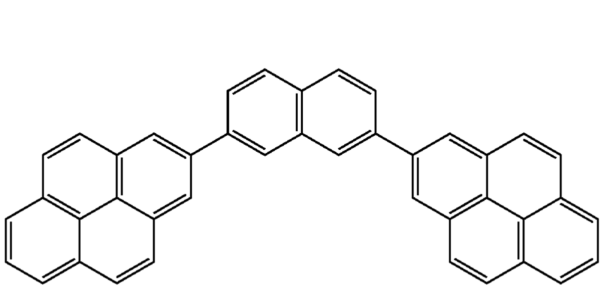
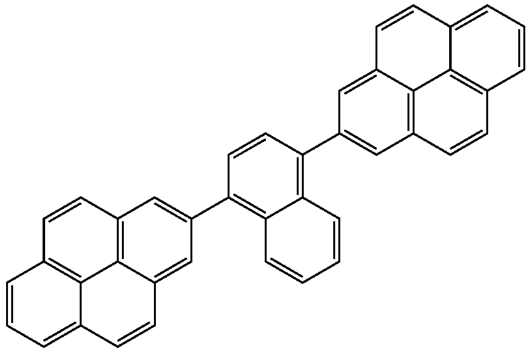
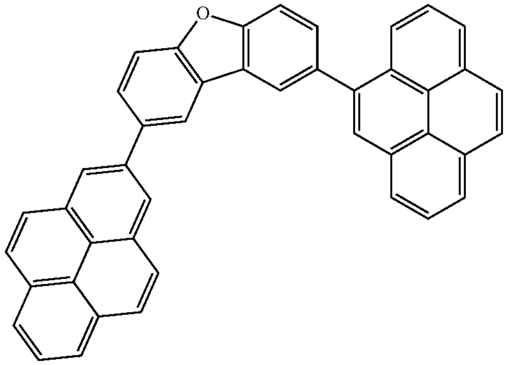
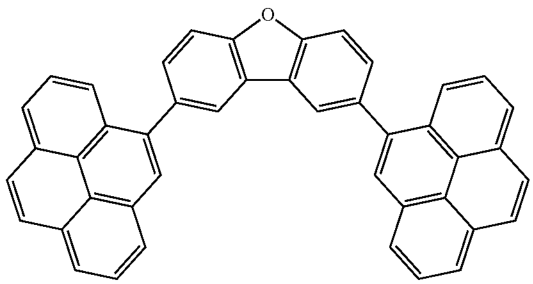
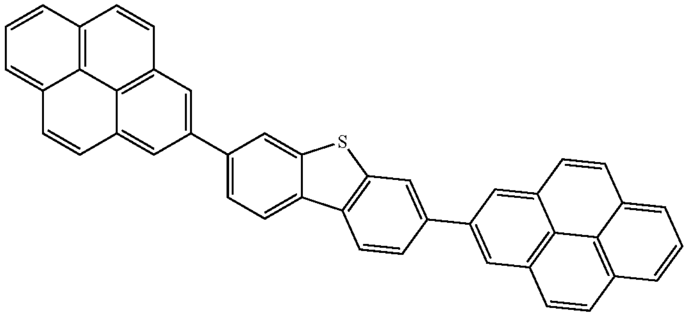
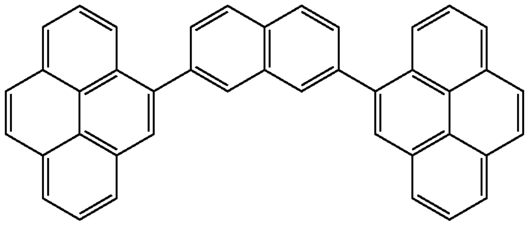
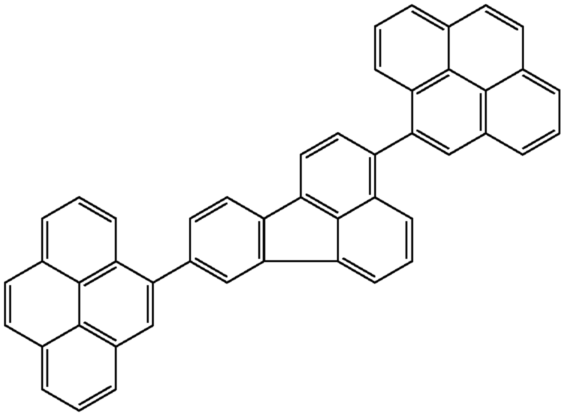
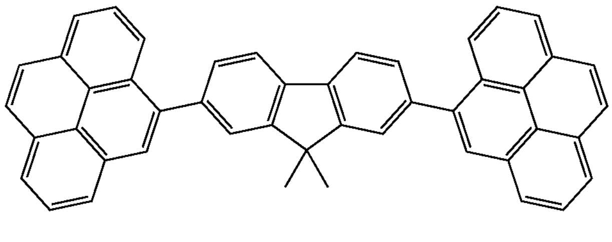

-continued
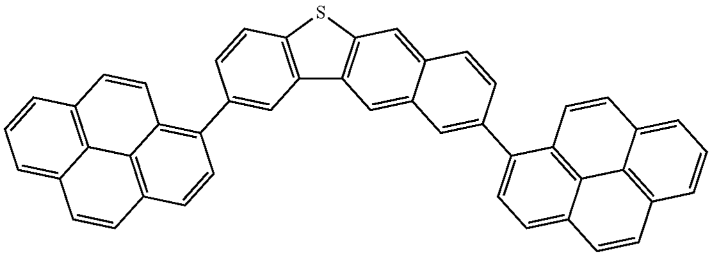
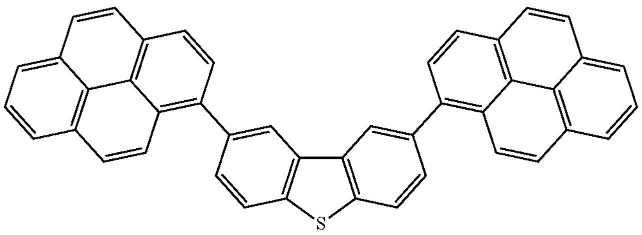
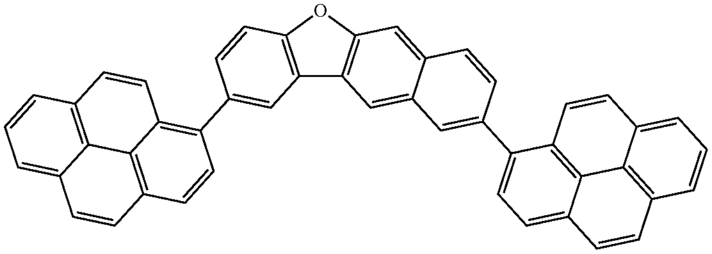
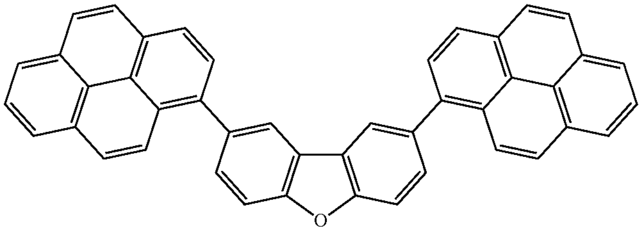
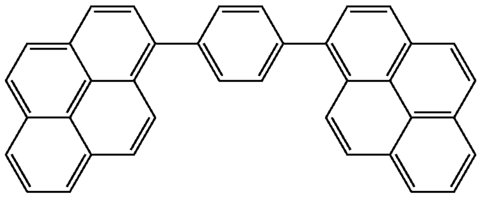
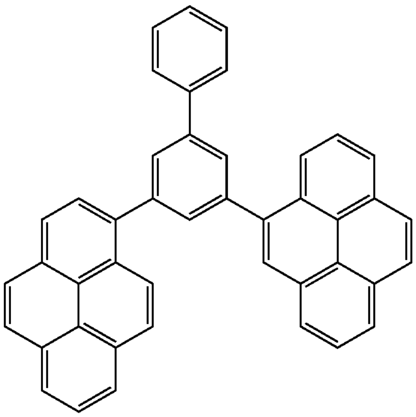
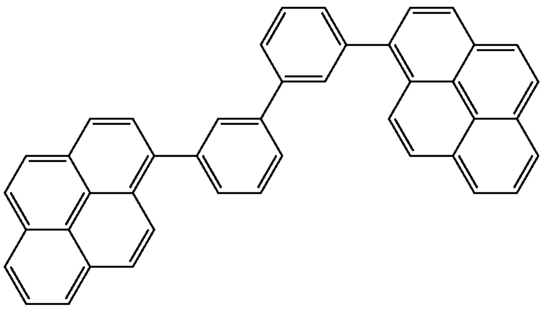

-continued

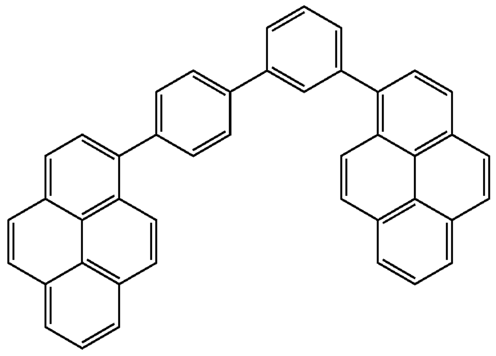

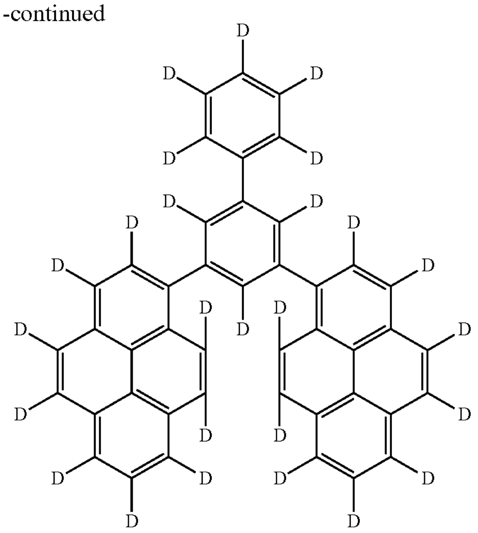

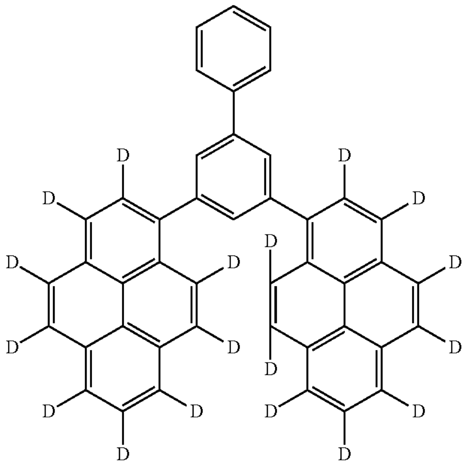

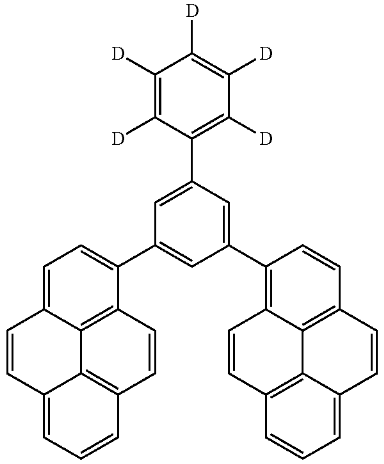

When the second host material is a benzanthracene derivative, the second host material is preferably a compound represented by a formula (H1 X) below.

Compound Represented by Formula (H1X)

(H1X)

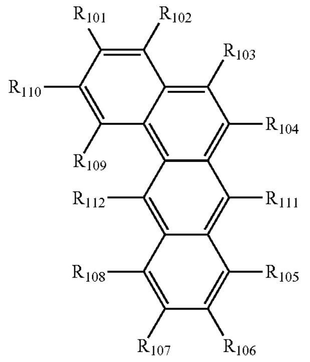

(H11X)

$*-(L_{101})_{mx}-Ar_{101}$

In the formula (H1X):

$R_{101}$ to $R_{112}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by $-Si(R_{901})(R_{902})(R_{903})$, a group represented by $-O-(R_{904})$, a group represented by $-S-(R_{905})$, a substituted or unsubstituted aralkyl group having 7 to 50 carbon atoms, a group represented by $-C(=O)R_{801}$, a group represented by $-COOR_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (H11X);

at least one of $R_{101}$ to $R_{112}$ is a group represented by the formula (H11X);

when a plurality of groups represented by the formula (H11X) are present, the plurality of groups represented by the formula (H11X) are mutually the same or different;

$L_{101}$ is a single bond, a substituted or unsubstituted arylene group having 6 to 50 ring carbon atoms, or a substituted or unsubstituted divalent heterocyclic group having 5 to 50 ring atoms;

$Ar_{101}$ is a substituted or unsubstituted aryl group having 6 to 50 ring carbon atoms, or a substituted or unsubstituted heterocyclic group having 5 to 50 ring atoms;

mx is 1, 2, 3, 4, or 5;

when two or more $L_{101}$ are present, the two or more $L_{101}$ are mutually the same or different;

when two or more $Ar_{101}$ are present, the two or more $Ar_{101}$ are mutually the same or different; and

* in the formula (H11X) represents a bonding position to a benz[a]anthracene ring in the formula (N1X).

In the organic EL device according to the exemplary embodiment, a group represented by the formula (H11X) is preferably a group represented by a formula (H111X) below.

(H111X)

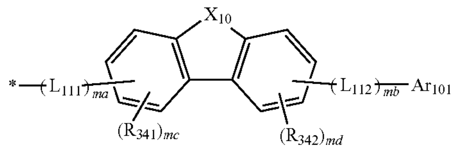

In the formula (H111X):

$X_{10}$ is $C(R_{343})(R_{344})$, an oxygen atom, a sulfur atom, or $NR_{345}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 1, 2, 3 or 4;

mb is 1, 2, 3 or 4;

ma+mb is 2, 3, or 4;

$Ar_{101}$ represents the same as $Ar_{101}$ in the formula (H11X), $R_{341}$, $R_{342}$, $R_{343}$, $R_{344}$ and $R_{345}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$Si(R_{901})(R_{902})(R_{903})$, a group represented by —O—$(R_{904})$, a group represented by —S—$(R_{905})$, a substituted or unsubstituted aralkyl group having 7 to 50 carbon atoms, a group represented by —$C(=O)R_{801}$, a group represented by —$COOR_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

mc is 3;

three $R_{341}$ are mutually the same or different;

and is 3; and three $R_{342}$ are mutually the same or different.

Among positions *1 to *8 of carbon atoms in a cyclic structure represented by a formula (H111aX) below in a group represented by the formula (H111X), is bonded to one of the positions *1 to *4, $R_{341}$ is bonded to each of three positions of the rest of *1 to *4, $L_{112}$ is bonded to one of the positions *5 to *8, and $R_{342}$ is bonded to each of three positions of the rest of *5 to *8.

(H111aX)

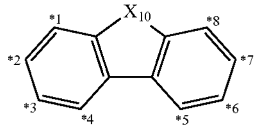

For instance, in a group represented by the formula (H111X), when $L_{111}$ is bonded to a carbon atom at a position *2 in the cyclic structure represented by the formula (H111aX) and $L_{112}$ is bonded to a carbon atom at a position *7 in the cyclic structure represented by the formula (H111aX), a group represented by the formula (H111X) is represented by a formula (H111bX) below.

(H111bX)

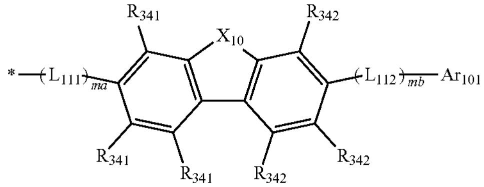

In the formula (H111bX):

$X_{10}$, $L_{111}$, $L_{112}$, ma, mb, $Ar_{101}$, $R_{341}$, $R_{342}$, $R_{343}$, $R_{344}$ and $R_{345}$ each independently represent the same as $X_{10}$, $L_{111}$, $L_{112}$, ma, mb, $Ar_{101}$, $R_{341}$, $R_{342}$, $R_{343}$, $R_{344}$ and $R_{345}$ in the formula (H111X);

a plurality of $R_{341}$ are mutually the same or different; and a plurality of $R_{342}$ are mutually the same or different.

In the organic EL device according to the exemplary embodiment, a group represented by the formula (H111X) is preferably a group represented by the formula (H111bX).

In the compound represented by the formula (H1X), it is preferable that ma is 1 or 2 and mb is 1 or 2.

In the compound represented by the formula (H1X), it is preferable that ma is 1 and mb is 1.

In the compound represented by the formula (H1X), $Ar_{101}$ is preferably a substituted or unsubstituted aryl group having 6 to 50 ring carbon atoms.

In the compound represented by the formula (H1X), it is preferable that $Ar_{101}$ is a substituted or unsubstituted phenyl group, a substituted or unsubstituted naphthyl group, a substituted or unsubstituted biphenyl group, a substituted or unsubstituted terphenyl group, a substituted or unsubstituted benz[a]anthryl group, a substituted or unsubstituted pyrenyl group, a substituted or unsubstituted phenanthryl group, or a substituted or unsubstituted fluorenyl group.

The compound represented by the formula (H1X) is also preferably a compound represented by a formula (H101X) below.

(H101X)

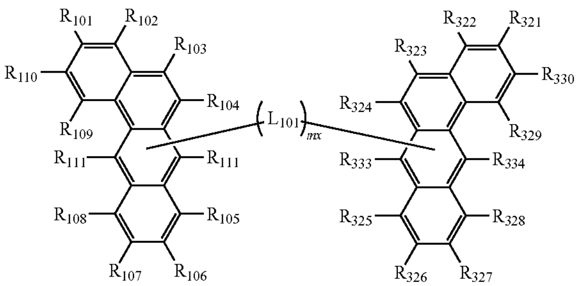

In the formula (H101X):

one of $R_{111}$ and $R_{112}$ represents a bonding position to $L_{101}$ and one of $R_{333}$ and $R_{334}$ represents a bonding position to $L_{101}$;

$R_{111}$ or $R_{112}$ not being a bonding position to $R_{101}$ to $R_{110}$, $R_{321}$ to $R_{330}$, and $L_{101}$, and $R_{333}$ or $R_{334}$ not being a bonding position to $L_{101}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$L_{101}$ is a single bond, a substituted or unsubstituted arylene group having 6 to 50 ring carbon atoms, or a substituted or unsubstituted divalent heterocyclic group having 5 to 50 ring atoms;

mx is 1, 2, 3, 4, or 5; and when two or more $L_{101}$ are present, the two or more $L_{101}$ are mutually the same or different.

In the compound represented by the formula (H1X), $L_{101}$ is preferably a single bond or a substituted or unsubstituted arylene group having 6 to 50 ring carbon atoms.

The compound represented by the formula (H1X) is also preferably a compound represented by a formula (H102X) below.

In the formula (H102X):

one of $R_{111}$ and $R_{112}$ represents a bonding position to $L_{111}$ or one of $R_{333}$ and $R_{334}$ represents a bonding position to $L_{112}$, $R_{111}$ or $R_{112}$ not being a bonding position to $R_{101}$ to $R_{110}$, $R_{321}$ to $R_{330}$, and $L_{111}$, and $R_{333}$ or $R_{334}$ not being a bonding position to $L_{112}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

$X_{10}$ is C($R_{343}$)($R_{344}$), an oxygen atom, a sulfur atom, or NR$_{345}$;

$L_{111}$ and $L_{112}$ are each independently a single bond, a substituted or unsubstituted arylene group having 6 to 50 ring carbon atoms, or a substituted or unsubstituted divalent heterocyclic group having 5 to 50 ring atoms;

ma is 1, 2, 3 or 4;

mb is 1, 2, 3 or 4;

ma+mb is 2, 3, 4 or 5;

$R_{341}$, $R_{342}$, $R_{343}$, $R_{344}$ and $R_{345}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COOR$_{802}$, a halogen atom, a cyano group, a nitro group, a substituted or unsubsti- (H102X)

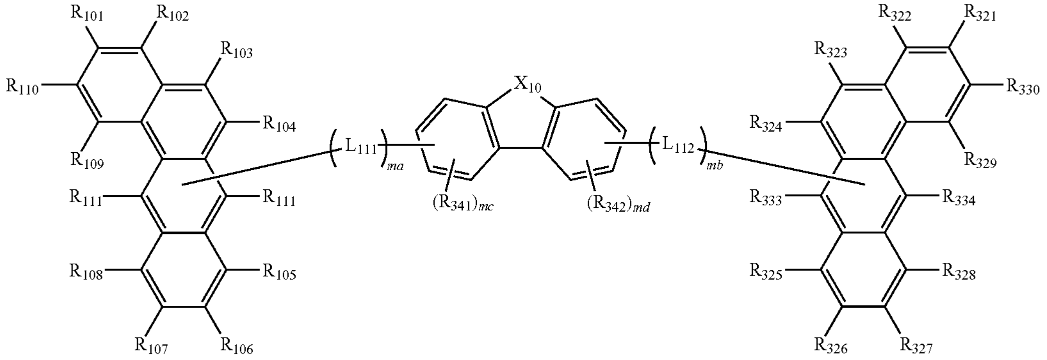

tuted aryl group having 6 to 50 ring carbon atoms, or a substituted or unsubstituted heterocyclic group having 5 to 50 ring atoms;

mc is 3;

three $R_{341}$ are mutually the same or different;

and is 3; and three $R_{342}$ are mutually the same or different.

In the compound represented by the formula (H1X), it is preferable that ma is 1 or 2 and mb is 1 or 2 in the formula (H102X).

In the compound represented by the formula (H1X), it is more preferable that ma is 1 and mb is 1 in the formula (H102X).

In the compound represented by the formula (H1X), it is also preferable that a group represented by the formula (H11X) is a group represented by a formula (H11AX) or a group represented by a formula (H11BX).

(H11AX)

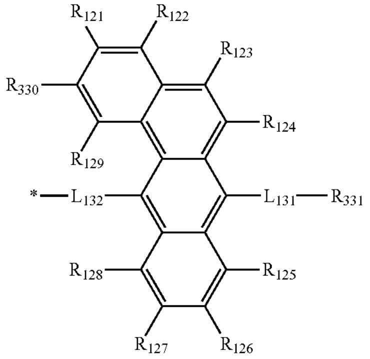

(H11BX)

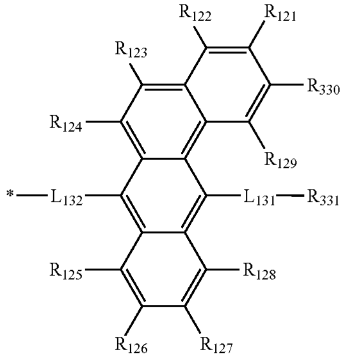

In the formula (H11AX) and the formula (H11BX):

$R_{121}$ to $R_{129}$, $R_{330}$, and $R_{331}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, or a substituted or unsubstituted heterocyclic group having 5 to 50 ring atoms;

when a plurality of groups represented by the formula (H11AX) are present, the plurality of groups represented by the formula (H11AX) are mutually the same or different;

when a plurality of groups represented by the formula (H11BX) are present, the plurality of groups represented by the formula (H11BX) are mutually the same or different;

$L_{131}$ and $L_{132}$ are each independently a single bond, a substituted or unsubstituted arylene group having 6 to 50 ring carbon atoms, or a substituted or unsubstituted divalent heterocyclic group having 5 to 50 ring atoms; and

* in each of the formulae (H11AX) and (H11BX) represents a bonding position to a benz[a]anthracene ring in the formula (H1X).

The compound represented by the formula (H1X) is also preferably a compound represented by a formula (H103X) below.

(H103X)

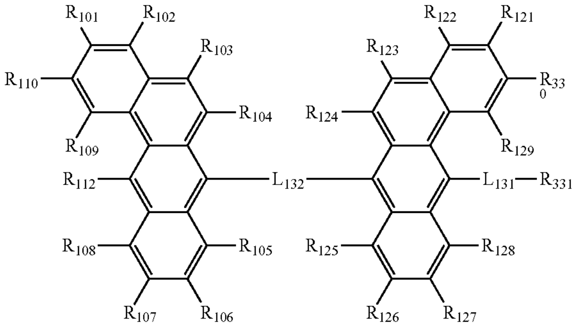

In the formula (H103X):

$R_{101}$ to $R_{110}$ and $R_{112}$ each represent the same as $R_{101}$ to $R_{110}$ and $R_{112}$ in the formula (H1X); and $R_{121}$ to $R_{129}$, $R_{330}$, $R_{331}$, $L_{131}$ and $L_{132}$ each represent the same as $R_{121}$ to $R_{129}$, $R_{330}$, $R_{331}$, $L_{131}$ and $L_{132}$ in the formula (H11BX).

In the compound represented by the formula (H1X), $L_{331}$ is also preferably a substituted or unsubstituted arylene group having 6 to 50 ring carbon atoms.

In the compound represented by the formula (H1X), $L_{332}$ is also preferably a substituted or unsubstituted arylene group having 6 to 50 ring carbon atoms.

In the compound represented by the formula (H1X), it is also preferable that two or more of $R_{101}$ to $R_{112}$ are each a group represented by the formula (H11X).

In the compound represented by the formula (H1X), it is preferable that two or more of $R_{101}$ to $R_{112}$ are a group represented by the formula (H11X) and $Ar_{101}$ in the formula (H11X) is a substituted or unsubstituted aryl group having 6 to 50 ring carbon atoms.

In the compound represented by the formula (H1X), it is also preferable that $Ar_{101}$ is not a substituted or unsubstituted benz[a]anthryl group, $L_{101}$ is not a substituted or unsubstituted benz[a]anthrylene group, and a substituted or unsubstituted aryl group having 6 to 50 ring carbon atoms as $R_{101}$ to $R_{110}$ not being a group represented by the formula (H11X) is not a substituted or unsubstituted benz[a]anthryl group.

In the compound represented by the formula (H1X), it is preferable that $R_{101}$ to $R_{112}$ not being a group represented by the formula (H11X) is each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

In the compound represented by the formula (H1X), it is preferable that $R_{101}$ to $R_{112}$ not being a group represented by the formula (H11X) are a hydrogen atom, a substituted or unsubstituted alkyl group having 1 to 50 carbon atoms, or a substituted or unsubstituted cycloalkyl group having 3 to 50 ring carbon atoms.

In the compound represented by the formula (H1X), it is preferable that $R_{101}$ to $R_{112}$ not being a group represented by the formula (H11X) are each a hydrogen atom.

The compound represented by the formula (H1X) can be manufactured by a known method.

Specific Examples of Compound Represented by Formula (H1X)

Specific examples of the compound represented by the formula (H1X) include compounds shown below. It should be noted that a compound represented by the formula (H1X) is by no means limited to the specific examples below.

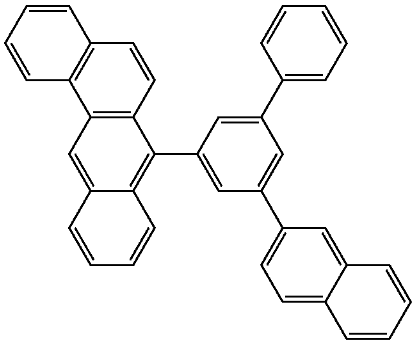

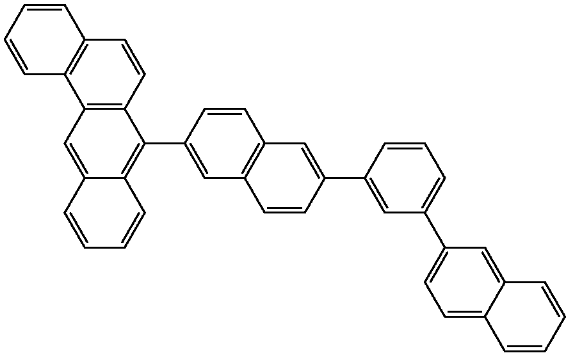

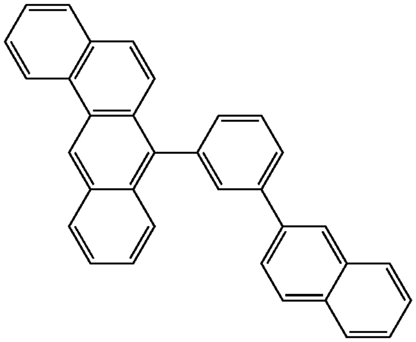

-continued

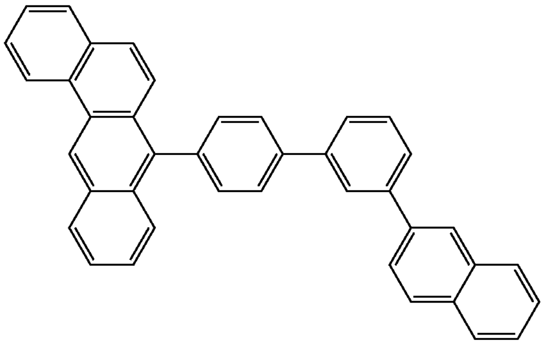

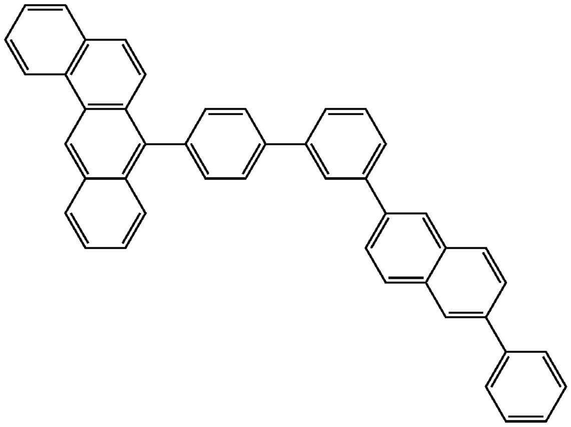

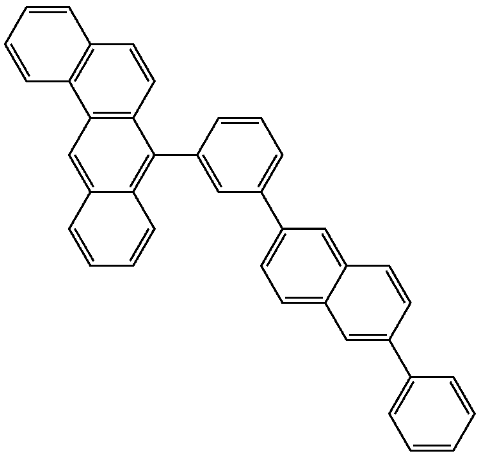

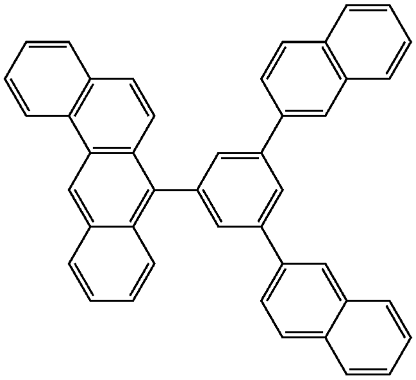

-continued
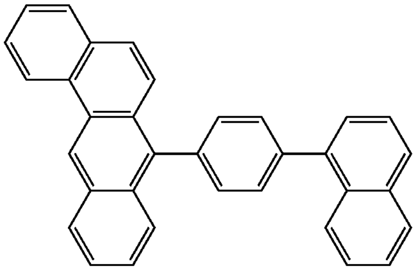
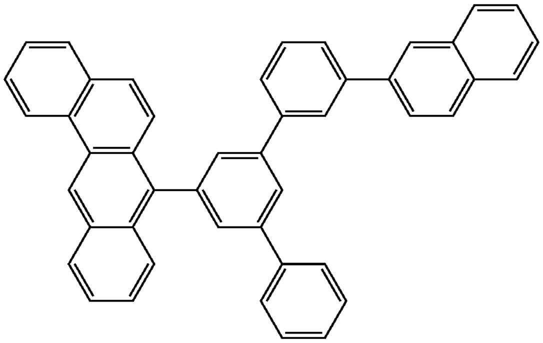
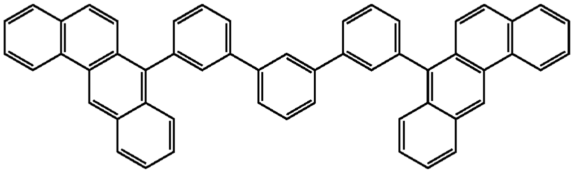
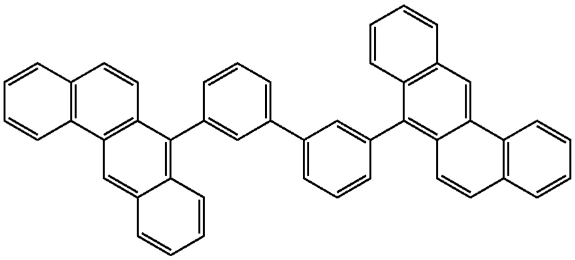
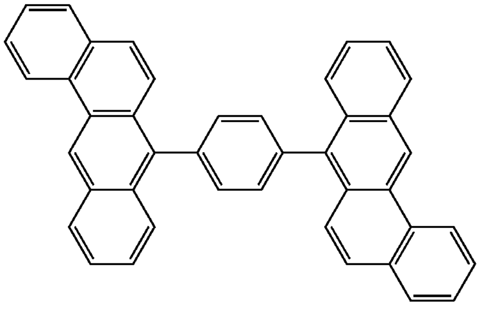
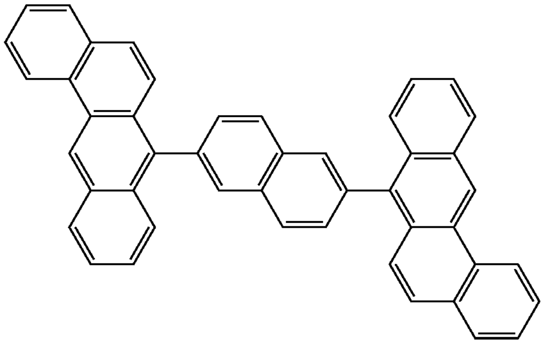
-continued
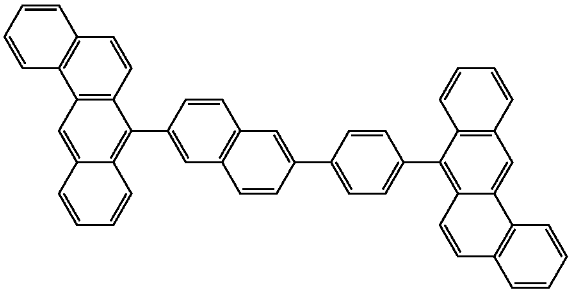
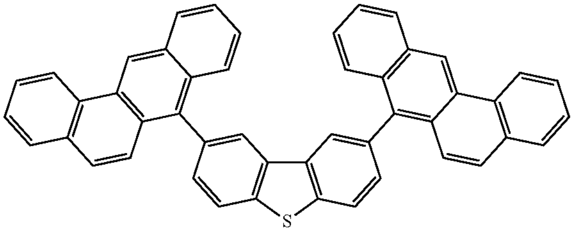
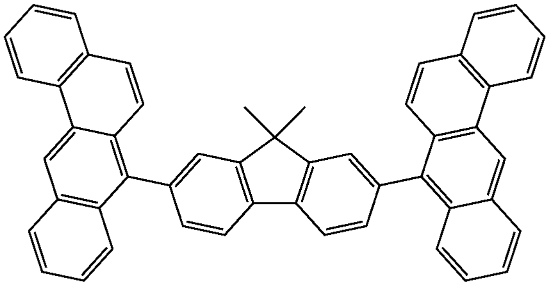
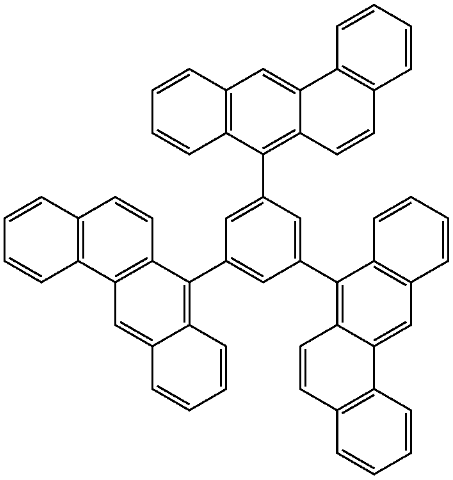
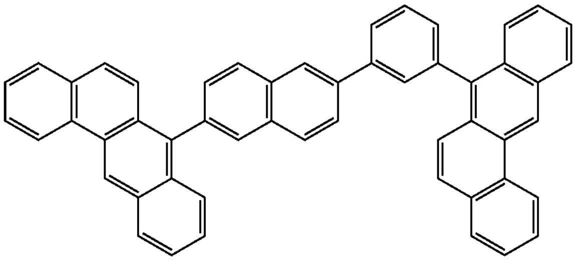

-continued

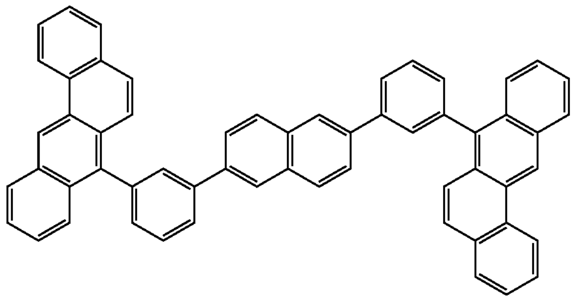

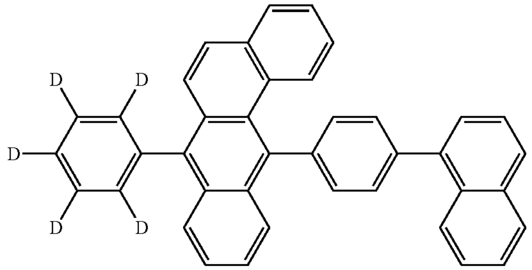

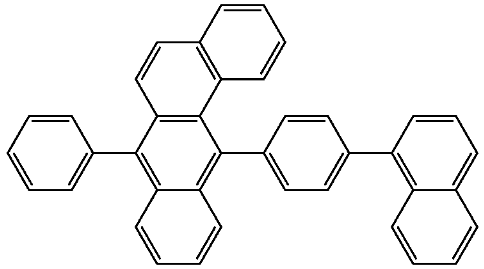

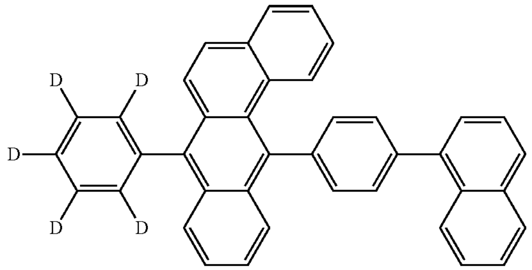

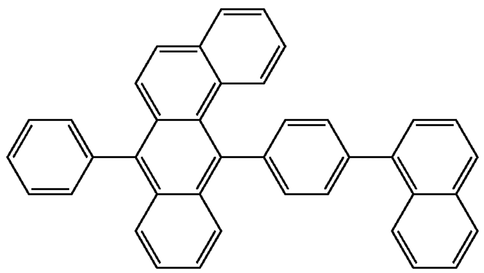

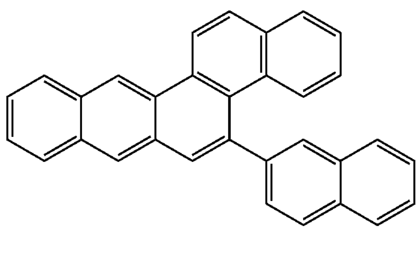

When the second host material is a benzoxanthene derivative, the second host material is preferably a compound represented by a formula (H14X) below.

Compound Represented by Formula (H14X)

(H14X)

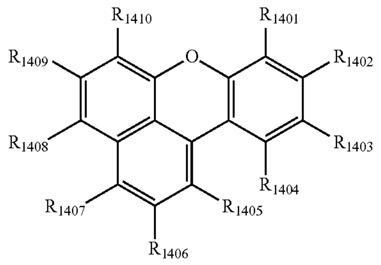

(H141)

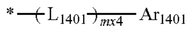

In the formula (H14X):

$R_{1401}$ to $R_{1410}$ are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a substituted or unsubstituted aralkyl group having 7 to 50 carbon atoms, a group represented by —C(═O)$R_{801}$, a group represented by —COO$R_{802}$, a halogen atom, a cyano group, a nitro group, a substituted or unsubstituted aryl group having 6 to 50 ring carbon atoms, a substituted or unsubstituted heterocyclic group having 5 to 50 ring atoms, or a group represented by the formula (H141);

at least one of $R_{1401}$ to $R_{1410}$ is a group represented by the formula (H141);

when a plurality of groups represented by the formula (H141) are present, the plurality of groups represented by the formula (H141) are mutually the same or different;

$L_{1401}$ is a single bond, a substituted or unsubstituted arylene group having 6 to 50 ring carbon atoms, or a substituted or unsubstituted divalent heterocyclic group having 5 to 50 ring atoms;

$Ar_{1401}$ is a substituted or unsubstituted aryl group having 6 to 50 ring carbon atoms, or a substituted or unsubstituted heterocyclic group having 5 to 50 ring atoms;

mx4 is 0, 1, 2, 3, 4 or 5;

when two or more $L_{1401}$ are present, the two or more $L_{1401}$ are mutually the same or different;

when two or more $Ar_{1401}$ are present, the two or more $Ar_{1401}$ are mutually the same or different; and

* in the formula (H141) represents a bonding position to a ring represented by the formula (H14X).

The compound represented by the formula (H14X) can be manufactured by a known method.

Specific Examples of Compound Represented by Formula (H14X)

Specific examples of the compound represented by the formula (H14X) include compounds shown below. It should be noted that the compound represented by the formula (H14X) is by no means limited to the specific examples below.

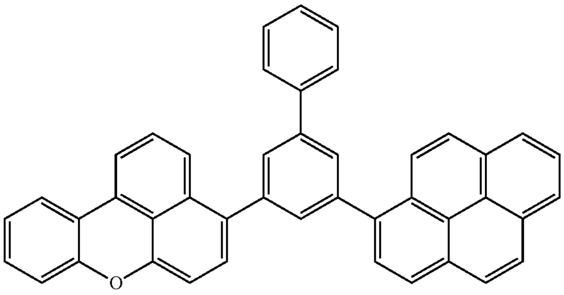
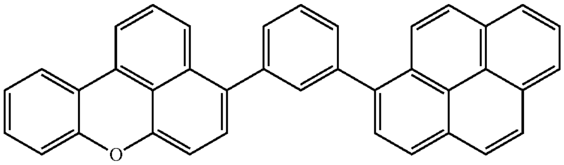
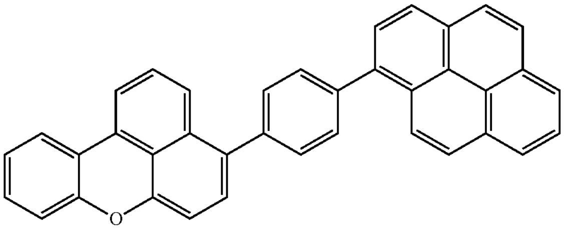
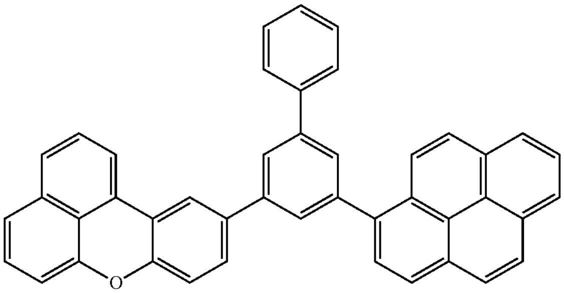
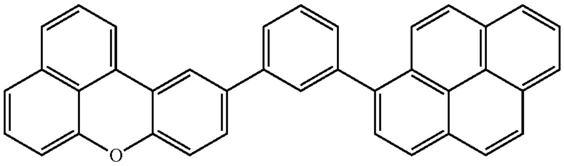
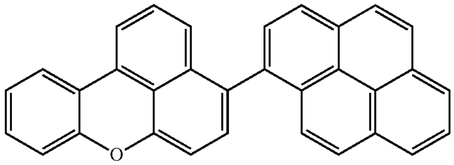
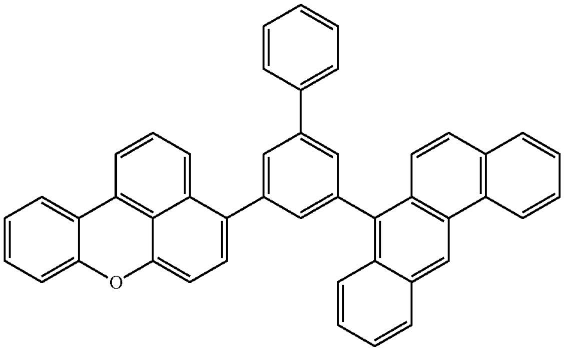
-continued
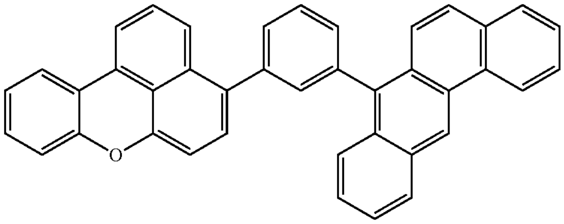
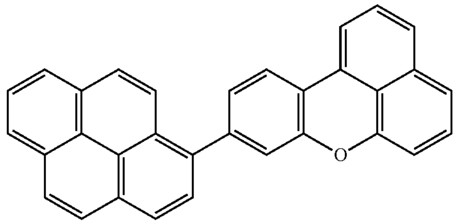
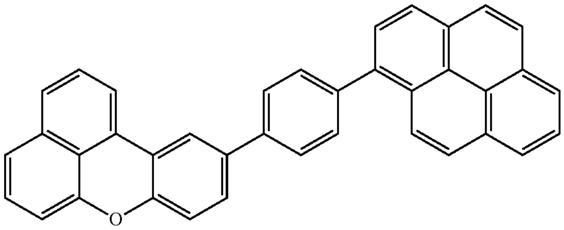
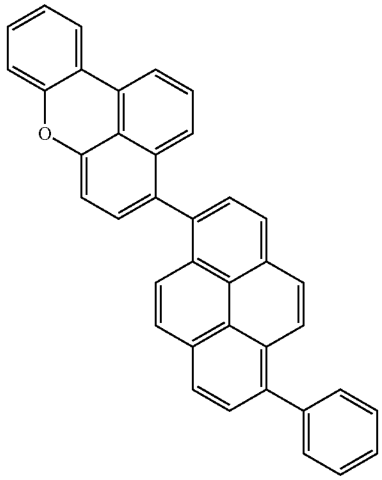
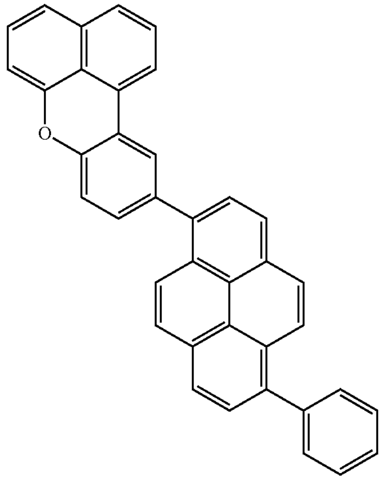

-continued

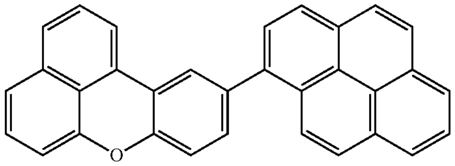

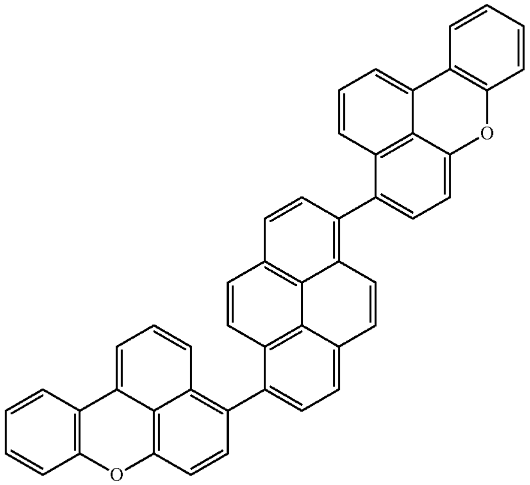

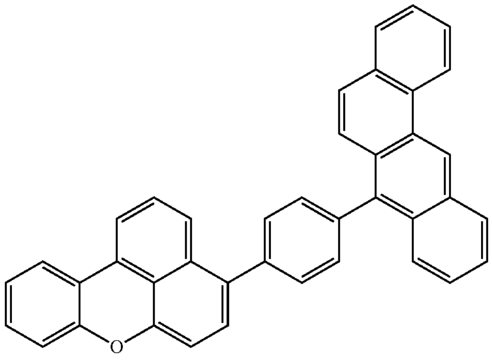

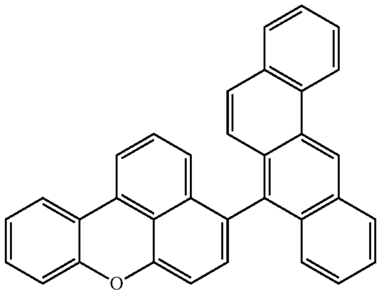

Second Dopant Material

Examples of the second dopant material include the compound according to the first exemplary embodiment, a pyrene derivative, a styrylamine derivative, a chrysene derivative, a fluoranthene derivative, a fluorene derivative, a diamine derivative, a triarylamine derivative, an aromatic amine derivative, and a tetracene derivative.

The second dopant material is preferably the compound according to the first exemplary embodiment, a compound represented by a formula (5) below, or a compound represented by a formula (6) below.

Compound Represented by Formula (5)

(5)

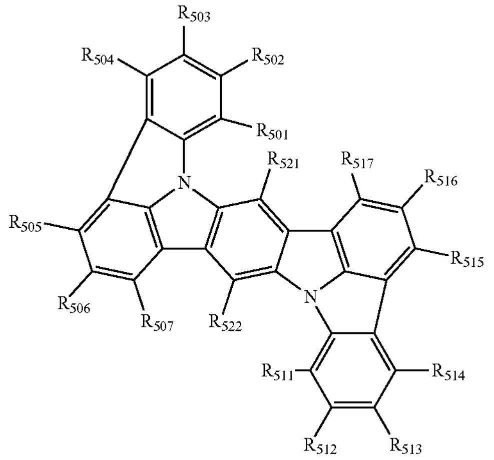

In the formula (5):

at least one combination of adjacent two or more of $R_{501}$ to $R_{507}$ and $R_{511}$ to $R_{517}$ are mutually bonded to form a substituted or unsubstituted monocyclic ring, mutually bonded to form a substituted or unsubstituted fused ring, or not mutually bonded;

$R_{501}$ to $R_{507}$ and $R_{511}$ to $R_{517}$ neither forming the substituted or unsubstituted monocyclic ring nor forming the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms; and $R_{521}$ and $R_{522}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

In the second dopant material, $R_{901}$, $R_{902}$, $R_{903}$, $R_{904}$, $R_{905}$, $R_{906}$, and $R_{907}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms, a substituted or unsubstituted alkyl group having 1 to 50 carbon atoms, or a substituted or unsubstituted aryl group having 6 to 50 ring carbon atoms; and when a plurality of $R_{901}$ are present, the plurality of $R_{901}$ are mutually the same or different;

when a plurality of $R_{902}$ are present, the plurality of $R_{902}$ are mutually the same or different;

when a plurality of $R_{903}$ are present, the plurality of $R_{903}$ are mutually the same or different;

when a plurality of $R_{904}$ are present, the plurality of $R_{904}$ are mutually the same or different;

when a plurality of $R_{905}$ are present, the plurality of $R_{905}$ are mutually the same or different;

when a plurality of $R_{906}$ are present, the plurality of $R_{906}$ are mutually the same or different; and when a plurality of $R_{907}$ are present, the plurality of $R_{907}$ are mutually the same or different.

"A combination of adjacent two or more of $R_{501}$ to $R_{507}$ and $R_{511}$ to $R_{517}$" refers to, for instance, a combination of $R_{501}$ and $R_{502}$, a combination of $R_{502}$ and $R_{503}$, a combination of $R_{503}$ and $R_{504}$, a combination of $R_{505}$ and $R_{506}$, a combination of $R_{506}$ and $R_{507}$, and a combination of $R_{501}$, $R_{502}$ and $R_{503}$.

In an exemplary embodiment, at least one, preferably two of $R_{501}$ to $R_{507}$ and $R_{511}$ to $R_{517}$ are groups represented by $—N(R_{906})(R_{907})$.

In an exemplary embodiment, $R_{501}$ to $R_{507}$ and $R_{511}$ to $R_{517}$ are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (52) below.

(52)

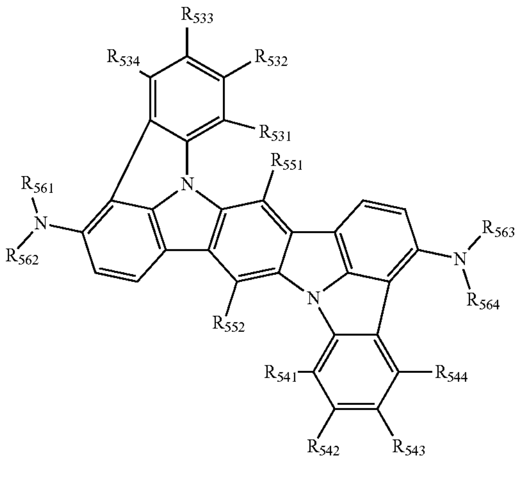

In the formula (52):

at least one combination of adjacent two or more of $R_{531}$ to $R_{534}$ and $R_{541}$ to $R_{544}$ are mutually bonded to form a substituted or unsubstituted monocyclic ring, mutually bonded to form a substituted or unsubstituted fused ring, or not mutually bonded;

$R_{531}$ to $R_{534}$, $R_{541}$ to $R_{544}$, $R_{551}$ and 8552 neither forming the substituted or unsubstituted monocyclic ring nor forming the substituted or unsubstituted fused ring are each independently a hydrogen atom, a substituted or unsubstituted aryl group having 6 to 50 ring carbon atoms, or a substituted or unsubstituted heterocyclic group having 5 to 50 ring atoms; and $R_{561}$ to $R_{564}$ are each independently a substituted or unsubstituted aryl group having 6 to 50 ring carbon atoms, or a substituted or unsubstituted heterocyclic group having 5 to 50 ring atoms.

In an exemplary embodiment, the compound represented by the formula (5) is a compound represented by a formula (53) below.

(53)

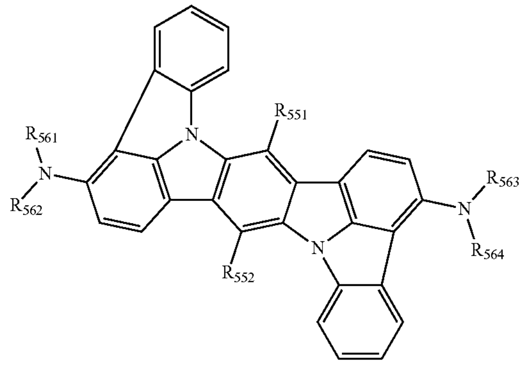

In the formula (53), $R_{551}$, $R_{552}$ and $R_{561}$ to $R_{564}$ each independently represent the same as $R_{551}$, $R_{552}$ and $R_{561}$ to $R_{564}$ in the formula (52).

In an exemplary embodiment, $R_{561}$ to $R_{564}$ in the formulae (52) and (53) are each independently a substituted or unsubstituted aryl group having 6 to 50 ring carbon atoms (preferably a phenyl group).

In an exemplary embodiment, $R_{521}$ and $R_{522}$ in the formula (5), and $R_{551}$ and $R_{552}$ in the formulae (52) and (53) are each a hydrogen atom.

In an exemplary embodiment, a substituent for the "substituted or unsubstituted" group in the formulae (5), (52) and (53) is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The compound represented by the formula (5) can be manufactured by a known method.

Specific Examples of Compound Represented by Formula (5)

Specific examples of the compound represented by the formula (5) include compounds shown below. It should be noted that the compound represented by the formula (5) is by no means limited to the specific examples below.

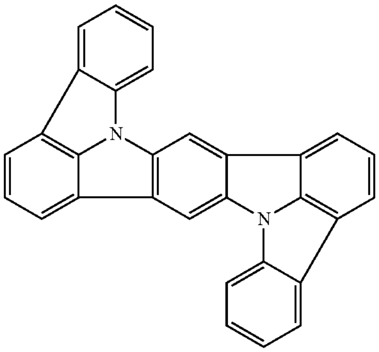
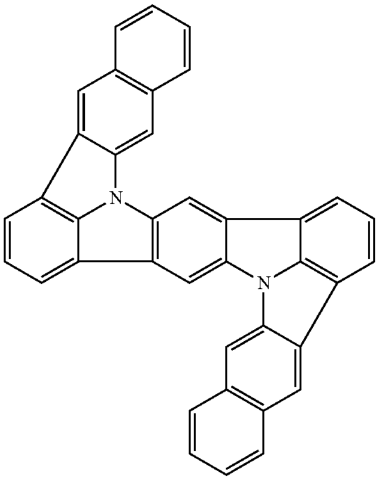
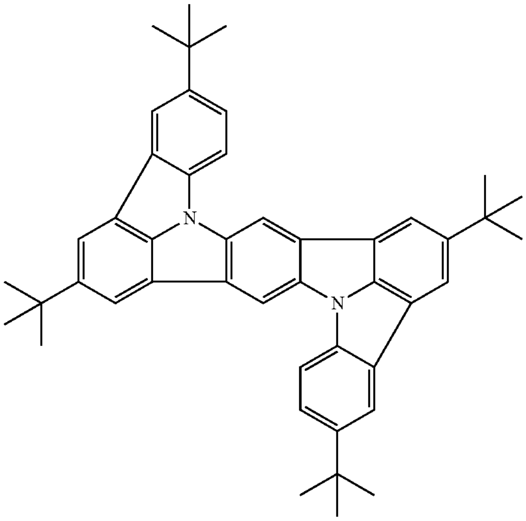
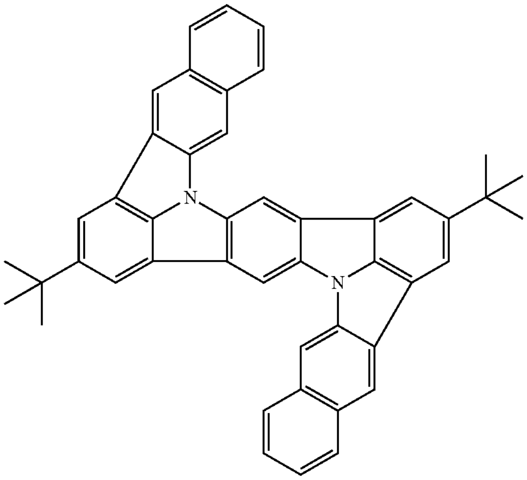
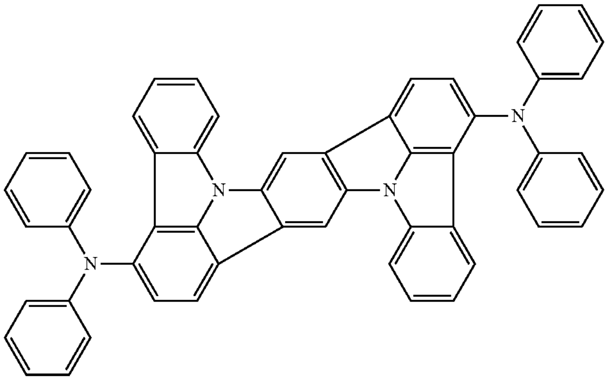

-continued
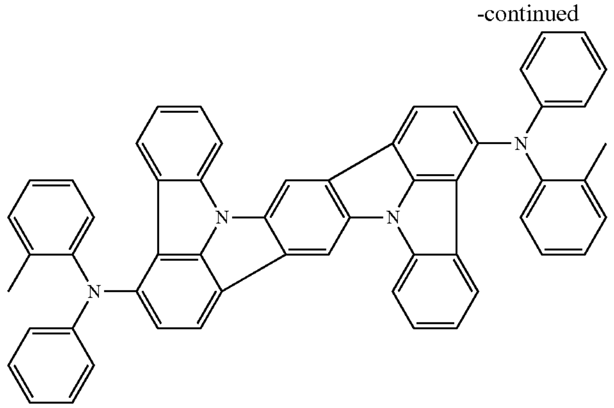
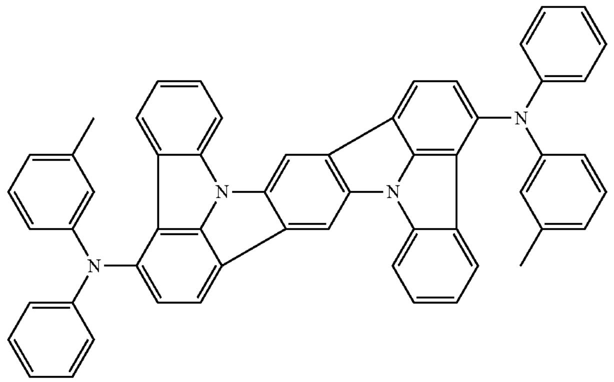
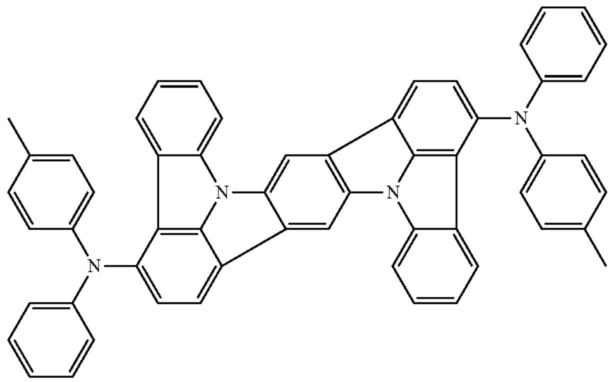
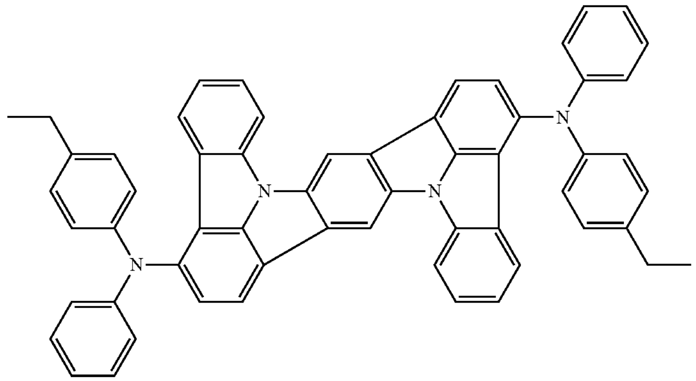

-continued
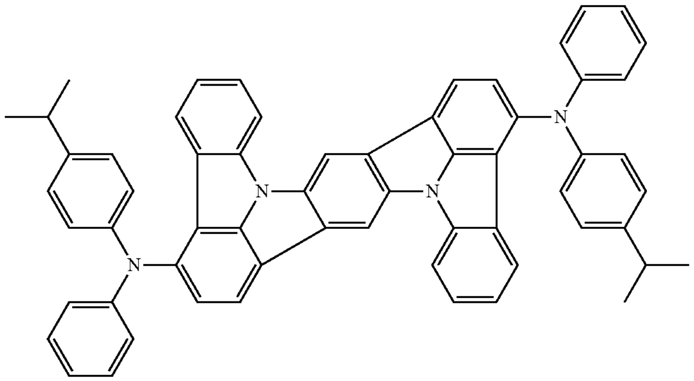
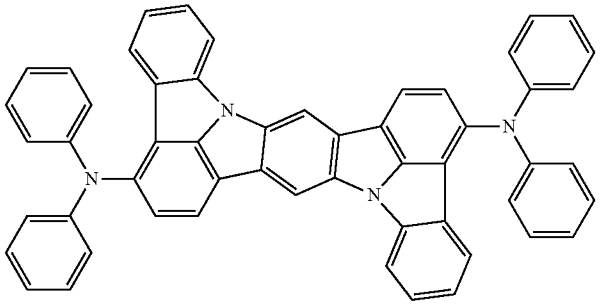
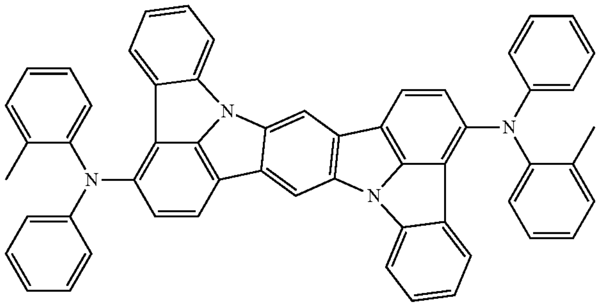
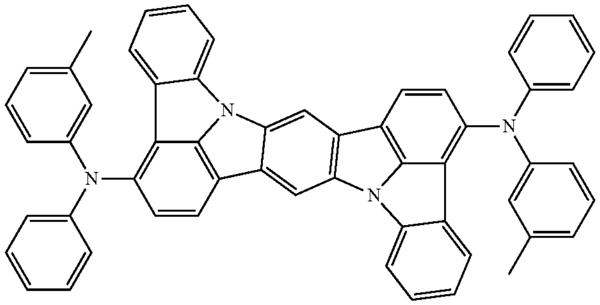
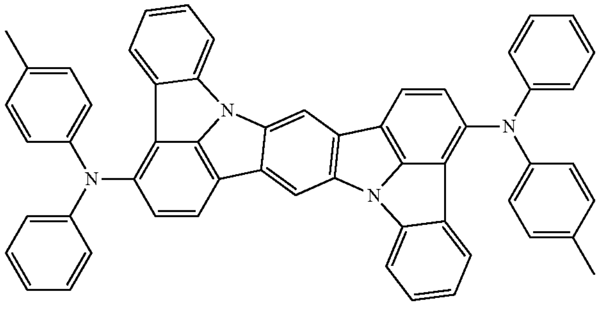

-continued
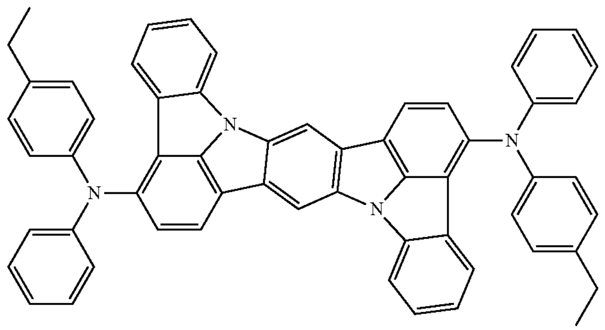
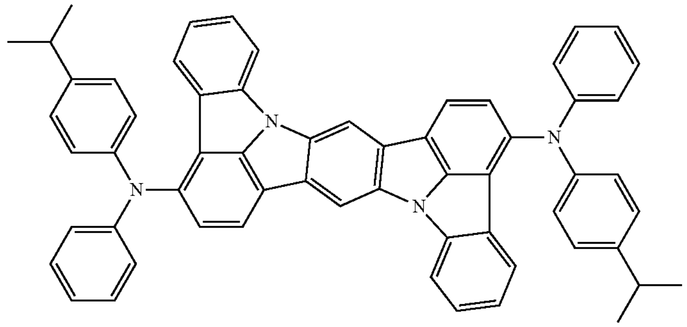
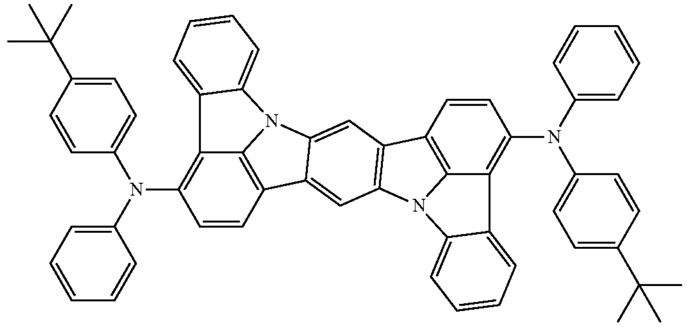
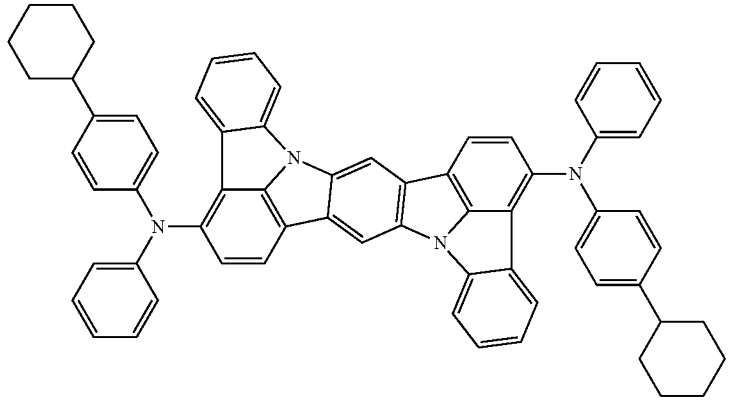

-continued
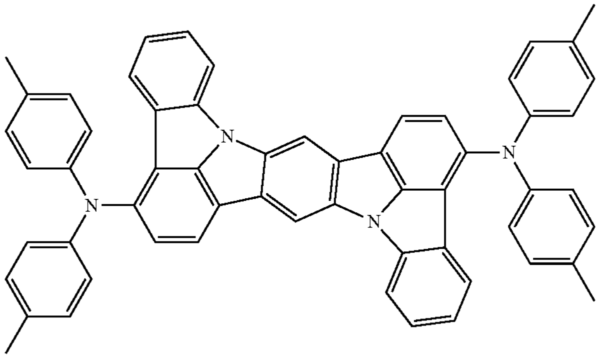
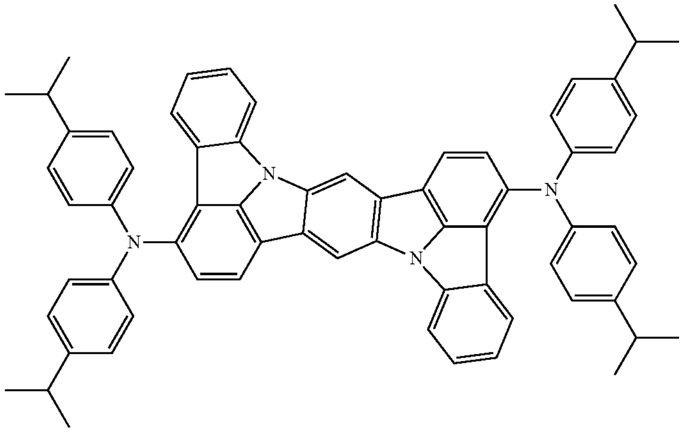
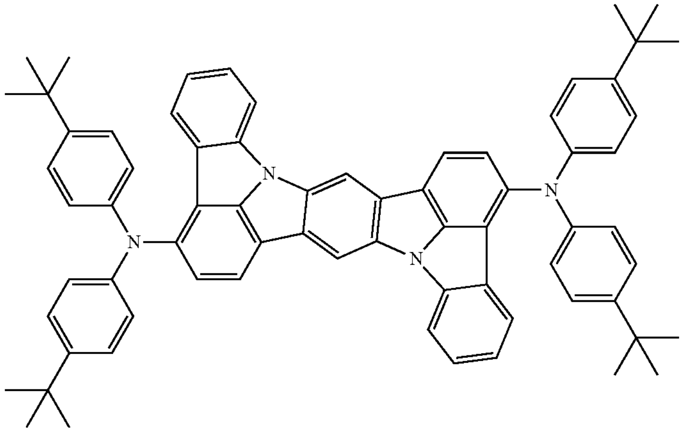
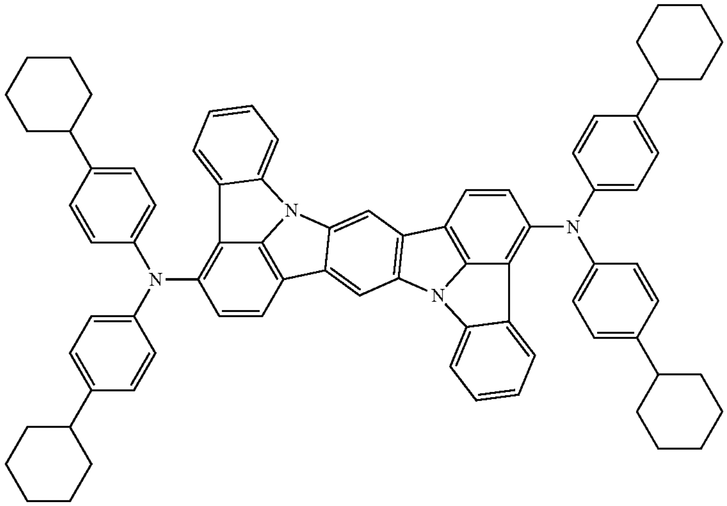

-continued
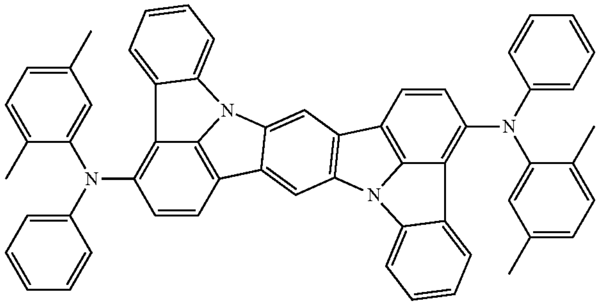
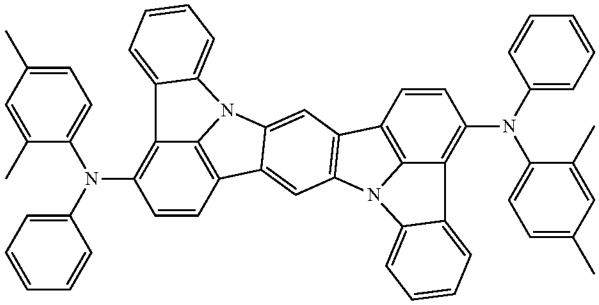
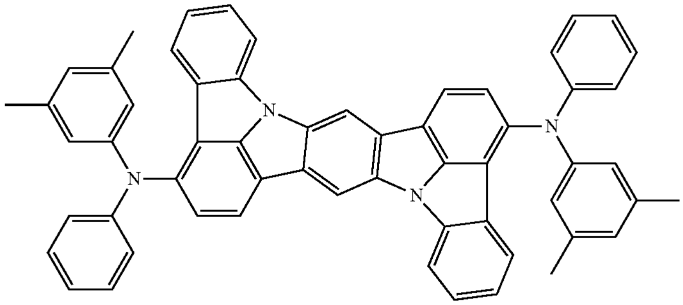
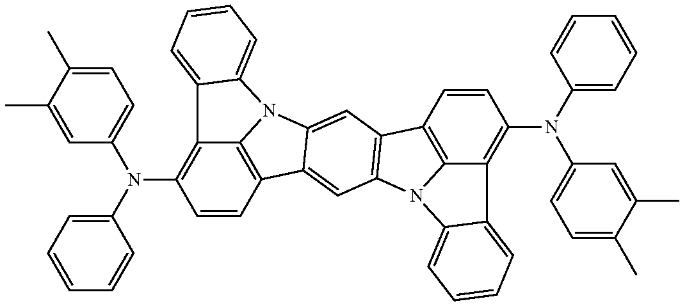
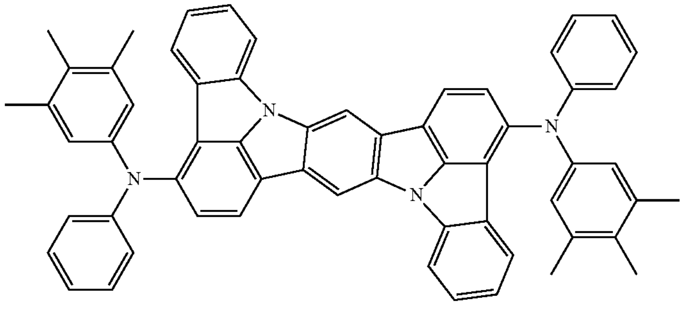

-continued
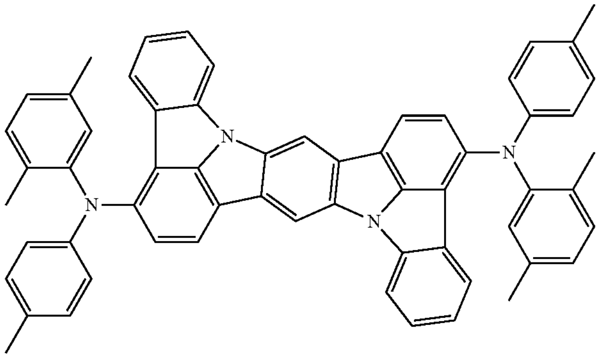
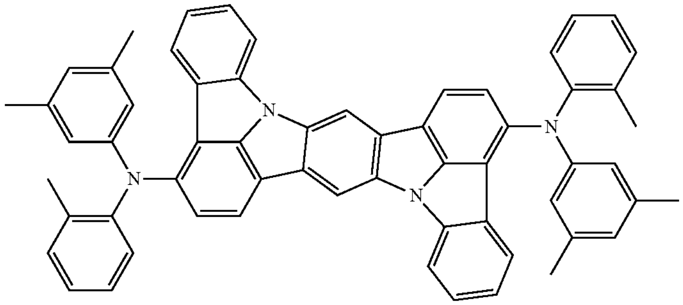
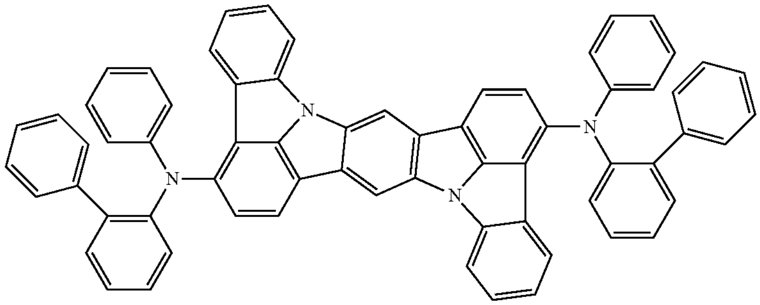
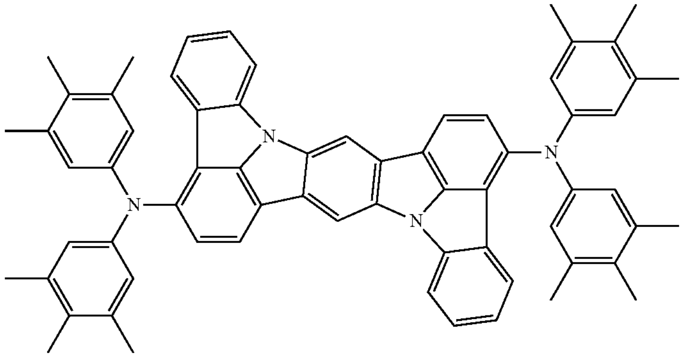

-continued
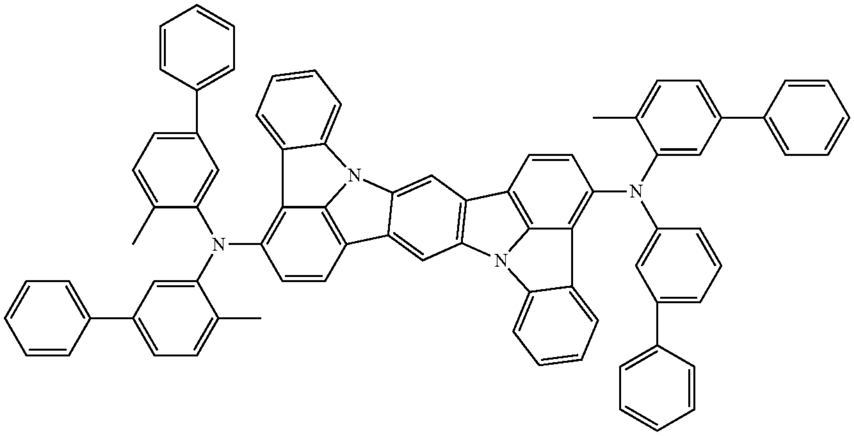
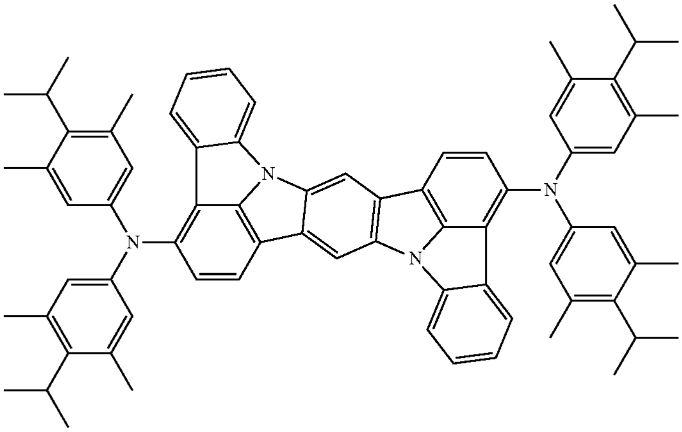
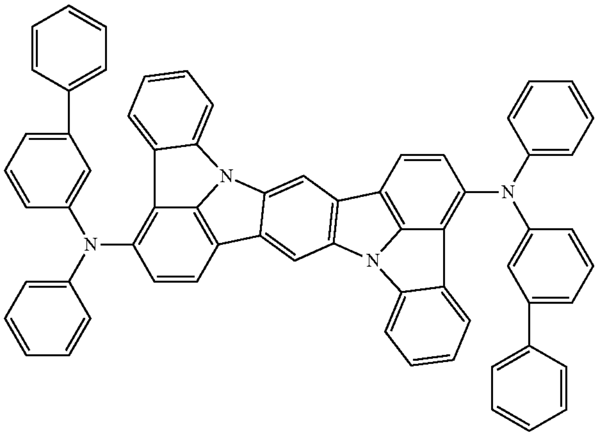
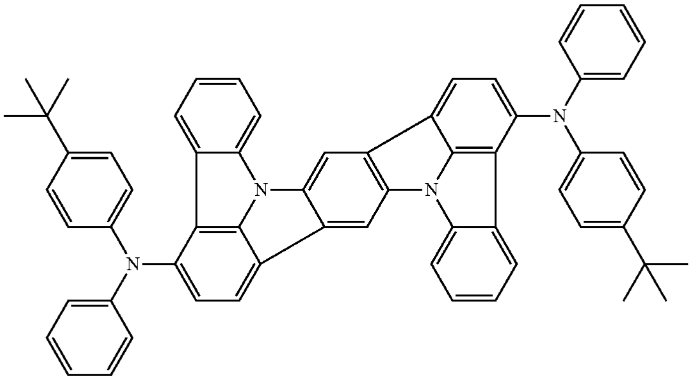

-continued
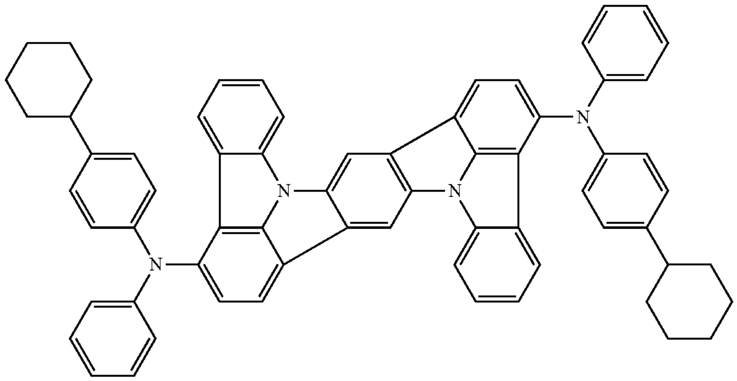
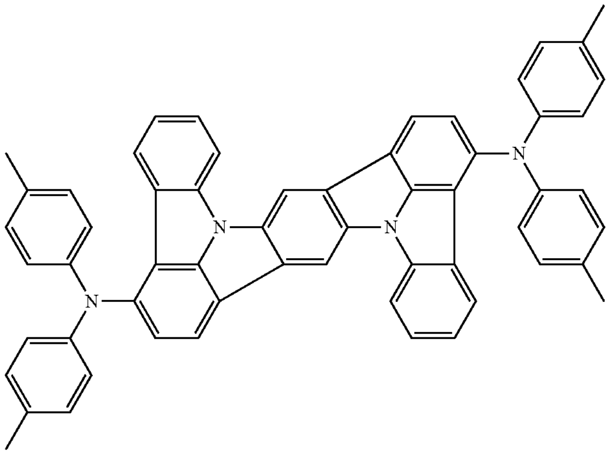
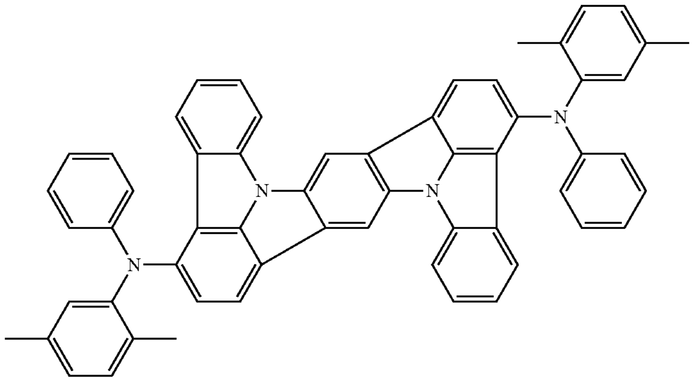
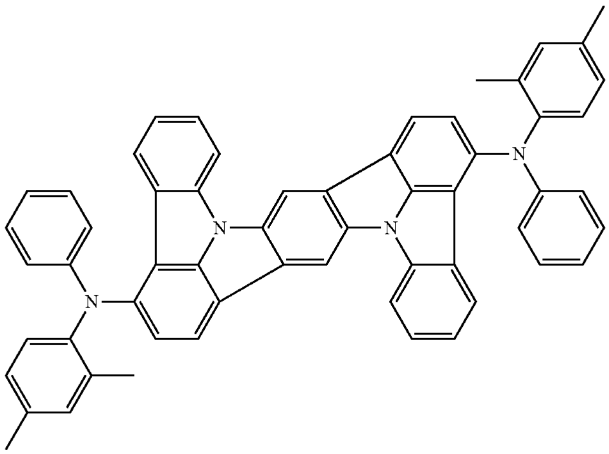

-continued
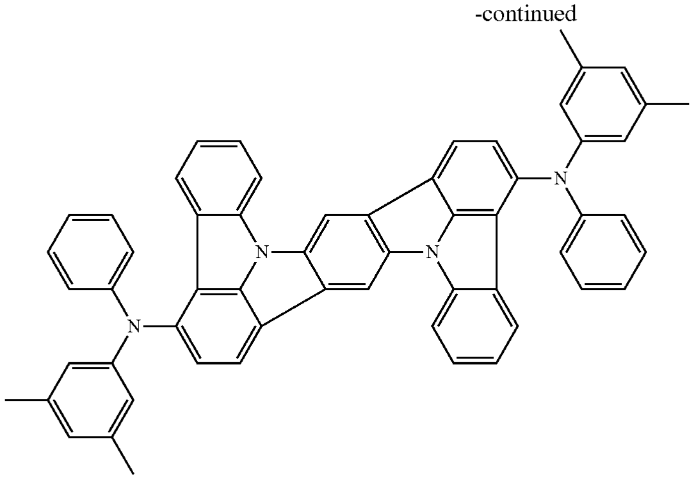
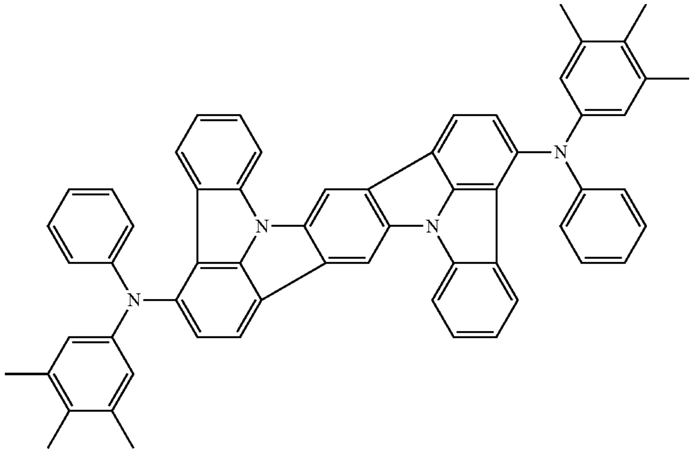
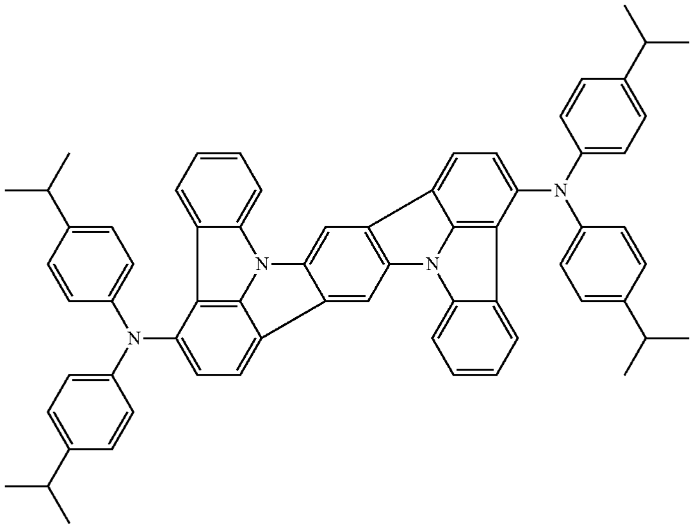

-continued
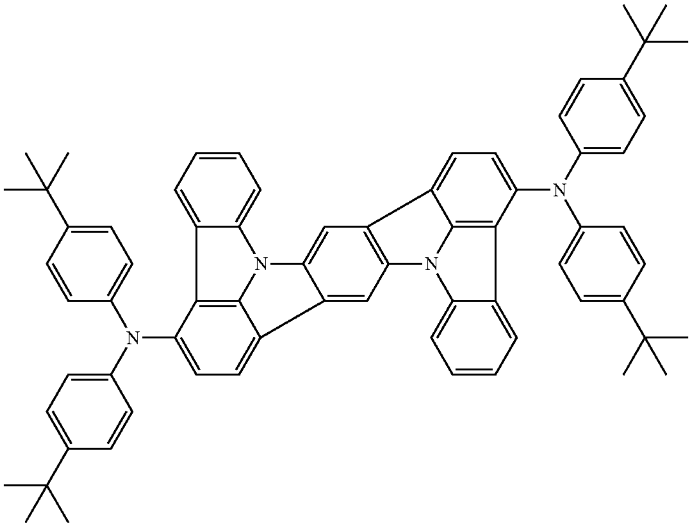
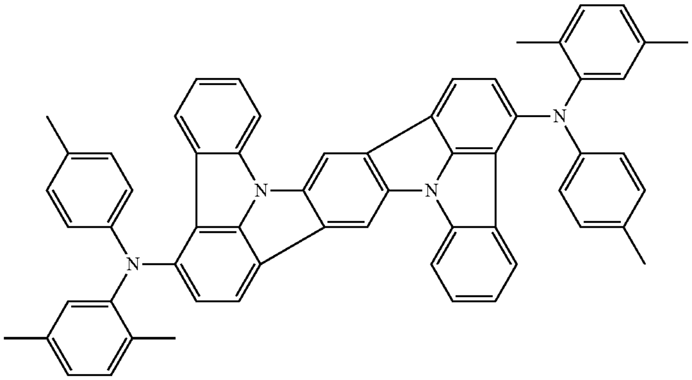
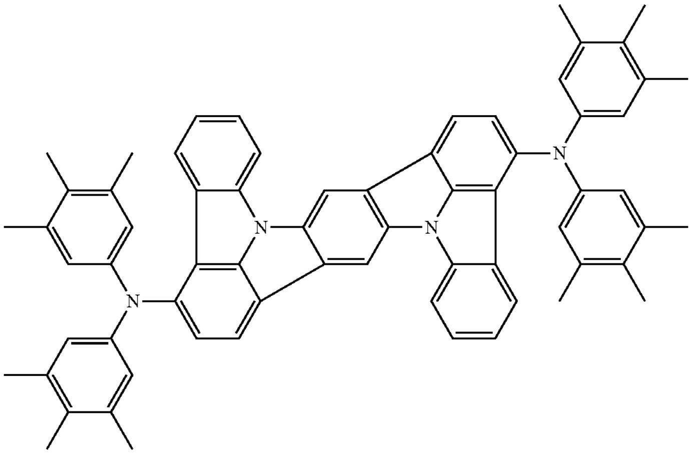
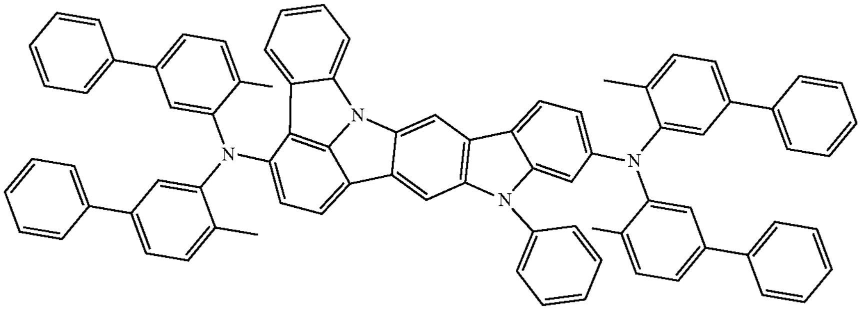

-continued
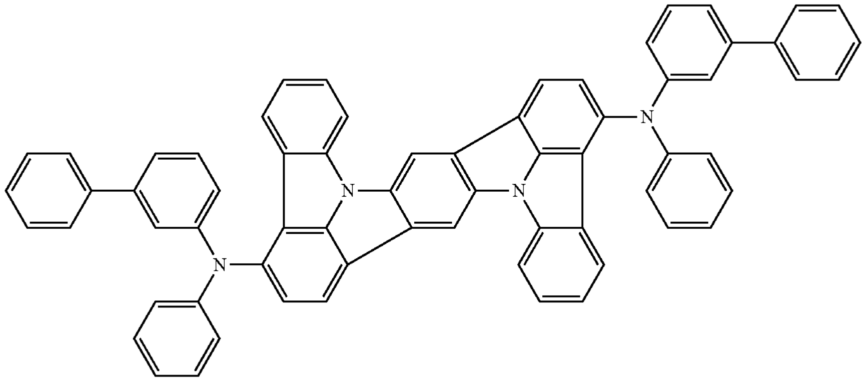
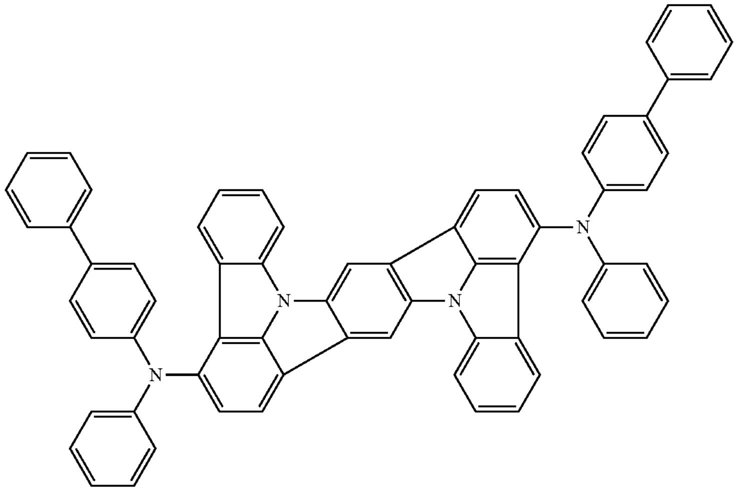
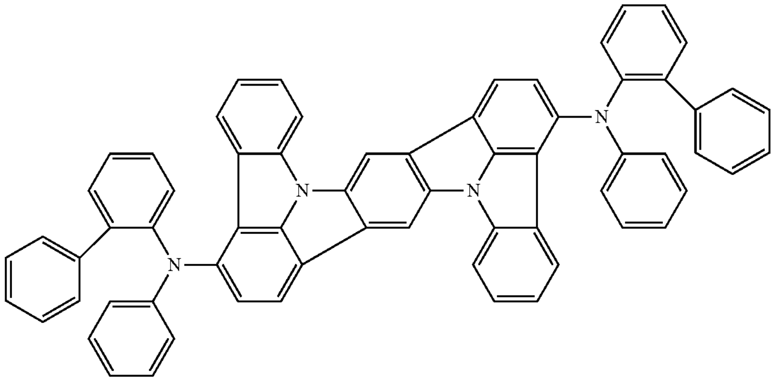
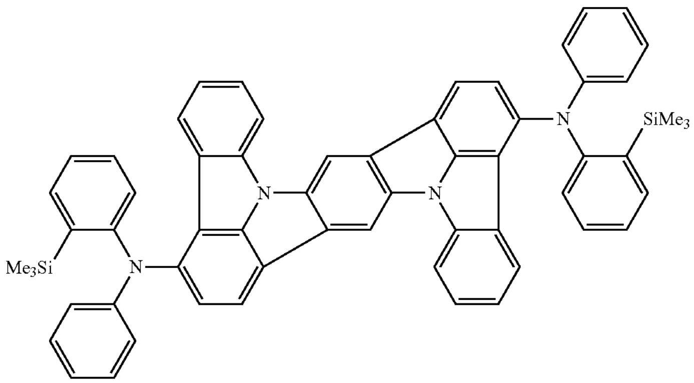

-continued
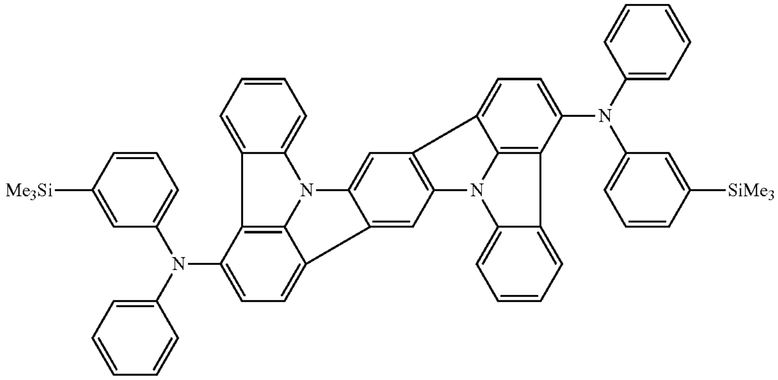
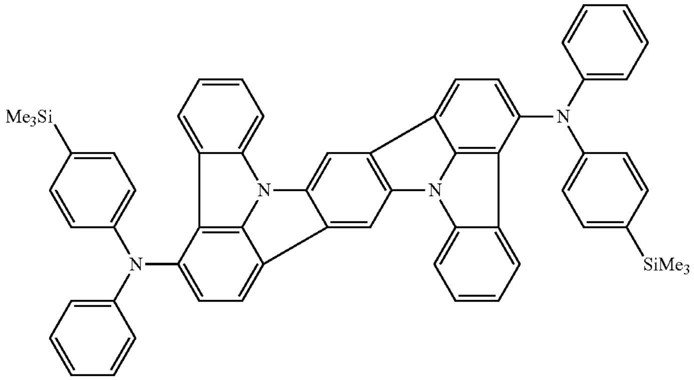
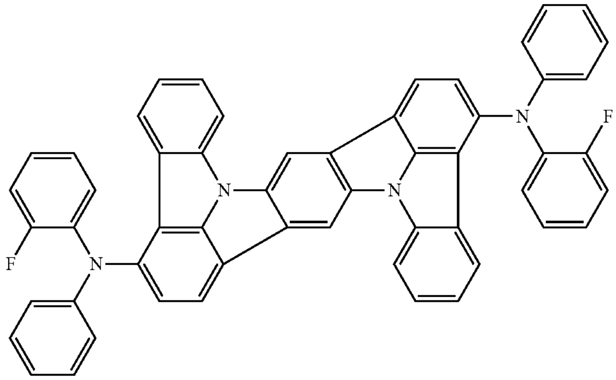
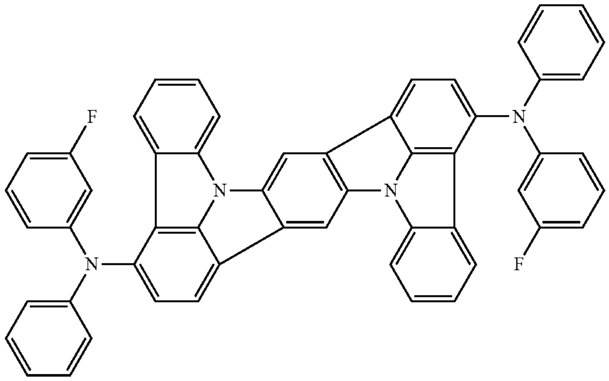

-continued
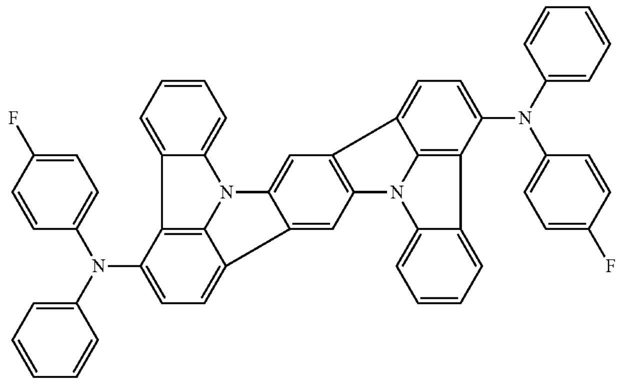
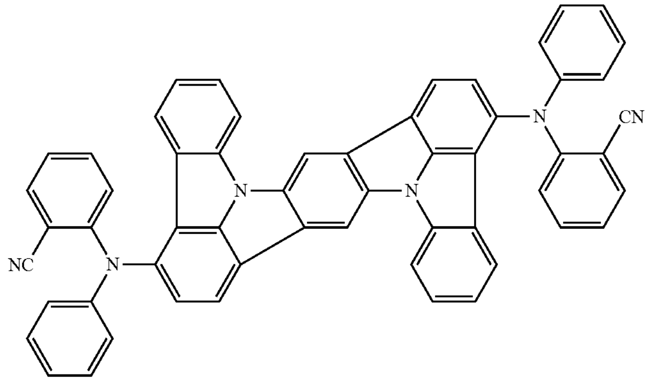
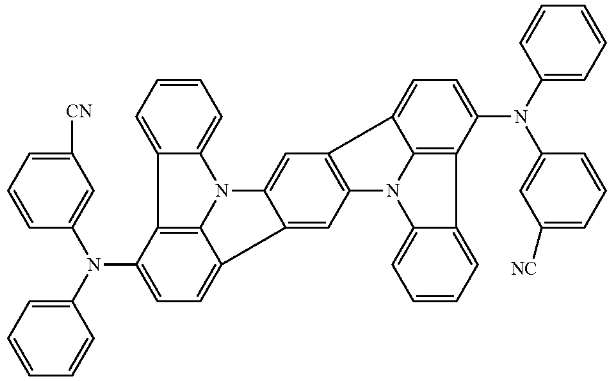
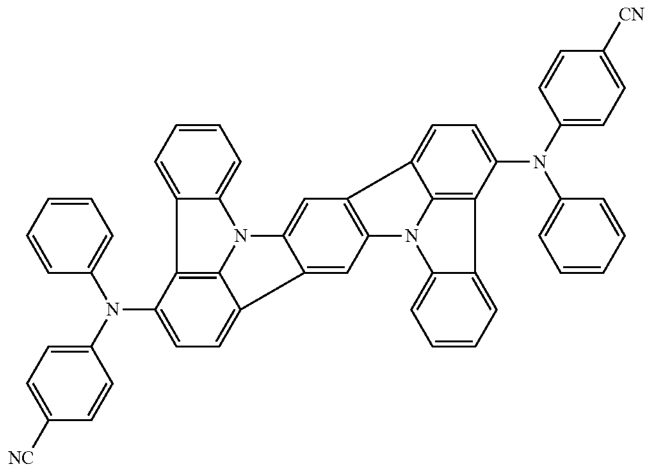

-continued
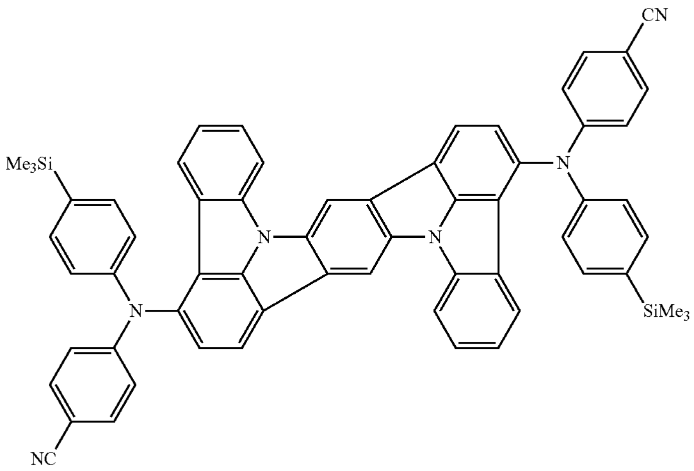
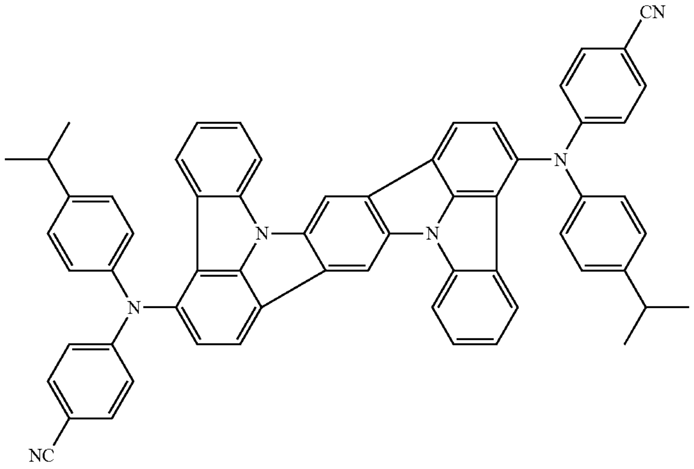
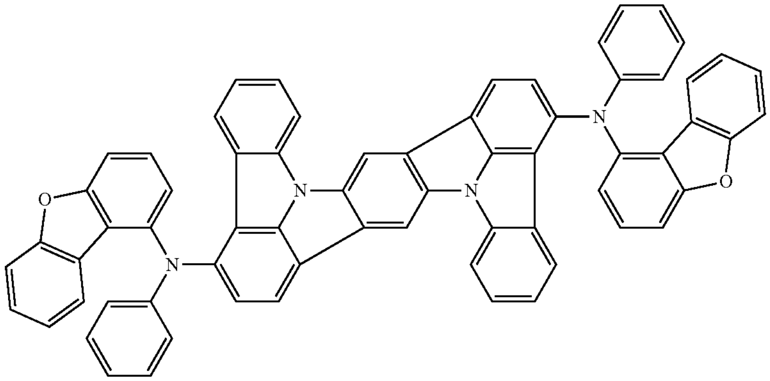
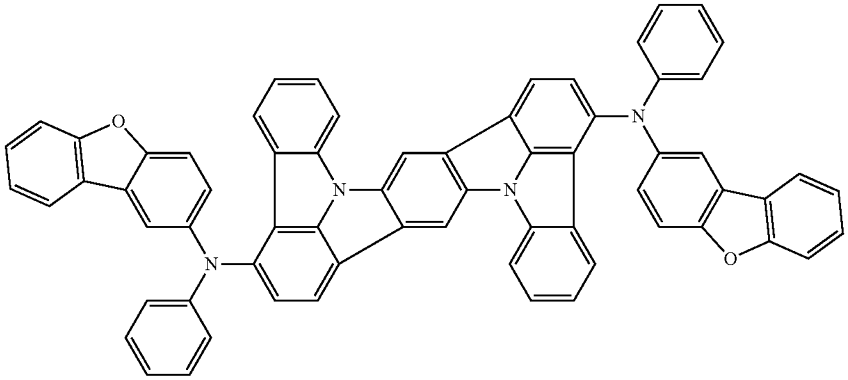

-continued
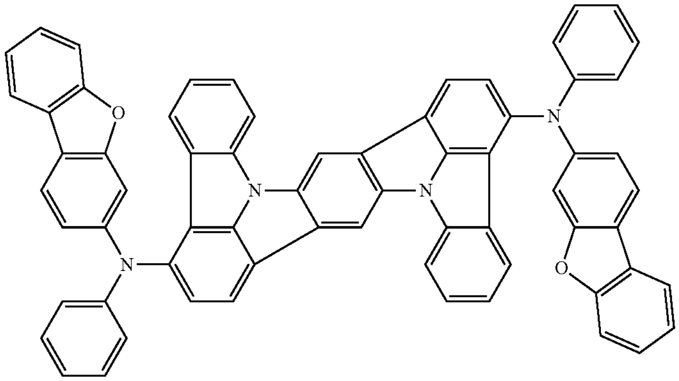
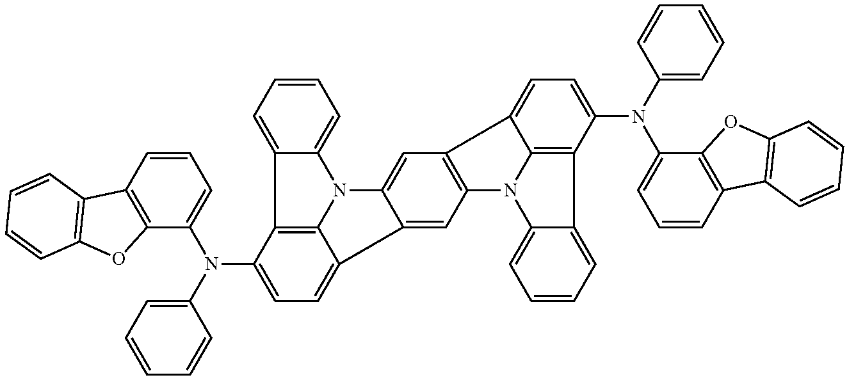
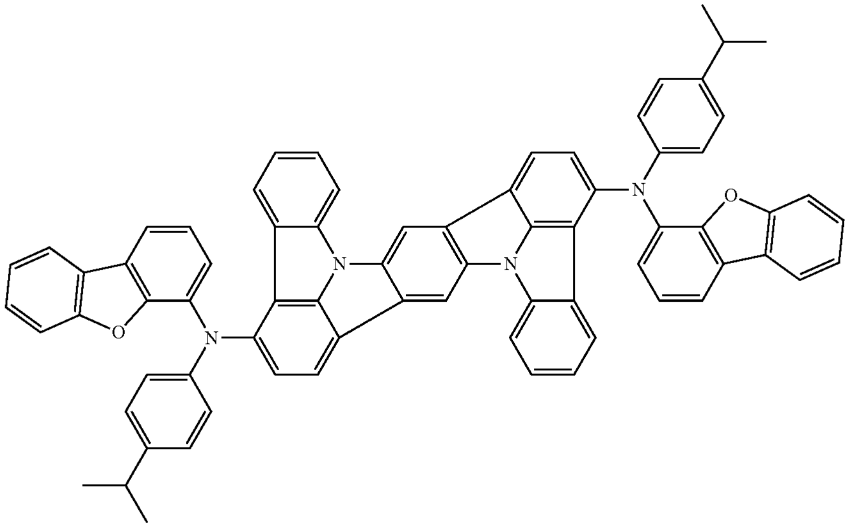
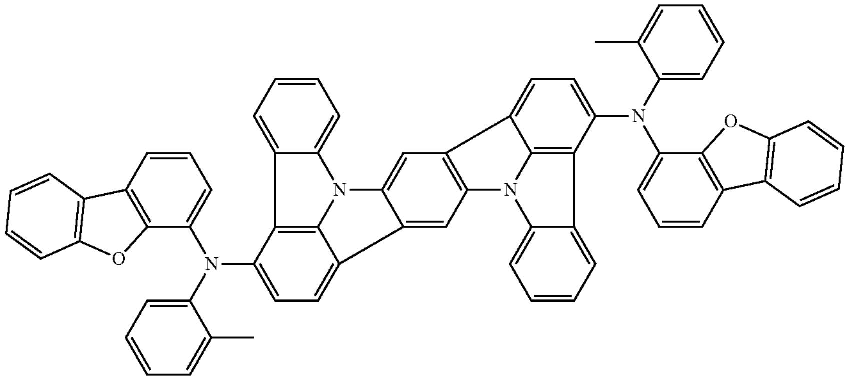

-continued
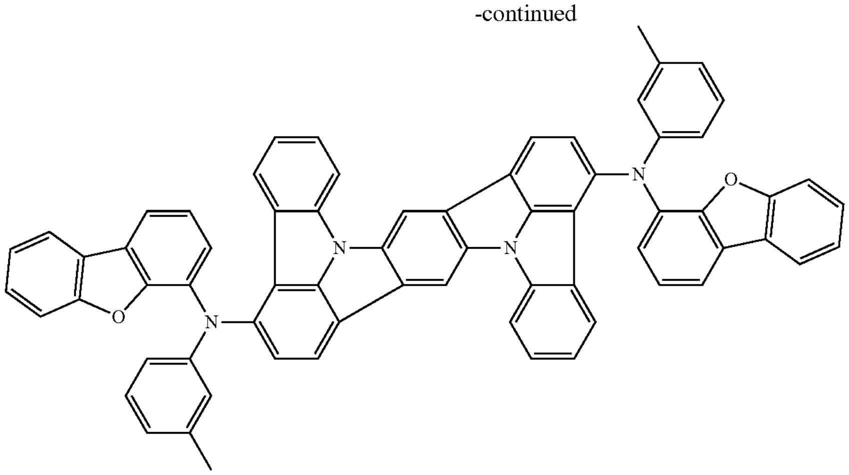
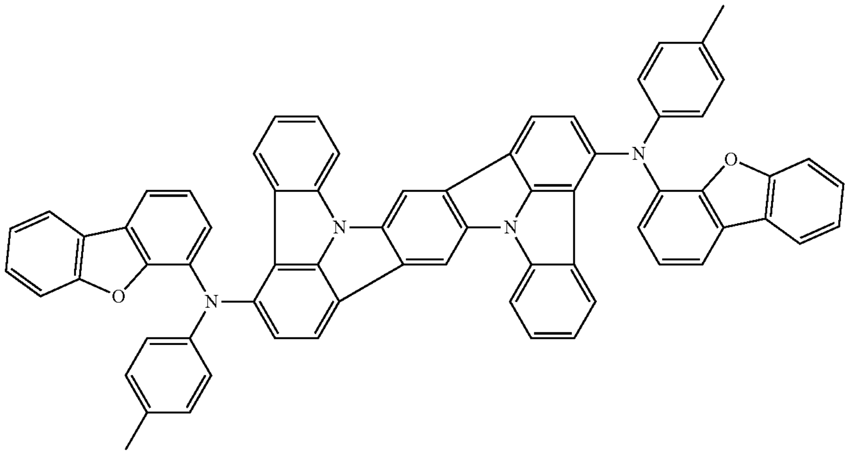
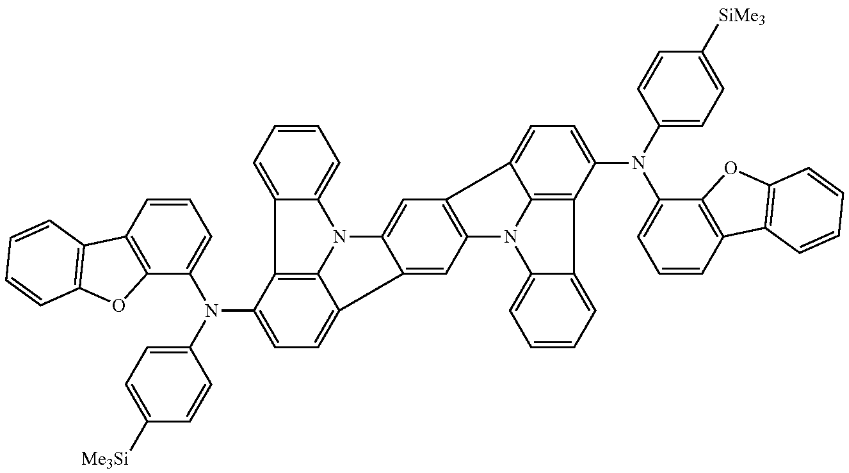

-continued
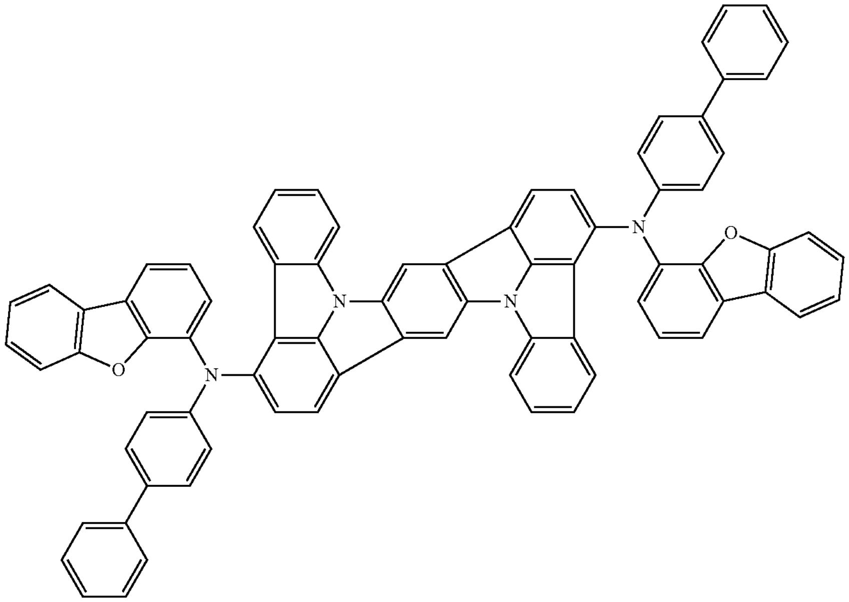
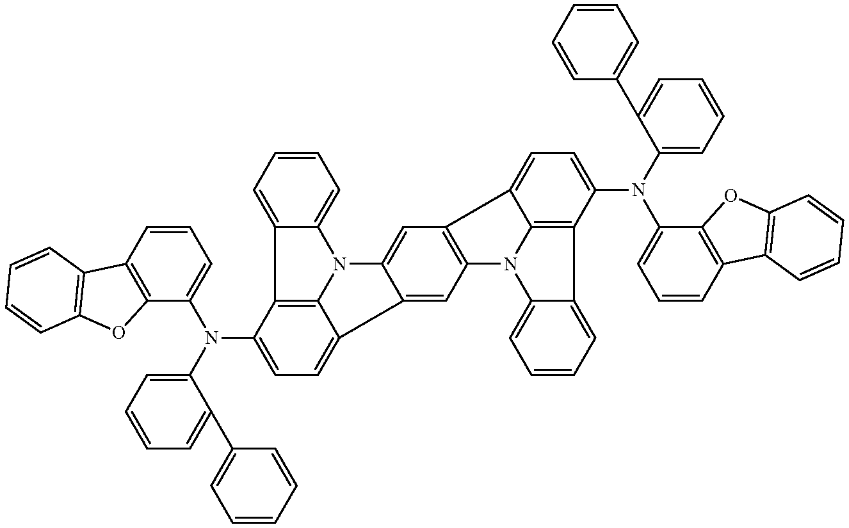
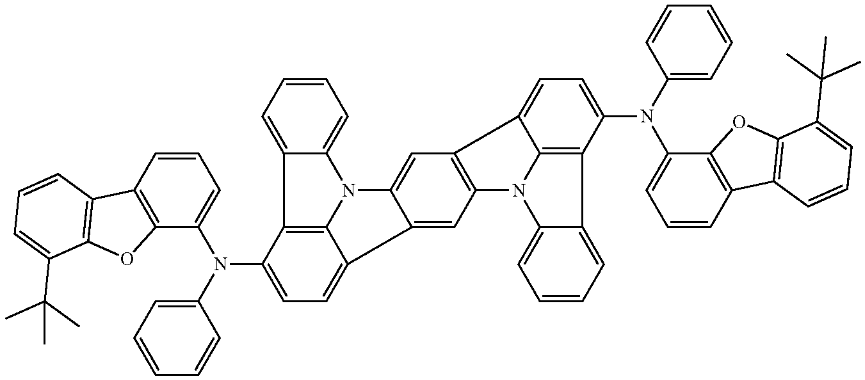

-continued
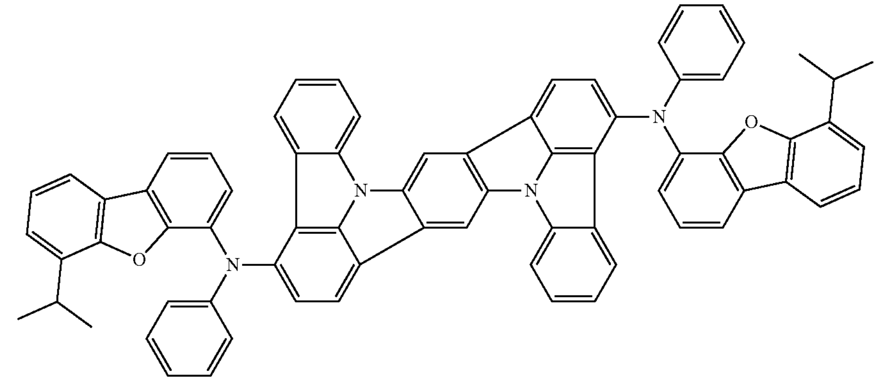
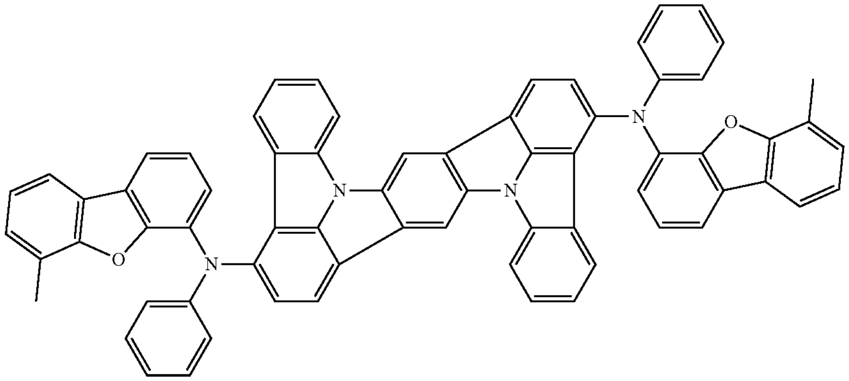
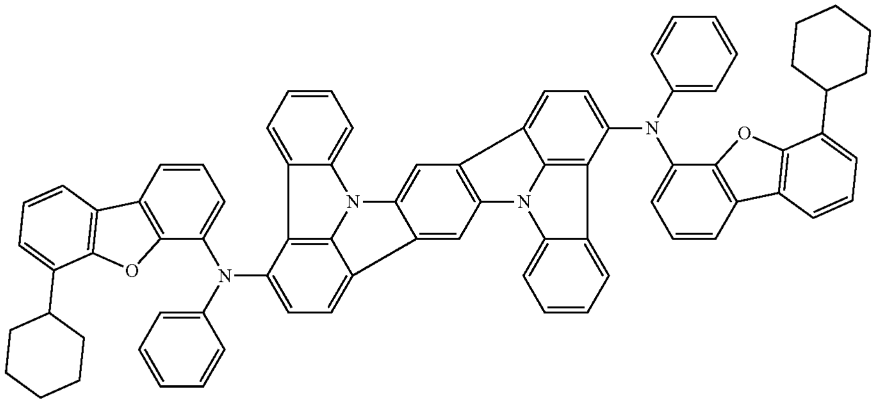
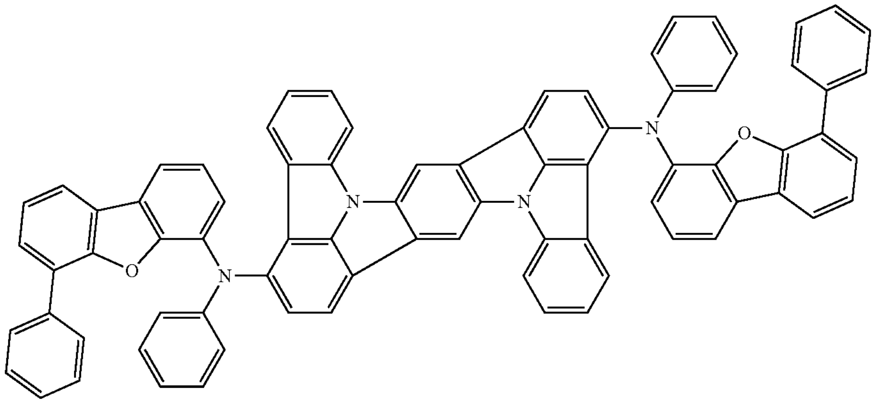

-continued
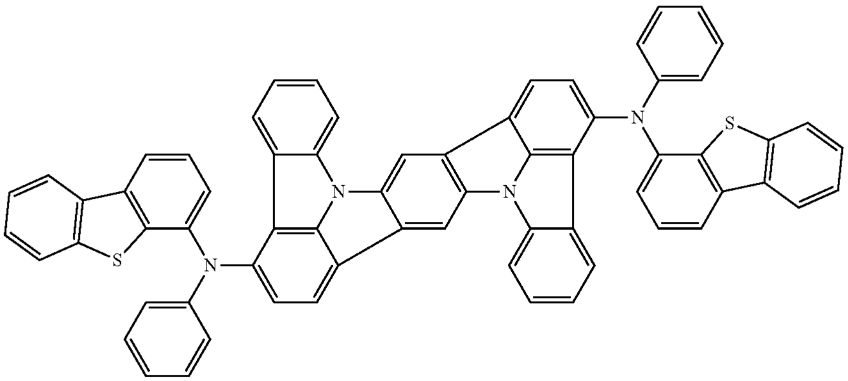
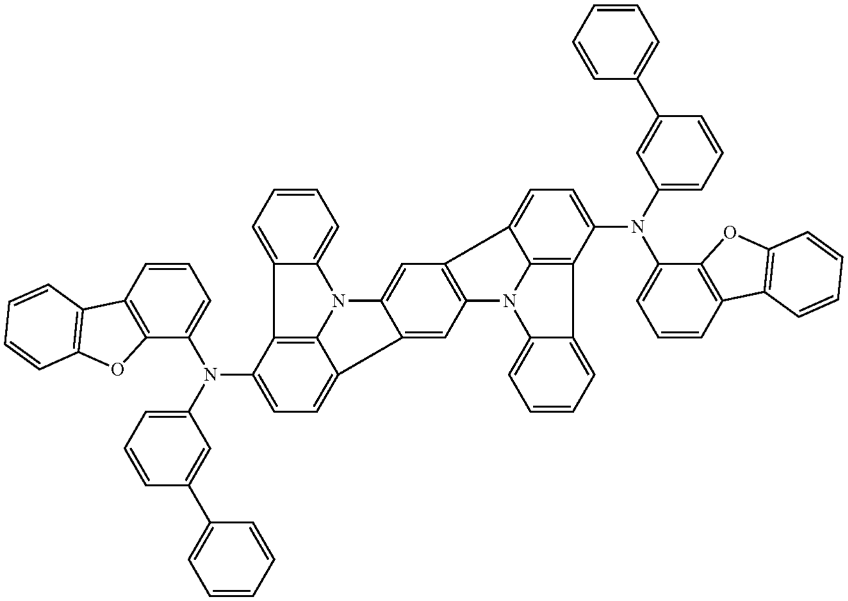
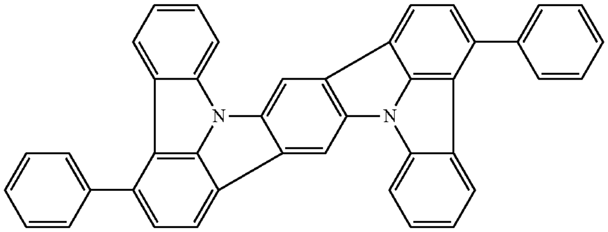
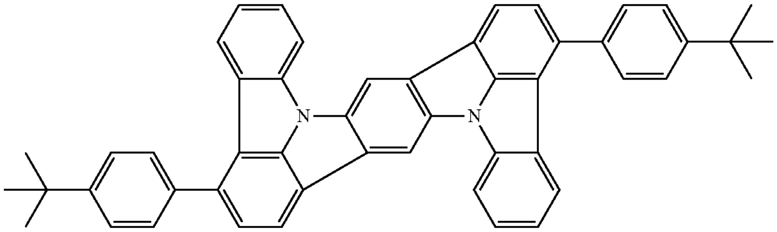
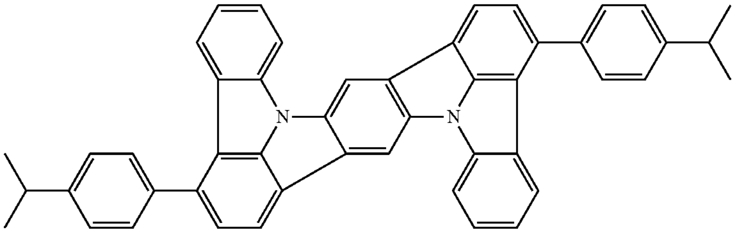

-continued
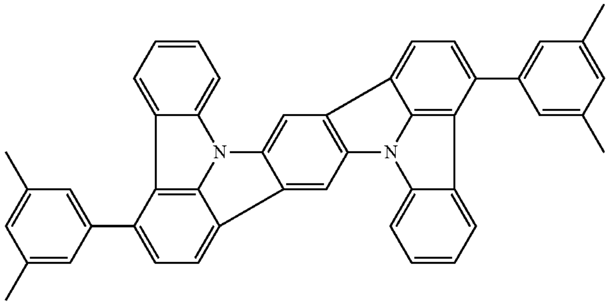
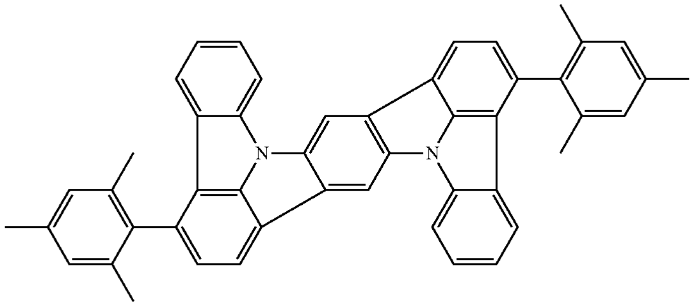
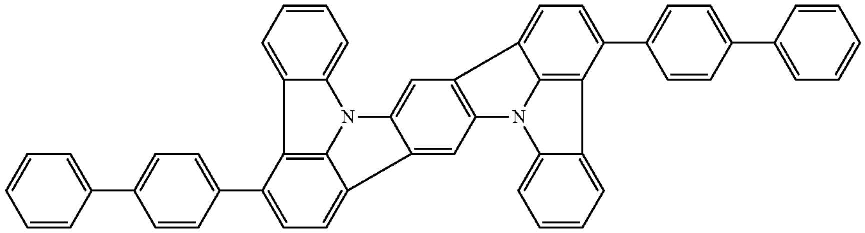
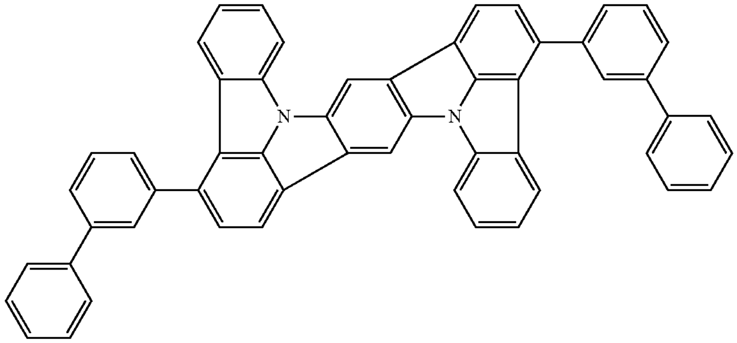
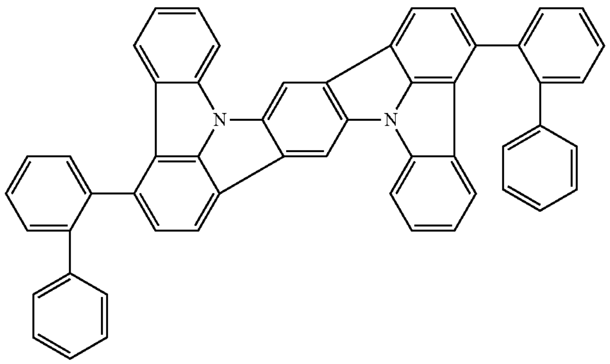

-continued
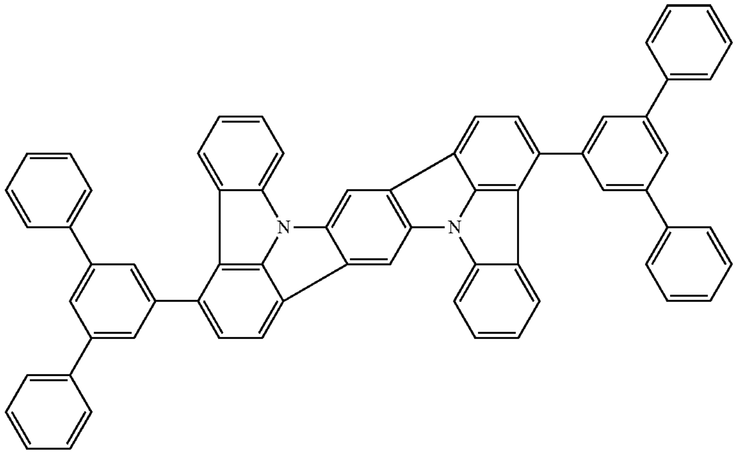
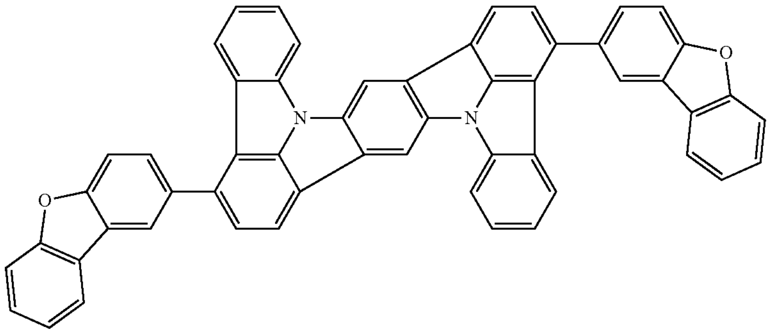
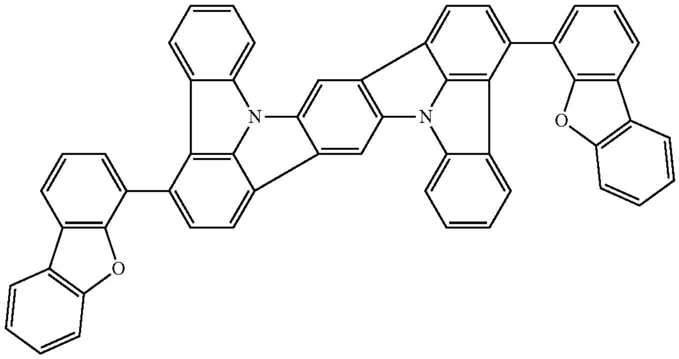
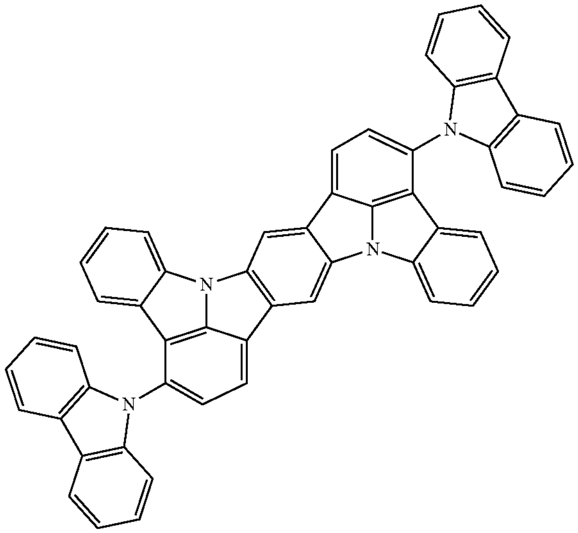

-continued
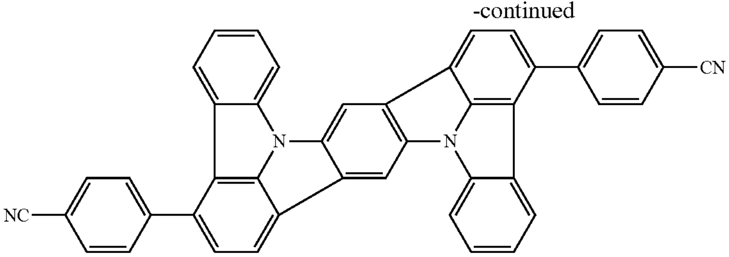
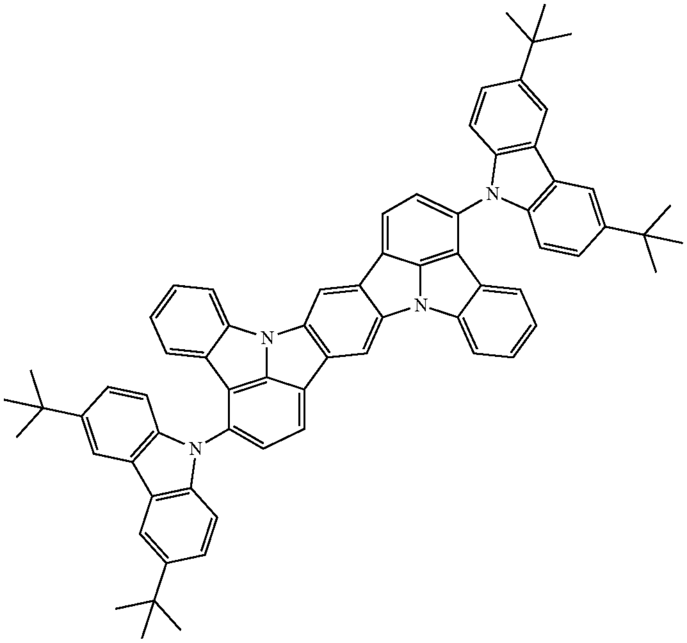
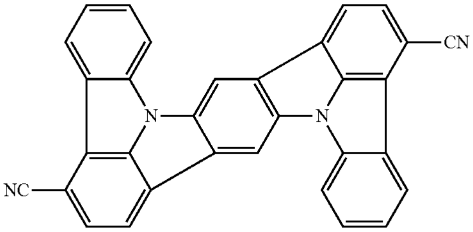
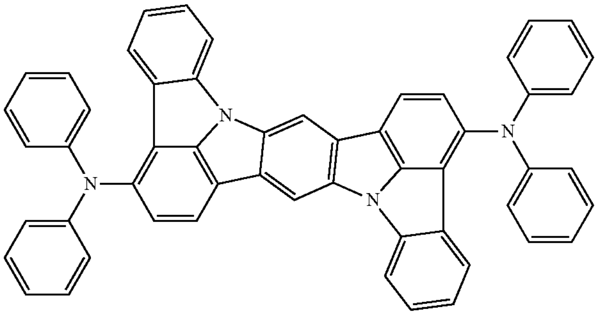
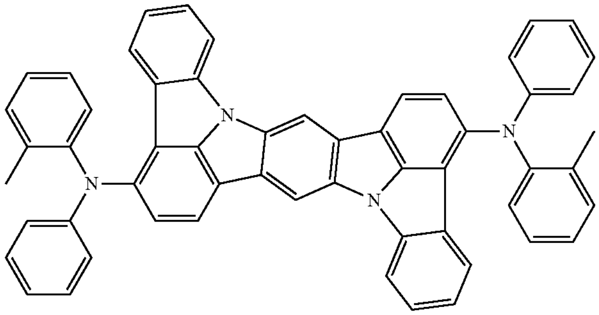

-continued
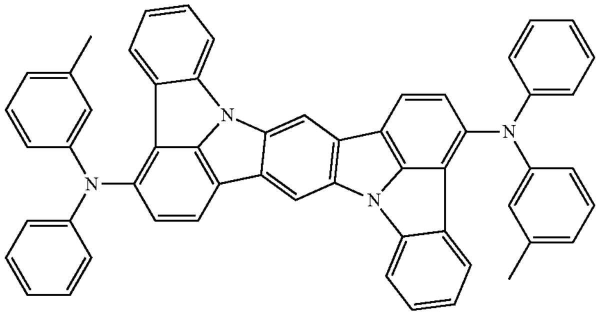
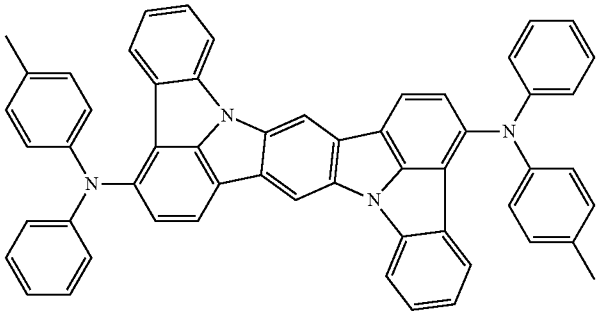
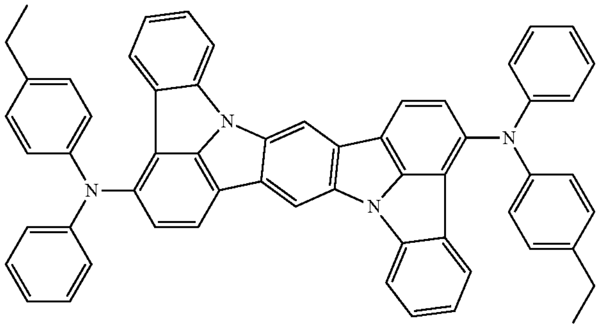
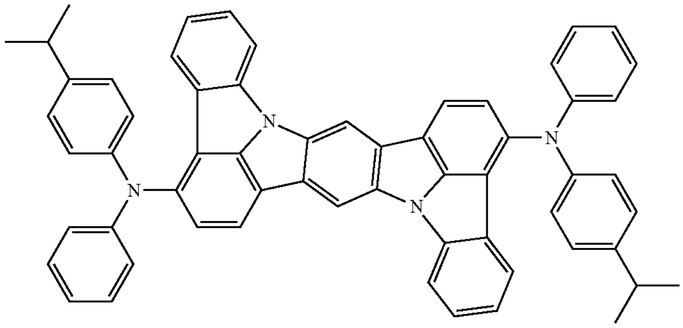
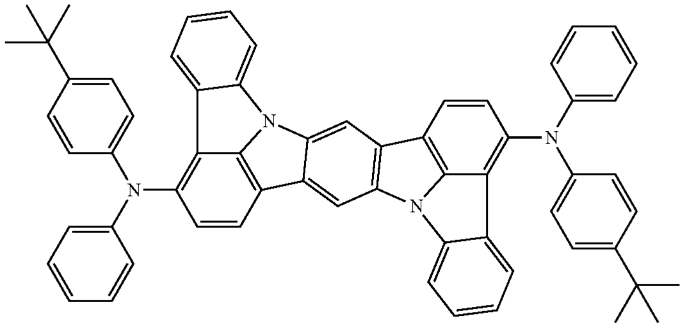

-continued
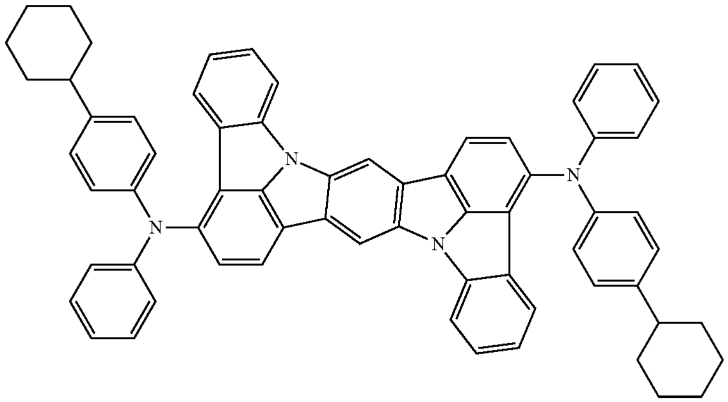
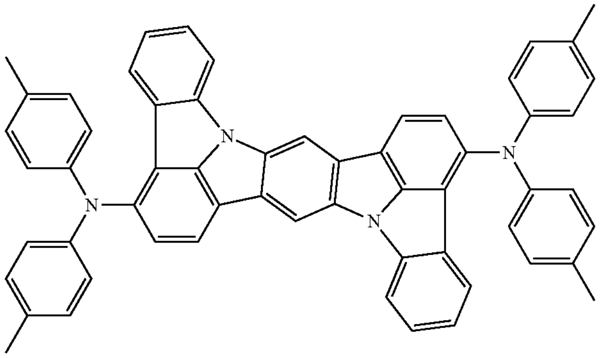
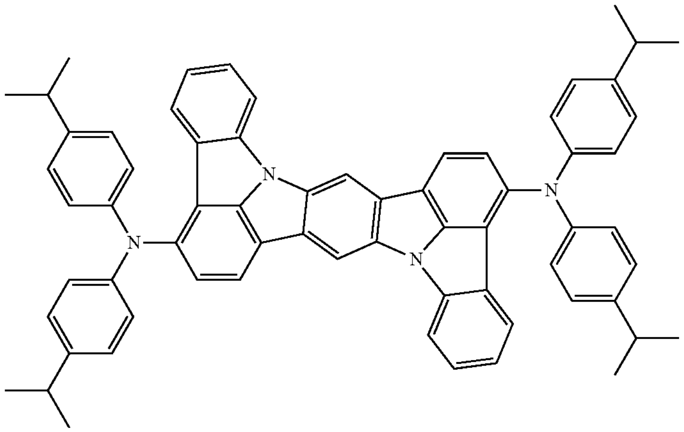
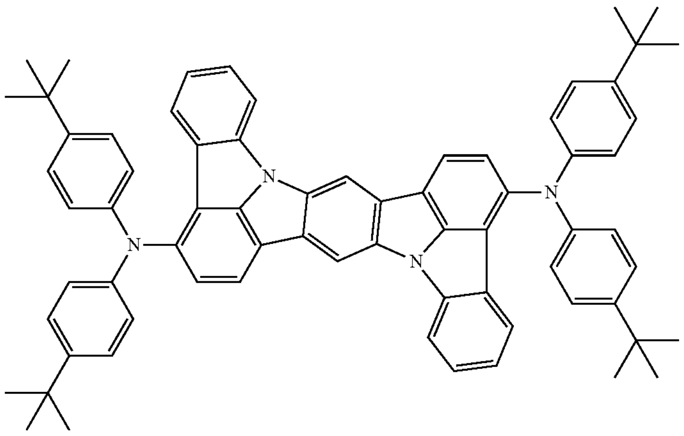

-continued
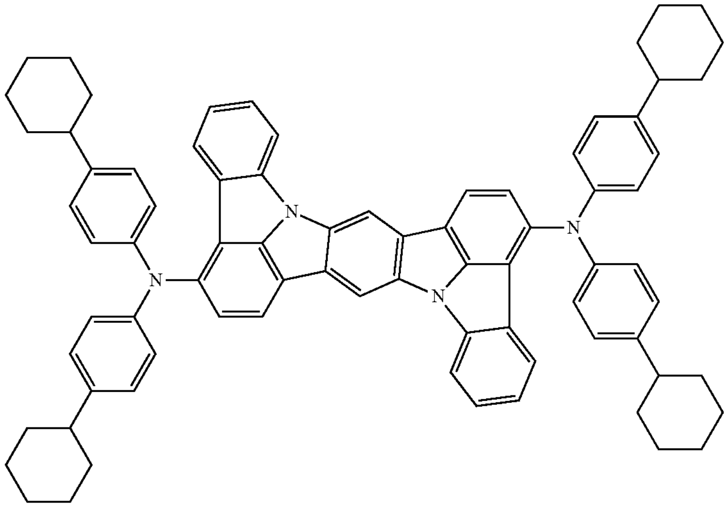
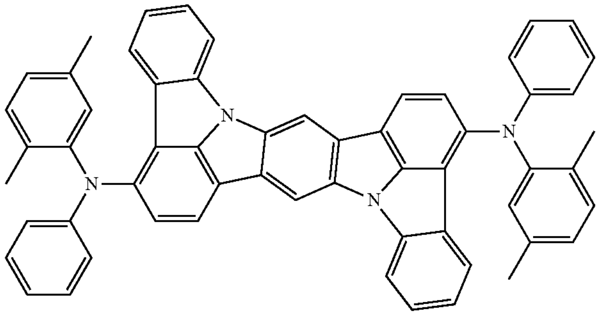
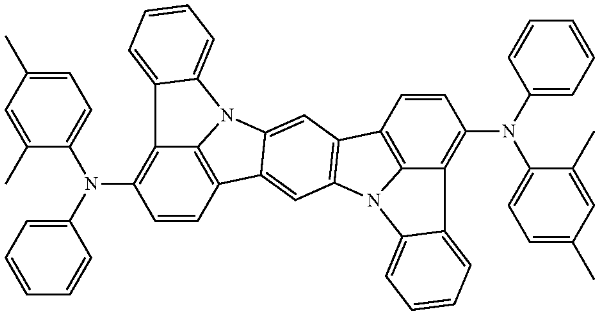
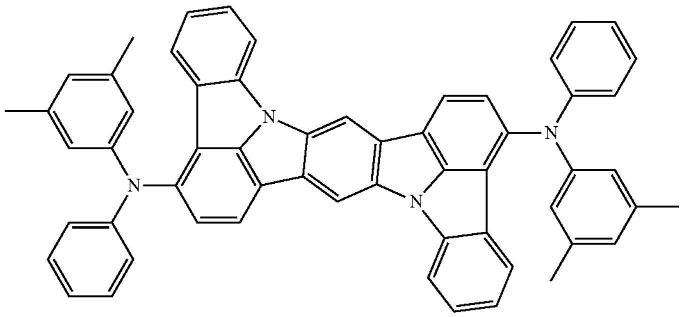

-continued
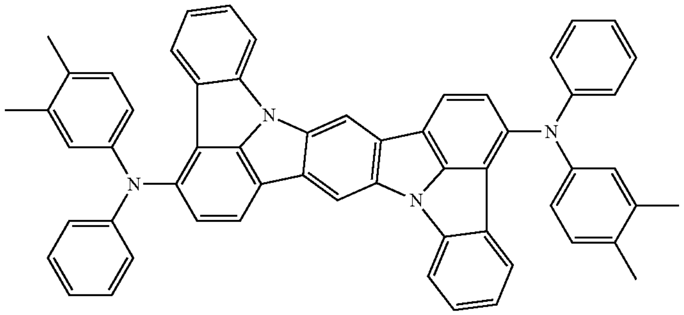
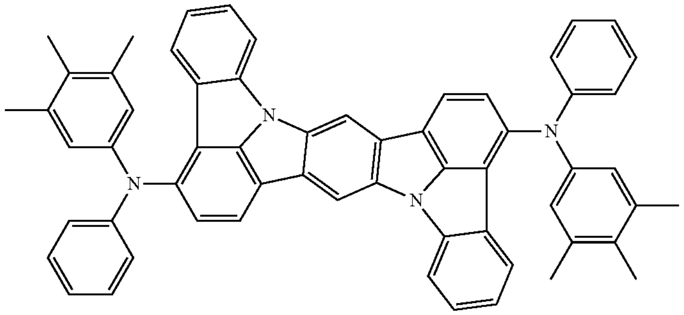
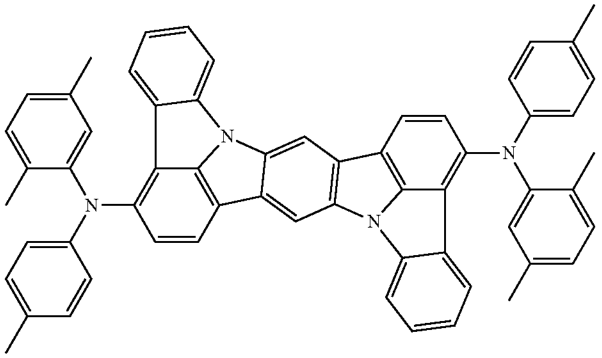
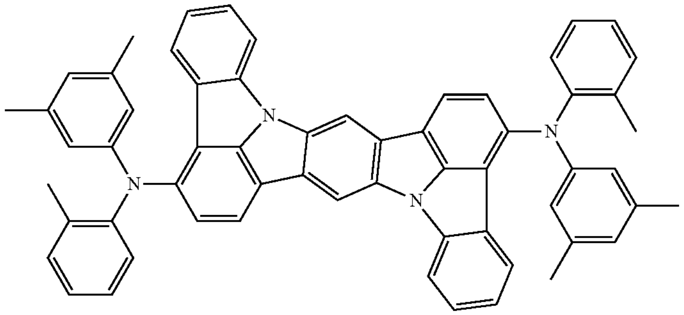
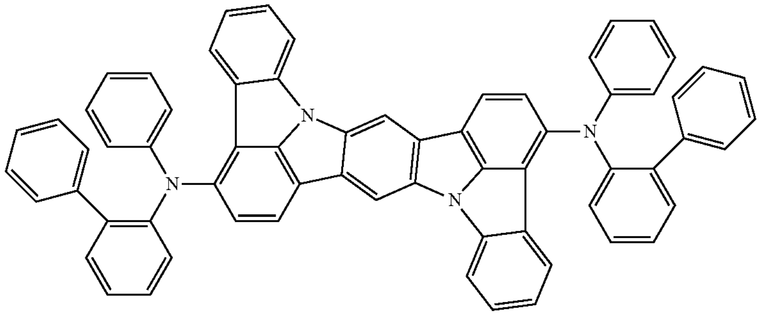

-continued
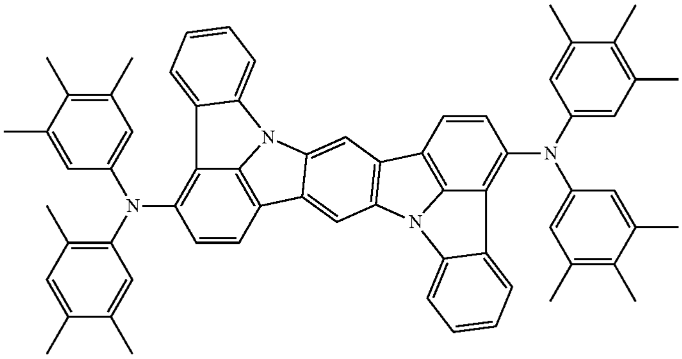
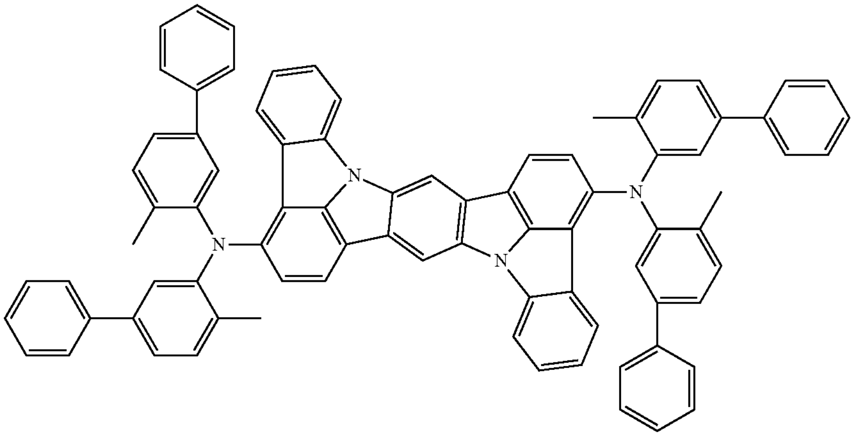
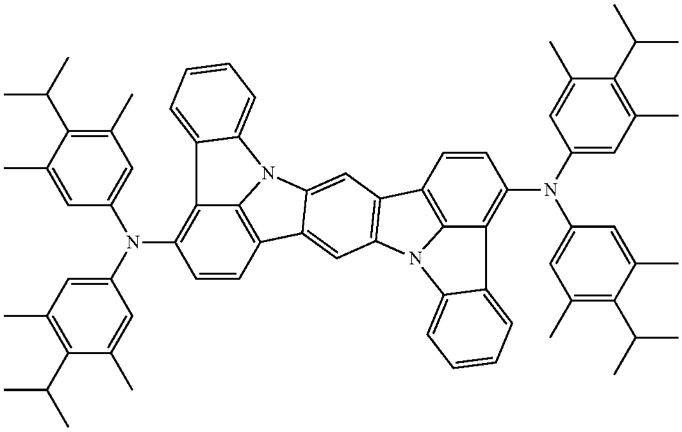
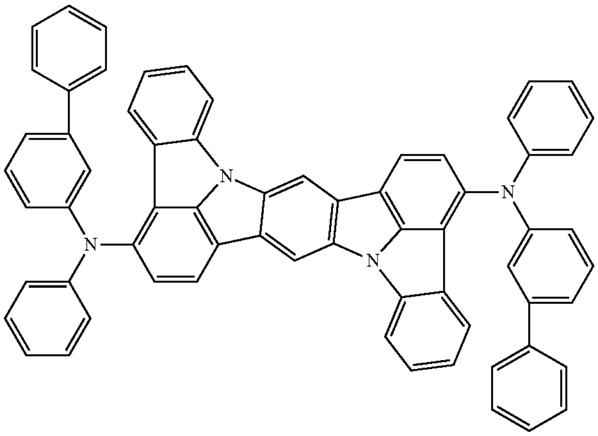

-continued
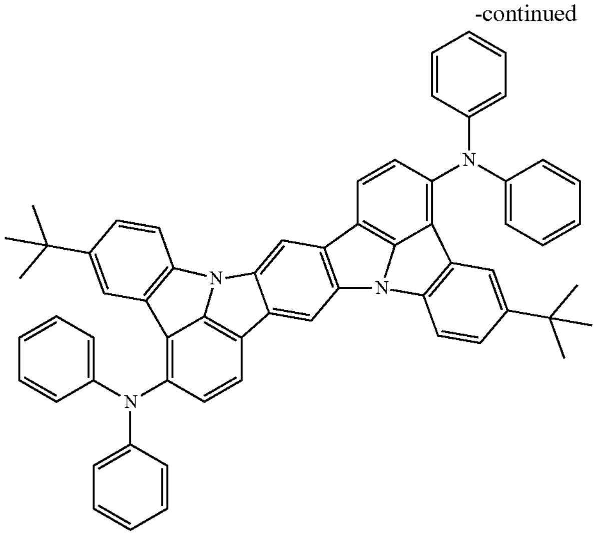
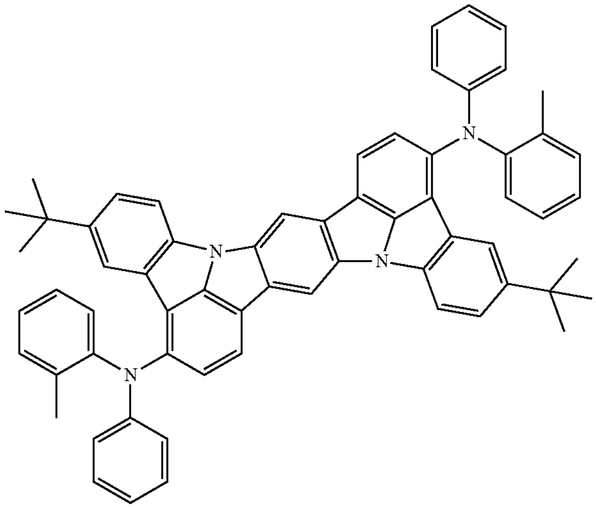
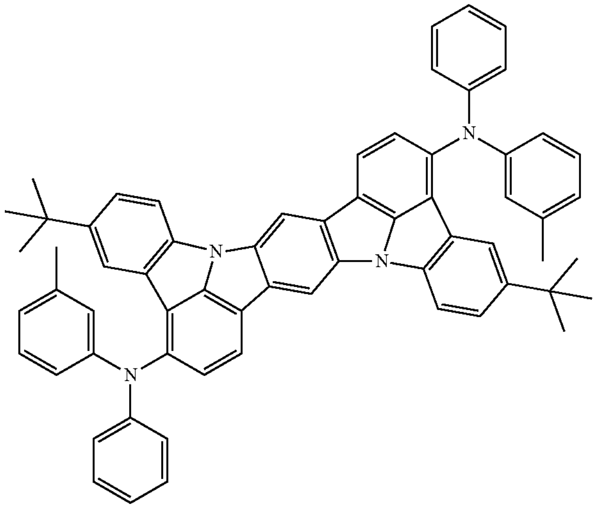

-continued
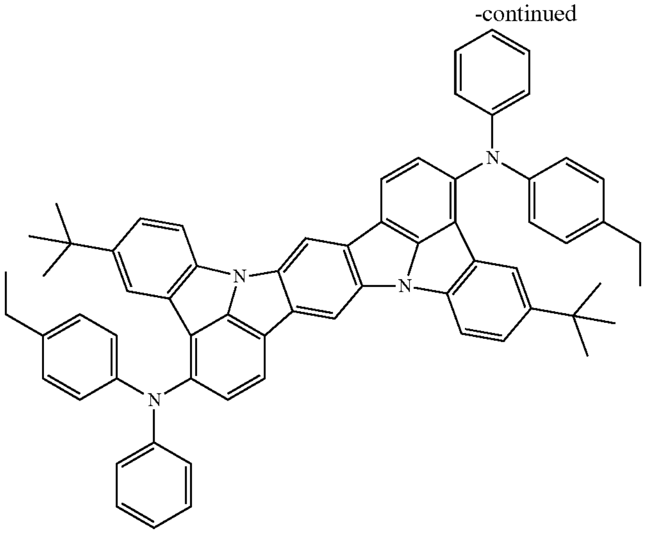
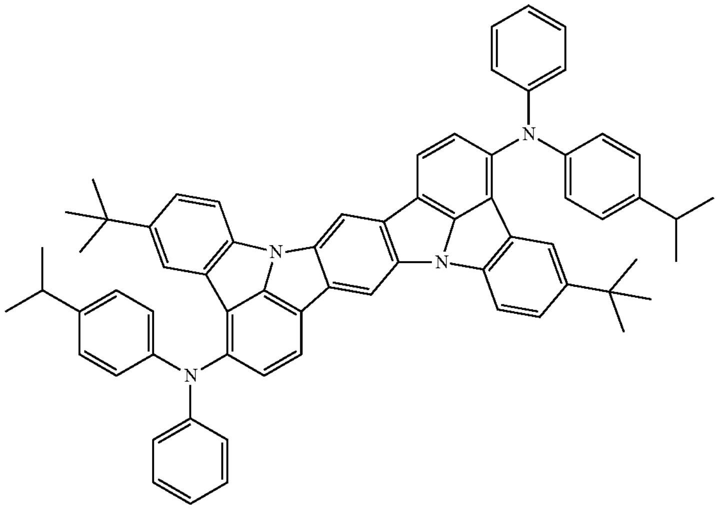
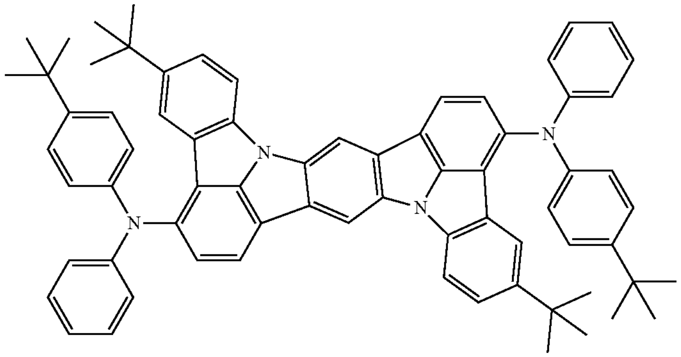

-continued
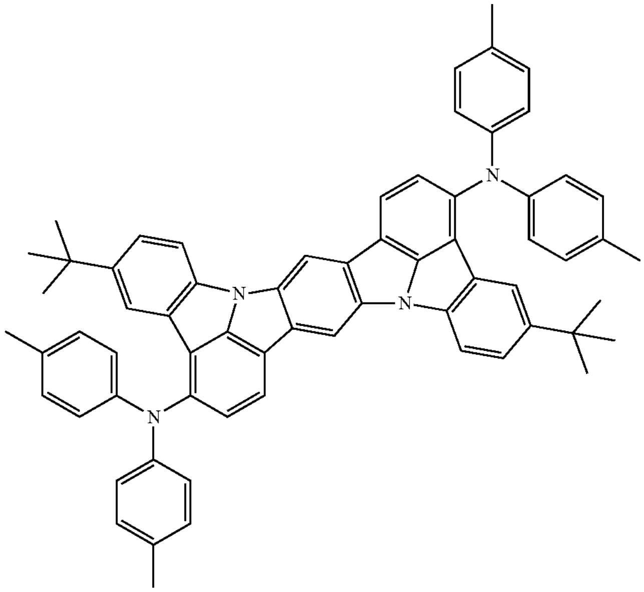
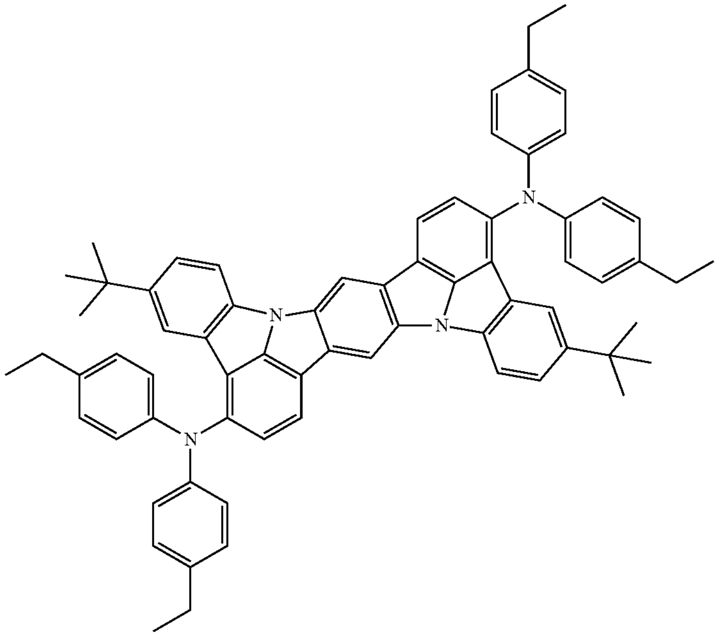

-continued
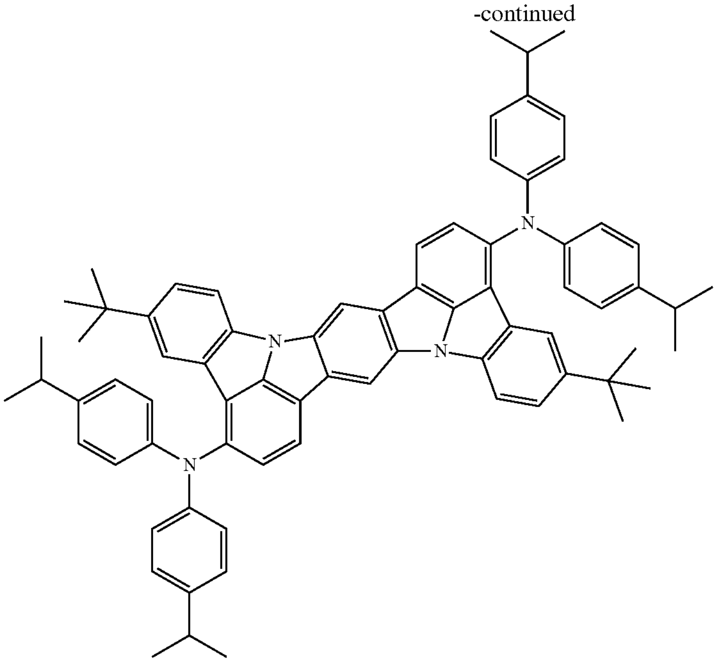
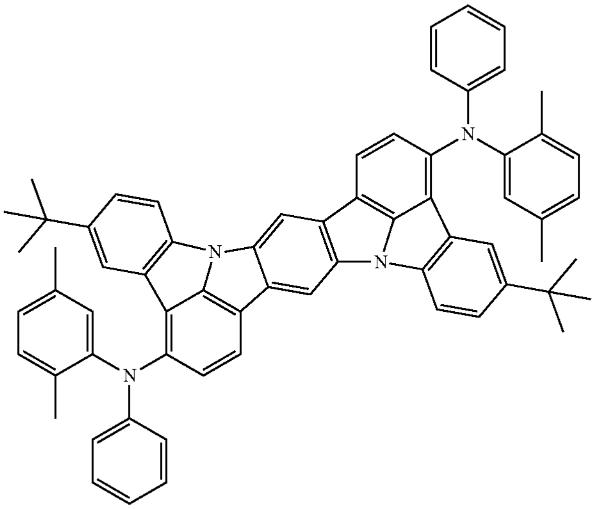
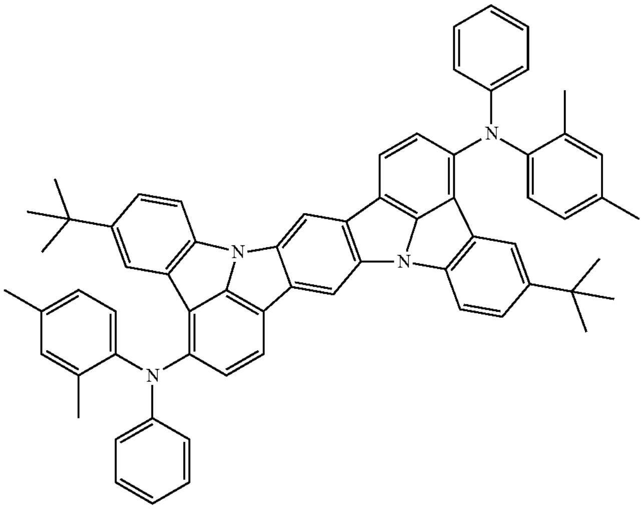

-continued
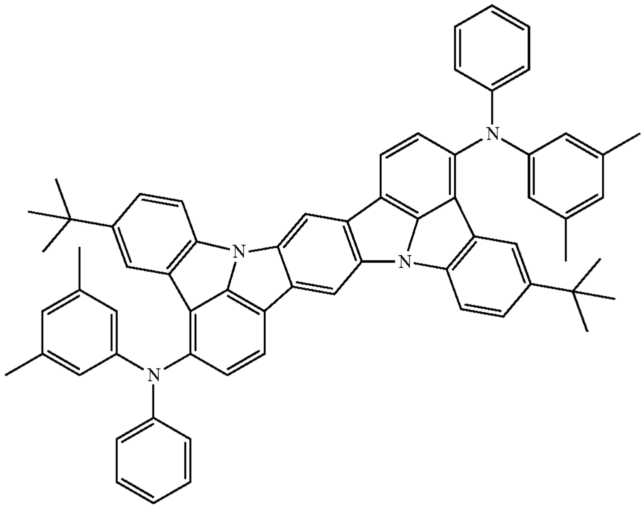
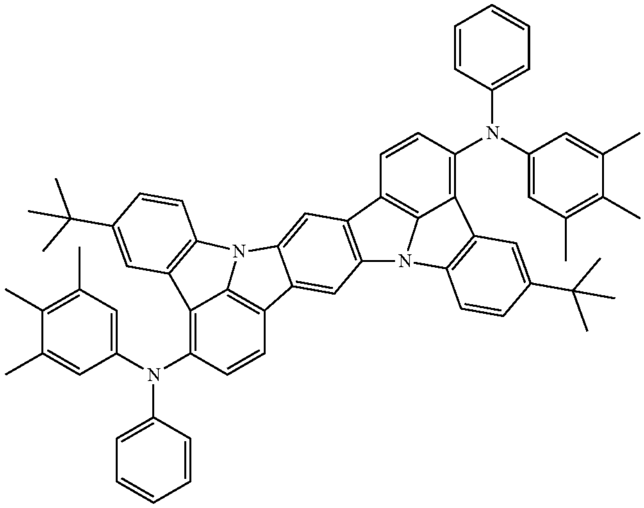
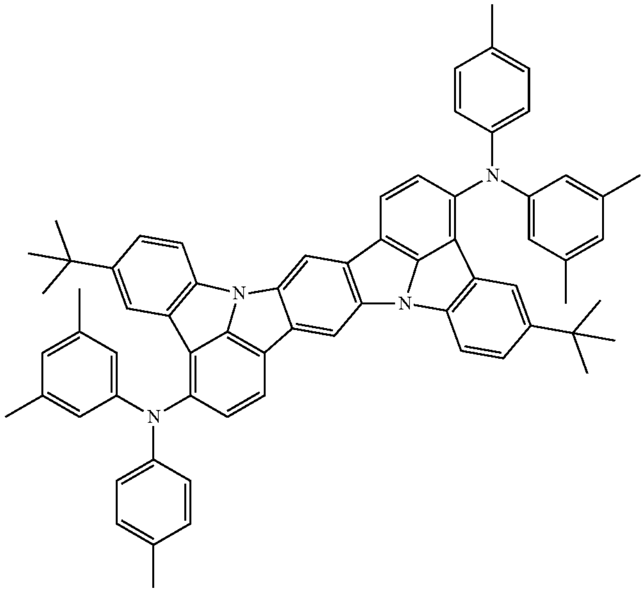

-continued
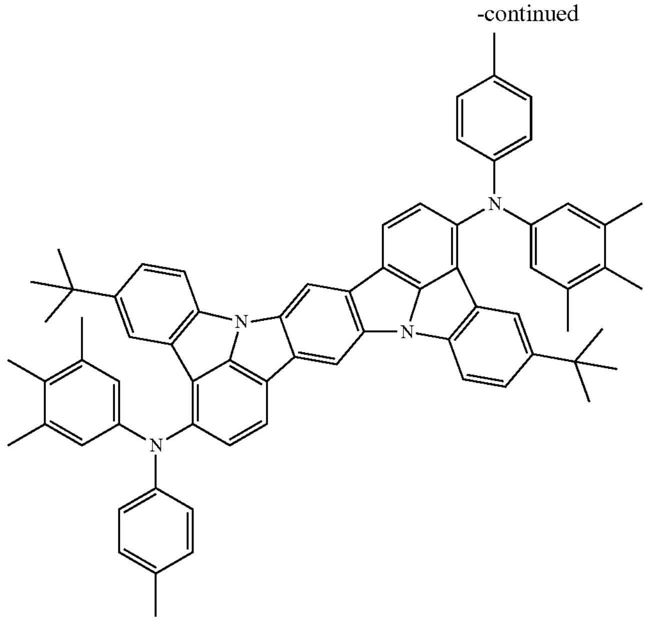
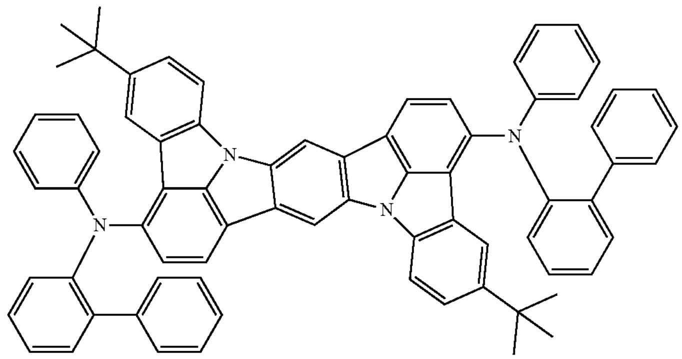
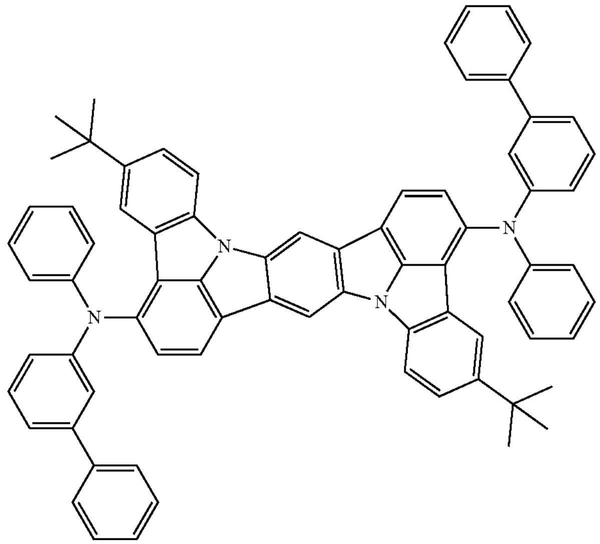

-continued
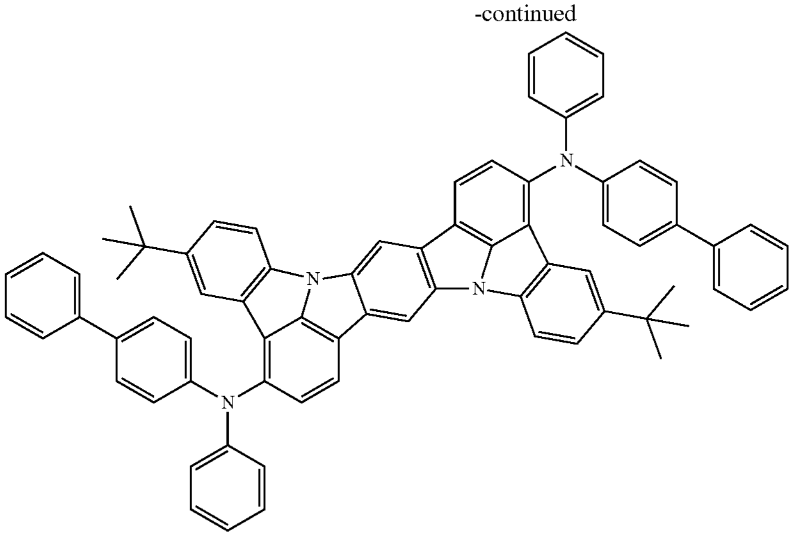
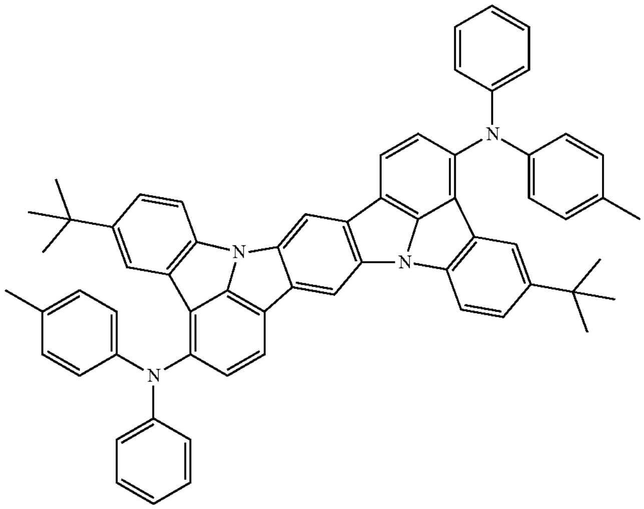
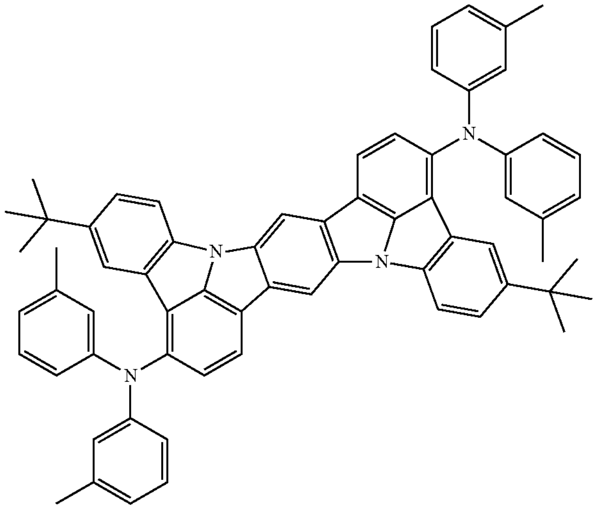

-continued
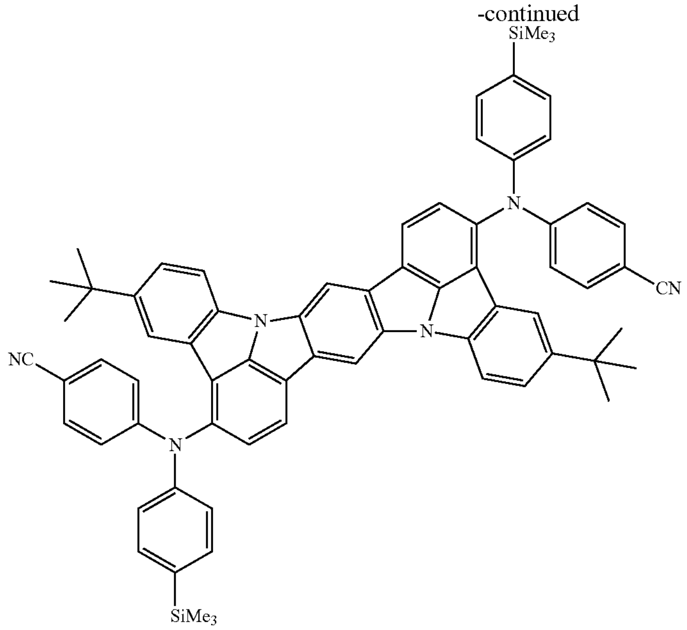
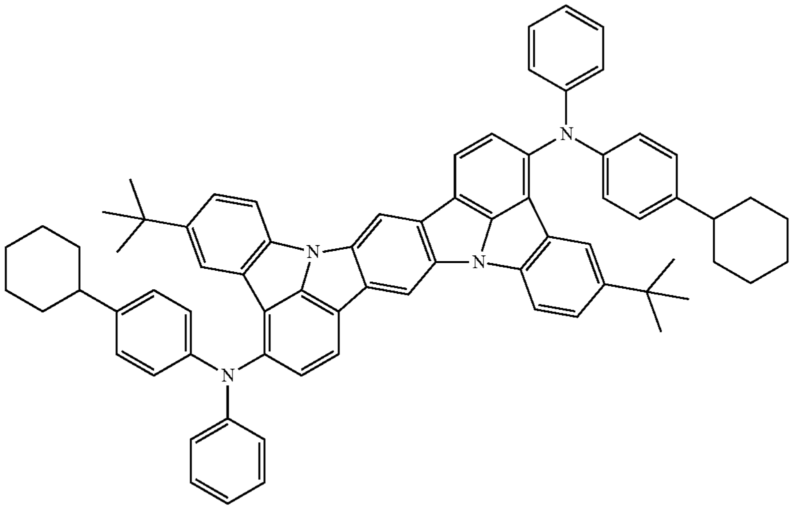
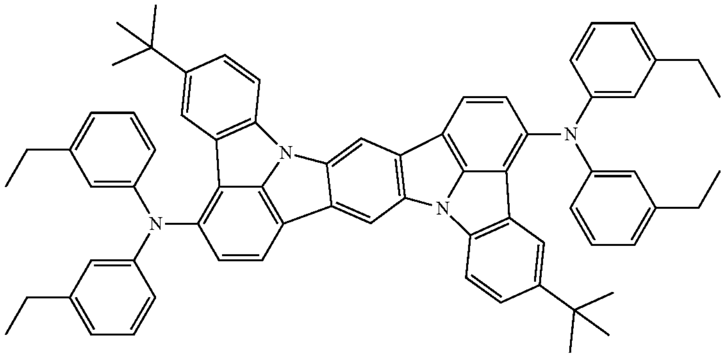

-continued
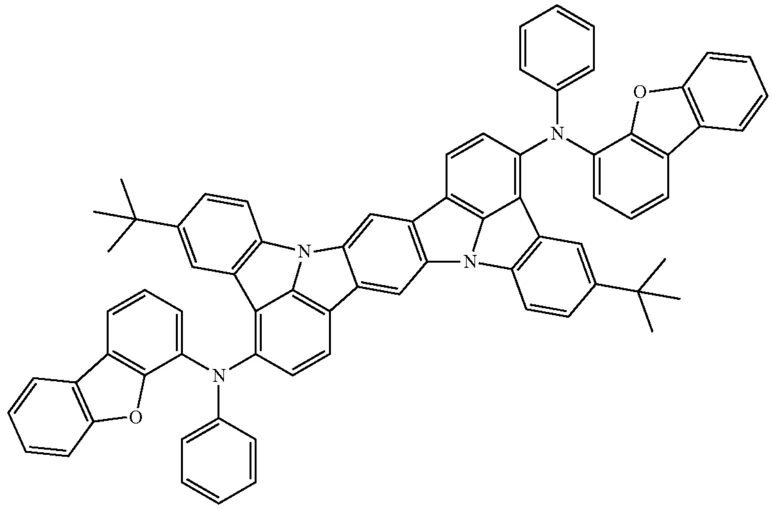
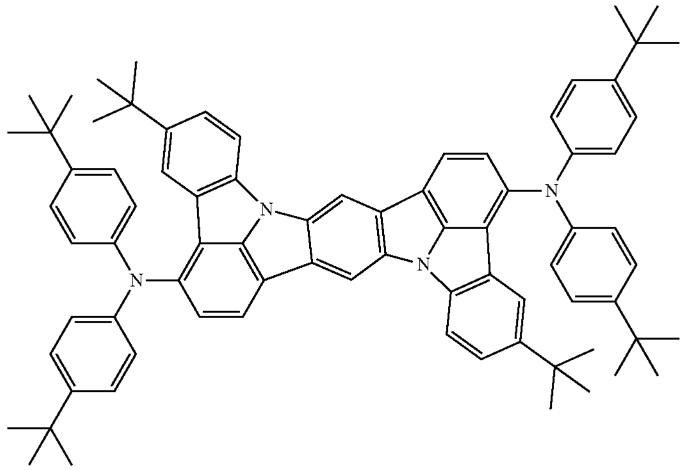
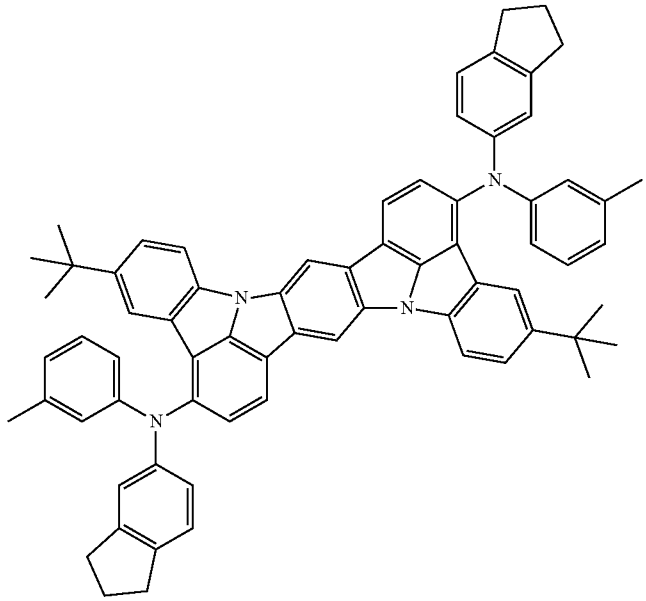

-continued
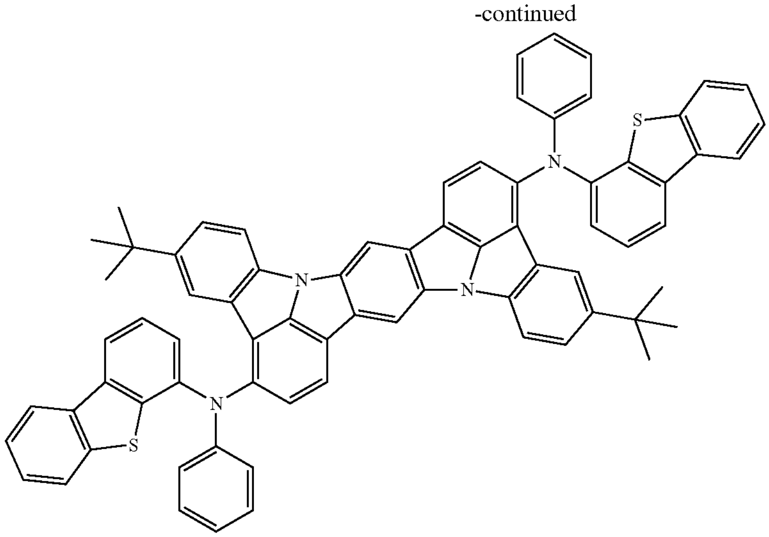
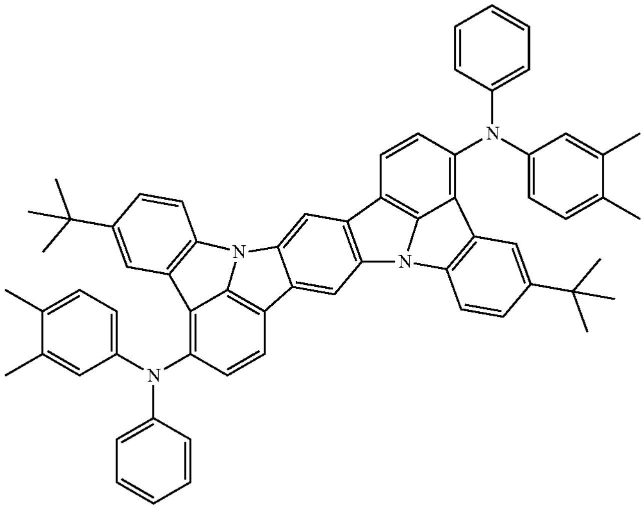
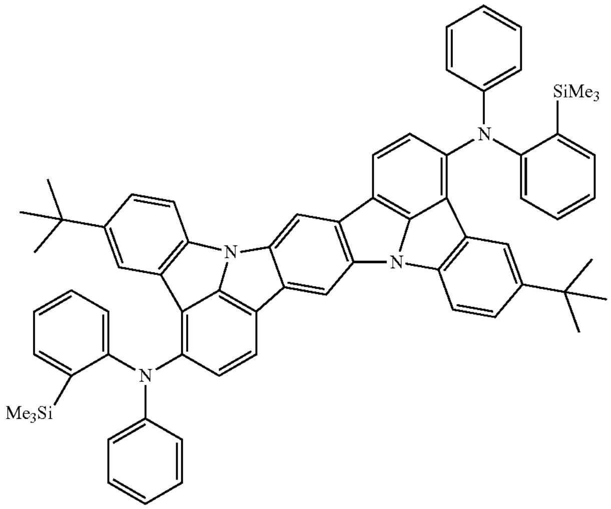

-continued
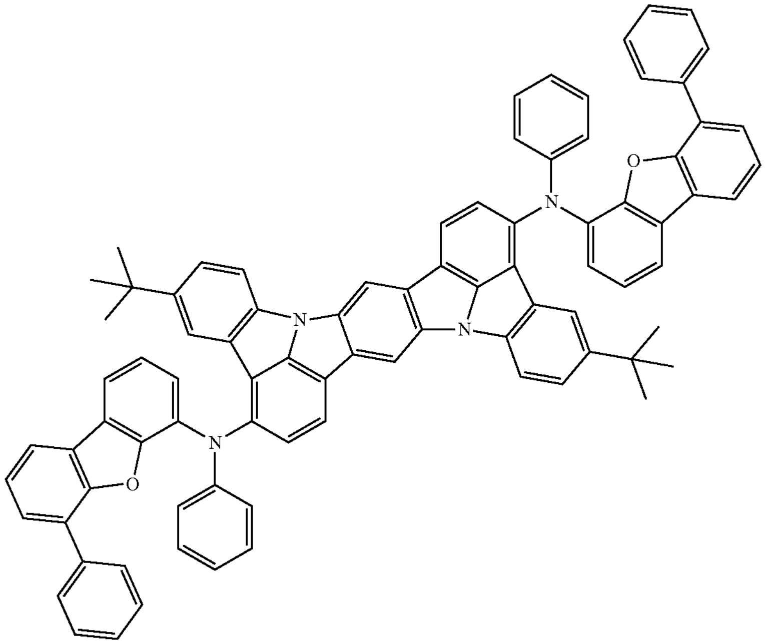
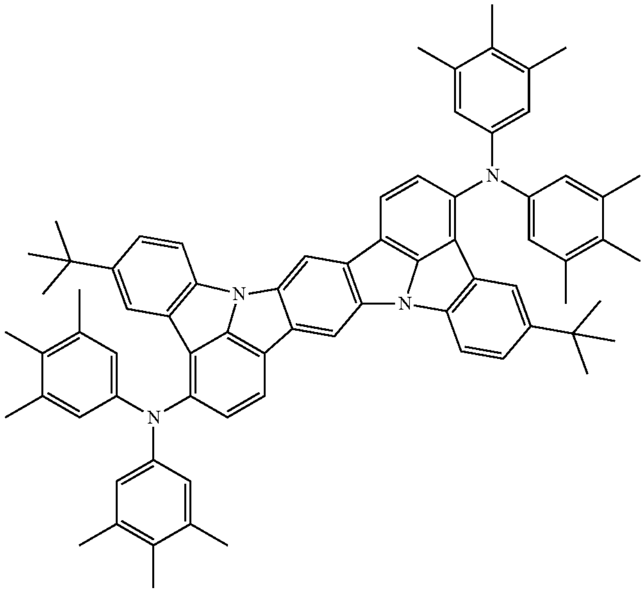

-continued
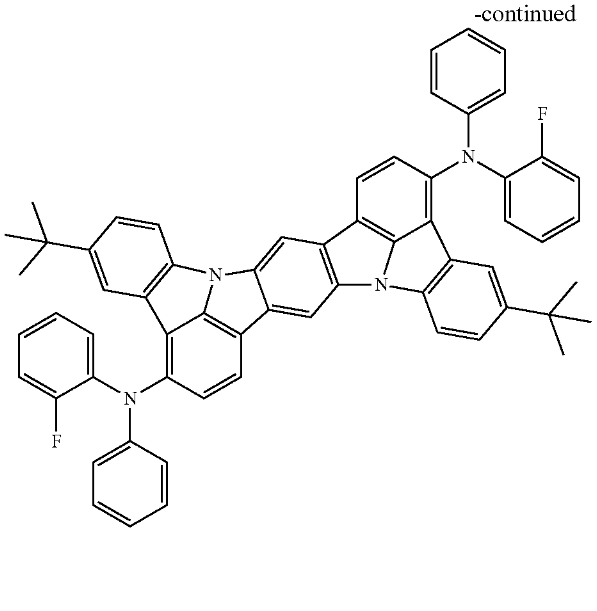
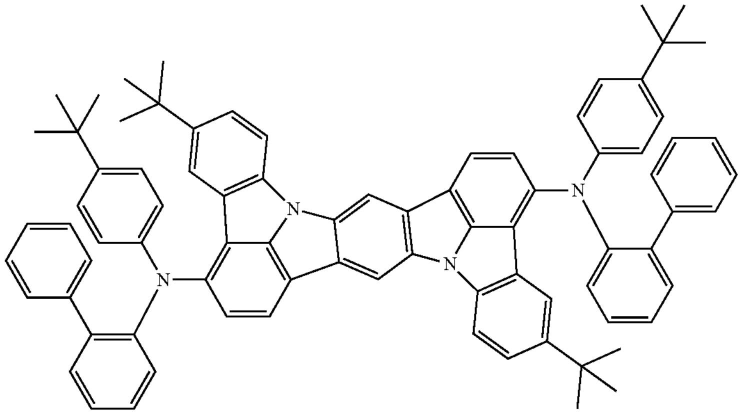
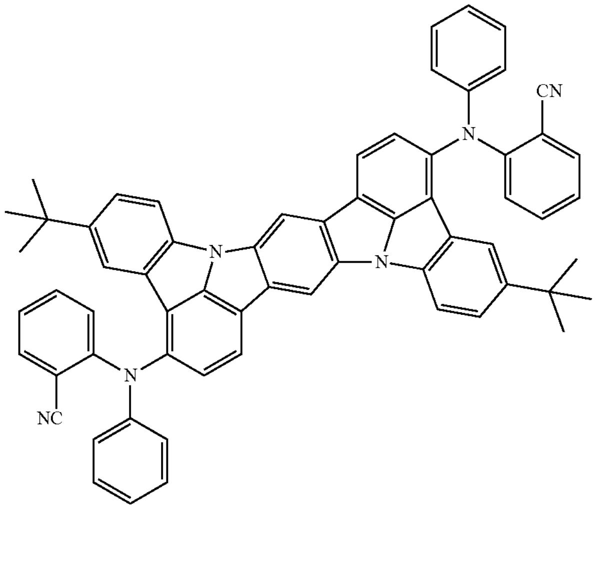

-continued
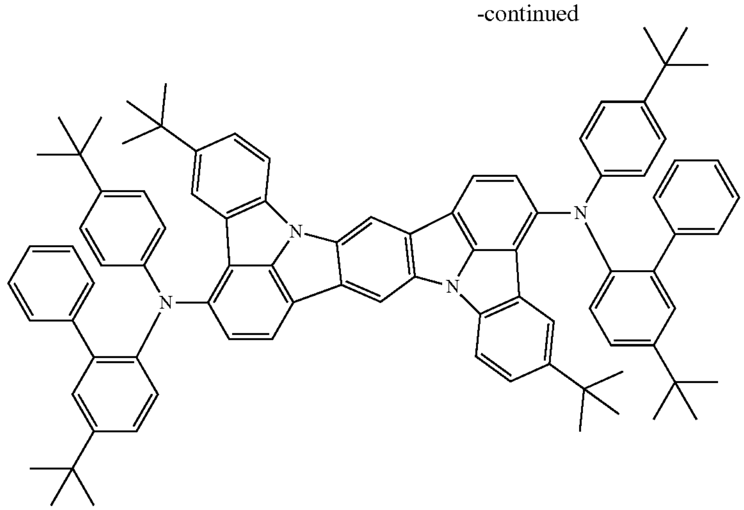
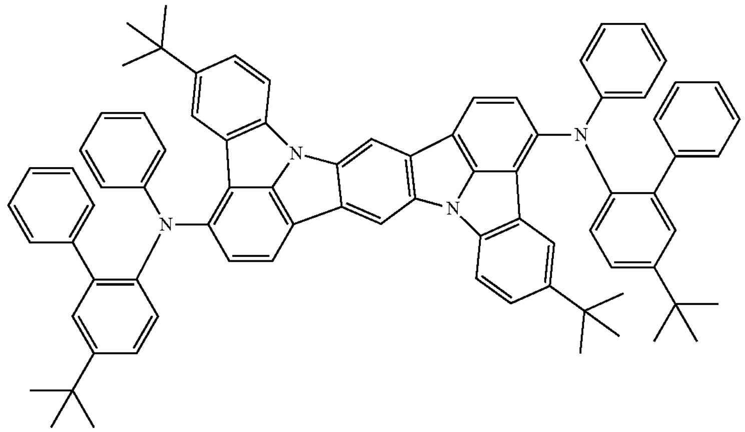
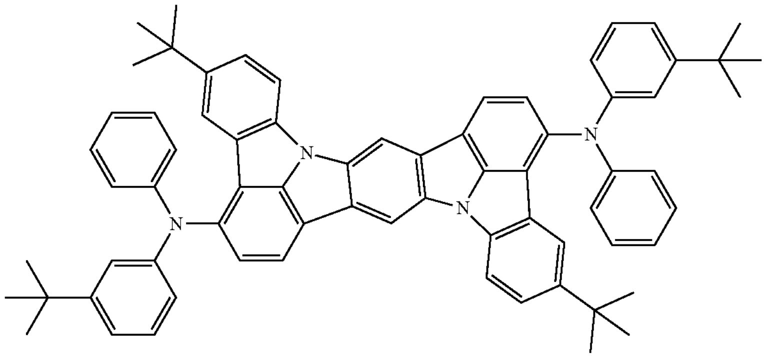

-continued
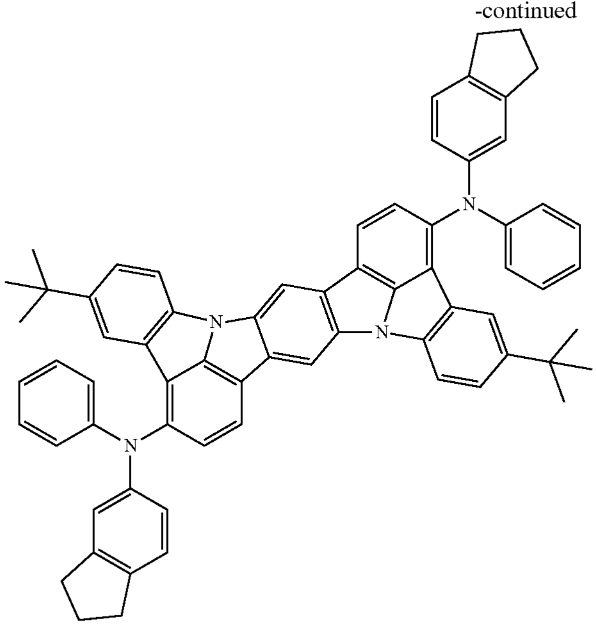
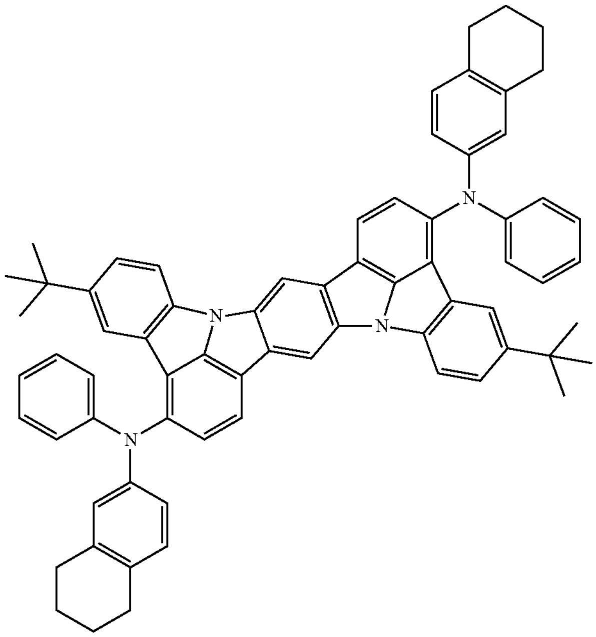

-continued
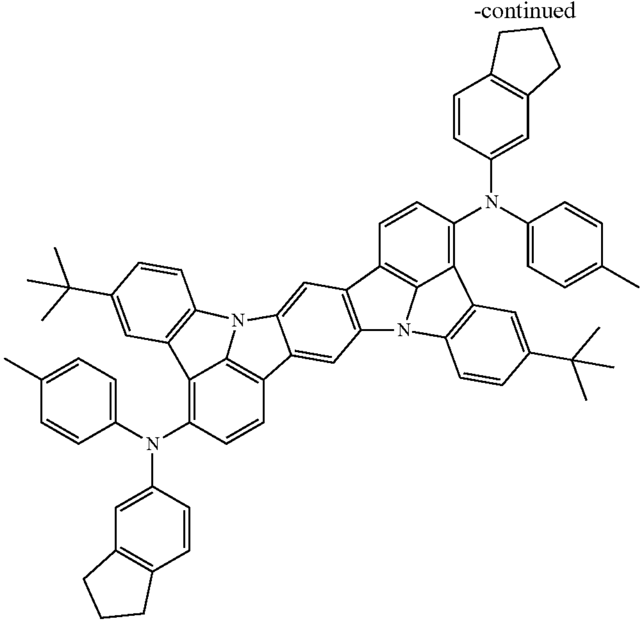
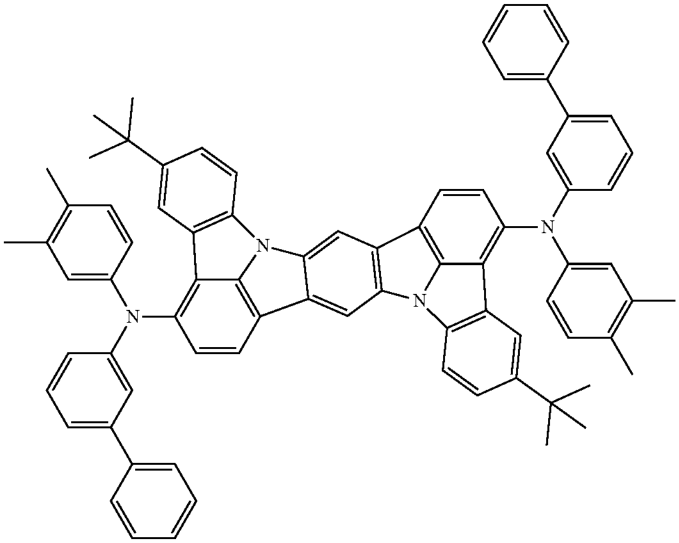
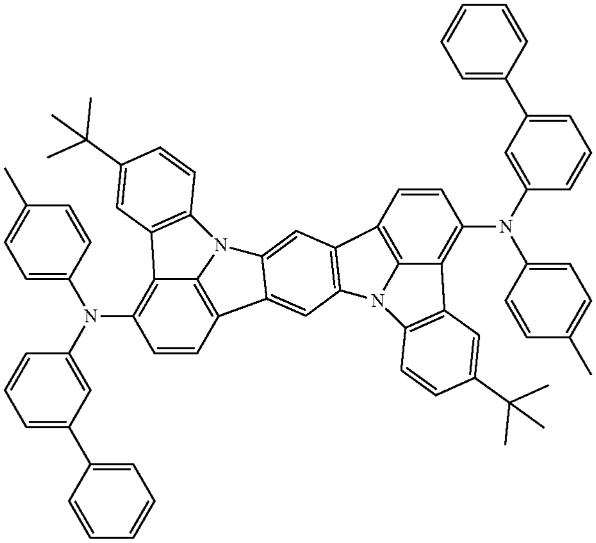

-continued
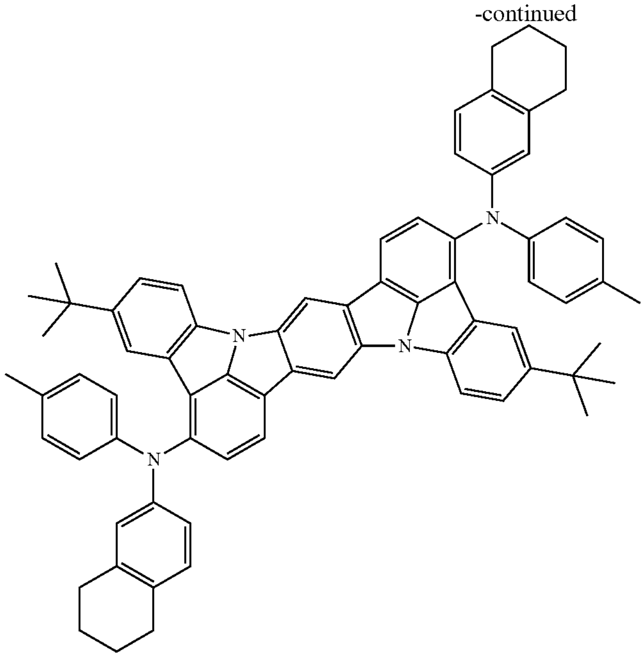
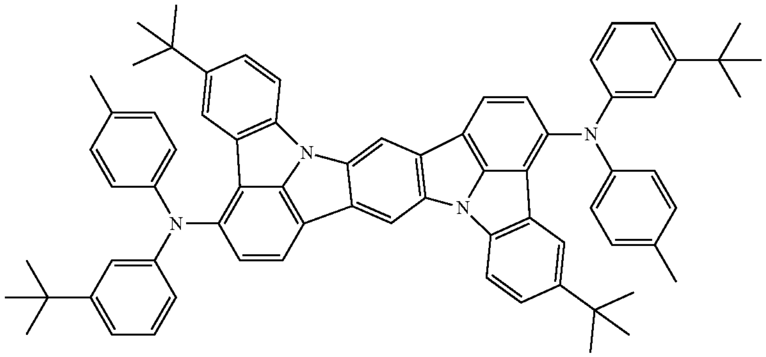
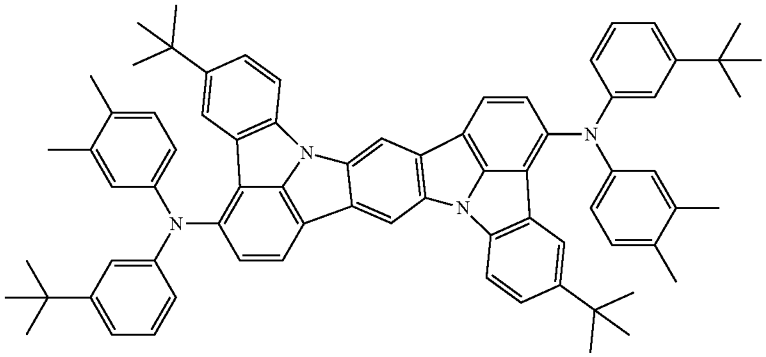

-continued
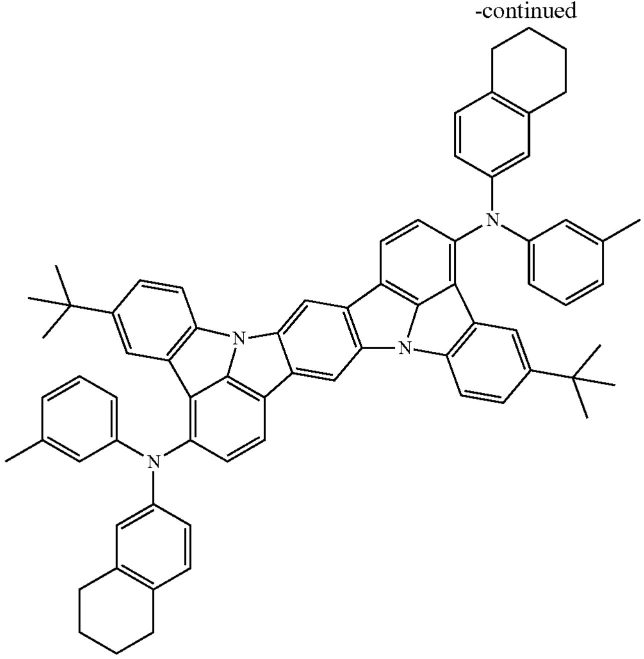
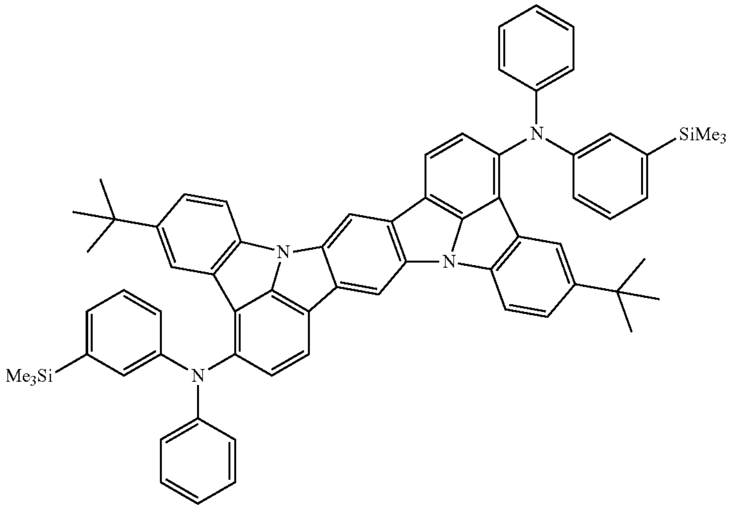
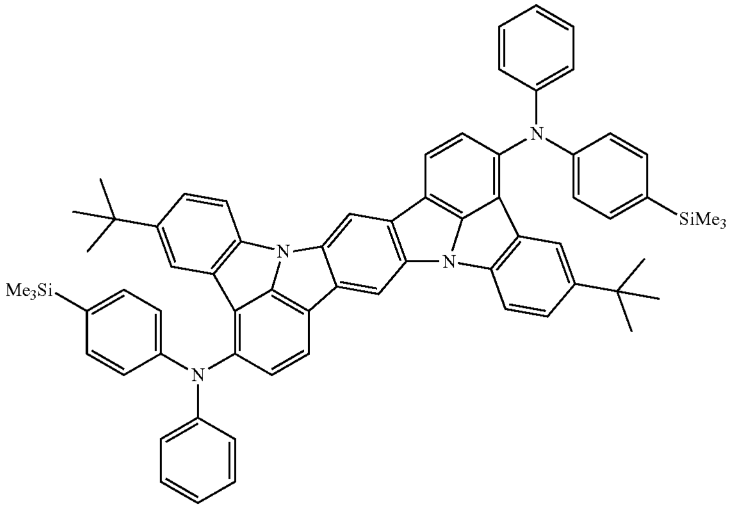

-continued
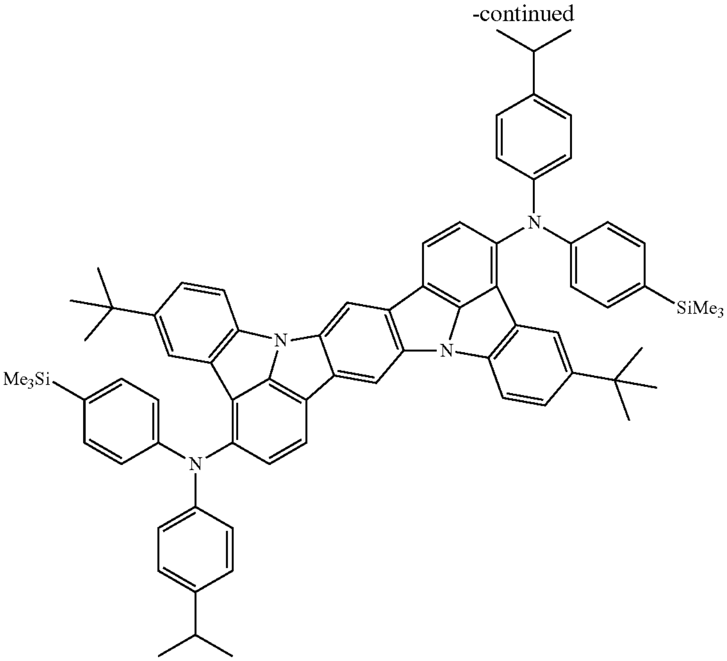
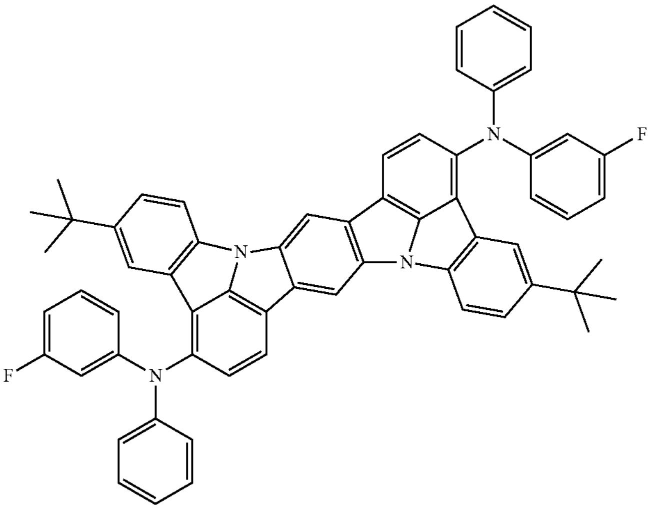
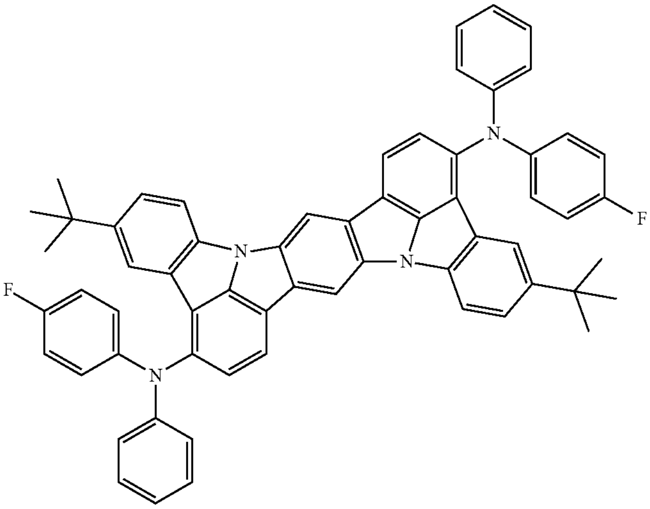

-continued
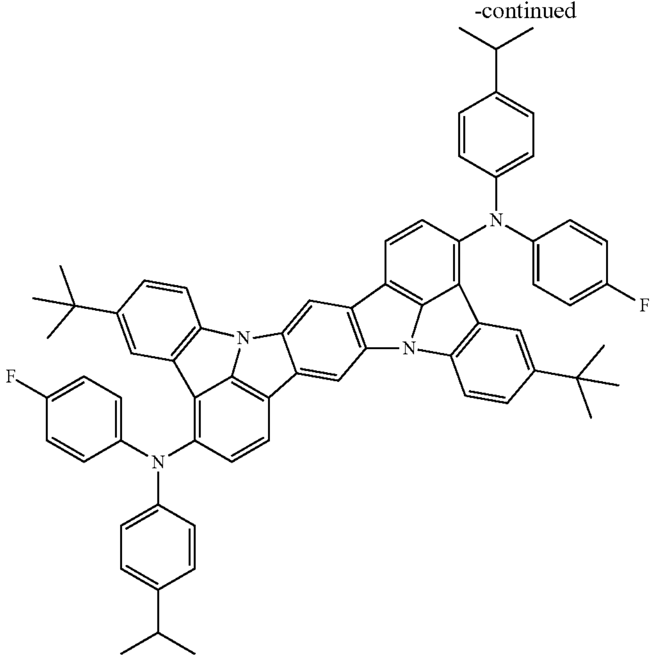
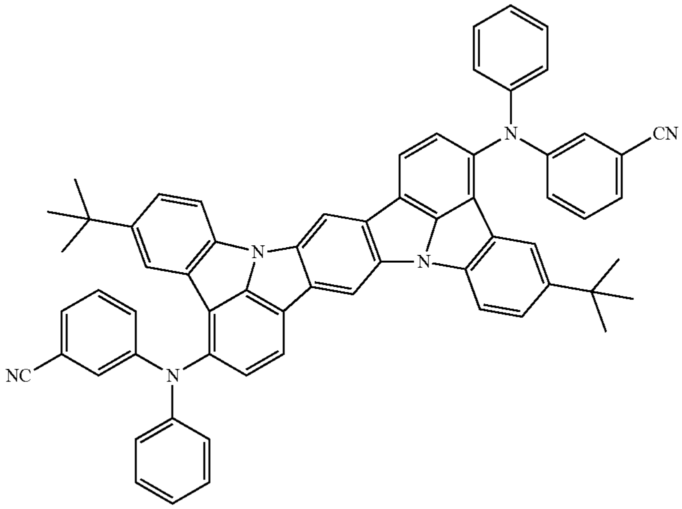
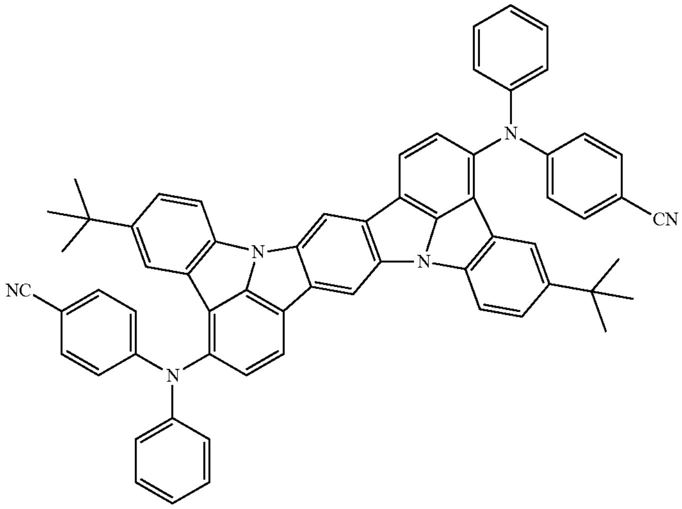

-continued
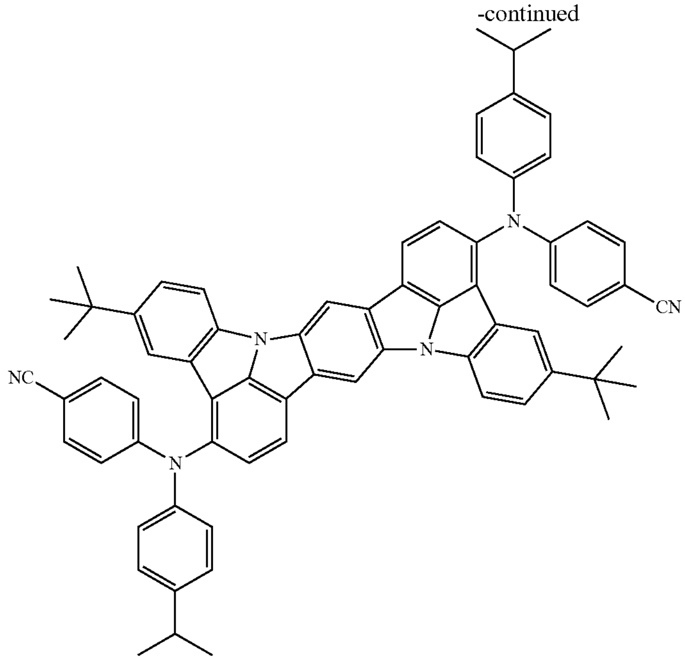
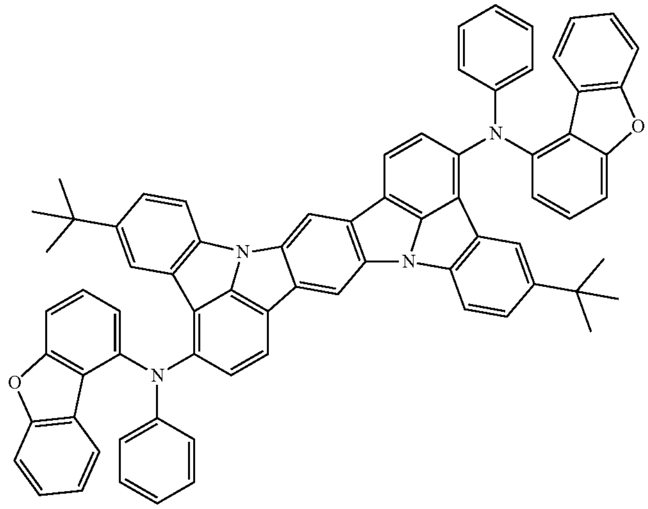
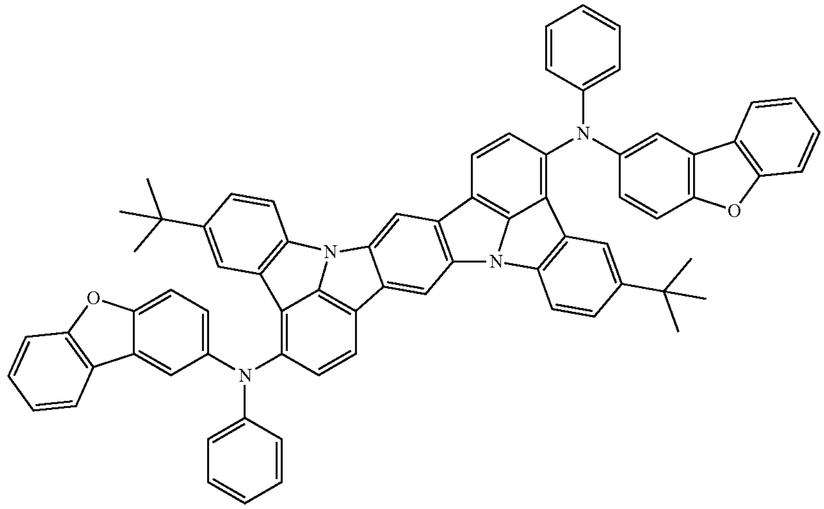

-continued
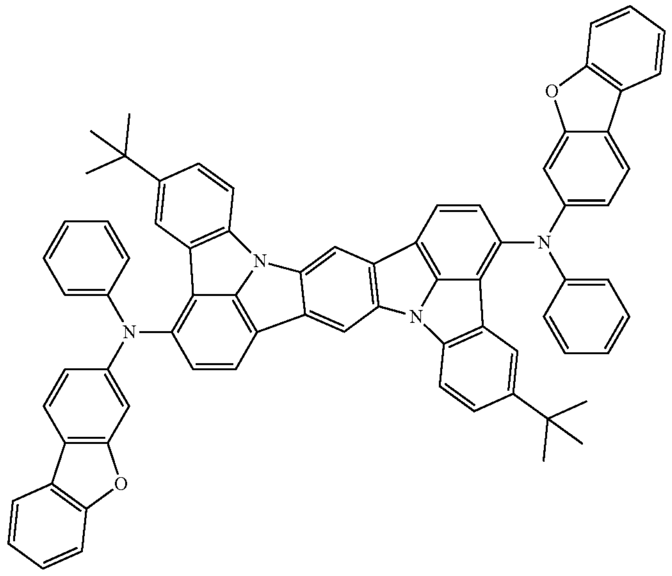
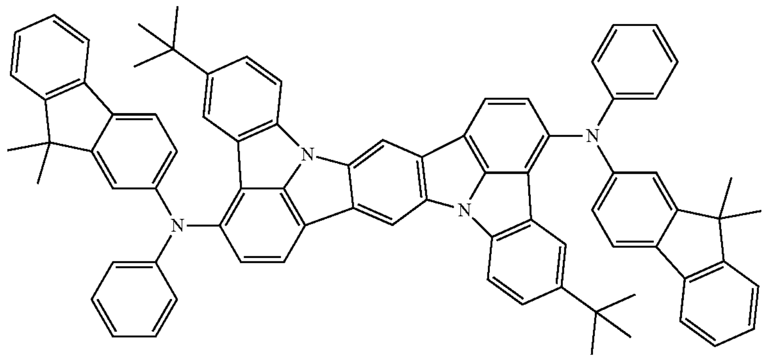
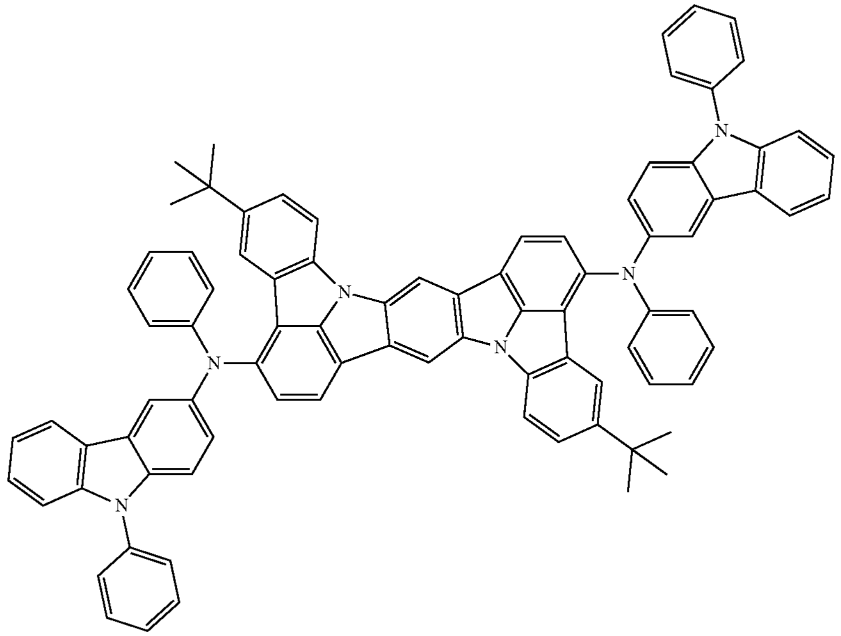

-continued
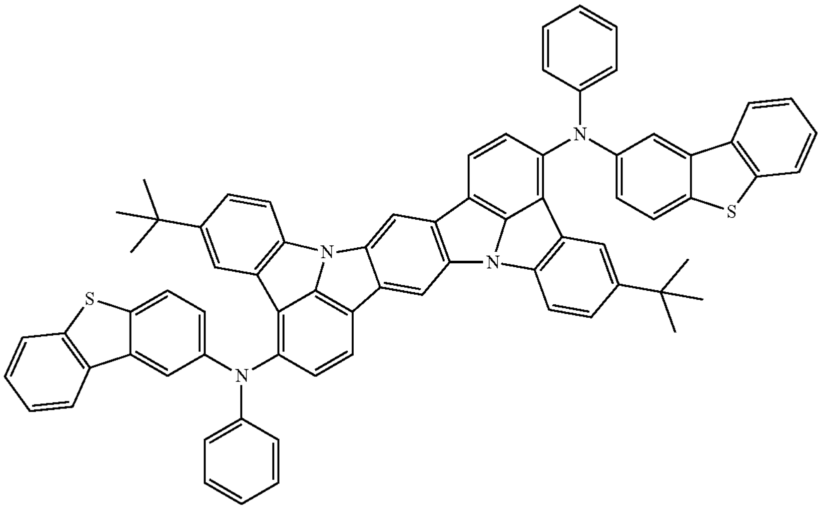
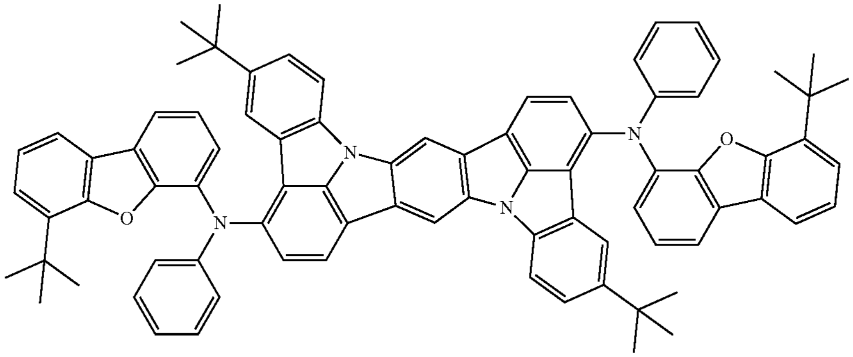
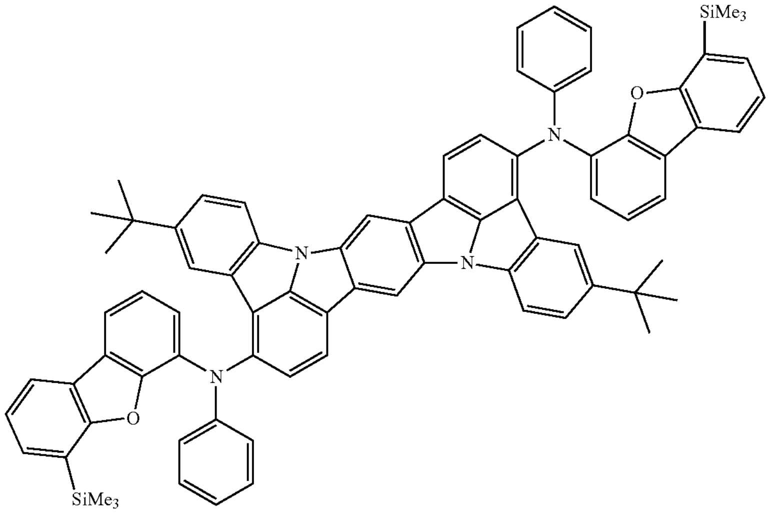

-continued

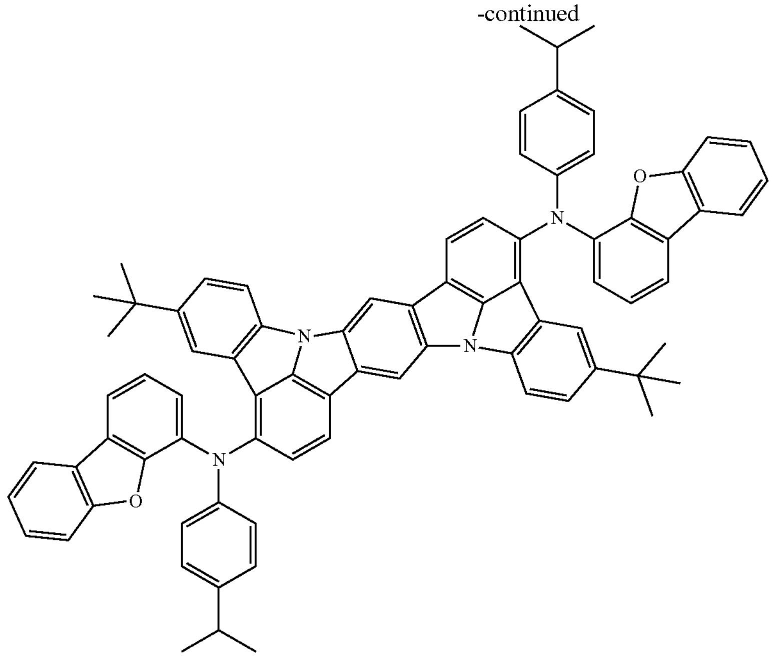

Compound Represented by Formula (6)

(6)

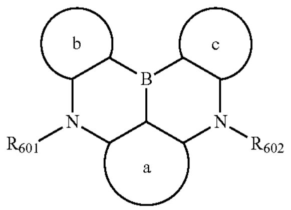

In the formula (6):

a ring, b ring and c ring are each independently a substituted or unsubstituted aromatic hydrocarbon ring having 6 to 50 ring carbon atoms, or a substituted or unsubstituted heterocycle having 5 to 50 ring atoms;

$R_{601}$ and $R_{602}$ are each independently bonded to the a ring, b ring or c ring to form a substituted or unsubstituted heterocycle, or not bonded to form no substituted or unsubstituted heterocycle; and $R_{601}$ and $R_{602}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms.

The a ring, b ring and c ring are each a ring (a substituted or unsubstituted aromatic hydrocarbon ring having 6 to 50 ring carbon atoms, or a substituted or unsubstituted heterocycle having 5 to 50 ring atoms) fused with the fused bicyclic structure formed of a boron atom and two nitrogen atoms at the center of the formula (6).

The "aromatic hydrocarbon ring" for the a, b, and c rings has the same structure as the compound formed by introducing a hydrogen atom to the "aryl group" described above.

Ring atoms of the "aromatic hydrocarbon ring" for the a ring include three carbon atoms on the fused bicyclic structure at the center of the formula (6).

Ring atoms of the "aromatic hydrocarbon ring" for the b ring and the c ring include two carbon atoms on a fused bicyclic structure at the center of the formula (6).

Specific examples of the "substituted or unsubstituted aromatic hydrocarbon ring having 6 to 50 ring carbon atoms" include a compound formed by introducing a hydrogen atom to the "aryl group" described in the specific example group G1.

The "heterocycle" for the a, b, and c rings has the same structure as the compound formed by introducing a hydrogen atom to the "heterocyclic group" described above.

Ring atoms of the "heterocycle" for the a ring include three carbon atoms on the fused bicyclic structure at the center of the formula (6). Ring atoms of the "heterocycle" for the b ring and the c ring include two carbon atoms on a fused bicyclic structure at the center of the formula (6). Specific examples of the "substituted or unsubstituted heterocycle having 5 to 50 ring atoms" include a compound formed by introducing a hydrogen atom to the "heterocyclic group" described in the specific example group G2.

$R_{601}$ and $R_{602}$ are optionally each independently bonded with the a ring, b ring, or c ring to form a substituted or unsubstituted heterocycle. The "heterocycle" in this arrangement includes the nitrogen atom on the fused bicyclic structure at the center of the formula (6). The heterocycle in the above arrangement optionally include a hetero atom other than the nitrogen atom. $R_{601}$ and $R_{602}$ bonded with the a ring, b ring, or c ring specifically means that atoms forming $R_{601}$ and $R_{602}$ are bonded with atoms forming the a ring, b ring, or c ring. For instance, $R_{601}$ may be bonded to the a ring to form a bicyclic (or tri-or-more cyclic) fused nitrogen-containing heterocycle, in which the ring including $R_{601}$ and the a ring are fused. Specific examples of the nitrogen-containing heterocycle include a compound corresponding to the nitrogen-containing bi(or-more)cyclic fused heterocyclic group in the specific example group G2.

The same applies to $R_{601}$ bonded with the b ring, $R_{602}$ bonded with the a ring, and $R_{602}$ bonded with the c ring.

In an exemplary embodiment, the a ring, b ring and c ring in the formula (6) are each independently a substituted or unsubstituted aromatic hydrocarbon ring having 6 to 50 ring carbon atoms.

In an exemplary embodiment, the a ring, b ring and c ring in the formula (6) are each independently a substituted or unsubstituted benzene ring or a substituted or unsubstituted naphthalene ring.

In an exemplary embodiment, $R_{601}$ and $R_{602}$ in the formula (6) are each independently a substituted or unsubstituted aryl group having 6 to 50 ring carbon atoms, or a substituted or unsubstituted heterocyclic group having 5 to 50 ring atoms, preferably a substituted or unsubstituted aryl group having 6 to 50 ring carbon atoms.

In an exemplary embodiment, the compound represented by the formula (6) is a compound represented by a formula (62) below.

(62)

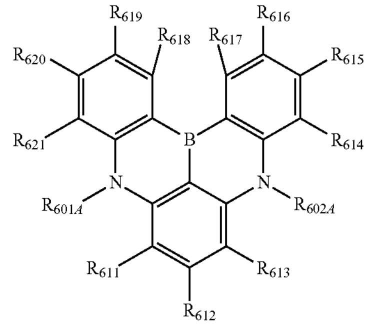

In the formula (62):

$R_{601A}$ is bonded with at least one selected from the group consisting of $R_{611}$ and $R_{621}$ to form a substituted or unsubstituted heterocycle, or not bonded to form no substituted or unsubstituted heterocycle;

$R_{602A}$ is bonded with at least one selected from the group consisting of $R_{613}$ and $R_{614}$ to form a substituted or unsubstituted heterocycle, or not bonded to form no substituted or unsubstituted heterocycle;

$R_{601A}$ and $R_{602A}$ not forming the substituted or unsubstituted heterocycle are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

at least one combination of adjacent two or more of $R_{611}$ to $R_{621}$ are mutually bonded to form a substituted or unsubstituted monocyclic ring, mutually bonded to form a substituted or unsubstituted fused ring, or not mutually bonded; and $R_{611}$ to $R_{621}$ not forming the substituted or unsubstituted heterocycle, not forming the substituted or unsubstituted monocyclic ring, and not forming the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{601A}$ and $R_{602A}$ in the formula (62) are groups corresponding to $R_{601}$ and $R_{602}$ in the formula (6), respectively.

For instance, $R_{601A}$ and $R_{611}$ are optionally bonded with each other to form a bicyclic (or tri-or-more cyclic) fused nitrogen-containing heterocycle, in which the ring including $R_{601A}$ and $R_{611}$ and a benzene ring corresponding to the a ring are fused. Specific examples of the nitrogen-containing heterocycle include a compound corresponding to the nitrogen-containing bi(or-more)cyclic fused heterocyclic group in the specific example group G2. The same applies to $R_{601A}$ bonded with $R_{621}$, $R_{602A}$ bonded with $R_{613}$, and $R_{602A}$ bonded with $R_{614}$.

At least one combination of adjacent two or more of $R_{611}$ to $R_{621}$ may be mutually bonded to form a substituted or unsubstituted monocyclic ring, or mutually bonded to form a substituted or unsubstituted fused ring.

For instance, $R_{611}$ and $R_{612}$ may be mutually bonded to form a structure in which a benzene ring, indole ring, pyrrole ring, benzofuran ring, benzothiophene ring or the like is fused to the six-membered ring bonded with $R_{611}$ and $R_{612}$, in which the formed fused ring are a naphthalene ring, carbazole ring, indole ring, dibenzofuran ring, or dibenzothiophene ring.

In an exemplary embodiment, $R_{611}$ to $R_{621}$ not contributing to the ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to the ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{611}$ to $R_{621}$ not contributing to the ring formation are each independently a hydrogen atom, or a substituted or unsubstituted alkyl group having 1 to 50 carbon atoms.

In an exemplary embodiment, $R_{611}$ to $R_{621}$ not contributing to the ring formation are each independently a hydrogen atom or a substituted or unsubstituted alkyl group having 1 to 50 carbon atoms, and at least one of $R_{611}$ to $R_{621}$ is a substituted or unsubstituted alkyl group having 1 to 50 carbon atoms.

In an exemplary embodiment, the compound represented by the formula (62) is a compound represented by a formula (63) below.

(63)

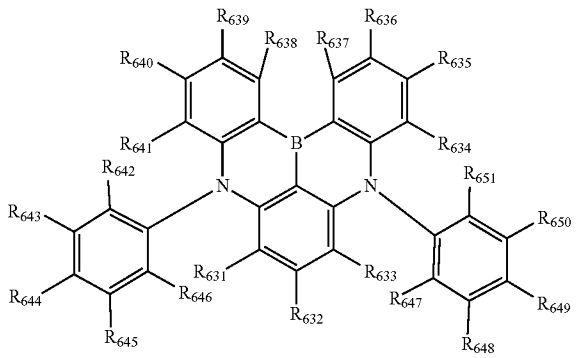

In the formula (63):

$R_{631}$ is bonded with $R_{646}$ to form a substituted or unsubstituted heterocycle, or not bonded to form no substituted or unsubstituted heterocycle;

$R_{633}$ is bonded with $R_{647}$ to form a substituted or unsubstituted heterocycle, or not bonded to form no substituted or unsubstituted heterocycle;

$R_{634}$ is bonded with $R_{651}$ to form a substituted or unsubstituted heterocycle, or not bonded to form no substituted or unsubstituted heterocycle;

$R_{641}$ is bonded with $R_{642}$ to form a substituted or unsubstituted heterocycle, or not bonded to form no substituted or unsubstituted heterocycle;

at least one combination of adjacent two or more of $R_{631}$ to $R_{651}$ are mutually bonded to form a substituted or unsubstituted monocyclic ring, mutually bonded to form a substituted or unsubstituted fused ring, or not mutually bonded; and $R_{631}$ to $R_{651}$ not forming the substituted or unsubstituted heterocycle, not forming the substituted or unsubstituted monocyclic ring, and not forming the substituted or unsubstituted fused ring are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —Si($R_{901}$)($R_{902}$)($R_{903}$), a group represented by —O—($R_{904}$), a group represented by —S—($R_{905}$), a group represented by —N($R_{906}$)($R_{907}$), a halogen atom, a cyano group, a nitro group, a substituted or unsubstituted aryl group having 6 to 50 ring carbon atoms, or a substituted or unsubstituted heterocyclic group having 5 to 50 ring atoms.

$R_{631}$ are optionally mutually bonded with $R_{646}$ to form a substituted or unsubstituted heterocycle. For instance, $R_{631}$ and $R_{646}$ are optionally bonded with each other to form a tri-or-more cyclic fused nitrogen-containing heterocycle, in which a benzene ring bonded with $R_{646}$, a ring including a nitrogen atom, and a benzene ring corresponding to the a ring are fused. Specific examples of the nitrogen-containing heterocycle include a compound corresponding to the nitrogen-containing tri(-or-more)cyclic fused heterocyclic group in the specific example group G2. The same applies to $R_{633}$ bonded with $R_{647}$, $R_{634}$ bonded with $R_{651}$, and $R_{641}$ bonded with $R_{642}$.

In an exemplary embodiment, $R_{631}$ to $R_{651}$ not contributing to the ring formation are each independently a hydrogen atom, a substituted or unsubstituted alkyl group having 1 to 50 carbon atoms, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to the ring formation are each independently a hydrogen atom, a substituted or unsubstituted aryl group having 6 to 50 ring carbon atoms, or a substituted or unsubstituted heterocyclic group having 5 to 50 ring atoms.

In an exemplary embodiment, $R_{631}$ to $R_{651}$ not contributing to the ring formation are each independently a hydrogen atom, or a substituted or unsubstituted alkyl group having 1 to 50 carbon atoms.

In an exemplary embodiment, $R_{631}$ to $R_{651}$ not contributing to the ring formation are each independently a hydrogen atom, or a substituted or unsubstituted alkyl group having 1 to 50 carbon atoms, and at least one of $R_{631}$ to $R_{651}$ is a substituted or unsubstituted alkyl group having 1 to 50 carbon atoms.

In an exemplary embodiment, the compound represented by the formula (63) is a compound represented by a formula (63A) below.

(63A)

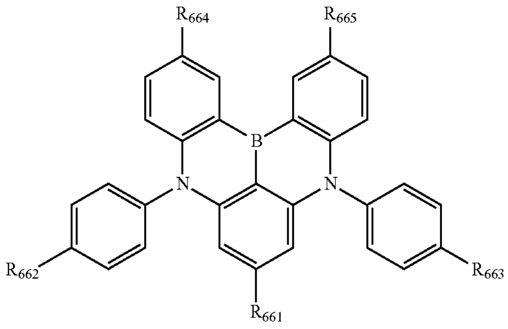

In the formula (63A):

$R_{661}$ is a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{662}$ to $R_{665}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms, or a substituted or unsubstituted aryl group having 6 to 50 ring carbon atoms.

In an exemplary embodiment, $R_{661}$ to $R_{665}$ are each independently a substituted or unsubstituted alkyl group having 1 to 50 carbon atoms.

In an exemplary embodiment, the compound represented by the formula (63) is a compound represented by a formula (63B) below.

(63B)

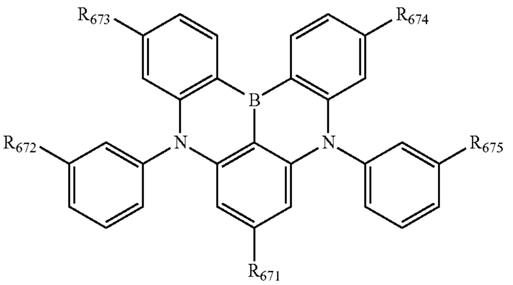

In the formula (63B):

$R_{671}$ and $R_{672}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, or a substituted or unsubstituted aryl group having 6 to 50 ring carbon atoms; and $R_{673}$ to $R_{675}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, or a substituted or unsubstituted aryl group having 6 to 50 ring carbon atoms.

In an exemplary embodiment, the compound represented by the formula (63) is a compound represented by a formula (63B') below.

(63B')

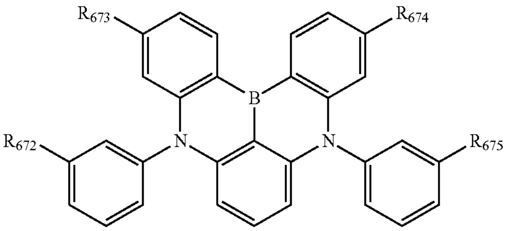

In the formula (63B'), $R_{672}$ to $R_{675}$ respectively independently represent the same as $R_{672}$ to $R_{675}$ in the formula (63B).

In an exemplary embodiment, at least one of $R_{671}$ to $R_{675}$ is a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{906})(R_{907})$, or a substituted or unsubstituted aryl group having 6 to 50 ring carbon atoms.

In an exemplary embodiment, $R_{672}$ is a hydrogen atom, a substituted or unsubstituted alkyl group having 1 to 50 carbon atoms, a group represented by —$N(R_{906})(R_{907})$, or a substituted or unsubstituted aryl group having 6 to 50 ring carbon atoms; and $R_{671}$ and $R_{673}$ to $R_{675}$ are each independently a substituted or unsubstituted alkyl group having 1 to 50 carbon atoms, a group represented by —$N(R_{906})(R_{907})$, or a substituted or unsubstituted aryl group having 6 to 50 ring carbon atoms.

In an exemplary embodiment, the compound represented by the formula (63) is a compound represented by a formula (63C) below.

(63C)

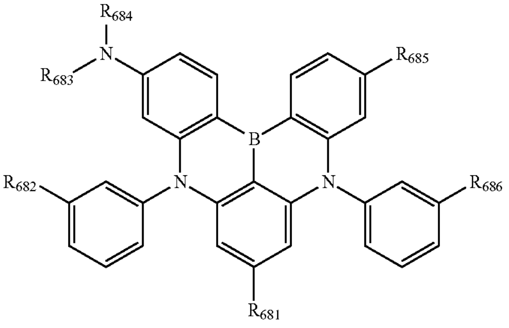

In the formula (63C):

$R_{681}$ and $R_{682}$ are each independently a hydrogen atom, a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms; and $R_{683}$ to $R_{686}$ are each independently a substituted or unsubstituted alkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, or a substituted or unsubstituted aryl group having 6 to 50 ring carbon atoms.

In an exemplary embodiment, the compound represented by the formula (63) is a compound represented by a formula (63C') below.

(63C')

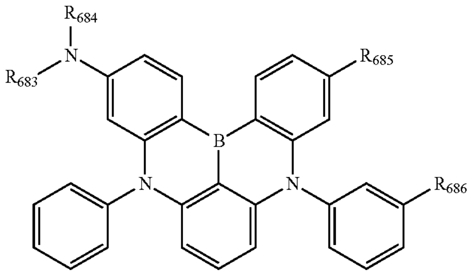

In the formula (63C'), $R_{683}$ to $R_{686}$ respectively independently represent the same as $R_{683}$ to $R_{686}$ in the formula (63C).

In an exemplary embodiment, $R_{681}$ to $R_{686}$ are each independently a substituted or unsubstituted alkyl group having 1 to 50 carbon atoms, or a substituted or unsubstituted aryl group having 6 to 50 ring carbon atoms.

In an exemplary embodiment, $R_{681}$ to $R_{686}$ are each independently a substituted or unsubstituted aryl group having 6 to 50 ring carbon atoms.

The compound represented by the formula (6) is producible by initially bonding the a ring, b ring and c ring with linking groups (a group including N—$R_{601}$ and a group including N—$R_{602}$) to form an intermediate (first reaction), and bonding the a ring, b ring and c ring with a linking group (a group including a boron atom) to form a final product (second reaction). In the first reaction, an amination reaction (e.g. Buchwald-Hartwig reaction) is applicable. In the second reaction, Tandem Hetero-Friedel—Crafts Reactions or the like is applicable.

The compound represented by the formula (6) can be manufactured by a known method.

Specific Examples of Compound Represented by Formula (6)

Specific examples of the compound represented by the formula (6) include compounds shown below. It should be noted that the compound represented by the formula (6) is by no means limited to the specific examples below.

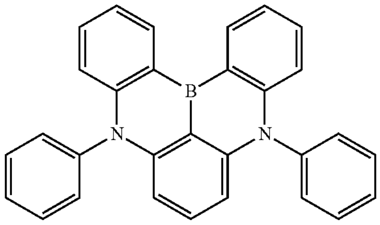

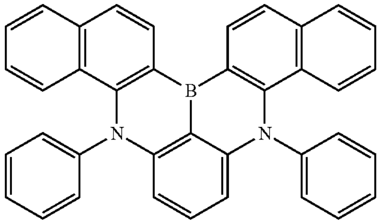

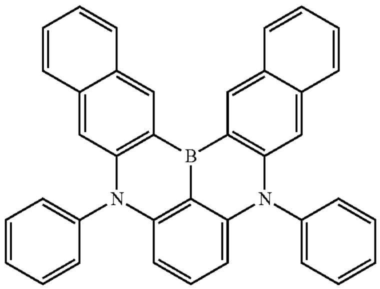

-continued

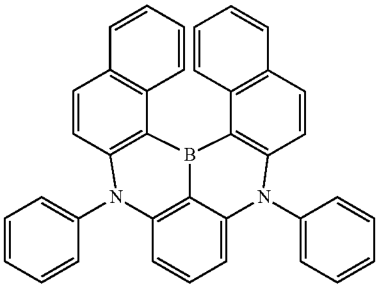

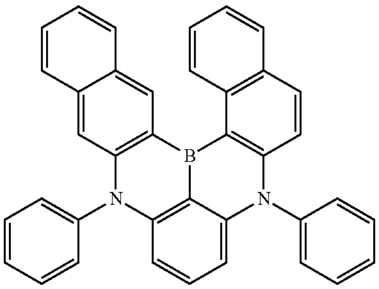

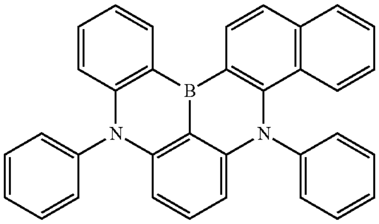

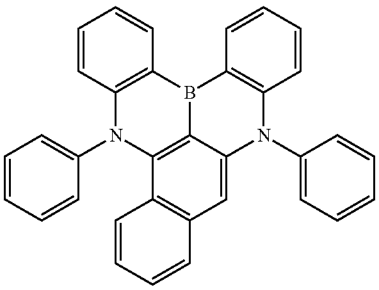

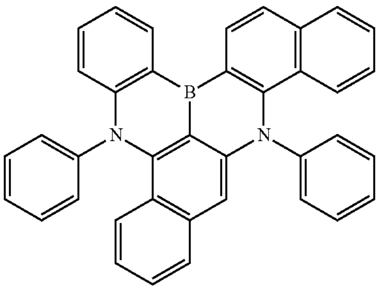

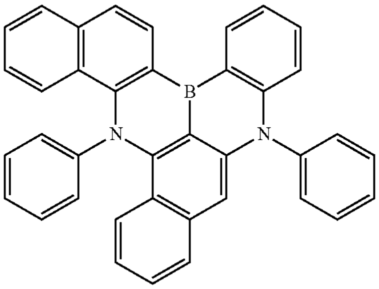

-continued
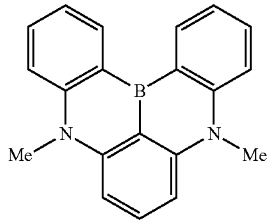
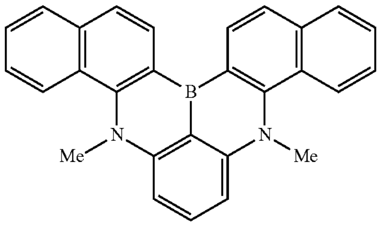
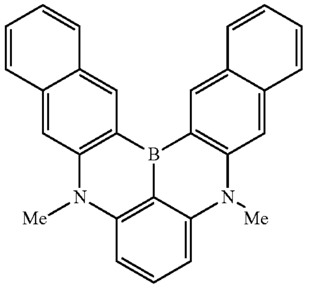
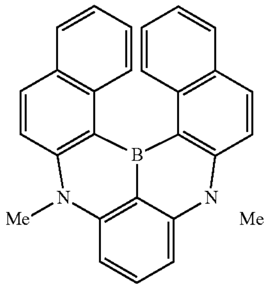
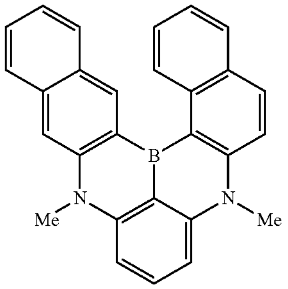
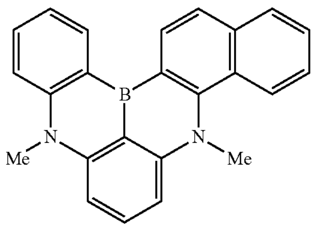
-continued
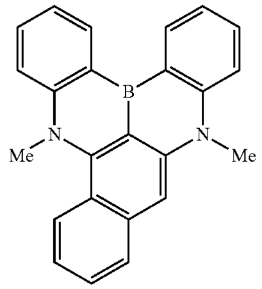
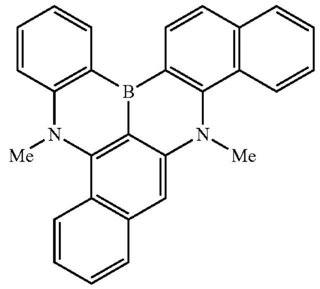
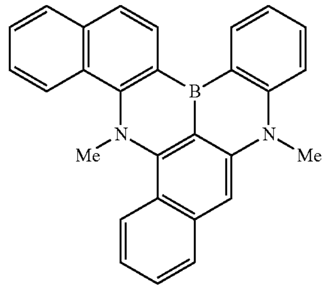
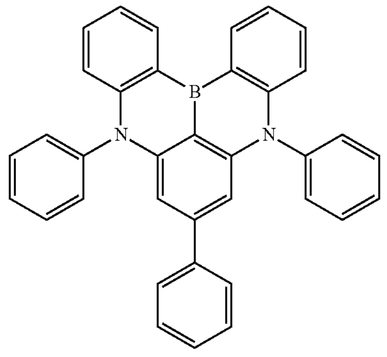
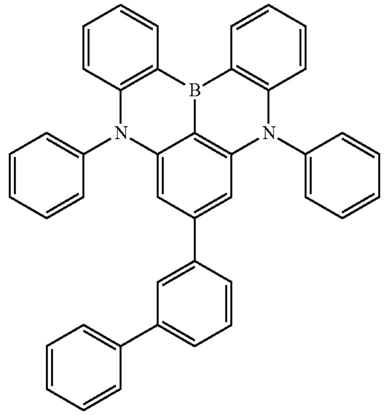

-continued
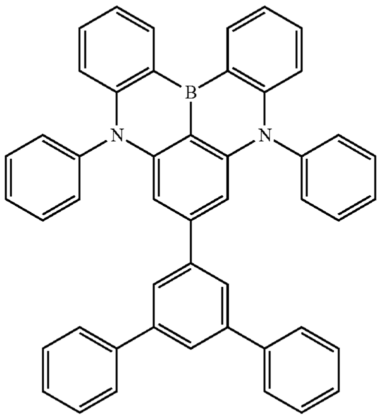
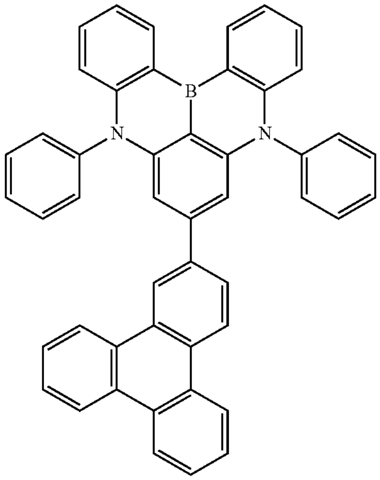
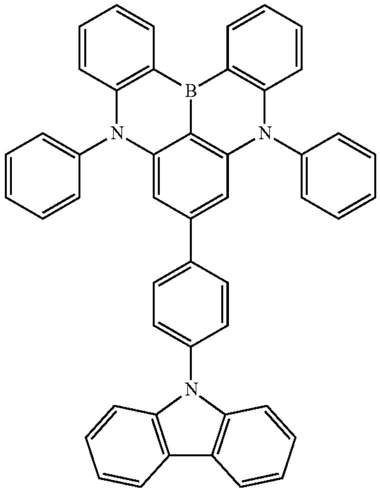
-continued
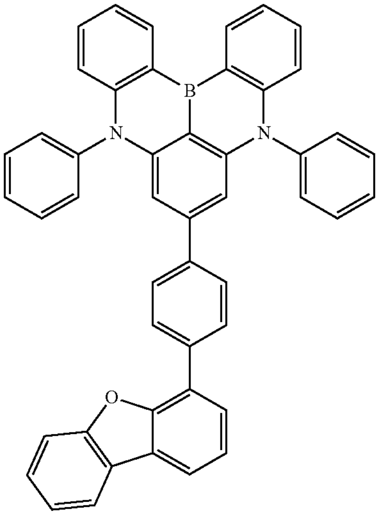
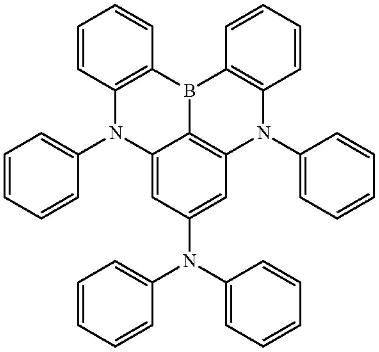
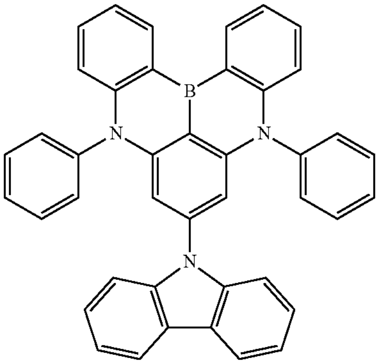
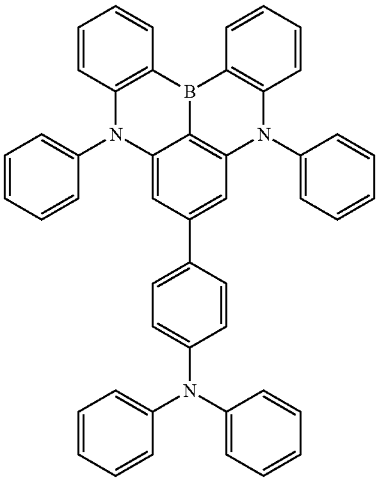

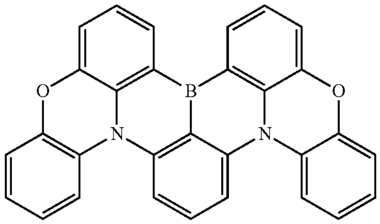
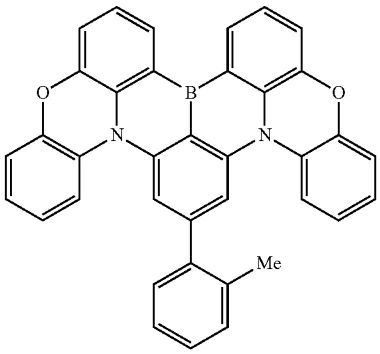
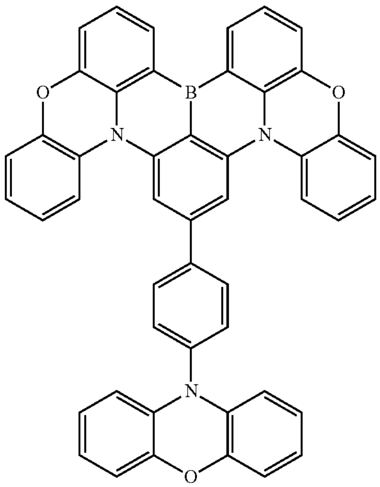
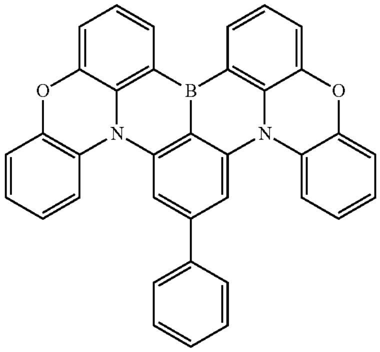
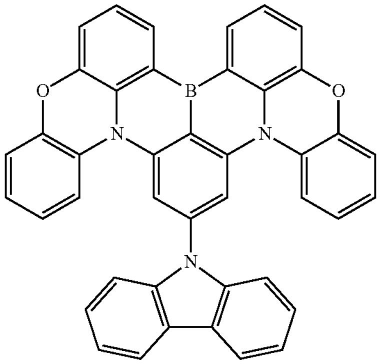
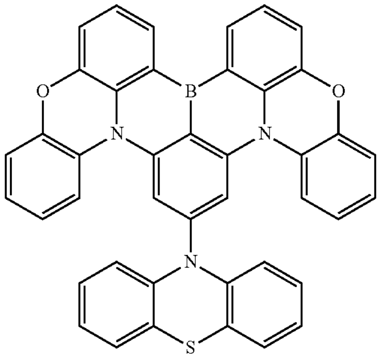
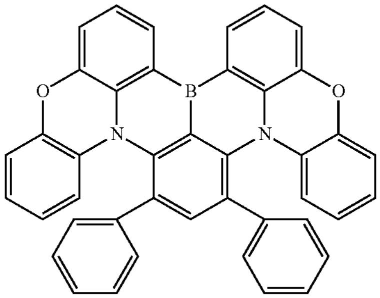
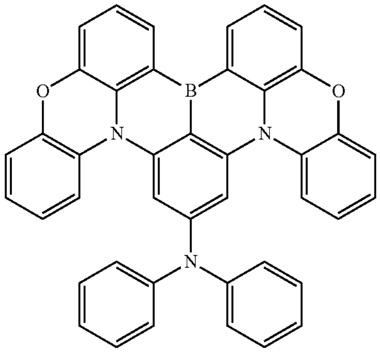

-continued
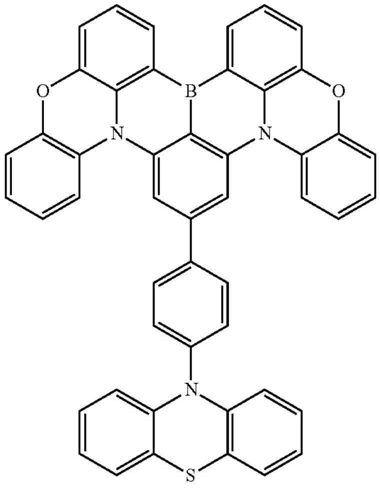
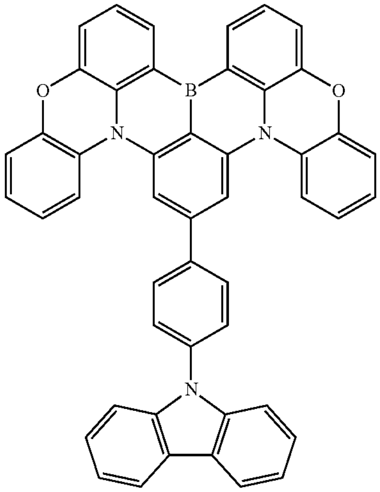
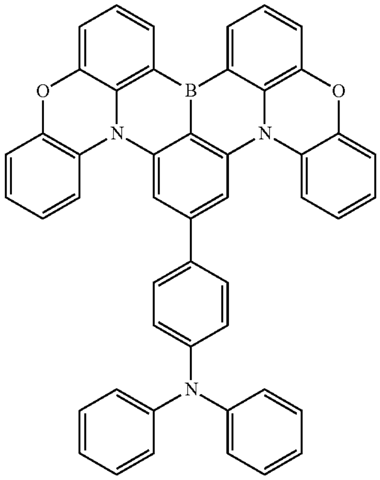
-continued
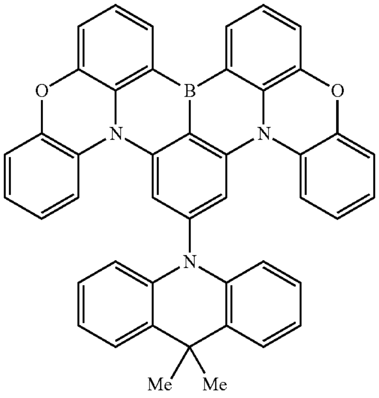
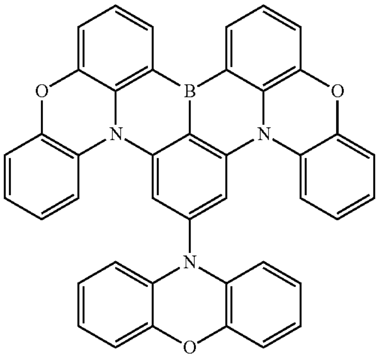
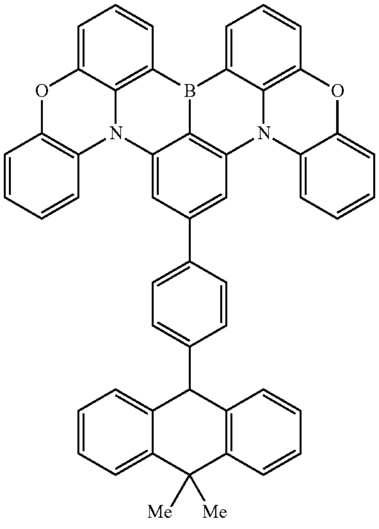
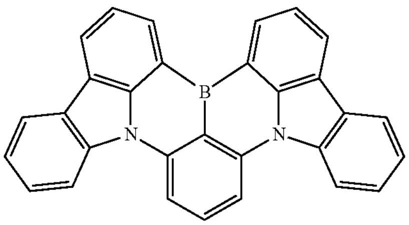

-continued
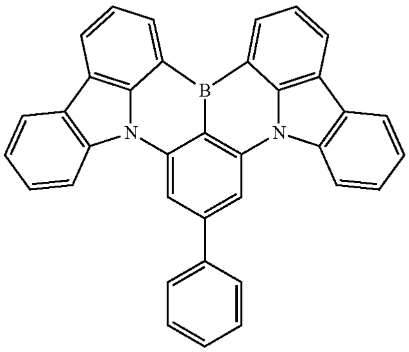
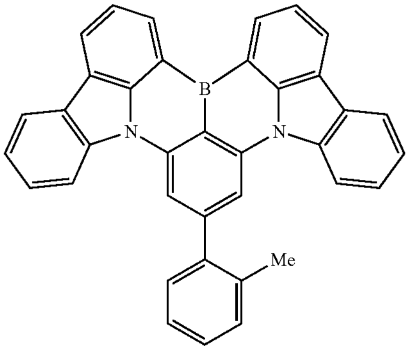
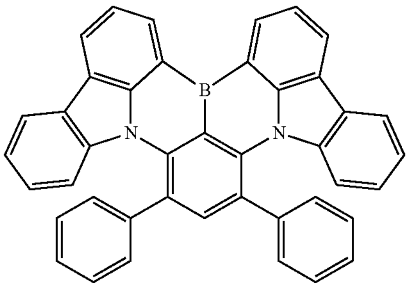
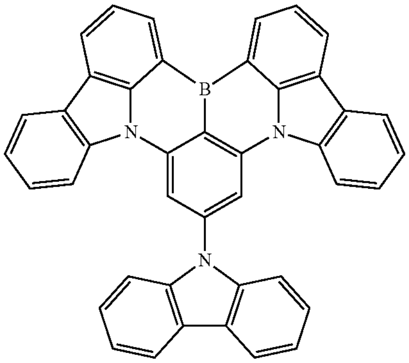
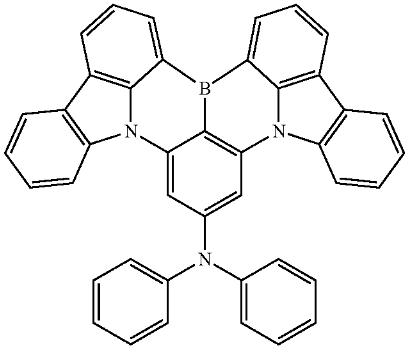
-continued
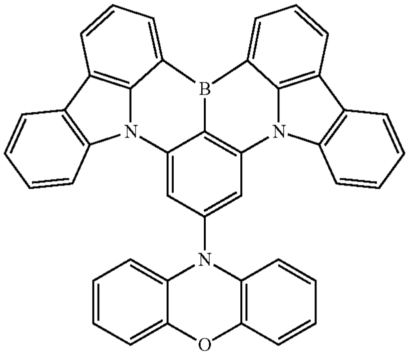
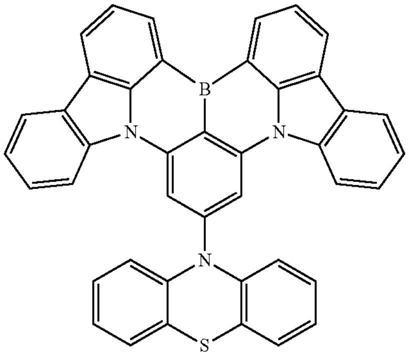
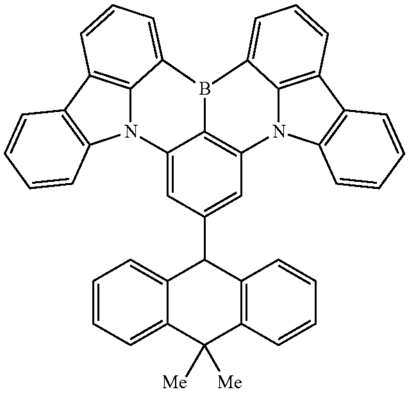
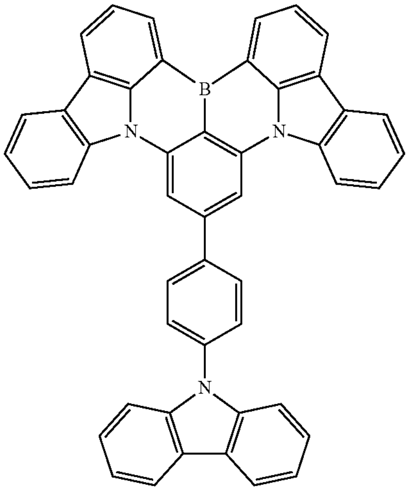

-continued
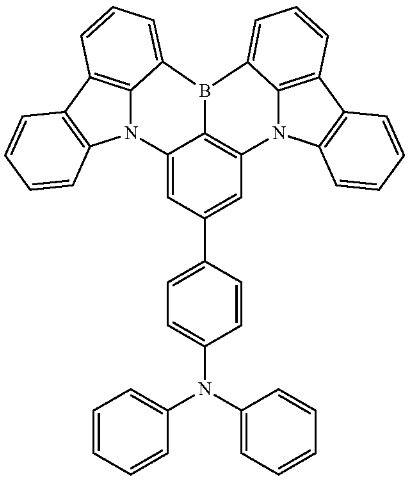
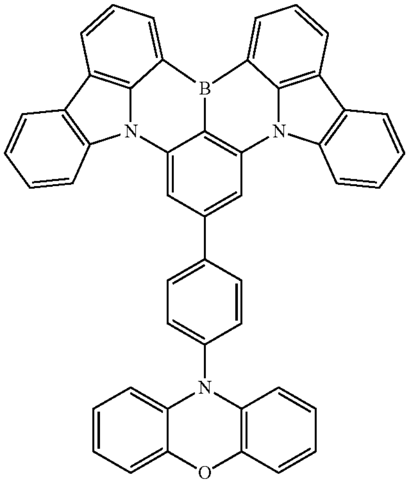
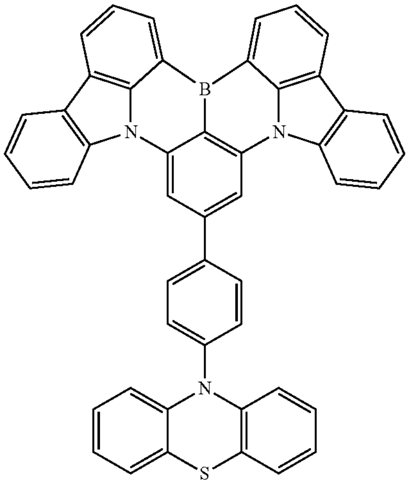
-continued
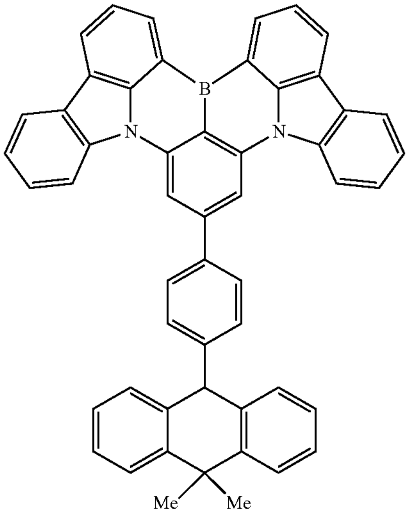
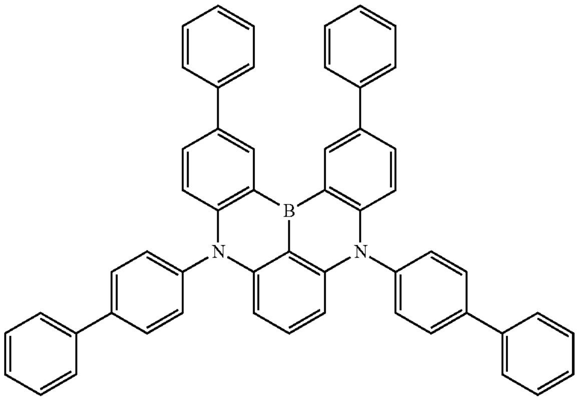
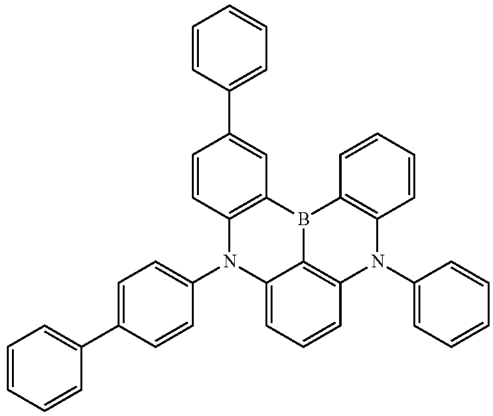
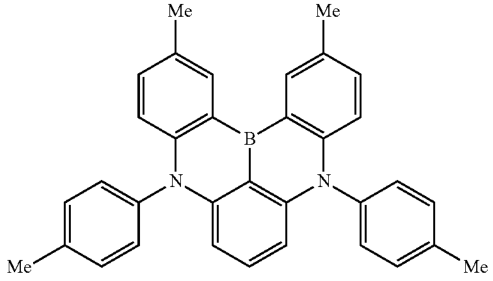

-continued
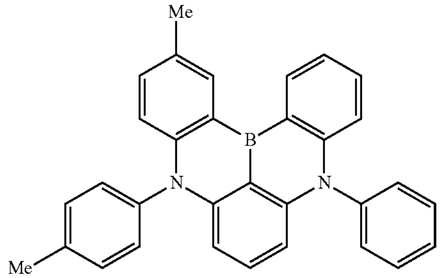
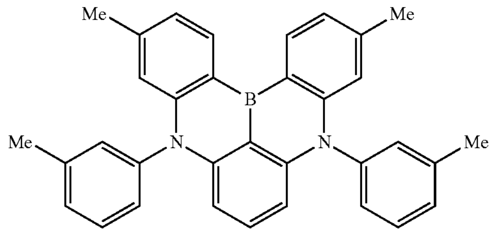
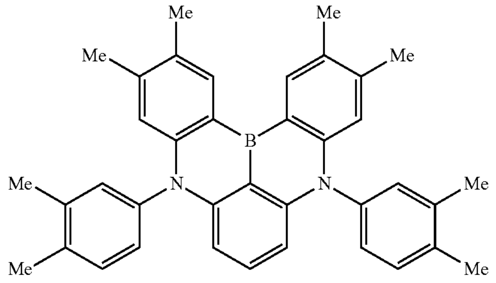
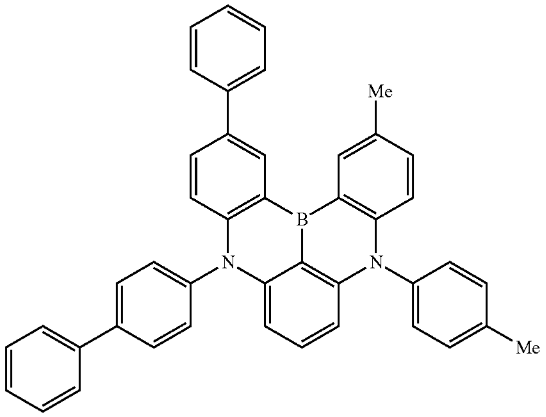
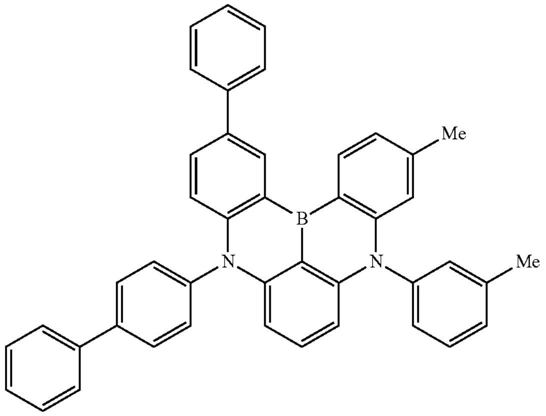
-continued
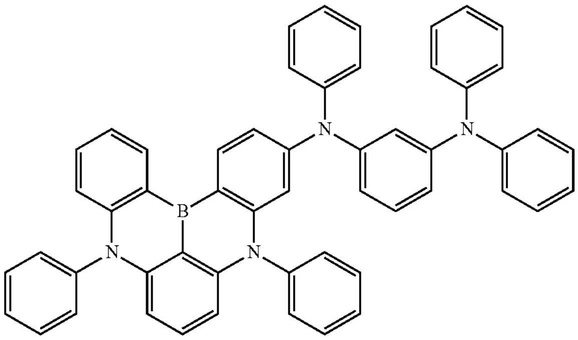
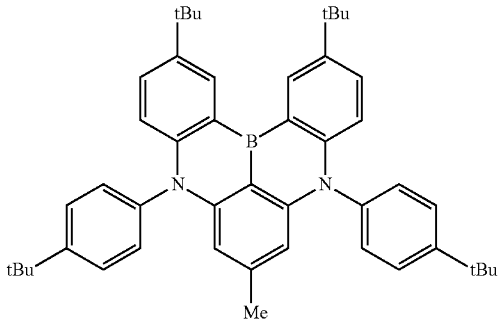 [SMILES: Cc1cc2c3c(c1)N(c1ccc(C(C)(C)C)cc1)c1ccc(C(C)(C)C)cc1B3c1cc(C(C)(C)C)ccc1N2c1ccc(C(C)(C)C)cc1]
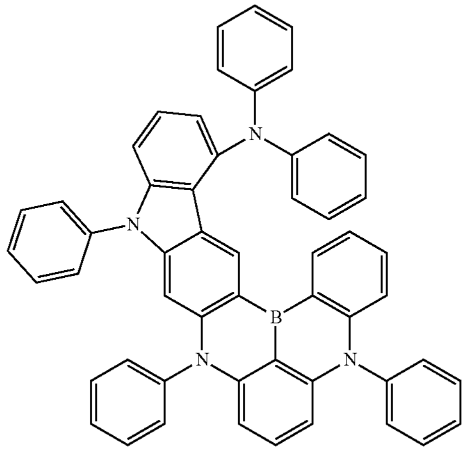
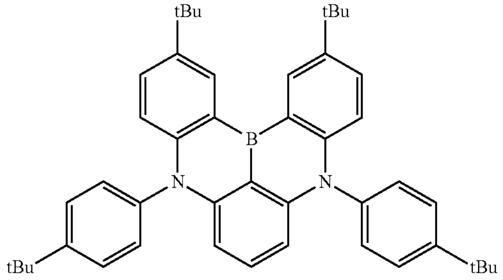
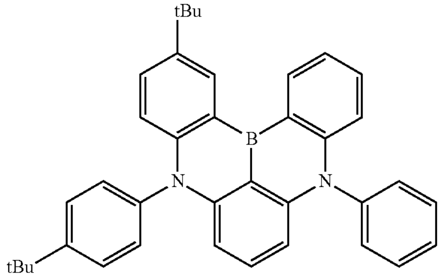

-continued
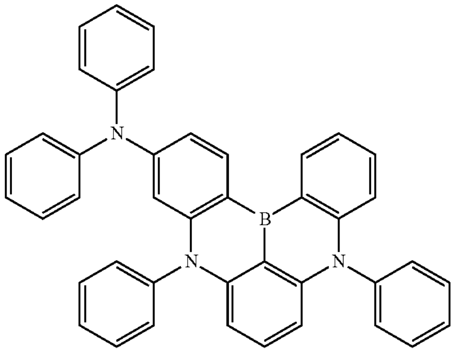
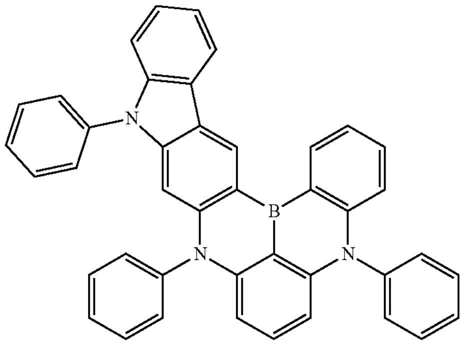
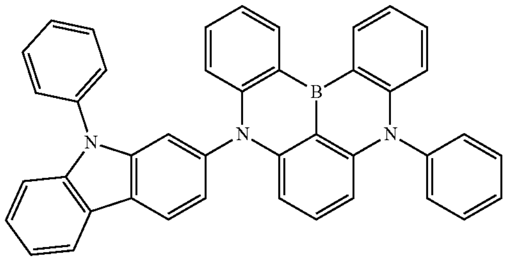
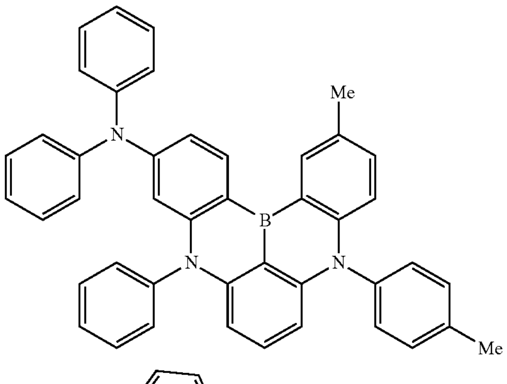
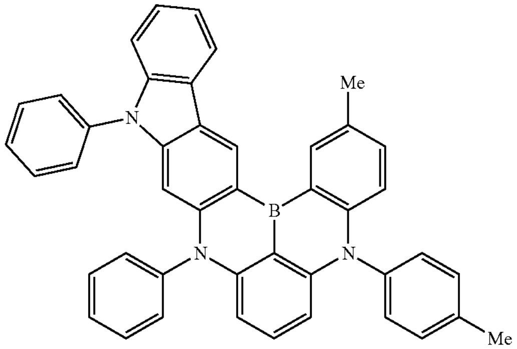
-continued
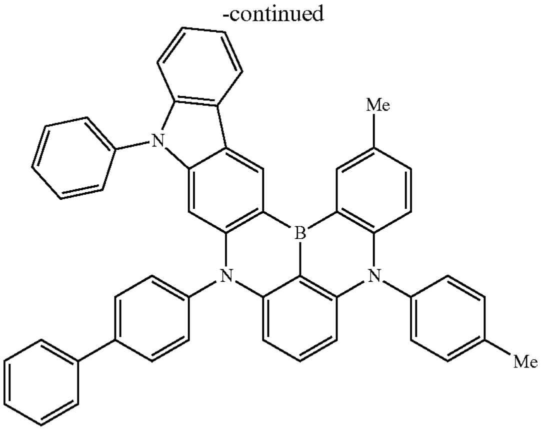
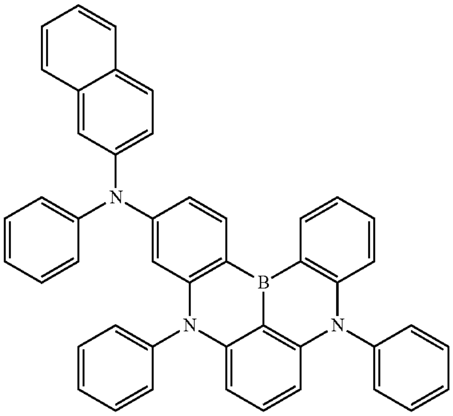
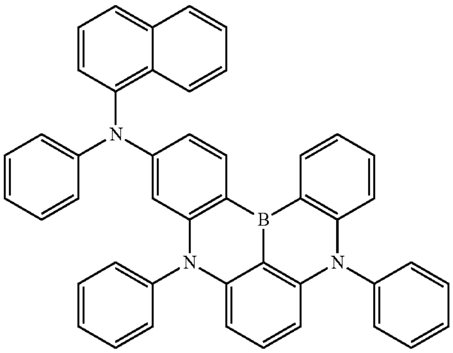
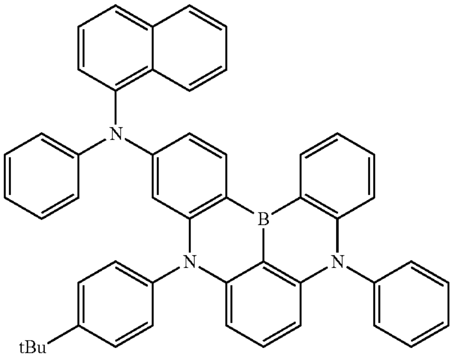

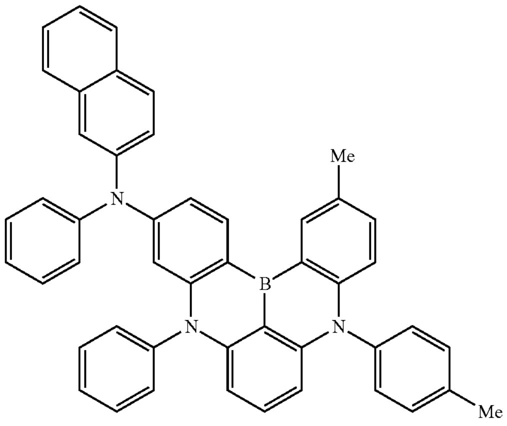
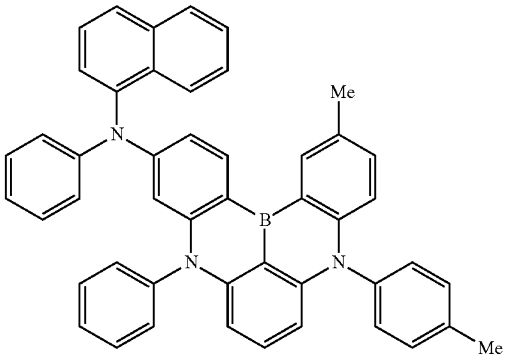
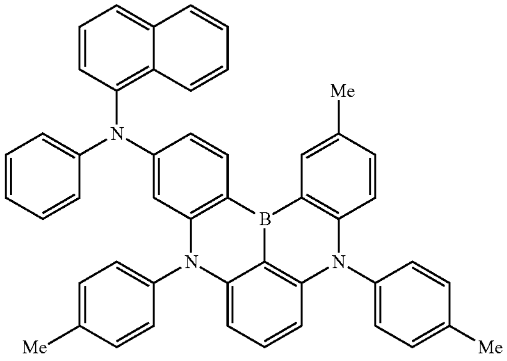
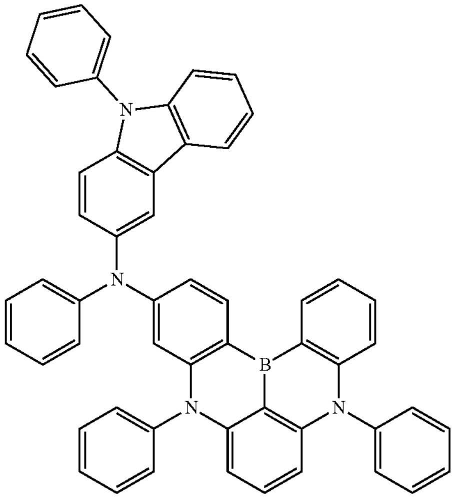
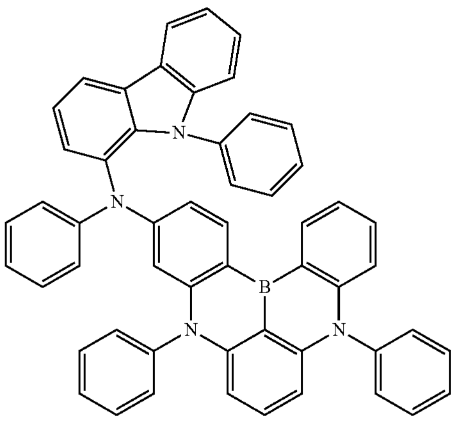
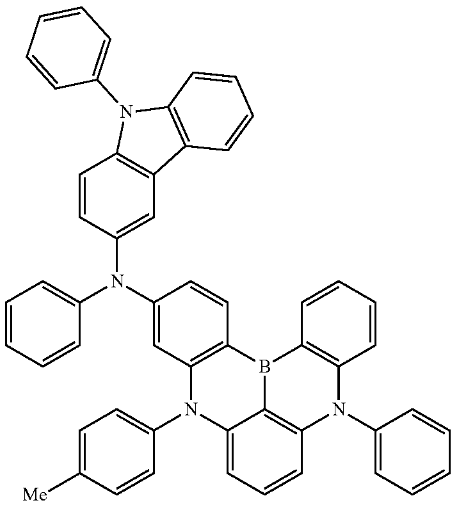
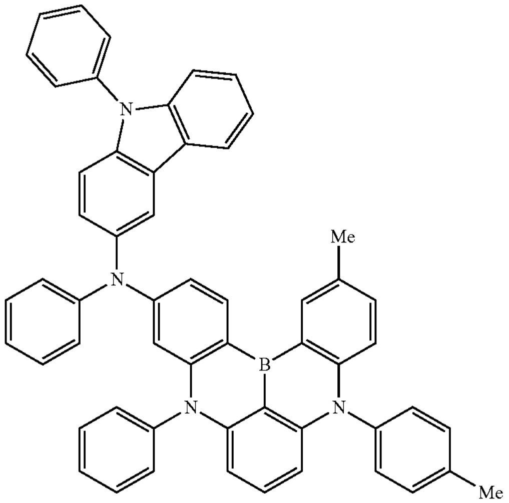

-continued
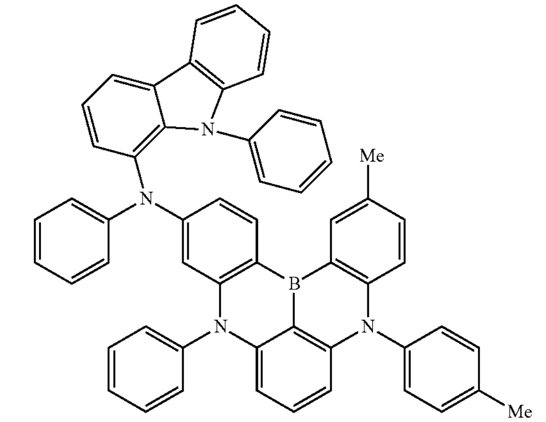
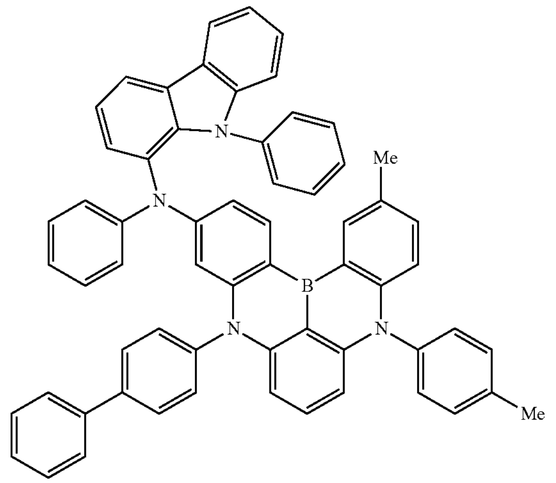
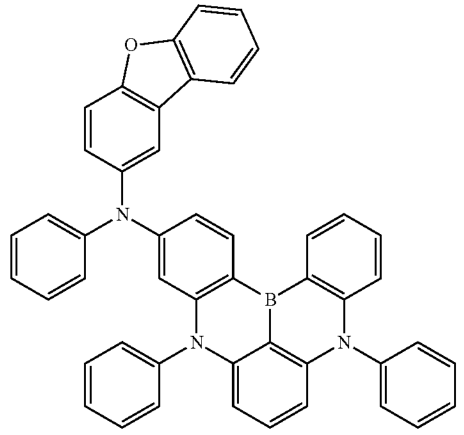
-continued
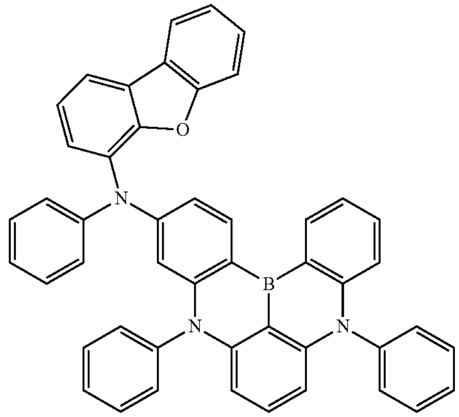
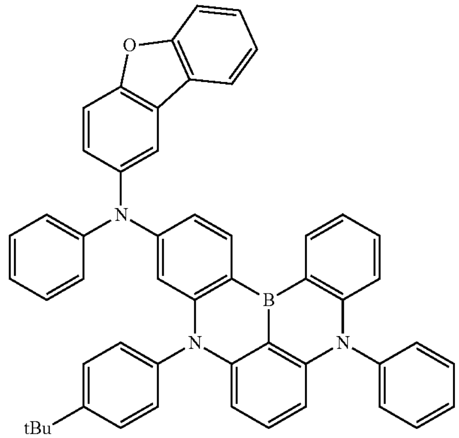
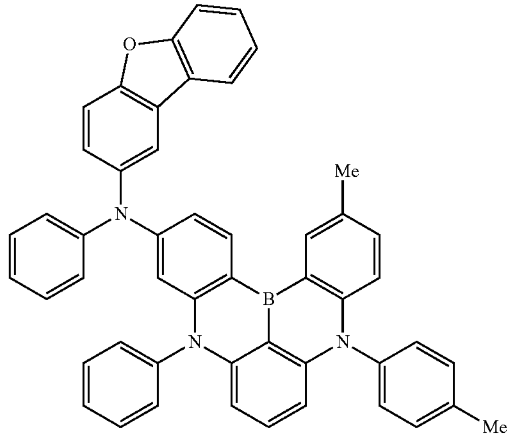
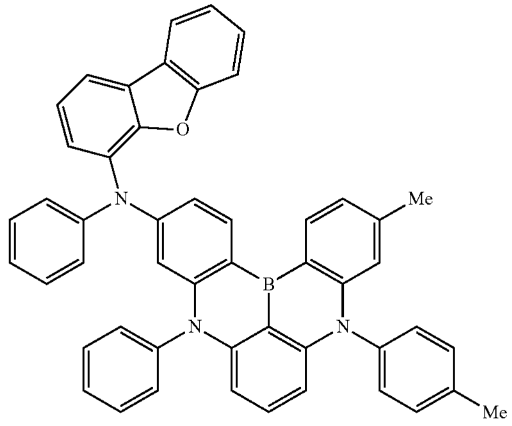

-continued
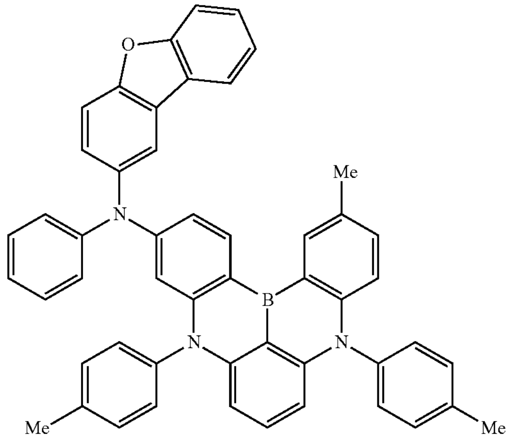
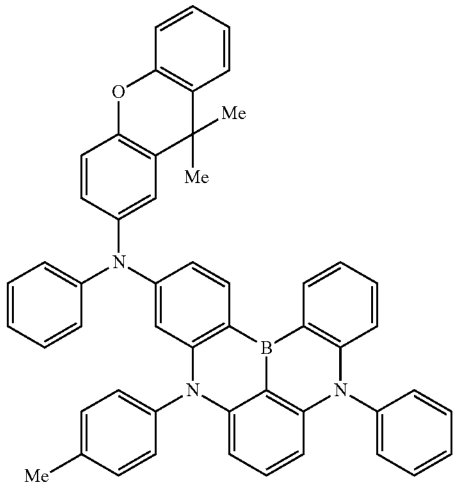
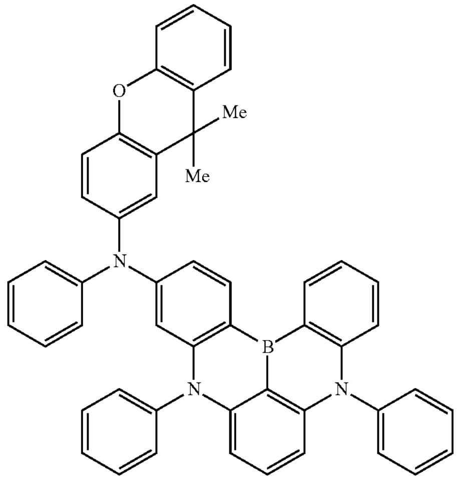
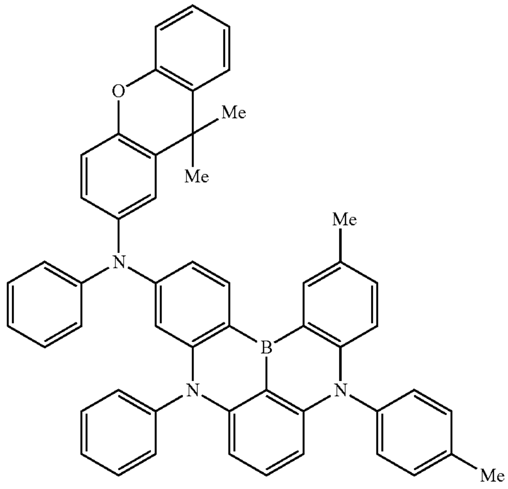
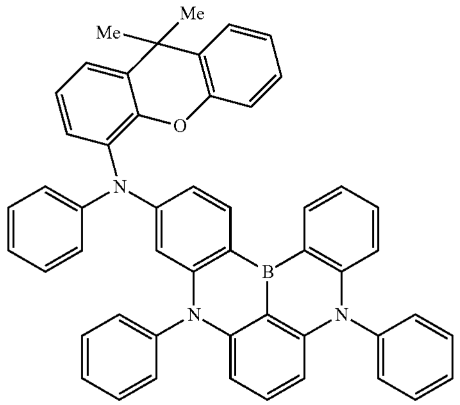
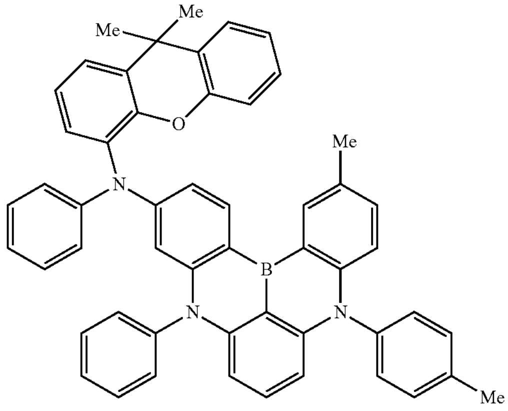
-continued -continued
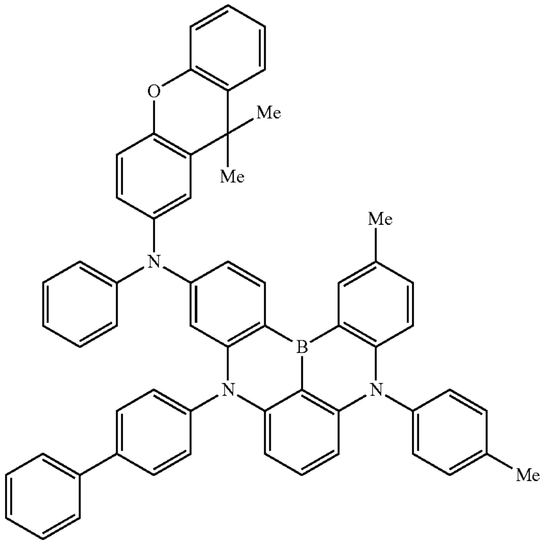
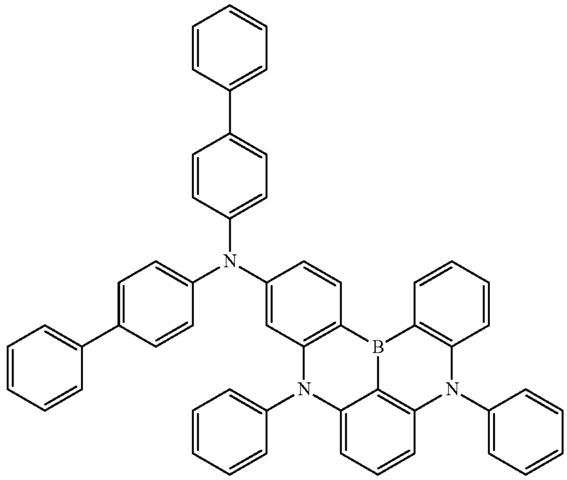
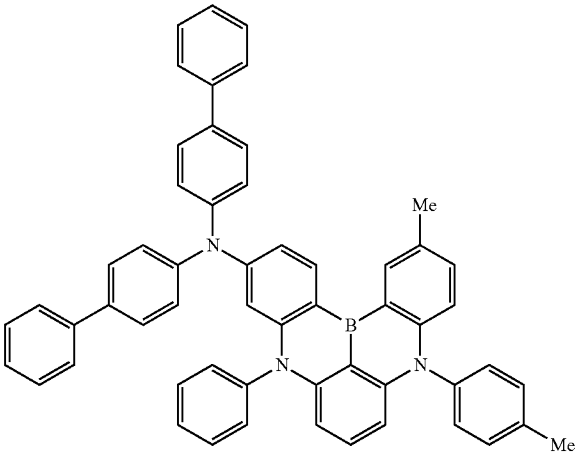
-continued
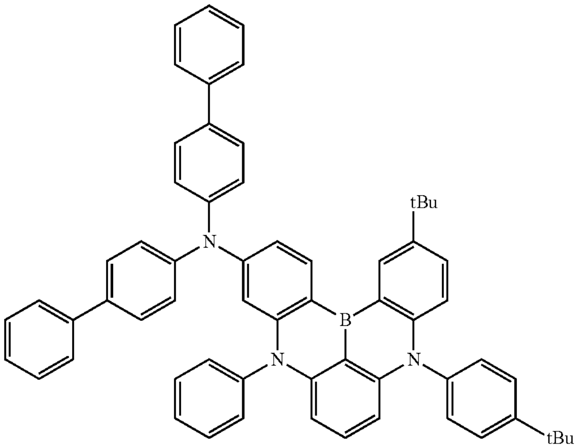
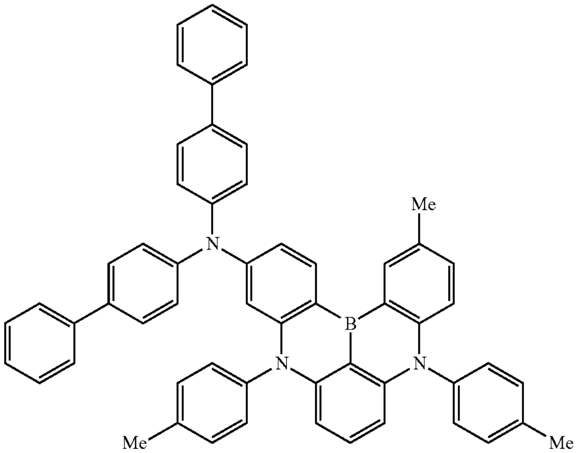 [SMILES: Cc1ccc(N2c3ccc(C)cc3B3c4ccc(N(c5ccc(-c6ccccc6)cc5)c5ccc(-c6ccccc6)cc5)cc4N(c4ccc(C)cc4)c4cccc2c43)cc1]
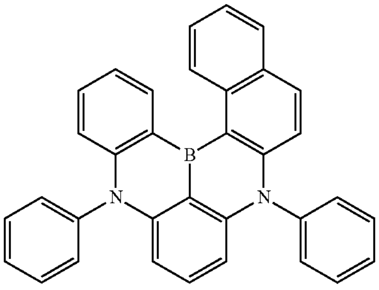
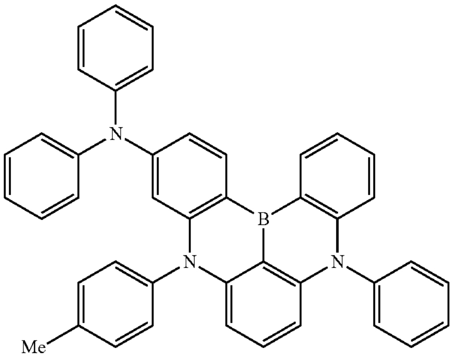

-continued
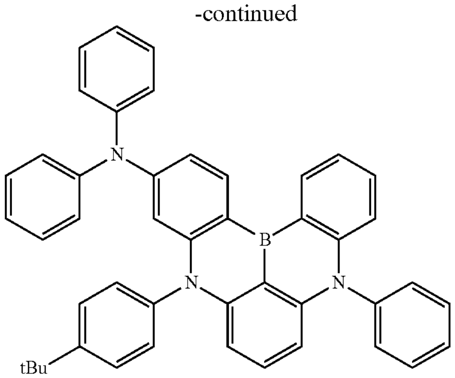
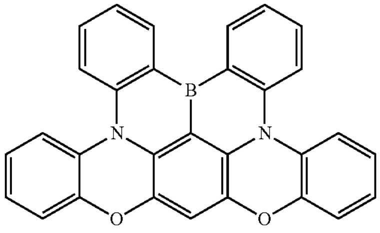
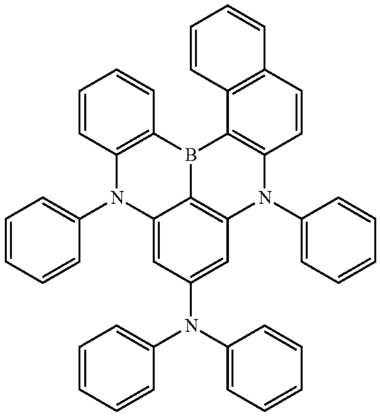
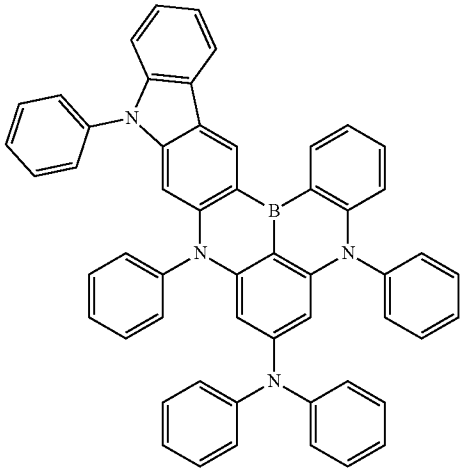
-continued
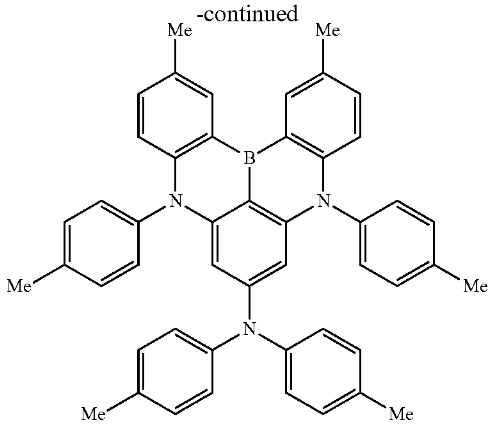
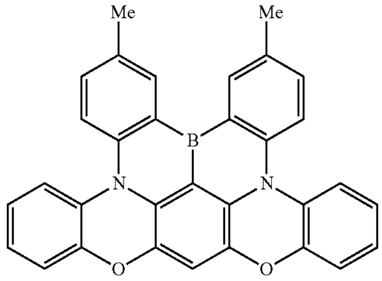
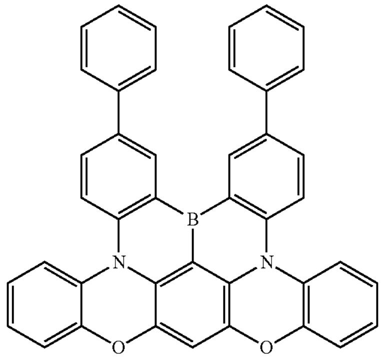
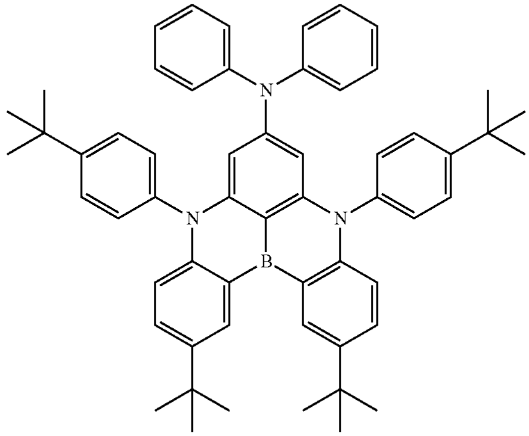

-continued
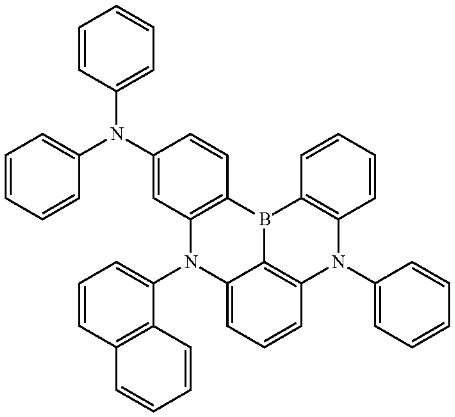
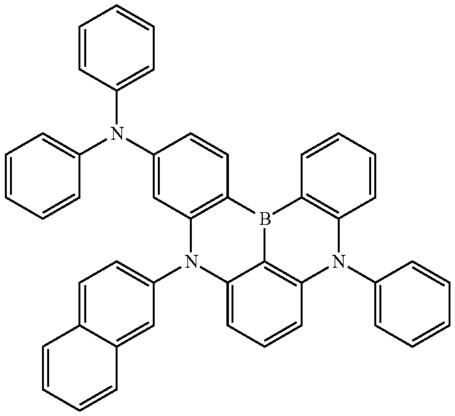
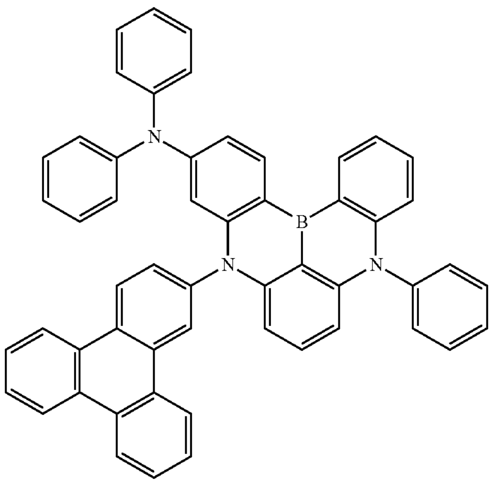
-continued
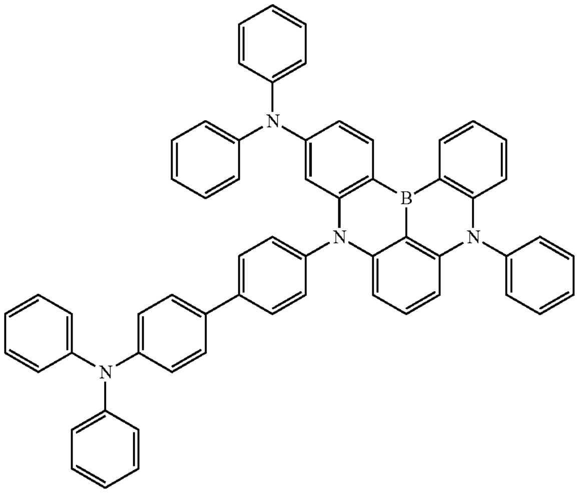
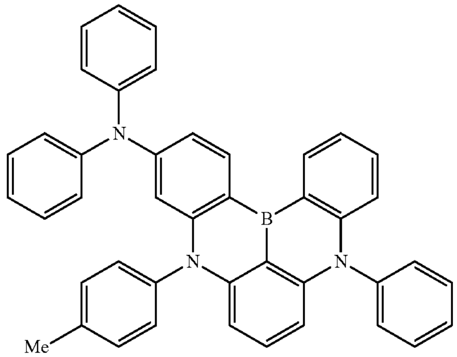
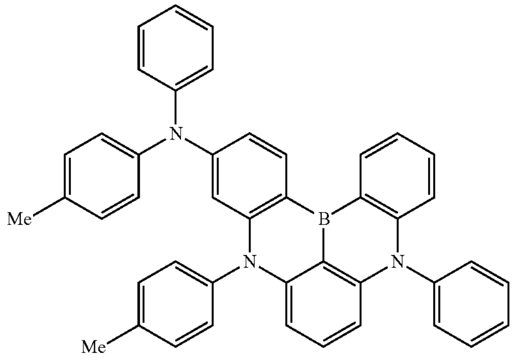
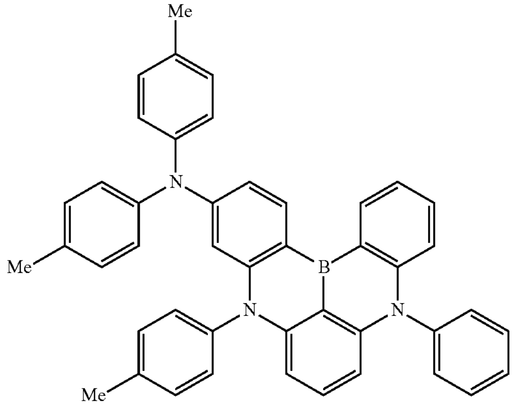

-continued
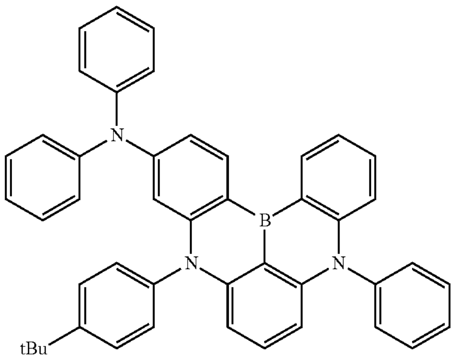
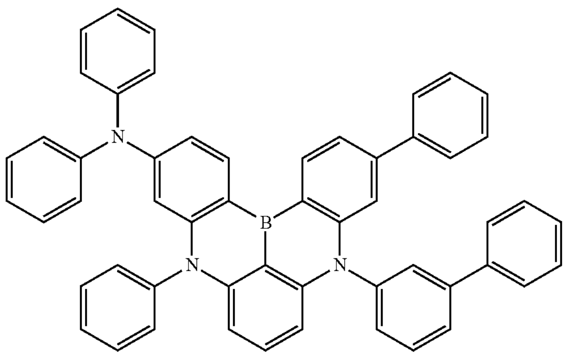
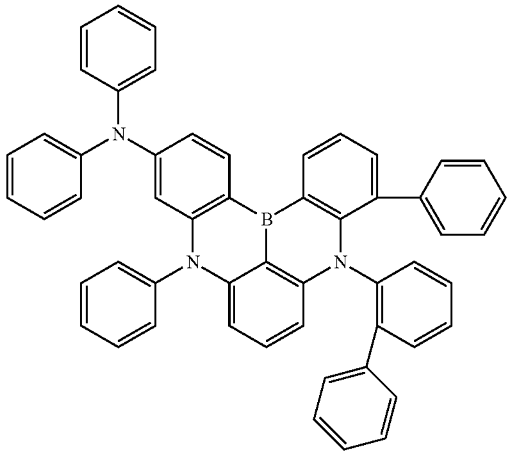
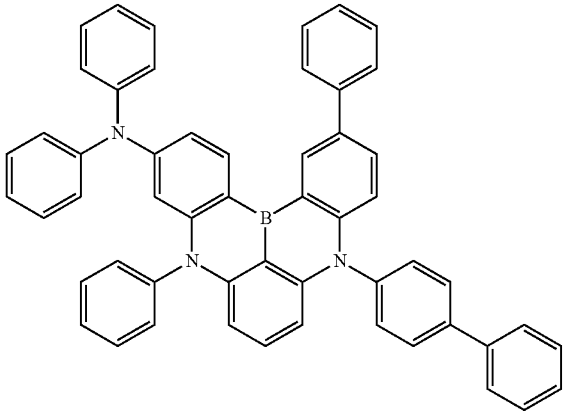
-continued
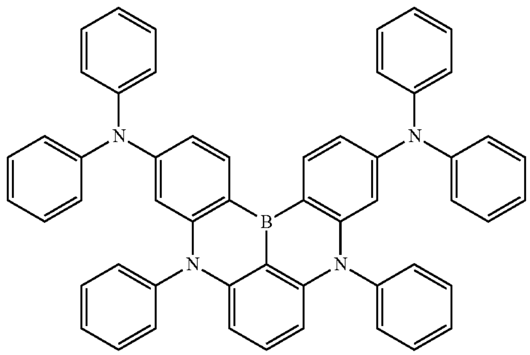
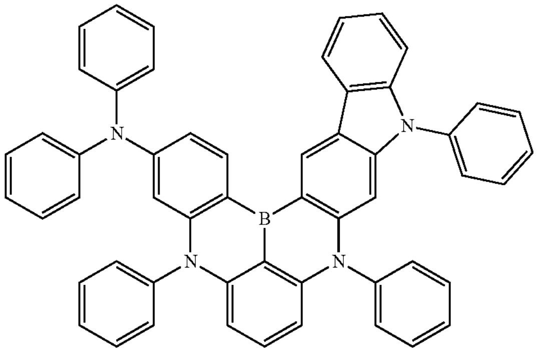
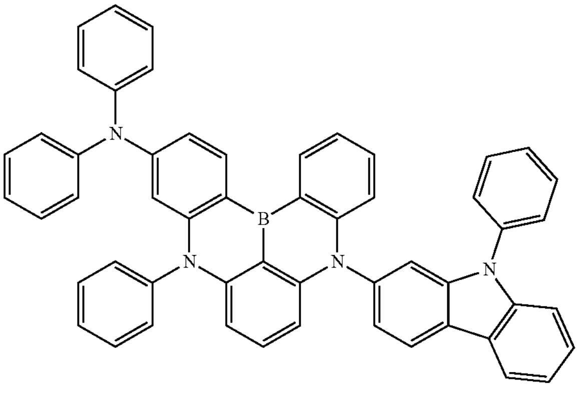
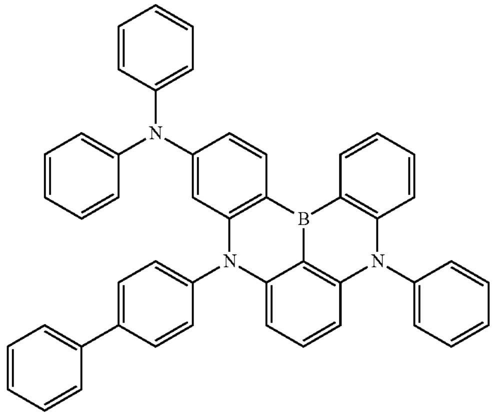

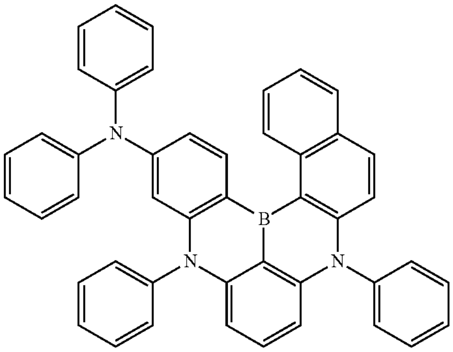
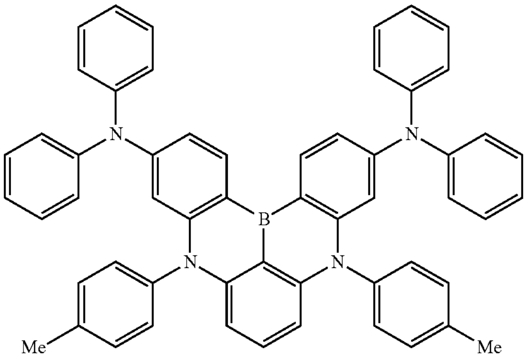
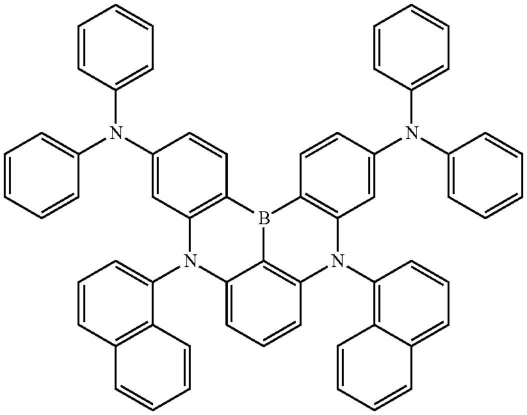
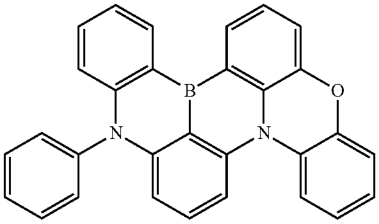
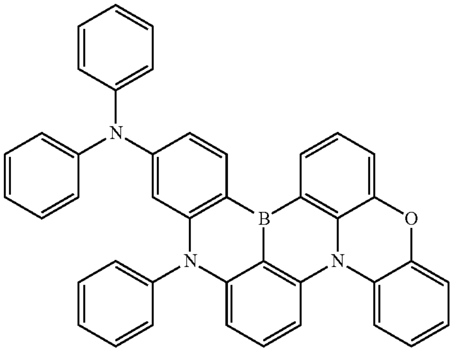
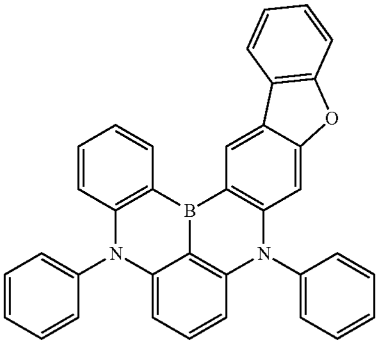
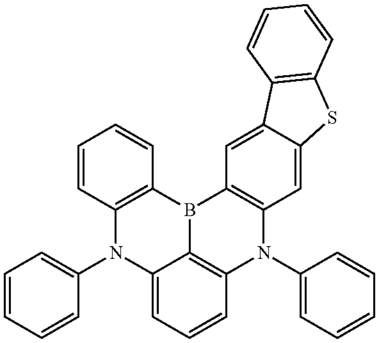
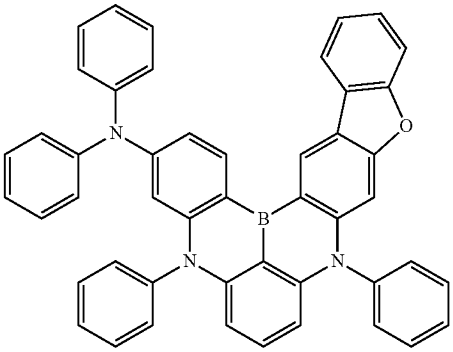
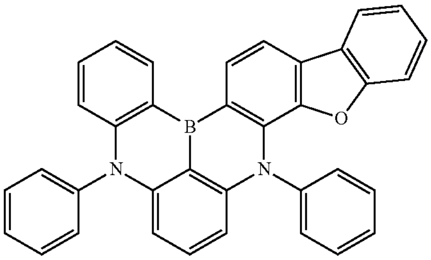
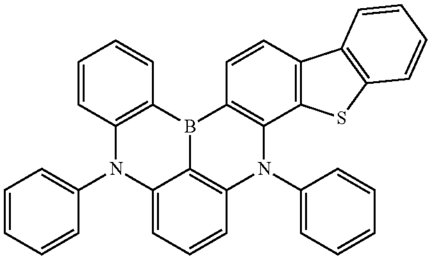

-continued

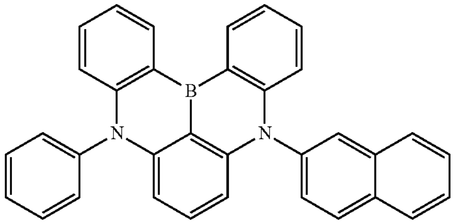

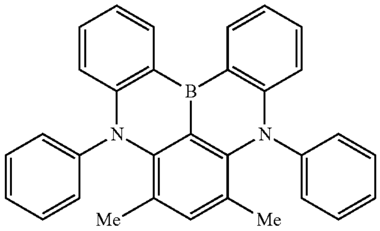

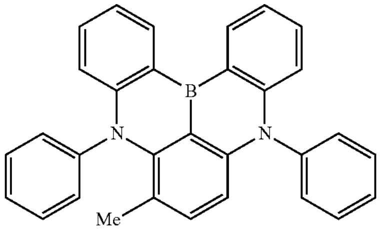

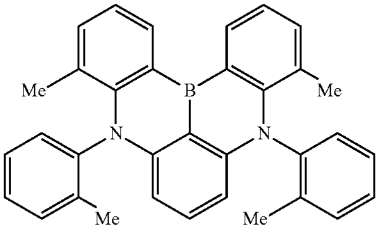

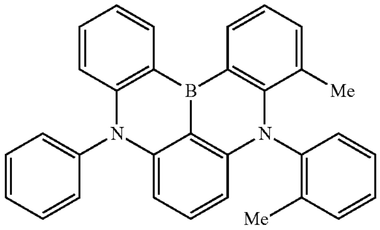

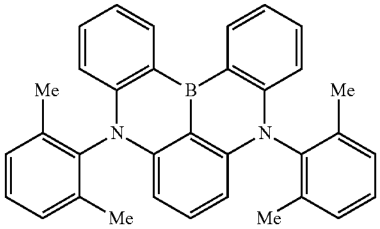

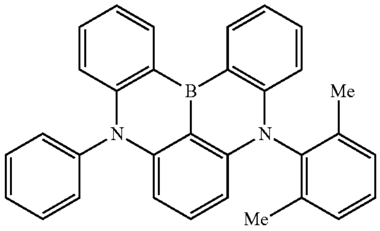

In the organic EL device according to the exemplary embodiment, a singlet energy $S_1$(H2) of the second host material and a singlet energy $S_1$(D2) of the second dopant material preferably satisfy a relationship represented by a numerical formula (Numerical Formula 20).

$$S_1(H2)>S_1(D2) \quad \text{(Numerical Formula 20)}$$

When the second host material and the second dopant material satisfy the relationship of the numerical formula (Numerical formula 20), singlet excitons generated on the second host material easily energy-transfer from the second host material to the second dopant material, thereby contributing to emission (preferably fluorescence) of the second dopant material.

In the organic EL device according to the exemplary embodiment, a triplet energy $T_1$(H2) of the second host material and a triplet energy $T_1$(D2) of the second dopant material preferably satisfy a relationship represented by a numerical formula (Numerical Formula 20A) below.

$$T_1(D2)>T_1(H2) \quad \text{(Numerical Formula 20A)}$$

When the second host material and the second dopant material satisfy the relationship represented by the numerical formula (Numerical Formula 20A), triplet excitons generated in the second emitting layer transfer not onto the second dopant material having higher triplet energy but onto the second host material, resulting in easy transfer to the first emitting layer.

In the organic EL device according to the exemplary embodiment, the second emitting layer contains the second dopant material preferably at 0.5 mass % or more, more preferably at more than 1.1 mass %, further preferably at 1.2 mass % or more, still further preferably at 1.5 mass % or more with respect to the total mass of the second emitting layer.

The second emitting layer contains the second dopant material preferably at 10 mass % or less, more preferably at 7 mass % or less, further preferably at 5 mass % or less with respect to the total mass of the second emitting layer.

In the organic EL device according to the exemplary embodiment, the second emitting layer contains the second host material preferably at 60 mass % or more, more preferably at 70 mass % or more, further preferably at 80 mass % or more, still further preferably at 90 mass % or more, still further preferably at 95 mass % or more, with respect to the total mass of the second emitting layer.

The second emitting layer preferably includes the second host material of 99 mass % or less with respect to a total mass of the second emitting layer.

When the second emitting layer contains the second host material and the second dopant material, the upper limit of a total content ratio of the second host material and the second dopant material is 100 mass %.

It is not excluded that the second emitting layer of the exemplary embodiment further contains a material(s) other than the second host material and the second dopant material.

The second emitting layer may include a single type of the second host material or may include two or more types of the second host material. The second emitting layer may include a single type of the second dopant material or may include two or more types of the second dopant material.

In the organic EL device according to the exemplary embodiment, a film thickness of the second emitting layer is preferably 3 nm or more, more preferably 5 nm or more. When the film thickness of the second emitting layer is 3 nm or more, the film thickness is thick enough for holes and electrons to recombine in the second emitting layer.

In the organic EL device according to the exemplary embodiment, the film thickness of the second emitting layer is preferably 15 nm or less, more preferably 10 nm or less. The film thickness of the second emitting layer being 15 nm or less is thin enough for triplet excitons to transfer to the first emitting layer.

In the organic EL device according to the exemplary embodiment, the film thickness of the second emitting layer is more preferably in a range from 3 nm to 15 nm.

Additional Layers of Organic EL Device

The organic EL device according to the exemplary embodiment may include one or more organic layers in addition to the first emitting layer and the second emitting layer. Examples of the organic layer include at least one layer selected from the group consisting of a hole injecting layer, a hole transporting layer, an emitting layer, an electron injecting layer, an electron transporting layer, a hole blocking layer, and an electron blocking layer.

For instance, the organic EL device according to the exemplary embodiment may include the anode, the second emitting layer, the first emitting layer, and the cathode in this order. However, by reversing the order of the second emitting layer and the first emitting layer, the organic EL device according to the exemplary embodiment may include the anode, the first emitting layer, the second emitting layer, and the cathode in this order. Regardless of the order of the first emitting layer and the second emitting layer, the effect obtained by layering the first emitting layer and the second emitting layer (i.e., the effect of prolonging the lifetime and the effect of improving the luminous efficiency of the device) can be expected by selecting a combination of the host materials satisfying the numerical formula (Numerical Formula 1) and containing the compound according to the first exemplary embodiment in the first emitting layer.

In the organic EL device according to the exemplary embodiment, the organic layer may consist of the first emitting layer and the second emitting layer. Alternatively, the organic layer may further include, for instance, at least one layer selected from the group consisting of a hole injecting layer, a hole transporting layer, an electron injecting layer, an electron transporting layer, a hole blocking layer, and an electron blocking layer.

It is preferable that the organic EL device according to the exemplary embodiment include the first emitting layer between the anode and the cathode, and the second emitting layer between the first emitting layer and the anode.

It is also preferable that the organic EL device according to the exemplary embodiment include the first emitting layer between the anode and the cathode, and the second emitting layer between the first emitting layer and the cathode.

It is preferable that the organic EL device according to the exemplary embodiment includes a hole transporting layer between the emitting layer and the anode.

It is preferable that the organic EL device according to the exemplary embodiment includes an electron transporting layer between the emitting layer and the cathode.

FIG. 2 schematically shows an exemplary arrangement of the organic electroluminescence device according to the fourth exemplary embodiment.

An organic EL device 1A includes the substrate 2, the anode 3, the cathode 4, and an organic layer 10A between the anode 3 and the cathode 4. The organic layer 10A includes a hole injecting layer 6, a hole transporting layer 7, a second emitting layer 52, a first emitting layer 51, an electron transporting layer 8, and an electron injecting layer 9 which are laminated on the anode 3 in this order.

FIG. 3 schematically shows another exemplary arrangement of the organic EL device according to the fourth exemplary embodiment.

An organic EL device 1B includes the substrate 2, the anode 3, the cathode 4, and an organic layer 10B between the anode 3 and the cathode 4. The organic layer 10B includes the hole injecting layer 6, the hole transporting layer 7, the first emitting layer 51, the second emitting layer 52, the electron transporting layer 8, and the electron injecting layer 9 which are laminated on the anode 3 in this order.

The invention is by no means limited to the arrangements of the organic EL device shown in FIGS. 2 and 3.

Third Emitting Layer

The organic EL device according to the exemplary embodiment may further include a third emitting layer.

It is preferable that the third emitting layer contains a third host material, the first host material, the second host material, and the third host material are mutually different, the third emitting layer at least contains a third dopant material, the first dopant material, the second dopant material, and the third dopant material are mutually the same or different, and the triplet energy $T_1$(H2) of the second host material and a triplet energy $T_1$(H3) of the third host material satisfy a relationship of a numerical formula (Numerical Formula 5) below.

$$T_1(H2)>T_1(H3) \quad \text{(Numerical Formula 5)}$$

The third dopant material is preferably a compound that emits light having the maximum peak wavelength of 500 nm or less, more preferably a compound that emits fluorescence having the maximum peak wavelength of 500 nm or less.

When the organic EL device according to the exemplary embodiment includes the third emitting layer, the triplet energy $T_1$(H1) of the first host material and the triplet energy $T_1$(H3) of the third host material preferably satisfy a relationship of a numerical formula (Numerical Formula 6).

$$T_1(H1)>T_1(H3) \quad \text{(Numerical Formula 6)}$$

The third host material is not particularly limited. However, for instance, the host material exemplified as the first host material and the second host material in the exemplary embodiment can be used.

The third dopant material is not particularly limited. However, for instance, the dopant material exemplified as the first dopant material and the second dopant material in the exemplary embodiment can be used.

In the organic EL device of the exemplary embodiment, the first emitting layer and the second emitting layer are preferably in direct contact with each other.

Herein, a layer arrangement in which the first emitting layer and the second emitting layer are in direct contact with each other can also encompass one of embodiments (LS1), (LS2) and (LS3) below.

(LS1) An embodiment in which a region containing both the first host material and the second host material in a mixed manner is generated in a process of vapor-depositing the compound of the first emitting layer and vapor-depositing the compound of the second emitting layer, and is present on the interface between the first emitting layer and the second emitting layer.

(LS2) An embodiment in which, when the first emitting layer and the second emitting layer each contain a luminescent compound (dopant material), a region containing the first host material, the second host material, and the luminescent compound in a mixed manner is generated in a process of vapor-depositing the compound of the first emitting layer and vapor-depositing the compound of the second emitting layer, and is present on the interface between the first emitting layer and the second emitting layer.

(LS3) An embodiment in which, when the first emitting layer and the second emitting layer each contain a luminescent compound, a region formed of the luminescent compound, a region formed of the first host material, or a region formed of the second host material is generated in a process of vapor-depositing the compound of the first emitting layer and vapor-depositing the compound of the second emitting layer, and is present on the interface between the first emitting layer and the second emitting layer.

When the organic EL device according to the exemplary embodiment includes the third emitting layer, it is preferable that the first emitting layer is in direct contact with the second emitting layer and the first emitting layer is in direct contact with the third emitting layer.

Herein, the layer structure in which "the first emitting layer is in direct contact with the third emitting layer" can also encompass, for instance, one of the following embodiments (LS4), (LS5) and (LS6).

(LS4) An embodiment in which a region containing both the first host material and the third host material in a mixed manner is generated in a process of vapor-depositing the compound of the first emitting layer and vapor-depositing the compound of the third emitting layer, and is present on the interface between the first emitting layer and the third emitting layer.

(LS5) An embodiment in which, when the first emitting layer and the third emitting layer each contain a luminescent compound (dopant material), a region containing the first host material, the third host material, and the luminescent compound in a mixed manner is generated in a process of vapor-depositing the compound of the first emitting layer and vapor-depositing the compound of the third emitting layer, and is present on the interface between the first emitting layer and the third emitting layer.

(LS6) An embodiment in which, when the first emitting layer and the third emitting layer each contain a luminescent compound, a region formed of the luminescent compound, a region formed of the first host material, or a region formed of the third host material is generated in a process of vapor-depositing the compound of the first emitting layer and vapor-depositing the compound of the third emitting layer, and is present on the interface between the first emitting layer and the third emitting layer.

When the organic EL device according to the exemplary embodiment includes an interposed layer, the interposed layer is preferably disposed between the first emitting layer and the second emitting layer.

The interposed layer is preferably a non-doped layer. The interposed layer is preferably a layer not containing a luminescent compound (dopant material). The interposed layer preferably does not contain a metal atom.

The interposed layer contains an interposed-layer material. The interposed-layer material is preferably not a luminescent compound.

The interposed-layer material is not particularly limited, however, preferably a material other than the luminescent compound.

Examples of the interposed-layer material include: 1) a heterocyclic compound such as an oxadiazole derivative, benzimidazole derivative, or phenanthroline derivative; 2) a fused aromatic compound such as a carbazole derivative, anthracene derivative, phenanthrene derivative, pyrene derivative or chrysene derivative; and 3) an aromatic amine compound such as a triarylamine derivative or a fused polycyclic aromatic amine derivative.

The interposed-layer material may be one or both of the first host material contained in the first emitting layer and the second host material contained in the second emitting layer.

When the interposed layer contains a plurality of interposed-layer materials, a content ratio of each interposed-layer material is preferably 10 mass % or more with respect to a total mass of the interposed layer.

The interposed layer contains the interposed-layer material preferably at 60 mass % or more, more preferably at 70 mass % or more, further preferably at 80 mass % or more, still further preferably at 90 mass % or more, still further preferably at 95 mass % or more, with respect to the total mass of the interposed layer.

The interposed layer may include a single type of the interposed-layer material or may include two or more types of the interposed-layer material.

When the interposed layer contains two or more interposed-layer materials, an upper limit of a total content ratio of the two or more interposed-layer materials is 100 mass %.

It is not excluded that the interposed layer in the organic EL device according to the fourth exemplary embodiment further contains a material(s) other than the interposed-layer material.

The interposed layer may be a single layer or a laminate of two or more layers.

A film thickness of the interposed layer is not particularly limited, however preferably in a range from 3 nm to 15 nm, more preferably from 5 nm to 10 nm per layer.

An arrangement of an organic EL device will be described. This arrangement is common to the organic EL devices according to the third and fourth exemplary embodiments. It should be noted that the reference numerals will be sometimes omitted below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, a mixture thereof, or the like having a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N, N'-bis(4-butylphenyl)-N, N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specifically, aromatic amine compounds such as 4,4'-bis[N-(1-naphthyl)-N-phenylamino]biphenyl (abbreviation: NPB), N, N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB) are usable. The above-described substances mostly have a hole mobility of $10^{-6}$ $cm^2/(V \cdot s)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

Electron Transporting Layer

It is preferable that the organic EL device according to the exemplary embodiment includes an electron transporting layer between the emitting layer and the cathode.

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the exemplary embodiment, a benzimidazole compound is suitably usable. The above-described substances mostly have an electron mobility of $10^{-6}$ $cm^2/Vs$ or more. It should be noted that any substance other than the above substance may be used for the electron transporting layer as long as the substance exhibits a higher electron transportability than the hole transportability. The electron transporting layer may be a single layer or a laminate of two or more layers formed of the above substance.

Further, a high polymer compound is usable for the electron transporting layer. For instance, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. The composite material exhibits excellent electron injecting performance and electron transporting performance since the electron donor generates electrons in the organic compound. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

A film thickness of each of the organic layers of the organic EL device in the exemplary embodiment is not limited unless otherwise specified in the above. In general, the thickness preferably ranges from several nanometers to 1 μm because excessively small film thickness is likely to cause defects (e.g. pin holes) and excessively large thickness leads to the necessity of applying high voltage and consequent reduction in efficiency.

Fifth Exemplary Embodiment

Electronic Device

An electronic device according to a fifth exemplary embodiment is installed with any one of the organic EL devices according to the above exemplary embodiments. Examples of the electronic device include a display device and a light-emitting device. Examples of the display device include a display component (e.g., an organic EL panel module), TV, mobile phone, tablet and personal computer. Examples of the light-emitting unit include an illuminator and a vehicle light.

Modification of Exemplary Embodiment(s)

The scope of the invention is not limited by the above-described exemplary embodiments but includes any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the organic layers satisfies the conditions described in the above exemplary embodiments and it is preferable that at least one of the emitting layers contains the compound of the first exemplary embodiment. When one of the plurality of the emitting layers contains the compound of the first exemplary embodiment, for instance, the rest of the emitting layers may be fluorescent emitting layers, or phosphorescent emitting layers with use of emission caused by electron transfer from the triplet state directly to the ground state.

When the organic EL device includes a plurality of emitting layers, these emitting layers may be mutually adjacently provided, or may form a so-called tandem organic EL device, in which a plurality of emitting units are layered via an intermediate layer.

For instance, a blocking layer may be provided adjacent to at least one of a side of the emitting layer close to the anode or a side of the emitting layer close to the cathode. The blocking layer is preferably provided in contact with the emitting layer to block at least any of holes, electrons, excitons or combinations thereof.

For instance, when the blocking layer is provided in contact with the side of the emitting layer close to the cathode, the blocking layer permits transport of electrons and blocks holes from reaching a layer provided closer to the cathode (e.g., the electron transporting layer) than the blocking layer. When the organic EL device includes the electron transporting layer, the blocking layer is preferably interposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) than the blocking layer. When the organic EL device includes the hole transporting layer, the blocking layer is preferably interposed between the emitting layer and the hole transporting layer.

Alternatively, the blocking layer may be provided adjacent to the emitting layer so that excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) than the blocking layer.

The emitting layer is preferably bonded with the blocking layer.

Specific structure, shape and the like of the components in the invention may be designed in any manner as long as an object of the invention can be achieved.

EXAMPLES

The invention will be described in further detail with reference to Example(s). It should be noted that the scope of the invention is by no means limited to Examples.

Compounds

Structures of a compound having a cyclic structure represented by the formula (1) and a cyclic structure represented by the formula (10) in a molecule are shown below as a compound in Example 1 and a compound used for manufacturing an organic EL device in Example 1A.

BD-1

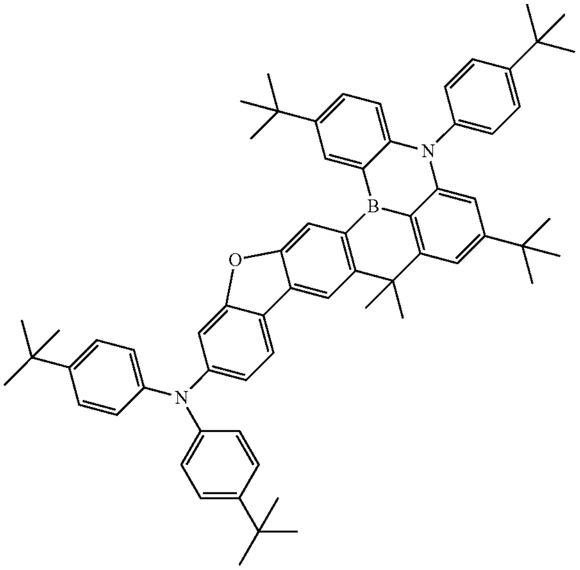

-continued

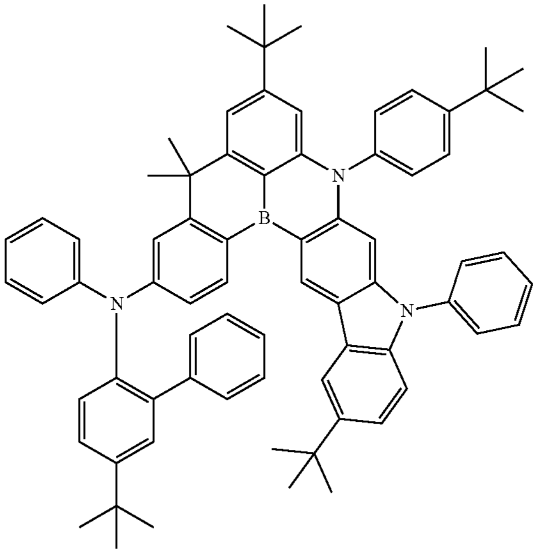

Structures of other compounds used for manufacturing the organic EL device in Example 1A are shown below.

HI

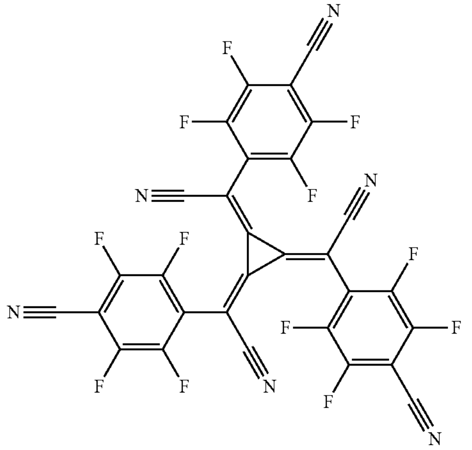

HT-1

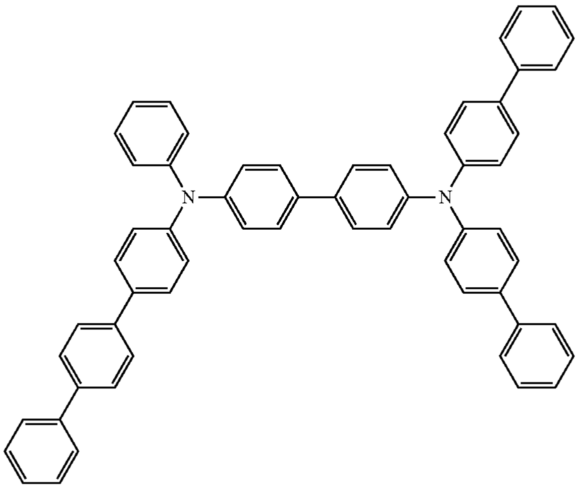

-continued

HT-2

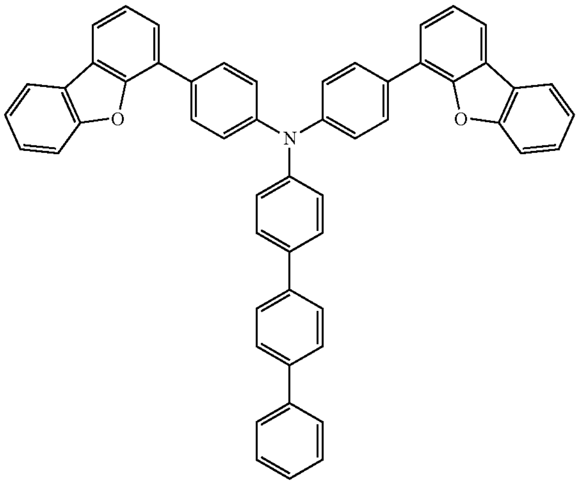

BH-1

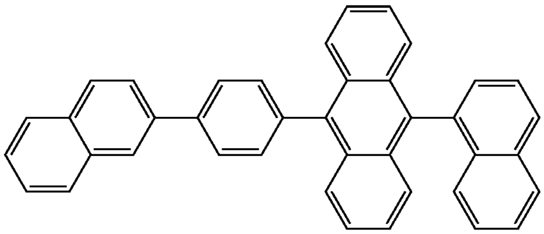

ET-1

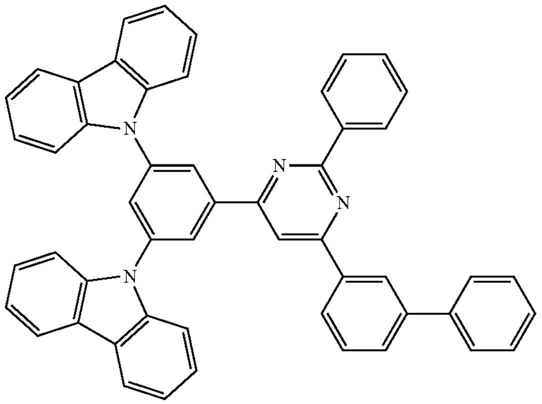

ET-2

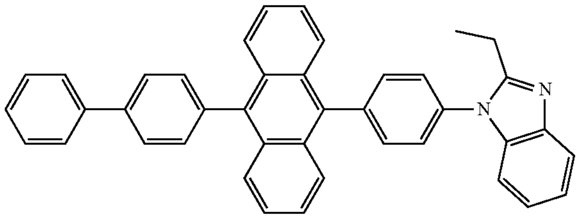

Structures of comparative compounds in Comparatives 1 and 2 are shown below.

Ref-1

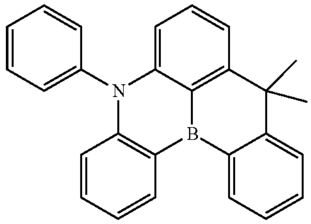

Ref-2

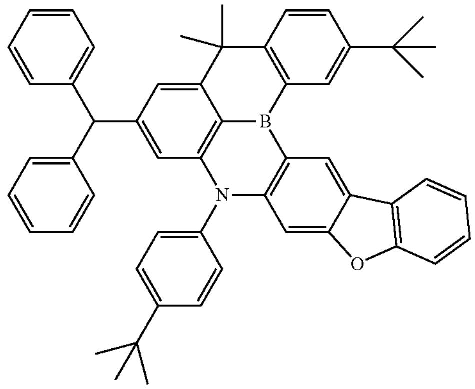

Evaluation of Compounds

Measurement of Maximum Fluorescence Peak Wavelength

A compound BD-1 was dissolved in toluene to prepare a solution of $5.0\times10^{-6}$ mol/L. The obtained solution was put into a quartz cell (optical path length: 1.0 cm). The maximum fluorescence peak wavelength when the solution was excited at 400 nm was measured using a fluorescence spectrum measurement device "fluorospectrophotometer FP-8300" (manufactured by JASCO Corporation). Measurement results are shown in Table 1.

Measurement of Photoluminescence Quantum Yield

The measurement target compound BD-1 was dissolved in toluene to prepare a solution of $5.0\times10^{-6}$ mol/L. The solution was then frozen and deaerated to prepare an argon saturated solution. The obtained solution was transferred to a quartz cell (optical path length: 1.0 cm). A photoluminescence quantum yield (PLQY) was measured using an absolute PL quantum yield measurement device "Hamamatsu Quantaurus-QY C11347" (manufactured by Hamamatsu Photonics Co., Ltd.). Measurement results are shown in Table 1.

Lowest Singlet Energy Level

Regarding the compound BD-1, a comparative compound Ref-1, and a comparative compound Ref-2, the lowest singlet energy level (S1 energy level) was calculated by TD-DFT calculation using B3LYP as hybrid functional and 6-31 g* as a basis function. All calculations were implemented using the Gaussian 16 software program available from Gaussian Inc. Results are shown in Table 1.

TABLE 1

| | Compound | PLQY (%) | Maximum Fluorescence Peak Wavelength (nm) | S1 Energy Level (eV) |
|---|---|---|---|---|
| Example 1 | BD-1 | 91 | 452 | 2.900 |
| Comparative 1 | Ref-1 | — | — | 3.292 |
| Comparative 2 | Ref-2 | — | — | 3.103 |

As shown in Table 1, the maximum fluorescence peak wavelength of the compound BD-1 in Example 1 is 452 nm. In contrast, the comparative compound Ref-1 in Comparative 1 and the comparative compound Ref-2 in Comparative 2, which are estimated to have higher S1 energy level than the compound BD-1 in Example 1, has an emission wavelength close to the short-wavelength side with respect to a blue emission wavelength (from 445 nm to 465 nm) suitable for display usage. Therefore, the comparative compound Ref-1 and the comparative compound Ref-2 are not suitable for being used as a material of an organic EL device for display usage.

Preparation of Organic EL Device

The organic EL devices were prepared and evaluated as follows.

Example 1A

A glass substrate (manufactured by Geomatec Co., Ltd.) having an Indium Tin Oxide (ITO) transparent electrode having a 130-nm thickness was used as an anode. This glass substrate having the ITO transparent electrode was cleaned with nitrogen plasma for 100 seconds. This treatment also improved hole injectability of ITO.

The cleaned glass substrate was attached to a substrate holder and transported into a vacuum vapor deposition apparatus.

Subsequently, a compound HT-1 and a compound HI were co-deposited on a surface of the ITO transparent electrode under pressure in a range from $10^{-8}$ mbar to $10^{-8}$ mbar at a deposition speed in a range from 0.2 Å/second to 1 Å/second, so that a 10-nm-thick hole injecting layer was formed. The compound HT-1 and the compound HI accounted in ratio for 97 mass % and 3 mass %, respectively, in the hole injecting layer.

Next, after the formation of the hole injecting layer, the compound HT-1 was vapor-deposited to form an 80-nm-thick first hole transporting layer.

After the formation of the first hole transporting layer, a compound HT-2 was vapor-deposited to form a 10-nm-thick second hole transporting layer.

Subsequently, a compound BH-1 (host material) and a compound BD-2 (dopant material) were co-deposited on the second hole transporting layer to form a 25-nm-thick emitting layer. The compound BH-1 and the compound BD-2 accounted in ratio for 98 mass % and 2 mass %, respectively, in the emitting layer.

A compound ET-1 was vapor-deposited on the emitting layer to form a 10-nm-thick first electron transporting layer (also referred to as a hole blocking layer).

A compound ET-2 was vapor-deposited on the first electron transporting layer to form a 15-nm-thick second electron transporting layer.

Next, lithium fluoride (LiF) was vapor-deposited on the second electron transporting layer to form a 1-nm-thick electron injecting layer.

Next, metal Al was vapor-deposited on the electron injecting layer to form a 50-nm-thick cathode.

The manufactured device was sealed with a glass cover and a desiccant under an inert nitrogen atmosphere containing water of less than 1 ppm and oxygen.

A device arrangement of the organic EL device of Example 1A is roughly shown as follows.

ITO(130)/HT-1:H1(10.97/0:3%)/HT-1(80)/HT-2(10)/BH-1:BD-2(25.98%:2%)/ET-1(10)/ET-2(15)/LiF(1)/Al(50)

Numerals in parentheses represent a film thickness (unit: nm). The numerals (97%:3%) represented by percentage in the parentheses indicate a ratio (mass %) between the compound HT-1 and the compound HI in the hole injecting layer. The numerals (98%:2%) represented by percentage in the parentheses indicate a ratio (mass %) between the host material (compound BH-1) and the dopant material (compound BD-2) in the emitting layer.

Evaluation of Organic EL Devices

The manufactured organic EL devices were evaluated as follows.

Evaluation results are shown in Table 2.

Maximum Peak Wavelength λp and Full Width at Half Maximum (FWHM) of Emission Spectrum Voltage was applied on the organic EL devices so that a current density was 10 mA/cm$^2$, where spectral radiance spectrum was measured by a spectroradiometer (CS-2000 manufactured by Konica Minolta, Inc.). The maximum peak wavelength λp (unit: nm) and a full width at half maximum (FWHM) of an emission spectrum (unit: nm) were obtained from the measured spectral radiance spectrum. FWHM is an abbreviation of full width at half maximum.

External Quantum Efficiency (EQE)

Voltage was applied on the organic EL devices so that a current density was 10 mA/cm$^2$, where spectral radiance spectrum was measured by a spectroradiometer (CS-2000 manufactured by Konica Minolta, Inc.). The external quantum efficiency EQE (unit: %) was calculated based on the obtained spectral-radiance spectra, assuming that the spectra was provided under a Lambertian radiation.

Lifetime LT95

Voltage was applied to the produced organic EL devices so that a current density was 50 mA/cm$^2$, where a time (LT95 (unit: h)) elapsed before a luminance intensity was reduced to 95% of the initial luminance intensity was measured. The luminance intensity was measured by a spectroradiometer CS-2000 (produced by Konica Minolta, Inc.).

TABLE 2

| | Emitting Layer | Evaluation | | | |
|---|---|---|---|---|---|
| | Dopant Material | EQE (%) | λ p (nm) | FMHW (eV) | LT95 (h) |
| Example 1A | BD-2 | 9.72 | 459 | 25 | 116 |

The results shown in Table 2 reveal that the organic EL device exhibits excellent performance when the compound BD-2 is used as a luminescent material (dopant material) of the organic EL device.

Synthesis Example

Synthesis of Compound BD-1

A method of synthesizing the compound BD-1 will be described below.

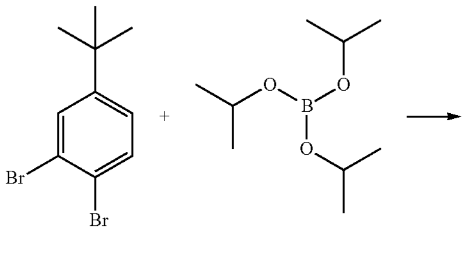

-continued

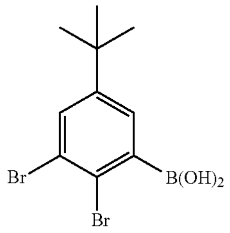

1-1

Manufacture of Intermediate 1-1

Under argon atmosphere, 2,2,6,6-tetramethyl piperidine (20.81 mL) was added to tetrahydrofuran (125 mL) and cooled to −78 degrees C., to which 2.5M n-butyl lithium pentane solution (49.3 mL) was then added dropwise. The resultant solution was stirred for 30 minutes at that temperature (−78 degrees C.), to which triisopropylborate (33.4 mL) was then added dropwise over 15 minutes. Subsequently, 50-mL tetrahydrofuran in which 1,2-bromo-4-t-butylbenzene (12.0 g) was dissolved was added dropwise to the above solution and stirred overnight for reaction. After the reaction, 1.0 N hydrochloric acid (150 mL) was added to the resultant solution, diluted with ethyl acetate, and an aqueous layer was extracted with ethyl acetate. The collected organic layer was washed with saturated saline and then dried over magnesium sulfate, and a solvent was distilled away under reduced pressure to obtain 18.3 g of a light yellow solid (yield 66%). As a result of mass spectrum analysis, this light yellow solid was a target intermediate 1-1 and had 335.02 [M−H] while a molecular weight was 335.83. This light yellow solid was used for a next reaction without being purified.

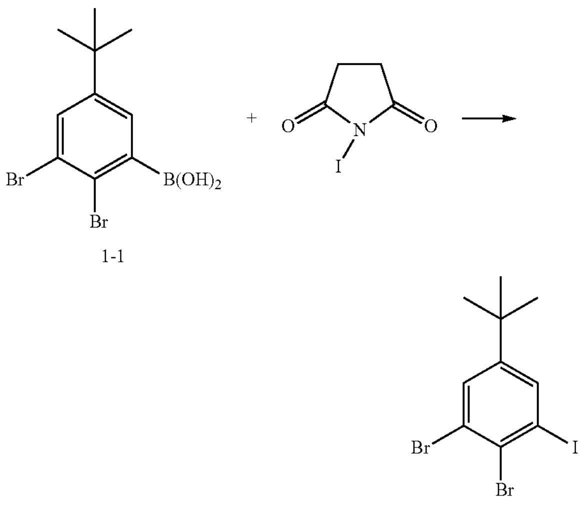

1-1

1-2

Manufacture of Intermediate 1-2

Under nitrogen atmosphere, the intermediate 1-1 (36.63 g) was suspended in acetonitrile (400 mL), to which potassium acetate (4.16 g) and N-iodosuccinimide (37.9 g) were added, and the obtained solution was stirred overnight at room temperature for reaction. A 10% aqueous sodium hydrogen sulfite solution was added to the stirred reaction solution, acetonitrile was distilled away under reduced pressure, and then the aqueous layer was extracted with ethyl acetate. The collected organic layer was washed with saturated saline and then dried over magnesium sulfate, and a solvent was distilled away under reduced pressure. The obtained residue was purified by silica-gel column chromatography to obtain 21.5 g of a white solid (yield 61%). This white solid was a target intermediate 1-2 as a result of $^{1}$H-NMR spectrum analysis.

$^{1}$H-NMR (300 MHz, $CD_2Cl_2$) δ 7.84 (d, J=2.2 Hz, 1H), 7.63 (d, J=2.2 Hz, 1H), 1.28 (s, 9H).

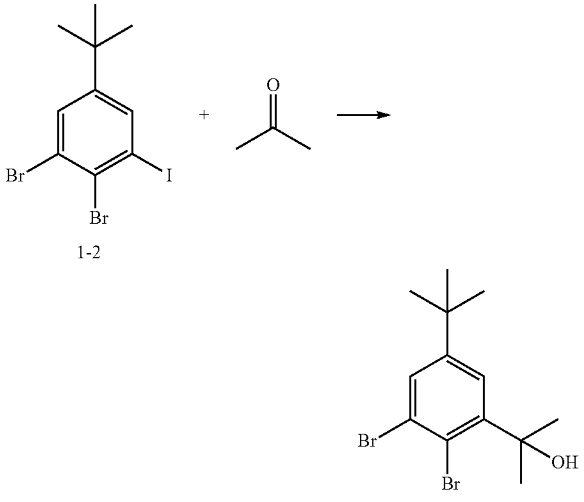

1-2

1-3

Manufacture of Intermediate 1-3

Under nitrogen atmosphere, tetrahydrofuran (93 mL) was added to the intermediate 1-2 (14 g) and cooled to −78 degrees C., to which a 2.0M isopropyl magnesium chloride tetrahydrofuran solution (17.59 mL) was then added dropwise, and the resultant solution was stirred for two hours at that temperature (−78 degrees C.). Subsequently, acetone (17.26 mL) was added to the solution over 10 minutes and the resultant solution was stirred overnight for reaction. After the stirred reaction solution was added with a saturated aqueous ammonium chloride solution, the aqueous layer was extracted with ethyl acetate. The collected organic layer was washed with saturated saline and then dried over magnesium sulfate, and a solvent was distilled away under reduced pressure. The obtained residue was purified by silica-gel column chromatography to obtain 4.22 g of a white solid (yield 36%). This white solid was a target intermediate 1-3 as a result of $^{1}$H-NMR spectrum analysis. $^{1}$H-NMR (300 MHz, DMSO-d6) δ 7.92 (d, J=2.5 Hz, 1H), 7.61 (d, J=2.4 Hz, 1H), 5.38 (s, 1H), 1.63 (s, 6H), 1.27 (s, 9H).

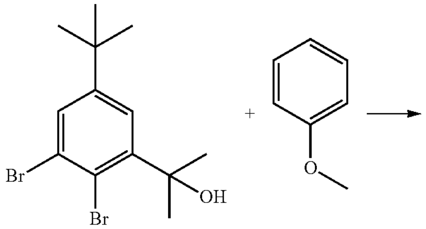

1-3

-continued

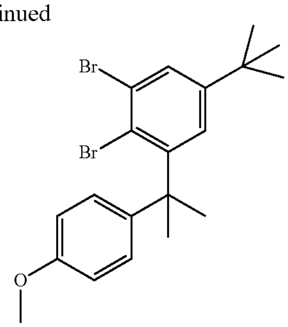

1-4

Manufacture of Intermediate 1-4

Under argon atmosphere, an intermediate 1-4 (6.9 g) and anisole (2.13 g) were added to methylene chloride (65 mL) and cooled to 0 degrees C., to which aluminum chloride (2.90 g) was then added. The resultant solution was stirred for four hours for reaction. After the stirred reaction solution was added with water, the aqueous layer was extracted with methylene chloride. The collected organic layer was washed with saturated saline, then dried over magnesium sulfate, and a solvent was distilled away under reduced pressure. The obtained residue was purified by silica-gel column chromatography to obtain 5.86 g of a white solid (yield 62%). This white solid was a target intermediate 1-4 as a result of $^{1}$H-NMR spectrum analysis.

$^{1}$H-NMR (300 MHz, $CD_2Cl_2$) δ 7.65 (d, J=2.3 Hz, 1H), 7.61 (d, J=2.3 Hz, 1H), 7.04-6.96 (m, 2H), 6.81-6.74 (m, 2H), 3.76 (s, 3H), 1.74 (s, 6H), 1.36 (s, 9H).

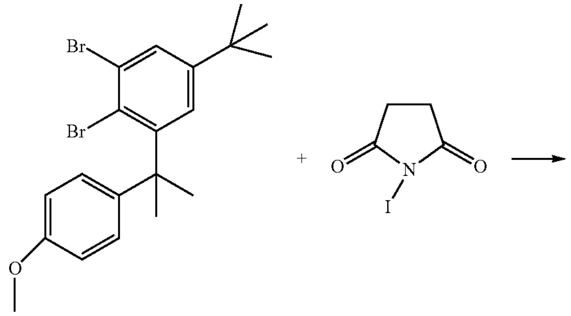

1-4

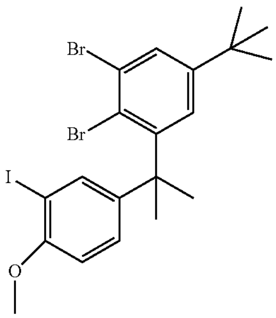

1-5

Manufacture of Intermediate 1-5

Under nitrogen atmosphere, the intermediate 1-4 (4.18 g) was suspended in acetonitrile (38 mL), to which N-iodosuccinimide (2.35 g) and trifluoroacetic acid (0.21 mL) were added, and the obtained solution was stirred overnight at room temperature for reaction. After the reaction, the resultant solution was washed with an aqueous sodium sulfite solution, diluted with toluene, and added with an aqueous sodium carbonate solution for neutralization, and the aqueous layer was then extracted with toluene. The collected organic layer was washed with saturated saline and then dried over magnesium sulfate, and a solvent was distilled away under reduced pressure. The obtained residue was purified by silica-gel column chromatography to obtain 5.07 g of a white solid (yield 92%). This white solid was a target intermediate 1-5 as a result of $^{1}$H-NMR spectrum analysis.

$^{1}$H-NMR (300 MHz, DMSO-d6) δ 7.70-7.62 (m, 2H), 7.42 (d, J=2.3 Hz, 1H), 6.97 (dd, J=8.6, 2.3 Hz, 1H), 6.88 (d, J=8.6 Hz, 1H), 3.78 (s, 3H), 1.69 (s, 6H), 1.34 (s, 9H).

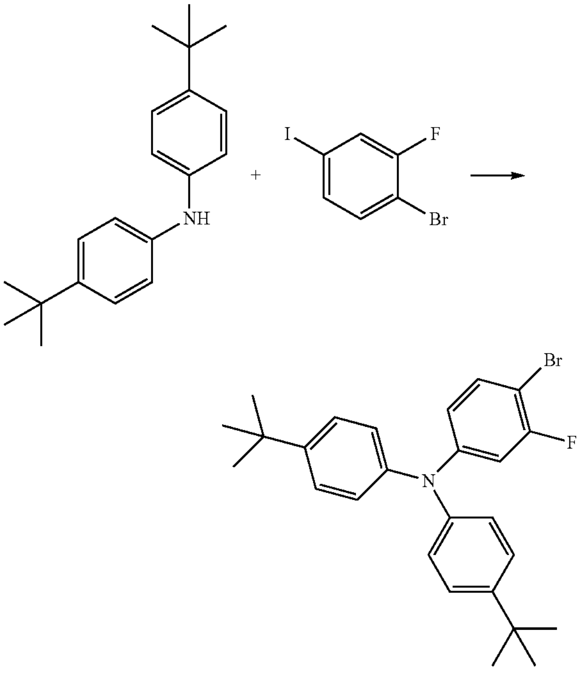

1-6

Manufacture of Intermediate 1-6

Under argon atmosphere, 1-bromo-2-fluoro-4-iodobenzene (22.45 g), bis(4-t-butylphenyl)amine (20.00 g) and sodium t-butoxide (9.56 g) were added to toluene (203 mL). Further, to the obtained solution, tris(dibenzylideneacetone) dipalladium (325 mg) and 4,5-bis(diphenylphosphino)-9,9-dimethylxanthene (822 mg) were added. After being deaerated and purged with argon, the obtained solution was stirred at 80 degrees C. for 16 hours. The stirred reaction solution was cooled to the room temperature and added with toluene to separate a solid by filtration. The filtrate was distilled away under reduced pressure. The obtained residue was purified by silica-gel column chromatography to obtain 31.69 g of a white solid (yield 96%). As a result of mass spectrum analysis, this white solid was a target intermediate 1-6 and had 454.2[M+H]$^{+}$ while a molecular weight was 453.15.

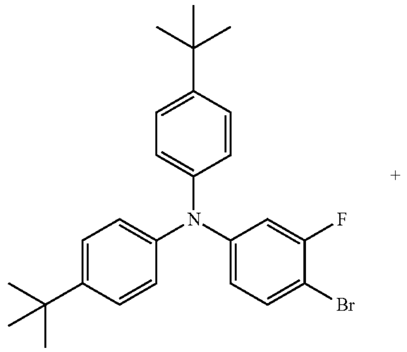

1-6

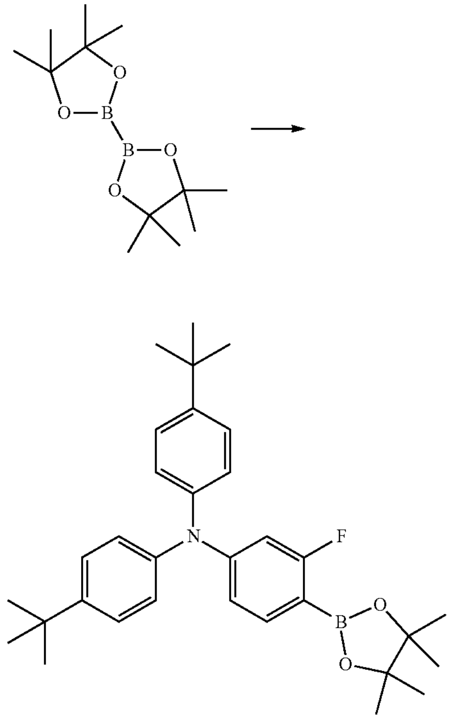

1-7

Manufacture of Intermediate 1-7

Under argon atmosphere, the intermediate 1-6 (29.51 g), bis(pinacolate)diborane (21.44 g) and potassium acetate (12.75 g) were added to toluene (325 mL). Further, to the obtained solution, tris(dibenzylideneacetone)dipalladium (1.19 g) and 2-dicyclohexylphosphino-2',4'-6'-triisopropyl-biphenyl (2.48 g) were added. After being deaerated and purged with argon, the obtained solution was stirred at 80 degrees C. for 16 hours. The stirred reaction solution was cooled to the room temperature and added with toluene to separate a solid by filtration. The filtrate was distilled away under reduced pressure. The obtained residue was purified by silica-gel column chromatography to obtain 28.23 g of a white solid (yield 87%). As a result of mass spectrum analysis, this white solid was a target intermediate 1-7 and had 502.4$[M+H]^+$ while a molecular weight was 501.49.

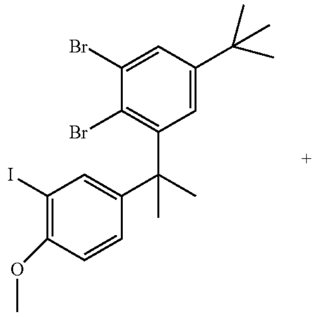

1-5

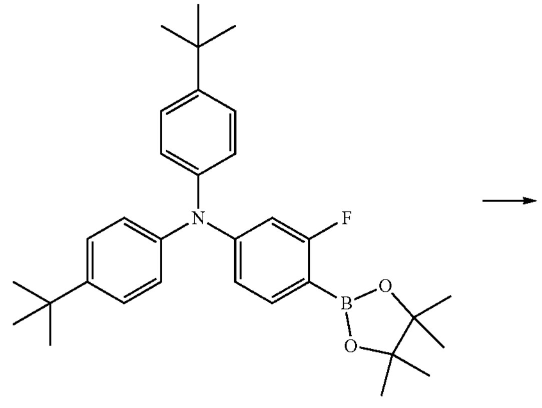

1-7

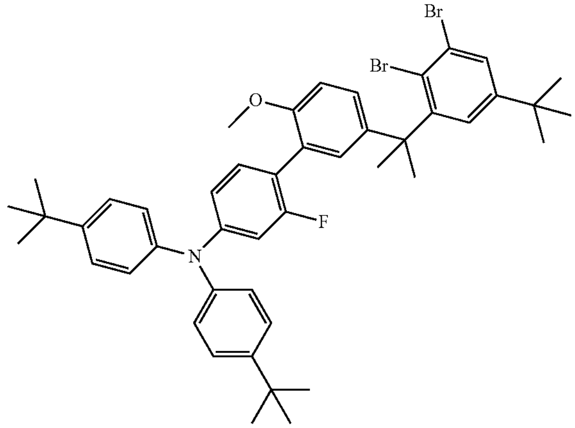

1-8

Manufacture of Intermediate 1-8

Under argon atmosphere, the intermediate 1-5 (3.00 g), the intermediate 1-7 (2.79 g), and potassium phosphate (2.25 g) were added to a mixture solvent of toluene (35 mL), 1,4-dioxane (17 mL), and water (26 mL). The obtained solution was added with tetrakistriphenylphosphine palladium (122 mg) and stirred for 6.5 hours at 75 degrees C. The stirred reaction solution was cooled to the room temperature and transferred to a separatory funnel, and the aqueous layer was extracted with toluene. The collected organic layer was washed with saturated saline and then dried over magnesium sulfate, and a solvent was distilled away under reduced pressure. The obtained residue was purified by silica-gel column chromatography to obtain 3.18 g of a white solid (yield 72%). As a result of mass spectrum analysis, this white solid was a target intermediate 1-8 and had 814.7$[M+H]^+$ while a molecular weight was 813.73.

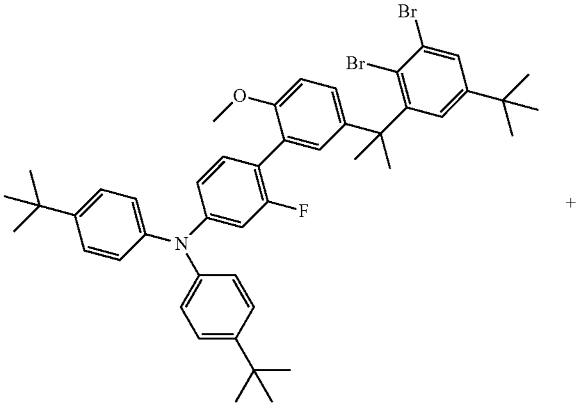

1-8

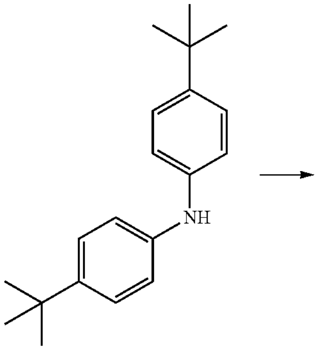

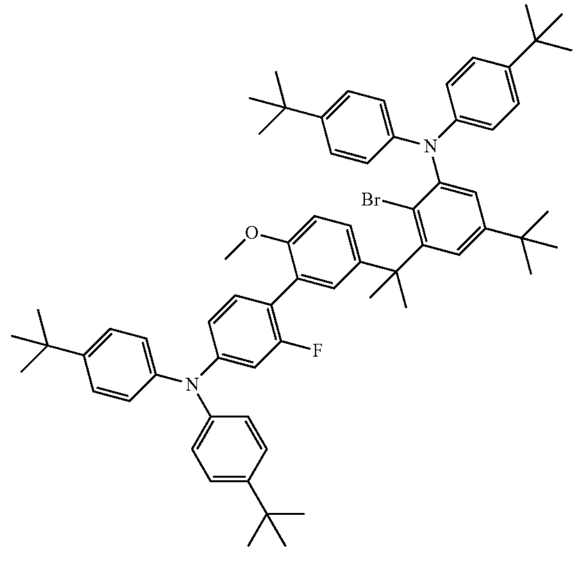

1-9

Manufacture of Intermediate 1-9

Under argon atmosphere, the intermediate 1-8 (3.19 g), bis(4-t-butylphenyl)amine (1.06 g) and sodium t-butoxide (750 mg) were added in xylene (40 mL). Further, to the obtained solution, tris(dibenzylideneacetone)dipalladium (70 mg) and tri-t-butylphosphonium tetrafluoroborate (90 mg) were added. After being deaerated and purged with argon, the obtained solution was stirred at 90 degrees C. for two hours. The stirred reaction solution was cooled to the room temperature and added with water, and the aqueous layer was extracted with ethyl acetate. The collected organic layer was washed with saturated saline and then dried over magnesium sulfate, and a solvent was distilled away under reduced pressure. The obtained residue was purified by silica-gel column chromatography to obtain 2.02 g of a white solid (yield 52%). As a result of mass spectrum analysis, this white solid was a target intermediate 1-9 and had 1038.7[M+H+Na]$^+$ while a molecular weight was 1014.27.

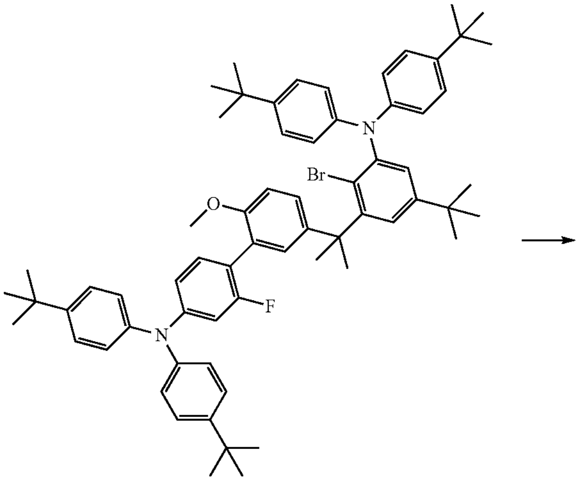

1-9

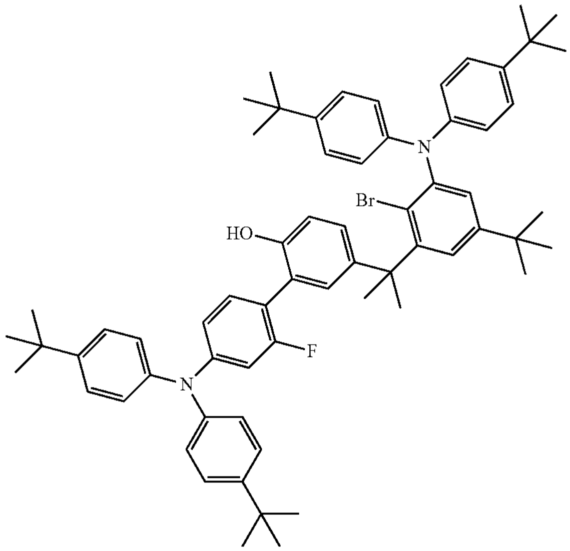

1-10

Manufacture of Intermediate 1-10

Under nitrogen atmosphere, the intermediate 1-9 (2.02 g) was added to methylene chloride (30 mL) and cooled to 0 degrees C. The obtained solution was added with a 1M solution of boron tribromide in methylene chloride (2.0 mL) and stirred overnight at room temperature. The stirred reaction solution was cooled to 0 degrees C. and added with an aqueous sodium hydrogencarbonate solution, and the aqueous layer was extracted with methylene chloride. The collected organic layer was washed with saturated saline and then dried over magnesium sulfate, and a solvent was distilled away under reduced pressure. The obtained residue was used for a next reaction without being purified. As a result of mass spectrum analysis, this residue was a target intermediate 1-10 and had 1001.5[M+H]$^+$ while a molecular weight was 1000.24.

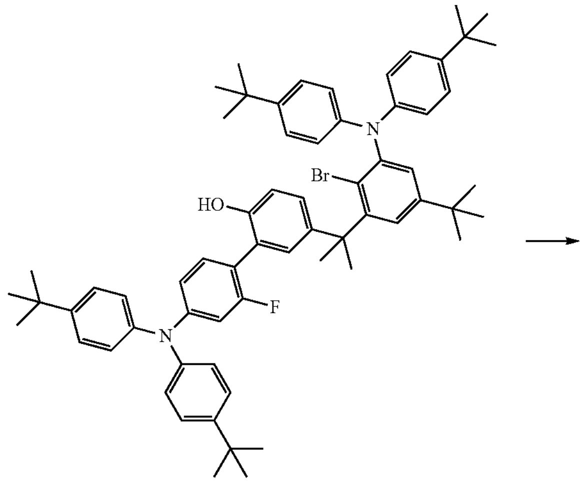

1-10

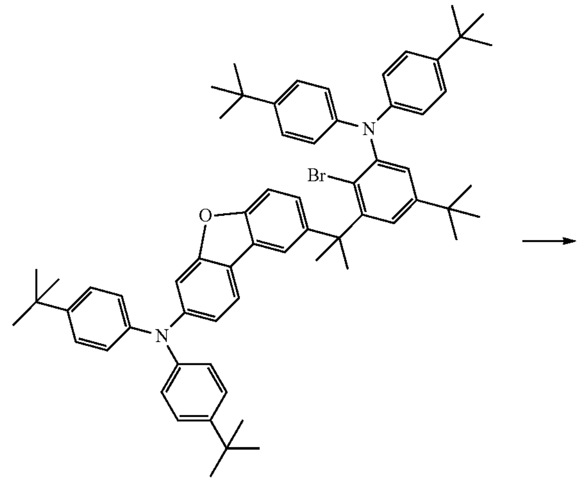

1-11

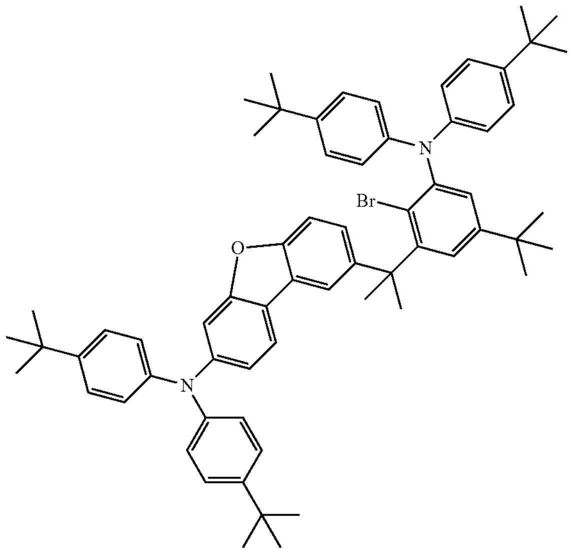

1-11

Manufacture of Intermediate 1-11

Under nitrogen atmosphere, the intermediate 1-10 (1.10 g) was added to dimethylformamide (10 mL), to which potassium carbonate (180 mg) was further added, and the obtained solution was stirred at 100 degrees C. for 22 hours. The stirred reaction solution was cooled to the room temperature and added with water, and the aqueous layer was extracted with methylene chloride. The collected organic layer was washed with saturated saline and then dried over magnesium sulfate, and a solvent was distilled away under reduced pressure. The obtained residue was purified by silica-gel column chromatography to obtain 975 mg of a light orange solid (yield 52%). As a result of mass spectrum analysis, this light orange solid was a target intermediate 1-11 and had 981.5[M+H]$^+$ while a molecular weight was 980.23.

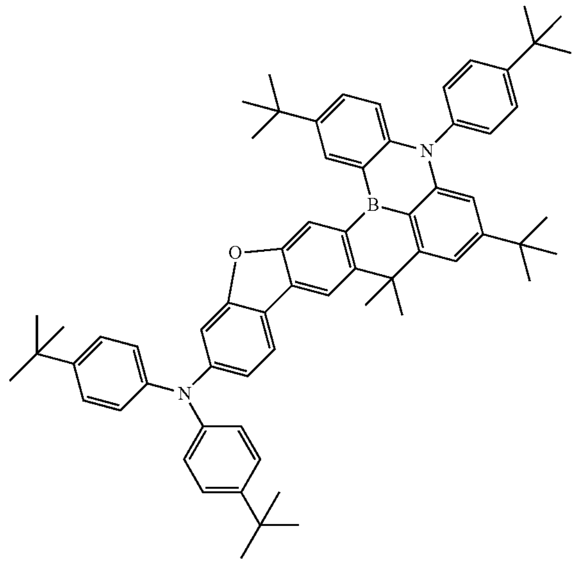

BD-1

Manufacture of Compound BD-1 Under argon atmosphere, the intermediate 1-11 (950 mg) was added to t-butylbenzene (27 mL) and cooled to 0 degrees C., to which 1.9M t-butyllithium pentane solution (1.0 mL) was added dropwise. After the dropwise addition, the temperature was raised to 45 degrees C. and the obtained solution was stirred for 15 minutes. The reaction mixture was then cooled to −55 degrees C., to which boron tribromide (0.18 mL) was added. The reaction mixture was raised to the room temperature and stirred for one hour. The stirred reaction solution was cooled to 0 degrees C., to which N,N-diisopropylethylamine (0.84 mL) was added. The reaction mixture was stirred at the room temperature until heat generation subsided, then heated to 165 degrees C. and stirred overnight. The stirred reaction solution was cooled to the room temperature and added with 1N sodium acetate solution. The precipitated solid was collected by filtration and washed with water and ethanol. The solid collected by filtration was suspended in methylene chloride, and the solid was collected by filtration and then further washed with methylene chloride to obtain 327 mg of an orange solid (36% yield). As a result of mass spectrum analysis, this orange solid was the target compound BD-1 and had 910.0[M+H]$^+$ while a molecular weight was 909.12.

Synthesis of Compound BD-2

A synthesis method of the compound BD-2 will be described below.

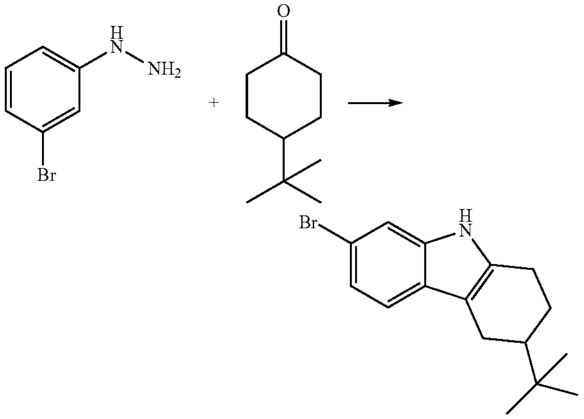

2-1

Manufacture of Intermediate 2-1

28.0 g (125 mmol) of (3-bromophenyl)hydrazine hydrochloride was dissolved in 270 mL of acetic acid and 19.4 g (125 mmol) of 4-(tert-butyl)cyclohexan-1-one was added.

The reaction mixture was stirred at 85 degrees C. for five hours under an inert atmosphere. The reaction mixture was poured into water and extracted with toluene. The organic layer was washed with an aqueous sodium hydrogencarbonate solution.

The organic layer was washed with saturated saline, dried over magnesium sulfate, filtered and concentrated. The crude product was used as an intermediate 2-1 for the next reaction without purification.

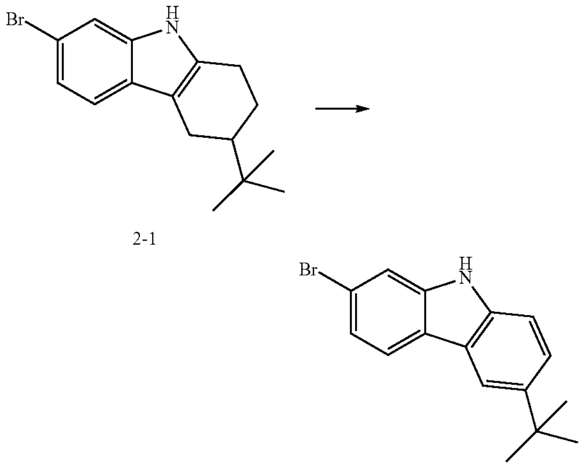

2-1

2-2

Manufacture of Intermediate 2-2

38.1 g (124 mmol) of the intermediate 2-1 was dissolved in 250 mL of toluene, and 56.5 g (249 mmol) of DDQ (2,3-dichloro-5,6-dicyano-1,4-benzoquinone) was added over 10 minutes gradually.

The reaction mixture was stirred at the room temperature for one hour. The reaction mixture was filtered and the organic layer was washed with a 10% solution of aqueous sodium hydroxide.

The organic layer was washed with saturated saline, dried over magnesium sulfate, filtered and concentrated. The crude product was used for the next reaction without purification.

The obtained isomers were separated by silica gel column chromatography using heptane and ethyl acetate (95:5) as eluents to provide 8.47 g (23% yield) of an intermediate 2-2. As a result of $^{1}$H-NMR spectrum analysis, the target intermediate 2-2 was identified.

A result of $^{1}$H-NMR spectrum analysis of the intermediate 2-2 is as follows. $^{1}$H NMR (300 MHz, DMSO-d6) δ: 11.24 (s, 1H), 8.17-8.00 (m, 2H), 7.63 (d, 1H), 7.51 (dd, 1H), 7.43 (dd, 1H), 7.26 (dd, 1H), 1.40 (s, 9H).

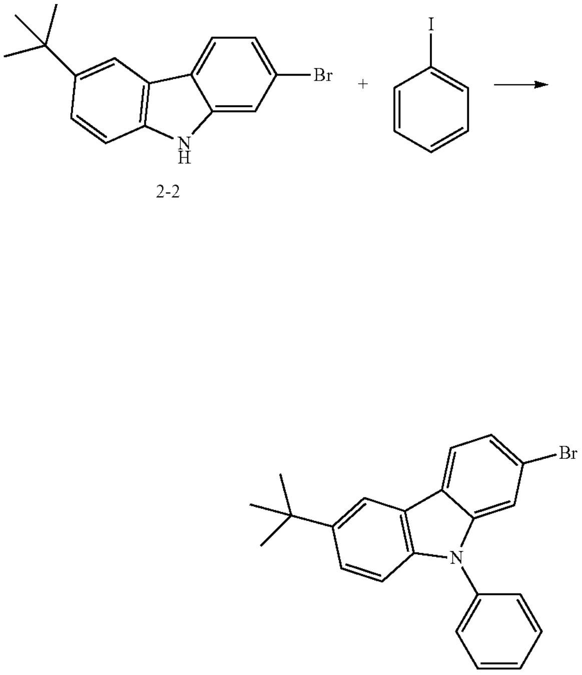

2-2

2-3

Manufacture of Intermediate 2-3

1.55 g (5.15 mmol) of the intermediate 2-2, 1.24 g (6.06 mmol) of iodobenzene, 48.1 mg (0.253 mmol) of copper iodide (I), 58.9 mg (0.515 mmol) of trans-1,2-cyclohexanediamine and 2.23 g (10.5 mmol) of potassium phosphate were suspended in 35 mL of toluene.

The reaction mixture was deaerated by bubbling argon for 10 minutes and then heated to 90 degrees C. for 48 hours under an inert atmosphere.

The reaction mixture was quenched with water and extracted with toluene. The organic layer was washed with saturated saline, dried over magnesium sulfate, filtered and concentrated.

The crude product was purified by silica gel column chromatography using heptane as an eluent to provide 1.61 g (83% yield) of an intermediate 2-3.

The analysis results of gas chromatography-mass spectrometry (GC-MS) of the intermediate 2-3 are as follows.

GC-MS: 377/379 [M+]

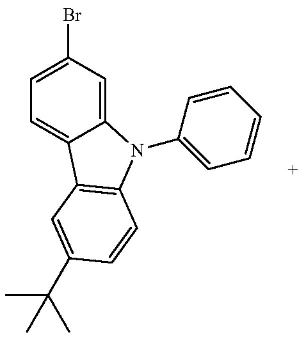

2-3

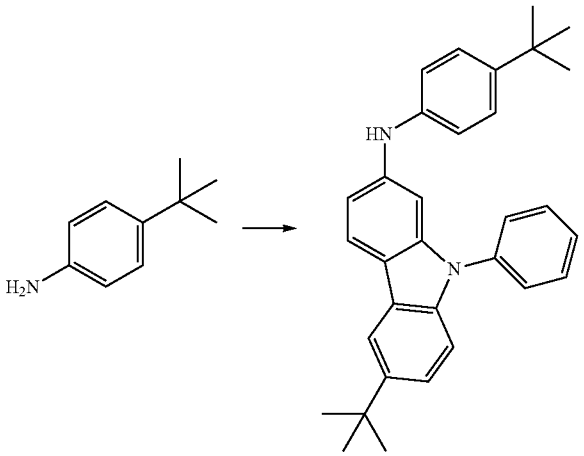

2-4

Manufacture of Intermediate 2-4

5.21 g (13.8 mmol) of the intermediate 2-3, 2.20 g (14.46 mmol) of 4-(tert-butyl)aniline and 3.41 g (34.4 mmol) of sodium tert-butoxide were suspended in 130 mL of toluene.

The suspension was deaerated by bubbling argon for 10 minutes, then 0.129 g (0.138 mmol) of tris(dibenzylideneacetone)dipalladium(0) and 0.350 g (0.551 mmol) of 2,2'-bis (diphenylphosphino)-1,1'-binaphthalene (BINAP) were added to the suspension.

The suspension was deaerated three times and refilled with argon before heating at 90 degrees C. for 19 hours.

The reactant was cooled to the room temperature, quenched with water and diluted with ethyl acetate.

The organic extracts were washed with water, dried over magnesium sulfate, and filtered. The solution was concentrated.

The crude product was purified by trituration in heptane to provide 3.95 g (64% yield) of an intermediate 2-4.

The analysis results of liquid chromatography-mass spectrometry (LC-MS) of the intermediate 2-4 are as follows.

LC-MS: 447.4/448.4 [M+H]+

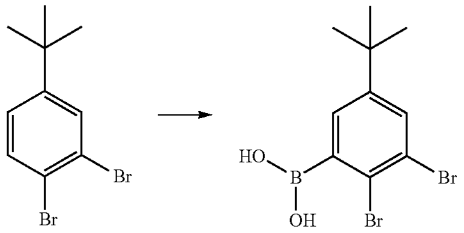

2-5

Manufacture of Intermediate 2-5

42.0 mL (249.0 mmol) of 2,2,6,6-tetramethylpiperidine was dissolved in 250 mL of THF (tetrahydrofuran). After the solution was cooled to −78 degrees C., 100 mL (250 mmol) of 2.5 M n-butyllithium in hexane was added dropwise to the solution via cannula for 30 minutes.

The solution was stirred at −78 degrees C. for 30 minutes.

67.0 mL (290.5 mmol) of triisopropyl borate was slowly added over 30 minutes and the mixture was stirred at −78 degrees C. for one hour, to which a solution of 24.24 g (83.0 mmol) of 1,2-dibromo-4-((tert)-butyl))benzene dissolved in 50 mL of THF was added dropwise at −78 degrees C. over 45 minutes.

Next, the mixture was stirred at the room temperature overnight.

The reaction mixture was poured into 300 mL of ice-cold 1N—HCl and the aqueous layer was extracted with ethyl acetate.

The organic layer was washed with saturated saline, dried over magnesium sulfate, filtered and concentrated.

The crude product was used as an intermediate 2-5 for the next reaction without purification.

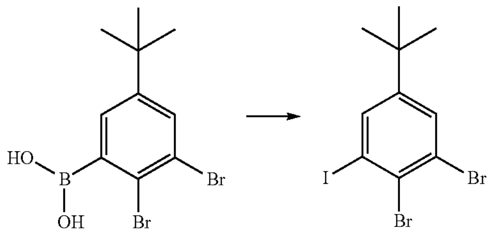

2-5 2-6

Manufacture of Intermediate 2-6

27.86 g (82.96 mmol) of the intermediate 2-5 and 1.63 g (16.59 mmol) of potassium acetate were suspended in 332 mL of acetonitrile.

22.4 g (99.55 mmol) of N-iodosuccinimide was then added to the suspension at the room temperature and the mixture was stirred overnight.

The reaction mixture was quenched with 300 mL of 10% aqueous sodium sulfite solution.

The aqueous layer was extracted with toluene. The organic layer was washed with saturated saline, dried over magnesium sulfate, filtered and concentrated.

The crude product was purified by silica gel column chromatography using heptane as an eluent to provide 22.1 g (61% yield) of an intermediate 2-6 as a white solid.

A result of $^1$H-NMR spectrum analysis of the intermediate 2-6 is as follows. $^1$H NMR (300 MHz, $CD_2Cl_2$) δ7.87 (d, 1H), 7.67 (d, 1H), 1.31 (s, 9H).

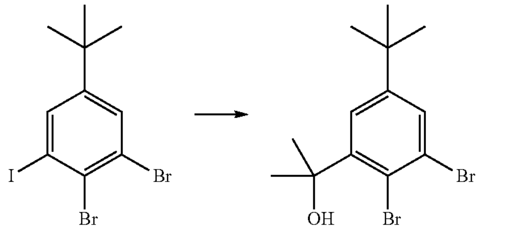

2-6 2-7

Manufacture of Intermediate 2-7

Under an inert atmosphere, 16.0 g (38.3 mmol) of the intermediate 2-6 was dissolved in 96 mL of THF and cooled to −10 degrees C.

20.3 mL (40.5 mmol) of 2M isopropylmagnesium chloride solution in THF was added dropwise and the solution was stirred at −10 degrees C. for one hour.

A solution of 4-mL (54.4 mmol) anhydrous acetone in 24-mL THF was added dropwise. The obtained solution was stirred at −10 degrees C. for 10 minutes before warming to the room temperature for one hour.

The reactant was quenched with a saturated ammonium chloride solution and extracted with ethyl acetate.

The organic layer was washed with saturated saline, dried over magnesium sulfate, filtered and concentrated.

The crude product was purified by silica gel column chromatography using heptane and ethyl acetate as eluents to provide 7.82 g (58% yield) of an intermediate 2-7 as white crystals.

A result of $^1$H-NMR spectrum analysis of the intermediate 2-7 is as follows. $^1$H NMR (300 MHz, DMSO-d6) δ7.92 (d, 1H), 7.61 (d, 1H), 5.38 (s, 1H), 1.63 (s, 6H), 1.27 (s, 9H).

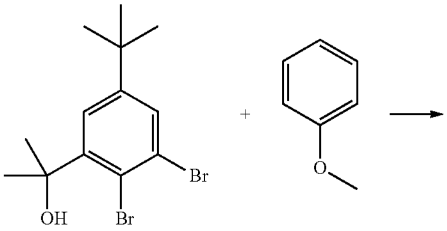

2-7

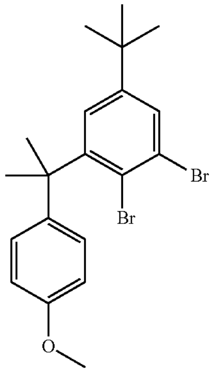

2-8

Manufacture of Intermediate 2-8

Under an inert atmosphere, 9.24 g (26.4 mmol) of the intermediate 2-7 and 2.95 mL (26.6 mmol) of anisole were dissolved in 105 mL of dichloromethane and cooled to 0 degrees C.

At this temperature, 3.91 g (29.0 mmol) of aluminum chloride was added gradually. The reactant was stirred at 0 degrees C. for 30 minutes before being quenched with water.

The reactant was extracted with dichloromethane. The organic layer was washed with saturated saline, dried over magnesium sulfate, filtered and concentrated.

The crude product was purified by silica gel column chromatography using heptane and dichloromethane as eluents to provide 8.20 g (71% yield) of an intermediate 2-8 as a colorless oily substance.

A result of $^1$H-NMR spectrum analysis of the intermediate 2-8 is as follows. $^1$H NMR (300 MHz, $CD_2Cl_2$) δ7.65 (d, 1H), 7.61 (d, 1H), 7.04-6.96 (m, 2H), 6.81-6.74 (m, 2H), 3.76 (s, 3H), 1.74 (s, 6H), 1.36 (s, 9H).

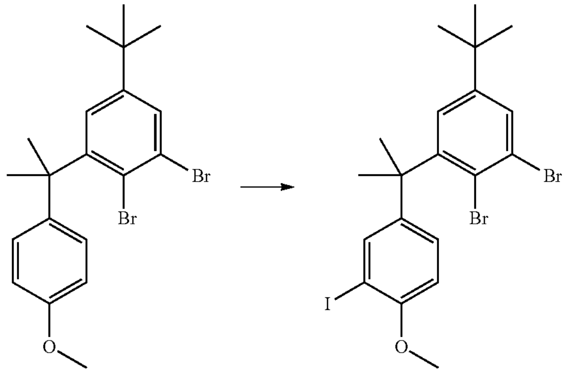

2-8 2-9

Manufacture of Intermediate 2-9

8.20 g (18.6 mmol) of the intermediate 2-8 was suspended in 75 mL of acetonitrile, to which 5.03 g (22.4 mmol) of N-iodosuccinimide and 0.5 mL (6.53 mmol) of trifluoroacetic acid were added.

The suspension was stirred at the room temperature for 24 hours, then cooled to 0 degrees C. and quenched with 10% aqueous sodium sulfite.

The obtained precipitate was filtered, washed with water and cold ethyl acetate to provide 5.13 g (49% yield) of an intermediate 2-9 as a white solid.

A result of $^1$H-NMR spectrum analysis of the intermediate 2-9 is as follows. $^1$H NMR (300 MHz, $CD_2Cl_2$) δ7.62 (s, 2H), 7.54 (d, 1H), 6.99 (dd, 1H), 6.72 (d, 1H), 3.83 (s, 3H), 1.73 (s, 6H), 1.36 (s, 9H).

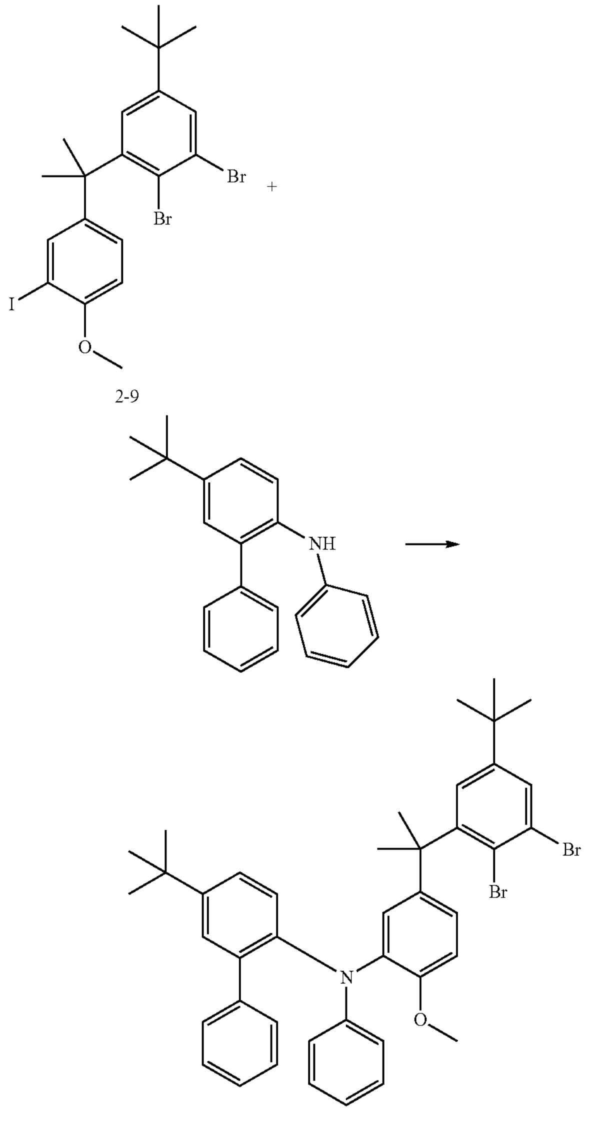

2-9

2-10

Manufacture of Intermediate 2-10

6.28 g (11.1 mmol) of the intermediate 2-9, 3.04 g (10.1 mmol) of 5-(tert-butyl)-N-phenyl-[1,1'-biphenyl]-2-amine, and 1.36 g (14.1 mmol) of sodium tert-butoxide were suspended in 100 mL of toluene.

The suspension was deaerated by bubbling argon for 10 minutes, then 0.115 g (0.126 mmol) of tris(dibenzylideneacetone)dipalladium(0) and 0.146 g (0.504 mmol) of tri-tert-butylphosphonium tetrafluoroborate were added.

The suspension was deaerated three times and refilled with argon before heating at 65 degrees C. for three hours.

The reactant was quenched with water, cooled to the room temperature, and diluted with ethyl acetate.

The organic extracts were washed with water, dried over magnesium sulfate, and filtered. The solution was concentrated.

The crude product was purified by trituration in heptane to provide 6.38 g (84% yield) of an intermediate 2-10.

The analysis results of liquid chromatography-mass spectrometry (LC-MS) of the intermediate 2-10 are as follows.

LC-MS: 738.3/740.3/742.3 [M+H]+

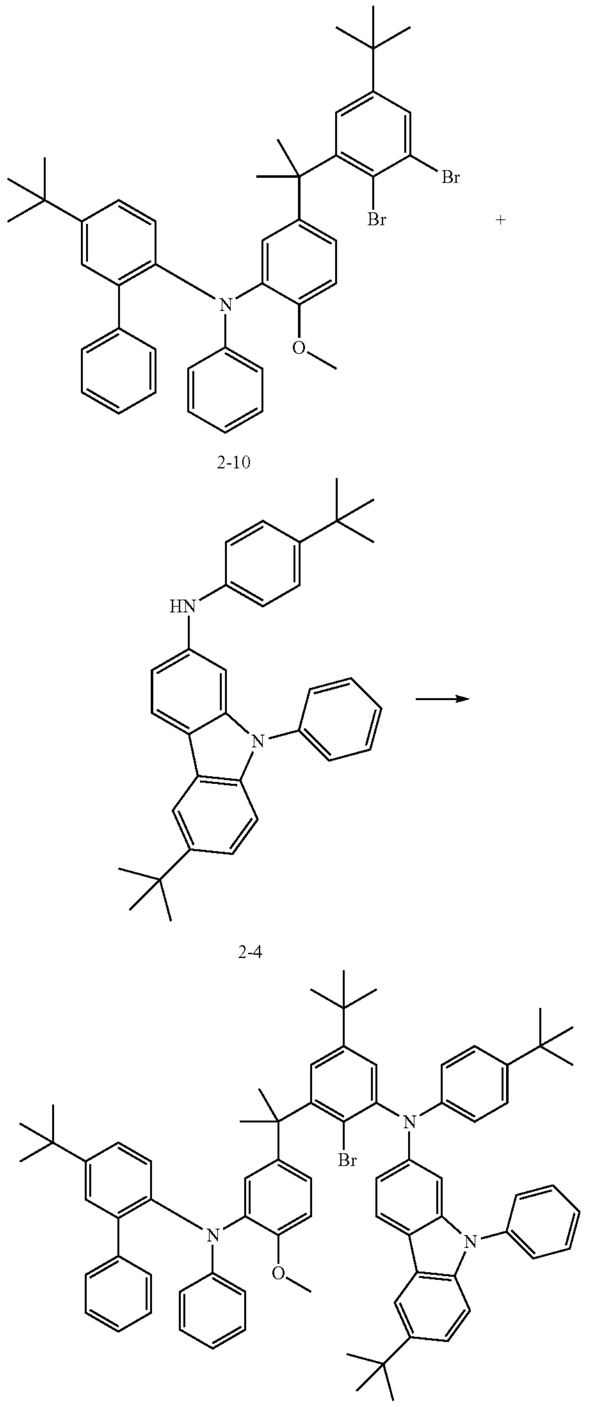

2-10

2-4

2-11

Manufacture of Intermediate 2-11

5.50 g (7.44 mmol) of the intermediate 2-10, 3.32 g (7.44 mmol) of the intermediate 2-4, and 1.79 g (18.6 mmol) of sodium tert-butoxide were suspended in 170 mL of xylene.

The suspension was deaerated by bubbling argon for 10 minutes, then 0.136 g (0.149 mmol) of tris(dibenzylideneacetone)dipalladium(0) and 0.173 g (0.595 mmol) of tri-tert-butylphosphonium tetrafluoroborate were added.

The suspension was deaerated three times, refilled with argon, and heated at 90 degrees C. for 2.5 hours.

The reaction was cooled to the room temperature, quenched with water and diluted with ethyl acetate.

The organic extracts were washed with water, dried over magnesium sulfate, and filtered. The solution was concentrated.

The crude product was purified by silica gel column chromatography using heptane and dichloromethane as eluents to provide 5.70 g (68% yield) of an intermediate 2-11 as a colorless oily substance.

The analysis results of liquid chromatography-mass spectrometry (LC-MS) of the intermediate 2-11 are as follows.

LC-MS: 1104.7/1106.7/1107.7 [M+H]+

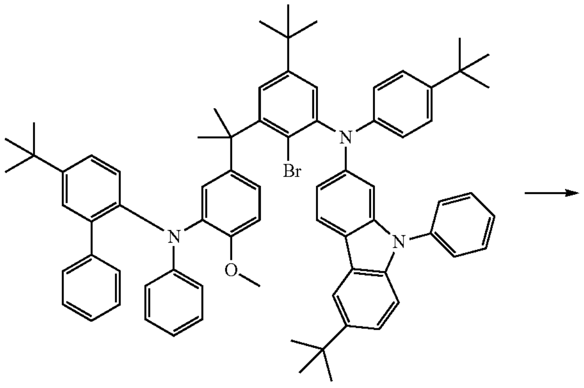

2-11

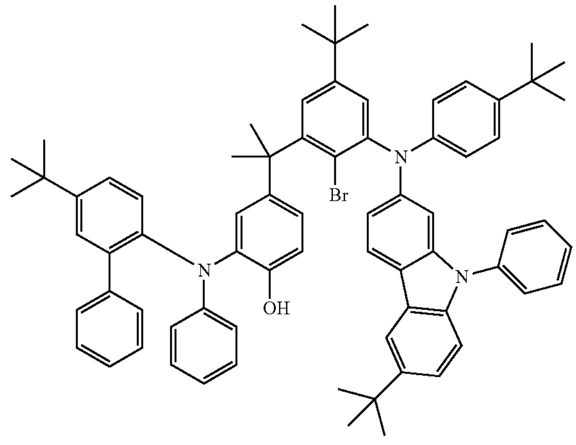

2-12

Manufacture of Intermediate 2-12

Under an inert atmosphere, 5.70 g (5.14 mmol) of the intermediate 2-11 was dissolved in 100 mL of dichloromethane and cooled to 0 degrees C.

7 mL (7.00 mmol) of a 1M solution of boron tribromide in dichloromethane was added dropwise at this temperature and the reactant was stirred overnight at the room temperature.

The reactant was quenched with water at 0 degrees C. and extracted with dichloromethane. The organic layer was washed with saturated saline, dried over magnesium sulfate, filtered and concentrated.

The crude product was purified by silica gel column chromatography using heptane and dichloromethane as eluents to provide 5.28 g (92% yield) of an intermediate 2-12 as a colorless oily substance.

The analysis results of liquid chromatography-mass spectrometry (LC-MS) of the intermediate 2-12 are as follows.

LC-MS: 1090.6/11092.6/1093.6 [M+H]+

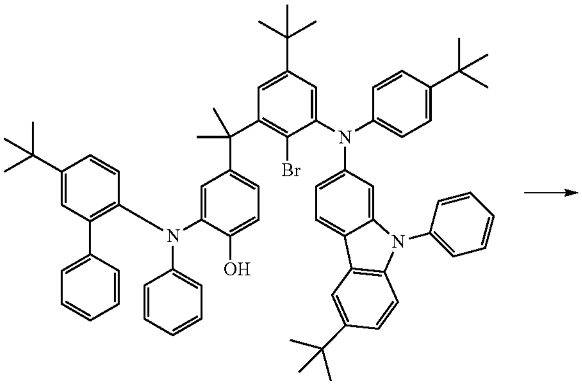

2-12

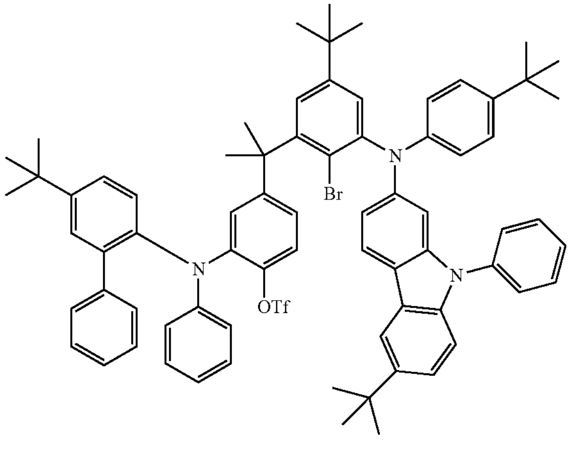

2-13

Manufacture of Intermediate 2-13

Under an inert atmosphere, 4.77 g (4.37 mmol) of the intermediate 2-12 was dissolved in 100 mL of dichloromethane and cooled to 0 degrees C.

1.21 mL (8.74 mmol) of triethylamine was added followed by 0.96 mL (5.68 mmol) of trifluoromethanesulfonic anhydride and the reactant was stirred at the room temperature for 30 minutes.

The reactant was quenched with saturated sodium bicarbonate at 0 degrees C. and extracted with dichloromethane.

The organic layer was washed with saturated saline, dried over magnesium sulfate, filtered and concentrated.

The crude product was purified by silica gel column chromatography using heptane and dichloromethane as eluents to provide 5.16 g (95% yield) of an intermediate 2-13 as a colorless oily substance.

The analysis results of liquid chromatography-mass spectrometry (LC-MS) of the intermediate 2-13 are as follows.

LC-MS: 1222.6/1224.6/1225.4 [M+H]+

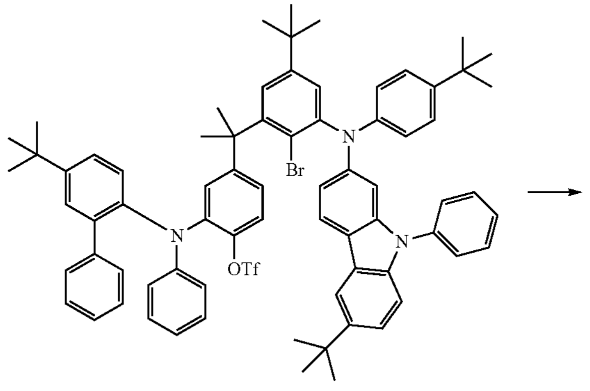

2-13

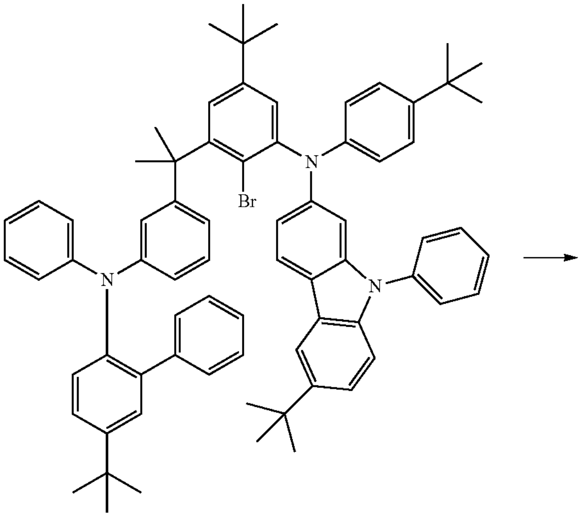

2-14

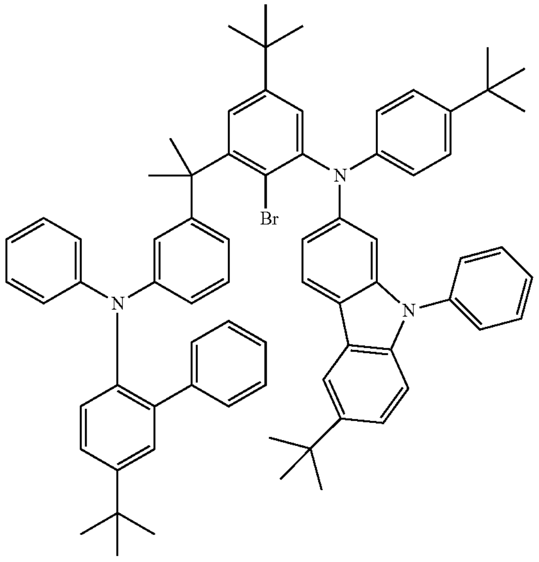

2-14

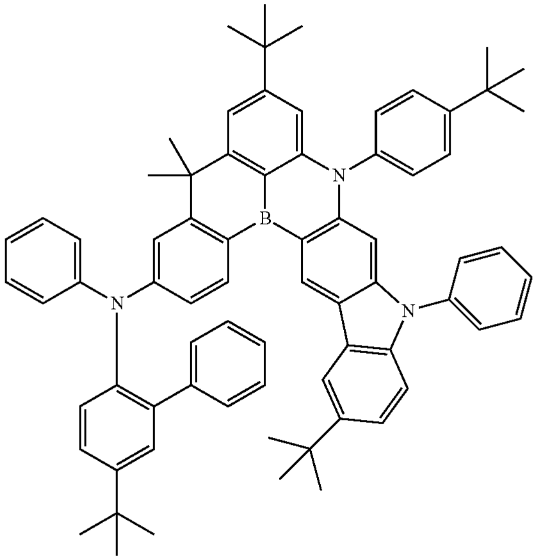

BD-2

Manufacture of Intermediate 2-14

3.64 g (2.98 mmol) of the intermediate 2-13 was dissolved in 30 mL of DMF (N, N-dimethylformamide).

The solution was deaerated by bubbling argon for 10 minutes and cooled to 0 degrees C.

47 mg (0.067 mmol) of bis(triphenylphosphine)palladium (II) chloride, 31 mg (0.074 mmol), 5 mL (35.9 mmol) of trimethylamine, and 0.92 mL (24.0 mmol) formic acid were added. The suspension was deaerated three times, refilled with argon, and heated at 80 degrees C. for 19 hours.

The reaction was cooled to the room temperature, quenched with water and diluted with ethyl acetate.

The organic extracts were washed with water, dried over magnesium sulfate, and filtered. The solution was concentrated.

The crude product was purified by silica gel column chromatography using heptane and dichloromethane as eluents to provide 2.70 g (84% yield) of an intermediate 2-14 as white foam.

The analysis results of liquid chromatography-mass spectrometry (LC-MS) of the intermediate 2-14 are as follows.

LC-MS: 1073.2/1074.7/1076.6 [M+H]+

Manufacture of Compound BD-2

Under an inert atmosphere, 2.91 g (2.71 mmol) of the intermediate 2-14 was dissolved in 90 mL of tert-butylbenzene and cooled to 0 degrees C.

2.85 mL (5.41 mmol) of 1.9 M tert-butyllithium solution in pentane was added dropwise.

The reactant was stirred at the room temperature for one hour, cooled to −30 degrees C. before 0.55 mL (5.82 mmol) of boron tribromide was added dropwise, and warmed to the room temperature.

After being stirred for three hours, the reactant was cooled to 0 degrees C., to which 4.5 mL (25.8 mmol) of N,N-diisopropylethylamine was added. The reactant was heated to 165 degrees C. for 16 hours.

After being cooled to the room temperature, the reactant was quenched with 10% saturated aqueous sodium acetate and extracted with ethyl acetate. The organic extracts were washed with water, dried over magnesium sulfate, and filtered. The solution was concentrated.

The crude product was purified by silica gel column chromatography using heptane and dichloromethane as eluents to provide 180 mg (6% yield) of the compound BD-2.

The analysis results of liquid chromatography-mass spectrometry (LC-MS) of the compound BD-2 are as follows.

LC-MS: 1003.6/1004.7/1005.7 [M+H]+

What is claimed is:

1. A compound represented by a formula (134-1) below, (134-1)

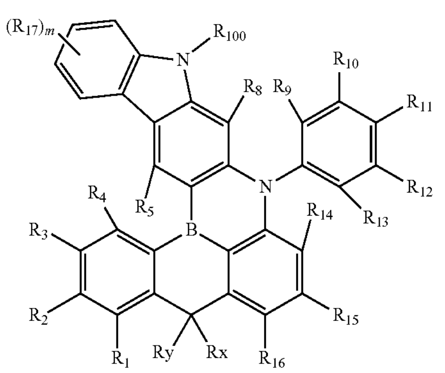

where in the formula (134-1)

at least one combination of adjacent two or more of $R_1$ to $R_5$ and $R_8$ to $R_{16}$ may be mutually bonded to form a substituted or unsubstituted monocyclic ring, mutually bonded to form a substituted or unsubstituted fused ring, or not mutually bonded;

at least one combination of adjacent two of $R_1$ to $R_5$ and $R_8$ to $R_{16}$ may be mutually bonded to form a cyclic structure represented by a formula (10)

(10)

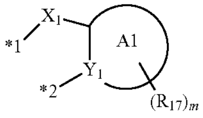

a combination of $R_4$ and $R_5$, a combination of $R_8$ and $R_9$, and a combination of $R_{13}$ and $R_{14}$ are not mutually bonded and do not form the cyclic structure represented by the formula (10);

$R_1$ to $R_5$ and $R_8$ to $R_{16}$ not forming the cyclic structure represented by the formula (10) are each independently a hydrogen atom, a substituted or unsubstituted alkyl group having 1 to 50 carbon atoms, a substituted or unsubstituted haloalkyl group having 1 to 50 carbon atoms, a substituted or unsubstituted alkenyl group having 2 to 50 carbon atoms, a substituted or unsubstituted alkynyl group having 2 to 50 carbon atoms, a substituted or unsubstituted cycloalkyl group having 3 to 50 ring carbon atoms, a group represented by —$N(R_{131})(R_{132})$, a group represented by —$Si(R_{133})(R_{134})(R_{135})$, a group represented by —O—$(R_{136})$, a group represented by —S—$(R_{137})$, a substituted or unsubstituted aralkyl group having 7 to 50 carbon atoms, a group represented by —C(=O)$R_{138}$, a group represented by —$COOR_{139}$, a halogen atom, a cyano group, a nitro group, a group represented by —P(=O)$(R_{140})(R_{141})$, a group represented by —$Ge(R_{142})(R_{143})(R_{144})$, a group represented by —$B(R_{145})(R_{146})$, a substituted or unsubstituted aryl group having 6 to 50 ring carbon atoms, or a substituted or unsubstituted heterocyclic group having 5 to 50 ring atoms;

a combination of $R_X$ and $R_Y$ are mutually bonded to form a substituted or unsubstituted monocyclic ring, mutually bonded to form a substituted or unsubstituted fused ring, or not mutually bonded; and $R_X$ and $R_Y$ forming neither the substituted or unsubstituted monocyclic ring nor the substituted or unsubstituted fused ring are each independently a substituted or unsubstituted alkyl group having 1 to 50 carbon atoms, in the formula (10):

a ring A1 is a substituted or unsubstituted aliphatic hydrocarbon ring having 3 to 50 ring carbon atoms, a substituted or unsubstituted aromatic hydrocarbon ring having 6 to 50 ring carbon atoms, or a substituted or unsubstituted heterocycle having 5 to 50 ring atoms;

m represents the number of $R_{17}$ bonded to the ring A1 and is an integer of 1 or more;

when a plurality of $R_{17}$ are present, the plurality of $R_{17}$ are mutually the same or different;

$X_1$ is $NR_{100}$, an oxygen atom, or a sulfur atom;

when a plurality of $X_1$ are present, the plurality of $X_1$ are mutually the same or different;

$Y_1$ is a carbon atom or a nitrogen atom; and

*1 and *2 each represent a bonding position to adjacent two of $R_1$ to $R_5$ and $R_8$ to $R_{16}$, at least one of $R_1$, $R_2$, $R_3$, $R_4$, $R_5$, $R_8$, $R_9$, $R_{10}$, $R_{11}$, $R_{12}$, $R_{13}$, $R_{14}$, $R_{16}$, or $R_{17}$ is a group represented by —$N(R_{131})(R_{132})$;

a combination of $R_{100}$, and one adjacent to $R_{100}$ among $R_1$ to $R_5$, $R_X$ to $R_{16}$, $R_{17}$, $R_{131}$ and $R_{132}$ that do not form the cyclic structure represented by the formula (10) are mutually bonded to form a substituted or unsubstituted monocyclic ring, mutually bonded to form a substituted or unsubstituted fused ring, or not mutually bonded;

a combination of $R_{131}$ and $R_{132}$ are mutually bonded to form a substituted or unsubstituted monocyclic ring, mutually bonded to form a substituted or unsubstituted fused ring, or not mutually bonded;

a combination of: at least one of $R_{131}$ or $R_{132}$ neither forming the substituted or unsubstituted monocyclic ring nor forming the substituted or unsubstituted fused ring; and at least one adjacent to $R_{131}$ or $R_{132}$ among $R_1$ to $R_5$, $R_8$ to $R_{16}$, $R_{17}$, and $R_{100}$ that do not form the cyclic structure represented by the formula (10) are mutually bonded to form a substituted or unsubstituted monocyclic ring, mutually bonded to form a substituted or unsubstituted fused ring, or not mutually bonded;

$R_{17}$ neither forming the substituted or unsubstituted monocyclic ring nor the substituted or unsubstituted fused ring each independently represent the same as $R_1$ to $R_5$ and $R_8$ to $R_{16}$ not forming the cyclic structure represented by the formula (10);

$R_{100}$, $R_{131}$ and $R_{132}$ forming neither the substituted or unsubstituted monocyclic ring nor the substituted or unsubstituted fused ring are each independently a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{100}$ are present, the plurality of $R_{100}$ are mutually the same or different;

when a plurality of $R_{131}$ are present, the plurality of $R_{131}$ are mutually the same or different;

when a plurality of $R_{132}$ are present, the plurality of $R_{132}$ are mutually the same or different;

$R_{133}$ to $R_{146}$ are each independently a hydrogen atom, a substituted or unsubstituted alkyl group having 1 to 50 carbon atoms, a substituted or unsubstituted cycloalkyl group having 3 to 50 ring carbon atoms, a substituted or unsubstituted aryl group having 6 to 50 ring carbon atoms, or a substituted or unsubstituted heterocyclic group having 5 to 50 ring atoms;

when a plurality of $R_{133}$ are present, the plurality of $R_{133}$ are mutually the same or different;

when a plurality of $R_{134}$ are present, the plurality of $R_{134}$ are mutually the same or different;

when a plurality of $R_{135}$ are present, the plurality of $R_{135}$ are mutually the same or different;

when a plurality of $R_{136}$ are present, the plurality of $R_{136}$ are mutually the same or different;

when a plurality of $R_{137}$ are present, the plurality of $R_{137}$ are mutually the same or different;

when a plurality of $R_{138}$ are present, the plurality of $R_{138}$ are mutually the same or different;

when a plurality of $R_{139}$ are present, the plurality of $R_{139}$ are mutually the same or different;

when a plurality of $R_{140}$ are present, the plurality of $R_{140}$ are mutually the same or different;

when a plurality of $R_{141}$ are present, the plurality of $R_{141}$ are mutually the same or different;

when a plurality of $R_{142}$ are present, the plurality of $R_{142}$ are mutually the same or different;

when a plurality of $R_{143}$ are present, the plurality of $R_{143}$ are mutually the same or different;

when a plurality of $R_{144}$ are present, the plurality of $R_{144}$ are mutually the same or different;

when a plurality of $R_{145}$ are present, the plurality of $R_{145}$ are mutually the same or different; and when a plurality of $R_{146}$ are present, the plurality of $R_{146}$ are mutually the same or different.

2. The compound according to claim 1, wherein a combination of $R_2$ and $R_3$ form a cyclic structure represented by the formula (10).

3. The compound according to claim 1, wherein the combination of $R_X$ and $R_Y$ are not mutually bonded.

4. The compound according to claim 1, wherein $R_1$ to $R_5$ and $R_8$ to $R_{16}$ not forming a cyclic structure represented by the formula (10) nor a cyclic structure represented by the formula (11) are each independently a hydrogen atom, a substituted or unsubstituted alkyl group having 1 to 50 carbon atoms, a group represented by —$N(R_{131})(R_{132})$, a substituted or unsubstituted aryl group having 6 to 50 ring carbon atoms, or a substituted or unsubstituted heterocyclic group having 5 to 50 ring atoms.

5. The compound according to claim 1, wherein in the formula (10):

the ring A1 is a substituted or unsubstituted aliphatic hydrocarbon ring having 3 to 50 ring carbon atoms, or a substituted or unsubstituted aromatic hydrocarbon ring having 6 to 50 ring carbon atoms;

$X_1$ is $NR_{100}$ or an oxygen atom; and

Y is a carbon atom.

6. The compound according to claim 1, wherein a combination of $R_2$ and $R_3$ form a cyclic structure represented by the formula (10);

$R_1$, $R_4$, $R_5$ and $R_8$ to $R_{16}$ do not form a cyclic structure represented by the formula (10);

$R_5$, $R_{11}$ and $R_{15}$ are each independently a hydrogen atom, or a substituted or unsubstituted alkyl group having 1 to 50 carbon atoms; and at least one $R_{17}$ in the formula (10) is a group represented by —$N(R_{131})$ $(R_{132})$.

7. The compound according to claim 1, wherein a combination of $R_2$ and $R_3$ form a cyclic structure represented by the formula (10);

among $R_1$, $R_4$, $R_5$ and $R_8$ to $R_{16}$ not forming a cyclic structure represented by the formula (10), $R_5$, $R_{11}$ and $R_{15}$ are each independently a hydrogen atom, a substituted or unsubstituted alkyl group having 1 to 50 carbon atoms, or a group represented by —$N(R_{131})$ $(R_{132})$; and at least one of $R_5$ or $R_{11}$ is a group represented by —$N(R_{131})(R_{132})$.

8. The compound according to claim 6, wherein $R_1$, $R_4$, $R_5$, $R_8$, $R_9$, $R_{10}$, $R_{12}$, $R_{13}$, $R_{14}$, and $R_{16}$ among $R_1$, $R_4$, $R_5$ and $R_8$ to $R_{16}$ not forming a cyclic structure represented by the formula (10) are each a hydrogen atom.

9. The compound according to claim 1, wherein a combination of $R_{131}$ and $R_{132}$ in a group represented by —$N(R_{131})(R_{132})$ are not mutually bonded.

10. The compound according to claim 1, wherein a cyclic structure represented by the formula (10) is at least one cyclic structure selected from the group consisting of a cyclic structure represented by a formula (101) below, a cyclic structure represented by a formula (102) below, and a cyclic structure represented by a formula (103) below, (101)

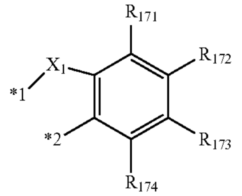

(102)

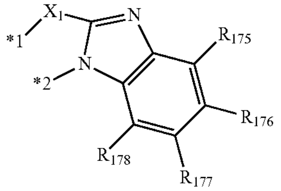

(103)

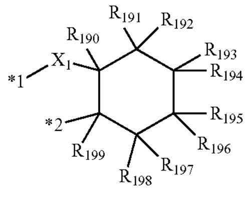

where in the formula (101):

at least one combination of adjacent two or more of $R_{171}$ to $R_{174}$ are mutually bonded to form a substituted or unsubstituted monocyclic ring, mutually bonded to form a substituted or unsubstituted fused ring, or not mutually bonded;

$R_{171}$ to $R_{174}$ forming neither the substituted or unsubstituted monocyclic ring nor the substituted or unsubstituted fused ring each independently represent the same as $R_{17}$ in the formula (10); and $X_1$ represents the same as $X_1$ in the formula (10), in the formula (102):

at least one combination of adjacent two or more of $R_{175}$ to $R_{178}$ are mutually bonded to form a substituted or unsubstituted monocyclic ring, mutually bonded to form a substituted or unsubstituted fused ring, or not mutually bonded;

$R_{175}$ to $R_{178}$ forming neither the substituted or unsubstituted monocyclic ring nor the substituted or unsubstituted fused ring each independently represent the same as $R_{17}$ in the formula (10); and $X_1$ represents the same as $X_1$ in the formula (10), in the formula (103):

at least one combination of adjacent two or more of $R_{190}$ to $R_{199}$ are mutually bonded to form a substituted or unsubstituted monocyclic ring, mutually bonded to form a substituted or unsubstituted fused ring, or not mutually bonded;

$R_{190}$ to $R_{199}$ forming neither the substituted or unsubstituted monocyclic ring nor the substituted or unsubstituted fused ring each independently represent the same as $R_{17}$ in the formula (10); and $X_1$ represents the same as $X_1$ in the formula (10), and

*1 and *2 in the formulae (101), (102), and (103) each represent a bonding position to adjacent two of $R_1$ to $R_5$ and $R_8$ to $R_{16}$.

11. The compound according to claim 10, wherein in the formula (101):

$R_{171}$ to $R_{174}$ forming neither the substituted or unsubstituted monocyclic ring nor the substituted or unsubstituted fused ring are each independently a hydrogen atom, a substituted or unsubstituted alkyl group having 1 to 50 carbon atoms, or a group represented by —$N(R_{131})(R_{132})$; and a combination of $R_{131}$ and $R_{132}$ are mutually bonded to form a substituted or unsubstituted monocyclic ring, mutually bonded to form a substituted or unsubstituted fused ring, or not mutually bonded;

in the formula (102):

$R_{175}$ to $R_{178}$ forming neither the substituted or unsubstituted monocyclic ring nor the substituted or unsubstituted fused ring are each independently a hydrogen atom, a substituted or unsubstituted alkyl group having 1 to 50 carbon atoms, or a group represented by —$N(R_{131})$ $(R_{132})$; and a combination of $R_{131}$ and $R_{132}$ are mutually bonded to form a substituted or unsubstituted monocyclic ring, mutually bonded to form a substituted or unsubstituted fused ring, or not mutually bonded;

in the formula (103):

$R_{190}$ to $R_{199}$ forming neither the substituted or unsubstituted monocyclic ring nor the substituted or unsubstituted fused ring are each independently a hydrogen atom, a substituted or unsubstituted alkyl group having 1 to 50 carbon atoms, or a group represented by —$N(R_{131})(R_{132})$; and a combination of $R_{131}$ and $R_{132}$ are mutually bonded to form a substituted or unsubstituted monocyclic ring, mutually bonded to form a substituted or unsubstituted fused ring, or not mutually bonded.

12. An organic-electroluminescence-device material comprising the compound according to claim 1.

13. An organic electroluminescence device comprising: a cathode, an anode, and at least one organic layer provided between the cathode and the anode, wherein at least one of the at least one organic layer comprises the compound according to claim 1.

14. The organic electroluminescence device according to claim 13, wherein the at least one organic layer comprises an emitting layer, and the emitting layer comprises the compound.

15. An electronic device comprising the organic electroluminescence device according to claim 13.

* * * * *